US010918426B2

(12) United States Patent
Peterson et al.

(10) Patent No.: US 10,918,426 B2
(45) Date of Patent: Feb. 16, 2021

(54) APPARATUS AND METHODS FOR TREATMENT OF A BONE

(71) Applicant: Conventus Orthopaedics, Inc., Maple Grove, MN (US)

(72) Inventors: Alex A. Peterson, Maple Grove, MN (US); Michael P. Brenzel, St. Paul, MN (US); Steve D. Kruse, St. Michael, MN (US); Todd A. Krinke, Buffalo, MN (US); Paul Hindrichs, Plymouth, MN (US); Troy Michael Siemers, Big Lake, MN (US); Jonathan Berndt, Crystal, MN (US); David Costello, Delano, MN (US); Umasuthan Srikumaran, Ellicott City, MD (US)

(73) Assignee: CONVENTUS ORTHOPAEDICS, INC., Maple Grove, MN (US)

( * ) Notice: Subject to any disclaimer, the term of this patent is extended or adjusted under 35 U.S.C. 154(b) by 0 days.

(21) Appl. No.: 16/027,338

(22) Filed: Jul. 4, 2018

(65) Prior Publication Data

US 2019/0105088 A1    Apr. 11, 2019

Related U.S. Application Data

(60) Provisional application No. 62/528,476, filed on Jul. 4, 2017.

(51) Int. Cl.
*A61B 17/74* (2006.01)
*A61B 17/72* (2006.01)
(Continued)

(52) U.S. Cl.
CPC ........ *A61B 17/744* (2013.01); *A61B 17/1725* (2013.01); *A61B 17/1728* (2013.01);
(Continued)

(58) Field of Classification Search
CPC .............. A61B 17/744; A61B 17/1778; A61B 17/1725; A61B 17/1728; A61B 17/7275;
(Continued)

(56) References Cited

U.S. PATENT DOCUMENTS

| 1,362,513 A | 12/1919 | Skinner |
| 1,344,327 A | 6/1920 | Wilson |

(Continued)

FOREIGN PATENT DOCUMENTS

| AU | 2008232900 | 10/2008 |
| CA | 2007210 A1 | 11/1990 |

(Continued)

OTHER PUBLICATIONS

US 7,063,700 B2, 06/2006, Michelson (withdrawn)
(Continued)

*Primary Examiner* — Tessa M Matthews
(74) *Attorney, Agent, or Firm* — Ice Miller LLP

(57) ABSTRACT

Apparatus and methods for treatment of a bone. The apparatus may include an implant. The implant may include an implant tail and an implant head configured to expand, inside the bone, from a collapsed state to an expanded state. The apparatus may include an intramedullary rod defining a central longitudinal rod axis. The intramedullary rod may include a guide segment configured to guide the implant head into the bone and support the implant tail. The intramedullary rod may include an elongated extension member spaced radially apart from the central longitudinal axis. The extension member may be configured to provide clearance for the implant head as the implant head is advanced, in the collapsed state, into the bone. The extension member may be configured to provide clearance for the implant head in the expanded state.

7 Claims, 79 Drawing Sheets

(51) Int. Cl.
  *A61B 17/56* (2006.01)
  *A61B 17/86* (2006.01)
  *A61B 17/80* (2006.01)
  *A61B 17/17* (2006.01)

(52) U.S. Cl.
  CPC ...... *A61B 17/1778* (2016.11); *A61B 17/7275* (2013.01); *A61B 17/742* (2013.01); *A61B 17/746* (2013.01); *A61B 17/8023* (2013.01); *A61B 17/8061* (2013.01); *A61B 17/8695* (2013.01); *A61B 17/175* (2013.01); *A61B 2017/564* (2013.01)

(58) Field of Classification Search
  CPC . A61B 17/742; A61B 17/746; A61B 17/8023; A61B 17/8061; A61B 17/8695
  See application file for complete search history.

(56) References Cited

U.S. PATENT DOCUMENTS

| | | |
|---|---|---|
| 1,493,240 A | 5/1924 | Bohn |
| 1,685,380 A | 9/1928 | Shultz |
| 2,137,710 A | 12/1937 | Anderson |
| 2,485,531 A | 1/1948 | Dzus et al. |
| 2,493,598 A | 1/1950 | Rozek |
| 2,537,070 A | 1/1951 | Longfellow |
| 2,580,821 A | 1/1952 | Nicola |
| 2,612,159 A | 9/1952 | Collison |
| 2,627,855 A | 2/1953 | Price |
| 2,730,101 A | 1/1956 | Hoffman |
| 2,780,223 A | 2/1957 | Haggland |
| 2,898,963 A | 8/1959 | Courtot |
| 3,029,811 A | 4/1962 | Yost |
| 3,030,951 A | 4/1962 | Mandarino |
| 3,143,915 A | 8/1964 | Tendler |
| 3,143,916 A | 8/1964 | Rice |
| 3,146,892 A | 9/1964 | White |
| 3,181,533 A | 5/1965 | Heath |
| 3,386,169 A | 6/1968 | Scialom |
| 3,486,500 A | 12/1969 | Ball et al. |
| 3,495,586 A | 2/1970 | Regenbogen |
| 3,517,128 A | 6/1970 | Hines |
| 3,561,437 A | 2/1971 | Orlich |
| 3,593,342 A | 7/1971 | Niebauer et al. |
| 3,602,218 A | 8/1971 | Riordan |
| 3,623,164 A | 10/1971 | Bokros |
| 3,640,280 A | 2/1972 | Slanker et al. |
| 3,702,611 A | 10/1972 | Fishbein |
| 3,710,789 A | 1/1973 | Ersek |
| 3,744,488 A | 7/1973 | Cox |
| 3,745,590 A | 7/1973 | Stubstad |
| 3,759,257 A | 9/1973 | Fischer et al. |
| 3,760,802 A | 9/1973 | Fischer et al. |
| 3,779,239 A | 12/1973 | Fischer et al. |
| 3,805,775 A | 4/1974 | Fischer et al. |
| 3,828,790 A | 8/1974 | Curtiss et al. |
| 3,835,859 A | 9/1974 | Roberts et al. |
| 3,886,600 A | 6/1975 | Kahn et al. |
| 3,909,853 A | 10/1975 | Lennox |
| 3,917,249 A | 11/1975 | Constantine |
| 3,946,445 A | 3/1976 | Bentley et al. |
| 3,970,075 A | 7/1976 | Sindelar et al. |
| 3,986,504 A | 10/1976 | Avila |
| 3,992,726 A | 11/1976 | Freeman et al. |
| 4,036,107 A | 7/1977 | Constantine |
| 4,091,806 A | 5/1978 | Aginsky |
| 4,101,985 A | 7/1978 | Baumann et al. |
| 4,124,026 A | 11/1978 | Berner et al. |
| 4,156,296 A | 5/1979 | Johnson et al. |
| 4,180,871 A | 1/1980 | Hamas |
| 4,190,044 A | 2/1980 | Wood |
| 4,193,139 A | 3/1980 | Walker |
| 4,194,250 A | 3/1980 | Walker |
| 4,203,444 A | 5/1980 | Bonnell et al. |
| 4,204,531 A | 5/1980 | Aginsky |
| 4,213,208 A | 7/1980 | Marne |
| 4,227,518 A | 10/1980 | Aginsky |
| 4,229,840 A | 10/1980 | Gristina |
| 4,231,121 A | 11/1980 | Lewis |
| 4,262,665 A | 4/1981 | Roalstad et al. |
| 4,273,128 A | 6/1981 | Lary |
| 4,274,398 A | 6/1981 | Scott et al. |
| 4,275,717 A | 6/1981 | Bolesky |
| 4,293,962 A | 10/1981 | Fuson |
| 4,313,434 A | 2/1982 | Segal |
| 4,349,922 A | 9/1982 | Agee |
| 4,352,212 A | 10/1982 | Greene et al. |
| 4,430,991 A | 2/1984 | Darnell |
| 4,438,762 A | 3/1984 | Kyle |
| 4,453,539 A | 6/1984 | Raftopoulos et al. |
| 4,473,070 A | 9/1984 | Matthews et al. |
| 4,485,816 A | 12/1984 | Krumme |
| 4,502,554 A | 3/1985 | Jones |
| 4,519,100 A | 5/1985 | Wills et al. |
| 4,522,200 A | 6/1985 | Stednitz |
| 4,530,114 A | 7/1985 | Tepic |
| 4,548,199 A | 10/1985 | Agee |
| 4,572,186 A | 2/1986 | Gould et al. |
| 4,573,448 A | 3/1986 | Kambin |
| 4,585,000 A | 4/1986 | Hershenson |
| 4,590,930 A | 5/1986 | Kurth et al. |
| 4,601,290 A | 7/1986 | Effron et al. |
| 4,608,965 A | 9/1986 | Anspach, Jr. et al. |
| 4,611,594 A | 9/1986 | Grayhack et al. |
| 4,619,122 A | 10/1986 | Simpson |
| 4,627,434 A | 12/1986 | Murray |
| 4,634,445 A | 1/1987 | Helal |
| 4,643,177 A | 2/1987 | Sheppard et al. |
| 4,644,951 A | 2/1987 | Bays |
| 4,646,738 A | 3/1987 | Trott |
| 4,655,203 A | 4/1987 | Tormala et al. |
| 4,660,557 A | 4/1987 | Collis |
| 4,662,371 A | 5/1987 | Whipple et al. |
| 4,665,906 A | 5/1987 | Jervis |
| 4,669,237 A | 6/1987 | Constantine |
| 4,674,488 A | 6/1987 | Nashef et al. |
| 4,705,027 A | 11/1987 | Klaue |
| 4,721,103 A | 1/1988 | Freedland |
| 4,730,608 A | 3/1988 | Schlein |
| 4,731,087 A | 3/1988 | Sculco et al. |
| 4,751,922 A | 6/1988 | DiPietropolo |
| 4,772,261 A | 9/1988 | Von Hoff et al. |
| 4,777,942 A | 10/1988 | Frey et al. |
| 4,782,833 A | 11/1988 | Einhorn et al. |
| 4,788,970 A | 12/1988 | Kara et al. |
| 4,790,302 A | 12/1988 | Colwill et al. |
| 4,809,793 A | 3/1989 | Hailey |
| 4,820,305 A | 4/1989 | Harms et al. |
| 4,865,604 A | 9/1989 | Rogozinski |
| 4,875,474 A | 10/1989 | Border |
| 4,886,062 A | 12/1989 | Wiktor |
| 4,914,818 A | 4/1990 | Hall et al. |
| 4,920,959 A | 5/1990 | Witzel et al. |
| 4,921,478 A | 5/1990 | Solano et al. |
| 4,941,466 A | 7/1990 | Romano |
| 4,946,459 A | 8/1990 | Bradshaw et al. |
| 4,954,126 A | 9/1990 | Wallsten |
| 4,955,916 A | 9/1990 | Carignan et al. |
| 4,969,888 A | 11/1990 | Scholten et al. |
| 4,973,257 A | 11/1990 | Lhotak |
| 4,978,349 A | 12/1990 | Frigg |
| 4,998,539 A | 3/1991 | Delsanti |
| 5,002,546 A | 3/1991 | Romano |
| 5,015,255 A | 5/1991 | Kuslich |
| 5,030,201 A | 7/1991 | Palestrant |
| 5,035,714 A | 7/1991 | Willert et al. |
| 5,047,055 A | 9/1991 | Bao et al. |
| 5,053,036 A | 10/1991 | Perren et al. |
| 5,057,103 A | 10/1991 | Davis |
| 5,059,193 A | 10/1991 | Kuslich |
| 5,059,206 A | 10/1991 | Winters |
| 5,062,845 A | 11/1991 | Kuslich et al. |
| 5,066,296 A | 11/1991 | Chapman et al. |

(56) References Cited

U.S. PATENT DOCUMENTS

| | | |
|---|---|---|
| 5,067,957 A | 11/1991 | Jervis |
| 5,071,407 A | 12/1991 | Termin et al. |
| 5,084,050 A | 1/1992 | Draenert |
| 5,100,423 A | 3/1992 | Fearnot |
| 5,102,413 A | 4/1992 | Poddar |
| 5,108,404 A | 4/1992 | Scholten et al. |
| 5,108,435 A | 4/1992 | Gustavson et al. |
| 5,112,333 A | 5/1992 | Fixel |
| 5,113,846 A | 5/1992 | Hiltebrandt et al. |
| 5,116,335 A | 5/1992 | Hannon et al. |
| 5,122,134 A | 6/1992 | Borzone et al. |
| 5,129,906 A | 7/1992 | Ross et al. |
| 5,133,767 A | 7/1992 | Frey et al. |
| 5,135,527 A | 8/1992 | Ender |
| 5,139,497 A | 8/1992 | Tilghman et al. |
| 5,151,103 A | 9/1992 | Tepic et al. |
| 5,169,402 A | 12/1992 | Elloy |
| 5,171,284 A | 12/1992 | Branemark |
| 5,174,374 A | 12/1992 | Hailey |
| 5,180,382 A | 1/1993 | Frigg et al. |
| 5,190,545 A | 3/1993 | Corsi et al. |
| 5,190,546 A | 3/1993 | Jervis |
| 5,190,548 A | 3/1993 | Davis |
| 5,197,966 A | 3/1993 | Sommerkamp |
| 5,197,967 A | 3/1993 | Wilson |
| 5,197,971 A | 3/1993 | Bonutti |
| 5,201,741 A | 4/1993 | Dulebohn |
| 5,203,773 A | 4/1993 | Green |
| 5,221,261 A | 6/1993 | Termin et al. |
| 5,236,431 A | 8/1993 | Gogolewski et al. |
| 5,242,017 A | 9/1993 | Hailey |
| 5,242,461 A | 9/1993 | Kortenbach et al. |
| 5,250,048 A | 10/1993 | Gundolf |
| 5,263,955 A | 11/1993 | Baumgart et al. |
| 5,269,785 A | 12/1993 | Bonutti |
| 5,275,602 A | 1/1994 | Shimizu et al. |
| 5,275,608 A | 1/1994 | Forman et al. |
| 5,281,225 A | 1/1994 | Vicenzi |
| 5,281,226 A | 1/1994 | Daydov et al. |
| 5,286,249 A | 2/1994 | Thibodaux |
| 5,306,310 A | 4/1994 | Siebels |
| 5,307,790 A | 5/1994 | Byrne |
| 5,314,486 A | 5/1994 | Zang et al. |
| 5,326,205 A | 7/1994 | Anspach et al. |
| 5,334,184 A | 8/1994 | Bimman |
| 5,358,405 A | 10/1994 | Imai |
| 5,370,697 A | 12/1994 | Baumgartner |
| 5,376,097 A | 12/1994 | Phillips |
| 5,376,100 A | 12/1994 | Lefebvre |
| 5,378,239 A | 1/1995 | Termin et al. |
| 5,380,328 A | 1/1995 | Morgan |
| 5,397,320 A | 3/1995 | Essig et al. |
| 5,401,269 A | 3/1995 | Buttner-Janz et al. |
| 5,415,660 A | 5/1995 | Campbell et al. |
| 5,423,823 A | 6/1995 | Schmieding |
| 5,431,671 A | 7/1995 | Nallakrishnan |
| 5,437,665 A | 8/1995 | Munro |
| 5,437,674 A | 8/1995 | Worcel et al. |
| 5,439,464 A | 8/1995 | Shapiro |
| 5,445,639 A | 8/1995 | Kuslich et al. |
| 5,454,365 A | 10/1995 | Bonutti |
| 5,458,599 A | 10/1995 | Adobbati |
| 5,458,648 A | 10/1995 | Berman et al. |
| 5,462,547 A | 10/1995 | Weigum |
| 5,467,763 A | 11/1995 | McMahon et al. |
| D365,634 S | 12/1995 | Morgan |
| 5,474,557 A | 12/1995 | Mai |
| 5,480,447 A | 1/1996 | Skiba |
| 5,484,439 A | 1/1996 | Olson et al. |
| 5,496,277 A | 3/1996 | Termin et al. |
| 5,496,330 A | 3/1996 | Bates et al. |
| 5,499,981 A | 3/1996 | Kordis |
| 5,501,695 A | 3/1996 | Anspach et al. |
| 5,505,734 A | 4/1996 | Caniggia et al. |
| 5,509,919 A | 4/1996 | Young |
| 5,512,037 A | 4/1996 | Russell et al. |
| 5,527,316 A | 6/1996 | Stone et al. |
| 5,531,792 A | 7/1996 | Huene |
| 5,536,267 A | 7/1996 | Edwards et al. |
| 5,540,693 A | 7/1996 | Fisher |
| 5,545,162 A | 8/1996 | Huebner |
| 5,549,679 A | 8/1996 | Kuslich |
| 5,554,163 A | 9/1996 | Shturman |
| 5,556,408 A | 9/1996 | Farhat |
| 5,571,098 A | 11/1996 | Domankevitz et al. |
| 5,571,189 A | 11/1996 | Kuslich |
| 5,578,035 A | 11/1996 | Lin |
| 5,582,577 A | 12/1996 | Lund et al. |
| 5,582,618 A | 12/1996 | Chin et al. |
| 5,586,983 A | 12/1996 | Sanders et al. |
| 5,586,985 A | 12/1996 | Putnam et al. |
| 5,586,990 A | 12/1996 | Hahnen et al. |
| 5,591,169 A | 1/1997 | Benoist |
| 5,591,170 A | 1/1997 | Spievack et al. |
| 5,597,378 A | 1/1997 | Jervis |
| 5,601,593 A | 2/1997 | Freitag |
| 5,602,935 A | 2/1997 | Yoshida et al. |
| 5,609,635 A | 3/1997 | Michelson |
| 5,620,414 A | 4/1997 | Campbell |
| 5,620,445 A | 4/1997 | Brosnahan et al. |
| 5,624,440 A | 4/1997 | Huebner |
| 5,624,447 A | 4/1997 | Myers |
| 5,626,580 A | 5/1997 | Brosnahan |
| 5,628,747 A | 5/1997 | Richelsoph |
| 5,645,589 A | 7/1997 | Li |
| 5,658,280 A | 8/1997 | Issa |
| 5,658,283 A | 8/1997 | Huebner |
| 5,660,188 A | 8/1997 | Groiso |
| 5,662,649 A | 9/1997 | Huebner |
| 5,667,509 A | 9/1997 | Westin |
| 5,674,295 A | 10/1997 | Ray et al. |
| 5,676,545 A | 10/1997 | Jones |
| 5,676,699 A | 10/1997 | Gogolewski et al. |
| 5,681,310 A | 10/1997 | Yuan et al. |
| 5,683,389 A | 11/1997 | Orsak |
| 5,685,826 A | 11/1997 | Bonutti |
| 5,693,011 A | 12/1997 | Onik |
| 5,697,981 A | 12/1997 | Ison et al. |
| 5,707,374 A | 1/1998 | Schmidt |
| 5,709,697 A | 1/1998 | Ratcliff et al. |
| 5,713,901 A | 2/1998 | Tock |
| 5,718,704 A | 2/1998 | Medoff |
| 5,725,531 A | 3/1998 | Shapiro |
| 5,725,541 A | 3/1998 | Anspach, III et al. |
| 5,728,047 A | 3/1998 | Edoga |
| 5,728,098 A | 3/1998 | Sherman et al. |
| 5,730,704 A | 3/1998 | Avitall |
| 5,741,266 A | 4/1998 | Moran et al. |
| 5,741,282 A | 4/1998 | Anspach et al. |
| 5,758,713 A | 6/1998 | Fallet |
| 5,779,703 A | 7/1998 | Benoist |
| 5,792,106 A | 8/1998 | Mische |
| 5,810,721 A | 9/1998 | Mueller et al. |
| 5,814,044 A | 9/1998 | Hooven |
| 5,817,098 A | 10/1998 | Albrektsson et al. |
| 5,824,095 A | 10/1998 | Di Maio, Jr. et al. |
| 5,827,289 A | 10/1998 | Reiley et al. |
| 5,827,312 A | 10/1998 | Brown et al. |
| D403,069 S | 12/1998 | Drewry et al. |
| 5,853,054 A | 12/1998 | McGarian et al. |
| 5,876,399 A | 3/1999 | Chia et al. |
| 5,879,352 A | 3/1999 | Filoso et al. |
| 5,879,355 A | 3/1999 | Ullmark |
| 5,885,258 A | 3/1999 | Sachdeva et al. |
| 5,885,282 A | 3/1999 | Szabo |
| 5,888,196 A | 3/1999 | Bonutti |
| 5,891,147 A | 4/1999 | Moskovitz et al. |
| 5,893,850 A | 4/1999 | Cachia |
| 5,897,556 A | 4/1999 | Drewry et al. |
| 5,908,423 A | 6/1999 | Kashuba et al. |
| 5,915,036 A | 6/1999 | Grunkin et al. |
| 5,919,195 A | 7/1999 | Wilson et al. |
| 5,925,039 A | 7/1999 | Landingham |
| 5,928,239 A | 7/1999 | Mirza |

(56) References Cited

U.S. PATENT DOCUMENTS

| | | |
|---|---|---|
| 5,935,127 A | 8/1999 | Border |
| 5,938,699 A | 8/1999 | Campbell |
| 5,941,878 A | 8/1999 | Medoff |
| 5,951,467 A | 9/1999 | Picha et al. |
| 5,951,556 A | 9/1999 | Faccioli et al. |
| 5,957,884 A | 9/1999 | Hooven |
| 5,964,698 A | 10/1999 | Fowle |
| 5,976,134 A | 11/1999 | Huebner |
| 5,980,525 A | 11/1999 | Bryant et al. |
| 5,984,932 A | 11/1999 | Yoon |
| 5,984,937 A | 11/1999 | Morse et al. |
| 5,997,538 A | 12/1999 | Asnis et al. |
| 6,001,099 A | 12/1999 | Huebner |
| 6,015,406 A | 1/2000 | Goble et al. |
| 6,019,762 A | 2/2000 | Cole |
| 6,019,947 A | 2/2000 | Kucherov |
| 6,022,376 A | 2/2000 | Assell et al. |
| 6,030,406 A | 2/2000 | Davis |
| 6,033,412 A | 3/2000 | Losken et al. |
| 6,045,564 A | 4/2000 | Walen |
| 6,048,309 A | 4/2000 | Flom et al. |
| 6,053,922 A | 4/2000 | Krause et al. |
| 6,056,750 A | 5/2000 | Lob |
| 6,068,642 A | 5/2000 | Johnson et al. |
| 6,068,648 A | 5/2000 | Cole et al. |
| 6,074,392 A | 6/2000 | Durham |
| 6,093,162 A | 7/2000 | Fairleigh et al. |
| 6,096,040 A | 8/2000 | Esser |
| 6,113,603 A | 9/2000 | Medoff |
| 6,120,472 A | 9/2000 | Singer |
| 6,120,504 A | 9/2000 | Brumback et al. |
| 6,123,704 A | 9/2000 | Hajianpour |
| 6,126,662 A | 10/2000 | Carmichael et al. |
| 6,127,597 A | 10/2000 | Beyar et al. |
| 6,129,762 A | 10/2000 | Li |
| 6,142,935 A | 11/2000 | Flom et al. |
| 6,143,012 A | 11/2000 | Gausepohl |
| 6,149,651 A | 11/2000 | Drewry et al. |
| 6,149,689 A | 11/2000 | Grundei |
| 6,156,069 A | 12/2000 | Amstutz |
| 6,162,223 A | 12/2000 | Orsak et al. |
| 6,162,224 A | 12/2000 | Huebner |
| 6,171,309 B1 | 1/2001 | Huebner |
| 6,174,312 B1 | 1/2001 | Laminger |
| 6,190,414 B1 | 2/2001 | Young et al. |
| 6,197,027 B1 | 3/2001 | Hajianpour |
| 6,200,330 B1 | 3/2001 | Benderev et al. |
| 6,216,573 B1 | 4/2001 | Moutafis et al. |
| 6,221,074 B1 | 4/2001 | Cole et al. |
| 6,221,102 B1 | 4/2001 | Baker et al. |
| 6,224,600 B1 | 5/2001 | Protogirou |
| 6,224,604 B1 | 5/2001 | Suddaby |
| 6,231,576 B1 | 5/2001 | Frigg et al. |
| 6,235,043 B1 | 5/2001 | Reiley et al. |
| 6,238,417 B1 | 5/2001 | Cole |
| 6,241,734 B1 | 6/2001 | Scribner et al. |
| 6,248,110 B1 | 6/2001 | Reiley et al. |
| 6,258,096 B1 | 7/2001 | Seki |
| 6,261,289 B1 | 7/2001 | Levy |
| 6,280,474 B1 | 8/2001 | Cassidy et al. |
| 6,296,639 B1 | 10/2001 | Truckai et al. |
| 6,299,642 B1 | 10/2001 | Chan |
| 6,302,915 B1 | 10/2001 | Cooney et al. |
| 6,306,141 B1 | 10/2001 | Jervis |
| 6,312,467 B1 | 11/2001 | Mcgee |
| 6,319,255 B1 | 11/2001 | Grundei et al. |
| 6,322,591 B1 | 11/2001 | Ahrens |
| 6,331,166 B1 | 12/2001 | Burbank et al. |
| 6,332,885 B1 | 12/2001 | Martella |
| 6,332,886 B1 | 12/2001 | Green et al. |
| 6,337,142 B2 | 1/2002 | Harder et al. |
| 6,344,026 B1 | 2/2002 | Burbank et al. |
| 6,348,053 B1 | 2/2002 | Cachia |
| 6,364,909 B1 | 4/2002 | Mcgee |
| 6,365,555 B1 | 4/2002 | Moser et al. |
| 6,375,666 B1 | 4/2002 | Mische |
| 6,375,682 B1 | 4/2002 | Fleischmann et al. |
| 6,383,188 B2 | 5/2002 | Kuslich et al. |
| 6,402,753 B1 | 6/2002 | Cole et al. |
| 6,411,729 B1 | 6/2002 | Grunkin |
| 6,416,517 B2 | 7/2002 | Harder et al. |
| 6,423,070 B1 | 7/2002 | Zeppelin |
| 6,440,138 B1 | 8/2002 | Reiley et al. |
| 6,447,514 B1 | 9/2002 | Stalcup et al. |
| 6,447,515 B1 | 9/2002 | Meldrum |
| 6,447,518 B1 | 9/2002 | Krause et al. |
| 6,454,810 B1 | 9/2002 | Lob |
| 6,468,207 B1 | 10/2002 | Fowler |
| 6,475,789 B1 | 11/2002 | Cech et al. |
| 6,488,685 B1 | 12/2002 | Manderson |
| 6,491,694 B1 | 12/2002 | Orsak |
| 6,511,481 B2 | 1/2003 | von Hoffmann et al. |
| 6,517,541 B1 | 2/2003 | Sesic |
| 6,527,775 B1 | 3/2003 | Warburton |
| 6,533,788 B1 | 3/2003 | Orbay |
| 6,540,770 B1 | 4/2003 | Tornier et al. |
| 6,544,267 B1 | 4/2003 | Cole et al. |
| 6,551,321 B1 | 4/2003 | Burkinshaw et al. |
| 6,554,833 B2 | 4/2003 | Levy et al. |
| 6,575,973 B1 | 6/2003 | Shekalim |
| 6,575,978 B2 | 6/2003 | Peterson |
| 6,582,467 B1 | 6/2003 | Teitelbaum et al. |
| 6,585,736 B2 | 7/2003 | Hajianpour |
| 6,585,770 B1 | 7/2003 | White et al. |
| 6,610,839 B1 | 8/2003 | Morin et al. |
| 6,613,052 B1 | 9/2003 | Kinnett |
| 6,613,054 B2 | 9/2003 | Scribner et al. |
| 6,617,110 B1 | 9/2003 | Cech et al. |
| 6,632,224 B2 | 10/2003 | Cachia et al. |
| 6,641,616 B1 | 11/2003 | Grundei |
| 6,645,210 B2 | 11/2003 | Manderson |
| 6,648,890 B2 | 11/2003 | Culbert et al. |
| 6,652,585 B2 | 11/2003 | Lange |
| 6,656,187 B1 | 12/2003 | Camino |
| 6,656,219 B1 | 12/2003 | Wiktor |
| 6,660,009 B1 | 12/2003 | Azar |
| 6,660,041 B1 | 12/2003 | Grundei |
| 6,676,665 B2 | 1/2004 | Foley et al. |
| 6,679,886 B2 | 1/2004 | Weikel et al. |
| 6,682,565 B1 | 1/2004 | Krishnan |
| 6,685,706 B2 | 2/2004 | Padget et al. |
| 6,689,138 B2 | 2/2004 | Léchot et al. |
| 6,692,496 B1 | 2/2004 | Wardlaw |
| 6,701,174 B1 | 3/2004 | Krause et al. |
| 6,709,433 B1 | 3/2004 | Schoenefeld |
| 6,711,432 B1 | 3/2004 | Krause et al. |
| 6,712,073 B2 | 3/2004 | Manderson |
| 6,712,858 B1 | 3/2004 | Grungei et al. |
| 6,719,761 B1 | 4/2004 | Reiley et al. |
| 6,719,793 B2 | 4/2004 | McGee et al. |
| 6,740,090 B1 | 5/2004 | Cragg et al. |
| 6,746,451 B2 | 6/2004 | Middleton et al. |
| 6,749,611 B2 | 6/2004 | Venturini et al. |
| 6,755,831 B2 | 6/2004 | Putnam et al. |
| 6,755,862 B2 | 6/2004 | Keynan |
| 6,761,722 B2 | 7/2004 | Cole et al. |
| 6,767,350 B1 | 7/2004 | Lob |
| 6,775,401 B2 | 8/2004 | Hwang et al. |
| 6,780,185 B2 | 8/2004 | Frei et al. |
| 6,783,530 B1 | 8/2004 | Levy et al. |
| 6,783,532 B2 | 8/2004 | Steiner et al. |
| 6,783,533 B2 | 8/2004 | Green et al. |
| 6,793,655 B2 | 9/2004 | Orsak |
| 6,793,659 B2 | 9/2004 | Putnam |
| 6,811,568 B2 | 11/2004 | Minamikawa |
| 6,827,723 B2 | 12/2004 | Carson |
| 6,827,743 B2 | 12/2004 | Eisermann et al. |
| 6,849,051 B2 | 2/2005 | Sramek et al. |
| 6,852,128 B2 | 2/2005 | Lange |
| 6,866,665 B2 | 3/2005 | Orbay |
| 6,887,243 B2 | 5/2005 | Culbert |
| 6,890,333 B2 | 5/2005 | von Hoffmann et al. |
| 6,893,444 B2 | 5/2005 | Orbay |
| 6,908,465 B2 | 6/2005 | von Hoffmann et al. |

(56) References Cited

U.S. PATENT DOCUMENTS

| | | |
|---|---|---|
| 6,911,046 B2 | 6/2005 | Schulter |
| 6,913,605 B2 | 7/2005 | Fletcher et al. |
| 6,923,813 B2 | 8/2005 | Phillips et al. |
| 6,923,817 B2 | 8/2005 | Carson et al. |
| 6,923,828 B1 | 8/2005 | Wiktor |
| 6,926,720 B2 | 8/2005 | Castañeda |
| 6,932,086 B1 | 8/2005 | Hajianpour |
| 6,942,666 B2 | 9/2005 | Overaker et al. |
| 6,942,668 B2 | 9/2005 | Padget et al. |
| 6,949,101 B2 | 9/2005 | McCleary et al. |
| 6,951,561 B2 | 10/2005 | Warren et al. |
| 6,953,313 B2 | 10/2005 | Tylosky |
| 6,975,894 B2 | 12/2005 | Wehrli et al. |
| 6,981,975 B2 | 1/2006 | Michelson |
| 6,984,248 B2 | 1/2006 | Hyde, Jr. |
| 6,986,771 B2 | 1/2006 | Paul et al. |
| 6,989,011 B2 | 1/2006 | Paul et al. |
| 6,991,656 B2 | 1/2006 | Mears |
| 7,008,425 B2 | 3/2006 | Phillips |
| 7,008,428 B2 | 3/2006 | Cachia et al. |
| 7,008,430 B2 | 3/2006 | Dong et al. |
| 7,011,662 B2 | 3/2006 | Lechot et al. |
| 7,018,332 B1 | 3/2006 | Masson et al. |
| 7,018,380 B2 | 3/2006 | Cole |
| 7,022,069 B1 | 4/2006 | Masson et al. |
| 7,025,789 B2 | 4/2006 | Chow et al. |
| 7,041,104 B1 | 5/2006 | Cole et al. |
| 7,041,138 B2 | 5/2006 | Lange |
| 7,048,542 B2 | 5/2006 | Von Arx et al. |
| 7,052,498 B2 | 5/2006 | Levy et al. |
| 7,063,701 B2 | 6/2006 | Michelson |
| 7,070,601 B2 | 7/2006 | Culbert et al. |
| 7,090,676 B2 | 8/2006 | Huebner et al. |
| 7,097,646 B2 | 8/2006 | Schantz |
| 7,097,648 B1 | 8/2006 | Globerman et al. |
| 7,122,033 B2 | 10/2006 | Wood |
| 7,122,043 B2 | 10/2006 | Greenhalgh et al. |
| 7,122,052 B2 | 10/2006 | Greenhalgh |
| 7,131,995 B2 | 11/2006 | Biedermann et al. |
| 7,137,987 B2 | 11/2006 | Patterson et al. |
| 7,141,054 B2 | 11/2006 | Vandewalle |
| 7,141,067 B2 | 11/2006 | Jones et al. |
| 7,147,640 B2 | 12/2006 | Huebner et al. |
| 7,153,307 B2 | 12/2006 | Scribner et al. |
| 7,153,309 B2 | 12/2006 | Huebner et al. |
| 7,160,302 B2 | 1/2007 | Warburton |
| 7,160,331 B2 | 1/2007 | Cooney et al. |
| 7,172,595 B1 | 2/2007 | Goble |
| 7,175,625 B2 | 2/2007 | Culbert |
| 7,179,024 B2 | 2/2007 | Greenhalgh |
| 7,189,237 B2 | 3/2007 | Huebner |
| 7,189,240 B1 | 3/2007 | Dekel |
| 7,195,589 B1 | 3/2007 | Masson et al. |
| 7,195,633 B2 | 3/2007 | Medoff et al. |
| 7,214,227 B2 | 5/2007 | Colleran et al. |
| 7,220,282 B2 | 5/2007 | Kuslich et al. |
| 7,229,441 B2 | 6/2007 | Trieu et al. |
| 7,235,079 B2 | 6/2007 | Jensen et al. |
| 7,237,556 B2 | 7/2007 | Smothers et al. |
| 7,255,712 B1 | 8/2007 | Steinberg |
| 7,258,692 B2 | 8/2007 | Thelen et al. |
| 7,264,622 B2 | 9/2007 | Michelson |
| 7,267,678 B2 | 9/2007 | Medoff |
| 7,282,053 B2 | 10/2007 | Orbay |
| 7,294,130 B2 | 11/2007 | Orbay |
| 7,300,449 B2 | 11/2007 | Mische et al. |
| 7,306,603 B2 | 12/2007 | Boehm et al. |
| 7,306,683 B2 | 12/2007 | Cheung et al. |
| 7,311,711 B2 | 12/2007 | Cole |
| D560,128 S | 1/2008 | Diederich et al. |
| 7,322,938 B2 | 1/2008 | Burbank et al. |
| 7,326,249 B2 | 2/2008 | Lange |
| 7,329,228 B2 | 2/2008 | Burbank et al. |
| 7,341,601 B2 | 3/2008 | Eisermann et al. |
| 7,344,539 B2 | 3/2008 | Serhan et al. |
| 7,354,453 B2 | 4/2008 | McAfee |
| 7,422,360 B2 | 9/2008 | Kozyuk |
| 7,465,318 B2 | 12/2008 | Sennett et al. |
| 7,476,226 B2 | 1/2009 | Weikel et al. |
| 7,481,815 B2 | 1/2009 | Fernandez |
| 7,485,119 B2 | 2/2009 | Thelen et al. |
| 7,488,320 B2 | 2/2009 | Middleton |
| 7,488,329 B2 | 2/2009 | Thelen et al. |
| D589,147 S | 3/2009 | Colleran et al. |
| 7,500,977 B2 | 3/2009 | Assell et al. |
| 7,507,241 B2 | 3/2009 | Levy et al. |
| 7,520,879 B2 | 4/2009 | Justis et al. |
| 7,527,632 B2 | 5/2009 | Houghton et al. |
| 7,547,324 B2 | 6/2009 | Cragg et al. |
| 7,563,263 B2 | 7/2009 | Orbay et al. |
| 7,569,061 B2 | 8/2009 | Colleran |
| 7,578,824 B2 | 8/2009 | Justin et al. |
| 7,588,575 B2 | 9/2009 | Colleran et al. |
| 7,588,577 B2 | 9/2009 | Fencl et al. |
| 7,588,588 B2 | 9/2009 | Spitler et al. |
| 7,601,152 B2 | 10/2009 | Levy et al. |
| 7,611,515 B2 | 11/2009 | Wolford et al. |
| 7,621,950 B1 | 11/2009 | Globerman et al. |
| 7,632,277 B2 | 12/2009 | Woll et al. |
| 7,632,310 B2 | 12/2009 | Clifford et al. |
| 7,666,226 B2 | 2/2010 | Schaller |
| 7,670,339 B2 | 3/2010 | Levy et al. |
| 7,670,374 B2 | 3/2010 | Schaller |
| 7,670,375 B2 | 3/2010 | Schaller |
| 7,682,364 B2 | 3/2010 | Reiley et al. |
| 7,695,471 B2 | 4/2010 | Cheung et al. |
| 7,695,502 B2 | 4/2010 | Orbay et al. |
| 7,704,251 B2 | 4/2010 | Huebner et al. |
| 7,708,742 B2 | 5/2010 | Scribner et al. |
| 7,713,271 B2 | 5/2010 | Warburton et al. |
| 7,717,472 B2 | 5/2010 | Johnson |
| 7,722,612 B2 | 5/2010 | Sala et al. |
| 7,722,626 B2 | 5/2010 | Middleman et al. |
| 7,727,264 B2 | 6/2010 | Orbay et al. |
| 7,731,720 B2 | 6/2010 | Sand et al. |
| 7,749,232 B2 | 7/2010 | Salerni |
| 7,758,500 B2 | 7/2010 | Boyd et al. |
| 7,785,368 B2 | 8/2010 | Schaller |
| 7,806,929 B2 | 10/2010 | Brown |
| 7,811,291 B2 | 10/2010 | Liu et al. |
| 7,828,802 B2 | 11/2010 | Levy et al. |
| 7,837,612 B2 | 11/2010 | Gill et al. |
| 7,842,041 B2 | 11/2010 | Liu et al. |
| 7,846,162 B2 | 12/2010 | Nelson et al. |
| 7,879,038 B2 | 2/2011 | Reiley et al. |
| 7,879,103 B2 | 2/2011 | Gertzman et al. |
| 7,905,909 B2 | 3/2011 | Orbay et al. |
| 7,909,825 B2 | 3/2011 | Saravia et al. |
| 7,909,827 B2 | 3/2011 | Reiley et al. |
| 7,909,873 B2 | 3/2011 | Tan-Malecki et al. |
| 7,914,533 B2 | 3/2011 | Nelson et al. |
| 7,931,689 B2 | 4/2011 | Hochschuler et al. |
| 7,942,875 B2 | 5/2011 | Nelson et al. |
| 7,959,634 B2 | 6/2011 | Sennett |
| 7,959,638 B2 | 6/2011 | Osorio et al. |
| 7,959,683 B2 | 6/2011 | Semler et al. |
| 7,967,827 B2 | 6/2011 | Osorio et al. |
| 7,967,865 B2 | 6/2011 | Schaller |
| 7,972,340 B2 | 7/2011 | Sand et al. |
| 7,988,735 B2 | 8/2011 | Yurek et al. |
| 8,007,498 B2 | 8/2011 | Mische |
| RE42,757 E | 9/2011 | Kuslich et al. |
| 8,012,210 B2 | 9/2011 | Lin et al. |
| 8,021,365 B2 | 9/2011 | Phan |
| 8,021,366 B2 | 9/2011 | Phan |
| 8,043,334 B2 | 10/2011 | Fisher et al. |
| 8,057,544 B2 | 11/2011 | Schaller |
| 8,092,536 B2 | 1/2012 | Ahrens et al. |
| 8,105,236 B2 | 1/2012 | Malandain et al. |
| 8,109,933 B2 | 2/2012 | Truckai et al. |
| 8,114,084 B2 | 2/2012 | Betts |
| 8,118,952 B2 | 2/2012 | Gall et al. |
| 8,128,627 B2 | 3/2012 | Justin et al. |
| 8,152,737 B2 | 4/2012 | Burbank et al. |

(56) References Cited

U.S. PATENT DOCUMENTS

| | | |
|---|---|---|
| 8,157,804 B2 | 4/2012 | Betts |
| 8,177,812 B2 | 5/2012 | Sankaran |
| 8,226,719 B2 | 7/2012 | Melsheimer et al. |
| 8,241,335 B2 | 8/2012 | Truckai et al. |
| 8,287,538 B2 | 10/2012 | Brenzel et al. |
| 8,287,539 B2 | 10/2012 | Nelson et al. |
| 8,287,541 B2 | 10/2012 | Nelson et al. |
| 8,317,791 B2 | 11/2012 | Phan |
| 8,353,911 B2 | 1/2013 | Goldin et al. |
| 8,366,717 B1 | 2/2013 | Jordan et al. |
| 8,366,773 B2 | 2/2013 | Schaller et al. |
| 8,409,211 B2 | 4/2013 | Baroud |
| 8,430,879 B2 | 4/2013 | Stoneburner et al. |
| 8,439,917 B2 | 5/2013 | Saravia et al. |
| 8,485,798 B2 | 7/2013 | Sheth et al. |
| 8,486,082 B2 | 7/2013 | Geisert et al. |
| 8,491,591 B2 | 7/2013 | Fürderer |
| 8,496,394 B2 | 7/2013 | Schneider |
| 8,496,657 B2 | 7/2013 | Bonutti et al. |
| 8,496,658 B2 | 7/2013 | Stoneburner et al. |
| 8,500,357 B2 | 8/2013 | Stahle |
| 8,505,638 B2 | 8/2013 | Ezell |
| 8,505,879 B2 | 8/2013 | Ruan |
| 8,506,199 B2 | 8/2013 | Rump et al. |
| 8,512,398 B2 | 8/2013 | Alkhatib |
| 8,568,413 B2 | 10/2013 | Mazur et al. |
| 8,579,537 B2 | 11/2013 | VanLandingham et al. |
| 8,597,276 B2 | 12/2013 | Vongphakdy et al. |
| 8,840,612 B2 | 9/2014 | Tontz |
| 8,906,022 B2 | 11/2014 | Krinke et al. |
| 8,951,251 B2 | 2/2015 | Willard |
| 8,961,518 B2 | 2/2015 | Taylor et al. |
| 9,095,438 B1 | 8/2015 | Wait |
| 9,155,574 B2 | 10/2015 | Saravia et al. |
| 9,216,023 B2 | 12/2015 | Schaller et al. |
| 9,247,970 B2 | 2/2016 | Teisen |
| 9,498,370 B2 | 11/2016 | Taylor et al. |
| 9,517,093 B2 | 12/2016 | Brenzel et al. |
| 9,636,226 B2 | 5/2017 | Hunt |
| 9,730,739 B2 | 8/2017 | Taylor et al. |
| 9,770,339 B2 | 9/2017 | Greenhalgh et al. |
| 9,788,870 B2 | 10/2017 | Brenzel et al. |
| 9,848,889 B2 | 12/2017 | Taylor et al. |
| 9,968,478 B2 | 5/2018 | Taylor et al. |
| 9,987,137 B2 | 6/2018 | Hunt et al. |
| 9,993,277 B2 | 6/2018 | Krinke et al. |
| 9,999,516 B2 | 6/2018 | Hunt |
| 10,022,132 B2 | 7/2018 | Wlodarski et al. |
| 10,076,342 B2 | 9/2018 | Wlodarski et al. |
| 10,092,333 B2 * | 10/2018 | Jansen ............... A61B 17/744 |
| 2001/0000186 A1 | 4/2001 | Bramlet et al. |
| 2001/0018588 A1 | 8/2001 | Harder et al. |
| 2001/0034526 A1 | 10/2001 | Kuslich et al. |
| 2001/0053912 A1 | 12/2001 | Frigg |
| 2002/0013600 A1 | 1/2002 | Scribner et al. |
| 2002/0015517 A1 | 2/2002 | Hwang et al. |
| 2002/0029081 A1 | 3/2002 | Scarborough et al. |
| 2002/0032444 A1 | 3/2002 | Mische |
| 2002/0055742 A1 | 5/2002 | Lieberman |
| 2002/0055785 A1 | 5/2002 | Harris |
| 2002/0065530 A1 | 5/2002 | Mische |
| 2002/0068974 A1 | 6/2002 | Kuslich et al. |
| 2002/0111629 A1 | 8/2002 | Phillips |
| 2002/0111690 A1 | 8/2002 | Hyde |
| 2002/0120269 A1 | 8/2002 | Lange |
| 2002/0120270 A1 | 8/2002 | Trieu et al. |
| 2002/0123750 A1 | 9/2002 | Eisermann et al. |
| 2002/0133153 A1 | 9/2002 | Hyde |
| 2002/0133156 A1 | 9/2002 | Cole |
| 2002/0133172 A1 | 9/2002 | Lambrecht et al. |
| 2002/0133175 A1 | 9/2002 | Carson |
| 2002/0138149 A1 | 9/2002 | Hyde |
| 2002/0143329 A1 | 10/2002 | Serhan et al. |
| 2002/0143333 A1 | 10/2002 | von Hoffman et al. |
| 2002/0143334 A1 | 10/2002 | Hoffmann et al. |
| 2002/0143335 A1 | 10/2002 | von Hoffman et al. |
| 2002/0147451 A1 | 10/2002 | Mcgee |
| 2002/0147455 A1 | 10/2002 | Carson |
| 2002/0165461 A1 | 11/2002 | Hayzelden et al. |
| 2002/0171208 A1 | 11/2002 | Lechot et al. |
| 2002/0173813 A1 | 11/2002 | Peterson et al. |
| 2002/0183758 A1 | 12/2002 | Middleton et al. |
| 2002/0191823 A1 | 12/2002 | Wehrli et al. |
| 2003/0040805 A1 | 2/2003 | Minamikawa |
| 2003/0055373 A1 | 3/2003 | Sramek et al. |
| 2003/0055425 A1 | 3/2003 | Hajianpour |
| 2003/0069582 A1 | 4/2003 | Culbert |
| 2003/0069645 A1 | 4/2003 | Ball et al. |
| 2003/0074075 A1 | 4/2003 | Thomas, Jr. et al. |
| 2003/0083660 A1 | 5/2003 | Orbay |
| 2003/0083662 A1 | 5/2003 | Middleton |
| 2003/0093076 A1 | 5/2003 | Venturini et al. |
| 2003/0097132 A1 | 5/2003 | Padget et al. |
| 2003/0097133 A1 | 5/2003 | Green et al. |
| 2003/0105461 A1 | 6/2003 | Putnam |
| 2003/0109932 A1 | 6/2003 | Keynan |
| 2003/0120273 A1 | 6/2003 | Cole |
| 2003/0130660 A1 | 7/2003 | Levy et al. |
| 2003/0153918 A1 | 8/2003 | Putnam et al. |
| 2003/0187449 A1 | 10/2003 | McCleary et al. |
| 2003/0216738 A1 | 11/2003 | Azar |
| 2003/0220641 A1 | 11/2003 | Thelen et al. |
| 2003/0220644 A1 | 11/2003 | Thelen et al. |
| 2003/0220646 A1 | 11/2003 | Thelen et al. |
| 2003/0220698 A1 | 11/2003 | Mears et al. |
| 2003/0225407 A1 | 12/2003 | Estrada |
| 2003/0233096 A1 | 12/2003 | Osorio et al. |
| 2004/0024410 A1 | 2/2004 | Olson, Jr. et al. |
| 2004/0039384 A1 | 2/2004 | Boehm et al. |
| 2004/0044413 A1 | 3/2004 | Schulter |
| 2004/0049192 A1 | 3/2004 | Shimizu |
| 2004/0078082 A1 | 4/2004 | Lange |
| 2004/0087956 A1 | 5/2004 | Weikel et al. |
| 2004/0092946 A1 | 5/2004 | Bagga et al. |
| 2004/0102774 A1 | 5/2004 | Trieu |
| 2004/0102777 A1 | 5/2004 | Huebner |
| 2004/0102778 A1 | 5/2004 | Huebner et al. |
| 2004/0102788 A1 | 5/2004 | Huebner et al. |
| 2004/0106925 A1 | 6/2004 | Culbert |
| 2004/0138665 A1 | 7/2004 | Padget et al. |
| 2004/0143264 A1 | 7/2004 | McAfee |
| 2004/0153080 A1 | 8/2004 | Dong et al. |
| 2004/0153114 A1 | 8/2004 | Reiley et al. |
| 2004/0153115 A1 | 8/2004 | Reiley et al. |
| 2004/0167528 A1 | 8/2004 | Schantz |
| 2004/0167561 A1 | 8/2004 | Boucher et al. |
| 2004/0167625 A1 | 8/2004 | Beyar et al. |
| 2004/0181221 A1 | 9/2004 | Huebner et al. |
| 2004/0193163 A1 | 9/2004 | Orbay |
| 2004/0193164 A1 | 9/2004 | Orbay |
| 2004/0193165 A1 | 9/2004 | Orbay |
| 2004/0193251 A1 | 9/2004 | Rudnick et al. |
| 2004/0193267 A1 | 9/2004 | Jones et al. |
| 2004/0208717 A1 | 10/2004 | Greenhalgh |
| 2004/0214311 A1 | 10/2004 | Levy |
| 2004/0220678 A1 | 11/2004 | Chow et al. |
| 2004/0230193 A1 | 11/2004 | Cheung et al. |
| 2004/0236327 A1 | 11/2004 | Paul et al. |
| 2004/0236328 A1 | 11/2004 | Paul et al. |
| 2004/0236339 A1 | 11/2004 | Pepper |
| 2004/0249375 A1 | 12/2004 | Agee et al. |
| 2004/0260289 A1 | 12/2004 | Padget et al. |
| 2004/0260297 A1 | 12/2004 | Padget et al. |
| 2004/0267269 A1 | 12/2004 | Middleton et al. |
| 2005/0010231 A1 | 1/2005 | Myers |
| 2005/0015129 A1 | 1/2005 | Mische |
| 2005/0015154 A1 | 1/2005 | Lindsey et al. |
| 2005/0033366 A1 | 2/2005 | Cole et al. |
| 2005/0043733 A1 | 2/2005 | Eisermann et al. |
| 2005/0049708 A1 | 3/2005 | Atkinson et al. |
| 2005/0049710 A1 | 3/2005 | O'Driscoll et al. |
| 2005/0065522 A1 | 3/2005 | Orbay |
| 2005/0065523 A1 | 3/2005 | Orbay |
| 2005/0065524 A1 | 3/2005 | Orbay |

(56) References Cited

U.S. PATENT DOCUMENTS

| | | |
|---|---|---|
| 2005/0065526 A1 | 3/2005 | Drew et al. |
| 2005/0070902 A1 | 3/2005 | Medoff |
| 2005/0085813 A1 | 4/2005 | Spitler et al. |
| 2005/0085818 A1 | 4/2005 | Huebner |
| 2005/0085824 A1 | 4/2005 | Castaneda |
| 2005/0085921 A1 | 4/2005 | Gupta et al. |
| 2005/0113836 A1 | 5/2005 | Lozier et al. |
| 2005/0113892 A1 | 5/2005 | Sproul |
| 2005/0113929 A1 | 5/2005 | Cragg et al. |
| 2005/0119749 A1 | 6/2005 | Lange |
| 2005/0124972 A1 | 6/2005 | Mische et al. |
| 2005/0125066 A1 | 6/2005 | Mcafee |
| 2005/0131407 A1 | 6/2005 | Sicvol et al. |
| 2005/0142163 A1 | 6/2005 | Hunter et al. |
| 2005/0143734 A1 | 6/2005 | Cachia et al. |
| 2005/0143827 A1 | 6/2005 | Globerman et al. |
| 2005/0154331 A1 | 7/2005 | Christie et al. |
| 2005/0159749 A1* | 7/2005 | Levy .............. A61B 17/68 606/62 |
| 2005/0177172 A1 | 8/2005 | Acker et al. |
| 2005/0182399 A1 | 8/2005 | Levine |
| 2005/0187627 A1 | 8/2005 | Ralph et al. |
| 2005/0192578 A1 | 9/2005 | Horst |
| 2005/0197537 A1 | 9/2005 | Bonadio et al. |
| 2005/0209557 A1 | 9/2005 | Carroll et al. |
| 2005/0216000 A1 | 9/2005 | Colleran et al. |
| 2005/0216007 A1 | 9/2005 | Woll et al. |
| 2005/0216008 A1 | 9/2005 | Zwirnmann et al. |
| 2005/0228391 A1 | 10/2005 | Levy et al. |
| 2005/0234472 A1 | 10/2005 | Huebner |
| 2005/0234498 A1 | 10/2005 | Gronemeyer et al. |
| 2005/0240188 A1 | 10/2005 | Chow et al. |
| 2005/0240190 A1 | 10/2005 | Gall et al. |
| 2005/0240193 A1 | 10/2005 | Layne et al. |
| 2005/0245928 A1 | 11/2005 | Colleran et al. |
| 2005/0251142 A1 | 11/2005 | Hoffmann et al. |
| 2005/0261779 A1 | 11/2005 | Meyer |
| 2005/0267483 A1 | 12/2005 | Middleton |
| 2005/0273138 A1 | 12/2005 | To et al. |
| 2005/0277936 A1 | 12/2005 | Siravo et al. |
| 2005/0277978 A1 | 12/2005 | Greenhalgh |
| 2005/0283154 A1 | 12/2005 | Orbay et al. |
| 2005/0283159 A1 | 12/2005 | Amara |
| 2005/0288676 A1 | 12/2005 | Schnieders et al. |
| 2005/0288795 A1 | 12/2005 | Bagga et al. |
| 2006/0002980 A1 | 1/2006 | Ringeisen et al. |
| 2006/0004362 A1 | 1/2006 | Patterson et al. |
| 2006/0004455 A1 | 1/2006 | Leonard et al. |
| 2006/0004462 A1 | 1/2006 | Gupta |
| 2006/0009771 A1 | 1/2006 | Orbay et al. |
| 2006/0015123 A1 | 1/2006 | Fencl et al. |
| 2006/0036240 A1 | 2/2006 | Colleran et al. |
| 2006/0036244 A1 | 2/2006 | Spitler et al. |
| 2006/0047787 A1 | 3/2006 | Agarwal et al. |
| 2006/0052788 A1 | 3/2006 | Thelen et al. |
| 2006/0058621 A1 | 3/2006 | Wehrli et al. |
| 2006/0058826 A1 | 3/2006 | Evans et al. |
| 2006/0064005 A1 | 3/2006 | Triano et al. |
| 2006/0064106 A1 | 3/2006 | Fernandez |
| 2006/0064164 A1 | 3/2006 | Thelen et al. |
| 2006/0064173 A1 | 3/2006 | Guederian et al. |
| 2006/0069392 A1* | 3/2006 | Renzi Brivio ......... A61B 17/72 606/64 |
| 2006/0079894 A1 | 4/2006 | Colleran et al. |
| 2006/0079905 A1 | 4/2006 | Beyar et al. |
| 2006/0085009 A1 | 4/2006 | Truckai et al. |
| 2006/0085070 A1 | 4/2006 | Kim |
| 2006/0089647 A1 | 4/2006 | Culbert et al. |
| 2006/0089648 A1 | 4/2006 | Masini |
| 2006/0089719 A1 | 4/2006 | Trieu |
| 2006/0095136 A1 | 5/2006 | McLuen |
| 2006/0100623 A1 | 5/2006 | Pennig |
| 2006/0100631 A1 | 5/2006 | Sullivan et al. |
| 2006/0100706 A1 | 5/2006 | Shadduck et al. |
| 2006/0106390 A1 | 5/2006 | Jensen et al. |
| 2006/0106394 A1 | 5/2006 | Colleran |
| 2006/0116689 A1 | 6/2006 | Albans et al. |
| 2006/0116773 A1 | 6/2006 | Cooney et al. |
| 2006/0122600 A1 | 6/2006 | Cole |
| 2006/0122610 A1 | 6/2006 | Culbert et al. |
| 2006/0122620 A1 | 6/2006 | Kim |
| 2006/0142760 A1 | 6/2006 | McDonnel |
| 2006/0142858 A1 | 6/2006 | Colleran et al. |
| 2006/0149281 A1 | 7/2006 | Reiley et al. |
| 2006/0149379 A1 | 7/2006 | Kuslich et al. |
| 2006/0155289 A1 | 7/2006 | Windhager et al. |
| 2006/0173454 A1 | 8/2006 | Spitler et al. |
| 2006/0178737 A1 | 8/2006 | Furcht et al. |
| 2006/0184192 A1 | 8/2006 | Markworth et al. |
| 2006/0187748 A1 | 8/2006 | Kozyuk |
| 2006/0189994 A1 | 8/2006 | Wolford et al. |
| 2006/0195103 A1 | 8/2006 | Padget et al. |
| 2006/0200061 A1 | 9/2006 | Warkentine |
| 2006/0200140 A1 | 9/2006 | Lange |
| 2006/0200143 A1 | 9/2006 | Warburton |
| 2006/0217726 A1 | 9/2006 | Maxy et al. |
| 2006/0217730 A1 | 9/2006 | Termanini |
| 2006/0229602 A1 | 10/2006 | Olsen |
| 2006/0235264 A1 | 10/2006 | Vassallo |
| 2006/0241629 A1 | 10/2006 | Krebs et al. |
| 2006/0241630 A1 | 10/2006 | Brunnett et al. |
| 2006/0241671 A1 | 10/2006 | Greenhalgh |
| 2006/0241776 A1 | 10/2006 | Brown et al. |
| 2006/0247637 A1 | 11/2006 | Colleran et al. |
| 2006/0264944 A1 | 11/2006 | Cole |
| 2006/0264945 A1 | 11/2006 | Edidin et al. |
| 2006/0264950 A1 | 11/2006 | Nelson et al. |
| 2006/0264951 A1 | 11/2006 | Nelson et al. |
| 2006/0264952 A1 | 11/2006 | Nelson et al. |
| 2006/0271049 A1 | 11/2006 | Zucherman et al. |
| 2006/0271053 A1 | 11/2006 | Schlapfer et al. |
| 2006/0271061 A1 | 11/2006 | Beyar et al. |
| 2006/0271198 A1 | 11/2006 | Mcafee |
| 2006/0276797 A1 | 12/2006 | Botimer |
| 2007/0012491 A1 | 1/2007 | Vasta |
| 2007/0016188 A1 | 1/2007 | Boehm et al. |
| 2007/0016198 A1 | 1/2007 | Boehm et al. |
| 2007/0016199 A1 | 1/2007 | Boehm et al. |
| 2007/0016211 A1 | 1/2007 | Botimer |
| 2007/0016283 A1 | 1/2007 | Greenhalgh et al. |
| 2007/0016300 A1 | 1/2007 | Kuslich |
| 2007/0027230 A1 | 2/2007 | Beyar et al. |
| 2007/0032567 A1 | 2/2007 | Beyar et al. |
| 2007/0032790 A1 | 2/2007 | Aschmann et al. |
| 2007/0043373 A1 | 2/2007 | Sala et al. |
| 2007/0049936 A1 | 3/2007 | Colleran et al. |
| 2007/0055379 A1 | 3/2007 | Stone et al. |
| 2007/0060941 A1 | 3/2007 | Reiley et al. |
| 2007/0066480 A1 | 3/2007 | Moser et al. |
| 2007/0073342 A1 | 3/2007 | Stone et al. |
| 2007/0073401 A1 | 3/2007 | Pointillart et al. |
| 2007/0093899 A1 | 4/2007 | Dutoit et al. |
| 2007/0100285 A1 | 5/2007 | Griffin et al. |
| 2007/0112427 A1 | 5/2007 | Christy et al. |
| 2007/0118132 A1 | 5/2007 | Culbert et al. |
| 2007/0123876 A1 | 5/2007 | Czartoski et al. |
| 2007/0123877 A1 | 5/2007 | Goldin et al. |
| 2007/0123886 A1 | 5/2007 | Meyer et al. |
| 2007/0123936 A1 | 5/2007 | Goldin et al. |
| 2007/0123995 A1 | 5/2007 | Thelen et al. |
| 2007/0129746 A1 | 6/2007 | Mische |
| 2007/0142919 A1 | 6/2007 | Cooney et al. |
| 2007/0173745 A1 | 7/2007 | Diederich et al. |
| 2007/0173835 A1 | 7/2007 | Medoff et al. |
| 2007/0173838 A1 | 7/2007 | Li |
| 2007/0173839 A1 | 7/2007 | Running et al. |
| 2007/0173843 A1 | 7/2007 | Matityahu |
| 2007/0173939 A1 | 7/2007 | Kim et al. |
| 2007/0179505 A1 | 8/2007 | Culbert |
| 2007/0198043 A1 | 8/2007 | Cox et al. |
| 2007/0213727 A1 | 9/2007 | Bottlang et al. |
| 2007/0219634 A1 | 9/2007 | Greenhalgh et al. |
| 2007/0225568 A1 | 9/2007 | Colleran |
| 2007/0225721 A1 | 9/2007 | Thelen et al. |

(56) References Cited

U.S. PATENT DOCUMENTS

| | | |
|---|---|---|
| 2007/0225726 A1 | 9/2007 | Dye et al. |
| 2007/0225810 A1 | 9/2007 | Colleran et al. |
| 2007/0233076 A1 | 10/2007 | Trieu |
| 2007/0233091 A1 | 10/2007 | Naifeh et al. |
| 2007/0233105 A1 | 10/2007 | Nelson et al. |
| 2007/0244485 A1 | 10/2007 | Greenhalgh et al. |
| 2007/0255287 A1 | 11/2007 | Rabiner |
| 2007/0270855 A1 | 11/2007 | Partin |
| 2007/0276392 A1 | 11/2007 | Beyar et al. |
| 2007/0276405 A1 | 11/2007 | Huebner et al. |
| 2007/0282443 A1 | 12/2007 | Globerman et al. |
| 2007/0283849 A1 | 12/2007 | Edidin et al. |
| 2007/0288097 A1 | 12/2007 | Hurowitz |
| 2008/0009868 A1 | 1/2008 | Gotfried et al. |
| 2008/0009874 A1 | 1/2008 | Meridew et al. |
| 2008/0009875 A1 | 1/2008 | Sankaran et al. |
| 2008/0009877 A1 | 1/2008 | Sankaran et al. |
| 2008/0012317 A1 | 1/2008 | Johnson |
| 2008/0015601 A1 | 1/2008 | Castro et al. |
| 2008/0019970 A1 | 1/2008 | Gorman |
| 2008/0021474 A1 | 1/2008 | Bonutti et al. |
| 2008/0039854 A1 | 2/2008 | Rabiner |
| 2008/0041629 A1 | 2/2008 | Aronstam et al. |
| 2008/0053575 A1 | 3/2008 | Cheung et al. |
| 2008/0058804 A1 | 3/2008 | Lechot et al. |
| 2008/0058934 A1 | 3/2008 | Malandain et al. |
| 2008/0065072 A1 | 3/2008 | Spitler et al. |
| 2008/0065073 A1 | 3/2008 | Perriello et al. |
| 2008/0065074 A1 | 3/2008 | Yeung et al. |
| 2008/0065140 A1 | 3/2008 | Bonutti |
| 2008/0071356 A1 | 3/2008 | Greenhalgh et al. |
| 2008/0077117 A1 | 3/2008 | Miller et al. |
| 2008/0077172 A1 | 3/2008 | Miller et al. |
| 2008/0077174 A1 | 3/2008 | Mische |
| 2008/0086133 A1 | 4/2008 | Kuslich et al. |
| 2008/0097332 A1 | 4/2008 | Greenhalgh et al. |
| 2008/0103501 A1 | 5/2008 | Ralph et al. |
| 2008/0103519 A1 | 5/2008 | Bonutti |
| 2008/0108996 A1 | 5/2008 | Padget et al. |
| 2008/0114364 A1 | 5/2008 | Goldin et al. |
| 2008/0119886 A1 | 5/2008 | Greenhalgh et al. |
| 2008/0125784 A1 | 5/2008 | Rabiner et al. |
| 2008/0125805 A1 | 5/2008 | Mische |
| 2008/0132896 A1 | 6/2008 | Bowen et al. |
| 2008/0133017 A1 | 6/2008 | Beyar et al. |
| 2008/0140078 A1 | 6/2008 | Nelson et al. |
| 2008/0140130 A1 | 6/2008 | Chan et al. |
| 2008/0149115 A1 | 6/2008 | Hauck et al. |
| 2008/0161805 A1 | 7/2008 | Saravia et al. |
| 2008/0161825 A1 | 7/2008 | Greenhalgh et al. |
| 2008/0167657 A1 | 7/2008 | Greenhalgh |
| 2008/0177261 A1 | 7/2008 | Mcminn |
| 2008/0183171 A1 | 7/2008 | Elghazaly et al. |
| 2008/0183211 A1 | 7/2008 | Lamborne et al. |
| 2008/0194868 A1 | 8/2008 | Kozyuk |
| 2008/0195104 A1 | 8/2008 | Sidebotham et al. |
| 2008/0195105 A1 | 8/2008 | Sidebotham et al. |
| 2008/0200915 A1 | 8/2008 | Globerman et al. |
| 2008/0200951 A1 | 8/2008 | Mcafee |
| 2008/0208202 A1 | 8/2008 | Williams |
| 2008/0208230 A1 | 8/2008 | Chin et al. |
| 2008/0208261 A1 | 8/2008 | Medoff |
| 2008/0208320 A1 | 8/2008 | Tan-Malecki et al. |
| 2008/0212405 A1 | 9/2008 | Globerman et al. |
| 2008/0221685 A9 | 9/2008 | Altarac et al. |
| 2008/0228192 A1 | 9/2008 | Beyar et al. |
| 2008/0249436 A1 | 10/2008 | Darr |
| 2008/0255560 A1 | 10/2008 | Myers et al. |
| 2008/0262495 A1 | 10/2008 | Coati et al. |
| 2008/0269742 A1 | 10/2008 | Levy et al. |
| 2008/0269745 A1 | 10/2008 | Justin |
| 2008/0269746 A1 | 10/2008 | Justin |
| 2008/0269747 A1 | 10/2008 | Justin |
| 2008/0269748 A1 | 10/2008 | Justin et al. |
| 2008/0269749 A1 | 10/2008 | Shalaby et al. |
| 2008/0269750 A1 | 10/2008 | Justin |
| 2008/0269776 A1 | 10/2008 | Justin et al. |
| 2008/0275448 A1 | 11/2008 | Sackett et al. |
| 2008/0275449 A1 | 11/2008 | Sackett et al. |
| 2008/0287950 A1 | 11/2008 | Frigg et al. |
| 2008/0287951 A1 | 11/2008 | Stoneburner et al. |
| 2008/0288003 A1 | 11/2008 | McKinley |
| 2008/0294163 A1 | 11/2008 | Chou et al. |
| 2008/0294166 A1 | 11/2008 | Goldin et al. |
| 2008/0294167 A1 | 11/2008 | Schumacher et al. |
| 2008/0294169 A1 | 11/2008 | Scott et al. |
| 2008/0294205 A1 | 11/2008 | Greenhalgh et al. |
| 2008/0319444 A9 | 12/2008 | Osorio et al. |
| 2009/0005782 A1 | 1/2009 | Chirico et al. |
| 2009/0012522 A1 | 1/2009 | Lob |
| 2009/0012564 A1 | 1/2009 | Chirico et al. |
| 2009/0018542 A1 | 1/2009 | Saravia et al. |
| 2009/0018656 A1 | 1/2009 | Clifford et al. |
| 2009/0018666 A1 | 1/2009 | Grundei et al. |
| 2009/0024204 A1 | 1/2009 | Greenhalgh et al. |
| 2009/0030468 A1 | 1/2009 | Sennett et al. |
| 2009/0048620 A1 | 2/2009 | Weiss et al. |
| 2009/0048629 A1 | 2/2009 | Rabiner |
| 2009/0048672 A1 | 2/2009 | Essenmacher |
| 2009/0054900 A1 | 2/2009 | Rabiner et al. |
| 2009/0069851 A1 | 3/2009 | Gillard et al. |
| 2009/0076517 A1 | 3/2009 | Reiley et al. |
| 2009/0088752 A1 | 4/2009 | Metzinger et al. |
| 2009/0088806 A1 | 4/2009 | Leyden et al. |
| 2009/0104586 A1 | 4/2009 | Cardoso et al. |
| 2009/0112196 A1 | 4/2009 | Rabiner et al. |
| 2009/0112330 A1 | 4/2009 | Grundei |
| 2009/0125028 A1 | 5/2009 | Teisen et al. |
| 2009/0131952 A1 | 5/2009 | Schumacher et al. |
| 2009/0131990 A1 | 5/2009 | Tipirneni et al. |
| 2009/0131992 A1 | 5/2009 | Greenhalgh et al. |
| 2009/0138015 A1 | 5/2009 | Conner et al. |
| 2009/0143781 A1 | 6/2009 | Mische |
| 2009/0143827 A1 | 6/2009 | Levy et al. |
| 2009/0149890 A1 | 6/2009 | Martin |
| 2009/0149956 A1 | 6/2009 | Greenhalgh et al. |
| 2009/0157080 A1 | 6/2009 | Warburton |
| 2009/0163918 A1 | 6/2009 | Levy et al. |
| 2009/0177206 A1 | 7/2009 | Lozier et al. |
| 2009/0177239 A1 | 7/2009 | Castro |
| 2009/0177241 A1 | 7/2009 | Bleich et al. |
| 2009/0204216 A1 | 8/2009 | Biedermann et al. |
| 2009/0216232 A1 | 8/2009 | Buford et al. |
| 2009/0228007 A1 | 9/2009 | Justin et al. |
| 2009/0228008 A1 | 9/2009 | Justin et al. |
| 2009/0275995 A1 | 11/2009 | Truckai et al. |
| 2009/0281628 A1 | 11/2009 | Oglaza |
| 2009/0292323 A1 | 11/2009 | Chirico et al. |
| 2009/0318926 A1 | 12/2009 | Christie |
| 2009/0318981 A1 | 12/2009 | Kang |
| 2010/0023010 A1 | 1/2010 | Nelson et al. |
| 2010/0082066 A1 | 4/2010 | Biyani |
| 2010/0087821 A1 | 4/2010 | Trip et al. |
| 2010/0094292 A1 | 4/2010 | Parrott |
| 2010/0094347 A1 | 4/2010 | Nelson et al. |
| 2010/0100184 A1 | 4/2010 | Krueger et al. |
| 2010/0114110 A1 | 5/2010 | Taft et al. |
| 2010/0114181 A1 | 5/2010 | Lob |
| 2010/0131019 A1 | 5/2010 | Lob |
| 2010/0137862 A1 | 6/2010 | Diao et al. |
| 2010/0137863 A1 | 6/2010 | Munro |
| 2010/0145397 A1 | 6/2010 | Overes et al. |
| 2010/0161061 A1 | 6/2010 | Hunt |
| 2010/0217325 A1 | 8/2010 | Hochschuler et al. |
| 2010/0222884 A1 | 9/2010 | Greenhalgh |
| 2010/0241120 A1 | 9/2010 | Bledsoe et al. |
| 2010/0241123 A1 | 9/2010 | Middleton et al. |
| 2010/0241176 A1 | 9/2010 | Lob |
| 2010/0249785 A1 | 9/2010 | Betts |
| 2010/0256638 A1 | 10/2010 | Tyber et al. |
| 2010/0286481 A1 | 11/2010 | Sharp et al. |
| 2010/0286692 A1 | 11/2010 | Greenhalgh et al. |
| 2011/0004308 A1 | 1/2011 | Marino et al. |
| 2011/0077650 A1 | 3/2011 | Braun et al. |

(56) References Cited

U.S. PATENT DOCUMENTS

| | | |
|---|---|---|
| 2011/0077651 A1 | 3/2011 | Lozier et al. |
| 2011/0087227 A1 | 4/2011 | Mazur et al. |
| 2011/0087257 A1 | 4/2011 | To et al. |
| 2011/0118740 A1 | 5/2011 | Rabiner et al. |
| 2011/0137312 A1* | 6/2011 | Mantovani ......... A61B 17/7233 606/63 |
| 2011/0137313 A1 | 6/2011 | Jensen et al. |
| 2011/0144645 A1 | 6/2011 | Saravia et al. |
| 2011/0178520 A1 | 7/2011 | Taylor et al. |
| 2011/0218585 A1 | 9/2011 | Krinke et al. |
| 2011/0282346 A1 | 11/2011 | Pham et al. |
| 2011/0295255 A1 | 12/2011 | Roberts et al. |
| 2011/0306975 A1 | 12/2011 | Kaikkonen et al. |
| 2011/0307021 A1 | 12/2011 | Anderson et al. |
| 2011/0307072 A1 | 12/2011 | Anderson et al. |
| 2011/0313537 A1 | 12/2011 | Anderson et al. |
| 2012/0016369 A1 | 1/2012 | O'Halloran et al. |
| 2012/0022651 A1 | 1/2012 | Akyuz et al. |
| 2012/0029633 A1 | 2/2012 | Anderson et al. |
| 2012/0065638 A1 | 3/2012 | Moore |
| 2012/0152872 A1 | 6/2012 | Didehvar |
| 2012/0172992 A1 | 7/2012 | Fockens |
| 2012/0179161 A1 | 7/2012 | Rains et al. |
| 2012/0209265 A1 | 8/2012 | Pool |
| 2012/0209273 A1 | 8/2012 | Zaretzka et al. |
| 2012/0226362 A1 | 9/2012 | Mische |
| 2012/0232533 A1 | 9/2012 | Veldman et al. |
| 2012/0239038 A1 | 9/2012 | Saravia et al. |
| 2012/0316648 A1 | 12/2012 | Lambrecht et al. |
| 2013/0006245 A1 | 1/2013 | Stoneburner et al. |
| 2013/0012942 A1 | 1/2013 | Nelson et al. |
| 2013/0018376 A1 | 1/2013 | Yoon et al. |
| 2013/0090655 A1* | 4/2013 | Tontz ................ A61B 17/7233 606/64 |
| 2013/0116693 A1 | 5/2013 | Nelson et al. |
| 2013/0123785 A1 | 5/2013 | Fonte |
| 2013/0165935 A1 | 6/2013 | Griffiths et al. |
| 2013/0204250 A1 | 8/2013 | McDevitt et al. |
| 2013/0204390 A1 | 8/2013 | Podolsky |
| 2013/0231665 A1 | 9/2013 | Saravia et al. |
| 2013/0231746 A1 | 9/2013 | Ginn et al. |
| 2013/0267953 A1 | 10/2013 | Brenzel et al. |
| 2013/0325007 A1 | 12/2013 | Beyar et al. |
| 2013/0345765 A1 | 12/2013 | Brockman et al. |
| 2013/0345821 A1 | 12/2013 | Jones et al. |
| 2014/0031823 A1 | 1/2014 | Mazur et al. |
| 2014/0074093 A9 | 3/2014 | Nelson et al. |
| 2014/0088707 A1 | 3/2014 | Donner et al. |
| 2014/0114368 A1 | 4/2014 | Lin et al. |
| 2014/0200618 A1 | 7/2014 | Donner et al. |
| 2014/0214045 A1 | 7/2014 | Felder et al. |
| 2014/0276840 A1 | 9/2014 | Richter et al. |
| 2014/0277177 A1 | 9/2014 | Gonzalez-Hernandez |
| 2014/0277570 A1 | 9/2014 | Behnam et al. |
| 2014/0288656 A1 | 9/2014 | Kuslich |
| 2015/0141996 A1 | 5/2015 | Taylor et al. |
| 2015/0173805 A1 | 6/2015 | Donner et al. |
| 2015/0196358 A1 | 7/2015 | Goshayeshgar |
| 2016/0030099 A1 | 2/2016 | Greenhalgh et al. |
| 2016/0128836 A1 | 5/2016 | Rabiner et al. |
| 2016/0175101 A1 | 6/2016 | Gonzalez-Hernandez |
| 2017/0303977 A1 | 10/2017 | Brenzel et al. |
| 2017/0319344 A1 | 11/2017 | Hunt |
| 2017/0319353 A1 | 11/2017 | Greenhalgh et al. |
| 2017/0325857 A1 | 11/2017 | Taylor et al. |
| 2017/0333102 A1 | 11/2017 | Peterson et al. |
| 2017/0360570 A1 | 12/2017 | Berndt et al. |
| 2018/0064540 A1 | 3/2018 | Hunt et al. |
| 2018/0085230 A1 | 3/2018 | Hunt |
| 2018/0193153 A1 | 7/2018 | Brenzel et al. |
| 2018/0199972 A1 | 7/2018 | Krinke et al. |
| 2019/0021746 A1 | 1/2019 | Wlodarski et al. |
| 2019/0269417 A1* | 9/2019 | Taylor ................ A61B 17/1637 |
| 2019/0374272 A1 | 12/2019 | Peterson et al. |

FOREIGN PATENT DOCUMENTS

| | | |
|---|---|---|
| CA | 2452508 A1 | 1/2003 |
| CA | 2609175 A1 | 12/2005 |
| CA | 2608693 A1 | 11/2006 |
| CA | 2537171 C | 8/2007 |
| CA | 2669737 A1 | 5/2008 |
| CA | 2670263 A1 | 5/2008 |
| CA | 2670438 A1 | 5/2008 |
| CA | 2678911 A1 | 9/2008 |
| CA | 2685046 A1 | 11/2008 |
| CA | 2727453 A1 | 12/2009 |
| CA | 2738478 A1 | 4/2010 |
| CN | 2326199 | 6/1999 |
| CN | 1530079 | 9/2004 |
| CN | 1533260 A | 9/2004 |
| CN | 2699849 Y | 5/2005 |
| CN | 1909848 A | 2/2007 |
| CN | 100379388 | 4/2008 |
| CN | 101208053 A | 6/2008 |
| CN | 101404946 | 4/2009 |
| CN | 101636119 A | 1/2010 |
| CN | 101795629 | 8/2010 |
| DE | 923085 | 7/1949 |
| DE | 3146065 A1 | 5/1983 |
| DE | 3234875 A1 | 3/1984 |
| DE | 8528770 | 1/1986 |
| DE | 198800197 U1 | 8/1988 |
| DE | 3922044 A1 | 2/1991 |
| DE | 4217236 | 11/1993 |
| DE | 202006017194 U1 | 2/2007 |
| DE | 102006016213 | 10/2007 |
| EP | 0145166 A2 | 6/1985 |
| EP | 145166 A2 | 6/1985 |
| EP | 145166 A3 | 8/1986 |
| EP | 253526 A1 | 1/1988 |
| EP | 263292 A1 | 4/1988 |
| EP | 275871 A1 | 7/1988 |
| EP | 0328883 | 8/1989 |
| EP | 355035 A2 | 2/1990 |
| EP | 381462 A2 | 8/1990 |
| EP | 396519 A1 | 11/1990 |
| EP | 401650 A1 | 12/1990 |
| EP | 409769 A1 | 1/1991 |
| EP | 420542 A1 | 4/1991 |
| EP | 440371 A1 | 8/1991 |
| EP | 442137 A1 | 8/1991 |
| EP | 475077 A2 | 3/1992 |
| EP | 487669 A1 | 6/1992 |
| EP | 491211 A1 | 6/1992 |
| EP | 508710 A1 | 10/1992 |
| EP | 525352 A1 | 2/1993 |
| EP | 611560 A1 | 8/1994 |
| EP | 745352 A2 | 12/1996 |
| EP | 546162 B1 | 9/1997 |
| EP | 807419 A2 | 11/1997 |
| EP | 819413 A2 | 1/1998 |
| EP | 931513 A2 | 7/1999 |
| EP | 0941037 | 9/1999 |
| EP | 0941037 B1 | 9/1999 |
| EP | 1099412 A2 | 5/2001 |
| EP | 1442729 A1 | 8/2001 |
| EP | 1132051 A2 | 9/2001 |
| EP | 674495 B1 | 11/2001 |
| EP | 1155661 A1 | 11/2001 |
| EP | 1203569 A1 | 5/2002 |
| EP | 900065 B1 | 6/2002 |
| EP | 1277442 A2 | 1/2003 |
| EP | 1300122 A2 | 4/2003 |
| EP | 1348384 A2 | 10/2003 |
| EP | 1354562 | 10/2003 |
| EP | 1372496 A1 | 1/2004 |
| EP | 1391186 A1 | 2/2004 |
| EP | 1098600 B1 | 3/2004 |
| EP | 1277442 A3 | 3/2004 |
| EP | 1396231 A1 | 3/2004 |
| EP | 1410765 A2 | 4/2004 |
| EP | 1442718 A1 | 8/2004 |
| EP | 1454592 A2 | 9/2004 |

(56) References Cited

FOREIGN PATENT DOCUMENTS

| | | |
|---|---|---|
| EP | 1459686 A2 | 9/2004 |
| EP | 1484077 A2 | 12/2004 |
| EP | 1079752 B1 | 1/2005 |
| EP | 1484077 A3 | 1/2005 |
| EP | 1495729 A1 | 1/2005 |
| EP | 1148825 B1 | 3/2005 |
| EP | 1148850 B1 | 4/2005 |
| EP | 1522268 A1 | 4/2005 |
| EP | 1227765 B1 | 5/2005 |
| EP | 1535579 A2 | 6/2005 |
| EP | 1563795 A1 | 8/2005 |
| EP | 1582159 A1 | 10/2005 |
| EP | 1582160 A1 | 10/2005 |
| EP | 1582161 A1 | 10/2005 |
| EP | 1582163 A1 | 10/2005 |
| EP | 1582164 A1 | 10/2005 |
| EP | 1634548 A2 | 3/2006 |
| EP | 1639953 A1 | 3/2006 |
| EP | 1669035 A1 | 6/2006 |
| EP | 1073371 B1 | 8/2006 |
| EP | 1454592 A3 | 8/2006 |
| EP | 1700572 A1 | 9/2006 |
| EP | 1702572 A2 | 9/2006 |
| EP | 1714618 A2 | 10/2006 |
| EP | 1787593 A1 | 5/2007 |
| EP | 1808143 A1 | 7/2007 |
| EP | 1815813 A2 | 8/2007 |
| EP | 1820462 A1 | 8/2007 |
| EP | 1011464 B1 | 1/2008 |
| EP | 1905367 A1 | 4/2008 |
| EP | 1905392 | 4/2008 |
| EP | 1905392 A1 | 4/2008 |
| EP | 1915959 A2 | 4/2008 |
| EP | 1920721 A2 | 5/2008 |
| EP | 1923019 A1 | 5/2008 |
| EP | 1277442 B1 | 7/2008 |
| EP | 1972308 A1 | 9/2008 |
| EP | 1982664 | 10/2008 |
| EP | 1987785 A2 | 11/2008 |
| EP | 2014261 A1 | 1/2009 |
| EP | 2025292 A1 | 2/2009 |
| EP | 1459689 B1 | 4/2009 |
| EP | 1484077 B1 | 6/2009 |
| EP | 1073371 B2 | 7/2009 |
| EP | 1459689 B3 | 11/2009 |
| EP | 3300676 | 4/2018 |
| ES | 2251888 | 5/2006 |
| FR | 2653006 A1 | 4/1991 |
| FR | 2686788 | 8/1993 |
| FR | 2781360 | 1/2000 |
| FR | 2861576 | 5/2005 |
| GB | 2173565 A | 10/1986 |
| GB | 2268068 A | 1/1994 |
| GB | 2274993 | 8/1994 |
| IE | 1582162 A1 | 10/2005 |
| JP | 1310664 A | 12/1989 |
| JP | 2000287983 | 10/2000 |
| JP | 2001506524 | 5/2001 |
| JP | 2001509040 | 7/2001 |
| JP | 200481681 | 3/2004 |
| JP | 2007125386 | 5/2007 |
| JP | 2008500140 A | 1/2008 |
| JP | 2008540037 A | 12/2008 |
| JP | 2009160399 | 7/2009 |
| JP | 2010510040 A | 4/2010 |
| JP | 2010510041 A | 4/2010 |
| JP | 2010510042 A | 4/2010 |
| JP | 2010522046 A | 7/2010 |
| JP | 2010524642 A | 7/2010 |
| JP | 2011523889 A | 8/2011 |
| JP | 2012504027 A | 2/2012 |
| JP | 2012518511 | 8/2012 |
| JP | 2013500073 | 1/2013 |
| RU | 2004104359 A | 2/2005 |
| WO | WO8904150 A1 | 5/1989 |
| WO | WO8907056 A1 | 8/1989 |
| WO | WO9003764 A1 | 4/1990 |
| WO | WO9011726 A1 | 10/1990 |
| WO | WO1991002493 A1 | 3/1991 |
| WO | WO9106260 A1 | 5/1991 |
| WO | WO9106265 A1 | 5/1991 |
| WO | WO9111962 A1 | 8/1991 |
| WO | WO1991011962 A1 | 8/1991 |
| WO | WO9119461 A1 | 12/1991 |
| WO | WO9424938 A1 | 11/1994 |
| WO | WO9427507 A1 | 12/1994 |
| WO | WO9428824 A2 | 12/1994 |
| WO | WO9514433 A1 | 6/1995 |
| WO | WO1995014433 A1 | 6/1995 |
| WO | WO9520362 A1 | 8/1995 |
| WO | WO9531159 A1 | 11/1995 |
| WO | WO9602202 A1 | 2/1996 |
| WO | WO9602203 A1 | 2/1996 |
| WO | WO9605783 A1 | 2/1996 |
| WO | WO9606041 A1 | 2/1996 |
| WO | WO9607161 A1 | 3/1996 |
| WO | WO9616607 A1 | 6/1996 |
| WO | WO9617557 A1 | 6/1996 |
| WO | WO9618354 A2 | 6/1996 |
| WO | WO1996018354 A2 | 6/1996 |
| WO | WO9625118 A1 | 8/1996 |
| WO | WO1996018354 A3 | 8/1996 |
| WO | WO9640476 A1 | 12/1996 |
| WO | WO9703611 A1 | 2/1997 |
| WO | WO1997003611 A1 | 2/1997 |
| WO | WO1997018775 A1 | 5/1997 |
| WO | WO9742602 A1 | 11/1997 |
| WO | WO9742912 A1 | 11/1997 |
| WO | WO9747251 A1 | 12/1997 |
| WO | WO9801077 A1 | 1/1998 |
| WO | WO9805261 A2 | 2/1998 |
| WO | WO1998007392 A1 | 2/1998 |
| WO | WO1998019616 A1 | 5/1998 |
| WO | WO9824380 A1 | 6/1998 |
| WO | WO9826725 A1 | 6/1998 |
| WO | WO9838918 A1 | 9/1998 |
| WO | WO9846169 A1 | 10/1998 |
| WO | WO9856301 A1 | 12/1998 |
| WO | WO9922661 A1 | 5/1999 |
| WO | WO9922662 A1 | 5/1999 |
| WO | WO9937219 A1 | 7/1999 |
| WO | WO1999047055 A1 | 9/1999 |
| WO | WO1999051149 A1 | 10/1999 |
| WO | WO1999053843 A1 | 10/1999 |
| WO | WO9955248 A1 | 11/1999 |
| WO | WO9962416 A1 | 12/1999 |
| WO | WO0009024 A1 | 2/2000 |
| WO | WO2000006037 A1 | 2/2000 |
| WO | WO00/13596 | 3/2000 |
| WO | WO0012036 A1 | 3/2000 |
| WO | WO2000012036 A1 | 3/2000 |
| WO | WO0021455 A1 | 4/2000 |
| WO | WO0025681 A1 | 5/2000 |
| WO | WO0028906 A1 | 5/2000 |
| WO | WO2007059243 A1 | 5/2000 |
| WO | WO0030551 A1 | 6/2000 |
| WO | WO0030569 A1 | 6/2000 |
| WO | WO0038586 A1 | 7/2000 |
| WO | WO0042954 A2 | 7/2000 |
| WO | WO0044319 A1 | 8/2000 |
| WO | WO0044321 A2 | 8/2000 |
| WO | WO0044946 A1 | 8/2000 |
| WO | WO0045712 A1 | 8/2000 |
| WO | WO0045714 A1 | 8/2000 |
| WO | WO0045715 A1 | 8/2000 |
| WO | WO0045722 A1 | 8/2000 |
| WO | WO0047119 A1 | 8/2000 |
| WO | WO0048534 A1 | 8/2000 |
| WO | WO0071038 A1 | 11/2000 |
| WO | WO0076414 A1 | 12/2000 |
| WO | WO0108571 A1 | 2/2001 |
| WO | WO0128443 A1 | 4/2001 |
| WO | WO0134045 A1 | 5/2001 |
| WO | WO0149193 A1 | 7/2001 |

(56) References Cited

FOREIGN PATENT DOCUMENTS

| | | |
|---|---|---|
| WO | WO01/54598 | 8/2001 |
| WO | WO0154598 A1 | 8/2001 |
| WO | WO0160268 A1 | 8/2001 |
| WO | WO2001060268 A1 | 8/2001 |
| WO | WO0176493 A1 | 10/2001 |
| WO | WO0176514 A2 | 10/2001 |
| WO | WO0178015 A2 | 10/2001 |
| WO | WO0180751 A1 | 11/2001 |
| WO | WO0185042 A1 | 11/2001 |
| WO | WO0213700 A2 | 2/2002 |
| WO | WO0213716 A1 | 2/2002 |
| WO | WO0217794 A1 | 3/2002 |
| WO | WO0224088 A2 | 3/2002 |
| WO | WO2002017794 A1 | 3/2002 |
| WO | WO0234107 A2 | 5/2002 |
| WO | WO0234148 A2 | 5/2002 |
| WO | WO0237935 A2 | 5/2002 |
| WO | WO0245606 A1 | 6/2002 |
| WO | WO0249517 A1 | 6/2002 |
| WO | WO02058575 A1 | 8/2002 |
| WO | WO2002067824 A2 | 9/2002 |
| WO | WO2002078555 A1 | 10/2002 |
| WO | WO02089683 A1 | 11/2002 |
| WO | WO2002096306 A1 | 12/2002 |
| WO | WO03007830 A1 | 1/2003 |
| WO | WO03013336 A2 | 2/2003 |
| WO | WO2002017794 A8 | 3/2003 |
| WO | WO03030760 A1 | 4/2003 |
| WO | WO2003043488 A2 | 5/2003 |
| WO | WO03047440 A2 | 6/2003 |
| WO | WO2003045257 A2 | 6/2003 |
| WO | WO03068090 A1 | 8/2003 |
| WO | WO2002017794 A9 | 9/2003 |
| WO | WO2004008949 A2 | 1/2004 |
| WO | WO04017817 A2 | 3/2004 |
| WO | WO2004021904 | 3/2004 |
| WO | WO2004030549 A1 | 4/2004 |
| WO | WO2004039271 | 5/2004 |
| WO | WO2004064603 A2 | 8/2004 |
| WO | WO2004078220 A2 | 9/2004 |
| WO | WO2004078221 A2 | 9/2004 |
| WO | WO2004086934 A2 | 10/2004 |
| WO | WO2004092431 A1 | 10/2004 |
| WO | WO2004093633 A2 | 11/2004 |
| WO | WO2004098453 A2 | 11/2004 |
| WO | WO2004/110292 | 12/2004 |
| WO | WO04103209 A2 | 12/2004 |
| WO | WO04110292 A2 | 12/2004 |
| WO | WO04110300 A2 | 12/2004 |
| WO | WO2004112661 A1 | 12/2004 |
| WO | WO05000159 A2 | 1/2005 |
| WO | WO2005020830 A1 | 3/2005 |
| WO | WO2005020833 A2 | 3/2005 |
| WO | WO2005023085 A2 | 3/2005 |
| WO | WO05032326 A2 | 4/2005 |
| WO | WO05032340 A2 | 4/2005 |
| WO | WO05039651 A2 | 5/2005 |
| WO | WO2005041799 A1 | 5/2005 |
| WO | WO2005044122 A1 | 5/2005 |
| WO | WO2005/048856 | 6/2005 |
| WO | WO2005051971 A1 | 6/2005 |
| WO | WO2005055874 A2 | 6/2005 |
| WO | WO2005020833 A3 | 7/2005 |
| WO | WO2005070314 A1 | 8/2005 |
| WO | WO2005092223 A2 | 10/2005 |
| WO | WO2005094693 A1 | 10/2005 |
| WO | WO2005094705 A2 | 10/2005 |
| WO | WO2005094706 A1 | 10/2005 |
| WO | WO2005096975 A2 | 10/2005 |
| WO | WO2005102196 A1 | 11/2005 |
| WO | WO2005107415 A2 | 11/2005 |
| WO | WO2005112804 A1 | 12/2005 |
| WO | WO2005112804 A1 | 12/2005 |
| WO | WO2005122931 A1 | 12/2005 |
| WO | WO2005122932 A2 | 12/2005 |
| WO | WO2005123171 A2 | 12/2005 |
| WO | WO2006011152 A2 | 2/2006 |
| WO | WO2006020530 A2 | 2/2006 |
| WO | WO2005112804 A9 | 3/2006 |
| WO | WO2006023793 A2 | 3/2006 |
| WO | WO2006026323 A2 | 3/2006 |
| WO | WO2006026323 A2 | 3/2006 |
| WO | WO2006026323 A9 | 4/2006 |
| WO | WO2006041460 A1 | 4/2006 |
| WO | WO2006041460 A1 | 4/2006 |
| WO | WO2006042188 A2 | 4/2006 |
| WO | WO2006042189 A2 | 4/2006 |
| WO | WO2006042334 A2 | 4/2006 |
| WO | WO2006034396 A3 | 5/2006 |
| WO | WO2006051547 A2 | 5/2006 |
| WO | WO2006055448 A1 | 5/2006 |
| WO | WO2006063083 A1 | 6/2006 |
| WO | WO2006066228 A2 | 6/2006 |
| WO | WO2006068682 A1 | 6/2006 |
| WO | WO2010065855 A1 | 6/2006 |
| WO | WO2006089929 A1 | 8/2006 |
| WO | WO2006090379 A2 | 8/2006 |
| WO | WO2006034436 A3 | 10/2006 |
| WO | WO2006108067 A2 | 10/2006 |
| WO | WO2006113800 A2 | 10/2006 |
| WO | WO2006116760 A2 | 11/2006 |
| WO | WO2006116761 A2 | 11/2006 |
| WO | WO2006124764 A1 | 11/2006 |
| WO | WO2006124764 A1 | 11/2006 |
| WO | WO2006124937 A2 | 11/2006 |
| WO | WO2006127904 A1 | 11/2006 |
| WO | WO2006127904 A1 | 11/2006 |
| WO | WO2007002933 A2 | 1/2007 |
| WO | WO2007008177 A1 | 1/2007 |
| WO | WO2007009107 A2 | 1/2007 |
| WO | WO2007009123 A2 | 1/2007 |
| WO | WO2007011994 A2 | 1/2007 |
| WO | WO2007012046 A2 | 1/2007 |
| WO | WO2007025236 A2 | 3/2007 |
| WO | WO2007040949 A2 | 4/2007 |
| WO | WO2007041665 A2 | 4/2007 |
| WO | WO2006124937 A3 | 5/2007 |
| WO | Wo2007053960 A1 | 5/2007 |
| WO | WO2007058943 A2 | 5/2007 |
| WO | WO2007059243 A1 | 5/2007 |
| WO | WO2007059246 A1 | 5/2007 |
| WO | WO2007059259 A1 | 5/2007 |
| WO | WO2007059259 A1 | 5/2007 |
| WO | WO2007065137 A2 | 6/2007 |
| WO | WO2007069251 A2 | 6/2007 |
| WO | WO2007073488 A2 | 6/2007 |
| WO | WO2007/078692 | 7/2007 |
| WO | WO2007/079237 | 7/2007 |
| WO | WO2007076308 A2 | 7/2007 |
| WO | WO2007076374 A2 | 7/2007 |
| WO | WO2007076376 A2 | 7/2007 |
| WO | WO2007076377 A2 | 7/2007 |
| WO | WO2007078692 A2 | 7/2007 |
| WO | WO2007079237 A2 | 7/2007 |
| WO | WO2007082151 A2 | 7/2007 |
| WO | WO2007084239 A2 | 7/2007 |
| WO | WO2007092813 A2 | 8/2007 |
| WO | WO2007092813 A2 | 8/2007 |
| WO | WO2007092841 A2 | 8/2007 |
| WO | WO2007092841 A2 | 8/2007 |
| WO | WO2007036815 A2 | 9/2007 |
| WO | WO2007114982 A1 | 10/2007 |
| WO | WO2007115108 A1 | 10/2007 |
| WO | WO2007117571 A2 | 10/2007 |
| WO | WO2007120539 A2 | 10/2007 |
| WO | WO2007092841 A3 | 11/2007 |
| WO | WO2007124130 A2 | 11/2007 |
| WO | WO2007127255 A2 | 11/2007 |
| WO | WO2007127260 A2 | 11/2007 |
| WO | WO2007131002 A2 | 11/2007 |
| WO | WO2007134134 A2 | 11/2007 |
| WO | WO2007079237 A3 | 12/2007 |
| WO | WO2007145824 A2 | 12/2007 |
| WO | WO2008004229 A2 | 1/2008 |

(56) References Cited

FOREIGN PATENT DOCUMENTS

| | | |
|---|---|---|
| WO | WO2008006117 A2 | 1/2008 |
| WO | WO2008016910 A2 | 2/2008 |
| WO | WO2008019397 A2 | 2/2008 |
| WO | WO2008035849 A1 | 3/2008 |
| WO | WO2008037454 A1 | 4/2008 |
| WO | WO2008043254 A1 | 4/2008 |
| WO | WO2008058960 A2 | 5/2008 |
| WO | WO2008059027 A2 | 5/2008 |
| WO | WO2008060277 | 5/2008 |
| WO | WO2008060277 A2 | 5/2008 |
| WO | WO2008063265 A1 | 5/2008 |
| WO | WO2008064346 A2 | 5/2008 |
| WO | WO2008064347 A2 | 5/2008 |
| WO | WO2008064347 A2 | 5/2008 |
| WO | WO2008064350 A2 | 5/2008 |
| WO | WO2008076330 A1 | 6/2008 |
| WO | WO2008076330 A1 | 6/2008 |
| WO | WO2008076357 A1 | 6/2008 |
| WO | WO2008094407 A1 | 8/2008 |
| WO | WO2007011353 A3 | 9/2008 |
| WO | WO2007092813 A3 | 9/2008 |
| WO | WO2008109566 A1 | 9/2008 |
| WO | WO2008112308 A1 | 9/2008 |
| WO | WO2008116170 A2 | 9/2008 |
| WO | WO2008116175 A2 | 9/2008 |
| WO | WO2008/121613 | 10/2008 |
| WO | WO2008118945 A1 | 10/2008 |
| WO | WO2008121608 A2 | 10/2008 |
| WO | WO2008132728 A1 | 11/2008 |
| WO | WO2008134287 A2 | 11/2008 |
| WO | WO2008134758 A1 | 11/2008 |
| WO | WO2008139456 A2 | 11/2008 |
| WO | WO2008144709 A2 | 11/2008 |
| WO | WO2008144709 A2 | 11/2008 |
| WO | WO2007078692 A3 | 12/2008 |
| WO | WO2008121608 A3 | 1/2009 |
| WO | WO2008134287 A3 | 1/2009 |
| WO | WO2009006622 A2 | 1/2009 |
| WO | WO2009007331 A2 | 1/2009 |
| WO | WO2009009772 A1 | 1/2009 |
| WO | WO2009010412 A1 | 1/2009 |
| WO | WO2009012347 A1 | 1/2009 |
| WO | WO2009026070 A1 | 2/2009 |
| WO | WO2009027325 A1 | 3/2009 |
| WO | WO2009039430 A1 | 3/2009 |
| WO | WO2006026323 A3 | 4/2009 |
| WO | WO2006026397 A3 | 4/2009 |
| WO | WO2009045751 A1 | 4/2009 |
| WO | WO2009059227 A1 | 5/2009 |
| WO | WO2009067568 | 5/2009 |
| WO | WO2009072125 A1 | 6/2009 |
| WO | WO2009076086 A1 | 6/2009 |
| WO | WO2008144709 A3 | 7/2009 |
| WO | WO2009088376 A1 | 7/2009 |
| WO | WO2009094478 A1 | 7/2009 |
| WO | WO2008060277 A3 | 9/2009 |
| WO | WO2008112912 A3 | 9/2009 |
| WO | WO2009132333 A2 | 10/2009 |
| WO | WO2009143374 A2 | 11/2009 |
| WO | WO2009143496 A1 | 11/2009 |
| WO | WO2008112875 A3 | 12/2009 |
| WO | WO2009146457 A1 | 12/2009 |
| WO | WO2009152270 A1 | 12/2009 |
| WO | WO2009152272 A1 | 12/2009 |
| WO | WO2009152273 A1 | 12/2009 |
| WO | WO2009132333 A3 | 1/2010 |
| WO | WO2010/017990 | 2/2010 |
| WO | WO2008139456 A3 | 2/2010 |
| WO | WO2010037038 A2 | 4/2010 |
| WO | WO2010056895 A1 | 5/2010 |
| WO | WO2010062379 A1 | 6/2010 |
| WO | WO2010091242 A1 | 8/2010 |
| WO | WO2010035156 A1 | 11/2010 |
| WO | WO2013/063145 A1 | 5/2013 |

OTHER PUBLICATIONS

US 7,201,752 B2, 04/2007, Huebner et al. (withdrawn)
"Proximal Humerus System 3.5," Medartis AG, Switzerland, 2018.
"The Gamma Locking Nail Operative Technique," Stryker Corporation, 2003.
"Compression Hip Screw," Smith & Nephew, Inc., Sep. 2004.
"Hip Fractures," OrthoInfo, Apr. 2009.
Jeong J. et al., "Effect of a Variable Prosthetic Neck-Shaft Angle and the Surgical Technique on Replication of Normal Humeral Anatomy," National Center for Biotechnology Information, U.S. National Library of Medicine, Aug. 2009.
"DHS/DCS Dynamic Hip and Condylar Screw System Technique Guide," Synthes, Inc., Mar. 2012.
"Gamma3© Long Nail R1.5 and R2.0," Stryker Corporation, 2014.
"Google Images," Google Inc., Jun. 28, 2017.
"Cylinder," Wikimedia Foundation, Inc., May 25, 2018.
"Curvature," Wikimedia Foundation, Inc., May 26, 2018.
Van Kampen et al, "Comparison of a New Intramedullary Scaffold to Volar Plating for Treatment of Distal Radius Fractures," J Orthop Trauma, Tampa, Florida, Nov. 26, 2012.
Pierannunzii, "Endoscopic and Arthroscopic Assistance in Femoral Head Core Decompression," Arthroscopy Techniques, vol. 1, No. 2, pp. e225-e230, Winston-Salem, North Carolina, Dec. 2012.
Strassmair, "Intramedullar Osteosynthesis for treatment of distal radius fractures," Orthopadie & Rheuma, Munchen, Germany, 2011.
"Surgical Technique: Advanced Core Decompression System," Wright Medical Technology, Inc., Memphis, Tennessee, Jan. 1, 2014.
"Conventus DRS Implant 2013 Coding and Reimbursement Guide," Conventus Orthopaedics, Inc., Maple Grove, Minnesota, Mar. 18, 2013.
"Conventus DRS—Distal Radius System," Conventus Orthopaedics, Inc., Maple Grove, Minnesota, Feb. 20, 2013.
"Conventus DRS Surgical Technique," Conventus Orthopaedics, Inc., Maple Grove, Minnesota, Aug. 20, 2012.
"Surgical Technique Conventus Distal Radius System," Conventus Orthopaedics, Inc., Maple Grove, Minnesota, Jan. 31, 2013.
"Conventus Distal Radius Reduction Jig," Conventus Orthopaedics, Inc., Maple Grove, Minnesota, Feb. 28, 2012.
"DRS Removal Summary," Conventus Orthopaedics, Inc., Maple Grove, Minnesota, Oct. 2, 2012.
"Biomechanical Testing Summary," Conventus Orthopaedics, Inc., Maple Grove, Minnesota, Oct. 10, 2012.
"Conventus Introduction and Summary," Conventus Orthopaedics, Inc., Maple Grove, Minnesota, Oct. 1, 2012.
"Clinical Investigation Overview," Conventus Orthopaedics, Inc, Maple Grove, Minnesota, Oct. 1, 2012.
"Conventus DRS, Instructions for Use," Conventus Orthopaedics, Inc., Maple Grove, Minnesota, Feb. 18, 2013.
"Conventus DRS, Procedure Instruments Instrument Tray," Conventus Orthopaedics, Inc., Maple Grove, Minnesota, Feb. 18, 2013.
"A New Intramedullary Device for Distal Radius Fracture Fixation Biomechanical Comparison to Volar Plating," Mayo Clinic, Rochester, Minnesota, Nov. 11, 2011.
Strassmair, M. et al., "A Novel Multi-Planar and Less Invasive Approach to Distal Radius Fracture Fixation—Early Clinical Experience," Conventus Orthopaedics, Inc., Maple Grove, Minnesota, 2011.
"Biological Vertebral Augmentation in Thoracic and Lumbal Fractures Using OptiMesh for Spineoplasty—A new minimal invasive procedure," Second International Congress for Biotechnologies for Spinal Surgery—Leipzig, Leipzig, Germany, 2011.
Strassmair et al., "A Novel, Multi-Planar and Less Invasive Approach to Distal Radius Fracture Fixation—A Prospective Case Series," Conventus Orthopaedics, Inc., Maple Grove, Minnesota, Sep. 12, 2014.
International Search Report for International Application No. PCT/US14/69907, dated Jun. 4, 2015.
Written Opinion for International Application No. PCT/US14/69907, dated Jun. 4, 2015.
App No. PCT/US2017/012322 International Search Report, dated Feb. 15, 2018.

(56) References Cited

OTHER PUBLICATIONS

App No. PCT/US2017/012322 Written Opinion of the International Searching Authority, dated Feb. 15, 2018.
App No. PCT/US2017/18857 International Search Report, dated Jul. 10, 2017.
App No. PCT/US2017/18857 Written Opinion of the International Searching Authority, dated Jul. 10, 2017.
App No. PCT/US2018/13208 International Search Report, dated Apr. 25, 2018.
App No. PCT/US2018/13208 Written Opinion of the International Searching Authority, dated Apr. 25, 2018.
App No. PCT/US2018/40834 International Search Report, dated Jan. 22, 2019.
App No. PCT/US2018/40834 Written Opinion of the International Searching Authority, dated Jan. 22, 2019.
App No. PCT/US 09/30971 International Search Report, dated Mar. 6, 2009.
App No. PCT/US 09/30971 Written Opinion of the International Searching Authority, dated Mar. 6, 2009.
App No. PCT/US2011/21074 International Search Report, dated May 23, 2011.
App No. PCT/US2011/21074 Written Opinion of the International Searching Authority, dated May 23, 2011.
App No. PCT/US2011/021735 International Search Report, dated May 25, 2011.
App No. PCT/US2011/021735 Written Opinion of the International Searching Authority, dated May 25, 2011.
App No. PCT/US2011/027597 International Search Report, dated Jul. 6, 2011.
App No. PCT/US2011/027597 Written Opinion of the International Searching Authority, dated Jul. 6, 2011.
App No. PCT/US2011/027602 International Search Report, dated Jul. 5, 4011.
App No. PCT/US2011/027602 Written Opinion of the International Searching Authority, dated Jul. 5, 2011.
Putnam, Matthew D., et al., "Distal Radial Metaphyseal Forces in an Extrinsic Grip Model: Implications for Post fracture Rehabilitation," American Society for Surgery of the Hand, 25A: 469-475, May 2000.
Higgins, Thomas F., et al., "A Biomechanical Analysis of Fixation of Intra-Articular Distal Radial Fractures with Calcium-Phosphate Bone Cement," The Journal of Bone and Joint Surgery, 84:1579-1586, Needham, Massachusetts, Sep. 2002.
Stoeckel et al., "Self-Expanding Nitinol Stents—Material and Design Considerations," Nitinol Devices & Components, Fremont, California, 2003.
Rozenthal, Tamara D., et al., "Functional Outcome and Complications After Volar Plating for Dorsally Displaced, Unstable Fractures of the Distal Radius," The Journal of Hand Surgery, 31A: 359-365, Mar. 2006.
Keast-Butler, Oliver, et al., "Biology Versus Mechanics in the Treatment of Distal Radial Fractures," The Journal of Orthopedic Trauma, 22: S91-S95, Philadelphia, Pennsylvania, Sep. 2008.
Mudgal, Chaitanya S., et al., "Plate Fixation of Osteoporotic Fractures of the Distal Radius," The Journal of Orthopedic Trauma, 22: S106-S115, 2008, Philadelphia, Pennsylvania, Sep. 2008.
Bogoch, Earl R., et al., "The Osteoporosis Needs of Patients with Wrist Fractures," The Journal of Orthopedic Trauma, vol. 22, No. 8, Supplement, Philadelphia, Pennsylvania, Sep. 2008.
Arora, Rohit, et al., "A Representative Case of Osteoporotic Distal Radius Fracture," The Journal of Orthopedic Trauma, vol. 22, No. 8, Supplement, Philadelphia, Pennsylvania, Sep. 2008.
Firoozabadi, Reza, et al., "Qualitative and Quantitative Assessment of Bone Fragility and Fracture Healing Using Conventional Radiography and Advanced Imaging Technologies—Focus on Wrist Fracture," The Journal of Orthopedic Trauma, vol. 22, No. 8, Supplement, Philadelphia, Pennsylvania, Sep. 2008.
Goldhan, Jorg, et al., "What Counts: Outcome Assessment After Distal Radius Fractures in Aged Patients," The Journal of Orthopedic Trauma, vol. 22, No. 8, Supplement, Philadelphia, Pennsylvania, Sep. 2008.
Hoang-Kim, Amy, et al., "Wrist Fractures in Osteoporotic Patients," The Journal of Orthopedic Trauma, vol. 22, No. 8, Supplement, Philadelphia, Pennsylvania, Sep. 2008.
Kettler, Mark, et al., "Do We Need to Include Osteoporosis in Today's Classification of Distal Radius Fractures?" The Journal of Orthopedic Trauma, vol. 22, No. 8, Supplement, Philadelphia, Pennsylvania, Sep. 2008.
Downing, Martin R., et al., "Assessment of Inducible Fracture Micromotion in Distal Radial Fractures Using Radiostereometry," The Journal of Orthopedic Trauma, vol. 22, No. 8, Supplement, Philadelphia, Pennsylvania, Sep. 2008.
Suhm, Norbert, et al., "Injectable Bone Cement Augmentation for the Treatment of Distal Radius Fractures: A Review," The Journal of Orthopedic Trauma, vol. 22, No. 8, Supplement, Philadelphia, Pennsylvania, Sep. 2008.
Van Lenthe, G. Harry, et al., "Quantification of Bone Structural Parameters and Mechanical Competence at the Distal Radius," The Journal of Orthopedic Trauma, vol. 22, No. 8, Supplement, Philadelphia, Pennsylvania, Sep. 2008.
Parkinson, Ian H., et al., "Whole Bone Geometry and Bone Quality in Distal Forearm Fracture," The Journal of Orthopedic Trauma, vol. 22, No. 8, Supplement, Philadelphia, Pennsylvania, Sep. 2008.
"Medtronic—Abdominal Stent Graft System, Instructions for Use," Medtronic, Inc., Minneapolis—Minnesota, 2008.
Jupiter, Jesse B., et al., "Operative Management of Distal Radial Fractures with 2.4-Millimeter Locking Plates. A Multicenter Prospective Case Series," The Journal of Bone and Joint Surgery, 91: 55-65, doi:10.2106-JBJS.G.01498, Needham, Massachusetts, Jan. 1, 2009.
App No. PCT/US2012/028145 International Search Report, dated Sep. 13, 2012.
App No. PCT/US2012/028145 Written Opinion of the International Searching Authority, dated Sep. 13, 2012.
Ilyas, Asif M., "Intramedullary Fixation of Distal Radius Fractures," Elsevier, Inc. on behalf of the American Society for Surgery of the Hand, New York, New York, Feb. 2009.
Figl, Markus, et al., "Volar Fixed-Angle Plate Osteosynthesis of Unstable Distal Radius Fractures: 12 Months Results," Springer, New York, New York, Feb. 19, 2009.
Photograph, OrthopaedicLIST, 2010, Wilmington, North Carolina.
Barnes, C. Lowry, et al., "Advanced Core Decompression System," Wright, 2008, Arlington, Tennessee.
"OptiMesh 1500E—Percutaneous Interbody Fusion Surgical Technique," Spineology Inc., Feb. 2010, Saint Paul, Minnesota.
Corti, G., et al., "Acute Vertebral Body Compression Fracture treated with OptiMesh—Indications, Applications and First Clinical Results," Eurospine, 2005, Uster-Zürich Switzerland.
Advanced Core Decompression System—Surgical Technique, Wright, 2010, Arlington, Tennessee.

* cited by examiner

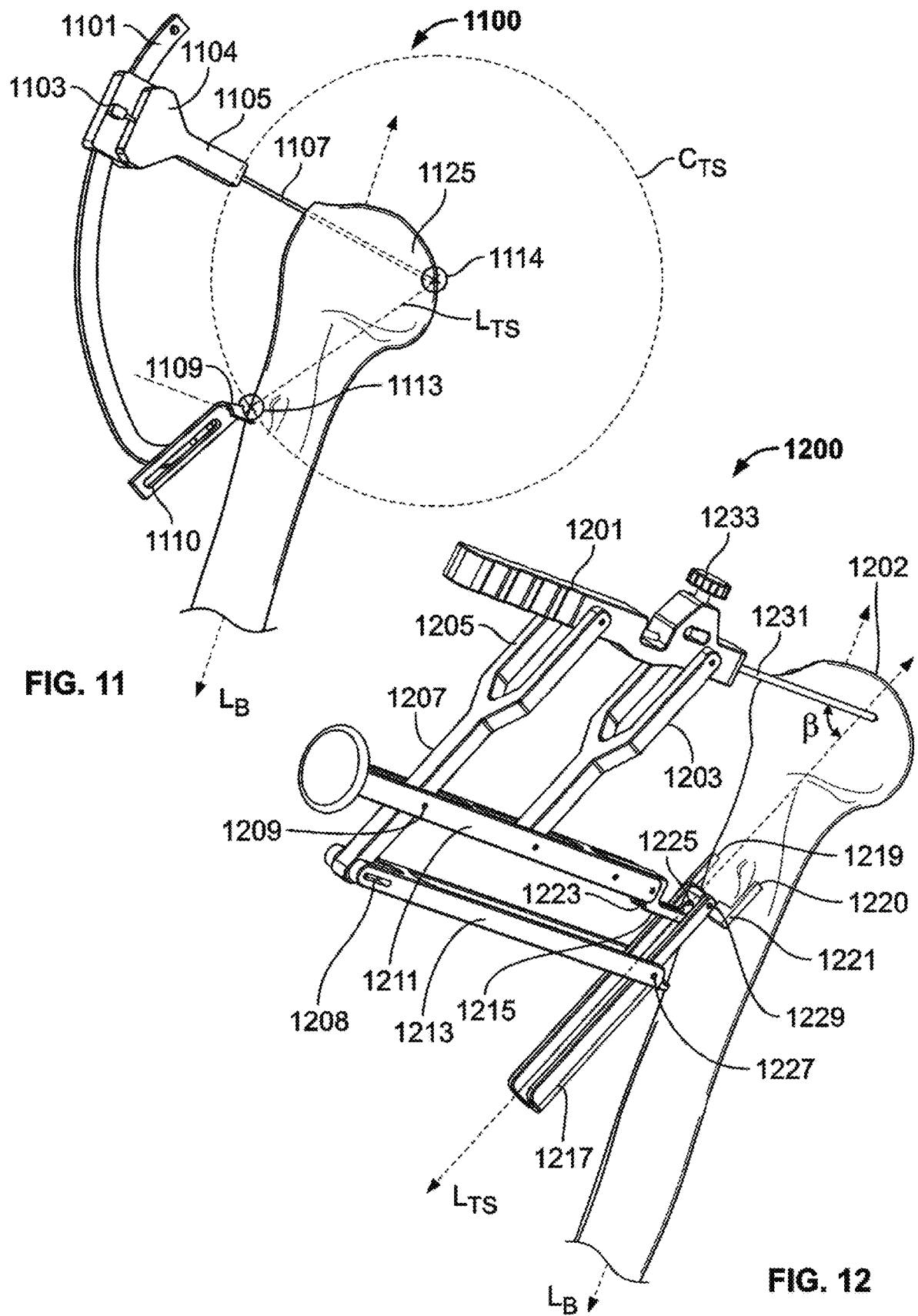

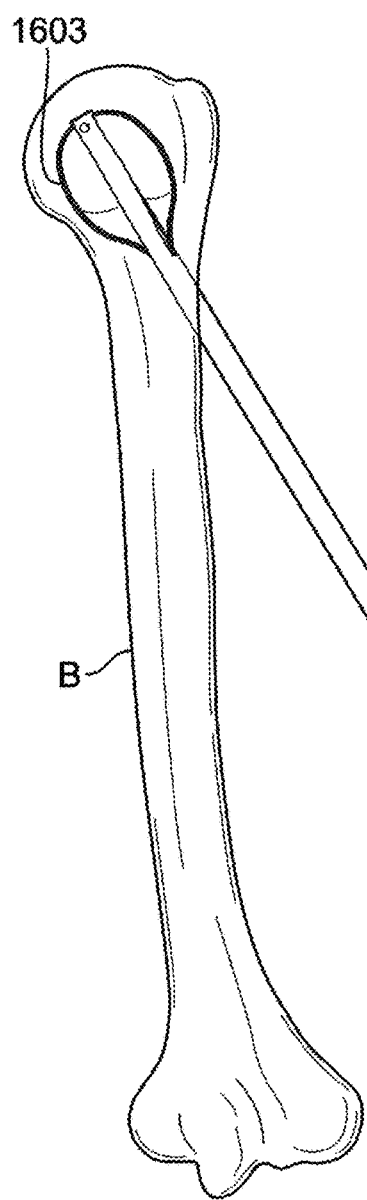
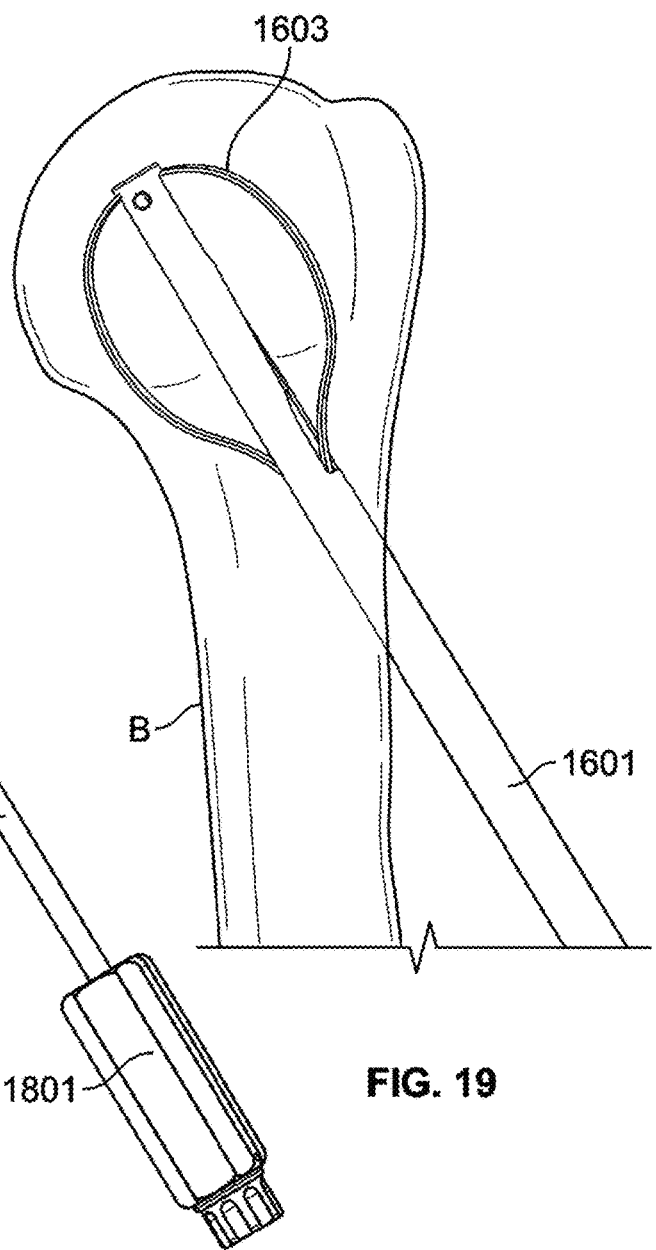
FIG. 18
FIG. 19

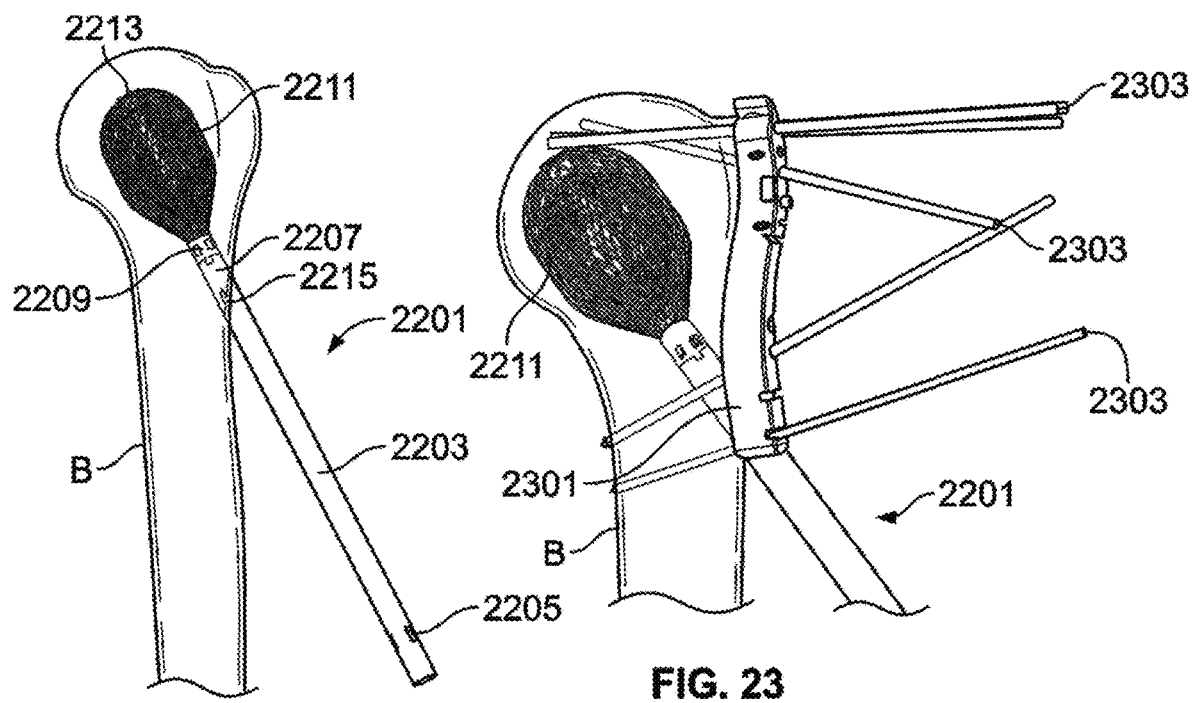
FIG. 22
FIG. 23
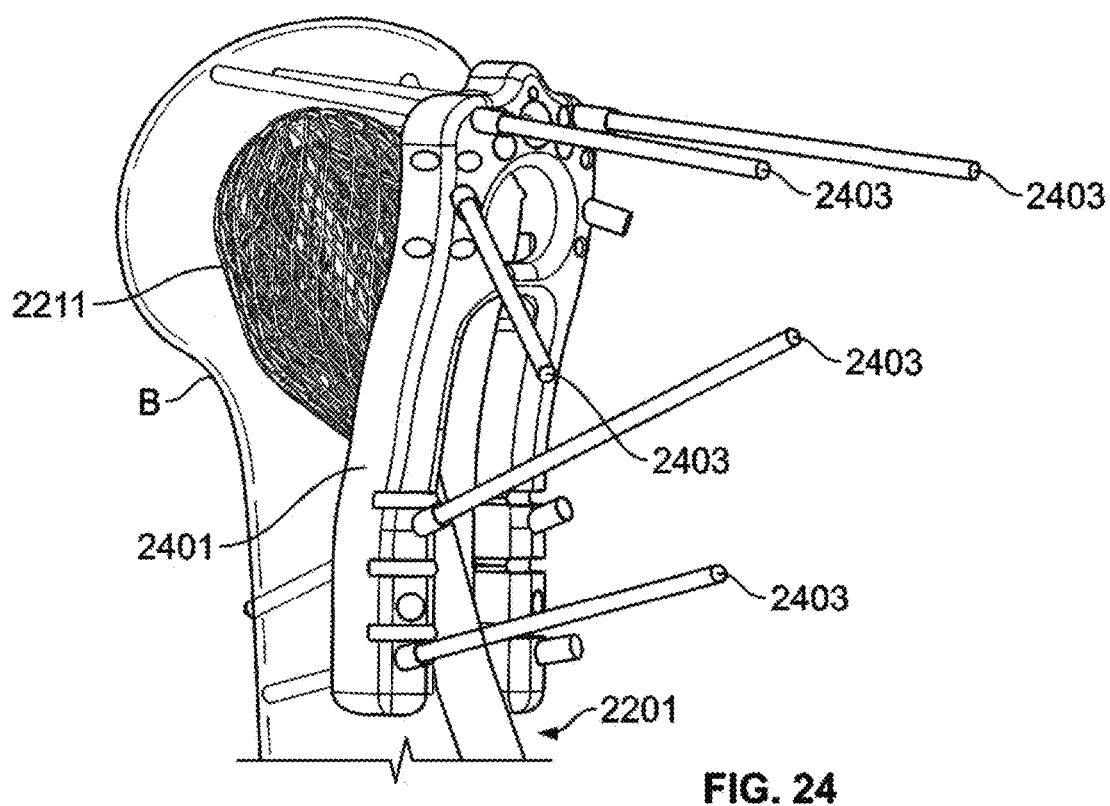
FIG. 24

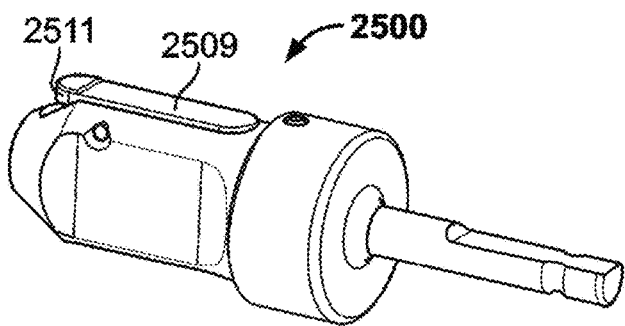
FIG. 25
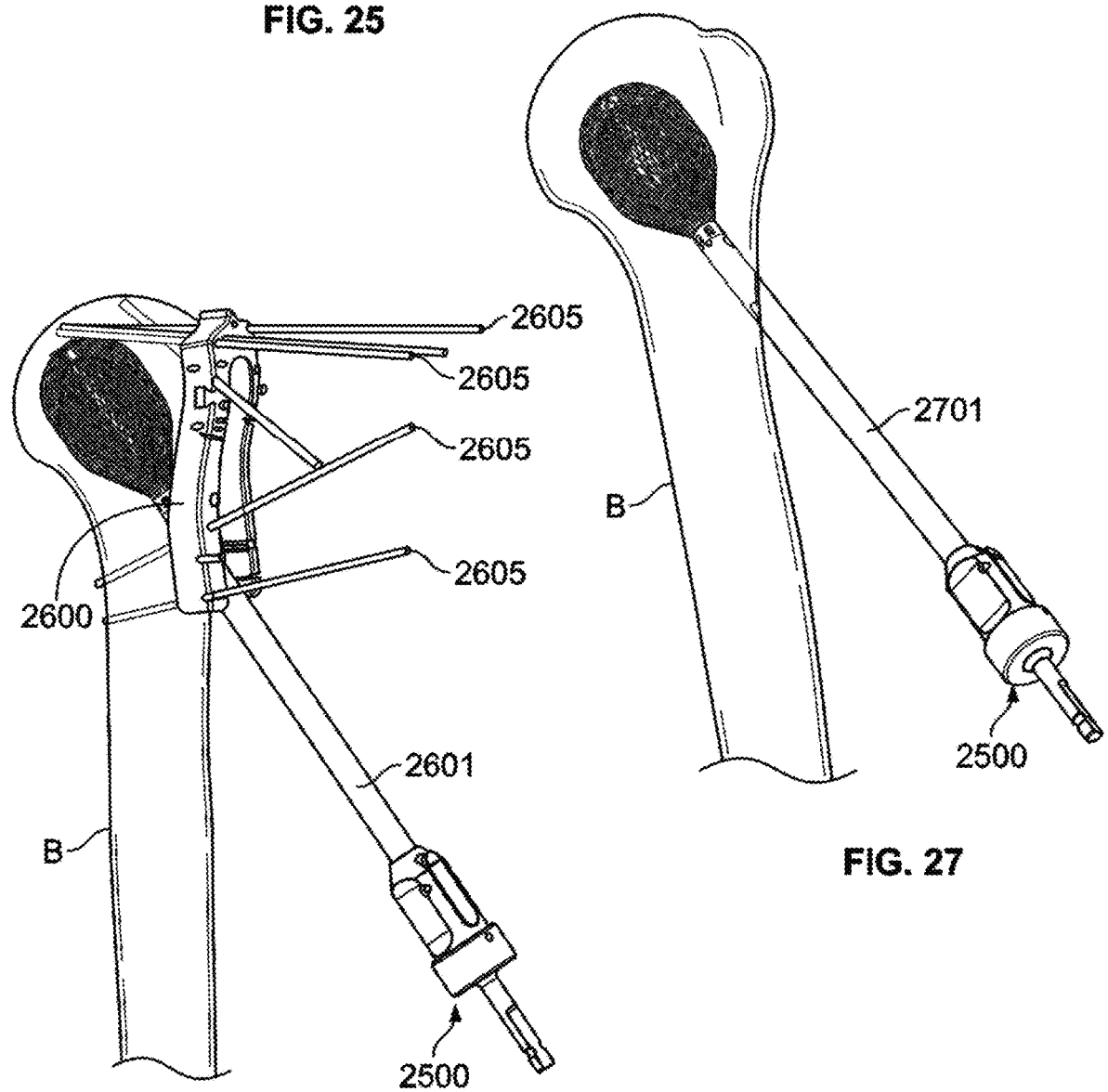
FIG. 27
FIG. 26

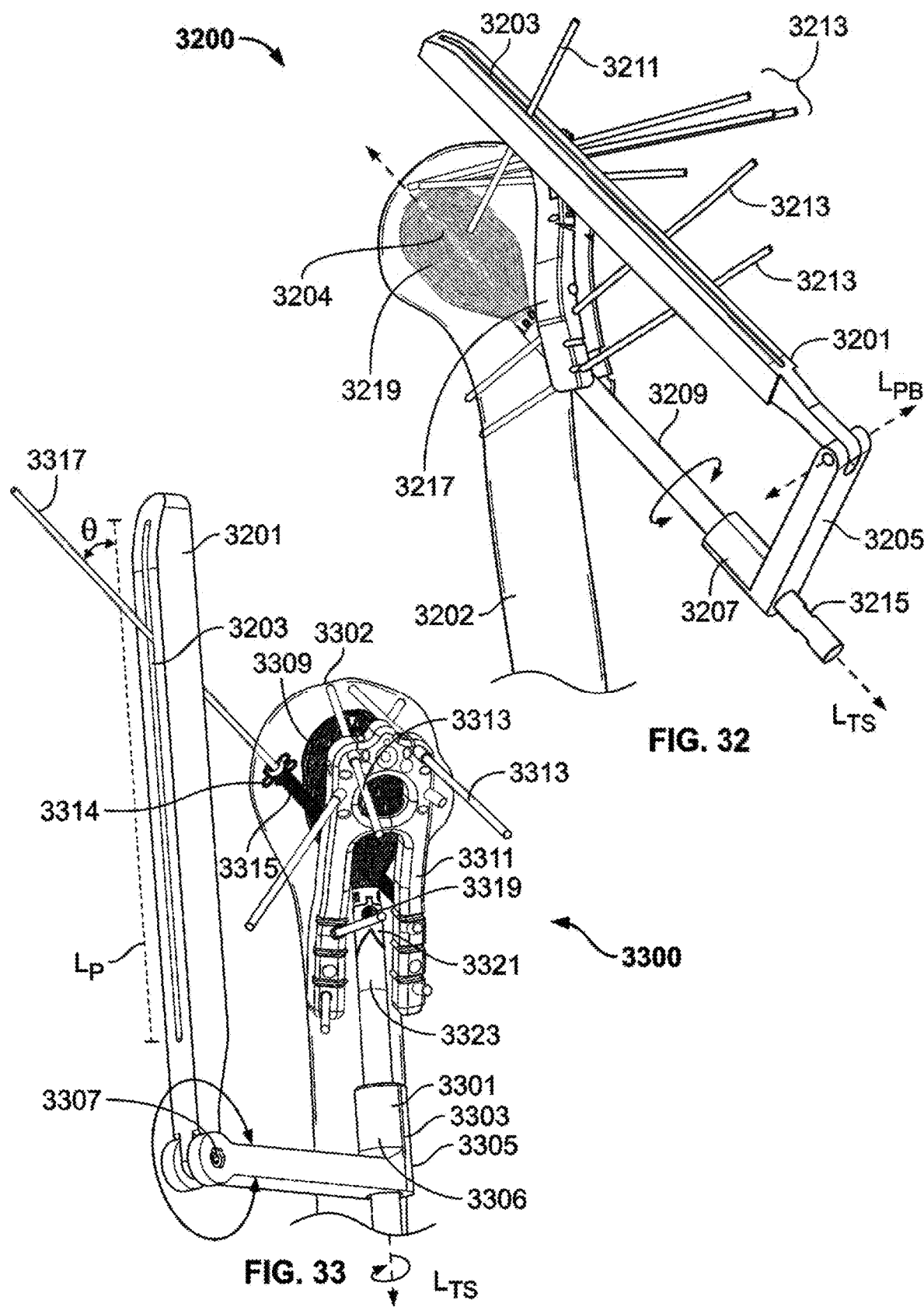

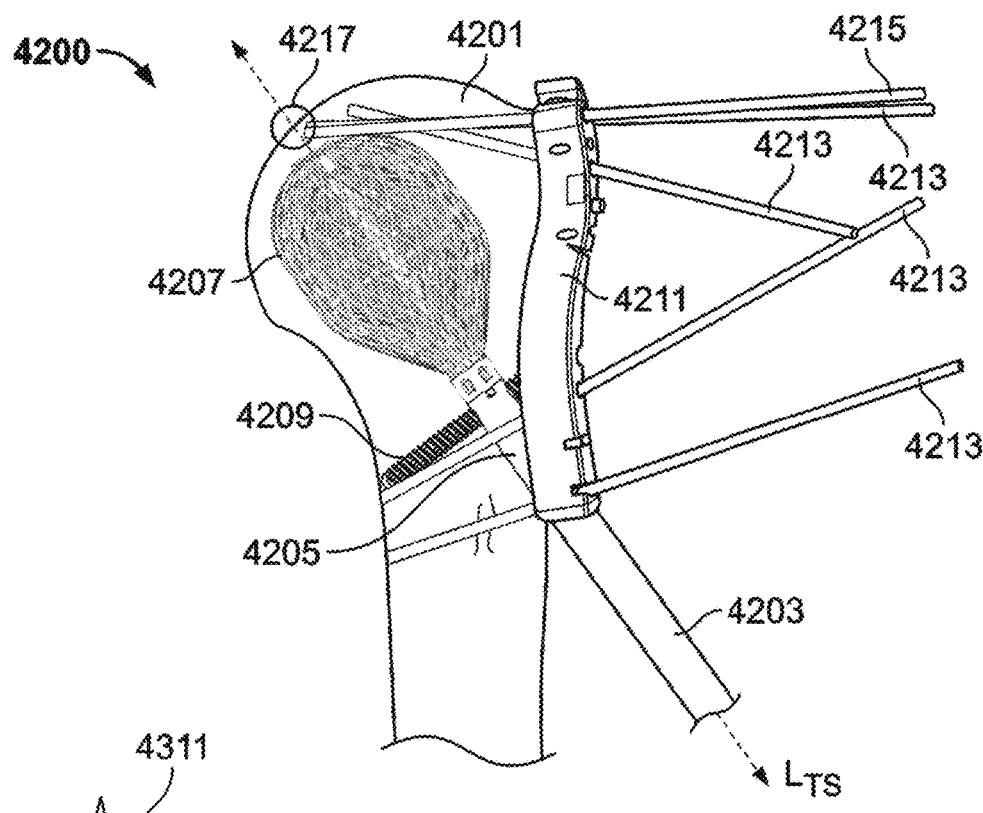
FIG. 42
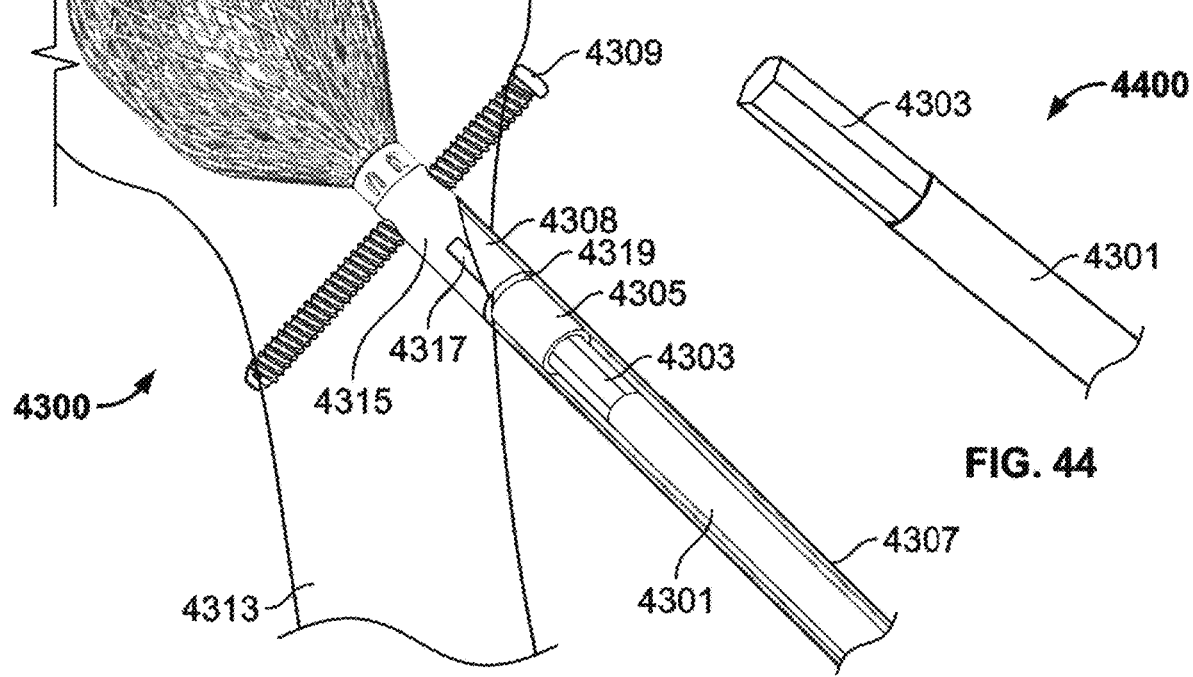
FIG. 43
FIG. 44

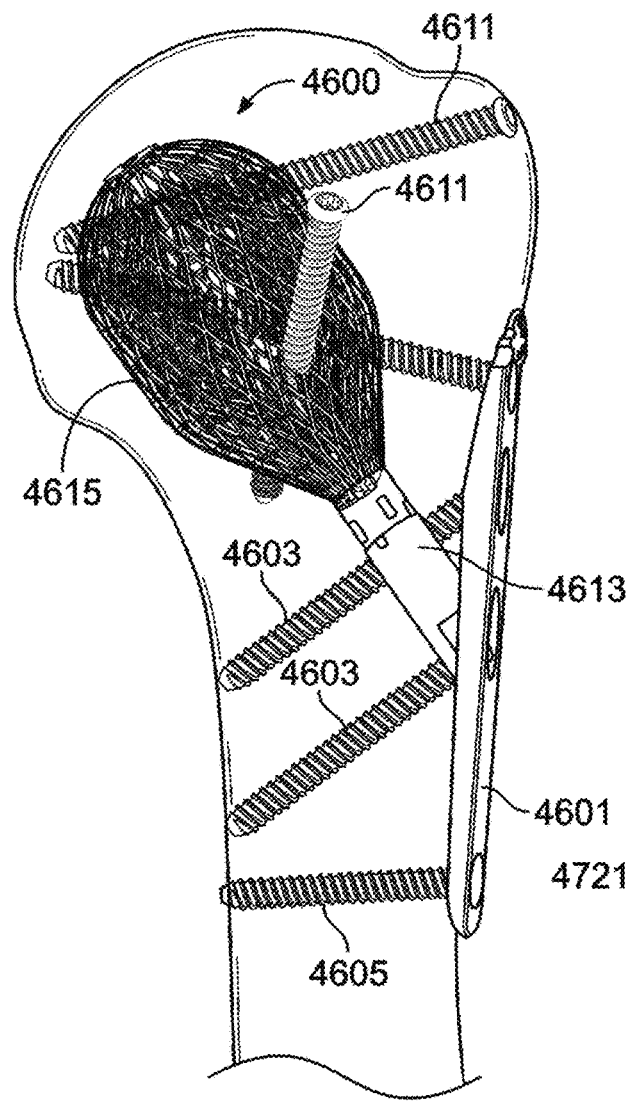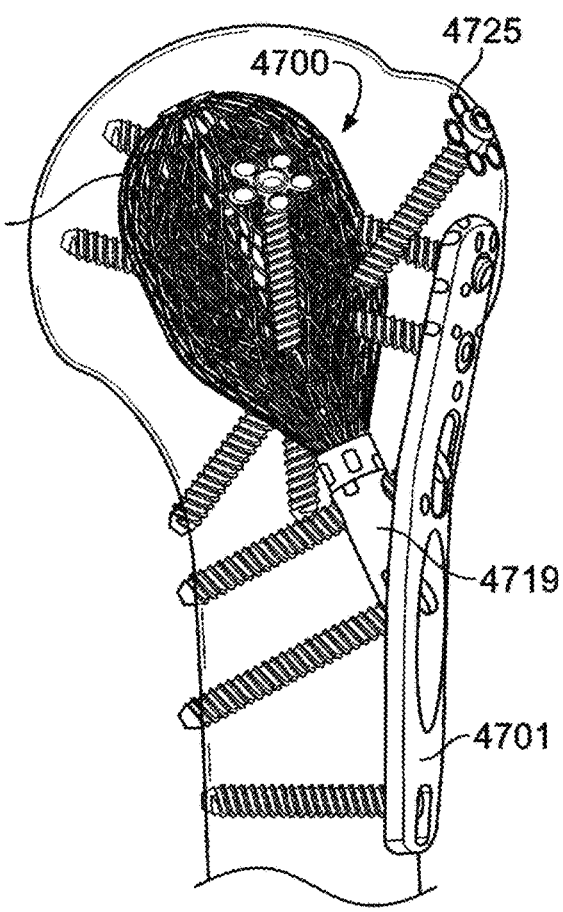
FIG. 46
FIG. 47

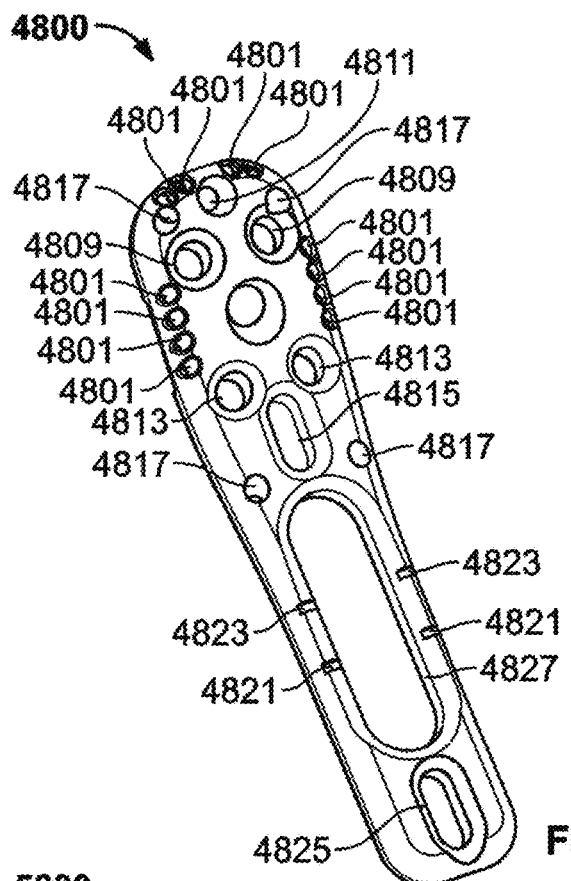
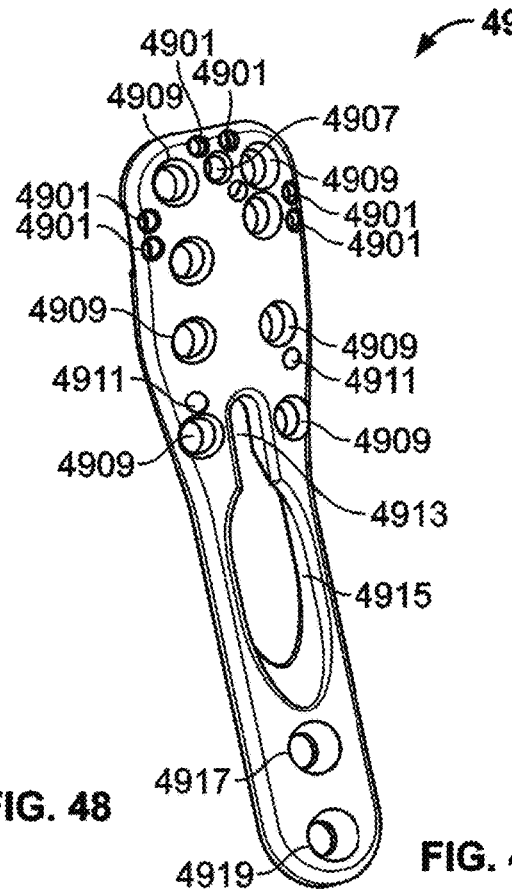
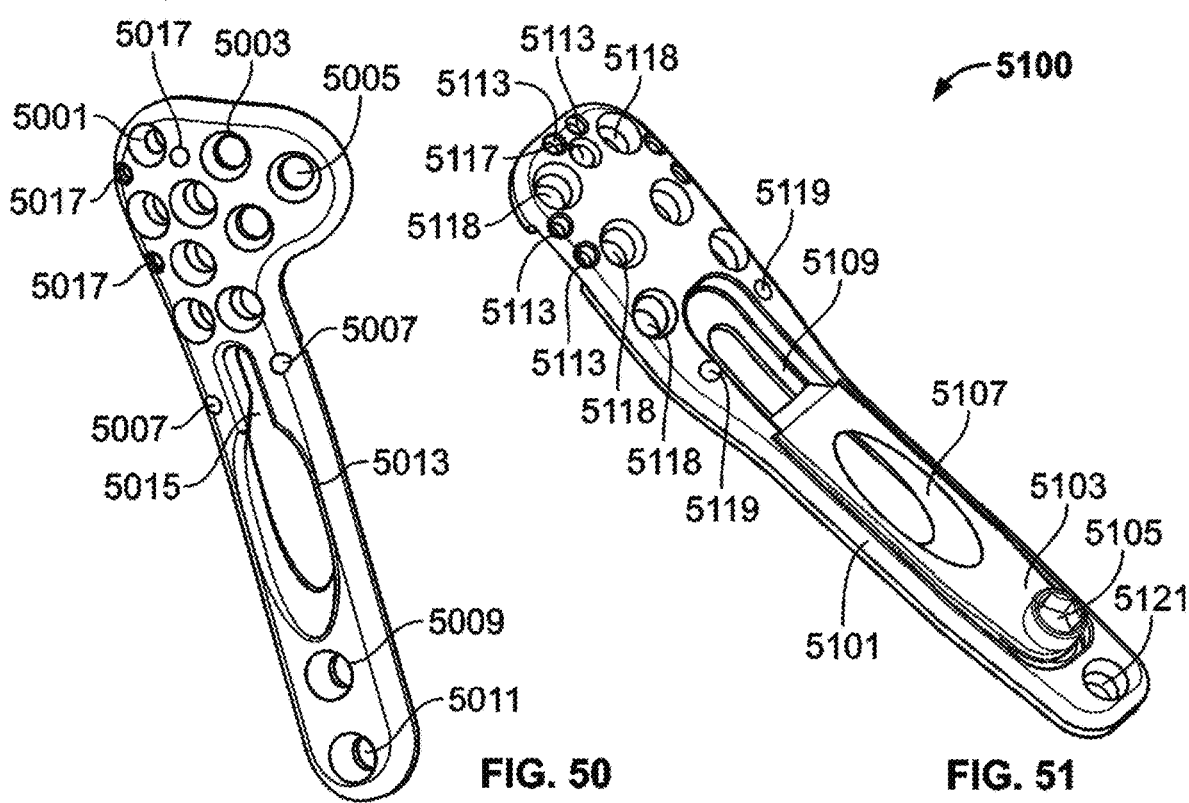
FIG. 48
FIG. 49
FIG. 50
FIG. 51

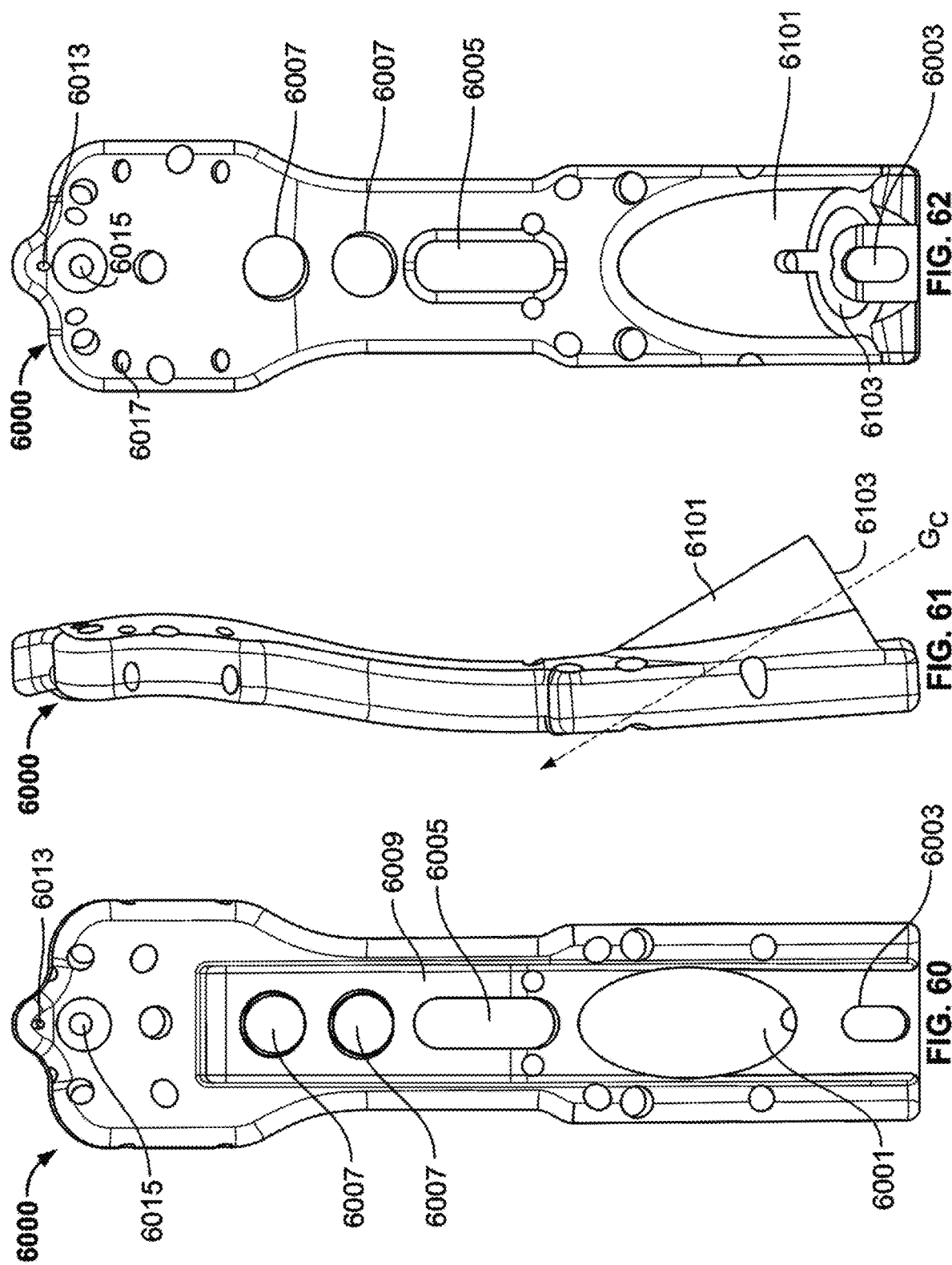

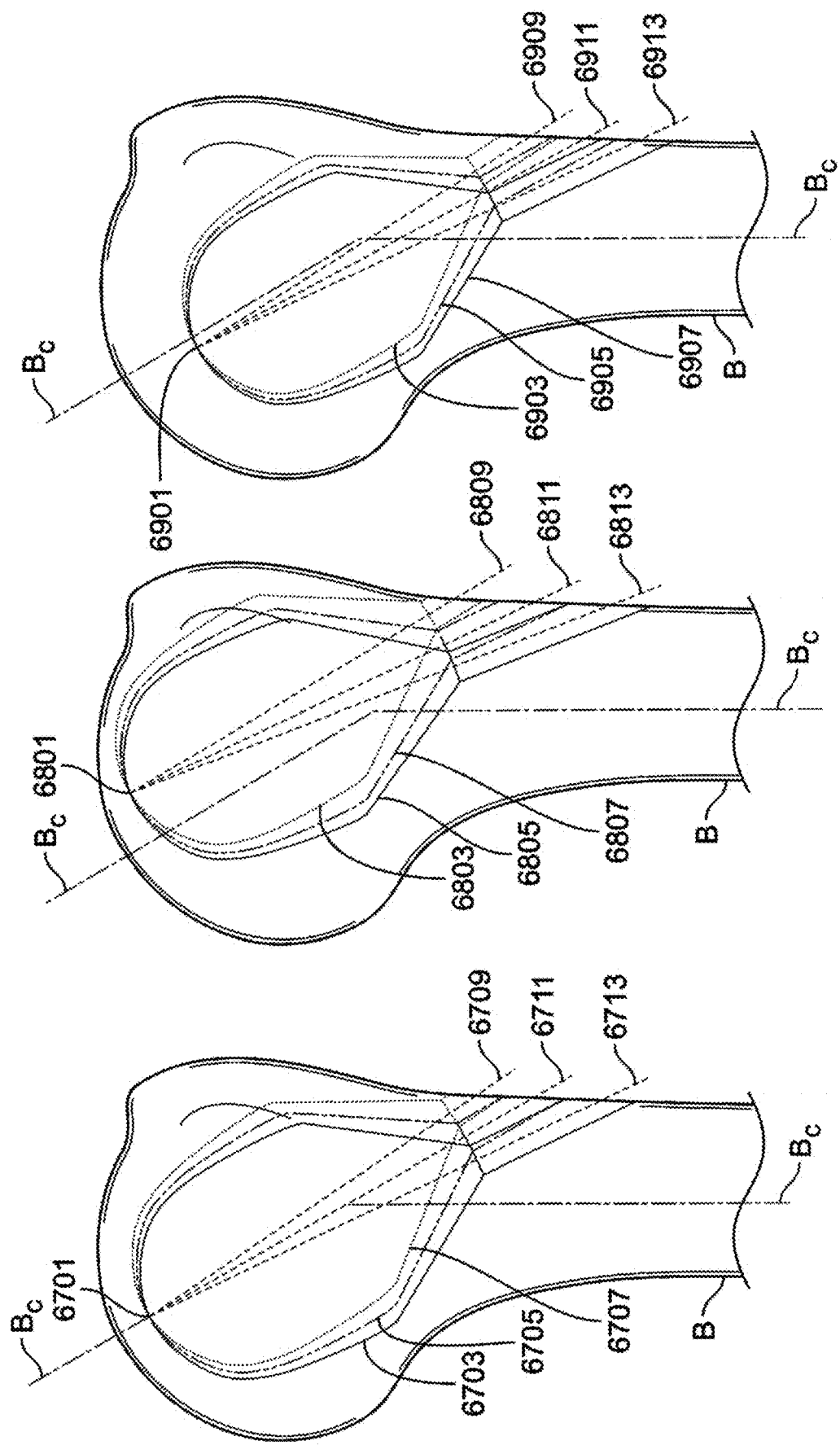

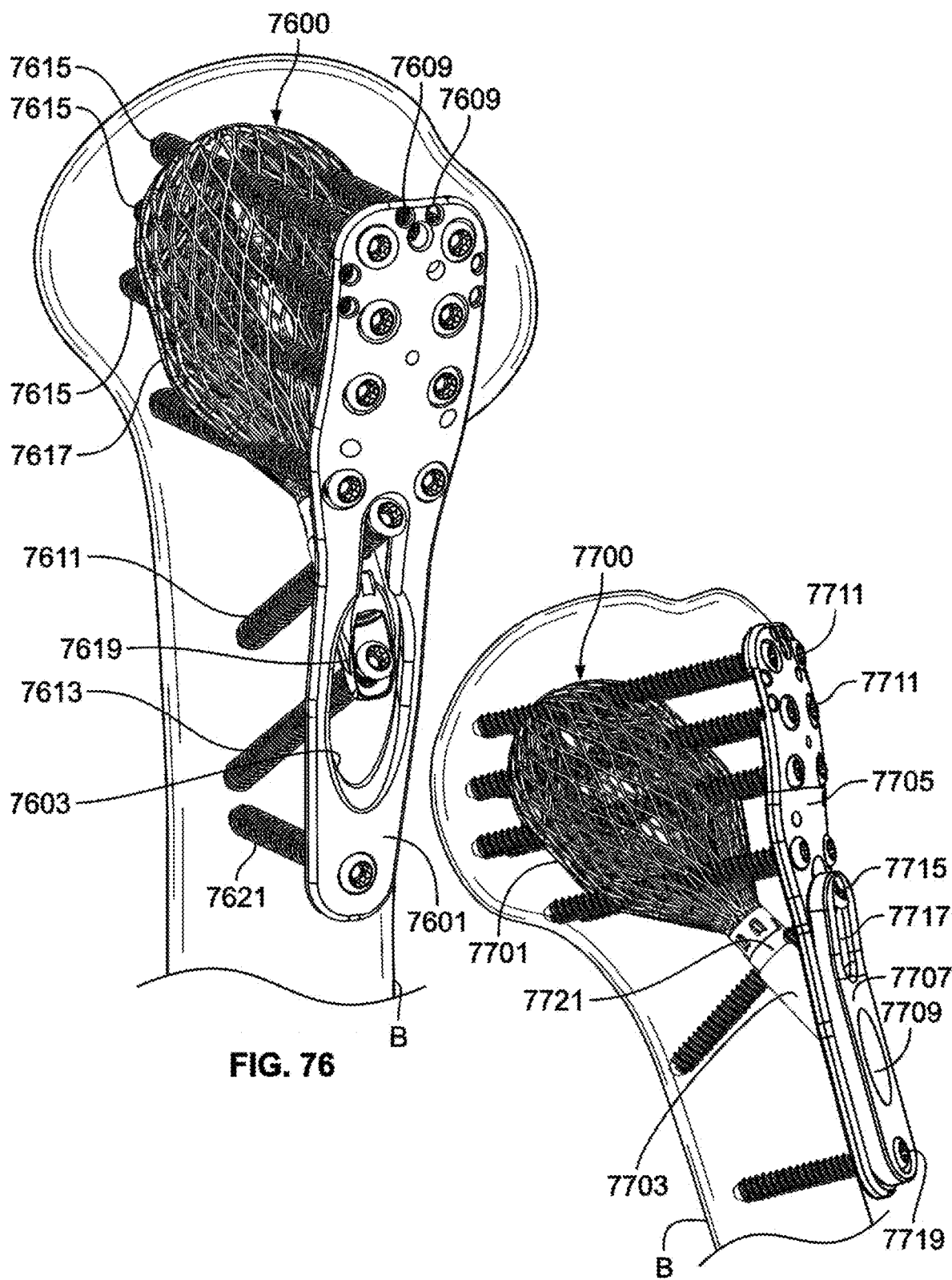

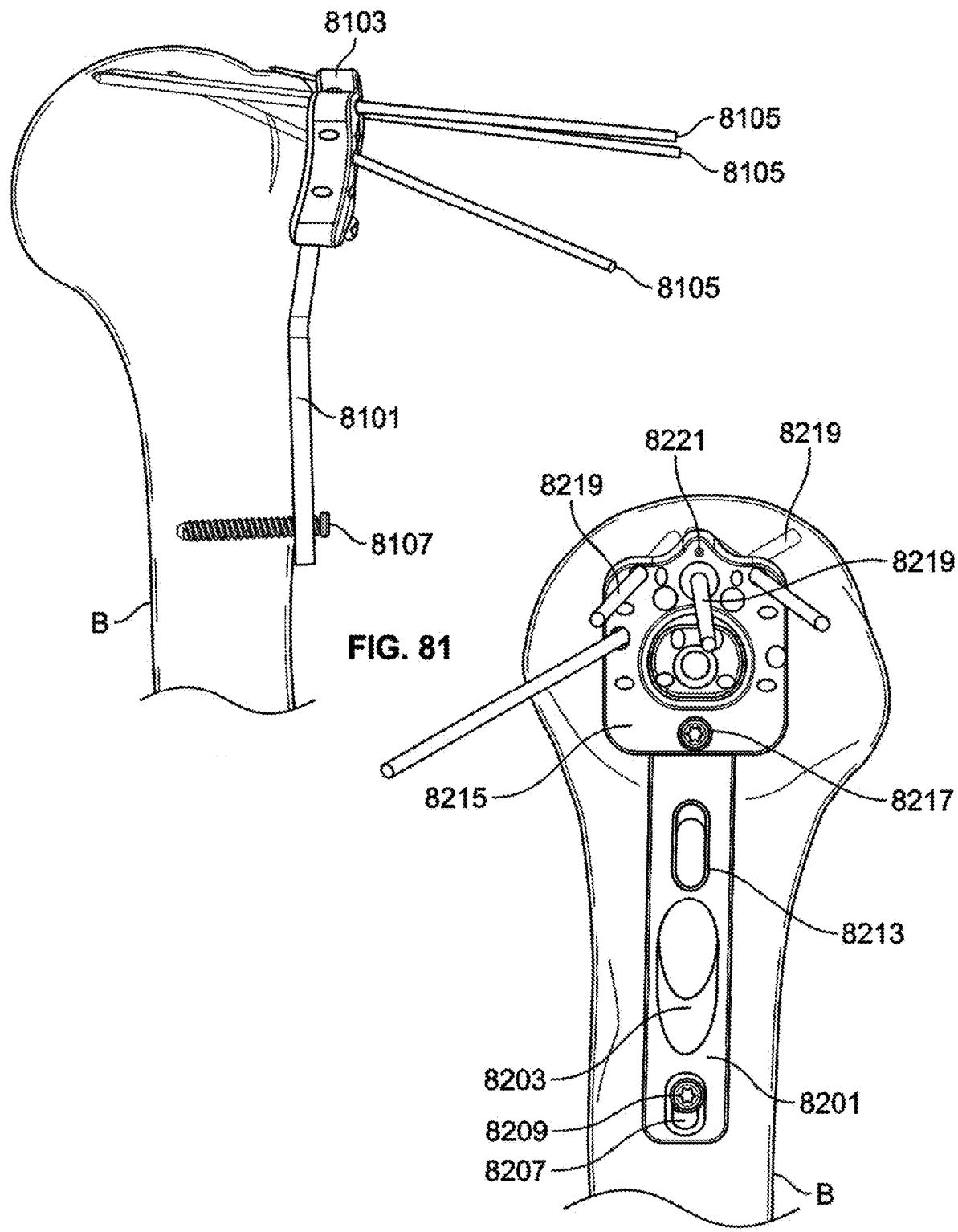

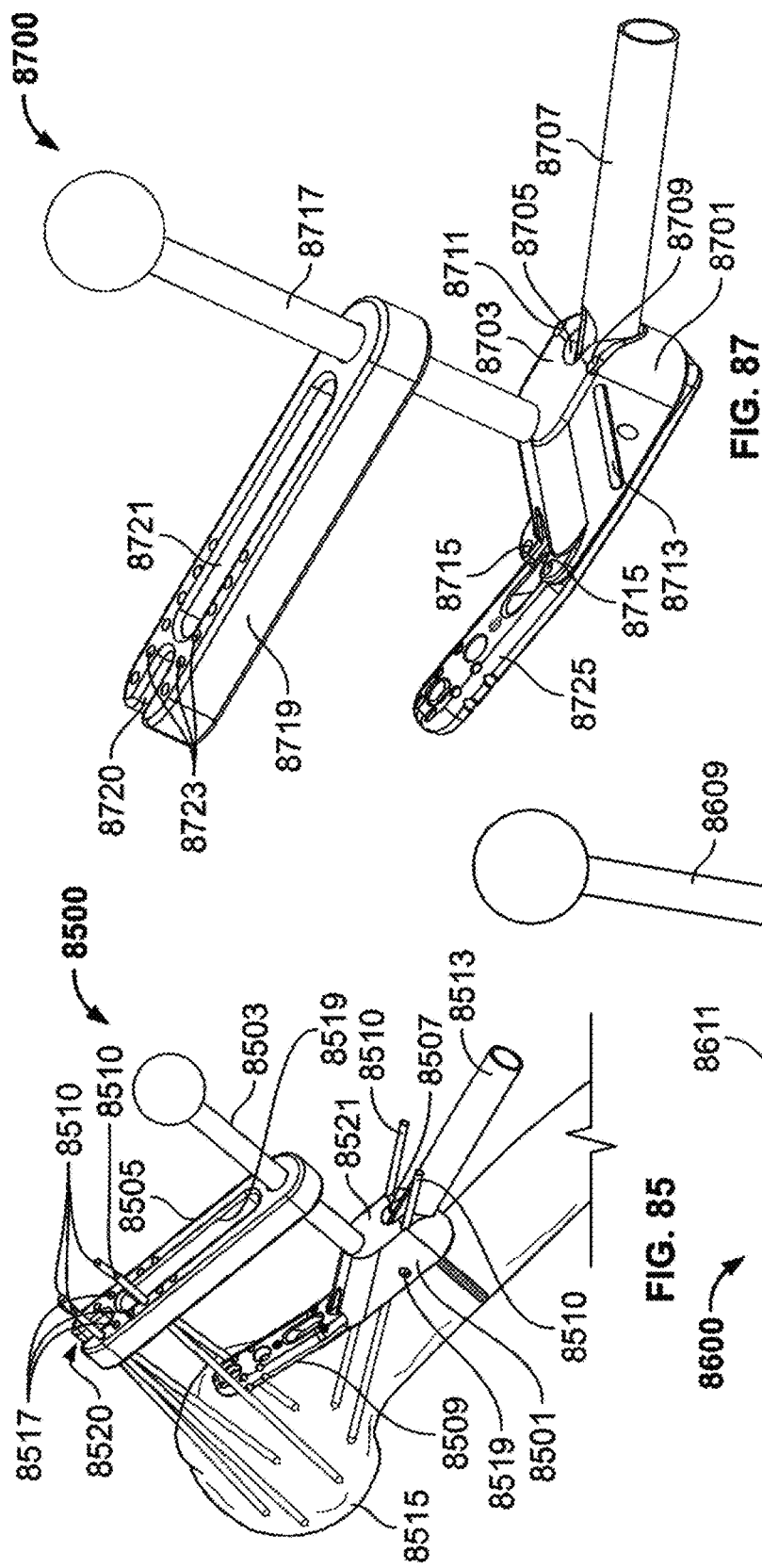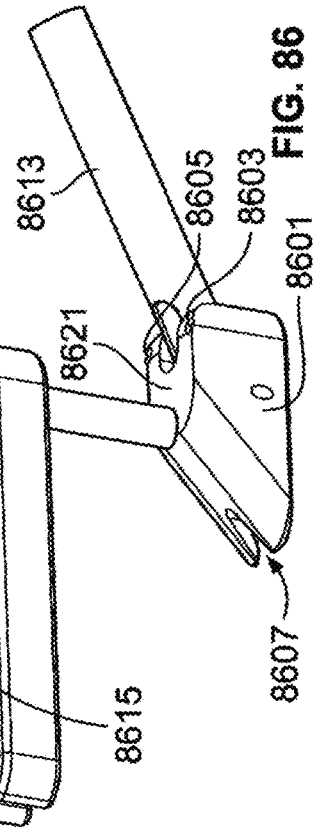

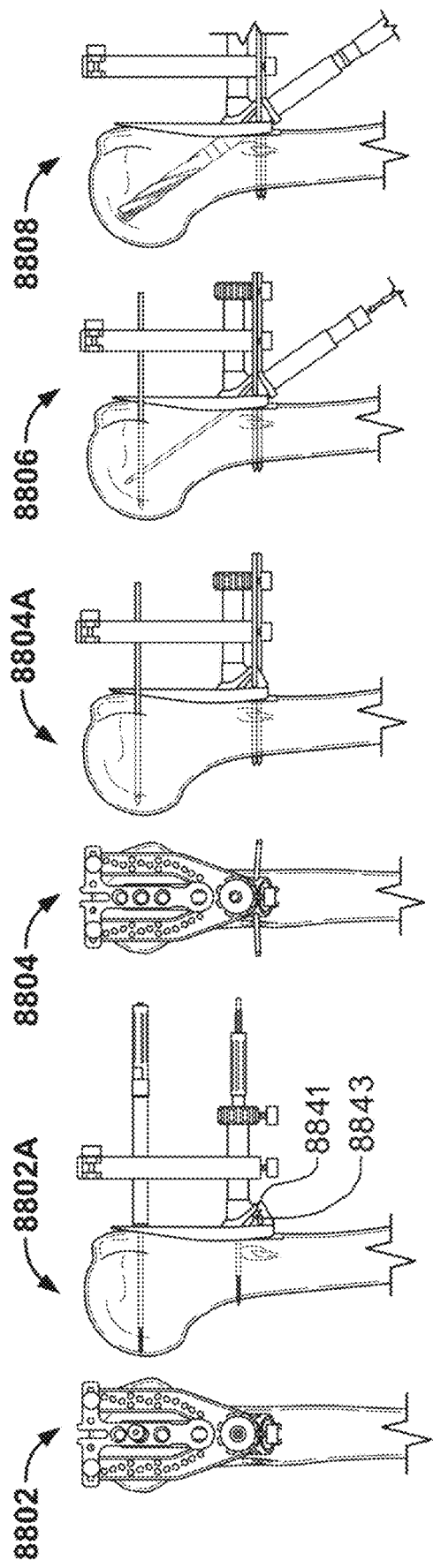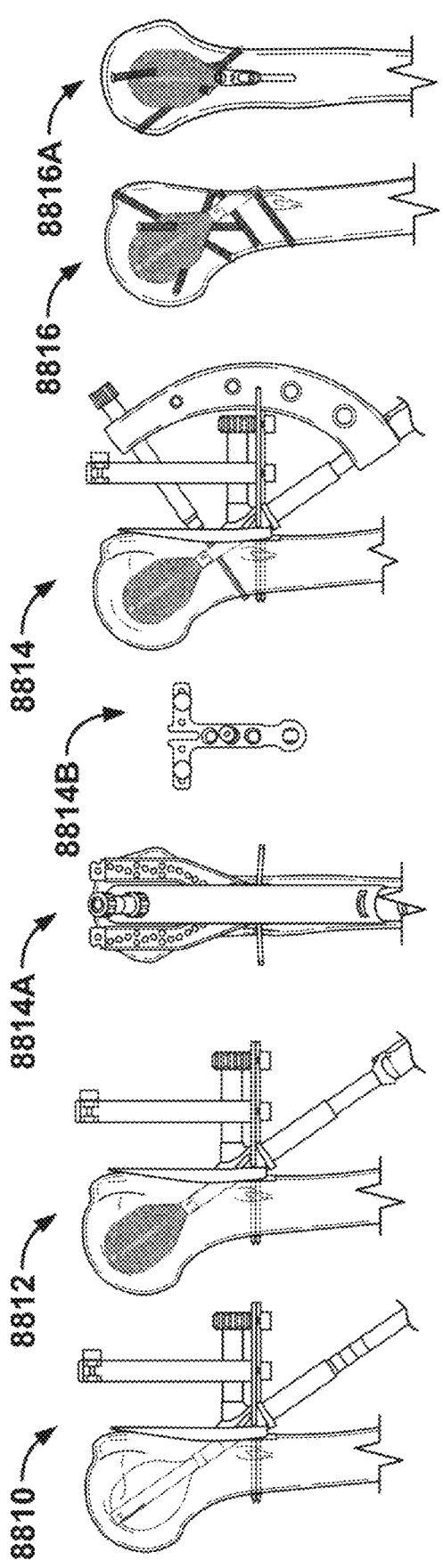
FIG. 88A

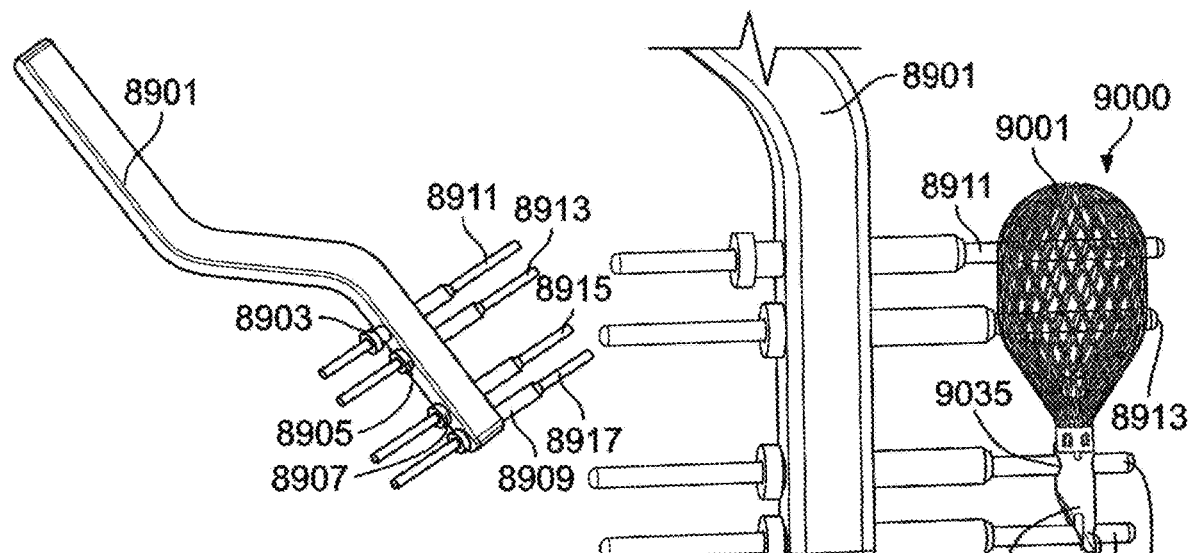
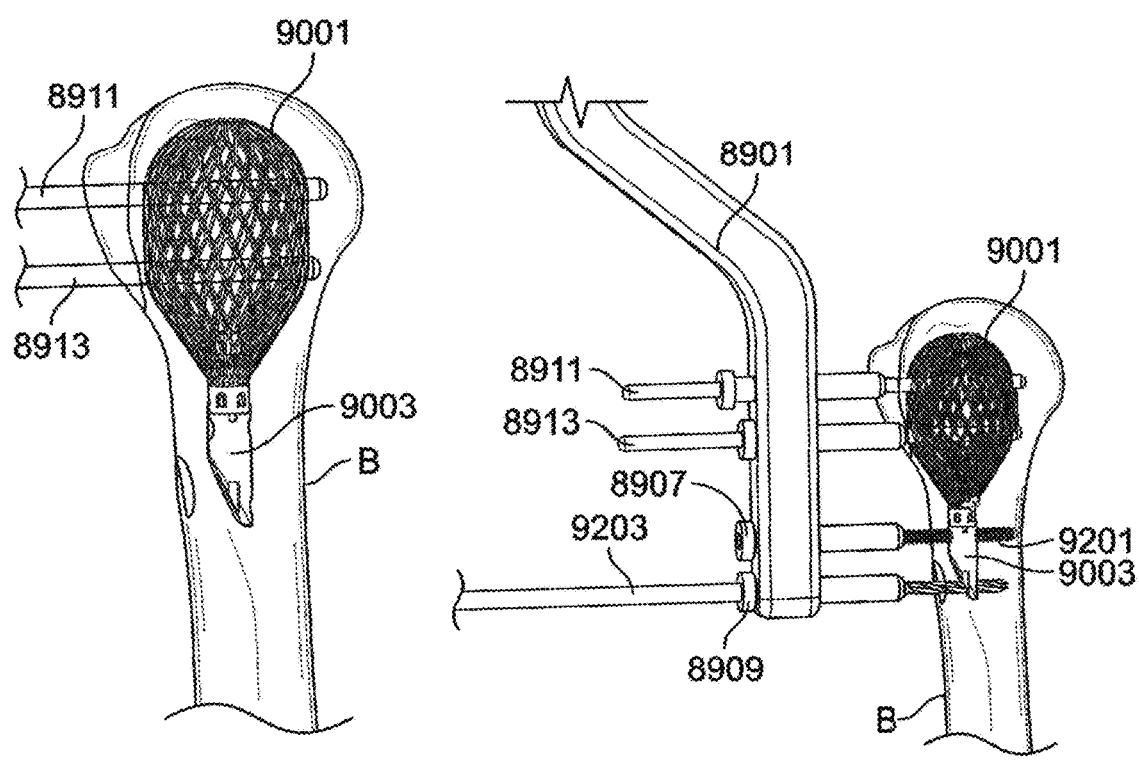

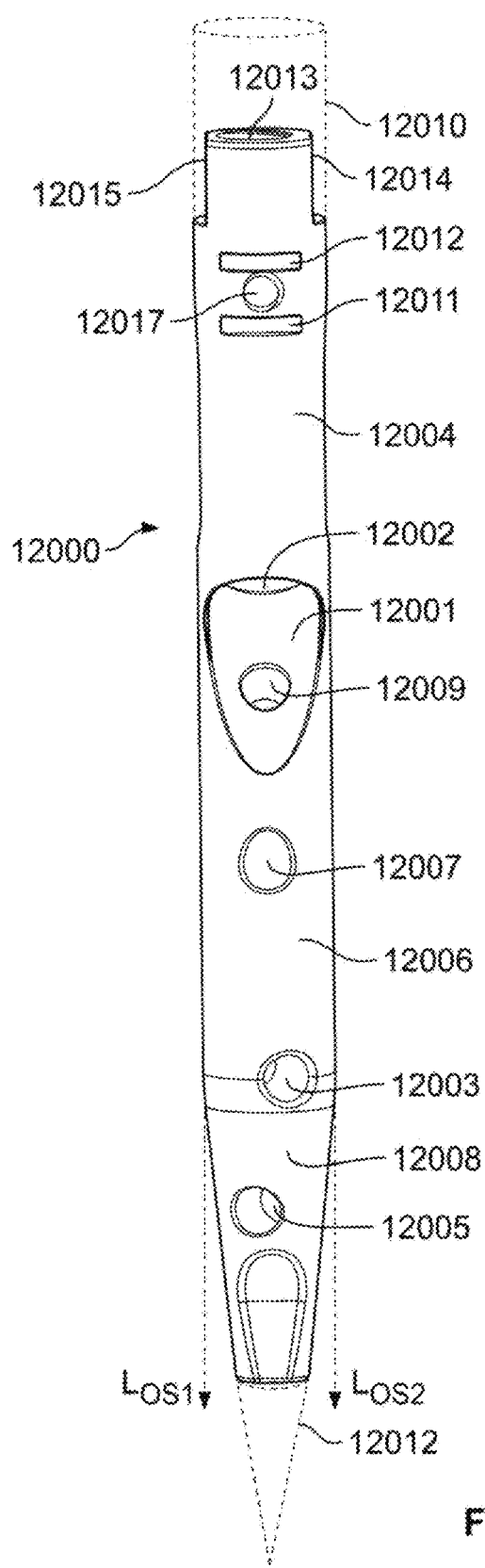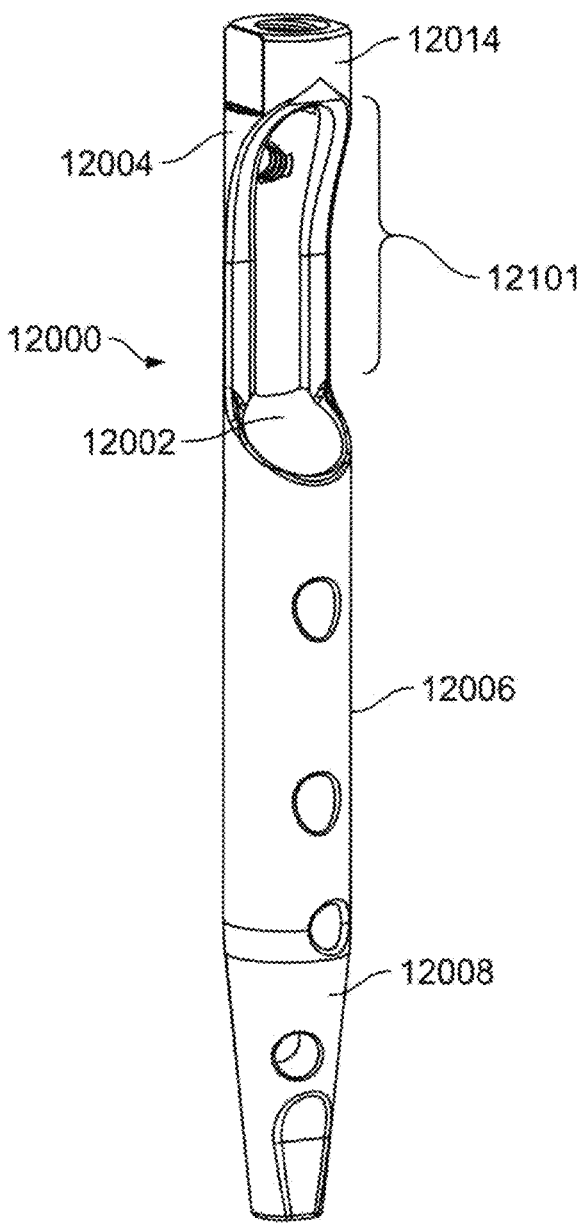
FIG. 120
FIG. 121

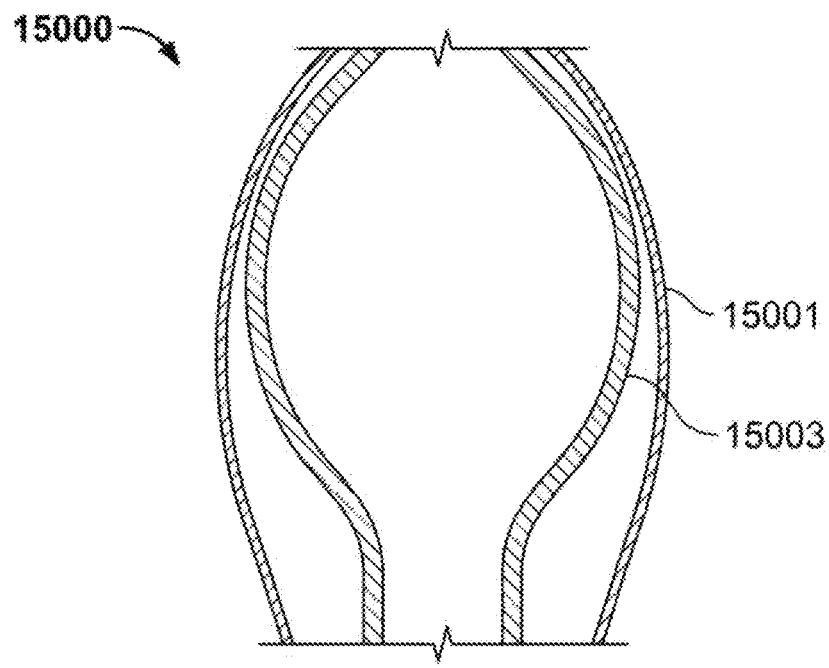
FIG. 150
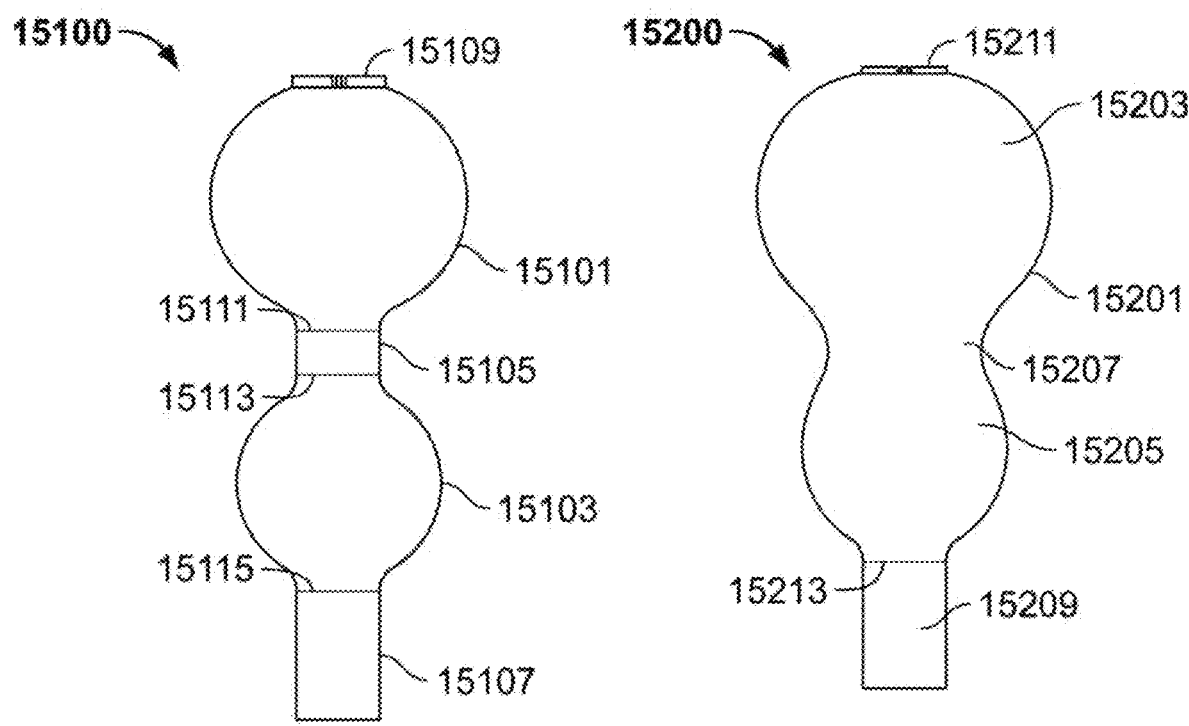
FIG. 151
FIG. 152

APPARATUS AND METHODS FOR TREATMENT OF A BONE

CROSS-REFERENCE TO RELATED APPLICATIONS

This application is a nonprovisional of U.S. Provisional Application No. 62/528,476, filed on Jul. 4, 2017, which is hereby incorporated herein by reference in its entirety.

BACKGROUND

Bone fracture fixation may involve using structures to counteract or partially counteract forces on a fractured bone or associated bone fragments. In general, fracture fixation may provide longitudinal (along the longitudinal axis of the bone), transverse (across the longitudinal axis of the bone), and rotational (about the longitudinal axis of the bone) stability. Fracture fixation may also preserve normal biologic and healing function.

Bone fracture fixation often involves addressing loading conditions, fracture patterns, alignment, compression force, and other factors, which may differ for different types of fractures. For example, midshaft fractures may have ample bone material on either side of the fracture in which anchors may be driven. End-bone fractures, especially near the articular surface may have thin cortical bone, soft cancellous bone, and relatively fewer possible anchoring locations.

Multi-segment fractures, of either the midshaft or end-bone, may require alignment and stability in a manner that generates adequate fixation in multiple directions.

Placement of the structures may be important for proper healing of the bone.

It would be desirable, therefore, to provide apparatus and methods for placement of structures.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which:

FIG. 11 shows illustrative apparatus and methods in accordance with principles of the invention.

FIG. 12 shows illustrative apparatus and methods in accordance with principles of the invention.

FIG. 18 shows illustrative apparatus and methods in accordance with principles of the invention.

FIG. 19 shows illustrative apparatus and methods in accordance with principles of the invention.

FIG. 22 shows illustrative apparatus and methods in accordance with principles of the invention.

FIG. 23 shows illustrative apparatus and methods in accordance with principles of the invention.

FIG. 24 shows illustrative apparatus and methods in accordance with principles of the invention.

FIG. 25 shows illustrative apparatus in accordance with principles of the invention.

FIG. 26 shows illustrative apparatus and methods in accordance with principles of the invention.

FIG. 27 shows illustrative apparatus and methods in accordance with principles of the invention.

FIG. 32 shows illustrative apparatus and methods in accordance with principles of the invention.

FIG. 33 shows illustrative apparatus and methods in accordance with principles of the invention.

FIG. 42 shows illustrative apparatus and methods in accordance with principles of the invention.

FIG. 43 shows illustrative apparatus and methods in accordance with principles of the invention.

FIG. 44 shows illustrative apparatus and methods in accordance with principles of the invention.
FIG. 46 shows illustrative apparatus and methods in accordance with principles of the invention.
FIG. 47 shows illustrative apparatus and methods in accordance with principles of the invention.
FIG. 48 shows illustrative apparatus in accordance with principles of the invention.
FIG. 49 shows illustrative apparatus in accordance with principles of the invention.
FIG. 50 shows illustrative apparatus in accordance with principles of the invention.
FIG. 51 shows illustrative apparatus in accordance with principles of the invention.
FIG. 60 shows illustrative apparatus in accordance with principles of the invention.
FIG. 61 shows illustrative apparatus in accordance with principles of the invention.
FIG. 62 shows illustrative apparatus in accordance with principles of the invention.
FIG. 67 shows an illustrative method in accordance with principles of the invention.
FIG. 68 shows an illustrative method in accordance with principles of the invention.
FIG. 69 shows an illustrative method in accordance with principles of the invention.
FIG. 76 shows illustrative apparatus and methods in accordance with principles of the invention.
FIG. 77 shows illustrative apparatus and methods in accordance with principles of the invention.
FIG. 81 shows illustrative apparatus and methods in accordance with principles of the invention.
FIG. 82 shows illustrative apparatus and methods in accordance with principles of the invention.
FIG. 85 shows illustrative apparatus and methods in accordance with principles of the invention.
FIG. 86 shows illustrative apparatus in accordance with principles of the invention.
FIG. 87 shows illustrative apparatus in accordance with principles of the invention.
FIG. 88A shows illustrative apparatus and methods in accordance with principles of the invention.
FIG. 89 shows illustrative apparatus in accordance with principles of the invention.
FIG. 90 shows illustrative apparatus and methods in accordance with principles of the invention.
FIG. 91 shows illustrative apparatus and methods in accordance with principles of the invention.
FIG. 92 shows illustrative apparatus and methods in accordance with principles of the invention.

FIG. 120 shows illustrative apparatus in accordance with principles of the invention.

FIG. 121 shows illustrative apparatus in accordance with principles of the invention.

FIG. 150 shows illustrative apparatus in accordance with principles of the invention.

FIG. 151 shows illustrative apparatus in accordance with principles of the invention.

FIG. 152 shows illustrative apparatus in accordance with principles of the invention.

DETAILED DESCRIPTION OF THE INVENTION

Figure 1:
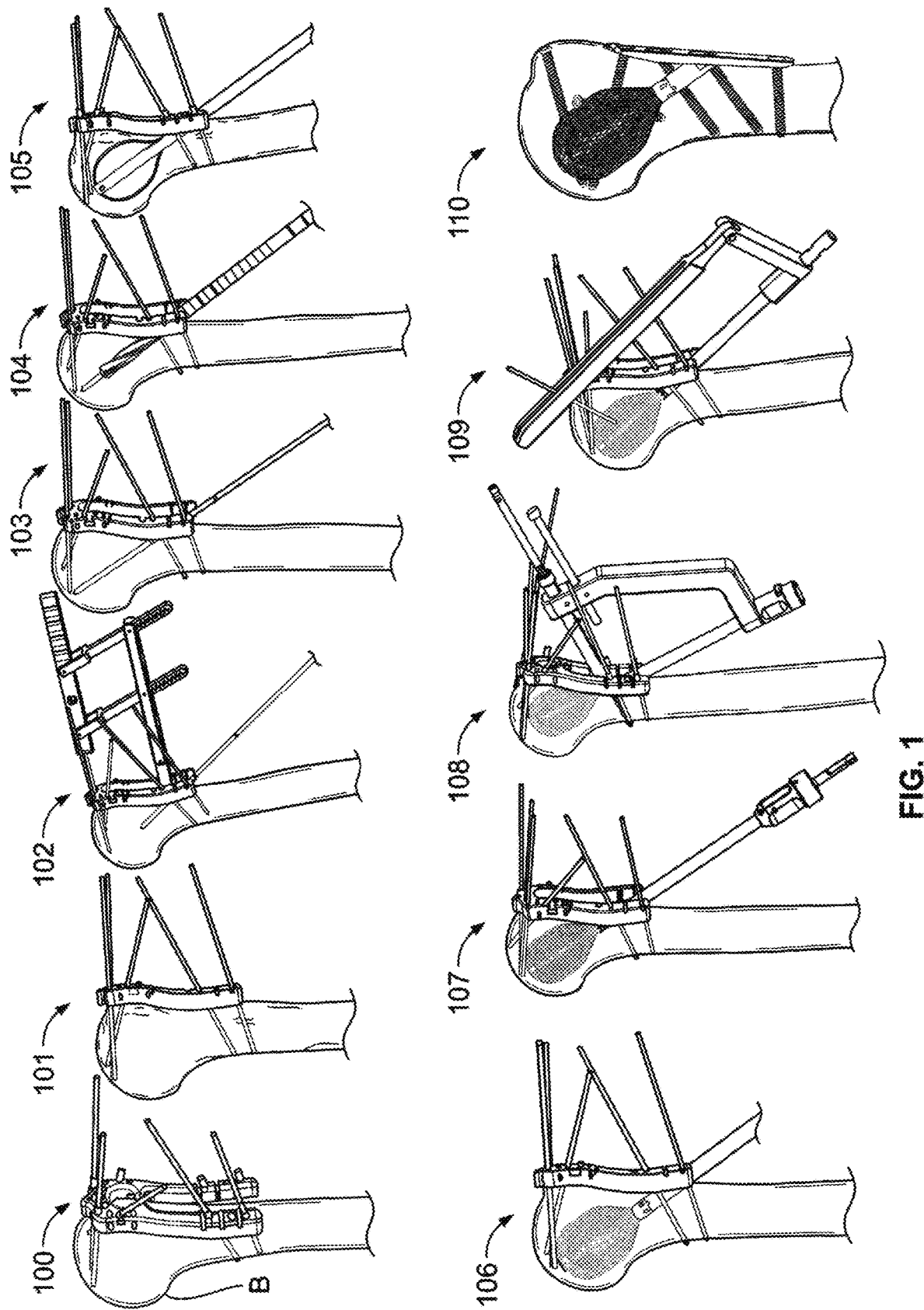
FIG. 1 shows illustrative apparatus and methods in accordance with principles of the invention.

Apparatus and methods for reducing a fracture of a bone are provided.

Apparatus and methods for implanting an implant into a target site in the bone are provided.

Apparatus and methods for securing the fractured bone are provided.

The apparatus may include, and the methods may involve, a jig. The jig may include features that spatially register external bone anatomy to an implant target site in the bone. The jig features may be used to direct one or more wires, screws, cavity preparation devices, plates and implants, or other suitable items, so that the implant may be delivered to the site.

The implant may include apparatus and methods described in U.S. patent application Ser. No. 12/353,855, filed on Jan. 14, 2009, now U.S. Pat. No. 8,287,538, U.S. patent application Ser. No. 13/043,190, filed on Mar. 8, 2011, now U.S. Pat. No. 8,906,022, and/or U.S. patent application Ser. No. 13/945,137, filed on Jul. 18, 2013, all of which are hereby incorporated by reference herein in their entireties.

Drilling and cavity preparation may be performed using apparatus and methods described in U.S. patent application Ser. No. 13/009,657, filed on Jan. 19, 2011, now U.S. Pat. No. 8,961,518, and/or U.S. patent application Ser. No. 14/568,301, filed on Dec. 12, 2014, both of which are hereby incorporated by reference herein in their entireties.

Reduction of a fracture and apparatus and methods for inserting an implant into a bone, may be performed using apparatus and methods described in U.S. patent application Ser. No. 13/043,330, filed on Mar. 8, 2011, and/or in U.S. patent application Ser. No. 13/414,695, filed on Mar. 7, 2012, both of which are hereby incorporated by reference herein in their entireties.

The implant may be an implant that is not expandable. The implant may be an expandable implant. The implant may self-expand when deployed and/or when rotated. The implant may be expanded using one or more actuating mechanisms. The implant may be radially expandable. The implant, when expanded, may form a mesh cage. The mesh cage may include interconnected cells. The implant, when expanded, may take on any suitable shape. The implant may be expanded from an unexpanded state to an expanded state. The unexpanded state may be a collapsed state.

The implant may be implanted in any suitable bone in the human body. The implant may be implanted in any suitable bone in an animal. A suitable bone may be a bone with a metaphyseal and a diaphyseal region, or any other suitable bone. For example, the bone may be a lateral condylar fracture in a horse. The lateral condylar fracture may be a fracture of the third metacarpal or cannon bone on the distal or lower end of the horse.

The implant may occupy a volume in the interior of the bone after it has been expanded. The implant may occupy the volume when the implant is positioned at the target site and expanded to form a mesh cage. The volume may define a three-dimensional area within the interior. The volume may occupy a portion of the interior. A volume occupied by the implant when the implant is positioned at a target site and radially expanded may be referred to herein as an 'implantation region.'

The implant may occupy a first volume when it is positioned at the target site prior to expansion. The implant may occupy a second volume when it is positioned at the target site and after it has been expanded.

The implant may include an implant head. The implant may include an implant tail. An implant shaft may be releasably coupled to the implant tail. The implant head may be formed from laser cut tube stock. The implant tail may be formed from laser cut tube stock. The implant head, when expanded, may form a mesh cage. The mesh cage may form a lattice-like structure defining a plurality of openings. The mesh cage may be an anchoring substrate. The mesh cage may be a mesh anchoring substrate.

The implant tail may be coupled to the implant head. The implant tail may be fixedly attached to the implant head, removably attached to the implant head, or of unitary or monolithic structure with the implant head. A portion of the implant tail may have a tubular shape. All of the implant tail may have a tubular shape. The implant tail may include a first end and a second end. The first end may be coupled to the implant head. The second end may be coupled to the implant shaft. The second end may be releasably coupled to the implant shaft.

The implant may include a base. The base may be positioned between the implant head and the implant tail.

The second end of the implant tail may be so shaped that, after the implant is implanted in the bone, the second end conforms to a contour of the bone surface abutting the second end. The second end may sit flush with the bone surface.

The second end may be so shaped that, after the implant is implanted in the bone, the second end sits below the bone surface. The second end may be so shaped that, after the implant is implanted in the bone, the second end protrudes above the bone surface.

The bone may be any suitable bone in the human body. The bone may define a longitudinal axis. The bone may include a surface contour. The surface contour may extend along a surface of the bone. The surface contour may be a two-dimensional or three-dimensional shape. The surface contour encompass two, three, four, or more different points or demarcation points on the surface of the bone. The points or lines may be at different elevations from the longitudinal axis. The points or lines may be at different angular displacements about the bone longitudinal axis. Thus, the surface contour may encompass a region of the bone surface having "topography" that varies longitudinally along the bone. Thus, the surface contour may encompass a region of the bone surface having "topography" that varies circumferentially about the bone.

The bone may include two or more surface contours. Each surface contour may extend along a portion of the bone surface.

A surface contour may include an anatomical landmark. A surface contour may include two or more anatomical landmarks. An anatomical landmark may include any anatomical structure of a bone in the human body that is used as an orientation point for medical measurements. A landmark may include a tuberosity, articular surface, condyle, a transitional location between a metaphyseal and a diaphyseal region, an end of a bone or any other suitable landmark. Exemplary landmarks may include a protuberance, such as a protuberance at a point on a bone where muscles or ligaments are attached, or any other suitable protuberance. When the bone is a proximal humerus, an anatomical landmark may include a greater tuberosity, an intertubercular groove, a lesser tuberosity, a surgical neck and an anatomical neck.

The apparatus may include the jig. The jig may be a reduction jig or any suitable jig or fixture. The jig may be used to facilitate the reduction of a bone fracture. The jig may be used to attain reduction of a bone fracture. The jig may be used to maintain reduction of the bone fracture. The jig may be used to facilitate provisional reduction of the fracture. The jig may be used to facilitate the securing of a bone. The bone may be any bone in the human body. The bone may be a fractured bone. The bone may be an osteoporotic bone. The bone may be a bone in need of therapeutic care.

The fracture may define one or more fragments or segments. For the purposes of this application, the term fragment and the term segment may be interchangeable. A segment or fragment may be used to call out any piece of a bone.

The jig may be shaped to span a fracture line of the fracture. The fracture line may be a typical fracture line. The fracture line may be an atypical fracture line. The jig, when secured to the fractured bone, may provide stability across one or more fracture lines of the bone. The jig, when secured to the bone, may provide stability across one or more planes defined by the bone. The jig may include a member that spans across a fracture site of a bone. The jig may include two members that span across a fracture site of the bone.

The bone may be a humerus bone. The jig may be applied to a proximal portion of the humerus bone. The jig may be shaped to span a typical fracture line of a proximal humeral fracture. A typical fracture line may be along a surgical neck of a proximal humerus.

The jig may be used with a plurality of surgical approaches. The surgical approaches may include a deltopectoral approach, a deltoid split approach, an antegrade approach, a percutaneous approach, and any other suitable approach. A percutaneous approach may be a surgical approach performed primarily through a small incision the skin.

The jig may be formed from any suitable material. The material may be biocompatible. The material may be radiopaque. Radiopaque materials may include plastic, carbon fiber or Polyetheretherketone ("PEEK"). The material may include metal such as stainless steel, Nitinol, other alloy, titanium alloys, aluminum alloys, composites of carbon fiber, or one or more plastics or epoxy resin. The jig may include a "soft" material. If the jig includes soft material, such as a plastic or epoxy resin, metal bushings may be incorporated into bores defined by the jig to provide more sound bearing surfaces for securing, penetrating and/or rotating members.

The reduction, provisional reduction and/or securing of a bone administered using the jig may assist a physician in repairing a bone fracture. The reduction, provisional reduction and/or securing of a bone administered using the jig may assist a physician in implanting the implant in an interior of a bone. For example, a shape of the jig and/or a plurality of holes defined by the jig may enable a physician to implant the implant in a bone interior without being obstructed by the jig and/or members supported by the jig. For example, the physician may implant an implant into an intramedullary canal of a bone without encountering obstruction by either the jig or members supported by the jig.

Two or more of the numerous jig features shown or described herein may be employed together in an individual jig.

The apparatus may include a plate. The plate may be releasably coupled to the jig. The plate may be used without the jig. The plate may be a surgical plate.

The plate may be formed from any suitable material such as a polymer, metal, composite such as a composite of carbon fiber, stainless steel, titanium alloys, aluminum alloys, Nitinol other alloy, a polymer or any other suitable material. The plate may provide buttressing support to a fracture. The plate may be removed from the bone prior to anchoring the implant to the bone. The plate may be anchored to the bone and to the implant and then left in place.

The plate may be used as a reduction jig or fixture. The plate may be used to facilitate the reduction of a bone fracture. The plate may be used to attain reduction of a bone fracture. The plate may be used to maintain reduction of the bone fracture. The plate may be used to facilitate provisional reduction of the fracture. The plate may be used to facilitate the securing of a bone. The bone may be any bone in the human body. The bone may be a fractured bone. The bone may be an osteoporotic bone. The bone may be a bone in need of therapeutic care.

The plate may be shaped to span a fracture line of the fracture. The fracture line may be a typical fracture line. The fracture line may be an atypical fracture line. The plate, when secured to the fractured bone, may provide stability across one or more fracture lines of the bone. The plate, when secured to the bone, may provide stability across one or more planes defined by the bone. The plate may include a member that spans across a fracture site of a bone. The plate may include two members that span across a fracture site of the bone.

The bone may be a humerus bone. The plate may be applied to a proximal portion of the humerus bone. The plate may be shaped to span a typical fracture line of a proximal humeral fracture. A typical fracture line may be along a surgical neck of a proximal humerus.

The plate may be used with a plurality of surgical approaches. The surgical approaches may include a deltopectoral approach, a deltoid split approach, an antegrade approach, a percutaneous approach, and any other suitable approach. A percutaneous approach may be a surgical approach performed primarily through a small incision the skin.

The reduction, provisional reduction and/or securing of a bone administered using the plate may assist a physician in repairing a bone fracture. The reduction, provisional reduction and/or securing of a bone administered using the plate may assist a physician in implanting the implant in an interior of a bone. For example, a shape of the plate and/or a plurality of holes defined by the plate may enable a physician to implant the implant in a bone interior without being obstructed by the plate and/or members supported by the plate. For example, the physician may implant an implant into an intramedullary canal of a bone without encountering obstruction by either the plate or members supported by the plate.

Two or more of the numerous plate features shown or described herein may be employed together in an individual plate.

The plate may include features that are shown and described herein in connection with the jig. The jig may include features that are shown and described herein in connection with the plate.

Apparatus disclosed herein may define a hole. The hole may point in a direction. The direction may be a direction of a central axis of the hole.

Apparatus disclosed herein may define a bottom surface. The bottom surface may complement a surface contour of a bone. The bottom surface may complement the surface contour of when the bottom surface is in contact with the bone. The bottom surface may complement the surface contour when the bottom surface is in contact with the bone.

The apparatus may include apparatus for, and the methods may involve, delivery of an implant at a target site in an interior of a bone. The bone may define a longitudinal axis. The bone may include a surface contour that extends along a surface of the bone between two or more points at different elevations from the longitudinal axis.

The apparatus may include the jig. The jig may have one or more features in common with any other jig or plate disclosed herein. The jig may include a bottom surface.

The jig may define one or more pluralities of holes (may be referred to herein as "fixation element holes"). The bottom surface may complement the surface contour. When the bottom surface is seated complementarily against the surface contour, a plurality of holes may point into the interior, but not into the volume to be occupied by the implant when the implant is positioned at the target site and radially expanded. The implant, when expanded, may form a mesh cage.

A plurality of holes may be sized to provide clearance for the implant in an interior of the bone.

A plurality of holes may be sized to receive fixation element. A fixation element, when passed through the plurality of holes, may engage the bone or fragment. Fixation elements that may be driven through one or more of the plurality of holes include pins, wires, K-wires, drills, needles, suture, cable, a threaded K-wire coupled to a nut to provide compression and/or threaded K-wires or any other suitable fixation element.

The plurality of holes may be located throughout the jig. The plurality of holes may be located throughout the jig so that fixation elements can be driven into a bone above and below a fracture line defined by a bone. The plurality of holes may assist a physician in securing the jig at a proper anatomical position on the bone. Fixation elements passed through the plurality of holes and into the bone may releasably couple the jig to the bone.

A fixation element hole may be sized too small to receive a screw.

Each of the fixation element holes may be smaller than holes for receiving screws ("screw holes"). Fixation element holes of the jig may be too small to receive a screw that can be received by a screw hole of the same jig.

Size ranges for the plurality of holes may include any size range suitable to one skilled in the art, for example a range between 1 mm and 6 mm.

Table 1 shows selected illustrative size ranges for a hole sized for receiving a fixation element having lower and upper limits.

TABLE 1

Selected fixation element hole sizes.
Fixation element hole diameter, illustrative ranges
(lower and upper limits, inclusive) (mm)

| Lower | Upper |
|---|---|
| <1.0 | 1.0 |
| 1.0 | 1.2 |
| 1.2 | 1.4 |
| 1.4 | 1.6 |
| 1.6 | 1.8 |
| 1.8 | 2.0 |
| 2.0 | 2.2 |
| 2.2 | 2.4 |
| 2.4 | 2.6 |
| 2.6 | 2.8 |
| 2.8 | 3.0 |
| 3.0 | 3.2 |
| 3.2 | 3.4 |
| 3.4 | 3.6 |
| 3.6 | 3.8 |
| 3.8 | 4.0 |
| 4.0 | 4.2 |
| 4.2 | 4.4 |
| 4.4 | 4.6 |
| 4.6 | 4.8 |
| 4.8 | 5.0 |
| 5.0 | 5.2 |
| 5.2 | 5.4 |
| 5.4 | 5.6 |
| 5.6 | 5.8 |
| 5.8 | 6.0 |
| 6.0 | >6.0 |

For example, for the plate configured to be applied to a proximal humerus bone, the plurality of holes may be 2.5 mm or smaller and a screw hole may be 3 mm or larger.

A screw hole may be sized too small to receive an unexpanded implant.

One or more of the plurality of holes may be internally threaded.

A threaded hole may receive a screw.

A threaded hole may receive an externally threaded bushing. The externally threaded bushing may define a bore. The bore may be sized to receive a fixation element. The bushing may assist a physician in guiding a fixation element through a hole defined by the jig and into a bone interior.

An internally threaded hole may be used as a K-wire bushing guide.

Two or more of the plurality of holes may be internally threaded.

All of the pluralities of holes may be internally threaded.

One or more of the plurality of holes may be not threaded.

The jig may define a bottom face. The bottom face may include the bottom surface. The bottom surface may define a portion of the bottom face. The bottom surface may define the bottom face. The bottom face may include two or more bottom surfaces.

The bottom surface may be a first bottom surface. The bottom face may include a second bottom surface. The second bottom surface may not complement a surface contour of the bone. The surface contour may be a first surface contour. The bone may include a second surface contour that extends along a surface of the bone between two or more points at different elevations from the longitudinal axis. The second bottom surface may complement the second surface contour. The surface contour may be a first surface contour, the bone may be a first bone and the longitudinal axis may be a second longitudinal axis. A second bone may include a second surface contour that extends along a surface of the second bone between two or more points at different elevations from a second longitudinal axis defined by the second bone. The second bottom surface may complement the second surface contour.

The jig may define a target hole. The target hole may be sized to receive a fixation element. A fixation element advanced through the target hole may be referred to herein as a "target wire." When the bottom surface of the jig is seated complementarily against the surface contour, the target hole may point to the target site. The target site may be a location in the bone interior where a physician may desire to position an end of the implant. The end of the implant may be an end of an implant head distal a physician when the implant is implanted in a bone.

The target hole may be tapered.

When a fixation element is advanced through the target hole and into an interior of a bone, a practitioner may position a tip of the fixation element at or near the target site. The practitioner may position the end of the implant at or near the point in the bone penetrated by the tip of the target wire. The head of the implant may be positioned at a point in the bone proximal to the point penetrated by the tip of the target wire. The head of the implant may be positioned at a point in the bone distal to the point penetrated by the tip of the target wire.

Where the bone is a proximal humerus bone, the target site may be a center of a head of the proximal humerus bone. When the bottom surface is seated complementarily against the surface contour, the target hole may point to a center-center location in the interior of the proximal humeral head. Driving a target wire through the target hole may advance the tip of the target wire towards the center-center location in the interior of the proximal humeral head.

Where the bone is a proximal humerus bone, the surface contour may include a greater tuberosity. The surface contour may include an intertubercular groove. The surface contour may include a deltoid insertion. The surface contour may include two or more of the greater tuberosity, the intertubercular groove and the deltoid insertion.

The implant may be a first implant and the volume may be a first volume. Each of the plurality of holes may point into the interior, but not into the first volume or into a second volume occupied by a second implant when the second implant is positioned at the target site and radially expanded. The second implant, when expanded, may form a mesh cage.

The jig may include an indicator. The indicator may be a notch, a slit, a depression, or any other suitable demarcation on a top or side face of the jig. When the bottom surface is seated complementarily against the surface contour, the indicator may register to a location on the surface for initiating an access hole for accessing the target site. A location on the surface for initiating an access hole may be referred to herein as an "access position." The access position may be a location on the surface adjacent the indicator. A distance between the location and the target site may correspond to a length of the implant.

An access hole may be initiated by drilling through the surface to form a hole. An access hole may be a hole on a surface of the bone through which a practitioner may access a target site in a bone interior. An access hole may be a hole on a surface of the bone for accessing the target site along a straight path.

The jig may include an indicator. The indicator on the jig may be spaced apart from the target hole. When the bottom surface of the jig is seated complementarily on a surface contour of a bone, a spatial separation between the target hole and the target site may have a second length. The second length may be known based on an anatomy of the bone.

The jig may include a first indicator and a second indicator. When the bottom surface is seated complementarily against the surface contour, the first indicator may register to a first location on the surface for initiating a first access hole for accessing the target site. When the bottom surface is seated complementarily against the surface contour, the second indicator may register to a second location on the surface for initiating a second access hole for accessing the target site. A distance between the first location and the target site may correspond to a first implant length. A distance between the second location and the target site corresponds to a second implant length. The first implant length may be different from the second implant length.

Where the jig includes a transverse member, a first longitudinal member and a second longitudinal member, the jig may include a first indicator and a second indicator. The first indicator may be located on the first longitudinal member. The second indicator may be located on the second longitudinal member. Each of the first indicator and the second indicator may register to a location on the bone for initiating an access hole.

The plurality of holes may include a first hole and a second hole. The first hole may point in a first direction. The second hole may point in a second direction. The first direction may be divergent from the second direction. The first direction may be convergent with the second direction. The first direction may be non-parallel with the second direction. The first direction may be parallel with the second direction.

The plurality of holes may point in non-parallel directions. Some of the plurality of holes may point in parallel directions. Some of the plurality of holes may point in different directions. Each the plurality of holes may point in a unique trajectory. None of the trajectories may be parallel.

None of the plurality of holes may transect the jig at a right angle. One or more of the trajectories defined by the plurality of holes may transect the jig at right angles. All of the trajectories defined by the plurality of holes may transect the jig at right angles.

When the bottom surface is seated complementarily against the surface contour, the jig may partially define an area on the surface of the bone for initiating an access hole for accessing the target site.

The jig may include a longitudinal member. The jig may be elongated along a longitudinal axis of the bone.

The jig may include a longitudinal member and a transverse member extending away from the longitudinal member. The transverse member may extend away from the longitudinal member. The transverse member may assist in stabilizing the fracture across a fracture line defined by the fractures site. The longitudinal member may include the bottom surface. The transverse member may include the bottom surface. The longitudinal member and the transverse member may include the bottom surface. The bottom surface may be a first bottom surface, the surface contour may be a first contour and the surface may be a first surface. The longitudinal member may include the first bottom surface. The transverse member may include a second bottom surface. The second bottom surface may complement a second surface contour that extends along a second surface of the bone between two or more points at different elevations from the longitudinal axis.

The jig may include a longitudinal member and a transverse member extending away from the longitudinal member. When bone is a proximal humerus bone, the surface contour may include a greater tuberosity and an intertubercular grove. The transverse member may include a first bottom surface complementing the greater tuberosity. The longitudinal member may include a second bottom surface complementing the intertubercular groove.

The jig may include a longitudinal member and a transverse member extending away from the longitudinal member. Where bone is a proximal humerus bone, the surface contour may include a greater tuberosity, an intertubercular grove and a deltoid insertion. The transverse member may include a first bottom surface complementing the greater tuberosity. The longitudinal member may include a second bottom surface complementing the intertubercular groove. The longitudinal member may include a third bottom surface distal the transverse member. The third bottom surface may complement the deltoid insertion and a lateral aspect of the humerus shaft.

The jig may include a positioning hole. The positioning hole may be located at an end of the jig. The positioning hole may be sized to receive a fixation element. When the bottom surface is seated complementarily against the surface contour, the positioning hole may point in a direction. The direction may be tangent to the bone. The direction may not transect a surface of the bone.

When the bone is proximal humerus bone, the direction may be tangent to a top of the greater tuberosity. A bottom surface of the jig extending away from the positioning hole may complement a surface contour of the humerus defined by a greater tuberosity. The bottom surface complementing the surface contour of the greater tuberosity may be used by a practitioner as a greater tuberosity locator. For example, positioning the bottom surface of the jig on the greater tuberosity may provide a physician with tactile feedback indicating that the jig has been properly positioned on the bone.

The jig may include a first longitudinal member, a second longitudinal member, a first transverse member and a second transverse member. The first transverse member may define a first end and a second end. The first longitudinal member may extend away from the first end. The second longitudinal member may extend away from the second end. The second transverse member may define a third end and a fourth end. The second transverse member may be positioned between the first longitudinal member and the second longitudinal member. The third end may adjoin the first longitudinal member along a length of the first longitudinal member. The fourth end may adjoin the second longitudinal member along a length of the second longitudinal member. The first longitudinal member may define a first longitudinal axis. The second longitudinal member may define a second longitudinal axis. The second transverse member may define a third longitudinal axis. The third longitudinal axis may transect the first longitudinal axis and the second longitudinal axis at a right angle. The third longitudinal axis may transect the first longitudinal axis and the second longitudinal axis at an oblique angle. The third longitudinal angle may transect the first longitudinal axis at a right angle and the second longitudinal axis at an oblique angle.

The jig may include a first longitudinal member, a second longitudinal member and a transverse member. The transverse member may define a first end and a second end. The first longitudinal member may extend away from the first end. The second longitudinal member may extend away from the second end. The bottom surface may be a first bottom surface, the surface contour may be a first surface contour and the surface may be a first surface. The bone may include a second surface contour that extends along a second surface of the bone between two or more points at different elevations from the longitudinal axis. The bone may include a third surface contour that extends along a third surface of the bone between two or more points at different elevations from the longitudinal axis. The transverse member may include the first bottom surface. The first longitudinal member may include a second bottom surface complementing the second surface contour. The second longitudinal member may include the third bottom surface complementing the third surface contour.

The jig may include a first longitudinal member, a second longitudinal member and a transverse member. The transverse member may define a first end and a second end. The first longitudinal member may extend away from the first end. The second longitudinal member may extend away from the second end. The bottom surface may be a first bottom surface, the surface contour may be a first surface contour, the surface may be a first surface, the bone may be a first bone and the longitudinal axis may be a first longitudinal axis. The second bone may include a second surface contour that extends along a second surface of the bone between two or more points at different elevations from a second longitudinal axis. The first longitudinal member may include the first bottom surface. The second longitudinal member may include a second bottom surface complementing the second surface contour. Both the first bone and the second bone may define a third surface contour. The transverse member may define a third bottom surface complementing the third surface contour.

The jig may include a first longitudinal member, a second longitudinal member and a transverse member. The transverse member may define a first end and a second end. The first longitudinal member may extend away from the first end. The second longitudinal member may extend away from the second end. The bone may be a left humerus. A second bone may be a right humerus. The transverse member may include the first bottom surface. The first bottom surface may complement a greater tuberosity of the left humerus and a greater tuberosity of the right humerus. The first longitudinal member may include a second bottom surface complementing an intertubercular groove of the left humerus. The second longitudinal member may include a third bottom surface complementing an intertubercular groove of the right humerus.

The jig may include one or more suturing holes. A suturing hole may allow for attachment of a suture to the jig. Attachment of a suture to the jig may facilitate tying the jig to soft tissue. The suturing holes may be sized for suturing. The suturing holes may have characteristics different from the plurality of holes.

The jig may be configured to receive the plate. The jig may define an opening for receiving the plate. The jig may partially define an area for receiving the plate. The jig may include a coupling mechanism for removably coupling the plate to the jig. When the jig includes a first longitudinal member, a second longitudinal member and a transverse member, the first longitudinal member may include a first coupling mechanism for removably coupling the plate to the jig. The second longitudinal member may include a second coupling mechanism for removably coupling the plate to the jig.

The jig may be configured to be releasably coupled to the plate. A first apparatus may be described herein as being configured to be releasably coupled to a second apparatus. Releasably coupled apparatus may be releasably coupled by a coupling mechanism. The coupling mechanism may include a screw for coupling the first apparatus to the second apparatus, a press fit, a toggle feature, a rotational hook mechanism and any other fastener concept known to those skilled in the art.

For example, the jig may define a first bore extending through the jig and the plate may define a second bore extending through the plate. The first bore and the second bore may be threaded. Driving a screw through the first bore and into the second bore may couple the jig to the plate. Any other suitable coupling mechanisms may be used to couple the jig to the plate.

The jig may include a first longitudinal member, a second longitudinal member and a transverse member. The transverse member may define a first transverse member end and a second transverse member end. The first longitudinal member may define a first longitudinal member end and a second longitudinal member end. The second longitudinal member may define a third longitudinal member end and a fourth longitudinal member end. The first transverse member end may adjoin the first longitudinal member end. The second transverse member end may adjoin the third longitudinal member end. The second longitudinal member end may adjoin the fourth longitudinal member end. The transverse member, the first longitudinal member and the second longitudinal member may define an opening for receiving the plate. When the transverse member is a first transverse member, a second transverse member may be positioned between, and connected to, the second longitudinal member and the fourth longitudinal member end. The transverse member, the first longitudinal member and the second longitudinal member may define an opening for receiving the plate. The first transverse member, the second transverse member, the first longitudinal member and the second longitudinal member may define an opening for receiving the plate.

The jig may be configured to provide therapy to a first bone and a second bone. The jig may include a first bottom surface and a second bottom surface. The first bottom surface may conform to a surface contour of the first bone.

The second bottom surface may conform to a surface contour of the second bone. The jig may include two or more bottom surfaces that conform to a surface contour of a first bone and two or more bottom surfaces that conform to a surface contour of a second bone.

For example, the first bone may be a right humerus. The first bone may include a first surface contour defined by a first greater tuberosity of the first bone and a second surface contour defined by a first intertubercular groove of the first bone. The second bone may be a proximal portion of a left humerus. The second bone may include a third surface contour defined by a second greater tuberosity of the second bone and a fourth surface contour defined by a second intertubercular groove of the second bone.

The transverse member may include a first bottom surface. The first bottom surface may complement the first surface contour and the third surface contour. The first longitudinal member may include a second bottom surface. The second bottom surface may complement the fourth surface contour. The second longitudinal member may include a third bottom surface. The third bottom surface may complement the second surface contour.

The jig may define an opening. When the bottom surface is seated complementarily against the surface contour, the opening may define an area on the surface of the bone for initiating an access hole for accessing the target site.

When the jig defines an opening, the opening may have a width. The width may be at least twice as wide as a diameter defined by the first holes. The width may be one and a half times as wide as a diameter defined by the first holes. The width may range from 6 mm to 8 mm. The width may range from 6 mm to 12 mm. The jig may have a longitudinal axis. The width may be perpendicular to the longitudinal axis. The opening may define a length. The length may have any suitable size. The length of the opening may range from 6 mm to 8 mm. The length of the opening may range from 6 mm to 12 mm. The opening may be sized to provide clearance for the implant in the non-expanded state. The implant, in the non-expanded state, may have a diameter. The diameter may be any suitable diameter. The diameter may be 7 mm, 8 mm, 9 mm, or any other suitable diameter.

When the jig defines an opening, the jig may include a guide. The guide may extend away from the opening. The guide may fix or partially fix an access angle used by a practitioner for preparing the access hole. The access angle may be an angle between a longitudinal central axis of the guide and a longitudinal axis of the bone. When the bottom surface is seated on the surface contour, a central axis defined by the guide may point to the target site. When the bottom surface is seated on the surface contour, a central axis defined by the guide may point in a direction that does not intersect with the target site.

The guide may assist a practitioner in preparing the access hole and advancing the implant through the access hole towards the target site. The guide may receive one or more bushings during a surgical procedure. The guide may be used to direct a fixation element through the access hole and into the interior of the bone. The guide may be used to direct a drill through the access hole and into the interior of the bone. The guide may be used to direct an unexpanded implant through the access hole and into the interior of the bone.

The guide may include a guide inner surface. The guide inner surface may be sized to provide clearance for an implant.

The guide may define a guide central axis extending through the guide inner surface. The guide inner surface may be cylindrical, partially cylindrical and partially flat, or any other suitable shape. The guide inner surface may include a cylindrical portion. The guide may be cut from a tube angled at an angle oblique to the jig. The tube may be cut away from the jig after it becomes tangent to the jig.

The guide may receive a bushing. The bushing may be used to protect soft tissue from drills or other instruments inserted into the jig. The bushing may direct a target wire into a bone at a fixed angle relative to a longitudinal axis of the bone. The bushing may direct a cavity preparation device into a bone at a fixed angle relative to a longitudinal axis of the bone. The busing may direct an implant into a bone at a fixed angle relative to a longitudinal axis of the bone. The bushing may include a collar that mates with the guide The guide may receive a bushing sized to receive a fixation element. The guide may receive a bushing sized to receive a drill. The guide may receive a bushing sized to receive a cavity preparation device. The guide may receive a bushing sized to receive an implant. The guide may receive a bushing sized to receive a drill, an implant and a cavity preparation device. A drill outer circumference, a cavity preparation device outer circumference and an implant outer circumference may be equal. The guide may receive a first bushing disposed within a second bushing. The first bushing may be sized to receive a fixation element. The second bushing may be sized to receive a drill. The second bushing may be sized to receive a cavity preparation device. The second bushing may be sized to receive an implant.

When the first bushing, disposed within the second bushing, is positioned in the guide, a practitioner may insert a fixation element through the first bushing. The practitioner may advance the fixation element towards the target site. The practitioner may confirm that the tip of the fixation element is positioned in a desired location within the interior. The desired location may be a target site. When a tip of the fixation element is positioned at the desired location, the practitioner may remove the first bushing from within the second bushing. The practitioner may drive a cannulated drill over the fixation element, through the second bushing and towards the target site. The practitioner may remove the first bushing and the fixation element and drive a solid drill towards the desired location. After drilling, the practitioner may remove the drill. After drilling, the practitioner may insert a cavity preparation device through the second bushing and into the interior. When the cavity is prepared, the practitioner may remove the cavity preparation device. When the cavity is prepared, the practitioner may insert an implant through the second bushing and into the interior.

The apparatus may include a bushing (may be referred to herein as an "insert"). The insert may be shaped to be inserted into the guide. The insert may define an insert outer surface. The insert outer surface may match the guide inner surface. The insert outer surface may define an insert outer central axis. The insert may include an insert inner surface. The insert inner surface may define a lumen. The insert inner surface may define an inner insert central axis. The guide may define a slot and the insert may include a projection. When the insert is seated within the guide the projection may be positioned within the insert.

A central axis defined by the guide may be parallel to the insert outer central axis. A central axis defined by the guide may be coaxial with the insert outer central axis. The guide central axis may be parallel to the insert inner central axis. The guide central axis may not be parallel to the insert inner central axis.

A practitioner may insert a fixation element through a first insert disposed within the guide and into the interior. The practitioner may determine that an access angle of the fixation element is undesirable. The practitioner may determine that the access angle is undesirable based at least in part on a position of the fixation element within the bone. The access angle may be an angle between a bone longitudinal axis and a first insert inner central axis. The practitioner may remove the first insert. The practitioner may place a second insert within the guide. The second insert may define a second insert inner central axis. Replacing the first insert with the second insert may change the access angle without necessitating moving the jig along the bone surface.

The apparatus may include apparatus for, and the methods may involve, delivery of an implant at a target site in an interior of a bone. The bone may define a longitudinal axis and include a surface contour. The surface contour may extend along a surface of the bone between two or more points at different elevations from the longitudinal axis.

The apparatus may include the jig. The jig may include a bottom surface. The jig may define a plurality of holes and a target hole. The bottom surface may complement the surface contour.

The apparatus may include the plate. The plate may be configured to be releasably coupled to the jig. The plate may define an opening.

When the bottom surface is seated complementarily against the surface contour and the plate is coupled to the jig, each of the plurality of holes may point into the interior but not into a volume occupied by the implant in the interior when the implant is positioned at the target site and radially expanded to form a mesh cage. When the bottom surface is seated complementarily against the surface contour and the plate is coupled to the jig, the target hole may point to the target site. When the bottom surface is seated complementarily against the surface contour and the plate is coupled to the jig, the opening may define an area on the surface of the bone for preparing an access hole for accessing the target site.

Each of the plurality of holes may be sized to receive a fixation element.

The plate may define a hole sized for receiving a screw (may be referred to herein as a "screw hole"). The screw may be any suitable screw, such as an anchoring screw or a surgical screw. The screw may be cannulated. The screw may not be cannulated. The screw hole may be threaded. The screw hole may be configured to receive a bushing. The bushing may assist a practitioner in guiding a screw through the screw hole. A screw hole may be too small to provide passage of the implant in an unexpanded state. The screw hole may be tapered.

The screw holes may be internally threaded. The screw holes may not be internally threaded. The screw holes may have a diameter. The diameter may be any suitable size.

Table 2 shows selected illustrative size ranges for a hole sized for receiving a screw having lower and upper limits.

TABLE 2

| Selected illustrative screw hole sizes. Screw hole diameter, illustrative ranges (lower and upper limits, inclusive) (mm) ||
|---|---|
| Lower | Upper |
| <1.0 | 1.0 |
| 1.0 | 1.2 |
| 1.2 | 1.4 |
| 1.4 | 1.6 |
| 1.6 | 1.8 |
| 1.8 | 2.0 |
| 2.0 | 2.2 |
| 2.2 | 2.4 |
| 2.4 | 2.6 |
| 2.6 | 2.8 |
| 2.8 | 3.0 |
| 3.0 | 3.2 |
| 3.2 | 3.4 |
| 3.4 | 3.6 |
| 3.6 | 3.8 |
| 3.8 | 4.0 |
| 4.0 | 4.2 |
| 4.2 | 4.4 |
| 4.4 | 4.6 |
| 4.6 | 4.8 |
| 4.8 | 5.0 |
| 5.0 | 5.2 |
| 5.2 | 5.4 |
| 5.4 | 5.6 |
| 5.6 | 5.8 |
| 5.8 | 6.0 |
| 6.0 | 6.2 |
| 6.2 | 6.4 |
| 6.4 | 6.6 |
| 6.6 | 6.8 |
| 6.8 | 7.0 |
| 7.0 | 7.2 |
| 7.2 | 7.4 |
| 7.4 | 7.6 |
| 7.6 | 7.8 |
| 7.8 | 8.0 |
| 8.0 | 8.2 |
| 8.2 | 8.4 |
| 8.4 | 8.6 |
| 8.6 | 8.8 |
| 8.8 | 9.0 |
| 9.0 | 9.2 |
| 9.2 | 9.4 |
| 9.4 | 9.6 |
| 9.6 | 9.8 |
| 9.8 | 10.0 |
| 10.0 | >10.0 |

When the bottom surface is seated complementarily against the surface contour and the plate is coupled to the jig, the screw hole may point into the interior and into a volume occupied by the implant in the interior when the implant is positioned at the target site and radially expanded to form a mesh cage. When the bottom surface is seated complementarily against the surface contour and the plate is coupled to the jig, the screw hole may point into the interior and not into a volume occupied by the implant in the interior when the implant is positioned at the target site and radially expanded to form a mesh cage.

The plate may define holes sized for receiving screws (may be referred to herein as "screw holes").

When the bottom surface is seated complementarily against the surface contour and the plate is coupled to the jig, the screw holes may point into the interior and into a volume occupied by the implant in the interior when the implant is positioned at the target site and radially expanded to form a mesh cage. When the bottom surface is seated complementarily against the surface contour and the plate is coupled to the jig, and the screw holes include a first screw hole and a second screw hole, the first screw hole may point into the interior and into a volume occupied by the implant in the interior when the implant is positioned at the target site and radially expanded to form a mesh cage. The second screw hole may point into the interior and into a volume occupied by the implant in the interior when the implant is positioned at the target site and radially expanded to form a mesh cage.

The plate may define a hole sized for receiving a fixation element (may be referred to herein as a "fixation element hole"). The plate may define holes sized for receiving fixation elements (may be referred to herein as "fixation element holes").

The opening may be a first opening. The jig may define a second opening. The plate may be positioned on the surface of the bone in an area defined by the second opening.

The jig may include a transverse member and a longitudinal member. When the plate is coupled to the jig, a first side of the plate may abut the transverse member. When the plate is coupled to the jig, a second side of the plate may abut the longitudinal member. When the plate is coupled to the jig, a first side of the plate may abut the transverse member and a second side of the plate may abut the longitudinal member.

The jig may include a transverse member and a longitudinal member. When the plate is coupled to the jig, the first side of the plate may be adjacent the transverse member. When the plate is coupled to the jig, a second side of the plate may be adjacent the longitudinal member. When the plate is coupled to the jig, the first side of the plate may be adjacent the transverse member and the second side of the plate may be adjacent the transverse member.

The jig may include a transverse member and a longitudinal member. When the plate is coupled to the jig, the first side of the plate may be adjacent to, but not in physical contact with, the transverse member. When the plate is coupled to the jig, a second side of the plate may be adjacent to, but not in physical contact with, the longitudinal member. When the plate is coupled to the jig, the first side of the plate may be adjacent to, but not in physical contact with, the transverse member and the second side of the plate may be adjacent to, but not in physical contact with, the transverse member.

The jig may include a transverse member, a first longitudinal member, and a second longitudinal member. The transverse member may define a first end and a second end. The first longitudinal member may extend away from the first end. The second longitudinal member may extend away from the second end. The plate may include a first side, a second side, and a third side. When the plate is coupled to the jig, the first side may abut the transverse member, the second side may abut the first longitudinal member and the third side may abut the second longitudinal member. When the plate is coupled to the jig, one of the sides of the plate may abut one of the members of the jig. When the plate is coupled to the jig, two of the sides of the plate may abut two of the members of the jig.

The jig may include a transverse member, a first longitudinal member, and a second longitudinal member. The transverse member may define a first end and a second end. The first longitudinal member may extend away from the first end. The second longitudinal member may extend away from the second end. The plate may include a first side, a second side, and a third side. When the plate is coupled to the jig, the first side may be adjacent the transverse member, the second side may be adjacent the first longitudinal member and the third side may be adjacent the second longitudinal member. When the plate is coupled to the jig, one of the sides of the plate may be adjacent one of the members of the jig. When the plate is coupled to the jig, two of the sides of the plate may be adjacent two of the members of the jig.

The jig may include a transverse member, a first longitudinal member, and a second longitudinal member. The transverse member may define a first end and a second end. The first longitudinal member may extend away from the first end. The second longitudinal member may extend away from the second end. The plate may include a first side, a second side, and a third side. When the plate is coupled to the jig, the first side may be adjacent to, but not in physical contact with, the transverse member, the second side may be adjacent to, but not in physical contact with, the first longitudinal member and the third side may be adjacent to, but not in physical contact with, the second longitudinal member. When the plate is coupled to the jig, one of the sides of the plate may be adjacent to, but not in physical contact with one of the members of the jig. When the plate is coupled to the jig, two of the sides of the plate may be adjacent to, but not in physical contact with, two of the members of the jig.

The jig may include an indicator. When the bottom surface is seated complementarily against the surface contour, the indicator may register to a location on the surface of the bone for initiating an access hole for accessing the target site. A distance between the location and the target site may correspond to a length of the implant.

The jig may include a first indicator and a second indicator. When the bottom surface is seated complementarily against the surface contour, the first indicator may register to a first location on the surface of the bone for initiating a first access hole for accessing the target site, and the second indicator may register to a second location on the surface of the bone for initiating a second access hole for accessing the target site. A distance between the first location and the target site may correspond to a first implant length. A distance between the second location and the target site may correspond to a second implant length. The first implant length may be different from the second implant length.

The plate may include an indicator. When the plate is coupled to the jig and the bottom surface is seated complementarily against the surface contour, the indicator may register to a location on the surface of the bone for initiating an access hole for accessing the target site. A distance between the location and the target site may correspond to a length of the implant.

The plate may include a first indicator and a second indicator. When the plate is coupled to the jig and the bottom surface is seated complementarily against the surface contour, the first indicator may register to a first location on the surface of the bone for initiating a first access hole for accessing the target site, and the second indicator may register to a second location on the surface of the bone for initiating a second access hole for accessing the target site. A distance between the first location and the target site may correspond to a first implant length. A distance between the second location and the target site may correspond to a second implant length. The first implant length may be different from the second implant length.

The plurality of holes defined by the jig may include a first hole and a second hole. The first hole may point in a first direction. The second hole may point in a second direction. The first direction may be divergent from the second direction.

The plurality of holes defined by the jig may include a first hole and a second hole. The first hole may point in a first direction. The second hole may point in a second direction. The first direction may be convergent with the second direction.

The plurality of holes defined by the jig may include a first hole and a second hole. The first hole may point in a first direction. The second hole may point in a second direction. The first direction may be non-parallel to the second direction.

The bone may be any suitable bone. The bone may be a proximal humerus bone. The target site may be a center of a head of the proximal humerus bone. The surface contour may include a greater tuberosity. The surface contour may include a deltoid insertion.

The jig may include a positioning hole. When the bone is a proximal humerus bone, when the bottom surface is seated complementarily against the surface contour, the positioning hole may point in a direction tangent to a top of a greater tuberosity.

The jig may include suturing holes.

The apparatus may include apparatus for, and the methods may involve, delivery of an implant at a target site in an interior of a bone. The bone may define a longitudinal axis. The bone may include a surface contour. The surface contour may extend along a surface of the bone between two or more points at different elevations from the longitudinal axis.

The apparatus may include a first jig. The first jig may have one or more features in common with any other jig or plate disclosed herein. The first jig may include a bottom surface. The first jig may define a plurality of holes. The first jig may define a target hole. The bottom surface may complement the surface contour.

The apparatus may include a second jig. The second jig may have one or more features in common with any other jig or plate disclosed herein. The second jig may be configured to be releasably coupled to the first jig. The second jig may define an opening.

When the bottom surface is seated complementarily against the surface contour and the first jig is releasably coupled to the second jig, each of the plurality of holes may point into the interior, but not into a volume occupied by the implant in the interior when the implant is positioned at the target site and radially expanded to form a mesh cage. When the bottom surface is seated complementarily against the surface contour and the first jig is releasably coupled to the second jig, the target hole may point to the target site. When the bottom surface is seated complementarily against the surface contour and the first jig is releasably coupled to the second jig, the opening may define an area on the surface of the bone for preparing an access hole for accessing the target site.

The second jig may include a guide. The guide may extend away from the bone surface and away from the opening.

The apparatus may further include an insert configured to be inserted into the guide. The guide may include a guide inner cylindrical surface. The guide may define a guide central axis. The insert may include an insert outer cylindrical surface and an insert inner cylindrical surface. The insert outer cylindrical surface may define an insert outer central axis. The insert inner cylindrical surface may define an insert inner central axis. The guide central axis may be parallel to the insert outer central axis and the guide central axis may not be parallel to the insert inner central axis. The guide central axis may be parallel to the insert outer central axis and the guide central axis may be parallel to the insert inner central axis.

The apparatus may further include the plate configured to be releasably coupled to a bottom surface of the second jig. The plate may have one or more features in common with any other jig or plate disclosed herein. the bottom surface of the second jig may define a recessed area. The plate may be positioned in the recessed area.

The apparatus may include apparatus for, and the methods may involve, delivery of an implant at a target site in an interior of a bone. The bone may define a longitudinal axis. The longitudinal axis may include a surface contour. The surface contour may extend along a surface of the bone between two or more points at different elevations from the longitudinal axis.

The apparatus may include the plate. The plate may have one or more features in common with any other jig or plate disclosed herein.

The plate may be thinner than a conventional plate. For example, for a given bone, a plate in accordance with the invention may be half as thick, two thirds as thick, or otherwise thinner than a conventional plate used for the given bone. A portion of the plate used for a proximal humerus may have a thickness of less than 2 mm, whereas a conventional plate may have a thickness of 4-6 mm. The thickness of the plate may vary along the length of the plate.

The plate may include a bottom surface. The bottom surface may complement the surface contour.

The plate may define first holes sized for receiving screws (may be referred to herein as "screw holes"). A screw received by a screw hole defined by the plate may be a compression screw, a lagging screw, or a locking screw. A head of a compression or lagging screw may not fully engage the plate, but may apply a compressional force to the plate. A head of a locking screw may fully engage the plate.

The plate may define second holes sized for receiving fixation elements.

The plate may define an opening. The opening may be sized for providing passage of the implant in a non-expanded state through the plate. When the bottom surface of the plate is seated complementarily on a surface contour of a bone, the opening defined by the plate may include an access position. When a bottom surface of the plate is seated complementarily on a surface contour of a bone, the opening may be positioned on the bone surface for providing passage of the implant through the plate. When a bottom surface of the plate is seated complementarily on a surface contour of a bone, the opening may be positioned for providing passage of the implant to the site.

The opening may be tapered.

The opening defined by the plate may have a width. The width may be at least twice as wide as a diameter defined by the screw holes. The width may be one and a half times as wide as a diameter defined by the first holes. The width may range from 6 mm to 8 mm. The width may range from 6 mm to 12 mm. The plate may have a longitudinal axis. The width may be perpendicular to the longitudinal axis. The opening may define a length. The length may have any suitable size. The length of the opening may range from 6 mm to 8 mm. The length of the opening may range from 6 mm to 12 mm.

The opening may be sized to provide clearance for the implant in the non-expanded state. The implant, in the non-expanded state, may have a diameter. The diameter may be any suitable diameter. The diameter may be 7 mm, 8 mm, 9 mm, or any other suitable diameter.

The plate may define a plate longitudinal axis. When the bottom surface is seated complementarily against the surface contour, the longitudinal axis may be aligned with a longitudinal axis of the bone. The opening may be elongated along the plate longitudinal axis. The plate may also define a short axis. The short axis may be transverse to the longitudinal axis.

When the bottom surface is seated complementarily against the surface contour, the first holes may point into the interior and into a volume occupied by the implant in the interior when the implant is positioned at the target site and radially expanded to form a mesh cage. When the bottom surface is seated complementarily against the surface contour, the second holes may point into the interior and not into the volume. When the bottom surface is seated complementarily against the surface contour, the opening may be positioned for providing passage of the implant to the site.

One or more of the first holes sized for receiving screws may not be threaded. One or more of the first holes sized for receiving screws may be internally threaded. A hole sized for receiving a screw may be referred to herein as a "screw hole." Holes sized for receiving screws may be referred to herein as "screw holes." A threaded screw hole may receive an externally threaded bushing. A threaded screw hole may be sized to receive a screw and a bushing inserted into the screw hole.

A screw hole may have a diameter. The diameter may be any suitable size. The diameter may range from 3 mm to 5 mm. The diameter may range from 2 mm to 6 mm. The diameter may range from 1 mm to 6 mm. The diameter may range from 0.035 of an inch to 6 mm or more. The largest diameter of a screw hole defined by the plate may be smaller than a diameter of a head of a screw received by the plate. This may enable the screw to engage the plate without passing through the plate. The screw may be a compression screw. The screw may be a locking screw.

The plate may define third holes sized for receiving screws. The third holes may have one or more features in common with the first holes. When the bottom surface is seated complementarily against the surface contour, the third holes may point into the interior and not into the volume. The plate may include a first end and a second end. The third holes may include a first third hole and a second third hole. The first third hold may be positioned at the first end. The second third hole may be positioned at the second end. The third holes may include a first third hole and two or more second third holes. The first third hold may be positioned at the first end. The two or more second third holes may be positioned at the second end.

The first holes may include a first screw hole and a second screw hole. The first screw hole may point in a first direction. The second screw hole may point in a second direction. The first direction may diverge from the second direction. The first direction may converge with the second direction. The first direction may be oblique with the second direction. The first direction may be parallel to the second direction.

The first screw hole may be spaced apart from a plate longitudinal axis by a first distance. The second screw hole may be spaced apart from the plate longitudinal axis by a second distance. The first distance may be equal to the second distance. The first distance may be greater than or less than the second distance. The plate may define a plate short axis. The plate short access may be perpendicular to the plate longitudinal axis. A plate short axis may transect the first screw hole and the second screw hole.

The plate may include a locking slot. The locking slot may be defined by the plate. The locking slot may be partially defined by the plate and extend into the opening. The locking slot may include a plurality of slots. The locking slot may include slots that are not perpendicular to a surface of the bone. One or more of the slots may engage a head of a screw. A head of a screw advanced through the locking slot may engage one of the slots. The slots may act as a locking feature for a screw.

The locking slot may define a locking slot longitudinal axis. The plate may define a plate longitudinal axis. The locking slot longitudinal axis may be parallel to the plate longitudinal axis. The locking slot longitudinal axis may be coaxial with the plate longitudinal axis.

The locking slot may include a slanted side. The slanted side may be positioned perpendicular to a plate longitudinal axis. The slanted side may slant in a direction perpendicular to an axis of the implant when the bottom surface of the plate is seated complementarily on the surface contour and the implant is implanted in the bone surface.

The implant, when expanded, may form a mesh cage with interconnected cells.

When the bottom surface is seated complementarily against the surface contour, the opening may define an area on the surface for preparing an access hole for accessing the target site.

The opening may have a width. The width may be at least twice as wide as a diameter defined by the first holes. The width may be at least one and a half times as wide as a diameter defined by the first holes. The width may extend along at least half of a plate short axis. The width may extend along at least two thirds of a plate short axis. The first holes may define a diameter ranging from 3 mm to 5 mm and the opening may define a width ranging from 6 mm to 8 mm. The opening may be sized to provide clearance for the implant. The implant may have a diameter, in a non-expanded state, ranging from 6 mm to 12 mm.

The opening may have a length. The length may be elongated along a length longitudinal axis. The plate may have a plate longitudinal axis. The length longitudinal axis may be parallel or coaxial with a plate longitudinal axis and the width may be perpendicular to the plate longitudinal axis. The length longitudinal axis may be oblique to the plate longitudinal axis and the width may be oblique to the plate longitudinal axis. The length longitudinal axis may be perpendicular to the plate longitudinal axis and the width may be parallel to the plate longitudinal axis.

The length of the opening may be longer than a diameter of an implant tail. The length may of the opening may be longer than the diameter of an implant shaft. The length may be sized to facilitate deployment of the implant through the plate at an angle oblique to the plate longitudinal axis. The length may be sized to facilitate deployment of the implant through the bone at an angle oblique to the bone longitudinal axis. The implant may be deployed through the plate at a 30° angle from a plate longitudinal axis. The implant may be deployed through the plate at a 45°, 44°, 43°, 42°, 41°, 40°, 39°, 38°, 37°, 36°, 35°, 34°, 33°, 32°, 31°, 30°, 29°, 28°, 27°, 26°, 25°, 24°, 23°, 22°, 21°, 20°, 19°, 18°, 17°, 16° or 15° angle, or at any angle in any range defined by any two of the foregoing angles, from a plate longitudinal axis. The length may be sized to facilitate deployment of the implant through the plate at two or more angles relative to a bone longitudinal axis. The length may be sized to facilitate deployment of the implant through the bone at two or more angles relative to a bone longitudinal axis.

The opening may be tapered. The opening may transect the plate at an angle oblique to a plate longitudinal axis. The width of the opening may be constant along the length of the opening. The width of the opening may vary along the length of the opening.

The plate may include a target hole. The target hole may be sized to receive a fixation element. When the bottom surface is seated complementarily against the surface contour, the target hole may point to the target site.

The plate may include a positioning hole. The positioning hole may be sized to receive a fixation element. When the bottom surface is seated complementarily against the surface contour, the positioning hole may point in a direction tangent to the bone surface.

The bone may be any suitable bone. When the bone is a proximal humerus bone, when bottom surface is seated complementarily against the landmark, the positioning hole may point in a direction tangent to a greater tuberosity.

The plate may define a plate longitudinal axis. The opening may be elongated along the plate longitudinal axis. The plate longitudinal axis may be aligned with a longitudinal axis of the bone when the bottom surface is seated complementarily against the surface contour. The plate may also define a short axis. The short axis may be transverse to the longitudinal axis. The short axis may be transverse to the plate longitudinal axis.

The plate may include holes having a diameter sized for suturing.

The apparatus may include the jig. The jig may be configured to be releasably coupled to the plate. The plate may define a top face. The jig may define a jig bottom surface. The jig bottom surface may be shaped to be positioned on at least a portion of the top face. The jig may be positioned on the plate when the jig bottom surface is seated on the at least a portion of the top face. The jig bottom surface may be seated on some of the top face. The jig bottom surface may be seated on all of the top face.

The jig bottom surface may be a first jig bottom surface. The jig may include a second jig bottom surface. When the first jig bottom surface is positioned on the plate, the second jig bottom surface may extend away from the plate. The second jig bottom surface may include a positioning hole. The second bottom surface may include one, two or more holes for receiving a fixation element. The second bottom surface may not conform to the plate.

The opening may be a plate opening. The jig may define a jig opening. When the jig is coupled to the plate, the jig opening may be positioned above the plate opening. The plate opening may define a plate opening central axis. The jig opening may define a jig opening central axis. The plate opening central axis may be coaxial with the jig opening central axis.

The plate may define a threaded plate bore. The jig may define a threaded jig bore. When the jig is positioned on the plate, the threaded jig bore may be positioned above the threaded plate bore. Driving a screw through the threaded jig bore and into the threaded plate bore may releasably couple the jig to the plate.

The jig may define third holes sized for receiving screws. Holes defined by the jig for receiving screws may be threaded. A threaded screw hole defined by the jig may receive an externally threaded bushing. A threaded screw hole may be sized to receive a screw and a bushing inserted into the screw hole. The largest diameter of a screw hole defined by the jig may be larger than a diameter of a head of a screw. This may enable the screw to pass through the screw hole defined by the jig without engaging the jig.

The jig may define fourth holes sized for receiving fixation elements. Fixation element holes defined by the jig may have one or more features in common with fixation element holes defined by the plate.

When the jig is coupled to the plate and the bottom surface is seated complementarily against the surface contour, the third holes may point into the interior and into the volume. When the jig is coupled to the plate and the bottom surface is seated complementarily against the surface contour, the fourth holes may point into the interior and not into the volume. When the jig is coupled to the plate, the third holes may be positioned above the first holes. When the jig is coupled to the plate, the fourth holes may be positioned above the second holes.

The jig may include a guide leading to the opening. The guide may be sized for providing passage of the implant in a non-expanded state through the opening.

The third holes may include a first third hole and a second third hole. The first third hole may point in a first direction. The second third hole may point in a second direction. The first direction may diverge from the second direction. The first direction may converge with the second direction. The first direction may be parallel to the second direction. The first direction may be oblique to the second direction.

The first third hole may be spaced apart from the second third hole along the jig longitudinal axis. The first third hole may be spaced apart from the jig longitudinal axis by a first distance. The second third hole may be spaced apart from the jig longitudinal axis by a second distance. The first distance may be equal to the second distance. The first distance may be greater than or less than the second distance. The jig may define a plate short axis. The jig short access may be perpendicular to the jig longitudinal axis. A jig short axis may transect the first third hole and the second third hole.

The jig may have a perimeter. The perimeter may define a channel. The channel may be an open channel. When the jig is coupled to the plate, a surface of the channel may be tangent to a hole defined by the plate. The hole defined by the plate may be one of the second holes. When a fixation element is advanced through the channel, the fixation element may define a fixation element central axis that is coaxial with a central axis of the hole. The channel may be an open channel that has an arcuate cross section. The second holes may include a fixation element hole. When the jig is coupled to the plate, the channel may be positioned above the fixation element hole. The channel may guide a fixation element into the fixation element hole. The channel may be used by a practitioner to guide a fixation element into a bone.

The jig may include an aperture. The aperture may extend through a thickness of the jig. The aperture may be sized to receive a first bushing. The aperture may also be sized to receive a second bushing. The aperture may include a first threaded opening sized to receive the first bushing. The aperture may include a second threaded opening sized to receive the second bushing. The first threaded opening may have an arcuate cross section. The second threaded opening may have an arcuate cross section.

The jig may include a positioning hole. When the jig is coupled to the plate and the bottom surface is seated complementarily against the surface contour, the positioning hole may point in a direction tangent to the bone surface. When the bone is a proximal humerus bone, when the bottom surface is seated complementarily against the surface contour and the jig is coupled to the plate, the positioning hole may define a direction tangent to a greater tuberosity.

When the jig includes a guide, the guide may include an aperture positioned on an outer face of the guide. The aperture may extend through a thickness of the guide. The aperture may be used by a practitioner to pass a threaded fixation element coupled to a nut through the guide and into a bone fragment. The nut may be seated on a top surface of the aperture. The nut may be used to provide compressional force to the bone fragment.

When the jig includes a guide, the guide may include a slot. The slot may be positioned on a guide opening. The guide opening may be configured to receive a bushing. The slot may be configured to engage a portion of a bushing inserted into the guide.

When a bottom surface of the jig conforms to a top surface of the plate and the jig is configured to be releasably coupled to the plate, a jig screw hole may define a jig screw hole central axis and a plate screw hole may define a plate screw hole central axis. When the jig is releasably coupled to the plate, the jig screw hole may be positioned above the plate screw hole. When the jig is releasably coupled to the plate, the jig screw hole central axis may extend along the plate screw hole central axis.

When a bottom surface of the jig conforms to a top surface of the plate and the jig is configured to be releasably coupled to the plate, each jig screw hole may define a jig screw hole central axis and each plate screw hole may define a plate screw hole central axis. When the jig is releasably coupled to the plate, each jig screw hole may be positioned above a plate screw hole. When the jig is releasably coupled to the plate, each jig screw hole may define a jig screw hole central axis that lies along a screw hole central axis defined by a screw hole positioned underneath each jig screw hole.

When a bottom surface of the jig conforms to a top surface of the plate and the jig is configured to be releasably coupled to the plate, one of the jig plurality of holes may define a jig hole central axis and a plate hole may define a plate hole central axis. When the jig is releasably coupled to the plate, the jig hole central axis be positioned above the plate hole. When the jig is releasably coupled to the plate, the jig hole central axis may extend along the plate hole central axis.

When a bottom surface of the jig conforms to a top surface of the plate and the jig is configured to be releasably coupled to the plate, each of the jig plurality of holes may define a jig hole central axis. When the jig is releasably coupled to the plate, some or all of the jig plurality of holes may be positioned above plate holes. When the jig is releasably coupled to the plate, some or all of the jig plurality of holes may define a jig hole central axis that extends along a plate hole central axis defined by a plate hole positioned underneath each of the some or all of the jig plurality of holes.

The apparatus may include apparatus for, and the methods may involve, delivery of an implant at a target site in an interior of a bone. The bone may define a longitudinal axis. The bone may include a surface contour. The surface contour may extend along a surface of the bone between two or more points at different elevations from the longitudinal axis.

The apparatus may include the jig. The jig may have one or more features in common with any other jig or plate disclosed herein. The jig may be configured to be releasably coupled to the plate. The plate may have one or more features in common with any other jig or plate disclosed herein. The plate may include a plate bottom surface. The plate bottom surface may complement the surface contour. The jig may include a jig bottom surface. The jig bottom surface may be shaped to conform to a top surface of the plate.

The jig may define a plurality of holes sized for receiving fixation elements. The jig may define screw holes sized for receiving screws. The jig may define an opening for passage of the implant in a non-expanded state through the jig and to the target site. The passage may be along a straight path oblique to a longitudinal axis of the jig.

When the jig is releasably coupled to the plate and the plate bottom surface is seated complementarily against the surface contour, the plurality of holes may point into the interior and into a volume occupied by the implant in the interior when the implant is positioned at the target site and radially expanded to form a mesh cage. When the jig is releasably coupled to the plate and the plate bottom surface is seated complementarily against the surface contour, the screw holes may point into the interior and not into the volume. When the jig is releasably coupled to the plate and the plate bottom surface is seated complementarily against the surface contour, the opening may be positioned for providing passage of the implant to the site.

The screw holes may be jig screw holes. The plate may define plate fixation element holes sized for receiving fixation elements and plate screw holes sized for receiving screws. When the jig is coupled to the plate, the plurality of holes may be positioned above the plate screw holes and the jig screw holes may be positioned above the plate screw holes.

The jig may include a guide. The guide may extend away from the opening. The guide may have an inner lumen. The inner lumen may define a central axis collinear with the path.

The jig bottom surface may be a first jig bottom surface. The jig may include a second jig bottom surface. The second jig bottom surface may include a positioning hole. When the jig is releasably coupled to the plate, the first jig bottom surface may be positioned on the plate and the second jig bottom surface may extend away from the plate. When the jig is releasably coupled to the plate and the plate bottom surface is seated complementarily against the surface contour, the positioning hole may point in a direction tangent to the bone surface.

The plate may define a threaded plate bore. The jig may define a threaded jig bore. When the bottom surface of the jig is positioned on the plate, the threaded jig bore may be positioned above the threaded plate bore. Driving a screw through the threaded jig bore and into the threaded plate bore may releasably couple the jig to the plate.

The screw holes may include a first screw hole and a second screw hole. The first screw hole may point in a first direction. The second screw hole may point in a second direction. The first direction may diverge from the second direction. The first direction may converge with the second direction. The first direction may be parallel to the second direction. The first direction may be oblique to the second direction.

The jig may have a perimeter that defines a channel. When the jig is coupled to the plate, a surface of the channel may be tangent to a hole defined by the plate. The hole defined by the plate may be one of the second holes. When a fixation element is advanced through the channel, the fixation element may define a fixation element central axis that is coaxial with a central axis of the hole. The channel may be an open channel that has an arcuate cross section. The second holes may include a fixation element hole. When the jig is coupled to the plate, the channel may be positioned above the fixation element hole. The channel may guide a fixation element into the fixation element hole.

The jig may define an aperture. The aperture may be sized to receive a first bushing. The aperture may be sized to receive a second bushing. The aperture may include a first threaded opening sized to receive a first bushing. The aperture may include a second threaded opening sized to receive the second bushing. The first threaded opening and the second threaded opening may both be open channels that each have an arcuate cross section.

The jig may include a positioning hole. When the jig is coupled to the plate and the plate bottom surface is seated complementarily against the surface contour, the positioning hole may point in a direction tangent to the bone surface. When the bone is a proximal humerus bone, when the plate bottom surface is seated complementarily against the surface contour and the jig is coupled to the plate, the positioning hole may point in a direction tangent to a greater tuberosity.

When the jig includes a guide, the guide may include an aperture. The aperture may be positioned on an outer face of the guide. The aperture may extend through a thickness of the guide.

When the jig includes a guide, the guide may include a slot. The slot may be positioned on a guide opening. The guide opening may be configured to receive a bushing. The slot may be configured to engage a portion of a bushing inserted into the guide.

The opening may be a jig opening. The plate may include a plate opening. The plate opening may be an opening for passage of the implant in a non-expanded state through the jig and to the target site. The passage may be along a straight path oblique to a longitudinal axis of the jig. When the jig is coupled to the plate, the jig opening may be positioned above the plate opening. When the jig is coupled to the plate, a central axis defined by the jig opening may be coaxial with a central axis defined by the plate opening.

The apparatus may include apparatus for, and the methods may involve, delivery of an implant at a target site in an interior of a bone. The bone may define a longitudinal axis. The bone may include a surface contour. The surface contour may extend along a surface of the bone between two or more points at different elevations from the longitudinal axis.

The apparatus may include the plate. The plate may have one or more features in common with any other jig or plate disclosed herein. The plate may include a bottom surface. The bottom surface may complement the surface contour. The plate may define a positioning hole. The plate may define first holes sized for receiving screws. The plate may define second holes sized for receiving fixation elements. The plate may define an opening sized for providing passage of the implant in a non-expanded state through the plate.

When the bottom surface is seated complementarily against the surface contour, the positioning hole may point in a direction tangent to the surface. When the bottom surface is seated complementarily against the surface contour, the first holes may point toward a volume occupied by the implant in the interior when the implant is positioned at the target site and radially expanded to form a mesh cage. When the bottom surface is seated complementarily against the surface contour, the second holes may point away from the volume. When the bottom surface is seated complementarily against the surface contour, the opening may be positioned for providing passage of the implant through the plate and to the site.

The bone may be any suitable bone. When the bone is a proximal humerus bone, the surface contour may include a greater tuberosity and the plate may be aligned with the greater tuberosity when the positioning hole points in a direction tangent to the greater tuberosity.

The plate may include a target hole.

The apparatus may include apparatus for, and the methods may involve, implanting the implant at a target site in an interior of a bone. The bone may define a longitudinal axis. The bone may include a surface contour that extends along a surface of the bone between two or more points at different elevations from the longitudinal axis.

The apparatus may include a first plate. The first plate may have one or more features in common with any other jig or plate disclosed herein. The first plate may include a bottom surface. The bottom surface may complement the surface contour. The plate may define first holes sized for receiving screws. The plate may define second holes sized for receiving fixation elements. The plate may define a first opening.

The apparatus may include a second plate. The second plate may have one or more features in common with any other jig or plate disclosed herein. The second plate may be shaped to be positioned in the first opening. The second plate may be configured to be anchored to the first plate. The second implant may be configured to be anchored to the implant when the second plate is positioned on the bone surface and the implant is implanted at the target site.

The second plate may define a second opening. The second opening may be sized for receiving a tail of the implant when the implant is implanted in the target site. The second opening may define a second opening circumference. The second opening circumference may be larger than an outer circumference defined by the tail of the implant.

When the bottom surface is seated complementarily against the surface contour, the first holes may point into the volume occupied by the implant in the interior when the implant is positioned at the target site and radially expanded to form a mesh cage. When the bottom surface is seated complementarily against the surface contour, the second holes may point into the interior and not into the volume.

The bottom surface may be a first bottom surface. The second plate may define a second bottom surface. The second bottom surface may conform to the surface contour.

The apparatus may include apparatus supporting the implant when the implant is implanted at a target site in an interior of a bone. The bone may define a longitudinal axis. The bone may include a surface contour. The surface contour may extend along a surface of the bone between two or more points at different elevations from the longitudinal axis.

The apparatus may include a first plate. The first plate may have one or more features in common with any other jig or plate disclosed herein. The first plate may include a first plate bottom surface. The first plate bottom surface may complement the surface contour. The first plate may define first holes sized for receiving screws. The first plate may define second holes sized for receiving fixation elements. The first plate may define a first opening.

The apparatus may include a second plate. The second plate may have one or more features in common with any other jig or plate disclosed herein. The second plate may be configured to be positioned on top of the first plate. The second plate may be configured to be releasably coupled to the first plate. The second plate may be configured to be anchored to the first plate. The second plate may include a screw hole for receiving an anchoring screw. The first plate may include a bore for receiving a screw. The anchoring screw may be advanced through the screw hole and into the bore to anchor the second plate to the first plate.

The second plate may include a second bottom surface conforming to a contour of a portion of a top surface of the first plate. The second plate may include a second opening. When the second plate is positioned on the first plate, the second opening may be positioned on top of the first opening. When the second plate is positioned on the first plate, a first opening central axis may be coaxial with a second opening central axis.

The second plate may include a tube. The tube may extend through the second opening at an angle oblique to a central axis of the second plate. When the second plate is positioned on the first plate and the first bottom surface is seated on the surface contour, the tube may extend through the second opening and the first opening and into the interior. The tube may extend into the interior at an angle oblique to a central axis of the second plate. The tube may extend into the interior at an angle oblique to a central axis of the first plate.

The tube may be sized for coaxially mounting to a tail of the implant when the implant is implanted in the target site. The tube may define an inner lumen. The inner lumen may have an inner lumen circumference. The inner lumen circumference may be larger than an outer circumference of the tail of the implant.

When the first bottom surface is seated complementarily against the surface contour, the first holes may point into a volume occupied by the implant in the interior when the implant is positioned at the target site and radially expanded to form a mesh cage. When the first bottom surface is seated complementarily against the surface contour, the second holes may point into the interior and not into the volume.

The apparatus may include apparatus for, and the methods may involve, delivery of an implant at a target site in an interior of a bone. The bone may define a longitudinal axis. The bone may include a surface contour. The surface contour may extend along a surface of the bone between two or more points at different elevations from the longitudinal axis.

The apparatus may include the jig. The jig may have one or more features in common with any other jig or plate disclosed herein. The jig may include a bottom surface. The bottom surface may complement the surface contour. The jig may define a plurality of holes.

The jig may define a positioning hole. When the bottom surface is seated complementarily against the surface contour, the positioning hole may point in a direction tangent to the bone surface.

The jig may define an opening for passage of the implant in a non-expanded state through the jig and to the target site. The passage may be a passage along a straight path oblique to a longitudinal axis of the jig.

The jig may include a guide. The guide may extend away from the bone surface and the opening. The guide may have an inner surface. The inner surface may define a central axis collinear with the path.

When the bottom surface is seated complementarily against the surface contour, each of the plurality of holes may point into the interior but not a volume occupied by the implant in the interior when the implant is positioned at the target site and radially expanded to form a mesh cage. When the bottom surface is seated complementarily against the surface contour, the opening may define an area on the surface for preparing an access hole for accessing the target site.

The jig may define a target hole. When the bottom surface is seated complementarily against the surface contour, the target hole may point to the target site.

The bone may be any suitable bone. When the bone is a proximal humerus bone, the direction may be tangent to a greater tuberosity. When the bone is a proximal humerus bone, the surface contour may include an intertubercular groove.

The apparatus may further include an insert. The insert may be configured to be inserted into the guide. The guide may include a guide inner cylindrical surface and defines a guide central axis. The insert may include an insert outer cylindrical surface and an insert inner cylindrical surface. The insert outer cylindrical surface may define an insert outer central axis. The insert inner cylindrical surface may define an insert inner central axis. The guide central axis may be parallel to the insert outer central axis and the guide central axis may not be parallel to the insert inner central axis. The guide central axis may be parallel to the insert outer central axis and the insert inner central axis.

The apparatus may include the plate. The plate may have one or more features in common with any other jig or plate disclosed herein. The plate may be configured to be releasably coupled to a bottom surface of the jig. The bottom surface of the jig may define a recessed area. The recessed area may be configured to receive the plate. The plate may be configured to be positioned in the recessed area. The recessed area may conform to a contour of a top face of the plate. The recessed area may conform to a contour of a perimeter of the plate.

The apparatus may include apparatus for, and the methods may involve, delivery of an implant at a target site in an interior of a bone. The bone may define a longitudinal axis. The bone may include a surface contour that extends along a surface of the bone between two or more points at different elevations from the longitudinal axis.

The apparatus may include the plate. The plate may have one or more features in common with any other jig or plate disclosed herein. The plate may include a plate bottom surface. The plate bottom surface may complement a first portion of the surface contour. The plate may define an opening.

The apparatus may include the jig. The jig may have one or more features in common with any other jig or plate disclosed herein. The jig may be configured to be releasably coupled to an end of the plate. The jig may include a jig bottom surface. The jig may define a plurality of holes. The jig bottom surface may complement a second portion of the surface contour.

When the jig bottom surface is seated complementarily against the second portion of the surface contour, each of the plurality of holes may point into the interior but not into a volume occupied by the implant in the interior when the implant is positioned at the target site and radially expanded to form a mesh cage. When the plate bottom surface is seated complementarily against the first portion of the surface contour, the opening may define an area on the surface for preparing an access hole accessing the target site.

The jig may define a target hole.

The jig may define a positioning hole. When the bone is a proximal humerus bone, the second portion of the surface contour may include a greater tuberosity and, when the jig bottom surface is seated complementarily against the greater tuberosity, the positioning hole may point in a direction tangent to the greater tuberosity.

The jig bottom surface may be a first jig bottom surface. The jig may include a second jig bottom surface. The second jig bottom surface may be configured to be positioned on a portion of a top surface of the plate. The second jig bottom surface may conform to a surface contour of the portion of the top surface of the plate.

When the jig is a first jig and the end is a first end, the apparatus may further include a second jig. The second jig may be configured to be releasably coupled to a second end of the plate. The second jig may include a guide. The guide may extend away from the opening.

The apparatus may include apparatus for, and the methods may involve, repairing a bone defining a longitudinal axis. The bone may define a longitudinal axis. The bone may include a surface contour. The surface contour may extend along a surface of the bone between two or more points at different elevations from the longitudinal axis.

The apparatus may include the implant. The implant may be implanted at a target site in an interior of the bone. The implant may have an implant tail and an implant head. A portion of the implant tail may have a tubular shape. The implant head may include an expandable mesh cage.

The apparatus may include the plate. The plate may have one or more features in common with any other jig or plate disclosed herein. The plate may include a bottom surface. The plate may include a tube extending away from the bottom surface. The tube may define a central axis. The central axis may be oblique to a longitudinal axis of the plate. The tube may be configured to be coaxially mounted on the implant tail.

The bottom surface may complement the surface contour. When the bottom surface is seated complementarily against the surface contour, the central axis may point to the target site.

The tube may have an outer diameter. The outer diameter may be lesser than a diameter of an access hole. The outer diameter may be large enough for passage of the implant in a non-expanded state.

The tube may have an inner diameter. The inner diameter may be greater than an outer diameter of the implant tail. The inner diameter may be large enough for passage of the implant in a non-expanded state. In operation, when the implant is implanted in the bone and the bottom surface of the plate abuts a surface of the bone, the tube may be coaxially mounted on the implant tail.

The plate may define a hole sized to receive a screw. The screw may be a screw for anchoring the plate to the implant. The hole sized to receive the screw may point in a direction. When the implant is implanted in the bone and the bottom surface of the plate abuts a surface of the bone, the direction may point to a bore defined by the implant tail. The bone may be sized to receive the screw. When the implant is implanted and expanded in the bone and the bottom surface of the plate abuts a surface of the bone, the direction may point to the implant head.

The plate may define a first screw hole and a second screw hole. The first screw hole may point in a first direction and the second screw hole may point in a second direction. When the implant is implanted in the bone and the bottom surface of the plate abuts a surface of the bone, the first direction may point to a bore defined by the implant tail. The bone may be sized to receive the screw. When the implant is implanted and expanded in the bone and the bottom surface of the plate abuts a surface of the bone, the first direction may point to the implant head. When the implant is implanted and expanded in the bone and the bottom surface of the plate abuts a surface of the bone, the second direction may point into an interior of the bone but not into a volume occupied by the implant in the interior.

The apparatus may include apparatus for, and the methods may involve, implanting the implant in an interior of a bone. The apparatus may include apparatus for supporting the implant after implantation. The implant may be implanted at a target site in the interior.

The bone may define a longitudinal axis. The bone may include a surface contour. The surface contour may extend along a surface of the bone between two or more points at different elevations from the longitudinal axis.

The apparatus may include the plate. The plate may have one or more features in common with any other jig or plate disclosed herein. The plate may define an internally threaded hole. The hole may point in a direction that is oblique to a longitudinal axis of the plate. The direction may be defined by a hole central axis.

The plate may include a bottom surface. The bottom surface may complement the surface contour. When the bottom surface is seated complementarily against the surface contour, the hole may define an area on the surface for preparing an access hole for accessing the target site. When the bottom surface is seated complementarily against the surface contour, the direction may point to the target site.

The apparatus may include a first externally threaded tube. The first externally threaded tube may be configured to mate with the internally threaded hole. When the first tube mates with the hole, the first tube may extend away from a surface of the bone.

The apparatus may include a second externally threaded tube. The second externally threaded tube may be configured to mate with the internally threaded hole. When the second tube mates with the hole the second tube may extend into the interior.

The first tube may define a first inner diameter. The first inner diameter may be greater than a diameter of the implant in a non-expanded state. In operation, the implant may be advanced through the first tube and towards the target site.

The second tube may define a second inner diameter. The second inner diameter may be greater than an outer diameter of a tail of the implant. In operation, when the implant is implanted in the bone, the first tube may be removed from the plate. In operation, when the implant is implanted in the bone, the second tube may be configured to be coaxially mounted on the tail. In operation, when the implant is implanted in the bone, the second tube may be coaxially mounted on the tail.

The plate may define holes sized for receiving screws. The plate may define holes sized for receiving fixation elements.

The apparatus may include, and the methods may involve, apparatus for delivery of an implant at a target site in an interior of a bone. The bone may define a longitudinal axis. The bone may include a surface contour. The surface contour may extend along a surface of the bone between two or more points at different elevations from the longitudinal axis.

The apparatus may include means for aligning the apparatus with the surface contour when the apparatus is in direct contact with the bone surface. Apparatus may be in direct contact with the bone surface when there is no intervening apparatus between the apparatus and the bone surface.

The apparatus may include means for guiding fixation elements into a bone interior. The guiding may provide clearance for expanding the implant inside the bone. The apparatus may include means for guiding a target wire toward the target site in the bone interior.

The bone may be a proximal humerus bone. The surface contour may include a first anatomical landmark. The first anatomical landmark may be a bicipital groove.

The surface contour may include a second anatomical landmark. The apparatus may include means for aligning the apparatus with the second anatomical landmark when the apparatus is in direct contact with the bone. The second anatomical landmark may be a greater tuberosity.

The means for guiding fixation elements may include a first means and a second means. The first means and the second means may be spaced apart from each other. The first means and the second means may guide the fixation elements along non-parallel paths. The first means and second means may guide the fixation elements along convergent paths. The first means and second means may guide the fixation elements along divergent paths. The first means and the second means may guide the fixation elements along parallel paths.

The apparatus may include means for identifying a location on the bone surface suitable for inserting the implant so that the head of the implant will be disposed at the target site.

The apparatus may include means for identifying an area on the surface of the bone that includes an access position.

The apparatus may include means for identifying a plurality of locations on the bone surface. Each of the plurality of locations may be suitable for inserting the implant having a length so that the head of the implant will be disposed at the target site.

The apparatus may include positioning means for positioning the apparatus relative to an anatomical landmark defined by the bone.

When the bone is a proximal humerus bone, the apparatus may include means for guiding a wire over a top of a greater tuberosity.

When the bone is a proximal humerus bone, the target site may be a center region in a head of the proximal humerus bone.

The apparatus may include means for guiding one or more devices into a bone interior at an acute angle relative to a longitudinal axis of the bone.

The apparatus may include means for guiding a drill into a bone interior at an acute angle relative to a longitudinal axis of the bone.

The apparatus may include means for guiding a cavity preparation device into a bone interior at an acute angle relative to a longitudinal axis of the bone.

The apparatus may include means for guiding the implant into a bone interior at an acute angle relative to a longitudinal axis of the bone.

The apparatus may include means for receiving anchoring members. The anchoring members may be configured to anchor the apparatus to the bone. The means for receiving the anchoring members may include means for guiding a fixation element into a head of the implant.

The means for receiving anchoring members may include means for guiding a fixation element into a tail of the implant. The means for receiving anchoring members may include means for guiding a fixation element into the bone.

The apparatus may include means for receiving the plate. The plate may define a hole for passage of the implant into the bone interior. The apparatus may include means for removably coupling the plate to the apparatus.

The apparatus may include means for receiving the jig. The jig may define a hole for passage of the implant into the bone interior. The apparatus may include means for removably coupling the jig to the apparatus.

The apparatus may include means for providing passage of the implant through the apparatus and into the bone interior.

The apparatus may include means for defining an area on the bone surface. The area on the bone surface may be for initiating an access hole. The implant may be deployed through the access hole.

The apparatus may include, and the methods may involve, apparatus for delivery of an implant at a target site in an interior of a bone. The bone may define a longitudinal axis. The bone may include a surface contour. The surface contour may extend along a surface of the bone between two or more points at different elevations from the longitudinal axis.

The apparatus may include an implant delivery base. The implant delivery base may have a base bottom surface.

The base bottom surface may complement the surface contour.

The base bottom surface may be shaped to nest in an opening of the plate. A portion of the base bottom surface may be shaped to nest in an opening of the plate.

The implant delivery base may have a base top surface. The base top surface may be flat. The base top surface may be curved. The base top surface may include a flat portion. The base top surface may include a curved portion.

The implant delivery base may define a channel. The channel may extend through an interior of the implant delivery base. The channel may extend away from the base bottom surface in a direction. The direction may define an angle oblique to the bottom surface. The channel may be sized to provide passage of the implant. The channel may be configured to receive a bushing. When the bottom surface is seated complementarily on the surface contour, a central axis of the channel may point towards the target site.

The base bottom surface may be shaped to nest in an opening of the plate. A portion of the base bottom surface may be shaped to nest in an opening of the plate. A bottom surface of the plate may complement the surface contour. When the implant delivery base is nested in an opening of the plate and the plate bottom surface is seated complementarily on the surface contour, a central axis of the channel may point towards the target site. The opening may define an area on the surface of the bone for preparing an access hole for accessing the target site.

The apparatus may include a post. The post may be supported by the implant delivery base. The post may extend away from the base top surface. The post may be releasably coupled to the implant delivery base. The post may be fixedly attached to the implant delivery base. The post may be cannulated. The cannula may be sized to receive a screw. The post may define a surface shaped to receive a reduction device.

The apparatus may include the reduction device. The reduction device may be configured to be slidingly coupled to the post. The reduction device may be releasably coupled to the post. The reduction device may be configured to slide along the post so that, in operation, a bottom surface of the reduction device is positioned on skin covering the bone.

The reduction device may be configured to be snapped onto the post. The reduction device may define an opening sized to be removably coupled to the post. The opening may be sized to fit on the surface defined by the post for receiving the reduction device. The opening may be sized to be coupled to an outer face of the post.

The apparatus may include the plate. The base bottom surface may be configured to releasably interconnect with the plate. The plate may define an opening. The opening may be sized for passage of an implant. A plate bottom surface may complement the surface contour. The base bottom surface may conform to a top face of the plate. The base bottom surface may conform to a portion of a top face of the plate. The base bottom surface may be shaped to nest in the opening of the plate. A first portion of the base bottom surface may be contoured to nest in the opening of the plate. A second portion of the base bottom surface may be contoured to seated on a top face of the plate. The base bottom surface may be shaped to be seated on a top face of the plate.

When the implant delivery base is coupled to the plate, the channel may extend away from the opening. When the plate bottom surface is seated complementarily on the surface contour and the implant delivery base is coupled to the plate, a central axis defined by the channel may point to the target site. The opening may define an area on the surface of the bone for preparing an access hole for accessing the target site.

The plate may define screw holes sized to receive screws. The screw holes may receive a bushing. The bushing may be sized to receive a screw. The bushing may be sized to receive a fixation element. When the plate bottom surface is seated complementarily against the surface contour, the screw holes may point into the interior, but not into a volume occupied by the implant in the interior when the implant is positioned at the target site and radially expanded to form a mesh cage.

The reduction device may define a plurality of holes. The plurality of holes may be sized for receiving fixation elements. Each of the plurality of holes may transect the reduction device at a right angle. When the base bottom surface is seated complementarily on the surface contour, each of the plurality of holes may point into the interior and not into a volume occupied by the implant when the implant is positioned at the target site and expanded to form a cage. Fixation elements driven through the plurality of holes and into the interior may provide clearance for the implant.

The implant may be a first implant. The reduction device may define a first plurality of holes and a second plurality of holes. The first plurality of holes may be positioned at a first distance away from a central axis of the reduction device. The first plurality of holes may point into the interior of the bone and not into a volume occupied by the first implant in the interior when the first implant is positioned at the target site and radially expanded to form a mesh cage. The first plurality of holes may include a first hole and a second hole. The first hole may be spaced apart from the second hole along a direction oblique to the central axis of the reduction device. The first hole may be spaced apart from the second hole along a direction perpendicular to the central axis of the reduction device. Each of the second plurality of holes may be displaced a second distance away from the central axis of the reduction device. The second plurality of holes may point into the interior of the bone and not into a volume occupied by a second implant in the interior when the second implant is positioned at the target site and radially expanded to form a mesh cage. The second plurality of holes may include a third hole and a fourth hole. The third hole may be spaced apart from the fourth hole along a direction perpendicular to the central axis of the reduction device. The third hole may be spaced apart from the fourth hole along a direction oblique to the central axis of the reduction device. The first volume may be different from the second volume. The second distance may be different from the first distance.

The reduction device may define a screw hole sized to receive a screw. The apparatus may include a bushing. The screw hole may be configured to receive the bushing.

The reduction device may define a plurality of holes. The holes may be sized for receiving fixation elements. The holes may be sized for receiving bushings. The holes may be sized for receiving screws. A top face of the reduction device may be flat. A top face of the reduction device may be curved.

When the base bottom surface is seated complementarily on the surface contour, the screw hole may point to a volume in the interior of the bone occupied by the implant in the interior when the implant is positioned at the target site and radially expanded to form a mesh cage.

The base bottom surface may be configured to releasably interconnect with the plate. The plate may define a plate screw hole sized to receive the screw. The plate may define a bottom surface complementing the surface contour. The reduction device may define a reduction device screw hole. When the implant delivery base is releasably coupled to the plate, a central axis defined by the reduction device screw hole may be coaxial with a central axis defined by the plate screw hole. When the bottom surface is seated complementarily on the surface contour and the implant delivery base is interconnected with the plate, the plate screw hole and the reduction device screw hole may point to a volume. The volume may be a volume occupied by the implant in the interior when the implant is positioned at the target site and radially expanded to form a mesh cage.

The base bottom surface may be configured to releasably interconnect with the plate. The plate may define a slot configured to engage a head of the screw. The plate may define a plate bottom surface complementing the surface contour. When the implant delivery base is interconnected with the plate, a central axis defined by the screw hole may pass through the slot. When the bottom surface of the plate is seated complementarily on the surface contour and the implant delivery base is interconnected with the plate, the screw hole may point to a volume. The volume may be a volume occupied by the implant in the interior when the implant is positioned at the target site and radially expanded to form a mesh cage.

The reduction device may define an aperture sized for receiving screws. The reduction device may define an aperture sized for receiving a fixation element. The aperture may extend along a longitudinal central axis of the reduction device. The base bottom surface may be configured to releasably interconnect with the plate. The plate may define a screw hole configured to engage a screw. The plate may define a plate bottom surface complementing the surface contour. When the implant delivery base is interconnected with the plate, a central axis defined by the screw hole may pass through the aperture without transecting the aperture. When the bottom surface of the plate is seated complementarily on the surface contour and the implant delivery base is interconnected with the plate, the screw hole may point to a volume occupied by the implant in the interior when the implant is positioned at the target site and expanded to form a cage.

The base bottom surface may be configured to releasably interconnect with the plate. The plate may define a slot configured to engage a head of a screw. The plate may define a plate bottom surface complementing the surface contour. When the bottom surface of the plate is seated complementarily on the surface contour and the implant delivery base is interconnected with the plate, a bore central axis of a bore defined by an implant tail of the implant, when the implant is positioned at the target site, may extend through the slot without transecting the slot. The bore central axis may extend through the aperture and transects a central longitudinal axis of the aperture.

The implant delivery base may define a first bore. The first bore may be positioned on the base top surface. The first bore may extend through the implant delivery base at an angle oblique to the base bottom surface. The implant delivery base may define a second bore. The second bore may be positioned on the base top surface. The second bore may extend through the base at an angle oblique to the base bottom surface. The first bore may be spaced apart from the second bore along a direction transverse to an implant delivery base bottom-surface longitudinal axis. The first bore may be spaced apart from the second bore along a direction perpendicular to a longitudinal axis of a bottom surface of the implant delivery base. The first bore and the second bore may both be sized to receive a fixation element.

When the top surface includes a curved portion, the first bore may extend thought the implant delivery base and form a notch on a shoulder defined by an outer surface of the channel. The top surface may include the shoulder. The implant delivery base may include a second bore having the same geometrical properties as the first bore disposed on an opposite side of the shoulder.

The implant delivery base may define a third bore. The third bore may be positioned on the base top surface. When the top surface includes a curved portion, the third bore may form a notch on the shoulder. The third bore may define a direction perpendicular to the implant delivery base central axis. The implant delivery base may define a fourth bore. The fourth bore may be positioned on the base top surface. When the top surface is curved, the fourth bore may be positioned on the shoulder. The fourth bore may have the same geometrical properties as the third bore and be disposed on an opposite side of the shoulder.

When the base bottom surface is seated complementarily on the surface contour, the first bore and the second bore may point into the interior, but not into a volume occupied by the implant in the interior, when the implant is positioned at the target site and radially expanded to form a mesh cage.

The post may define an inner lumen. The inner lumen may be sized for advancing a screw through the inner lumen. When the bottom surface is seated complementarily against the surface contour and the implant is implanted in the bone, the inner lumen may define an inner lumen central axis. The inner lumen central axis may be coaxial with a central axis of a bore defined by a tail of the implant.

The implant delivery base may include a longitudinal member. The longitudinal member may extend away from the channel. The longitudinal member may extend away from the channel along a longitudinal axis defined by the bottom surface.

A bottom face of the longitudinal member may include the base bottom surface. When the base bottom surface is seated complementarily on the surface contour, the longitudinal member may extend along the longitudinal axis of the bone.

The longitudinal member may define a screw hole sized for receiving a screw. The longitudinal member may define a slot sized for receiving a screw. The longitudinal member may include a recess for engaging the plate.

The apparatus may include, and the methods may involve, apparatus for positioning an implant in an implantation region inside a fractured bone. The apparatus may include an elongated base member. The apparatus may include an elongated targeting member. The apparatus may include a first swing arm. The first swing arm may be pivotally affixed to the base member. The first swing arm may be pivotally affixed to the targeting member.

The apparatus may include a second swing arm. The second swing arm may be pivotally affixed to the base member. The second swing arm may be pivotally affixed to the targeting member.

The base member may define a longitudinal axis. The first swing arm may be pivotally affixed to the base member at a first position along the longitudinal axis of the base member. The second swing arm may be pivotally affixed to the base member at a second position along the longitudinal axis of the base member. The first position along the longitudinal axis of the base member may be spaced apart from the second position along the longitudinal axis of the base member.

The targeting member may define a longitudinal axis. The first swing arm may be pivotally affixed to the targeting member at a first position along the longitudinal axis of the targeting member. The second swing arm may be pivotally affixed to the targeting member at a second position along the longitudinal axis of the targeting member. The first position along the longitudinal axis of the targeting member may be spaced apart from the second position along the longitudinal axis of the targeting member.

A first distance spacing the first position along the longitudinal axis of the base member apart from the second position along the longitudinal axis of the base member may be equal to, or substantially equal to, a second distance spacing the first position along the longitudinal axis of the targeting member apart from the second position along the longitudinal axis of the targeting member.

The first and second swing arms may be pivotally affixed to the base member and pivotally affixed to the targeting member. The first and second swing arms may be pivotally affixed to the base member and to the targeting member such that the first and second swing arms are maintained parallel to each other. The first and second swing arms may be pivotally affixed to the base member and to the targeting member such that the base member and the targeting member are maintained parallel to each other.

The base member may define a receptacle. The receptacle may extend along a longitudinal axis of the base member. The receptacle may be sized to receive a fixation element. The receptacle may receive the fixation element at a position on the fixation element that is operatively external to the bone. The receptacle may be sized such that the base member fits snugly over the fixation element. For example, the fixation element may be a K-wire. The receptacle may be sized to receive a length of a shaft of the K-wire.

A tip of the fixation element may be positioned inside a bone. The tip may identify a target site inside the bone. The fixation element may be referred to herein as a target wire. The bone may be any suitable bone. For example, the bone may be a radius, a humerus or any other bone shown below in FIG. 3. When the bone is a humerus, the tip may be positioned in a head of the humerus.

The base member may include a set screw. The set screw may be configured to lock the base member to the fixation element when a tip of the fixation element is in the bone and a shaft of the fixation element that is operatively outside the bone is positioned within the receptacle.

When the fixation element is positioned within the receptacle, the targeting member, in operation, may move along a circumference of a circle centered at the tip of the fixation element that is within the bone. The tip of the fixation element may identify a distal end of a target site for the implant inside the bone. A distal end of the targeting member may move along the circumference.

When the targeting member, in operation, moves along the circumference, the targeting member may indicate an access position. The targeting member may indicate the access position at an intersection of the circumference and an outer surface of the bone. The targeting member may indicate the access position regardless of an angle between a longitudinal axis of the fixation element and a longitudinal axis of the bone.

The tip of the fixation element (when positioned in the bone) and the access position may define a longitudinal axis. The longitudinal axis defined by the tip of the fixation element and the access position may correspond to a longitudinal axis of an implantation region inside the bone. The longitudinal axis of an implantation region may define an angle, with respect to a longitudinal axis of the bone, at which an implant may be positioned inside the bone.

The targeting member may include an indicator. The indicator may be positioned at an end of the targeting member. In operation, the indicator may be positioned at a distal end of the targeting member. The indicator may be positioned at an end of the targeting member that, in operation, is configured to intersect an outer surface of the bone.

The receptacle defined by the base member may be configured to position the base member with respect to the fixation element. The receptacle may be configured to position the base member with respect to the fixation element such that, in operation, an indicator of the targeting member is positioned on a circumference of a circle centered at the tip of the fixation element.

A position of the indicator with respect to a tip of the fixation element (when the tip is positioned inside the bone) may define a radius of the circle. The radius of a circle centered at a tip of the fixation element may correspond to a length of an implant inserted into the bone. The position of the indicator may be determined by a position of the base member with respect to the fixation element. The position of the indicator may be determined by a length of the receptacle along a longitudinal axis of the base member. Apparatus may be adjustable to identify an appropriate access position for different size implants. For example, a length of the receptacle may be adjustable.

The first and second swing arms may space the base member apart from the targeting member. The first and second swing arms may position an indicator of the targeting member on a circumference of the circle centered about the tip of the bone penetrating member.

When a fixation element is positioned within the receptacle, the targeting member may be positioned with respect to the bone such that when, in operation, the targeting member contacts an outer surface of the bone, the targeting member defines an access position on the outer surface of the bone.

The access position may be a location on the outer surface of the bone where an access hole may be initiated. The access hole may be formed by drilling at the access position. The access position may define a length of an implantation region inside the bone. For example, a maximum length of an implantation region may extend from a tip of a fixation element positioned inside the bone to the access position on the outer surface of the bone. The access position may define a longitudinal axis that extends from a proximal end of the implantation region to a distal end of the implantation region. The distal end of the implantation region may correspond to a target site inside the bone. The target site may correspond to a tip of a fixation element positioned inside the bone. The proximal end of the implantation region may correspond to the access position.

The targeting member may include a first concave surface. The first concave surface may be configured to guide a drill into the bone at the access position. The first concave surface may be configured to guide a drill into the bone such that the drill is oriented substantially perpendicular to a longitudinal axis of the bone.

The targeting member may include a second concave surface. The second concave surface may be configured to guide a drill into the bone. The second concave surface may be configured to guide a drill into the bone at the access position. The second concave surface may be configured to guide a drill into the bone at the access position such that the drill is oriented at an oblique angle to a longitudinal axis of the bone. The angle may be less than 90 degrees and greater than 5 degrees. The angle may define a longitudinal axis of an implantation region.

The first swing arm may include an elongated body. The first swing arm may include a clevis. The first swing arm may be pivotally affixed to the base member by a pin that passes through the clevis and through the base member. The base member may include a clearance holes for receiving the pin.

The targeting member may include a channel. The channel may have a longitudinal axis. The first swing arm may be pivotally affixed within the channel by a pin that passes through the first swing arm and passes perpendicular to the longitudinal axis of the channel. The targeting member may include a pair of clearance holes. A first clearance hole may be on a first side of the channel. A second clearance hole may be on a first side of the channel. The first and second clearance holes may be positioned such that the pin inserted into the first and second clearance holes traverses the channel. The pin may pass through the first clearance hole, pass through a clearance hole in the first swing arm and pass through the second clearance hole.

A targeting member may include a gripper. A gripper may be affixed to the targeting member. A gripper may be affixed to a distal end of the targeting member. The gripper may be configured to stabilize the targeting member on an outside surface of the bone. The gripper may be configured to stabilize the targeting member on an outside surface of the bone when, in operation, the fixation element is positioned inside the receptacle and the targeting member contacts the outside surface of the bone.

The gripper may include a first projection. The gripper may include a second projection. The first projection may be spaced apart from the second projection by a distance. The distance may be greater than a width of the targeting member. The distance may be less than or equal to a width of the bone. The distance may be configured to stabilize the targeting member against an anatomical landmark of a bone. For example, the distance may be determined based on a width of a tuberosity on the bone. The distance may be greater than a width of the tuberosity. The anatomical landmark may be on an outer surface of the bone.

The first projection may be substantially parallel to the second projection. The gripper may be pivotally affixed to the targeting member. The gripper may be rigidly affixed to the targeting member.

When the bone is a humerus, the gripper may be configured to stabilize the targeting member on a humeral shaft of the humerus. In operation, when the targeting member contacts the outside surface of the bone, the first projection and the second projection may be aligned with a longitudinal axis of the implantation region. Being aligned may include being parallel or substantially parallel.

A targeting member may include a guide channel. The guide channel may be pivotally affixed to the targeting member. The guide channel may be pivotally affixed to a distal end of the targeting member. The guide channel may include an elongated concave surface. The guide channel may define a longitudinal axis. The guide channel may be configured such that when, in operation, the targeting member contacts an outer surface of the bone, the guide channel defines a longitudinal axis of the implantation region.

In operation, when the targeting member contacts an outer surface of the bone, the guide channel may define an angle between a longitudinal axis of the bone and the longitudinal axis of the implantation region. The angle may be any suitable angle. For example, the angle may be oblique with respect to the longitudinal axis of the bone. The angle may be perpendicular to a longitudinal axis of the bone.

A targeting member may include an angular stopping member. The angular stopping member may be pivotally affixed to the guide channel. The angular stopping member may be pivotally affixed to a swing arm. For example, the angular stopping member may be pivotally affixed to the second swing arm.

In operation, when the targeting member contacts an outside surface of the bone, the angular stopping member may be configured to support the guide channel. The angular stopping member may support the guide channel with respect to the access position. When the targeting member contacts the outside surface of the bone, the angular stopping member may be configured to support the guide channel along a longitudinal axis that is defined by the access position and a target site inside the bone. The target site may correspond to a tip of a target wire inserted into the bone. The guide channel may define a longitudinal axis of the implantation region.

When, in operation, the targeting member contacts an outside surface of the bone, the angular stopping member may be configured to support the guide channel at an angle to a longitudinal axis of the bone. The angle may be oblique. The angle may correspond to an angle between the longitudinal axis of the bone and a longitudinal axis of the implantation region. For example, the angle may be less than 90 degrees and greater than 5 degrees.

The angular stopping member may include a pair of opposing slots. A swing arm may be pivotally affixed to the angular stopping member by a pin that passes through the swing arm and into the pair of opposing slots. The pin may translate within the opposition slots. In operation, when the targeting member contacts the outer surface of the bone, movement of the pin in the opposing slots may adjust an angle between the guide channel and the longitudinal axis of the bone.

The apparatus may include, and the methods may involve, apparatus for identifying an access position on an outer surface of a bone. The apparatus may include a base member. The base member may be elongated. The base member may include a first sleeve. The first sleeve may be configured to slide over a length of a fixation element that is operational external to the bone. The fixation element may be a target wire. The base member may include a second sleeve. The second sleeve may be positioned at a proximal end of the base member. The apparatus may include a curved member. The curved member may be slidably mounted in the second sleeve.

When the first sleeve is positioned over the fixation element, the curved member may be configured to indicate the access position. When a tip of the fixation element is positioned inside the bone, an end of the curved member may be positioned on a circumference of a circle centered at the tip.

The fixation element may be inserted into the bone in a direction that, with respect to the bone, is lateral to medial. An end of the curved member may include a guide. The guide, when positioned at the at the access position, may indicate an angular direction for inserting an implant into the bone.

The angular direction may be aligned along a diameter of the circle centered at the tip of the target wire. A radius of the circle centered at the tip of the target wire may correspond to a length of the implant. The access position may lie on a circumference of the circle centered about the tip of the target wire when the tip is operationally inside the bone.

The curved member may be configured to indicate an access position on the circumference independent of a position of the base member with respect to a longitudinal axis of the bone. The curved member may be configured to indicate the access position independent of an angle between a longitudinal axis of the fixation element (when a tip of the fixation element is operatively inside the bone) and a longitudinal axis of the bone.

When the first sleeve is positioned over a portion of the fixation element that is operatively external to the bone, a longitudinal axis of the first sleeve may be positioned substantially perpendicular to a longitudinal axis of the bone. When the first sleeve is positioned over a portion of the fixation element that is operatively external to the bone, a longitudinal axis of the first sleeve may be positioned at an oblique angle to a longitudinal axis of the bone. When the bone is a humerus, a longitudinal axis of the implantation region passes through a head of the humerus.

The apparatus may include, and the methods may involve, apparatus for a guide for directing a fixation element into a tail of an implant. A fixation element may be a K-wire, anchor, screw or any suitable fixation device. The implant may be positioned inside a bone. The bone may be any suitable bone. For example, the bone may be any of the bones show below in FIG. 3. The tail may define a hole for clearance of a fixation element. The guide may include a guide tube. The guide may include a collar. The guide may include a bracket. The bracket may include a first end that holds the collar. The bracket may include a second end that holds the guide tube. The bracket may orient a longitudinal axis of the collar substantially perpendicular to a longitudinal axis of the guide tube.

The guide may be configured to cooperate with a shaft of an implant. The shaft may be tubular. The shaft may be elongated. The shaft may be configured to slide concentrically into the collar of the guide. The shaft may include a first end that is configured to engage the tail of the implant. The shaft may include a second end that is configured to engage the collar of the guide. When the first end of the shaft is engaged with the tail and the second end of the shaft is engaged with the collar, the guide tube may be aligned with the hole defined by the tail of the implant.

When the guide tube is aligned with the hole defined by the tail, the guide tube may direct an anchor through the bone and through the clearance hole defined by the tail. When the implant is deployed in the bone, the clearance hole may be positioned below an outer surface of the bone. When the implant is deployed in the bone, the clearance hole may not be visible from a vantage point outside the bone.

The hole may be a first hole. The tail may define a second hole. The first and second holes may define an emplacement axis. When the tail is circular, the emplacement axis may correspond to a diameter of the tail. A longitudinal axis of a fixation element positioned within the first and second holes may be aligned with the emplacement axis. When a first end of the implant shaft is engaged with the tail and a second end of the elongated implant shaft is engaged with the collar of the guide, a longitudinal axis of the guide tube may be aligned along the emplacement axis.

The second end of the bracket may include a passageway. The passageway may hold the guide tube. The passageway may orient the guide tube relative to the collar.

The passageway may define a longitudinal axis. The guide tube may be slidable in the passageway along the longitudinal axis. When the collar is engaged with the implant shaft, the guide tube may be slidable within the passageway between the bracket and the bone.

The guide tube may include a first flanged end. The guide tube may include a second flanges end. The first flanged end and the second flanged end may be spaced apart from each other along a longitudinal axis of the guide tube. The first and second flanged ends may prevent the guide tube from sliding out of the passageway.

The second end of the bracket may include a gasket. The gasket may be positioned in the bracket such that the gasket surrounds the guide tube when the guide tube in positioned in the passageway. The gasket may provide a friction fit that holds the guide tube at a position along a longitudinal axis of the passageway.

When the implant shaft is engaged with the collar, the guide tube may define a longitudinal axis that is substantially perpendicular to the implant shaft.

The guide tube may be a first guide tube. The second end of the bracket may hold a second guide tube. The second end of the bracket may include a first passageway and a second passageway. The first guide tube may be slidably mounted in the first passageway. The second guide tube may be slidably mounted in the second passageway.

A first end of the elongated implant shaft may engage a tail of the implant. A second end of the implant shaft may engage the collar. A clearance hole may be defined by the tail. The clearance hole may be a first hole. The bracket may align a first guide tube with the first hole defined by the tail. The bracket may align the second guide tube with a second hole defined by the tail.

The collar may include a key. The implant shaft may include a keyseat. The key may be configured to be releasably seated in the keyseat. The key may be configured to be releasably seated in the keyseat when the implant shaft is inserted into the collar. When the key is seated in the keyseat, the implant shaft may be axially and rotationally locked with respect to the collar.

The key may be a releasable key. The collar may include a static key. The implant shaft may include a slot that is configured to receive the static key. Engagement of the static key and the slot may be configured to align the releasable key with the keyseat. When the implant shaft is engaged with the tail of the implant, seating the key of the collar in the keyseat of the implant shaft may align the longitudinal axis of the guide tube with a clearance hole and/or an emplacement axis of the tail.

The implant shaft may include a first keyseat. The implant shaft may include a second keyseat. Seating a key of the collar in the first keyseat may space the collar a first distance apart from an end of the implant shaft. Seating a key of the collar in the second keyseat may space the collar a second distance from an end of the implant shaft. The end of the implant shaft may be the first end that is configured to engage the tail.

Apparatus are provided for directing fixation element from outside a bone, through the bone and into a volume defined by an implant positioned inside the bone. The volume maybe defined by an expandable web (alternatively referred to herein as expandable mesh or cage) of the implant. The implant may be positioned inside the bone. Apparatus may include an implant shaft. The implant shaft may be tubular. The implant shaft may define a longitudinal axis. The implant shaft may be configured to engage an implant positioned inside the bone. The implant shaft may engage a tail of the implant. The implant shaft may extend outside the bone.

Apparatus may include a collar that is configured to slidably engage the implant shaft. The collar may slide over the implant shaft. The collar may slidably engage the implant shaft at a position on the implant shaft that is operatively outside the bone.

The apparatus may include a boom. The boom may include an elongated passageway;

The apparatus may include a neck. The neck may include a first end. The first end of the neck may be fixed to the collar. The neck may include a second end. The second end of the neck may be fixed to the boom. When the collar is slidably engaged with the implant shaft, the elongated passageway may be positioned to direct a fixation element from outside the bone, through the bone and into the volume defined by the implant.

The boom may be positioned on the neck such that that the fixation element does not contact a central axis member of the implant. For example, the neck may position the boom to be "off center" with respect to a central longitudinal axis of the implant. The neck may position the boom such that the passageway is spaced apart from the central axis member of the implant.

When the collar is slidably engaged with the implant shaft, the elongated passageway maybe positioned substantially parallel to the implant shaft. The elongated passageway may be configured to direct a fixation element into the volume defined by the implant. When the collar is slidably engaged with the implant shaft, the elongated passageway may be configured to direct a fixation element into the volume defined by the implant at or near a center longitudinal axis of the implant.

When the collar is slidably engaged with the implant shaft, the elongated passageway maybe configured to direct a fixation element into the volume defined by the implant such that the fixation element is deflected by a center axis member of the implant.

The collar may be rotatable about the implant shaft. Rotating the collar about the implant shaft may position the elongated passageway about an outer perimeter of the volume defined by the implant.

The boom may be pivotally affixed to the neck. The boom may be pivotally affixed to the neck such that a longitudinal axis defined by the passageway is oriented at an oblique angle with a longitudinal axis defined by the implant shaft.

When a fixation element passes through the elongated passageway and into the bone, the boom may be configured to pivot such that fixation element is no longer within the elongated passageway (without removing the fixation element from the bone). After pivoting the boom, the collar may be rotatable at least 180 degrees about the implant shaft. After pivoting the boom, the collar may be rotatable 360 degrees about the implant shaft.

The collar may include a pair of kerfs. The pair of kerfs may separate a first trough from a second trough. When the collar is sildably engaged with the implant shaft, the first and second troughs may be spread apart by the implant shaft. When the collar is sildably engaged with the implant shaft, the first and second troughs may apply pressure to an outer surface of the implant shaft. The pressure applied by the first and second troughs may provide a friction fit that holds the collar in a position about the longitudinal axis of the implant shaft.

The apparatus may include, and the methods may involve, a washer. The washer may be a surgical washer that is implantable in a human body. The washer may define a central aperture. The central aperture may have a circumference. The washer may define an offset aperture. The offset aperture may be spaced apart from the central aperture at a position with respect to the circumference of the central aperture.

The central aperture may have a diameter that is larger than a diameter of the offset aperture. The washer may include solid material that joins the offset aperture to the central aperture. The washer may include a second offset aperture. The washer may include two or more offset apertures. The second offset aperture may be spaced apart from the central aperture and spaced apart from the first offset aperture. The central aperture and an offset aperture form a figure eight shape.

The apparatus may include, and the methods may involve, a suturable washer. The suturable washer may include an inner circumference that defines a central aperture. The suturable washer may include an outer perimeter that encloses the inner circumference. The outer perimeter may define a non-circular shape. The suturable washer may include solid material between the inner circumference and the outer perimeter. The suturable washer may include an offset circumference that is enclosed by the outer perimeter. The offset circumference may define an offset aperture.

The suturable washer may include solid material between an arc length of the offset circumference and a corresponding length of the outer perimeter covering the arc length. The solid material may vary in thickness between the arc length of the offset circumference and the length of the outer perimeter covering the arc length.

The suturable washer may include a first thickness of solid material between a first arc length of the offset circumference and a corresponding first length of the outer perimeter covering the first arc length. The suturable washer may include a second thickness of solid material between a second arc length of the offset circumference and an arc length of the inner circumference opposing the second arc length. The second thickness may be greater than the first thickness.

The suturable washer may include a uniform thickness of solid material between a first arc length of the offset circumference and a corresponding length of the outer perimeter covering the first arc length. The suturable washer may include a variable thickness of solid material between a second arc length of the offset circumference and an arc length of the inner circumference convexly opposing the second arc length.

An offset circumference may be a first offset circumference. The suturable washer may include a second offset circumference that is enclosed by the outer perimeter. The second offset circumference may define a second offset aperture. The first offset circumference may be equal in length to the second offset circumference.

The suturable washer may include a first segment of solid material between a first arc length of the first offset circumference and a corresponding length of the outer perimeter covering the first arc length. The suturable washer may include a second segment of solid material between a second arc length of the second offset circumference and a corresponding second length of the outer perimeter covering the second arc length.

The first segment of solid material may be spaced apart from the second segment of solid material. The spacing may be defined by the outer perimeter. The first arc length may be positioned convexly opposing the second arc length. A distance spacing the first segment of solid material apart from the second segment of solid material may vary along the convexly opposing first and second arc lengths. A distance spacing the first segment of solid material apart from the second segment of solid material may vary along the outer perimeter.

The suturable washer may include a first arc length of the first offset circumference that is positioned convexly opposing a second arc length of the inner circumference. The suturable washer may include a third arc length of the second offset circumference that is positioned convexly opposing a fourth arc length of the inner circumference.

The suturable washer may include solid material between an arc length of the offset circumference and an arc length of the inner circumference convexly opposing the arc length of the offset circumference. Solid material may vary in thickness between an arc length of the offset circumference and a convexly opposing arc length of the inner circumference.

The suturable washer may include an offset aperture that is moveable about an axis. The axis may be tangential to an inner circumference that defines the central aperture and tangential to an offset circumference. The axis may be a longitudinal axis that passes between an inner circumference and an offset circumference. An offset aperture may be bent to allow for sutures to be threaded through the offset aperture. The offset aperture may be bent after a fixation element is inserted into the central aperture. A fixation element inserted into the central aperture may engage the bone and affix the washer to the bone.

An inner circumference that defines central aperture may also define a first plane. An outer perimeter of a washer may define a second plane. The first plane may be spaced apart from the second plane. The first plane may be substantially parallel to the second plane.

In operation, when the washer is positioned on an outside surface of a bone, the outer perimeter of the washer may be positioned closer to the bone than a central aperture of the washer. A distance spacing the outer perimeter apart from the central aperture may correspond to a distance spacing the first plane apart from the second plane.

In operation, when a washer is positioned on an outside surface of a bone, a central aperture of the washer may be positioned closer to the bone than the outside perimeter of the washer. A distance spacing the outer perimeter apart from the central aperture may correspond to a distance spacing the first plane apart from the second plane.

In operation, when suturable washer is positioned on an outside surface of a bone, the outer perimeter may be positioned closer to the bone than the central aperture. A distance spacing the outer perimeter apart from the central aperture may correspond to a distance spacing the first plane apart from the second plane.

An inner circumference that defines the central aperture may also define a first plane. An offset circumference may define a second plane. The first plane may be positioned at an oblique angle to the second plane.

The apparatus may include, and the methods may involve, an implantable, suturable washer. The washer may define a central aperture. The central aperture may include a central circumference. The washer may define an offset aperture. An offset aperture may include an offset circumference. The offset aperture may be fixed at a position along the central circumference.

The offset aperture may be a first offset aperture. The position may be a first position. The washer may define a second offset aperture. The second aperture may be fixed at a second position along the central circumference.

The central circumference of the washer may define a central plane. The offset circumference of the offset aperture may define an offset plane. The offset aperture may be moveable with respect to the central aperture. The offset aperture may be moveable with respect to the central aperture when the central aperture is fixed to the bone. The offset aperture may be moveable with respect to the central aperture such that movement of the offset aperture changes an angle between the central plane and the offset plane. The offset aperture may be moveable with respect to the central aperture such that movement of the offset aperture does not change the position of the offset aperture with respect to the central circumference.

First and second offset apertures may each be independently moveable with respect to the central aperture. A washer may include two or more offset apertures. Each of the offset apertures may be moveable with respect to the central aperture.

The apparatus may include, and the methods may involve, an implantable, suturable washer. The washer may include a central aperture that defines a central plane. The central aperture may be defined by a central circumference. The washer may include a flanged outer skirt. The flanged outer skirt may encircle the central aperture. The flanged outer skirt may define an outer plane.

The washer may include a mid-section. The mid-section may extend between the central aperture and the flanged outer skirt. The mid-section may space the central plane apart from the outer plane. The mid-section may define a surface. A slope of the surface may vary between the central plane and the outer plane.

The washer may include a plurality of offset apertures. The plurality of offset apertures may be distributed circumferentially around the central aperture. Each of the plurality of offset apertures may include an offset circumference. The mid-section of the washer may include a first arc length of the offset circumference. The flanged outer skirt of the washer may include a second arc length of the offset circumference.

A washer may include a rim surrounding the central aperture. In operation, when a fixation element, such as an anchor, is driven through the central aperture into a bone, the rim may be pressed against the bone by a head of the anchor.

In operation, when an anchor is driven through the central aperture into a bone, the flanged outer skirt and the mid-section of the washer may space the rim apart from the bone. In operation, when an anchor is driven through the central aperture of the washer into a bone, the mid-section of the washer may be positioned concavely facing an outer surface of the bone.

In operation, when an anchor is driven through the central aperture of the washer into a bone, the mid-section of the washer may be positioned convexly facing an outer surface of the bone. When the mid-section is convexly facing the outer surface of the bone, an offset aperture of the washer may be spaced apart from the bone.

Apparatus for coupling an implant positioned inside a bone to a tool positioned outside the bone is provided. The apparatus may include a tail of the implant. The tail may include an internally threaded segment. The tail may include a beveled segment.

The apparatus may include an implant shaft. The implant shaft may be a hollow implant shaft. The implant shaft may include a beveled segment. The beveled segment of the implant shaft may be configured to mate with the beveled segment of the tail. The implant shaft may include a flange positioned inside the implant shaft. The flange may define an aperture.

The apparatus may include a locking screw. The locking screw may be cannulated. The locking screw may include a threaded segment. The threaded segment may slide past the flange inside the hollow tube when the locking screw is inserted into the hollow implant shaft. For example, the major diameter of the threaded segment of the locking screw may be less than a diameter of the aperture defined by the flange.

The locking screw may include a shoulder. The shoulder may abut the flange when the locking screw is inserted into the implant shaft. When the locking screw is inserted into the implant shaft and the threaded segment of the locking screw engages the internally threaded segment of the tail, the locking screw may axially lock the implant shaft to the tail.

The implant shaft may include one or more fingers protruding from the beveled segment of the implant shaft. The tail may include one or more indentations that are configured to mate with the one or more fingers of the implant shaft. When the locking screw threadedly engages the tail, the one or more fingers may mate with the one or more indentations. When the one or more fingers mate with the one or more indentations, the implant shaft may be rotational fixed with respect to the tail.

Apparatus and methods for repairing a bone are provided. The bone may be fractured. Apparatus and methods may be used to repair the fracture. For example, apparatus and methods may be used to reduce the fracture. Apparatus and methods may be used to maintain a reduction of fracture.

Apparatus may include the implant. The implant may include the implant tail. The implant may include the implant head. The tail may be expandable. The tail may be configured to self-expand. The tail may be non-expandable.

The implant may have a collapsed state. In the collapsed stated, the implant may have a uniform diameter. The head may be expandable. The head may be configured to self-expand. The head may not be expandable.

The head may be configured to expand, inside the bone from a collapsed state into an expanded state.

Apparatus may include an intramedullary rod. The rod may define a central longitudinal rod axis. The rod may define an outer surface. The outer surface may be any suitable surface.

The rod may define a cylindrical outer surface. The rod may define a conical outer surface. The rod may include a first segment that defines a cylindrical outer surface and a second segment that defines a conical outer surface.

The rod may include a guide segment. The guide segment may be configured to guide an implant head into the bone. The guide segment may be configured to support the implant tail. The guide segment may support the implant tail after the implant head is positioned inside the bone.

The rod may include an elongated extension member. The elongated extension member may be spaced radially apart from the central longitudinal rod axis. The elongated extension member may be configured to provide clearance, with respect to an outer surface of the rod, for tools inserted into the bone. Without the clearance provided by dimensions of the elongated members, the tools would be obstructed by an outer surface of the rod. Exemplary tools may include a drill, implant, wire, anchor, reamer, guide tube or any other suitable tool may be inserted into the bone to repair the bone.

For example, the elongated extension member may provide clearance for the implant head as the implant head is advanced, in the collapsed state, through the guide segment into the bone. The elongated member may provide clearance that allows the implant head to be positioned inside the bone without being obstructed by an outer surface of the rod.

The elongated extension member may provide clearance for the implant head in the expanded state. The elongated member may allow the implant head to expand without being obstructed by an outer surface of the rod.

The rod further may include a ring-shaped segment. The ring-shaped segment may bridge between the guide segment and the elongated extension member. The central longitudinal rod axis may pass through the ring-shaped segment. The central longitudinal axis may pass through an aperture of the ringed-shaped segment. The ringed-shaped segment may be part of the guide segment.

The rod may define a cylindrical volume.

The guide segment may be defined by a conical-shaped volume subtracted or removed from the cylindrical volume. A diameter of a base of the conical-shaped volume may have a diameter that is less than a diameter of the cylindrical volume.

The implant tail may include a first anchor receiving feature. The guide segment may include a guide surface defining a central longitudinal guide axis. The guide segment may include a second anchor receiving feature. The second anchor receiving feature may define a central longitudinal anchor axis. The central longitudinal anchor axis of the second anchor receiving feature may be perpendicular to, or substantially perpendicular to, the central longitudinal guide axis.

In operation, the implant tail may be supported by the guide surface. The implant tail may be supported by the guide surface such that the first anchor receiving feature and the second anchor receiving feature are aligned to receive the same anchor. Targeting tools positioned outside the bone may direct the anchor into the first anchor receiving feature and into the second anchor receiving feature.

The rod may include an outer surface. The outer surface may define a cylindrical surface. The outer surface may define a conical surface.

The rod may include a first body segment. The first body segment may extend along a first length of the central longitudinal rod axis. The first body segment may define a uniform diameter along the first length. The rod may include a second body segment. The second body segment may extend along a second length of the central longitudinal rod axis. The second body segment may define a diameter that varies along the second length.

The guide segment may include an inner radius. The guide segment may include an outer radius. The guide segment may include a guide surface. The guide surface may be defined by a thickness between the inner and outer radii. The guide surface may be defined by a cylindrical surface that intersects the guide segment.

The cylindrical guide surface may be an oblique, cylindrical surface. The cylindrical guide surface may have a diameter greater than a maximum diameter defined by the guide segment. The cylindrical guide surface may have a diameter smaller than a maximum diameter defined by the guide segment.

A length of the rod may be cannulated. A cannulated length of the rod may be threaded. The guide segment may have a length. A length of the guide segment may extend along the central longitudinal rod axis. A length of the guide segment may be cannulated. A length of the guide segment may be threaded.

The rod may include a first cannulated length. The rod may include a second cannulated length. The second cannulated length may be threaded. The second cannulated length may be spaced apart from the first length, along the central longitudinal rod axis, by a third length. The elongated extension member may extend along the third length.

The central longitudinal rod axis may intersect the central longitudinal guide axis at an angle. The angle of intersection may define a slope of the guide surface. For example, if the angle of intersection is θ, the slope of the guide surface may be defined as tan(θ). The angle of intersection may be any suitable value. For example, the angle of intersection may be less than 90 degrees. The angle of intersection may be between 45 and 15 degrees.

An outer surface of the rod may define a cylindrical surface. The cylindrical surface may be a first cylindrical surface. The implant, in the collapsed state, may define a second cylindrical surface. A diameter of the second cylindrical surface may be smaller than a diameter of the first cylindrical surface.

The guide segment may define a cylindrical outer surface. The elongated extension member may include the cylindrical outer surface. The elongated extension member may include an outer arc length. The outer arc length may be less than a maximum circumference of the cylindrical outer surface. The arc length may be less than half of the maximum circumference. The elongated extension member may have a thickness. The thickness may be less than a radius of the cylindrical outer surface.

The elongated extension member may define a length along the central longitudinal rod axis. The elongated extension member may define an outer surface area. The outer surface area defined by the elongated extension member may be less than an outer surface area of the length of the guide segment along the central longitudinal axis.

The elongated extension member may include a first mating feature. The first mating feature may be configured to mate with a second mating feature. The rod may be a first rod. A second rod may include the second mating feature. The first rod may be inserted into the bone. The second rod may extend from inside the bone outside the bone. Mating of the first and second mating features may allow force to be transferred the first rod.

The force may be applied to the second rod. The force may be transferred from the second rod to the first rod. The force may be transferred from the second rod to the first rod via the elongated extension member of the first rod. The force may be transferred from the second rod to the first rod along a central longitudinal rod axis of the first rod. The force may be transferred to the first rod without deforming the first rod. In operation the force transferred to the first rod may be sufficient to drive the first rod into the bone.

A mating feature may define a depression. The depression may be defined relative to an outer surface of a rod. A first mating feature may include a first depression. The first mating feature may include a second depression. The second depression may be spaced apart from the first depression. The second depression may be spaced apart from the first depression along a central longitudinal axis of the rod.

The elongated extension member may include an anchor receiving feature. The first depression may be spaced apart from the second depression by a diameter of the anchor receiving feature. The anchor receiving feature may be threaded.

A mating feature may include a depression and an edge of the elongated extension member. The edge of the elongated extension member may be an end of the rod. A mating feature may define an aperture in the elongated extension member. A mating feature may include a protrusion. The protrusion may extend from an outer surface of the rod.

The rod may include a third mating feature. The third mating feature may be configured to mate with a tool positioned outside the rod.

The rod may include a tapered segment. The tapered segment may be configured to displace tissue inside the bone. In operation, as the rod is inserted into the bone, the tapered segment may displace tissue inside the bone. A guide segment of the rod may define a longitudinal guide axis. The longitudinal guide axis may be oblique to a central longitudinal axis of the rod. The elongated extension member may define a longitudinal extension axis. The longitudinal extension axis may be parallel to, or substantially parallel to, the central longitudinal rod axis.

The rod may include a plurality of anchor receiving features. The plurality of anchor receiving features may include a first anchor receiving feature. The first anchor receiving feature may define a first longitudinal axis. The first longitudinal axis may be oblique to a central longitudinal rod axis.

The plurality of anchor receiving features may include a second anchor receiving feature. The second anchor receiving feature may define a second longitudinal axis. The second longitudinal axis may be oblique to the central longitudinal rod axis.

The first longitudinal axis (defined by the first anchor receiving feature) may be positioned in a first plane. The first plane may be perpendicular to, or substantially perpendicular to, the central longitudinal rod axis. The second longitudinal axis (defined by the second anchor receiving feature) may be positioned in a second plane. The second plane may be parallel to, or substantially parallel to, the first plane and perpendicular to, or substantially perpendicular to, the central longitudinal rod axis.

The first longitudinal axis (defined by the first anchor receiving feature) may intersect the second longitudinal axis (defined by the second anchor receiving feature).

The plurality of anchor receiving features may include a third anchor receiving feature. The third anchor receiving feature may define a third longitudinal axis. The third longitudinal axis may be oblique to the central longitudinal rod axis and transverse to the first and second planes.

Methods for repairing a bone are provided. The repairing may include reducing a fracture in the bone. The methods may include maintaining a reduction of the fracture and promoting healing of the fracture.

Methods may include positioning a first rod perpendicular to, or substantially perpendicular to, a longitudinal axis of a second rod. Methods may include locking the first rod to the second rod. The locking may include driving an anchor, guided by a cannulated segment of the second rod, into a threaded anchor receiving feature of the first rod. The first rod may be locked to second rod outside the bone.

Methods may include inserting the first rod into an intramedullary cavity of the bone. Methods may include inserting the first rod into the bone though an articular surface-region of the bone. Methods may include inserting the first rod into the bone through any desirable accessible region of the bone.

Inserting the first rod into the bone may include applying a force to the second rod. The second rod may be locked to the first rod such that the force drives the first rod into the bone without deforming the first rod. The mating of the first and second mating features may reduce likelihood that the force applied to the second rod deforms the first rod.

The inserting may include driving the first rod into a femur along a femoral-shaft axis of the femur. The inserting may include driving the first rod into a humerus along a longitudinal axis defined by the humerus.

Methods may include securing targeting tools to the second rod. Methods may include using the targeting tools, securing the first rod to the bone.

Methods may include using one or more apertures in the targeting tools and positioning an anchor in a receiving feature of the first rod. The positioning may include mating a first mating feature of the first rod with a second mating feature of the second rod. The mating may include fitting the first mating feature into the second mating feature. The mating may include fitting the second mating feature into the first mating feature.

Methods may include positioning a joint linking the first rod to the second rod inside the bone. Methods may include affixing the targeting tools to the second rod outside the bone. Methods may include using the targeting tools, guiding a drill into the bone. Methods may include using a guide surface of the first rod, guiding the drill into the bone.

Methods may include using the targeting tools, guiding a reamer into the bone. Methods may include using a guide surface of the first rod, guiding the reamer into the bone.

Methods may include using the targeting tools guiding an anchor into an anchor receiving feature of the first rod that is obscured by an outside surface of the bone.

Methods may include positioning the implant inside the bone. Methods may include expanding the implant inside the bone. Methods may include using the targeting tools, securing the expandable implant to the bone.

Methods may include using a guide surface of the first rod, positioning the implant inside the bone. Methods may include securing the implant to the first rod. The implant may be secured to the first by driving an anchor from an outside on the bone, into the bone through the implant and through the first rod. The anchor may be guided into the bone, implant and rod using the targeting tools secured to the second rod.

The bone may be any suitable bone Si (see Table 5, below). For, example, the bone may be a humerus. The bone may be a femur. Methods may include securing the implant to a humerus such that a central longitudinal axis of the implant is positioned, relative to a central longitudinal axis of the first rod, at an angle that conforms to an angle of inclination of the humerus.

Methods may include securing the implant to a humerus such that a central longitudinal axis of the implant is positioned, relative to a central longitudinal axis of the humerus, at an angle that conforms to an angle of inclination of the humerus.

Methods may include expanding the implant within a head region of a bone. For example, methods may include expanding the implant within a head region of humerus. Methods may include expanding the implant within a head region of femur.

The bone may be a femur. Methods may include securing the implant to a femur such that a central longitudinal axis of the implant is positioned, relative to a central longitudinal axis of the rod, at an angle that conforms to an angle of inclination of the femur. Methods may include securing the implant to a femur such that a central longitudinal axis of the implant is positioned, relative to a central longitudinal axis of the femur, at an angle that conforms to an angle of inclination of the femur.

Methods may include affixing a third rod to the first rod. The third rod may be affixed to the first rod such that a central longitudinal axis of the first rod is parallel to, or substantially parallel to, a central longitudinal axis of the third rod. Methods may include securing targeting tools to the third rod. The targeting tools may be secured to the third rod outside the bone. A joint linking the first rod to the third rod may be positioned inside the bone.

Methods may include removing the targeting tools after the first rod is secured to the bone. Methods may include removing the second rod after the first rod is secured to the bone. Methods may include removing the second rod and the targeting tools after the first rod and the implant are secured to the bone.

Methods may include using a guide surface of the first rod, inserting the implant into the bone. The implant may be inserted into the bone using an access hole in cortical bone. A practitioner may provide access to the guide surface after the first rod is inserted into the bone by drilling the access hole. A drill used to form the access hole may be guided by a guide surface of the targeting tools secured to the second rod.

The targeting tools may be secured to the second rod by aligning a cut-out in the targeting tools with a rib that protrudes from an outer surface of the second rod. The targeting tools may be secured to the second rod by positioning a set screw of the targeting tools into a cut-out in the rib.

The apparatus may include, and the methods may involve, an elongated member. The elongated member may be configured to be coupled to the implant. The implant may include the implant tail.

The elongated member may include a sleeve. The sleeve may have a sleeve longitudinal axis. The apparatus may include an anchoring base. The anchoring base may be fixed to, and extend away from, the sleeve. The apparatus may include a threaded member. The threaded member may be fixed to the anchoring base and extend along the sleeve longitudinal axis. The threaded member may be spaced radially apart from the sleeve to define an annular space for receiving the implant tail.

The elongated member may not include a threaded member. The sleeve may be configured to be coupled to the implant tail using a snap-fit mechanism. The sleeve may define an inner threaded surface for screwing onto an outer threaded surface of the implant tail. The sleeve may be configured to be coupled to the implant tail by driving a screw through a hole defined by the sleeve and into a hole defined by the implant tail, the implant tail hole being coaxial with the sleeve hole.

The sleeve may define, transverse to the longitudinal axis, a constant outside diameter. The sleeve may define, transverse to the longitudinal axis, an outside diameter that varies along a length of the sleeve.

The anchoring base may define, transverse to an anchoring base longitudinal axis, a constant outside diameter. The anchoring base may define, transverse to an anchoring base longitudinal axis, an outside diameter that varies along a length of the anchoring base. The outside diameter may decrease along the length. A largest value of the outside diameter may be adjacent the sleeve.

The sleeve may define a first outside diameter transverse to the longitudinal axis. The anchoring base may define a second outside diameter, equal to the first outside diameter, transverse to the longitudinal axis.

The anchoring base may include a hollow mesh structure defining a plurality of openings. The anchoring base may define a base longitudinal axis. The mesh structure may extend circumferentially around the longitudinal axis. The mesh structure may have a first outside diameter transverse to a mesh longitudinal axis along a first portion of a length of the mesh structure and a second outside diameter, different from the first outside diameter, transverse to a mesh longitudinal axis along a second portion of the length of the mesh structure. The mesh structure may include a plurality of struts. The plurality of openings may be defined by the struts.

The anchoring base may include a first end. The anchoring base may include a second end, opposite the first end. The hollow mesh structure may be disposed between the first end and the second end. The sleeve may extend away from the first end. The second end may be tapered.

The anchoring base may define a hole. The hole may be a screw hole. A cross-section of the hole, transverse to a central axis of the hole, may be circular. The hole may have a first diameter parallel to an anchoring base longitudinal axis and a second diameter extending circumferentially about the anchoring base longitudinal axis, wherein the first length is at least double the second length. The hole may be a slot. The slot may be sized to receive an anchor. The anchor may be a screw.

The hole may be a first hole. The anchoring base may define a second hole, the second hole being spaced apart from the first hole along a longitudinal axis of the anchoring base. The first hole may have a first central axis pointing in a first direction. The second hole may have a second central axis pointing in a second direction different from the first direction. The second hole may have a second central axis pointing in a second direction perpendicular to the first direction. The second hole may have a second central axis pointing in a second direction parallel to the first direction.

The hole may be a first hole. The anchoring base may define a plurality of holes, the plurality of holes including the first hole. Each hole may be spaced apart from an adjacent hole along a longitudinal axis of the anchoring base.

The hole may be a first hole. The anchoring base may define a second hole extending through the anchoring base. The second hole may be spaced circumferentially apart, about an anchoring base longitudinal axis, from the first hole. A central axis extending through the first hole may transect a central axis extending through the second hole.

The anchoring base may include a first end and a second end opposite the first end. The anchoring base may include a plurality of longitudinal struts. Each strut may be coupled to, and extend between, the first and second end. Each strut may be and spaced apart from an adjacent strut circumferentially about an anchoring base longitudinal axis.

The apparatus may include the implant. The implant may include the implant head and the implant tail. The implant tail may include an inner threaded portion. The implant may include the implant base. The implant base may be positioned between the head and the tail. The implant tail may be sized to be seated in the annular space. The inner threaded portion may be threaded to mate with the threaded member. An inner face of the sleeve may have a circumference. An outer face of the implant tail may have the circumference. An outer face of the implant tail may have a circumference slightly smaller than the circumference.

In operation, the implant may be coupled to the elongated member, the implant tail may be seated in the annular space and the threaded member may engage the inner threaded portion. In operation, the implant may be coupled to the elongated member, the implant tail and a portion of the implant base may be seated in the annular space and the threaded member may engage the inner threaded portion. In operation, the implant may be coupled to the elongated member, the implant tail and the implant base may be seated in the annular space and the threaded member may engage the inner threaded portion.

The implant tail may be cylindrical. In operation, the implant may be coupled to the elongated member and the implant may fill the annular space. In operation, the implant may be coupled to the elongated member and the implant may fill a portion of the annular space.

The implant tail may have an angled face oblique to an implant tail longitudinal axis. In operation, the implant may be coupled to the elongated member and the implant may fill a portion of the annular space.

The implant tail may define a first hole and a second hole opposite the first hole across an implant tail longitudinal axis. The sleeve may define a third hole and a fourth hole across the sleeve longitudinal axis. In operation, the implant may be coupled to the elongated member and the first, second, third and fourth hole may be coaxial.

The sleeve and anchoring base, together, may be monolithic. The sleeve, threaded member and anchoring base, together, may be monolithic. The anchoring base and threaded member, together, may be monolithic.

The anchoring base may not define an opening.

The sleeve longitudinal axis may be coaxial with an anchoring base longitudinal axis. The sleeve longitudinal axis may be oblique to an anchoring base longitudinal axis.

The apparatus may include, and the methods may involve, a first expandable implant and a second expandable implant. The first expandable implant may be the implant. The second expandable implant may be the implant.

The first expandable implant may include a first base coupled to a first implant head. The first head, when expanded, may form a first mesh cage. The second expandable implant may include a second base coupled to a second implant head. The second head, when expanded, may form a second mesh cage. The first base may be configured to be coupled to the second base such that an outer face of the first base is positioned within an inner face of the second base.

In operation, the outer face of the first base may be positioned within the inner face of the second base and the first base may be coupled to the second base. An outer face of the first base may be threaded.

An inner face of the second base may be threaded to mate with the threads on the first base.

An inner face of the second base may be sized to receive an outer face of the first base.

The first base may define a protrusion. The second base may define a window. In operation, the outer face of the first base may be positioned within the inner face of the second base and the protrusion may extend through the window to couple the first base to the second base.

The second base may define a protrusion. The first base may define an opening. In operation, the outer face of the first base may be positioned within the inner face of the second base and the protrusion may extend through the opening to couple the first base to the second base.

In operation, the first base may be coupled to the second base, the first cage may define a first central axis and the second cage may define a second central axis coaxial with the first central axis. In operation, the first base may be coupled to the second base, the first cage may define a first central axis, and the second cage may define a second central axis oblique to the first central axis.

In operation, the first base may be coupled to the second base. The first head, when expanded, may define a first volume and the second head, when expanded, may define a second volume that is greater than the first volume. The first head, when expanded, may define a first volume and the second head, when expanded, may define a second volume that is different from the first volume.

The first implant may include a first shaft extending away from the first base. The second base may include a second shaft extending away from the second base. The first shaft may be configured to be coupled to the second shaft such that an outer face of the first shaft is positioned within an inner face of the second shaft.

The apparatus may include, and the methods may involve, the implant base having a first end and, opposite the first end, a second end. The apparatus may include a first mesh cage fixed to, and extending away from, the first end. The apparatus may include a second mesh cage fixed to, and extending away from, the second end. The first mesh cage may be expandable. The second mesh cage may be expandable.

The first mesh cage may be the implant head. The second mesh cage may be the implant head.

The base, the first and the second cage may together be formed from a monolithic laser-cut tube. The base and the first cage may together be formed from a first laser-cut tube. The second cage may be formed from a second laser-cut tube.

The first cage may define a first central axis. The second cage may define a second central axis coaxial with the first central axis. The second cage may define a second central axis oblique to the first central axis.

The implant base may define a hole. The hole may be a screw hole. The screw hole may be a first screw hole. The implant base may define a second screw hole.

The implant base may be cylindrical. The implant base may have an outside diameter perpendicular to a base longitudinal axis. The outside diameter may vary along a length of the base.

The first mesh cage may define a first volume. The second mesh cage may define the first volume. The second mesh cage may define a second volume different from the first volume.

The apparatus may include, and the methods may involve, a first mesh cage having a first hub and a first base. The apparatus may include a second mesh cage having a second hub and a second base. The apparatus may include a first elongated member extending between the first base and the second hub. The apparatus may include a second elongated member coupled to, and extending away from, the second base.

The first mesh cage may be expandable between a collapsed configuration and an expanded configuration. The second mesh cage may be expandable between a collapsed configuration and an expanded configuration.

The first mesh cage may be the implant head. The second mesh cage may be the implant head.

The first mesh cage may define a first central axis. The second mesh cage may define a second central axis. The first elongated member may define a third central axis. The second elongated member may define a fourth central axis. The first, second, third and fourth central axis may be coaxial.

The first elongated member may define a hole sized for receiving an anchor, such as a screw. The second elongated member may define a hole sized for receiving an anchor, such as a screw. The first elongated member may define a plurality of holes. The holes may be screw holes. The second elongated member may define a plurality of holes. The holes may be screw holes.

The first elongated member may include a hollow cylindrical mesh structure extending along a length of the first member. The mesh structure may extend circumferentially about a central axis of the first member. The second elongated member may include a hollow cylindrical mesh structure extending along a length of the second member. The mesh structure may extend circumferentially about a central axis of the second member.

The first mesh cage may define a first volume. The second mesh cage may define a second volume greater than the first volume. The second mesh cage may define the first volume.

The apparatus may include an intramedullary rod. The second elongated member may extend through a bore defined by the intramedullary rod.

The methods, which may involve the apparatus shown and described herein, may include a method for treating a bone having an interior. The method may include selecting a first implant having a first expandable mesh head and a first base. The method may include selecting a second implant having a second expandable mesh head and a second base. The method may include coupling the first base to the second base. The method may also include positioning the first and second implants in the interior.

The first implant may be the implant. The second implant may be the implant.

The positioning may be performed after the coupling. The positioning may be performed before the coupling.

The coupling may include threadingly engaging threads defined on an outer face of the first base with threads defined on an inner face of the second base. The coupling may include inserting the first base into the second base. The coupling may include advancing an inner face of the first base along an outer face of the second base.

The method may include, prior to the inserting, expanding the first expandable cage. The method may include, prior to the inserting, expanding the second expandable cage.

The method may include, after the inserting, expanding the first expandable cage. The method may include, after the inserting, expanding the second expandable cage.

The apparatus may include, and the methods may involve, a first intramedullary rod defining a screw hole having a central axis. The apparatus may include a second intramedullary rod configured to be coupled to the first rod. The apparatus may include the implant. The implant may be configured to be coupled to an end of the second rod. The implant may include the implant head that, when expanded, defines a volume. In operation, the second rod may be coupled to the first rod, the implant may be coupled to the second rod, the implant head may be in an expanded state and the central axis may point to the volume.

The hole may be a first hole and the central axis may be a first central axis. The first rod may define a second hole. The second hole may define a second central axis oblique to the first central axis. In operation, the second rod may be coupled to the first rod, the implant may be coupled to the second rod, the implant head may be in an expanded state and the second central axis may point to the volume. The first central axis may be parallel to the second central axis. The first central axis may be oblique to the second central axis.

The implant may include the implant base. The implant base may extend away from the implant head.

The end of the second rod may define an opening sized to receive the implant base.

An inner face of the implant base may include threads. An outer face of the end of the second rod may include threads configured to threadingly engage the threads on the inner face of the implant base.

An outer face of the implant base may include threads. The end of the second rod may define a threaded opening configured to threadingly engage the threads on the outer face of the implant base.

The implant may be a first implant. The expandable head may be a first expandable head. The apparatus may include a second implant. The second implant may include a second expandable head. The second implant may be configured to be coupled to an end of the second rod.

The second implant may include a base extending away from the second head. The end of the second rod may define an opening sized to receive the second implant base. The base may include threads, and the end of the second rod may be configured to threadingly engage the threads.

The end of the second rod may be a first end. The apparatus may include a third implant. The third implant may include a third expandable head. The third expandable head may be configured to be coupled to a second end of the second rod.

The third implant may include a base extending away from the third head. The second end of the second rod may define an opening sized to receive the third base. The base may include threads, and the second end of the second rod may be configured to threadingly engage the threads.

The apparatus may include, and the methods may involve, a cannulated intramedullary rod having a first end and a second end opposite the first end and the implant. The implant may be configured to be coupled to the first end. The implant may include the implant head, the implant tail and the implant base extending between the head and the tail. The apparatus may include an end cap configured to be coupled to the second end. The implant may be configured to be coupled to the first end such that the implant head extends away from the first end and the implant tail is seated in an interior of the rod.

The apparatus may include a threaded member coupled to, and extending away from, the end cap along a central axis of the end cap. An inner face of the implant tail may be threaded. The threaded member may be threaded to mate with the implant tail. In operation, the threaded member may extend through an interior of the rod, along a longitudinal axis of the rod, and may be engaged with the implant threaded surface.

The implant base may be a portion of the implant tail.

The methods, which may involve the apparatus shown and described herein, may include a method for repairing a bone. The bone may have a surface and an interior. The bone may have an elongated portion, a head including an articular surface, and a neck positioned between the elongated portion and the head.

The method may include placing a first intramedullary rod and the implant including a mesh cage coupled to an end of the first rod in the interior such that at least a portion of the mesh cage is positioned in the head. The method may include placing a second intramedullary rod in the interior such that the second rod extends along a length of the elongated portion. The placing may include coupling the second rod to the first rod.

The method may include advancing a screw through a hole defined by the second intramedullary rod. The method may include anchoring a distal end of the screw in the head of the articular surface. The anchoring may include driving the distal end into the mesh cage.

The method may include coupling the first rod to the implant. The implant may include a base extending away from the mesh cage. The base may include threads. The coupling of the mesh cage to the first rod may include threadingly engaging the base with a threaded portion of the first rod.

The method may include coupling the first rod to the implant. The implant may include a base extending away from the mesh cage. The coupling of the first rod to the implant may include positioning the base in an opening defined by the first rod.

The method may include threadingly engaging threads on a face of the hub with threads on a face of the rod. The method may include threadingly engaging threads on a face of the base with threads on a face of the rod.

When the mesh cage is an expandable mesh cage the method may include expanding the mesh cage. After the expanding, and before the placing of the first rod, the method may include coupling the mesh cage to the first rod.

When the mesh cage is an expandable mesh cage the method may include, after the positioning of the first rod and the implant in the head of the bone, expanding the mesh cage. The first rod may be cannulated. The implant may include an implant tail coupled to the mesh cage. Expanding the mesh cage may include advancing a threaded member along an interior of the first rod and engaging the threaded member with threads in an inner surface of the implant tail.

The method may include, after the expanding of the mesh cage, placing an end cap on a second end of the first rod, the second end being opposite the first end.

When the mesh cage is an expandable mesh cage the method may include expanding the mesh cage from a first volume to a second volume.

The coupling of the second rod to the first rod may include positioning the first rod in an opening defined by the second rod. The coupling of the second rod to the first rod may include positioning the second rod in an opening defined by the first rod.

When the screw is a first screw, the implant is a first implant, the mesh cage is a first mesh cage, and an end of the second rod is coupled to a second implant including a second mesh cage, the method may include advancing a second screw through the surface and into the second cage.

When the end of the second rod is a first end and a second end of the second rod is coupled to a third mesh cage, the method may include advancing a third screw through the surface and into the third cage When the screw is a first screw and the hole is a first hole, the method may include driving a second screw through a second hole defined by the second intramedullary rod. The method may also include anchoring a distal end of the second screw in the head. The anchoring may comprise driving the distal end of the second screw into the mesh cage.

The first screw may be advanced through the first hole along a first axis. The second screw may be advanced through the second hole along a second axis. The first axis may be parallel to the second axis. The first axis may be oblique to the second axis.

The methods, which may involve the apparatus shown and described herein, may include a method for repairing a bone having a surface and an interior. The bone may have an elongated portion, a head including an articular surface, and a neck positioned between the elongated portion and the head.

The method may include placing an intramedullary rod coupled to a mesh cage at an end of the rod in the interior such that at least a portion of a mesh cage is positioned in the head. The mesh cage may be the implant head. The method may include placing a plate on the surface. The placing may include coupling the plate to the rod. The method may include driving a screw through a hole defined by the plate. The method may also include anchoring a distal end of the screw in the head. The anchoring may comprise driving the distal end into the mesh cage.

The method may include, before the placing of the rod, coupling the mesh cage to the rod. The method may include, before the placing of the rod and the coupling of the plate to the rod, expanding the mesh cage. The method may include expanding the mesh cage in the interior.

The end of the rod may be a first end. The coupling of the plate and the rod may include placing a second end of the rod inside an opening defined by the plate. The second end may be opposite the first end.

When the screw is a first screw and the hole is a first hole, the method may include driving a second screw through a second hole defined by the plate. The method may also include anchoring a distal end of the second screw in the head, the anchoring comprising driving the distal end of the second screw into the mesh cage.

The first screw may be advanced through the first hole along a first axis. The second screw may be advanced through the second hole along a second axis. The first axis may be parallel to the second axis. The first axis may be oblique to the second axis.

The methods, which may involve the apparatus shown and described herein, may include a method for repairing a bone having a surface and an interior. The method may include placing an intramedullary rod in the interior. The method may include advancing an expandable implant through a lumen defined by an interior of the rod. The method may include positioning the expandable implant in the interior such that a head of the implant is in the interior. The method may include expanding the head to form a mesh cage. The method may include anchoring the rod to the bone. The anchoring may include driving a first screw through the surface and into the mesh cage.

The methods, which may involve the apparatus shown and described herein, may include a method for implanting an expandable implant in an interior of a calcaneus bone having a bone surface. The method may include making an incision in soft tissue covering a posterior facet of the bone below a termination point, on the bone, of an Achilles' Tendon. The method may include providing, through the incision, an access hole on the bone surface. The method may include advancing the expandable implant through the access hole and into the interior. The method may include positioning a distal end of the implant in the interior. The method may include expanding the implant in the interior to form a mesh cage. The implant may be expanded such that such that a first portion of the mesh cage is adjacent a sinus tarsi space and a second portion of the mesh cage is adjacent a distal facet of the bone.

When the incision is a first incision the method may include making a second incision in soft tissue covering a lateral side of the posterior facet of the calcaneus. The method may include visualizing a position of a sinus space relative to a talus bone through the second incision.

The method may include, after the expanding, anchoring a distal end of a screw in the interior. The anchoring may include driving the screw through the bone surface and advancing a distal tip of the screw into the mesh cage.

The method may include positioning a plate on the posterior facet of the bone. The method may include, after the expanding, driving a screw through a hole defined by the plate and into the mesh cage.

The positioning of the plate may be performed after the advancing the expandable implant into the interior. The positioning of the plate may be performed before the advancing of the expandable implant into the interior. The advancing may be performed through an opening in the plate.

The methods, which may involve the apparatus shown and described herein, may include a method for implanting an expandable implant in an interior of a calcaneus bone having a bone surface. The method may include forming a split in an Achilles's tendon extending along a posterior facet of the bone. The method may include making an incision, through the split, in soft tissue covering the posterior portion facet. The method may include providing, through the incision, an access hole on the bone surface. The method may include advancing the expandable implant through the access hole and into the interior. The method may include positioning a distal end of the implant in the interior. The method may include expanding the implant in the interior to form a mesh cage such that a portion of the mesh cage is adjacent a distal facet of the calcaneus.

When the incision is a first incision the method may include making a second incision in soft tissue covering a lateral side of the posterior facet of the calcaneus. The method may include visualizing a position of a sinus tarsi space relative to a talus bone through the second incision.

The method may include, after the expanding, anchoring a distal end of a screw in the interior. The anchoring may include driving the screw through the bone surface. The anchoring may include advancing a distal tip of the screw into the expandable implant.

The method may include positioning a plate on the posterior facet. The method may include driving a screw through a hole defined by the plate and into the implant.

The positioning of the plate may be performed after the advancing the expandable implant. The positioning of the plate may be performed before the advancing the expandable implant. The advancing may be performed through an opening in the plate.

The methods, which may involve the apparatus shown and described herein, may include a method for implanting an expandable implant in an interior of a calcaneus bone having a bone surface. The method may include making an incision in soft tissue covering a distal facet of the bone. The method may include providing, through the incision, an access hole on the bone surface. The method may include advancing the expandable implant through the access hole and into the interior. The method may include positioning a distal end of the implant in the interior and perpendicular to, or substantially perpendicular to, a longitudinal axis extending along a length of the bone. The method may include expanding the implant in the interior to form a mesh cage such that a hub of the implant is adjacent the talus.

When the incision is a first incision the method may include making a second incision in soft tissue covering a lateral side of a posterior facet of the calcaneus. The method may include visualizing a position of a sinus space relative to a talus bone through the second incision.

The method may include, after the expanding, anchoring a distal end of a screw in the interior. The anchoring may include driving the screw through the bone surface. The method may include advancing a distal tip of the screw into the expandable implant.

The method may include positioning a plate on the distal facet. The method may include driving a screw through a hole defined by the plate and into the implant.

The apparatus may include, and the methods may involve, a first mesh that defines a longitudinal axis and is expandable about the axis and a second mesh that is expandable about the axis between the axis and the first mesh. Each of the first and second mesh may be configured to be longitudinally fixed to a central axis member that lies along the axis. The first mesh may have a first stress-strain modulus corresponding to compression of the first mesh along a direction not parallel to the axis. The second mesh may have a second stress-strain modulus corresponding to compression of the second mesh along the direction. "Modulus" may be an "effective modulus," in that it may be an extrinsic property of the mesh, and may depend on one or more parameters, such as one or more of those shown in Table 3, or any other suitable parameters.

TABLE 3

| Illustrative modulus parameters |
| --- |
| Illustrative modulus parameters |
| Mesh thickness (wall thickness of tube, if mesh is made from a tube) |
| Mesh axial length (expanded state) |
| Mesh radius (expanded state) |
| Mesh void fraction (percent of mesh surface corresponding to void) |
| Mesh cell density |

The second modulus may be greater than the first modulus. The second modulus may be 1.5, 2, 2.5, 3, 3.5, 4, 4.5, 5, 5.5, 6, 6.6, 7, 7.5, 8, 8.5, 9, 9.5, 10, 10.5, 11, 11.5, 12, 12.15, 13, 13.15 or 14 times greater than the first modulus The first mesh may have a first thickness. The second mesh may have a second thickness. The second thickness may be greater than the first thickness.

The first mesh may be formed from a first material having a first stress-strain modulus corresponding to compression of the first mesh along a direction not parallel to the axis. The second mesh may be formed from a second material having a second stress-strain modulus corresponding to compression of the second mesh along the direction. The second modulus may be greater than the first modulus.

The first material may be formed from super elastic materials including nitinol, NiTiCu, titanium alloys, nickel alloys, spring steel alloys, carbon fiber composites, carbon-graphene, shape-memory polymers, polyisoprene-based polymers, calcium iron arsenide $CaFe_2As_2$ and similar materials. The second material may be formed from super elastic materials different from the first material including nitinol, NiTiCu, titanium alloys, nickel alloys, spring steel alloys, carbon fiber composites, carbon-graphene, shape-memory polymers, polyisoprene-based polymers, calcium iron arsenide $CaFe_2As_2$ and similar materials.

The first thickness may be in the range 0.010 in. to 0.020 in. The second thickness may be in the range 0.015 in. to 0.040 in.

Table 4 shows selected illustrative first and second thickness ranges.

TABLE 4

Selected illustrative first and second thickness ranges.
Illustrative thickness ranges (lower and upper limits, inclusive) (in.)

| First thickness | | Second thickness | |
|---|---|---|---|
| Lower | Upper | Lower | Upper |
| <0.010 | 0.011 | <0.015 | 0.015 |
| 0.011 | 0.012 | 0.015 | 0.016 |
| 0.012 | 0.013 | 0.016 | 0.017 |
| 0.013 | 0.014 | 0.017 | 0.018 |
| 0.014 | 0.015 | 0.018 | 0.019 |
| 0.015 | 0.016 | 0.019 | 0.02 |
| 0.016 | 0.017 | 0.02 | 0.021 |
| 0.017 | 0.018 | 0.021 | 0.022 |
| 0.018 | 0.019 | 0.022 | 0.023 |
| 0.019 | 0.020 | 0.023 | 0.024 |
| 0.020 | >0.020 | 0.024 | 0.025 |
| | | 0.025 | 0.026 |
| | | 0.026 | 0.027 |
| | | 0.027 | 0.028 |
| | | 0.028 | 0.029 |
| | | 0.029 | 0.03 |
| | | 0.03 | 0.031 |
| | | 0.031 | 0.032 |
| | | 0.032 | 0.033 |
| | | 0.033 | 0.034 |
| | | 0.034 | 0.035 |
| | | 0.035 | 0.036 |
| | | 0.036 | 0.037 |
| | | 0.037 | 0.038 |
| | | 0.038 | 0.039 |
| | | 0.039 | 0.04 |
| | | 0.040 | >0.04 |

The apparatus may include, and the methods may involve, the implant head that includes a mesh anchoring substrate that is expandable away from a longitudinal axis of the substrate, and the base. The base may define an opening for receiving along the axis an elongated support having a catch.

The apparatus may include the support. The support may be configured to engage a hub at an end of the substrate that is opposite the base. The apparatus may also include a latch extending from the base in a direction away from the substrate. The latch may be configured to engage the catch to prevent withdrawal of the elongated support from the base.

The latch may include an arm and a protrusion from the arm. The latch may be configured to insert the protrusion into a recess in the elongated support when the protrusion is positioned at the recess. The catch may define a limit of the recess.

The base may define a cylindrical outer surface at a first radius from the axis. The arm may have a length that is disposed at the first radius in a state in which the protrusion is in the recess. The length may be disposed at second radius that is greater than the first radius in a state in which the protrusion is in contact with the elongated member at a location outside the recess.

The elongated support may define a recess. The recess may include the catch.

The anchoring substrate may be pretreated to induce contraction of the substrate along the axis. The contraction may collapse the anchoring substrate. The contraction may increase frictional engagement between the latch and the wall.

The support may include a threaded member. The threaded member may be configured to reduce a length of the support by threaded engagement with an internally threaded cannulated member. Reduction of the length may expand the anchoring substrate.

The apparatus may include, and the methods may involve, the implant that includes a mesh anchoring substrate that is expandable away from a longitudinal axis of the substrate and the tail at an end of the substrate. The tail may be configured for sliding engagement in a slot of the plate. The slot in operation may fix the implant relative to the plate axially along the axis, rotationally about the axis, and rotationally about the plate.

The apparatus may include the plate. The plate may be keyed to a groove in the tail. The plate may define a clearance opening having a first width, and the slot, the slot having a second width that is less that the first width. The first width may be greater than a diameter of the tail. The second width may be less than the diameter. The second width may be greater than a thickness of the tail at the groove.

The groove may be a plurality of grooves. The grooves may define a sliding direction along which the plate is configured to slide for insertion of the tail in the slot. In operation the sliding direction may be oblique to the axis.

The apparatus may include, and the methods may involve, the implant head that includes a mesh anchoring substrate that is expandable away from an elongated central support and the support. The support may define a transverse bore that in operation is disposed between a first end of the substrate and a second end of the substrate.

The bore may be sized for clearance of a screw that is configured for penetration and engagement of the substrate. The bore may have a diameter that is 0.0005"-0.001" smaller than a thread diameter of a screw that is configured for penetration and engagement of the substrate. The thread diameter may be a largest thread diameter on the screw.

An inner face of the bore may include threads for threadingly engaging a screw that is configured for penetration and engagement of the substrate.

The methods, which may involve the apparatus shown and described herein, may include a method for treating a bone having a bone surface and a bone interior. The method may include one or more steps from any other method disclosed herein.

The bone may define a longitudinal axis. The bone may include a surface contour. The surface contour may extend along the bone surface between two or more points at different elevations from the longitudinal axis.

The method for treating a bone having a bone surface and a bone interior may include making an incision in soft tissue covering the bone surface. The method may include placing a jig in direct contact with the bone surface. The placing may include seating a bottom surface of the jig complementarily against the surface contour. The bottom surface of the jig may complement the surface contour.

Direct contact with the bone surface may encompass a method in which there is no apparatus intervening between the jig or the plate and the bone surface.

After placing the jig on the bone surface, the method may include driving a first fixation element through a first hole defined by the jig and into a first fragment of the bone. After placing the jig on the bone surface, the method may also include driving a second fixation element through a second hole defined by the jig and into a second fragment of the bone.

The method may include removing the jig from the bone surface prior to closing the incision.

The method may include providing an access hole on the bone surface. The method may include inserting an implant through the access hole and into the bone interior.

The method may include closing the incision.

The bone may be a humerus bone. A portion of the bone being treated may include a proximal portion of the humerus bone. Making the incision may include making a deltopectoral incision. Making the incision may include making a deltoid split incision.

When the bone is a proximal humerus bone, the surface contour may include a greater tuberosity. The surface contour may include an intertubercular groove. The surface contour may include a deltoid insertion. The placing the jig may include aligning a first portion of the bottom surface of the jig with the greater tuberosity. The placing the jig may include aligning a second portion of the bottom surface of the jig with the intertubercular groove. The placing the jig may include aligning a third portion of the bottom surface of the jig with the deltoid insertion.

When the bone is a proximal humerus bone, the placing the jig may include palpitating a location of a lateral condyle. The placing the jig may include determining a position on the bone surface along a longitudinal axis of the humerus bone. The position may be a predetermined distance from the lateral condyle. The placing the jig may include aligning a member of the jig with the position.

When the bone is a proximal humerus bone, the placing the jig may include radiographically aligning a member of the jig with a surgical neck of the humerus bone. The surgical neck may be located at a base of a head of a proximal portion of the humerus bone.

The method may include releasably anchoring the jig to the bone.

The first hole and the second hole may be included in a plurality of holes. The plurality of holes may be defined by the jig. The method may include providing a plurality of fixation elements. The method may include guiding each of the fixation elements through one of the plurality of holes and into the bone interior.

The first hole may be spaced apart from the second hole. The guiding may include guiding the first fixation element and the second fixation element into the bone interior along convergent paths. The guiding may include guiding the first fixation element and the second fixation element into the bone interior along divergent paths. The guiding may include guiding the first fixation element and the second fixation element into the bone interior along parallel paths.

The method may include radially expanding the implant in the bone interior to form a mesh cage. The expanded implant may occupy a volume in the bone interior. The guiding the fixation elements may provide clearance for the volume.

The method may include radially expanding the implant in the bone interior to form a mesh cage. The expanded implant may occupy a region. The region may not be intersected by the fixation elements.

The method may include, when the bone is a proximal humerus bone, driving a target wire through a targeting hole defined by the jig and toward a center of an interior of a head of the proximal humerus bone. The method may include positioning a tip of the target wire in the center of the interior of the head.

The method may include, when the bone is a proximal humerus bone, driving a target wire through a targeting hole defined by the jig and tangent to a top of a greater tuberosity of the proximal humerus bone.

The placing the jig may include, when the bone is a proximal humerus bone, positioning a target defined by the jig. The target hole defined by jig may be positioned to point in a direction that intersects with a center region on a head of the proximal humerus bone.

The method may include driving a target wire through a target hole defined by the jig.

The providing the access hole may include advancing a fixation element through the bone surface toward a space in the bone that was penetrated by a tip of the target wire. The tip of the target wire may be at least partially retracted prior to advancing the fixation element.

The providing the access hole may include selecting a location on the bone adjacent a demarcation point included on the jig. The providing the access hole may include advancing a fixation element through the selected location toward a space in the bone that was penetrated by a tip of the target wire.

The providing the access hole may include selecting a demarcation point included on the jig from a plurality of demarcation points. Each demarcation point may correspond to an implant having a length. The providing the access hole may also include advancing a fixation element through a location on the surface of the bone adjacent the selected demarcation point and toward a space in the bone that was penetrated by a tip of the target wire. The implant inserted in the bone interior may have a length associated with the selected demarcation point.

The providing the access hole may include coupling a targeting apparatus to the target wire. The providing the access hole may include guiding a pointer included in the targeting apparatus onto a location the bone surface. The providing the access hole may include advancing a fixation element through the location and toward a space in the bone that was penetrated by a tip of the target wire.

The providing the access hole may include coupling a targeting apparatus to the target wire. The providing the access hole may include guiding a pointer included in the targeting apparatus onto a location on the bone surface. The providing the access hole may include identifying an angle relative to the bone surface at which the pointer abuts the bone surface and extends away from the bone surface. The providing the access hole may include advancing a fixation element through the location, at the identified angle, and toward a space in the bone that was penetrated by a tip of the target wire.

The providing the access hole may include removing a fixation element extending through the bone surface, wherein a tip of the fixation element is positioned adjacent a tip of the target wire. The providing the access hole may include inserting a drill through an opening on the bone surface initiated by the fixation element and advancing the drill towards the tip of the target wire. The providing the access hole may include inserting a drill through an opening on the bone surface initiated by the fixation element and advancing the drill towards the target site.

The providing the access hole may include inserting a cannulated drill over a fixation element, wherein a tip of the fixation element is positioned adjacent a tip of the target wire. The providing the access hole may include advancing the drill along the fixation element and towards an end of the fixation element positioned adjacent the target site. The providing the access hole may include advancing the drill along the fixation element and towards the target site.

The method may include providing a cavity in the bone interior. The cavity may extend away from the access hole. The implant may be inserted through the access hole and into the cavity.

The providing the cavity may include advancing a cannulated drill over the fixation element and towards the target site. The providing the cavity may include inserting a cavity preparation device through the access hole. The providing the cavity may include expanding the cavity preparation device. The providing the cavity may include rotating the cavity preparation device to cut material in the bone interior.

The method may include inserting an implant through the access hole. The method may include advancing an end of the implant to the target site. The method may include radially expanding the implant in the cavity. The method may include positioning an end of the implant disposed in the interior at the target site. The method may include radially expanding the implant in the cavity to form a mesh cage. The method may include rotating the implant in the cavity.

The method may include decoupling a first handle from an implant shaft. The method may include coupling a second handle to the implant shaft. The method may include rotating the implant within the cavity. The rotating may be driven by rotation of the second handle.

The method may include anchoring the implant to the bone. The anchoring may include coupling an anchoring jig onto a shaft of the implant. The anchoring may include guiding a screw through the anchoring jig. The anchoring may include guiding a screw through the bone surface. The anchoring may include guiding a screw into a tail of the implant.

The anchoring jig may be a first jig. The anchoring may include decoupling the first anchoring jig from the shaft. The anchoring may include coupling a second anchoring jig onto the shaft. The anchoring may include guiding a plurality of fixation elements through an elongated passageway defined by the second anchoring jig and into a head of the implant.

The method may include driving cannulated screws over the fixation elements and into the head of the implant. The method may include decoupling the shaft from the tail of the implant.

The anchoring may include placing the plate in direct contact with a bone surface. The placing may include positioning the plate so that a shaft of the implant extends through an opening defined by the plate. The anchoring may include coupling an anchoring jig onto the shaft. The anchoring may include guiding a screw through the anchoring jig, through the bone surface and into a tail of the implant.

The method may include anchoring the implant and the plate to the bone.

The anchoring may include placing the plate in direct contact with the bone surface. The placing may include positioning the plate so that a shaft of the implant extends through an opening defined by the plate. The anchoring may include coupling an anchoring jig onto the shaft. The anchoring may include fastening the plate to the tail of the implant by guiding a screw through the anchoring jig, through the plate and into a tail of the implant.

The anchoring may be a first anchoring jig. The method may include coupling a second anchoring jig to the shaft. The method may include guiding a plurality of fixation elements through a space defined by the second anchoring jig and into the head of the implant. The method may include driving cannulated screws over the fixation elements and into the head of the implant. The method may include decoupling the shaft from the tail of the implant.

The method may include driving a screw through a hole defined by the plate and into the head of the implant. The method may include driving a screw through a hole defined by the plate and into the bone interior. The method may include coupling a bushing to the hole. The method may include driving a screw through the bushing and into the hole.

The anchoring may include placing the plate in direct contact with the bone surface. The placing may include positioning the plate so that a shaft of the implant extends through an opening defined by the plate. The anchoring may include coupling an anchoring jig onto the shaft. The anchoring may include guiding a screw through the anchoring jig and into a tail of the implant. The anchoring may include driving a screw through the plate and into the tail of the implant.

The method may include sliding a tube over a shaft attached to a tail of the implant until the plate abuts the bone surface. The tube may extend away from the plate at an oblique angle relative to a bottom surface of the plate. When the plate abuts the bone surface, the tube may be coaxially mounted on a tail of the implant. When the plate abuts the bone surface, the tube may be positioned in the bone interior. The method may include anchoring the plate to the implant.

The plate may be a first plate. The anchoring may include sliding a tube over a shaft attached to a tail of the implant until a second plate abuts the bone surface. The tube may extend away from the second plate at an oblique angle relative to a bottom surface of the second plate. When the second plate abuts the bone surface, the tube may be coaxially mounted on the tail of the implant and positioned in the bone interior. The anchoring may also include anchoring the second plate to the first plate.

The plate may be a first plate. Anchoring may include placing a second plate on the first plate. The placing the second plate may include positioning the second plate so that a shaft of the implant extends through an opening defined by the second plate. The anchoring may also include anchoring the second plate to the first plate.

The method may include placing the plate in direct contact with the bone surface. The plate may include a plate opening. The providing the access hole may be performed on a surface of the bone defined by the plate opening.

The plate may include a bottom surface. The bottom surface may complement the surface contour. The placing the plate may include seating a plate bottom surface complementarily on surface contour.

The jig may define a recess. The placing the plate may include placing the plate in the recess.

The placing the plate may include placing a first edge of the plate adjacent to a longitudinally extending leg of the jig. The placing the plate may include placing a second edge of the plate adjacent to a transverse leg of the jig.

The placing the plate may include placing a portion of a bottom surface of the plate in physical contact with a portion of a top surface of the jig. The placing the plate may include placing a top surface of the plate in physical contact with a portion of a bottom surface of the jig.

The method may include coupling the plate to the jig.

The method may include driving a target wire through a target hole defined by the jig. The method may include driving a fixation element through a positioning hole defined by the jig.

The method may include identifying a location on the bone for preparation of an access hole. The location on the bone may be defined by the plate opening. The method may include advancing a fixation element through the location and toward a space in the bone that was penetrated by a tip of the target wire.

The identifying may include coupling a targeting apparatus to the target wire. The identifying may also include guiding a pointer included in the targeting apparatus onto the bone surface defined by the plate opening.

The identifying may include selecting a location on the bone adjacent a demarcation point included on the plate and defined by the plate opening. The identifying may also include advancing a fixation element through the selected location toward a space in the bone that was penetrated by a tip of the target wire.

The method may include providing an access hole. The method may include providing a cavity in the bone interior. The cavity may extend away from the access hole. The providing the cavity may include inserting a cavity preparation device through the access hole. The providing the cavity may include expanding the cavity preparation device. The providing the cavity may include rotating the cavity preparation device to cut material in the bone interior.

The method may include inserting an implant into the cavity. The method may include radially expanding the implant in the cavity to form a mesh cage.

The method may include removing the plate from the bone surface. The method may include anchoring the implant to the bone.

The method may include anchoring the plate and the implant to the bone. The anchoring may include driving a screw through the plate and into a head of the implant. The anchoring may include driving a screw through the plate and into a tail of the implant. The anchoring may include driving a screw through the plate and into the bone interior.

The method may include attaching a washer to one or more of the screws before using the screw for anchoring.

The jig may be a first jig. The method may include removably coupling a second jig to the plate. The second jig may include a guide extending away from the bone surface and extending away from the plate opening.

The method may include removably coupling the second jig to the first jig.

The method may include providing an access hole on the bone surface. The providing the access hole may include inserting a drill through the guide. The providing the access hole may include drilling an access hole through the bone surface.

The method may include inserting a cavity preparation device through the guide and the access hole and into the bone interior. The method may include preparing a cavity in the bone interior. The method may include inserting an implant through the guide and the access hole into the cavity. The method may include radially expanding the implant in the cavity to form a mesh cage.

The method may include providing an access hole on the bone surface. The providing may include inserting an insert into the guide. The providing may include inserting a drill through the insert. The providing may include drilling an access hole through the bone surface. A central axis of the insert may not be parallel to a central axis of the guide. A central axis of the insert may be parallel to a central axis of the guide.

The method may include inserting a cavity preparation device through the insert and the access hole and into the bone interior. The method may include preparing a cavity in the bone interior. The method may include inserting an implant through the insert and the access hole into the cavity. The method may include radially expanding the implant in the cavity to form a mesh cage.

The method may include decoupling the second jig from the plate. The method may include removing the second jig from the plate. The method may include anchoring the plate and the implant to the bone.

The method may include removing the plate from the bone surface. The method may include anchoring the implant to the bone.

The jig may be a first jig. The method may include placing a second jig in direct contact with the bone surface. A portion of the second jig may abut the first jig. The second jig may include a guide extending away from the bone surface. The method may include removably coupling the second jig to the first jig.

The method may include providing an access hole on the bone surface. The providing may include inserting a drill through the guide and into the bone interior.

The method may include inserting a cavity preparation device through the guide and access hole and into the bone interior. The method may include expanding and rotating the cavity preparation device in the bone interior to create a cavity. The method may include inserting an implant through the guide and the access hole. The method may include positioning the implant in the cavity. The method may include radially expanding the implant in the cavity to form a mesh cage.

The method may include providing an access hole on the bone surface. The providing the access hole may include inserting an insert into the guide. The providing the access hole may include inserting a drill through the insert. The providing the access hole may include drilling an access hole through the bone surface. A central axis of the insert may not be parallel to a central axis of the guide. A central axis of the insert may be parallel to a central axis of the guide.

The method may include selecting an access angle for drilling into the bone. The access angle may be different from an access angle defined by the guide. The access angle defined by the guide may be a central axis of the guide. The method may include inserting an insert into the guide. A central axis of the insert may define the selected angle.

The method may include decoupling the second jig from the first jig. The method may include removing the second jig from the bone surface. The method may include anchoring the implant to the bone.

The method may include placing the plate on the bone surface, a tail of the implant being positioned in a plate opening. After placing the plate on the bone surface, the method may include anchoring the plate and the implant to the bone.

The method may include placing the plate in direct contact with the bone surface. The plate may include a threaded hole. The method may include screwing a first bushing into the threaded hole. The first bushing may extend away from the bone surface. The method may include providing an access hole on the bone surface. The providing may include inserting a drill through the first bushing. The method may include implanting an implant through the first bushing into the bone interior.

The method may include radially expanding the implant to form a mesh cage. The method may include decoupling an implant shaft from an implant tail. The method may include unscrewing the first bushing from the threaded hole. The method may include screwing a second bushing into the threaded hole. Screwing the second bushing into the threaded hole may advance the second bushing into the bone interior. Screwing the second bushing into the threaded hole may coaxially mount the second bushing onto the tail of the implant.

The methods, which may involve the apparatus shown and described herein, may include methods for bone fracture repair. The methods may include a method for treating a bone having a bone surface and a bone interior. The method may include one or more steps from any other method disclosed herein.

The method for treating a bone having a bone surface and a bone interior may include providing an access hole on the bone surface. The method may include inserting an implant through the access hole. The method may include implanting the implant in the bone interior. The method may include placing the plate in direct contact with the bone surface. The placing may include positioning the plate so that a shaft of the implant extends through an opening defined by the plate. The method may include decoupling the implant shaft from the implant tail.

The method may include anchoring the plate to the implant. The anchoring may include driving a fixation element through the plate and an implant head. The anchoring may include driving a fixation element through the plate and an implant tail. The anchoring may include driving a fixation element through the plate and the bone surface.

The method may include radially expanding the implant in the bone interior to form a mesh cage.

The plate may be a first plate. The method may include sliding a tube over a shaft attached to the tail of the implant until a second plate abuts the bone surface and abuts a recess defined by the first plate. The tube may extend away from the second plate at an oblique angle relative to a bottom surface of the second plate. When the second plate abuts the bone surface, the tube may be coaxially mounted on the tail of the implant and is positioned in the bone interior. The method may include anchoring the second plate to the first plate.

The anchoring may include placing a second plate in a recess defined by the first plate. The placing the second plate may include engaging the tail of the implant with the second plate. The method may include anchoring the second plate to the first plate.

The methods, which may involve the apparatus shown and described herein, may include methods for bone fracture repair. The methods may include a method for treating a bone having a bone surface and a bone interior.

The method for treating a bone having a bone surface and a bone interior may include providing an access hole on the bone surface. The method may include inserting an implant through the access hole. The method may include implanting the implant in the bone interior. The method may include radially expanding the implant in the bone interior to form a mesh cage. The method may include sliding a tube over a shaft attached to a tail of the implant until the plate abuts the bone surface. The tube may extend away from the plate at an oblique angle relative to a bottom surface of the plate. When the plate abuts the bone surface, the tube may be coaxially mounted on the tail of the implant and is positioned in the bone interior.

The method may include anchoring the implant to the bone. The method may include anchoring the plate to the bone. The method may include anchoring the plate to the implant.

The methods, which may involve the apparatus shown and described herein, may include a method for treating a bone having a bone surface and a bone interior. The method may include one or more steps from any other method disclosed herein.

The method for treating a bone having a bone surface and a bone interior may include placing the plate in direct contact with the bone surface. The plate may include a threaded hole. The method may include screwing a first bushing into the threaded hole. The first bushing may extend away from the bone surface. The method may include providing an access hole on the bone surface. The providing may include inserting a drill through the first bushing.

The method may include inserting an implant through the first bushing. The method may include implanting the implant in the bone interior.

The method may include radially expanding the implant to form a mesh cage. The method may include decoupling an implant shaft from a tail of the implant.

The method may include unscrewing the first bushing from the threaded hole. The method may include screwing a second bushing into the threaded hole. Screwing the second bushing into the threaded hole may advance the second bushing into the bone interior. Screwing the second bushing into the threaded hole may coaxially mount the second bushing onto the tail of the implant.

The method may include anchoring the implant to the bone. The method may include anchoring the plate to the bone. The method may include anchoring the plate to the implant.

The methods, which may involve the apparatus shown and described herein, may include a method for treating a bone having a bone surface and a bone interior. The method may include one or more steps from any other method disclosed herein.

The method for treating a bone having a bone surface and a bone interior may include placing the plate in direct contact with the bone surface. The plate may include a plate opening.

The method may include providing an access hole on the bone surface through the plate opening. The method may include inserting an implant through the access hole and into the bone interior through the plate opening. The implant may be an expandable mesh cage. The method may include radially expanding the implant in the interior to form a mesh cage.

The bone may be a proximal humerus bone. The method may include making a deltopectoral incision in soft tissue covering the bone. The method may include making a deltoid split incision in soft tissue covering the bone.

The bone may define a longitudinal axis. The bone may include a surface contour. The surface contour may extend along the bone surface between two or more points at different elevations from the longitudinal axis. A bottom surface of the plate may complement the surface contour. The placing the plate may include seating the bottom surface of the plate complementarily on the surface contour.

When the bone is a proximal humerus bone, the surface contour may include a greater tuberosity. The surface contour may include an intertubercular groove. The surface contour may include a deltoid insertion. The placing the plate may include aligning a first portion of the bottom surface of the plate with the greater tuberosity. The placing the plate may include aligning a second portion of the bottom surface of the plate with the intertubercular groove. The placing the plate may include aligning a third portion of the bottom surface of the plate with the deltoid insertion.

When the bone is a proximal humerus bone, the placing the plate may include palpitating a location of a lateral condyle. The placing the plate may include determining a position on the bone surface along a longitudinal axis of the humerus bone. The position may be a predetermined distance from the lateral condyle. The placing the plate may include aligning a member of the plate with the position.

When the bone is a proximal humerus bone, the placing the plate may include radiographically aligning a member of the plate with a surgical neck at a base of a head of the proximal humerus bone.

The method may include releasably anchoring the plate to the bone.

The method may include driving a fixation element through a hole defined by the plate and into the bone interior.

The hole may be one of a plurality of holes. The method may include providing a plurality of fixation elements. The method may include guiding each of the fixation elements through one of the plurality of holes and into the bone interior.

The hole may be a first hole. The fixation element may be a first fixation element. The method may include providing a second fixation element. The method may include guiding the first fixation element through the first hole and into the bone interior. The method may include guiding the second fixation element through a second hole and into the bone interior. The first hole may be spaced apart from the second hole. The guiding may include guiding the first fixation element and the second fixation element into the bone interior along convergent paths. The guiding may include guiding the first fixation element and the second fixation element into the bone interior along divergent paths.

The expanded implant may occupy an area in the bone interior. The guiding the fixation elements may provide clearance for the area. The expanded implant may occupy a region that is not intersected by the fixation elements.

In the embodiments where the bone is a proximal humerus bone, the method may include driving a target wire through a targeting hole defined by the plate and toward a center of an interior of a head of the proximal humerus bone. The method may include positioning a tip of the target wire in the center of the interior of the head. The method may include driving a target wire through a positioning hole defined by the plate and tangent to a top of a greater tuberosity.

In the embodiments where the bone is a proximal humerus bone, the placing the plate may include positioning a targeting defined by the plate to point in a direction that intersects with a center region on a head of the proximal humerus bone.

The method may include driving a target wire through a target hole defined by the plate.

The providing the access hole may include advancing a fixation element through a location on the bone surface defined by the plate opening and toward a space in the bone that was penetrated by a tip of the target wire.

The providing the access hole may include selecting a location on the bone adjacent a demarcation point included on the plate. The location on the bone may be defined by the plate opening. The providing the access hole may include advancing a fixation element through the selected location toward a space in the bone that was penetrated by a tip of the target wire.

The providing the access hole may include selecting a demarcation point included on the plate from a plurality of demarcation points. Each demarcation point may correspond to an implant of a corresponding length. The providing the access hole may include advancing a fixation element through a location on the bone adjacent the selected demarcation point and toward a space in the bone that was penetrated by a tip of the target wire. The location on the bone may be defined by the plate opening. The implant may have a length equal to a length of an implant corresponding to the selected demarcation point.

The providing the access hole may include coupling a targeting apparatus to the target wire. The providing the access hole may include guiding a pointer included in the targeting apparatus onto a location the bone surface. The location on the bone surface may be defined by the plate opening. The providing the access hole may include advancing a fixation element through the location and toward a space in the bone that was penetrated by a tip of the target wire.

The providing the access hole may include coupling a targeting apparatus to the target wire. The providing the access hole may include guiding a pointer included in the targeting apparatus onto a location on the bone surface. The location on the bone surface may be defined by the plate opening. The providing the access hole may include identifying an angle relative to the bone surface at which the pointer abuts the bone surface and extends away from the bone surface. The providing the access hole may include advancing a fixation element through the location, at the identified angle, and toward a space in the bone that was penetrated by a tip of the target wire.

The providing the access hole may include removing a fixation element extending through the bone surface, wherein a tip of the fixation element is positioned adjacent a tip of the target wire. The providing the access hole may include inserting a drill through an opening on the bone surface initiated by the fixation element and advancing the drill towards the tip of the target wire. The providing the access hole may include inserting a drill through an opening on the bone surface initiated by the fixation element and advancing the drill towards the target site.

The providing the access hole may include inserting a cannulated drill over a fixation element, wherein a tip of the fixation element is positioned adjacent a tip of the target wire. The providing the access hole may include advancing the drill along the fixation element and towards an end of the fixation element positioned adjacent the target site. The providing the access hole may include advancing the drill along the fixation element and towards the target site.

The method may include providing a cavity in the bone interior. The cavity may extend away from the access hole. The implant may be inserted through the access hole and into the cavity.

The providing the cavity may include inserting a cavity preparation device through the access hole. The providing the cavity may include expanding the cavity preparation device. The providing the cavity may include rotating the cavity preparation device to cut material in the bone interior.

The method may include radially expanding the implant in the cavity.

The method may include decoupling a first handle from an implant shaft. The method may include coupling a second handle to the implant shaft. The method may include rotating the implant within the cavity. The rotating may be driven by rotation of the second handle.

The method may include removing the plate from the surface of the bone. After removing the plate from the surface of the bone, the method may include anchoring the implant to the bone.

The method may include anchoring the plate to the bone and the implant.

The anchoring may include coupling an anchoring jig onto a shaft of the implant. The anchoring may include guiding a screw through the plate, through the bone surface and into a tail of the implant.

The anchoring may include driving a screw through the plate and into a head of the implant. The anchoring may include driving a screw through the plate and into a tail of the implant. The anchoring may include driving a screw through the plate and into the bone interior.

The anchoring may include providing a plurality of screws. The anchoring may include driving each of the plurality of screws through a threaded hole defined by the plate. Each of the screws may engage a head of the implant.

The anchoring jig may be a first anchoring jig. The anchoring may include decoupling the first anchoring jig from the shaft. The anchoring may include coupling a second anchoring jig onto the shaft. The anchoring may include guiding a plurality of fixation elements through a space defined by the second anchoring jig and into a head of the implant. The method may include driving cannulated screws over the fixation elements and into the head of the implant. The method may include decoupling the shaft from the tail of the implant.

The method may include sliding a washer onto a head of one of the cannulated screws. The method may include bending an eyelit of the washer to conform with the surface contour of the bone. The method may include suturing soft tissue to the eyelit of the washer.

When the plate is a first plate, the method may include sliding a tube over a shaft attached to a tail of the implant until a second plate abuts the bone surface. The tube may extend away from the second plate at an oblique angle relative to a bottom surface of the second plate. When the second plate abuts the bone surface, the tube may be coaxially mounted on a tail of the implant and positioned in the bone interior. The method may include anchoring the second plate to the first plate.

When the plate is a first plate, the method may include sliding a tube over a shaft attached to a tail of the implant until a second plate abuts a recess defined by the second plate. The tube may extend away from the second plate at an oblique angle relative to a bottom surface of the second plate. When the second plate abuts the recess surface, the tube may be coaxially mounted on a tail of the implant. When the second plate abuts the recess surface, the second plate may be positioned in the bone interior. The method may also include anchoring the second plate to the first plate.

When the plate is a first plate, the method may include positioning a second plate in a recess defined by the first plate so that a shaft of the implant extends through an opening defined by the second plate. The method may include anchoring the second plate to the first plate.

The method may include placing a jig on the plate. The placing the jig may include positioning a portion of a bottom surface of the jig on a top surface of the plate.

The method may include coupling the jig to the plate.

The method may include driving a target wire through a targeting hole defined by the jig.

The method may include driving a fixation element through a positioning hole defined by the jig.

The method may include providing a plurality of fixation elements. The method may include driving each of the plurality of fixation elements through a hole defined by the jig.

The method may include providing a bushing. The method may include coupling the bushing to a threaded screw hole defined by the jig. The method may include advancing a screw through the bushing and into an implant head.

The method may include removing jig from the plate prior to closing an incision.

The jig may be a first jig. The method may include placing a second jig on the plate. The second jig may include a guide. The guide may extend away from the plate opening. The providing the access hole may include inserting a drill through the guide. The inserting the implant through the access hole may include the implant through the guide. The method may include removing the first jig and the second jig from the plate prior to closing the incision.

The method may include removably coupling a jig to the plate. The jig may include a guide extending away from the bone surface and extending away from the plate opening. The providing the access hole may include inserting a drill through the guide. The inserting the implant through the access hole may include inserting the implant through the guide. The method may include removing the jig from the plate prior to closing the incision. The method may include removing the jig from the plate prior to anchoring the plate to the bone.

The method may include anchoring the plate to the implant. The anchoring may include driving a screw through a hole defined by the jig, through a hole defined by the plate, and into the implant.

The providing the access hole may include inserting an insert into the guide. The providing the access hole may include inserting a drill through the insert. The providing the access hole may include drilling the access hole through the bone surface. A central axis of the insert may not be parallel to a central axis of the guide. A central axis of the insert may be parallel to a central axis of the guide.

The providing the access hole may include inserting an insert into the guide. The providing the access hole may include inserting a drill through the insert. The providing the access hole may include drilling the access hole through the bone surface. Inserting the insert into the guide may dispose a central axis of the insert parallel to a central axis of the guide. Inserting the insert into the guide may dispose a central axis of the insert oblique to a central axis of the guide.

The method may include inserting a cavity preparation device through the guide and the access hole and into the bone interior. The method may include preparing a cavity in the bone interior. The method may include inserting an implant through the guide and into the cavity. The method may include radially expanding the implant in the cavity to form a mesh cage.

The method may include inserting a cavity preparation device through the insert and the access hole and into the bone interior. The method may include preparing a cavity in the bone interior. The method may include inserting an implant through the insert and the access hole into the cavity. The method may include radially expanding the implant in the cavity to form a mesh cage.

The method may include driving a fixation element through a hole defined by the jig and into the bone interior. The hole may be one of a plurality of holes. The method may include providing a plurality of fixation elements. The method may include guiding each of the fixation elements through one of the plurality of holes defined by the jig and into the bone interior. The expanded implant may occupy a volume in the bone interior. The guiding the fixation elements may provide clearance for the volume. The expanded implant may occupy a region that is not intersected by the fixation elements.

When the bone is a proximal humerus bone, the method may include driving a target wire through a target hole defined by the jig and toward a center of an interior of a head of the proximal humerus bone. The method may include positioning a tip of the target wire in the center of the interior of the head. When the bone is a proximal humerus bone, the method may include driving a target wire through a positioning hole defined by the jig and tangent to a top of a greater tuberosity.

When the bone is proximal humerus bone, the placing the plate may include positioning a target hole defined by the plate to define a direction that intersects with a center region on a head of the proximal humerus bone.

The method may include driving a target wire through a target hole defined by the jig.

The plate may include a guide. Providing the access hole may include advancing a fixation element through the guide toward a space in the bone that was penetrated by a tip of the target wire.

The method may include providing a cavity in the bone interior. The cavity may extend away from the access hole. The implant may be inserted through the guide, through the access hole and into the cavity. The providing the cavity may include advancing a cannulated drill over the fixation element, through the guide and to the target site. The providing the cavity may include inserting a cavity preparation device through the access hole. The providing the cavity may include expanding the cavity preparation device. The providing the cavity may include rotating the cavity preparation device to cut material in the bone interior.

The method may include inserting an implant through guide and through the access hole. The method may include advancing an end of the implant to the target site. The method may include radially expanding the implant in the cavity.

The method may include decoupling a first handle from an implant shaft. The method may include coupling a second handle to the implant shaft. The method may include rotating the implant within the cavity. The rotation may be driven by rotation of the second handle.

The method may include removing the plate and the jig from the surface of the bone. The method may include anchoring the implant to the bone after removing the plate and the jig from the surface of the bone.

The method may include coupling a nested bushing to a threaded screw hole defined by jig. The method may include driving a fixation element through a first hole defined by the nested bushing. The method may include removing a first portion of the nested bushing. The method may include driving a cannulated drill over the fixation element and through a second hole defined by the nested bushing. The method may include removing the cannulated drill and a second portion of the nested bushing. The method may include driving a cannulated screw over the fixation element and through a third hole defined by the nested bushing. The method may include advancing the screw into the bone interior and into a head of the implant such that the screw anchors the implant to the plate and a head of the screw is engaged with the plate.

The anchoring may include driving a screw through the jig and plate into a head of the implant. The anchoring may include driving a screw through the jig and plate and into a tail of the implant. The anchoring may include driving a screw through the jig and plate and into the bone interior.

The anchoring may include providing a plurality of screws. The anchoring may include driving each of the plurality of screws through a threaded hole defined by the jig. Each of the screws may engage the plate and a head of the implant.

The method may include sliding a washer onto a head of one of the cannulated screws. The method may include bending an eyelet of the washer to conform with the surface contour of the bone. The method may include suturing soft tissue to the eyelit of the washer.

The method may include decoupling an implant shaft from an implant tail.

The methods, which may involve the apparatus shown and described herein, may include a method for treating a bone having a bone surface and a bone interior.

The method for treating a bone having a bone surface and a bone interior may include making an incision in soft tissue covering the bone surface. The method may include placing a jig in direct contact with the bone surface. A bottom surface of the jig may complement the surface contour.

The jig may include a jig opening. The jig may include a guide extending away from the jig opening. The method may include driving a fixation element through a hole defined by the jig and into the bone interior. The method may include preparing an access hole on the surface. An access position for preparing the access hole may be defined by the jig opening.

The method may include inserting an implant through the guide, through the access hole and into the bone interior. The method may include radially expanding the implant to form a mesh cage. The method may include removing the jig from the bone surface prior to closing the incision. The method may include closing the incision.

The placing the jig may include aligning the bottom surface of the jig with the surface contour. The placing the jig may include complementarily seating the bottom surface of the jig with the surface contour.

The method may include inserting a drill through the guide to provide the access hole. The method may include inserting a cavity preparation device through the access hole. The method may include preparing a cavity in the bone interior. The method may include inserting the implant through the access hole and into the cavity.

After removing the jig, the method may include anchoring the implant to the bone. The anchoring may include driving screws through the jig and into the implant. The driving the screws may not anchor the jig to the bone.

After removing the jig from the bone, the method may include placing the plate onto the bone surface. The placing the plate may include positioning the plate so that a shaft of the implant extends through an opening defined by the plate. The placing the plate may include positioning the plate so that an opening defines by the plate abuts a tail of the implant.

The method may include anchoring the plate to the implant. The method may include decoupling the shaft from the implant prior to closing the incision.

After removing the jig from the bone, the method may include sliding a tube over a shaft attached to a tail of the implant until the plate abuts the bone surface. The tube may extend away from the plate at an oblique angle relative to a bottom surface of the plate. When the plate abuts the bone surface, the tube may be coaxially mounted on the tail of the implant. When the plate abuts the bone surface, the tube may be positioned in the bone interior.

The method may include anchoring the plate to the implant. After anchoring the plate to the implant, the method may include decoupling the shaft from the tail.

A method for identifying an access position on a bone is provided. The access position may identify a location on an outer surface of the bone for drilling a hole in the bone. The hole may be utilized for delivery of an implant into an implantation region inside the bone. The method may include positioning a tip of a fixation element inside the bone. The fixation element may be a target wire. The method may include sliding a base member over a length of the fixation element that is operatively external to the bone.

The method may include positioning a curved member that is slidably affixed to the base member. The positioning may include positioning the curved member such that an end of the curved member rests on an outside surface of the bone, thereby identifying the access position.

The fixation element may be inserted into the bone at an angle to a longitudinal axis of the bone. The angle may be between 30 degrees and 150 degrees.

The method may include sliding the curved member within a sleeve of the base member such that the end of the curved member moves along a circumference of a circle centered about the tip of the fixation element. The method may include sliding the curved member such that the end of the curved member sweeps out an arc of the circumference in a direction that is substantially proximal to distal with respect to a longitudinal axis of the bone.

When the bone is a humerus, the method may include positioning the tip of the fixation element inside a head of the humerus. When the bone is a humerus, the method may include inserting the fixation element into a head of the humerus in a direction that, with respect to the bone, is lateral to medial. When the bone is a humerus, the method may include comprising inserting the tip of the fixation element at a proximal end of a greater tuberosity of the humerus.

When the bone is a humerus, the method may include inserting the tip of the fixation element into a head of the humerus in a direction that, with respect to the bone, is lateral to medial. When the bone is a humerus, the may include inserting the tip of a fixation element into a head of the humerus in a direction that, with respect to the bone, is anterior to posterior.

A method for securing an implant positioned inside a bone is provided. The method may include driving a fixation element from outside the bone into the bone and into an implant positioned inside the bone. The method may include sliding a washer onto the fixation element. The washer may include a central aperture and an offset aperture.

The method may include sliding a cannulated bone anchor onto the fixation element. The method may include driving the cannulated anchor along the fixation element through the central aperture, into the bone and into the implant.

The method may include suturing a muscle, a ligament and/or a tendon to the washer. The method may include suturing a muscle, a ligament and/or a tendon by passing, threading or weaving the suture through one or more offset apertures of the washer.

The method may include bending the offset aperture of the washer. After bending the offset aperture, the method may include suturing a muscle, a ligament and/or a tendon to the washer. After bending the offset aperture, the method may include passing, threading or weaving the suture through one or more offset aperture of the washer.

The washer may include a plurality of offset apertures. The method may include passing, threading or weaving a surgical suture through the plurality of apertures. The method may include tying a suture to the washer. The washer may include an arcuate shaped member that defines an arc of an outer perimeter of the offset aperture. The method may include tying a surgical suture at a position on the arcuate shaped member.

The methods, which may involve the apparatus shown and described herein, may include a method for treating a bone having a bone surface and a bone interior. The method may include one or more steps from any other method disclosed herein.

The method may include making an incision in soft tissue covering the bone surface. The method may include sliding an implant delivery base through the incision.

The method may include seating a bottom surface of the implant delivery base complementarily against a surface contour. The bottom surface of the implant delivery base may complement the surface contour. The bone may define a longitudinal axis and include the surface contour. The surface contour may extend along the bone surface between two or more points at different elevations from the longitudinal axis.

After placing the implant delivery base on the bone surface, the method may include seating a reduction device on skin located around the incision. The seating may include sliding the reduction device along a post supported by the implant delivery base. The method may include driving a fixation element through the reduction device and into the bone. The reduction device may be used to attain reduction of the bone. The reduction device may be used to maintain reduction of the bone.

The method may include implanting an implant through a channel defined by the implant delivery base and into an interior of the bone. The method may include expanding the implant to form a mesh cage. The expanded implant may occupy a volume in the bone interior. The driving the fixation element through the reduction device may not transect the volume. The driving the fixation element through the reduction device may provide clearance for the expanded implant.

When the bone is a proximal humerus, the incision may be made at a deltoid insertion on a lateral aspect of the humerus.

The method may include driving a first fixation element through a first hole defined by the implant delivery base and into a first fragment of the bone. The method may include driving a second fixation element through a second hole defined by the implant delivery base and into a second fragment of the bone. The first fixation element and the second fixation element may not transect the volume.

The method may include driving a plurality of fixation elements through holes defined by the reduction device. Driving the plurality of fixation elements may provide clearance for the expanded implant in the bone interior.

The placing may include placing the bottom surface on the bone surface at predetermined distance from an anatomical feature defined by the bone. When the bone is a proximal humerus bone, the anatomical feature may include an articular surface of a greater tuberosity.

The method may include identifying a target site within the bone interior. Identifying the target site may include inserting a bushing into the channel. Identifying the target site may include driving a fixation element through the bushing and into the bone interior. Identifying the target site may include verifying that a tip of the fixation element is positioned at the target site.

The method may include removing the implant delivery base from the bone surface prior to closing the incision.

The methods, which may involve the apparatus shown and described herein, may include a method for treating a bone having a bone surface and a bone interior.

The method may include making an incision in soft tissue covering the bone surface. The method may include sliding the plate coupled to an implant delivery base through the incision. The method may include seating a bottom surface of the plate complementarily against a surface contour. The bottom surface of the plate may complement the surface contour. The bone may define a longitudinal axis. The bone may include the surface contour. The surface contour may extend along the bone surface between two or more points at different elevations from the longitudinal axis.

After placing the plate on the bone surface, the method may include seating a reduction device on skin located around the incision. The seating may include sliding the reduction device along a post supported by the implant delivery base. The method may include driving a fixation element through the reduction device and into the bone. The method may include driving a fixation element through the reduction device and into the bone.

The method may include implanting an implant through a channel defined by the implant delivery base and into an interior of the bone. The method may include expanding the implant to form a mesh cage. The expanded implant may occupy a volume in the bone interior. The fixation element may not transect the volume. Driving the fixation element may provide clearance for the expanded implant in the bone interior.

When the bone is a proximal humerus, the incision may be made at a deltoid insertion on a lateral aspect of the humerus.

The method may include driving a first fixation element through a first hole defined by the implant delivery base and into a first fragment of the bone. The method may include driving a second fixation element through a second hole defined by the implant delivery base and into a second fragment of the bone. The first fixation element and the second fixation element may not transect the volume.

The method may include driving a plurality of fixation elements through holes defined by the reduction device. Driving the plurality of fixation elements may provide clearance for the expanded implant in the bone interior.

The placing may include placing the bottom surface on the bone surface at predetermined distance from an anatomical feature defined by the bone. When the bone is a proximal humerus, the anatomical feature may include an articular surface of a greater tuberosity.

The method may include identifying a target site. The identifying may include inserting a bushing into the channel. The identifying may include driving a fixation element through the bushing and into the bone interior. The identifying may include verifying that a tip of the fixation element is positioned in a predetermined location within the bone interior.

The method may include anchoring the plate to the bone. The anchoring may include inserting a bushing into a screw hole defined by the reduction device. The anchoring may include advancing a screw through the bushing and into a hole defined by the plate.

The method may include anchoring the plate to the bone. The anchoring may include inserting a first bushing into a reduction device screw hole. The anchoring may include advancing a fixation element through the first bushing and into the plate screw hole. The anchoring may include replacing the first bushing with a second bushing. The anchoring may include advancing a cannulated screw along the fixation element and into the plate screw hole.

The method may include decoupling the implant delivery base from the plate prior to closing the incision.

The apparatus may include, and the methods may involve, apparatus for directing a fixation element into a bone. The apparatus may include a first bushing. The apparatus may include a second bushing. The second bushing may be configured to nest within the first bushing. The apparatus may include a third bushing. The third bushing may be configured to nest within the second busing.

The first bushing may include a cannulated longitudinal segment. The cannulated longitudinal segment may be externally threaded.

The second bushing may include a first cannulated longitudinal segment. The first cannulated longitudinal segment may have a first external diameter. The second bushing may include a second cannulated longitudinal segment. The second cannulated longitudinal segment may have a second external diameter. The second diameter may be greater than the first diameter.

The first cannulated longitudinal segment of the second bushing may be configured to fit within a cannulated longitudinal segment of the first bushing.

The second bushing may include a key. The key may be positioned between the first and second longitudinal segments of the second bushing. The first bushing may include a key seat. The key seat may be configured to receive the key when, in operation, the first cannulated segment of the second bushing is nested within the longitudinal segment of the first bushing.

In operation, when the key is seated in the key seat, the second bushing may be rotational fixed, about its longitudinal axis, with respect to the first bushing. The key may be hexagonally shaped. The key may have any suitable geometric shape. The keyseat may have a geometric shape that corresponds to the geometric shape of the key.

The second bushing may include a third cannulated longitudinal segment. The third cannulated segment may have a third external diameter. The third external diameter may be greater than the first or second external diameters.

The second bushing may include a longitudinal segment. The longitudinal segment of the second bushing may include a pair of kerfs. In operation, when a fixation element is inserted into the second bushing, the pair of kerfs may allow the longitudinal segment of the second bushing to expand about a central longitudinal axis of the second bushing. Pressure applied by the longitudinal segment may provide a friction fit that holds the fixation element in a position along the longitudinal axis of the second bushing.

The first bushing may be cannulated. The first bushing may have a first internal diameter. The second bushing may be cannulated. The second bushing may have a second internal diameter. The third bushing may be cannulated. The third bushing may have a third internal diameter. The first internal diameter may be greater than the second internal diameter. The second internal diameter may be greater than the third internal diameter.

The first bushing may be configured to receive a fixation element. The fixation element may be threaded. The fixation element maybe cannulated. For example, the fixation element may be a cannulated screw. The internal diameter of the first bush may be large enough to receive the cannulated screw. The internal diameter of the first bushing may be sized to direct a screw along a longitudinal axis defined by the first bushing.

The first bushing may include an externally threaded longitudinal segment. The externally threaded longitudinal segment of the first bushing may be configured to engage an internally threaded screw hole defined by the plate. The plate may be any suitable plate described herein. An external diameter of the first bushing may be sized such that the externally threaded segment of the first bushing may engage a screw hole defined by plates described herein.

The second bushing may be configured to receive a surgical drill. For example, the internal diameter of the second bushing may be large enough to receive an 8-millimeter drill. The internal diameter of the second bushing may be sized to direct a tool along a longitudinal axis defined by the second bushing. An external diameter of the second bushing may be sized such that the second bushing may be nested within the first bushing.

The third bushing may be configured to receive a fixation element. For example, an internal diameter of the third bushing may be sized to receive an unthreaded K-wire. The internal diameter of the third bushing may be sized to direct the fixation element along a longitudinal axis defined by the third bushing.

The third bushing may include a first longitudinal segment. The third bushing may include a second longitudinal segment. The third bushing may include a based longitudinal segment. A pair of kerfs may divide a length of the base longitudinal segment into the first longitudinal segment and the second longitudinal segment. The pair of kerfs may allow the first and second longitudinal segments to expand about a central longitudinal axis of the third bushing. The central longitudinal axis may be defined by the base longitudinal segment.

The first longitudinal segment may include a first semi-circular cross section. The second longitudinal segment may include a second semi-circular cross section.

The first longitudinal segment may define a first longitudinal axis. The second longitudinal segment may define a second longitudinal axis. In a first state, the first longitudinal axis may form a first angle with the central longitudinal axis. In the first state, the second longitudinal axis may form a second angle with the central longitudinal axis. The second angle may be equal or substantially equal to the first angle.

In a second state, the first longitudinal axis may form a third angle with the central longitudinal axis. In the second state, the second longitudinal axis may form a fourth angle with the central longitudinal axis. The fourth angle may be equal or substantially equal to the third angle. The third angle may be greater than the first angle. The fourth angle may be greater than the second angle.

The first state may correspond to state, when in operation, the third bushing is not nested within the second bushing. The second state corresponds to when the third bushing is nested within the second bushing. When the third bushing is not nested within the second bushing, the first and second longitudinal segments may be spaced from the central longitudinal axis by a greater distance than when the third bushing is nested within the second bushing. When the third bushing is nested within the second bushing, the internal diameter of the second bushing may compress the first and second longitudinal segments of the third bushing about a central longitudinal axis of the third bushing.

The first state may correspond to when, in operation, the third bushing is nested within the second bushing. The second state may correspond to when, in operation, the third bushing is nested within the second bushing and the first and second longitudinal segments are further compressed about the central longitudinal axis of the third bushing. For example, when the third bushing is nested within the second bushing the first and second longitudinal segments of the third bushing may apply outward pressure to the second bushing. The outward pressure may provide a friction fit that maintains the third bushing within the second bushing. Compressing the first and second longitudinal segments may reduce the pressure applied to the second bushing and allow the third bushing to be more easily removed from the second bushing.

Methods for directing a tool from an outside of a bone into the bone are provided. The tool may include a screw, K-wire, drill or any other suitable tool. Methods may include positioning a bushing with respect to the bone. The bushing may be positioned by threadedly engaging the bushing with the plate. The plate may be affixed to the bone.

Methods may include driving a first tool through the bushing into the bone. The bushing may direct the first tool into the bone along a longitudinal axis defined by the bushing. The first tool may be a K-wire. Methods may include separating a first component from the bushing. The first component may be separable from the bushing without removing the first tool from the bone.

Methods may include driving a second tool though the bushing into the bone. The bushing may direct the second tool into the bone along a longitudinal axis defined by the bushing. Driving the second tool through the bushing may expand a diameter of the second component.

Methods may include driving the second tool over the first tool. The second tool may include a drill. The second tool may be a cannulated drill. The cannulated drill may fit over the first tool. Methods may include separating a second component from the bushing. The second component may be separable from the bushing without removing the first tool from the bone.

Methods may include driving a third tool through the bushing into the bone. The bushing may direct the third tool into the bone along a longitudinal axis defined by the bushing. Methods may include driving the third tool over the first tool. The third tool may include a screw. The screw may be a cannulated screw. The cannulated screw may be driven through the bushing and over the first tool. Methods may include separating a third component of the bushing from the plate affixed to the bone.

Methods may include applying pressure to the first component before separating the first component from the bushing. The pressure may compress first and second longitudinal segments of the first component about a central longitudinal axis of the bushing. The pressure may decrease a diameter of the first component.

An exemplary method may include applying the jig to a surface of the bone. The jig may be applied while maintaining provisional reduction of the bone. The provisional reduction of the bone may be maintained manually. The provisional reduction may be maintained with fixation elements. A fixation element may pass through a positioning hole of the jig. The fixation element passing through the positioning hole may be used to align the jig with an anatomical landmark of the bone.

When the bone is a proximal humerus, a fixation element passing through the positioning hole may be used to position the jig with a top of a greater tuberosity. A fixation element may be used to position an anterior jig leg over a bicipital groove. The jig may include a transverse member and a longitudinal member extending away from the transverse member. Positioning the jig relative to the top of the greater tuberosity and/or the bicipital groove may position a center of the jig frame on the bone just lateral to an insertion of the pectoralis major tendon.

The method may include driving fixation elements through fixation element holes defined by the jig and into the humeral head. The method may include driving one or more temporary screws through screw holes defined by the jig and into the humeral head. A temporary screw may be non-locking. A temporary screw may have a length longer than a screw. A temporary screw may have a length longer than a locking screw. A temporary screw may be used to capture a bone fragment. A temporary screw may be used to apply a force to the captured bone fragment. A temporary screw may be used to stabilize a bone or a bone fragment. A temporary screw may be removed from the bone surface and replaced with a screw. A temporary screw may be replaced with a locking screw.

Proper alignment of the humeral head to the humeral shaft may be confirmed by a practitioner using fluoroscopy or any other suitable method. Fixation elements may be placed through the jig and into a humeral shaft. When proper alignment is confirmed, any fixation element external to the jig may be removed to avoid interfering with the preparation of bone interior for of the implant. A target wire may be inserted through the jig. A tip of the target wire may be advanced 3-5 mm from the articular surface of the humeral head. When proper placement of the tip of the target wire is confirmed, preparation of an access hole may commence.

Example Procedure

Set up operating room. Provide radiolucent fracture table or other suitable C-arm/table combination such that anterior/posterior ("AP") and lateral images may be obtained without unnecessary patient movement or provisional fixation disruption. C-arm may be left in place during surgery. C-arm may be rotated to obtain AP and lateral images.

This example, which may include one or more of activities I-VII below, or one or more of their listed subactivies, or one or more activities that are not listed, may employ apparatus and methods shown in one or more of FIGS. 4-84 and 96-108. This example is described using the jig. This example may be used with the plate or a plate and jig combination described herein.

I. Fracture Reduction and Provisional Stabilization
  Apply jig while maintaining provisional reduction manually or with temporary reduction wires.
  Use 0.062 in. K-wire to align jig with top of greater tuberosity. Position anterior edge of jig adjacent to biceps tendon groove such that the center of the jig aligns slightly lateral to the pectoralis major insertion.
  Direct the 0.062" K-wire toward the center, in lateral view, of the humeral head.
  Insert K-wires or temporary screws through jig into humeral head.
  Radiographically confirm proper alignment of humeral head to humeral shaft.
  Drill with 3 mm non-cannulated drill and place screw through distal hole in plate or insert K-wires through jig into humeral shaft.
  Remove any K-wires that may be external to jig that may interfere with site preparation and implant delivery.

II. Provide Access
  Place a bushing sized to receive a drill and a bushing sized to receive a K-wire into a guide included in the jig, the K-wire bushing being nested inside the drill bushing (see, for example, FIG. 65).
  Drive 2.0 or 2.5 mm K-wire through the wire guide bushing into humeral head.
  Radiographically confirm that tip of K-wire is located centrally within the humeral head (target site) in AP and lateral views.
  Remove wire guide bushing.
  Place 8.0 mm cannulated drill through drill guide bushing and advance drill slowly with spindle rotating at high speed to reach target location.

III. Site Preparation
  Insert the fully collapsed cavity preparation device into the drill guide bushing and advance the instrument to the target location.
  Radiographically confirm site preparation instrument position.
  Rotate the entire site preparation instrument three times.
  Slightly expand the site preparation instrument cutting flutes by rotating the site preparation instrument expansion knob clockwise ¼ turn (one click).
  Rotate the entire site preparation instrument three more times.
  Repeat: Expand flutes by one click and rotate the entire site preparation instrument three times until tactile or audible feedback is received and/or until radiography indicates that the cutting flutes are nearing the cortical wall. The site preparation instrument does not need to be fully expanded; the implant is effective in a wide range of diameters.
  Collapse the site preparation instrument by rotating the expansion dial counter-clockwise until it stops.
  Remove site preparation instrument from the access site.
  K-wires that interfere with the instrument may be removed.

IV. Cage Implant Delivery, Rotation, and Locking
  Advance implant through drill guide bushing and up to target location. Deploy implant head by rotating delivery device knob clockwise.
  Attach implant rotation instrument to implant shaft.
  Manually rotate cage multiple times to properly seat cage.
  Confirm that release lever of implant rotation instrument is aligned with center of jig.
  Radiographically confirm expansion of cage.
  Tighten cage-locking screw to lock cage in expanded state.

V. Distal Targeting/Implant Fixation
  Attach distal targeting apparatus to implant shaft.
  Confirm that cage-locking screw is fully advanced prior to drilling.
  Drill bicortically using 3.0 mm non-cannulated drill
  Measure length for screw using graduations on drill.
  Insert 3.5 mm cannulated screw.

VI. Humeral Head Screws
  Thread a drill guide bushing sized to receive a drill into a screw hole defined by the jig, the drill guide bushing including a K-wire bushing nested within an inner lumen of the drill guide bushing.
  Place 0.062" K-wire through the K-wire bushing.
  Remove K-wire bushing.
  Measure length for screw using depth gauge.
  Drill near cortex with 2.9.mm cannulated drill.
  Remove drill guide bushing.
  Place 3.5 mm cannulated screw.

VII. Proximal Targeting/Fragment Fixation
  Attach apparatus for directing fixation elements to implant shaft.
  Insert 0.062" K-wires for through the apparatus for guiding cannulated screws into the implant head.
  Measure for screw length using depth gauge.
  Drill using 2.9 mm cannulated drill over K-wire.
  Insert 3.5 mm cannulated screws over the K-wires and through the cage to secure fragments. (Stacked suture washers may be used with any fragment screw for buttress of poor quality bone or attachment of suture.

Two or more washers may be stacked.) Two bicortical screws across the fracture line may enhance biomechanical integrity. One suture per eyelet may be provided.

Remove cage delivery tube utilizing 5/32" hex driver.

VIII. Distal Screws and Closure

Drill, measure, and insert one or more distal 3.5 mm screws.

Remove K-wires.

Repair cuff attaching suture to suture washers and/or suture attachment points on optional plate.

Close incisions.

Perform post-operative protocols for surgical treatment of proximal humerus fractures.

The steps of illustrative methods may be performed in an order other than the order shown and/or described herein. Some embodiments may omit steps shown and/or described in connection with the illustrative methods. Some embodiments may include steps that are neither shown nor described in connection with the illustrative methods. Illustrative method steps may be combined. For example, one illustrative method may include steps shown in connection with another illustrative method.

Some embodiments may omit features shown and/or described in connection with the illustrative apparatus. Some embodiments may include features that are neither shown nor described in connection with the illustrative apparatus. Features of illustrative apparatus may be combined. For example, one illustrative embodiment may include features shown in connection with another illustrative embodiment.

Embodiments may involve some or all of the features of the illustrative apparatus and/or some or all of the steps of the illustrative methods.

The illustrative apparatus and therapeutic scenarios will now be described now with reference to the accompanying drawings in the Figures, which form a part hereof. It is to be understood that other embodiments may be utilized and that structural, functional and procedural modifications may be made without departing from the scope and spirit of the present disclosure.

For the sake of clarity, figures may illustrate therapeutic treatment of bones without showing fracture lines.

Figure 2:
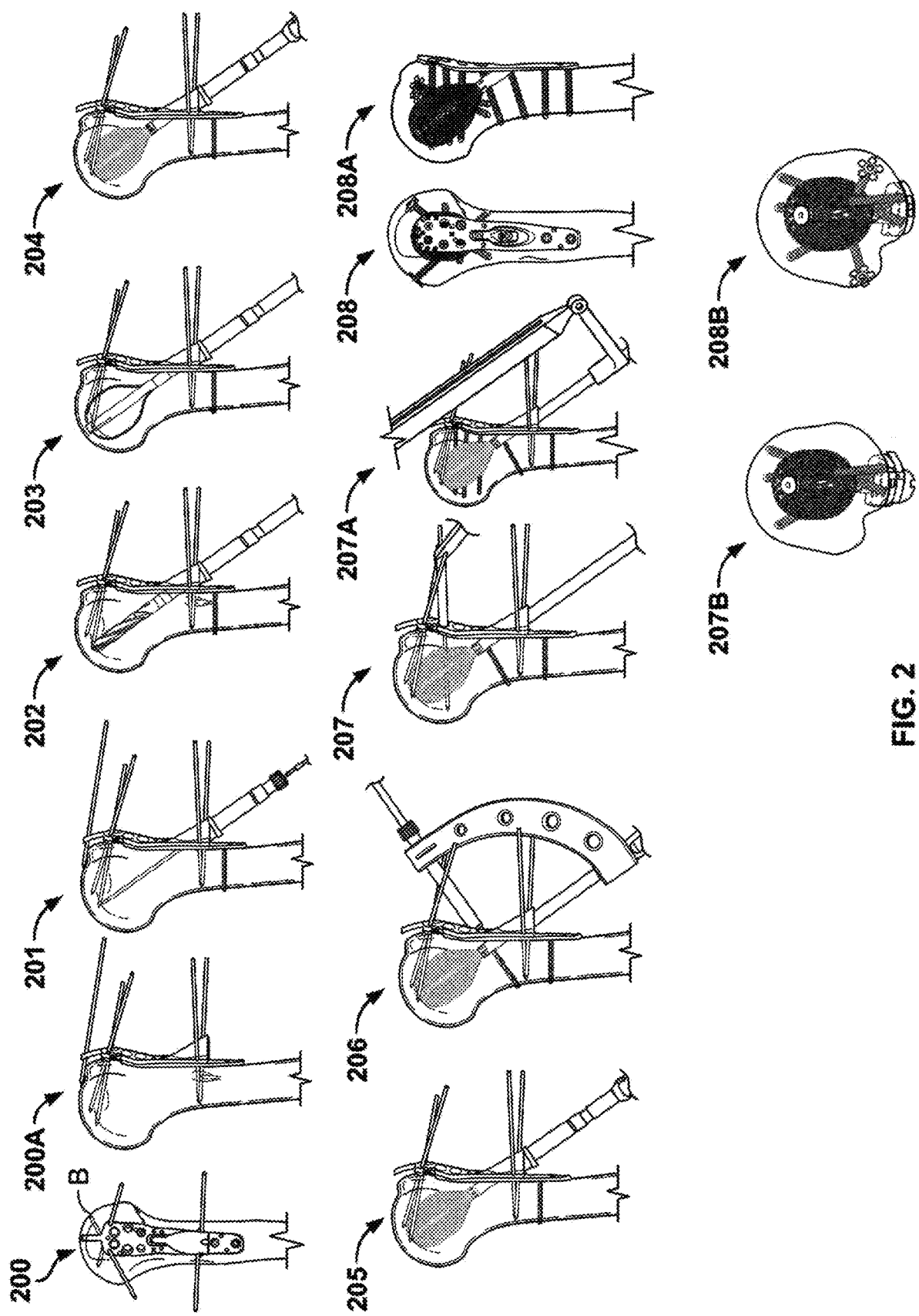
FIG. 2 shows illustrative apparatus and methods in accordance with principles of the invention.

FIGS. 1 and 2 illustrate steps that may be performed by using apparatus shown and described herein.

FIG. 1 shows an illustrative procedure for inserting an implant in a bone such as bone B. The illustrative procedure shown in FIG. 1 is shown using a jig and K-wires. The illustrative procedure may be used with any jig, plate, or jig and plate combination disclosed herein.

The illustrative procedure may include one of more of the steps shown in FIG. 1.

At steps 100 and 101, a fracture may be reduced and stabilized by complementarily seating a jig on an anatomical landmark of bone B. The seating registers the jig holes to define K-wire trajectories that lead into bone B, but away from a volume in the interior of B that will be prepared for and occupied by the implant. The seating registers a target hole defined by the jig to the target site. A target hole may be registered to a target site when the target hole points in a direction that transects the target site. The seating places a large jig opening in position for reception of the implant. The K-wires position the various bone fragments (not shown) for later anchoring to the implant.

At step 102, an implant location may be targeted. A hinged positioning device is registered, at the proximal end of the jig, to the target site. A distal limb of the positioning device points to a location for drilling of an access hole. A K-wire is inserted toward the target site.

At step 103, an access site of the implant may be confirmed using a template (not shown).

At step 104, a cannulated drill is inserted over the K-wire to access medullary space.

At step 105, a cavity for receiving the implant may be prepared using a cavity preparation device.

At step 106, the implant may be deployed in the cavity.

At step 107, the implant may be seated in the cavity by rotating the implant. A handle may be attached to an implant shaft to effect the rotation. The implant may be locked in the expanded state.

At step 108, apparatus for directing an anchor is attached to the implant shaft. This registers anchor direction features to the tail of the implant, in which there is disposed an anchor receiving feature.

At step 109, the anchor direction apparatus is replaced by a guide for directing K-wires. The guide has a channel that parallels the center line of the implant so that K-wires may be driven toward the center of the implant at different angles relative to the shaft.

At step 110 the implant may be secured to the bone and/or fractured bone segments using one or more screws, plates and/or washers.

FIG. 2 shows an illustrative procedure for inserting an implant in bone B. The illustrative procedure shown in FIG. 2 is shown using a plate removably coupled to a jig. The jig may be positioned on a top face of the plate. The illustrative procedure may be used with any jig, plate, or jig and plate combination disclosed herein.

The illustrative procedure may include one of more of the steps shown in FIG. 2.

At step 200, the fracture may be reduced and stabilized by complementarily seating a jig and a plate on an anatomical landmark of a bone such as bone B. The seating registers the jig holes to define K-wire trajectories that lead into bone B, but away from a volume in the interior of B that will be prepared for and occupied by the implant. The K-wires are shown is a skewed orientation to help fasten the jig to the bone. The seating registers a target hole defined by the jig to the target site. The seating places a large jig or plate opening in position for reception of the implant. The K-wires position the various bone fragments (not shown) for later anchoring to the implant.

At step 200A, the view has been rotated to show a side view of the plate under the jig and a slanted guide, registered to the target site, that will receive instrumentation and the implant.

At step 201, an implant location may be targeted. Bushings down-size the guide to fit a K-wire, which is inserted toward the target site. An access angle for implanting the implant into the interior may be confirmed using a template (not shown). Confirming the access angle may include inserting a bushing into a guide defined by the jig and advancing a K-wire through the guide and into an interior of the bone. If the access angle is undesirable, the K-wires may be removed and the guide and plate may be repositioned on the bone. If the access angle is undesirable, the bushing may be removed and replaced with an angled bushing. The angled bushing may have an oblique bore that modifies the access angle, relative to the guide central axis.

At step 202, a drill is inserted to access medullary space. The drill may be inserted over the K-wire. Appropriate bushing may be provided for the drill.

At step 203, a cavity for receiving the implant may be prepared using a cavity preparation device.

At step 204, the implant may be deployed in the cavity.

At step 205, the implant may be seated in the cavity by rotating the implant. A handle may be attached to an implant shaft to effect the rotation. The implant may be locked in the expanded state.

At step 206, apparatus for directing an anchor is attached to the implant shaft. This registers anchor direction features to the tail of the implant, in which there is disposed an anchor receiving feature.

At step 207A, K-wires may be driven through the implant head using the guide for directing K-wires. Anchors may be driven through the plate and the implant head.

At step 207B the implant may be secured to the bone and/or fractured bone segments using one or more screws, plates and/or washers.

At steps 208, 208A and 208B the implant may be secured to the bone. The implant may be secured to the bone by driving cannulated screws over the fixation elements positioned in step 207 and step 207A. Step 208 may also include securing the implant to the bone and/or fractured bone segments using one or more screws, plates and/or washers. The implant may be secured to the bone by driving a screw through the bone and into the implant, driving a screw through the plate and into the implant and bone and/or driving a screw through the plate and into the bone.

Figure 2A:
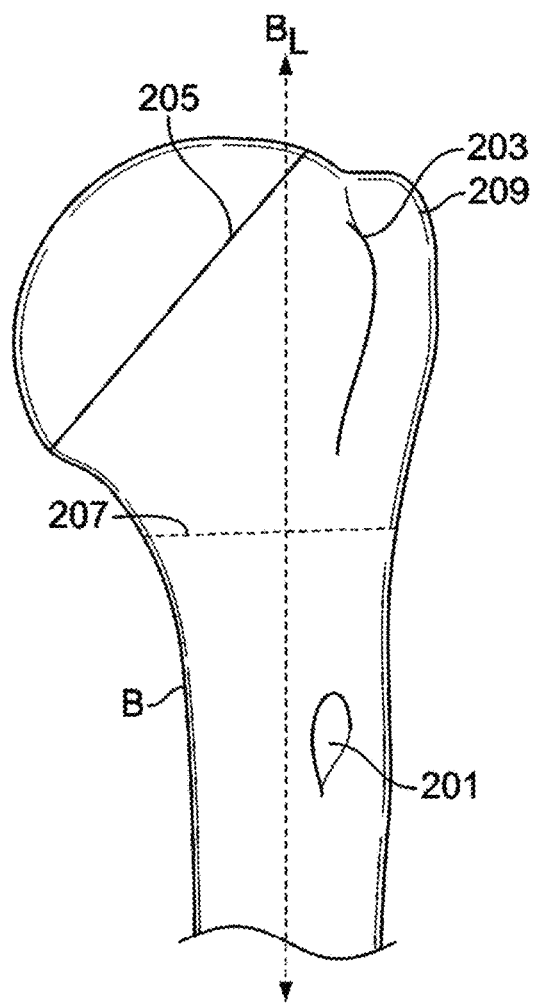
FIGS. 2A and 2B show portions of a humerus bone.

FIG. 2A shows bone B from in lateral projection. In FIG. 2A, bone B is a humerus. A proximal portion of the humerus is illustrated in FIG. 2A. For the purposes of the application, "proximal" may refer to a location closer to a patient's core, and "distal" may refer to a location further away from the patient's core. A proximal portion of the humerus may be referred to herein as the proximal humerus.

The proximal humerus may include greater tuberosity 209, lesser tuberosity 203, surgical neck 207, head of humerus 205 and deltoid tuberosity 201. $B_L$ is a longitudinal axis defined by the proximal humerus.

Figure 2B:
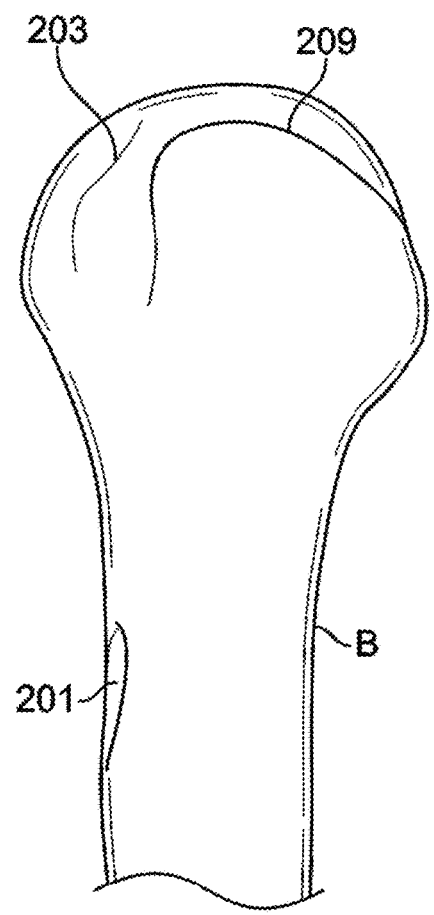

FIG. 2B shows a view of the proximal humerus that is different from the view illustrated in FIG. 2A.

Figure 2C:
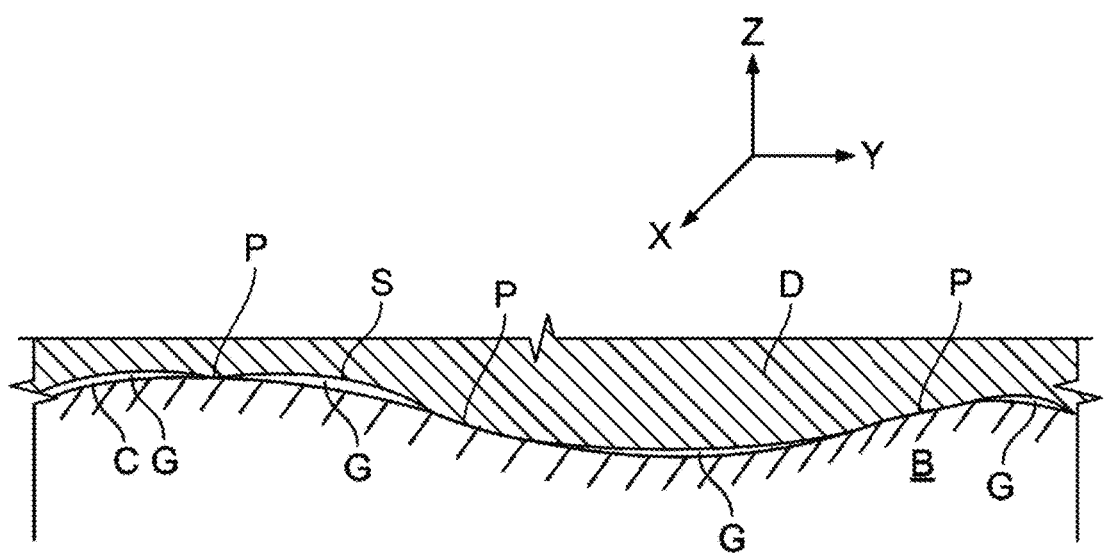
FIG. 2C shows conceptually a relationship between apparatus, in accordance with the principles of the invention, and anatomy.

FIG. 2C shows conceptually device D complementarily seated against contour C of an anatomical feature or landmark on bone B. Contour C may have a height z that varies in one or both of directions x and y. Device D has bottom surface S that complements contour C. The complementary seating dictates the placement of device D.

Gaps G may intervene between bottom surface S and contour C. S may be complementarily seated against C based on discrete points of contact P. The discrete points of contact may be spaced apart from each other.

Bottom surface S may be coincident with contour C. When bottom surface S is coincident with contour C, no gaps may intervene between bottom surface S and contour C.

Figure 3:
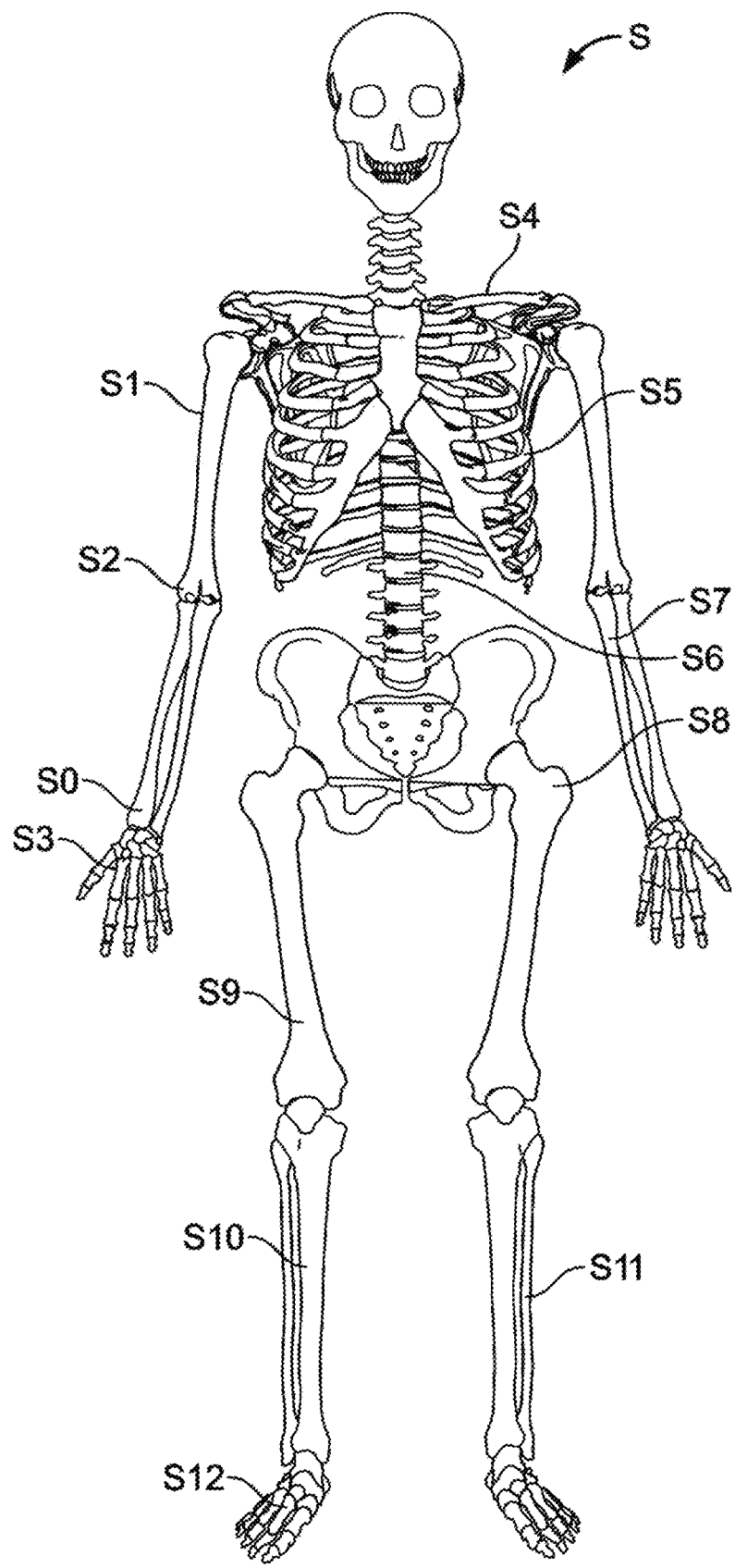
FIG. 3 shows a human skeleton.

FIG. 3 shows illustrative anatomy in connection with which the apparatus and methods may be used. FIG. 3 shows illustrative skeleton S. Skeleton S may include illustrative bones $S_i$ in which apparatus and methods in accordance with the principles of the invention may be used.

The apparatus and methods may be used in connection with "hollow" bones. The hollow bones may include cortical tissue. The hollow bones may include cancellous tissue. Cortical tissue may be referred to as "tissue." Cancellous tissue may be referred to as "tissue." Other matter in the interior of a bone may be considered "tissue." The bone may be considered "tissue."

The apparatus and methods may be used to create a space inside a bone. The bone may be any bone Si included in Table 5 below. The space may be a cavity. The tissue may be inside the bone. The space may be created by breaking up the tissue. The space may be created by removing the tissue from the bone. The space may be created as part of a therapeutic procedure. The apparatus and methods may displace tissue by imparting mechanical energy to the tissue, for example, through one or more of expanding motion, rotational motion, axial motion, compressive motion, cutting motion, and any other suitable motions.

The apparatus and methods may be used to deploy an implant in the space created inside the bone. The apparatus and methods may be used to anchor the implant to the bone. The implant may be any implant disclosed herein. The implant may be used together with any plate disclosed herein. The apparatus and methods disclosed herein may be used in any bone in the body.

Illustrative bones Si in which apparatus and methods in accordance with the principles of the invention may be used are included in Table 5 below. Table 5 may include a partial list of bones Si.

TABLE 5

Bones $S_i$.

| Bone | Reference numeral in FIG. 3 |
| --- | --- |
| Distal Radius | $S_0$ |
| Humerus | $S_1$ |
| Proximal Radius and Ulna (Elbow) | $S_2$ |
| Metacarpals | $S_3$ |
| Clavicle | $S_4$ |
| Ribs | $S_5$ |
| Vertebrae | $S_6$ |
| Ulna | $S_7$ |
| Hip | $S_8$ |
| Femur | $S_9$ |
| Tibia | $S_{10}$ |
| Fibula | $S_{11}$ |
| Metatarsals | $S_{12}$ |

Apparatus and methods described above may be utilized in any bone Si included in Table 5 above, or any other bone in the human body.

Apparatus and methods illustrated in the figures are shown in reference to a bone 'B'. The apparatus and methods described in respect to bone 'B' may be utilized in any bone Si included in Table 5 above, or any other bone in the human body.

Figure 4:
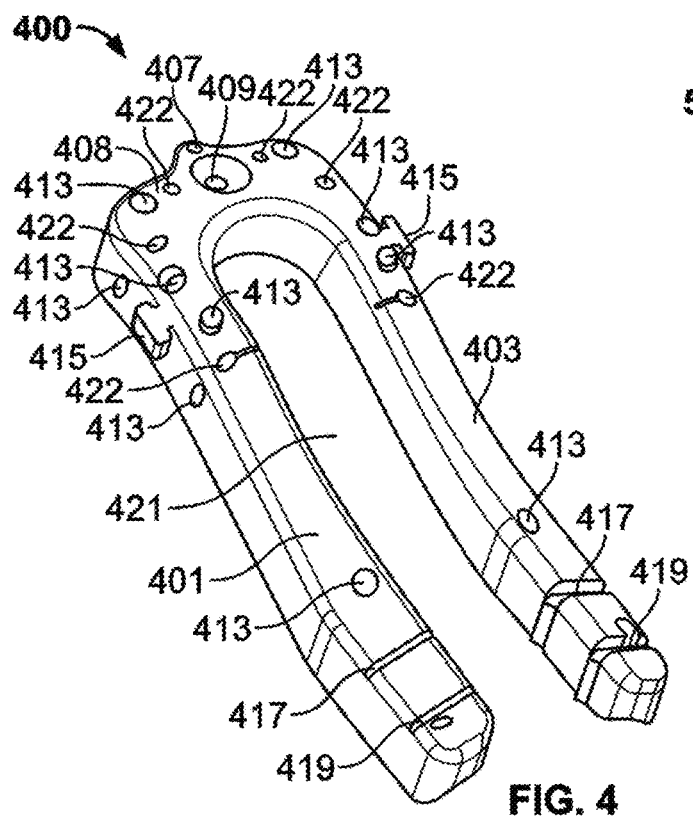
FIG. 4 shows illustrative apparatus in accordance with principles of the invention.

FIG. 4 shows illustrative jig 400. Illustrative jig 400 may include transverse member 408, first longitudinal member 401 and second longitudinal member 403. Transverse member 408, first longitudinal member 401 and second longitudinal member 403 may together define opening 421. A plate may be positioned in opening 421.

Jig 400 may include indicators 419 and indicators 417. Indicators 417 may register to a first location on the bone surface for initiating a first access hole. Indicators 419 may register to a second location on the bone surface for initiating a second access hole.

Jig 400 may include a bottom surface (not shown). The bottom surface may conform to a surface contour of a bone. When the bottom surface of jig 400 is seated complementarily against the surface contour, target hole 409 may point in a direction. The direction may point to a target site. A target site may be a location in the bone interior where a physician may desire to position an end of an implant. The end of the implant may be an end of an implant head distal the physician when the implant is implanted in the bone.

Jig 400 may include positioning hole 407. When the bottom surface is seated complementarily against the surface contour, positioning hole may point in a direction tangent to a greater tuberosity.

Jig 400 may include a first bottom surface. The first bottom surface may extend along at least a portion of a bottom face of longitudinal member 401 and along at least a portion of a bottom face of transverse member 408. The first bottom surface may conform to a surface contour of a first bone, for example a left humerus or a right humerus. Jig 400 may also include a second bottom surface. The second bottom surface may extend along at least a portion of a bottom face of longitudinal member 403 and along at least a portion of a bottom face of transverse member 408. The second bottom surface may conform to a surface contour of a second bone, for example a right humerus or a left humerus.

Jig 400 may include plurality of holes 413. When the bottom surface of the jig is seated complementarily against the surface contour, each of the plurality of holes may point into an interior of the bone. Each of the plurality of holes may not point not into a volume occupied by an implant in the interior. The volume may be a volume occupied by the implant when the implant is positioned at the target site in the interior and radially expanded to form a mesh cage. The volume may be referred to alternately herein as an implantation region.

Jig 400 may include suture holes 422. Jig 400 may include cleats 415. Cleats 415 may be used to anchor suture lines to jig 400. A physician may pass a suture through one or more suture holes 422 and then wrap the suture line around cleat 415.

Jig 400 may include bushings (not shown). The bushings may be screwed or placed onto holes defined by the jig. Each of the bushings may be used to guide a fixation element through the jig and into an interior of a bone.

Figure 5:
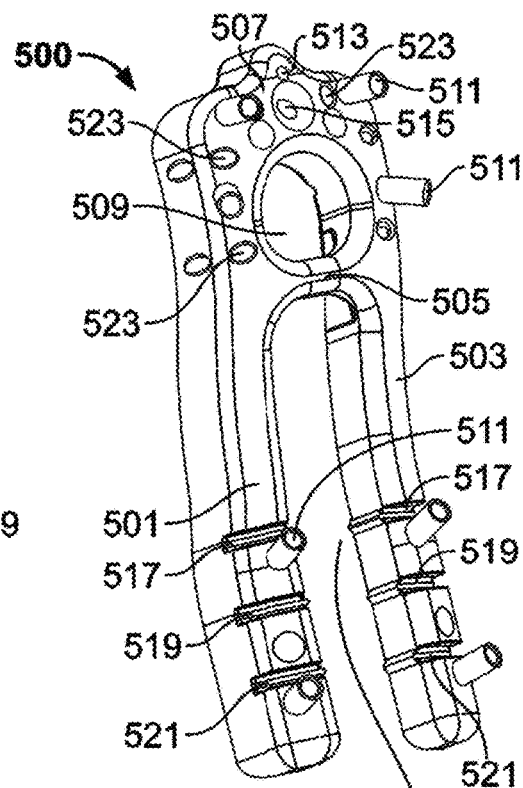
FIG. 5 shows illustrative apparatus in accordance with principles of the invention.

FIG. 5 shows illustrative jig 500. Illustrative jig 500 may include first transverse member 507, second transverse member 505, first longitudinal member 501 and second longitudinal member 503. First transverse member 507, second transverse member 505, first longitudinal member 501 and second longitudinal member 503 may define hole 509. Hole 509 may be used to access a plate positioned under jig 500. Hole 509 may provide clearance for driving a screw into a bone B.

Second transverse member 505, first longitudinal member 501 and second longitudinal member 503 may surround area 502. A plate may be positioned in area 502.

Second transverse member 505 may provide jig 500 with additional rigidity in comparison with jig 400. Second transverse member may provide extra support along a bone when jig 500 is positioned on the bone.

Jig 500 may include indicators 517, indicators 519 and indicators 521. Jig 500 may include positioning hole 513. Jig 500 may include target hole 515. Jig 500 may include a plurality of holes 511. In FIG. 500, bushings 511 are shown to be screwed into some of the holes 511. Bushings 511 may assist a physician in guiding a fixation element through jig 500 and into a bone interior. Jig 500 may include suture holes 523.

Jig 500 may include a bottom surface (not shown). The bottom surface may conform to a surface contour of a bone.

Figure 6:
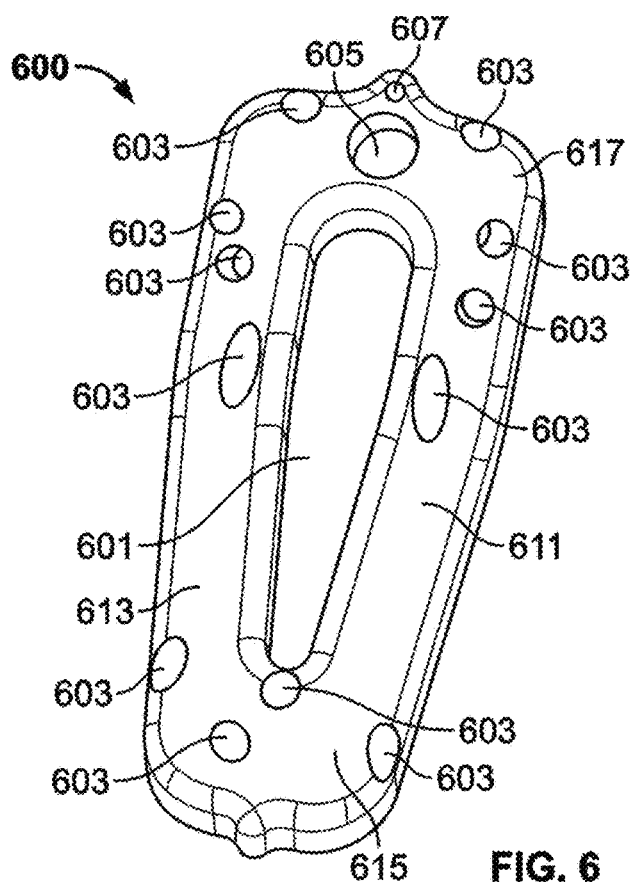
FIG. 6 shows illustrative apparatus in accordance with principles of the invention.

FIG. 6 shows illustrative jig 600. Illustrative jig 600 may include first transverse member 617, second transverse member 615, first longitudinal member 611 and second longitudinal member 613. First transverse member 617, second transverse member 615, first longitudinal member 611 and second longitudinal member 613 may together define opening 601. An access hole may be prepared at a portion of the bone defined by opening 601.

Jig 600 may include target hole 605 and positioning hole 607. Jig 600 may include a plurality of holes 603.

Jig 600 may include a bottom surface (not shown). The bottom surface may conform to a surface contour of a bone.

Figure 7:
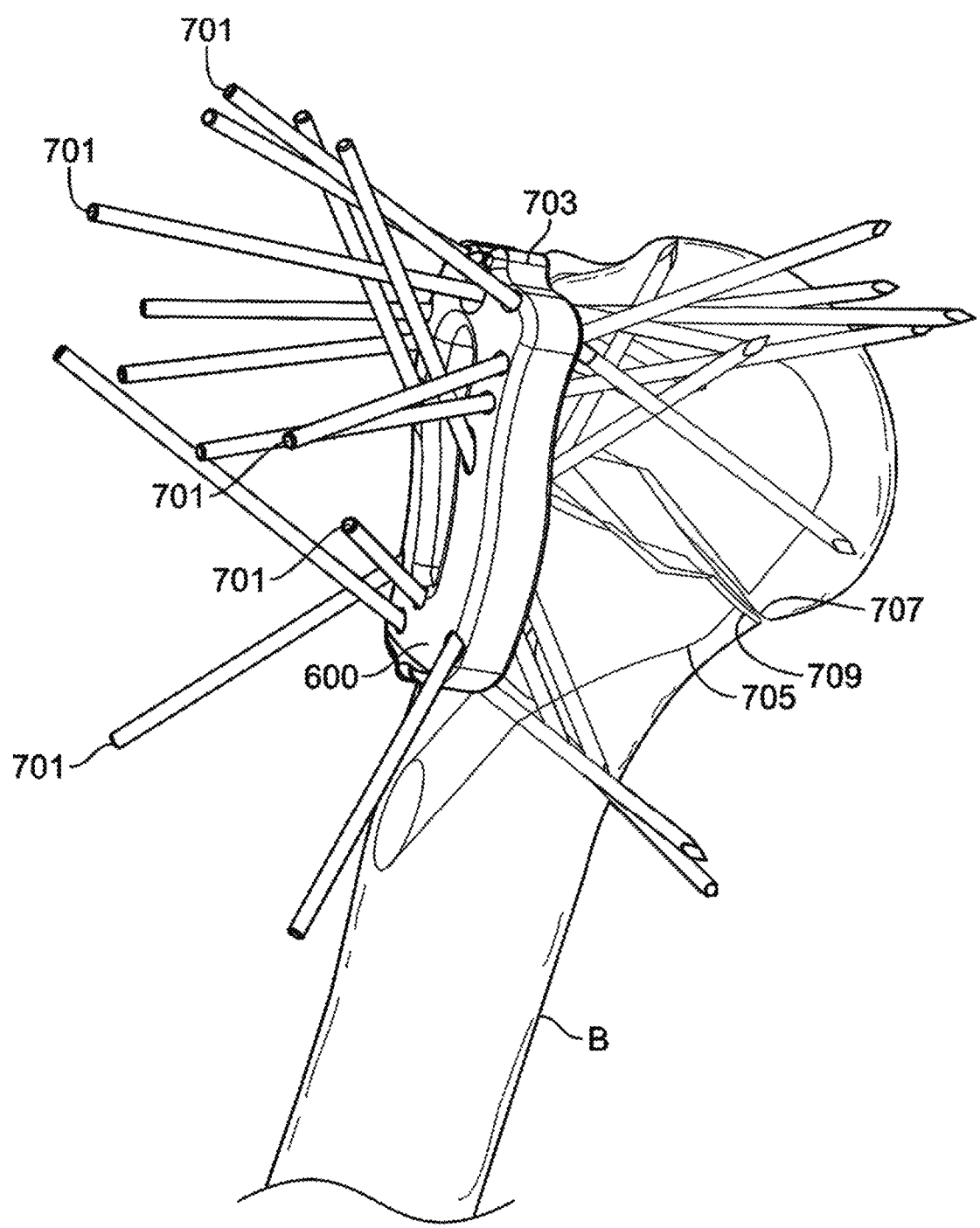
FIG. 7 shows illustrative apparatus and methods in accordance with principles of the invention.

FIG. 7 shows illustrative jig 600 positioned on bone B. Bone B may be a humerus bone. Jig 600 may be positioned on a lateral aspect of the proximal humerus bone. Bone B may be a fractured bone having bone fragment 707 and bone fragment 709. Jig 600 may be positioned over the fracture line defined by bone fragment 707 and bone fragment 709.

The bottom surface of jig 600 may be seated complementarily against a surface contour defined by B. When the bottom surface of jig 600 is seated complementarily against the surface contour, head 703 of jig 600 may be positioned flush with a top of a greater tuberosity on bone B.

Fixation elements 703 may be driven through the plurality of holes defined by jig 600 and into an interior of bone B. FIG. 7 illustrates exemplary trajectories of fixation elements 703. The exemplary trajectories may facilitate the reduction of the broken bone segments. The exemplary trajectories may secure broken bone B. At least one fixation element is shown driven through the fracture, assisting in securing together both parts of bone B.

The exemplary trajectories may preserve an open or unobstructed region in the interior of bone B in which the implant can be inserted into the bone. Fixation elements 703 may penetrate the interior of bone B without penetrating volume 705. Volume 705 may be a volume occupied in the interior of the bone by an implant when the implant is positioned at the target site and radially expanded to form a mesh cage. Volume 705 may be referred to alternately as an implantation region.

Figure 8:
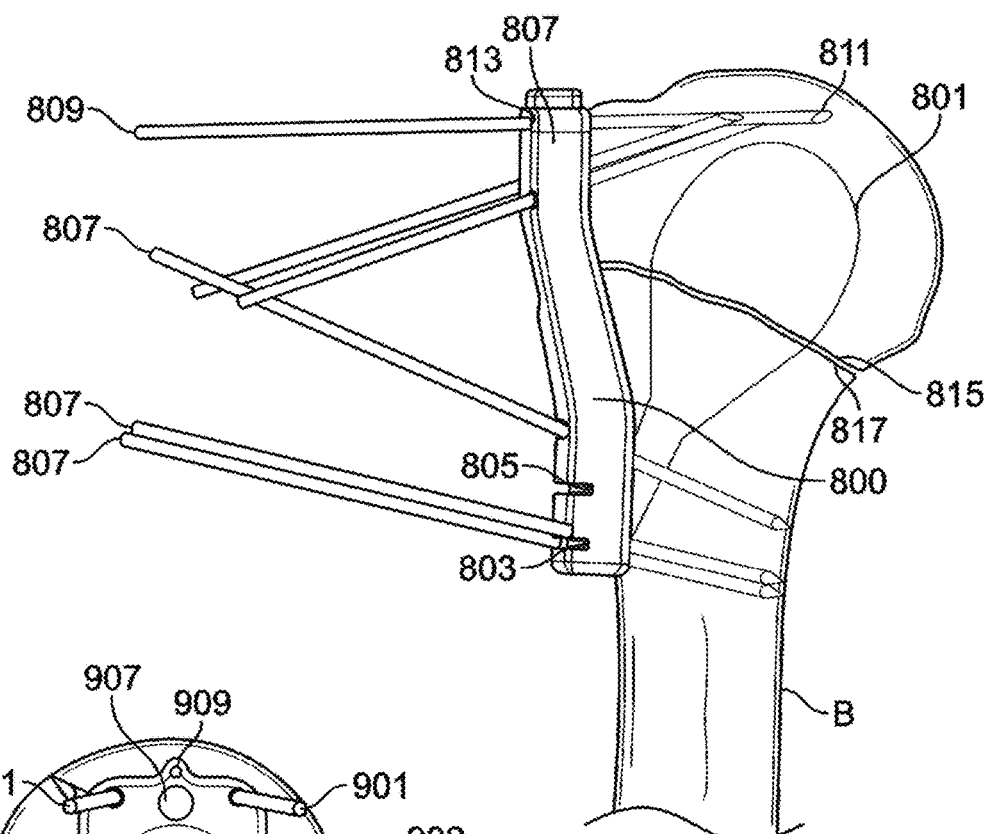
FIG. 8 shows illustrative apparatus and methods in accordance with principles of the invention.

FIG. 8 shows illustrative jig 800 positioned on bone B. In FIG. 8, bone B may be a proximal humerus. Bone B may have a fractured proximal humeral head. Bone B may include bone segment 805 and bone segment 807.

Jig 800 may include a bottom surface (not shown) complementing a surface contour defined by bone B. In FIG. 8, the bottom surface may be seated complementarily against the surface contour.

Jig 800 may include target hole 813. Target wire 809 may be driven through target hole 813 and into bone B. Tip 811 of target wire 809 may be positioned at a target site. The target site may be a location in bone B for implanting an implant.

Jig 800 may include indicator 803 and indicator 805.

Jig 800 may define a plurality of holes. In FIG. 8, fixation elements 807 are shown passing through the plurality of holes and into an interior of bone B. The plurality of holes may position fixation elements 807 in the interior but not in volume 801. Volume 801 may be a volume occupied in the interior of the bone by an implant when the implant is positioned at the target site and radially expanded to form a mesh cage.

Figure 9:
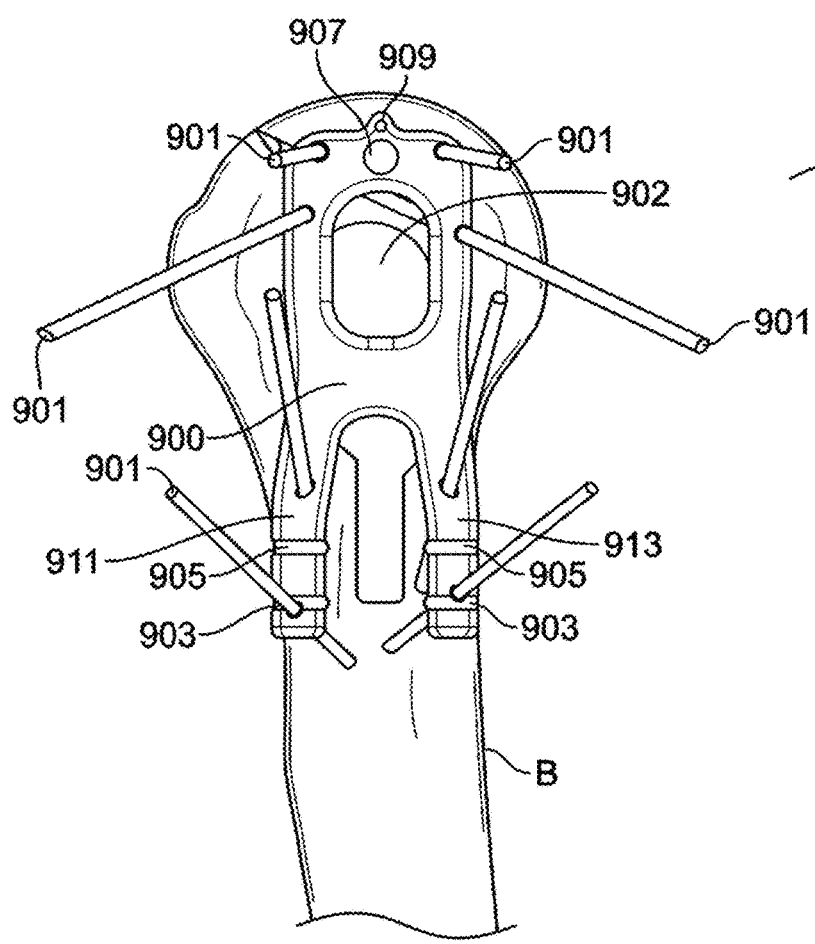
FIG. 9 shows illustrative apparatus and methods in accordance with principles of the invention.

FIG. 9 shows illustrative jig 900 positioned on bone B. In FIG. 9, bone B may be a proximal humerus. Bone B may have a fractured proximal humeral head.

Jig 900 may include a bottom surface (not shown) complementing a surface contour defined by bone B. In FIG. 9, the bottom surface may be seated complementarily against the surface contour.

A shape of jig 900 may provide a large supportive surface area on bone B while providing bone visibility during a surgical procedure. Driving fixation elements 901 through jig 900 on each side of the fracture may assist in securing the fracture during the surgical procedure.

Jig 900 may include distal leg member 911 and distal leg member 913. Distal leg member 911 and distal leg member 913 may be positioned on either side of the proximal humeral shaft to allow for access to bone B through an access hole without obstructing the access hole. Indicators 905 may indicate an area on bone B for initiating a first access hole. Indicators 905 may indicate a second area on bone B for initiating a second access hole. A practitioner may initiate an access hole between indicators 903. A practitioner may initiate an access hole between indicators 905.

Jig 900 may define a plurality of holes. Jig 900 may define positioning hole 909 and target hole 907.

In FIG. 9, fixation elements 901 are shown passing through the plurality of holes and into the interior of bone B. The plurality of holes may position fixation elements 901 in the interior but not in volume 901. Volume 901 may be a volume occupied in the interior of the bone by an implant when the implant is positioned at a target site in the interior and radially expanded to form a mesh cage. The target site may be defined by a target wire passing through target hole 907 and into bone B.

Figure 10:
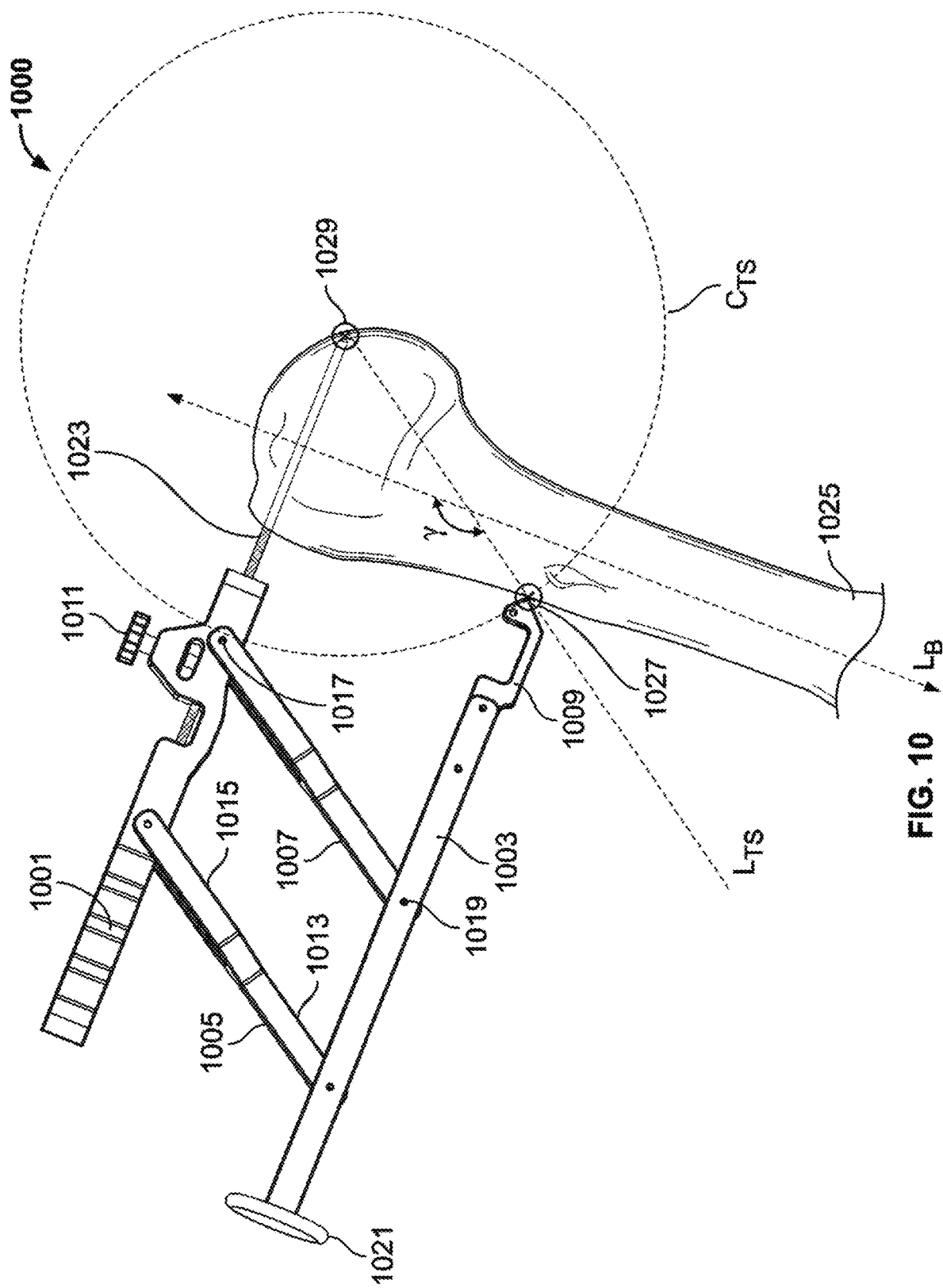
FIG. 10 shows illustrative apparatus and methods in accordance with principles of the invention.

FIG. 10 shows illustrative therapeutic scenario 1000. Scenario 1000 shows a targeting apparatus positioned on bone 1025. Bone 1025 may include one or more features of bone B or any suitable bone shown in FIG. 3. Therapeutic scenario 1000 may include positioning the implant inside bone 1025. Bone 1025 defines longitudinal axis $L_B$. Bone 1025 may be a humerus or any other suitable bone shown in FIG. 3. Apparatus 1000 may be used to identify an access position for inserting the implant into an implantation region of bone 1025.

Therapeutic scenario 1000 shows elongated base member 1001. Therapeutic scenario 1000 shows elongated targeting member 1003. Therapeutic scenario 1000 shows first swing arm 1005. First swing arm 1005 is pivotally affixed to base member 1001. First swing arm 1005 is pivotally affixed to base member 1001. First swing arm 1005 may be pivotally affixed to base member 1001 at any suitable position along a longitudinal axis of base member 1001.

First swing arm 1005 may include elongated body 1013. First swing arm 1005 may include clevis 1015. First swing arm 1005 may be pivotally affixed to base member 1001 by a pin (not shown) that passes through clevis 1015 and base member 1001.

Targeting member 1003 may include one or more channels (not shown). Each channel may have a longitudinal axis. First swing arm 1005 may be pivotally affixed to targeting member 1003 by a pin that passes through targeting member 1003, trough elongated portion 1013 of first swing arm 1005 and passes perpendicular to the longitudinal axis of the channel.

First swing arm 1005 is pivotally affixed to the targeting member 1003. First swing arm 1005 may be positioned at any suitable position along a longitudinal axis of targeting member 1003.

Therapeutic scenario 1000 shows second swing arm 1007. Second swing arm 1007 may be pivotally affixed to base member 1001. For example, second swing arm 1007 may be pivotally affixed to base member 1001 by a pin (not shown) that passes through aperture 1017 in base member 1001. Aperture 1017 may be positioned at any suitable position along a longitudinal axis of base member 1001.

Second swing arm 1007 may be pivotally affixed to targeting member 1003. For example, second swing arm 1007 may be pivotally affixed to targeting arm 1003 by a pin (not shown) that passes through aperture 1019 in targeting arm 1003. Aperture 1019 may be a positioned at any suitable position along a longitudinal axis of targeting arm 1003.

Pivotal connections to base member 1001 and targeting member 1003 may position first swing arm 1005 parallel to second swing arm 1007. Pivotal connection to first swing arm 1005 and second swing arm 1007 may position base member 1001 parallel to targeting member 1003.

Base member 1001 may define a receptacle (shown in notch, but not numbered) that is configured to receive fixation element 1023. The receptacle may extend along a longitudinal axis of base member 1001.

A tip of fixation element 1023 may be positioned inside bone 1025. The tip of fixation element 1023 when positioned inside bone 1025 may define a proximal end of the implantation region. The tip of fixation element 1023 may be positioned within bone 1025 using fluoroscopy or other suitable imaging techniques.

The receptacle defined by base member 1001 may be configured to receive fixation element 1023 at a position on fixation element 1023 that is operatively external to bone 1025. Fixation element 1023 may include a K-wire. For example, fixation element 1023 may be a 0.062" K-wire.

When fixation element 1023 is positioned on proximal end of bone 1025 and fixation element 1023 is positioned inside the receptacle of base member 1001, first swing arm 1005 and second swing arm 1007 are configured to allow gravity to pull targeting member 1003 in a distal direction along axis $L_B$.

Base member 1001 may include set screw 1011. Set screw 1011 may be configured to lock base member 1001 to fixation element 1023. Base member 1001 may be locked to fixation element 1023 after fixation element 1023 is inserted into bone 1025. Fixation element 1023 may be inserted into bone 1025 at a position relative to an anatomical landmark of bone 1025. For example, when bone 1025 is a humerus, fixation member 1023 may be positioned relative to a greater tuberosity of the humerus. Fixation member 1023 may be positioned relative to a head of the humerus.

Base member 1001 may be locked to fixation element 1023 after a suitable position of the tip of fixation element 1023 has been verified using a suitable imaging technique. A suitable position of the tip may be inside a head of a humerus. A suitable position of the tip may include a center of the humeral head in a lateral view.

When fixation element 1023 is positioned within the receptacle, targeting member 1003, in operation, moves along a circumference $C_{TS}$ of a circle centered at the tip of fixation element 1023. When base member 1001 is positioned on fixation member 1023, swing arms 1005 and 1007 allow targeting member 1003 to move along circumference $C_{TS}$.

When targeting member 1003 moves along circumference $C_{TS}$, targeting member 1003 identifies access position 1027 at an intersection of circumference $C_{TS}$ and an outer surface bone 1025. Access position 1027 may correspond to a position, on an outside surface of bone 1025, for drilling an access hole into bone 1025. The access hole may provide access to an interior of bone 1025. The access hole may provide access to the implantation region.

The tip of fixation element 1023 and access position 1027 define longitudinal axis $L_{TS}$ of the implantation region inside bone 1025.

Longitudinal axis $L_{TS}$ defines angle γ, with respect to longitudinal axis $L_B$ of bone 1025. Angle γ corresponds to an angle at which the implant will be positioned, relative to axis $L_B$ inside bone 1025.

Targeting member 1003 may include indicator 1009. Indicator 1009 may be positioned at a proximal end of targeting member 1003. Indicator 1009 may be configured to indicate access position 1027 on bone 1025 at the intersection of the outer surface of bone 1025 circumference $C_{TS}$. A length of the implant may correspond to a distance from a center of the circle to access position 1027.

The receptacle defined by base member 1001 may be configured to position base member 1003 with respect to fixation element 1023 such that, in operation, indicator 1009 is positioned on circumference $C_{TS}$.

Targeting member 1003 may include a first concave surface (not shown) that is configured to guide a drill into bone 1025 when the drill is oriented substantially perpendicular to axis $L_B$. Targeting member 1003 may include a second concave surface (not shown) that is configured to guide a drill into bone 1025 at angle γ. Indicator 1009 may include the first and second concave surfaces.

Therapeutic scenario 1000 shows finger support 1021. Pressure applied to finger support 1021 may hold indicator 1009 at access position 1027.

FIG. 11 shows illustrative therapeutic scenario 1100. Scenario 1100 shows a targeting apparatus positioned on bone 1125. Bone 1125 may include one or more features of Bone B or any suitable bone shown in FIG. 3. Apparatus shown in therapeutic scenario 1100 may be used to identify access position 1113 on an outer surface of bone 1125. Access position 1113 indicates a position on bone 1025 for inserting an implant into an implantation region inside bone 1125.

Therapeutic scenario 1100 shows base member 1104. Base member 1104 may include first sleeve 1105. First sleeve 1105 may be configured to slide over a length of fixation element 1107 that protrudes from bone 1125.

Base member 1104 may include second sleeve 1103. Therapeutic scenario 1100 shows curved member 1101. Curved member 1101 is slidably mounted in second sleeve 1103.

Curved member 1101 may indicate access position 1113 when first sleeve 1105 is positioned over fixation element 1107.

A tip of fixation element 11107 may be positioned inside bone 1125. When first sleeve 1105 is positioned over fixation element 1107, distal flute 1109 of curved member 1101 is positioned on circumference $C_{TS}$ of a circle centered at the tip 1114 of fixation element 1107. Distal flute 1109 is oriented to guide a drill bit perpendicularly into the bone to initiate a hole. The angle of the drill bit can then be backed off to establish a trajectory along $L_{TS}$.

Therapeutic scenario 1100 shows that fixation element 1107 is inserted into bone 1125 in a direction that is lateral-to-medial.

A distal end of curved member 1101 may include guide 1110. Guide 1110, when positioned against an outer surface of bone 1125 at access position 1113, indicates an angular direction, along axis $L_{TS}$, for drilling and for inserting the implant into bone 1125.

When fixation element 1107 is inserted into sleeve 1105, curved member 1101 may be configured to identify access position 1113 independent of a distance, along longitudinal axis $L_B$ of bone 1125.

When fixation element 1107 is inserted into sleeve 1105, curved member 1101 may be configured to identify access position 1113 independent of an angle between fixation element 1107 and longitudinal axis $L_{TS}$ of the implantation region.

Fixation element 1107 may be positioned at any suitable angle to longitudinal axis $L_B$. For example, a longitudinal axis of fixation element 1107 may be positioned substantially perpendicular to $L_B$. A longitudinal axis of fixation element 1107 may be positioned at an oblique angle to $L_B$.

In operation, guide 1110 may define a longitudinal axis $L_{TS}$ of the implantation region based on a position of tip 1114 of fixation element 1107 inside the bone 1125.

Bone 1125 may be a humerus. In operation, guide 1110 may define a longitudinal axis $L_{TS}$ of the implantation region that passes through a head of the humerus.

FIG. 12 shows illustrative therapeutic scenario 1200. Scenario 1200 shows a targeting apparatus positioned on bone 1202. Therapeutic scenario 1200 shows apparatus that may have one or more features in common with apparatus shown in in FIG. 10.

Base member 1201 may include set screw 1233 for securing base member 1201 to fixation element 1231. Therapeutic scenario 1200 shows clevis 1205 and clevis 1203 for pivotally affixing swing arms to base member 1201. Therapeutic scenario 1200 shows targeting member 1211. Targeting member 1211 may include indicator 1215.

Indicator 1215 may include concave guide surface 1223. In operation, when base member 1201 is positioned on fixation element 1231, indicator 1215 may be positioned on an outer surface of bone 1202 and identify an access position (such as access position 1027 shown in FIG. 10).

Surfaces 1223 and 1225 are the same or similar to surfaces present on indicator 1009, and indicator 1009 may include such surfaces. Surface 1223, as used in FIG. 10, can guide a drill that is aligned with member 1003 perpendicularly into the bone. After a starter hole is made, the drill bit can be backed off and angled along $L_{TS}$. Surface 1225, as used in FIG. 10, then guides the drill along $L_{TS}$.

Indicator 1215 may include concave surface 1223. When indicator 1215 is positioned at the access position, concave surface 1223 may be used to guide a surgical drill (not shown) into bone 1202. The scenario may be a scenario in which member 1213 is not present and does not obstruct the drill. Concave surface 1223 may be configured to orient the surgical drill with respect to an outer surface of bone 1202 to reduce the likelihood that the surgical drill will slide off of bone 1202. For example, concave surface 1223 may be configured to orient the surgical drill substantially perpendicular to $L_B$.

Indicator 1215 may include concave surface 1225. When indicator 1215 is positioned at an access position, concave surface 1225 is oriented to guide a surgical drill (not shown) into bone 1202 along axis $L_{TS}$. Indicator 1215 may include a channel (not shown) that allows the surgical drill to be rotated, without removing the drill from bone 1202, from being positioned in concave surface 1223 to being positioned in concave surface 1225.

Therapeutic scenario 1200 shows gripper 1221. Gripper 1221 is affixed to targeting member 1211. Gripper 1221 may stabilize targeting member 1211 on an outside surface of bone 1202. Gripper 1221 may stabilize targeting member 1211 on an outside surface of bone 1202, when targeting member 1211 contacts the outside surface of bone 1202. When bone 1202 is a humerus, gripper 1221 may be configured to stabilize targeting member 1211 on a humeral shaft of the humerus.

Gripper 1221 may include first projection 1219. Gripper 1221 may include second projection 1220. First projection 1219 is substantially parallel to second projection 1220. First projection 1219 is spaced apart from second projection 1220. First projection 1219 may be spaced apart from second projection 1220 by a distance. The distance may be greater than a width of targeting member 1211. The distance may be less than or equal to a width of bone 1202.

Gripper 1221 may be pivotally affixed to targeting member 1211.

When targeting member 1211 contacts an outside surface of bone 1202, first projection 1219 and second projection 1220 may be aligned with a longitudinal axis $L_{TS}$ of the implantation region.

Therapeutic scenario 1200 shows guide channel 1217. Guide channel 1217 may be pivotally affixed to indicator 1215. Guide channel 1217 may be pivotally affixed to indicator 1215 by a pin (not shown) that passes through aperture 1229.

Guide channel 1217 may include an elongated concave surface. Guide channel 1217 may be configured such that, in operation, when targeting member 1211 contacts an outer surface of bone 1202, guide channel 1217 defines longitudinal axis $L_{TS}$. Axis $L_{TS}$ may correspond to a longitudinal axis of the implantation region.

In operation, apparatus shown FIG. 12 may define an access position (such as access position 1027 shown in FIG. 10) on an outer surface of bone 1202. At the access position, guide channel 1217 defines longitudinal axis $L_{TS}$. Guide channel 1217 may define axis $L_{TS}$ at any suitable angle β between $L_{TS}$ and fixation element 1231. Apparatus shown in FIG. 12 may be configured to define any suitable axis $L_{TS}$ that passes through a center of a circle centered on a proximal end of bone penetrating 1231 inserted into bone 1202. Guide channel 1217 may guide a drill or other tool into bone 1202 along axis $L_{TS}$.

Therapeutic scenario 1200 shows angular stopping member 1213. Angular stopping member 1213 may be pivotally affixed to guide channel 1217. Guide channel 1217 may be pivotally affixed to angular stopping member 1213 by a pin (not shown) that passes through aperture 1227. Angular stopping member 1213 is pivotally affixed to swing arm 1207. Swing arm 1207 is pivotally affixed to targeting member 1211. Swing arm 1207 may be pivotally affixed to targeting member 1211 by a pin (not shown) that passes through aperture 1207.

Angular stopping member 1213 may be configured to support guide channel 1217. For example, in operation, when base member 1201 is positioned on fixation element 1231, targeting member 1213 may be configured to contact an outside surface of bone 1202. In operation, angular stopping member 1213 may be configured to support guide channel 1217 at an angle between $L_B$ and $L_{TS}$.

Angular stopping member 1217 may include first slot 1208 and a second slot (not shown) opposing slot 1208. Swing arm 1207 is pivotally affixed to angular stopping member 1213 by a pin (not shown) that passes through swing arm 1207 and rests in the first and second opposing slots.

In operation, when targeting member 1213 contacts the outside surface of bone 1202, movement of the pin in the first and second opposing slots adjusts an angle of guide channel 1217 relative to $L_B$.

Figure 13:
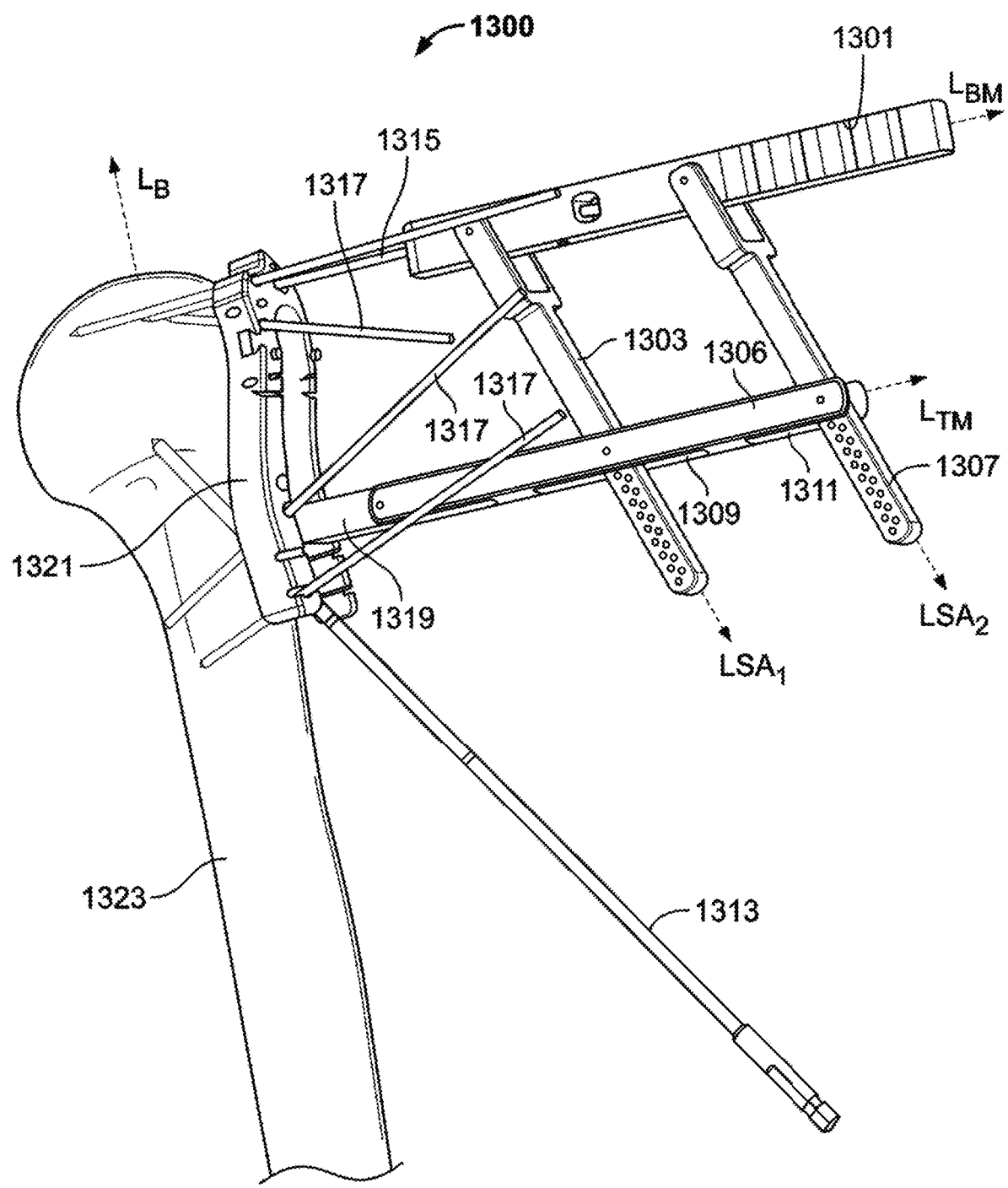
FIG. 13 shows illustrative apparatus and methods in accordance with principles of the invention.

FIG. 13 shows therapeutic scenario 1300. Scenario 1300 shows a targeting apparatus positioned on bone 1323. The targeting apparatus may be used to identify an access position on bone 1323. A hole may be drilled at the access position. An implant may be deployed into an interior of bone 1323 through the hole drilled at the access position.

Target wire 1315 may be inserted into bone 1323. A position to target wire 1315 inside bone 1323 may be verified using fluoroscopy or other imaging techniques. A proximal tip of target wire 1315 may correspond to a proximal end of an implantation region inside bone 1323.

Jig 1321 may be placed on an outer surface of bone 1323. Jig 1321 may be positioned on bone 1323 by inserting jig 1321 over a shaft of target wire 1315. Target wire 1315 may be inserted into bone 1323 after jig 1321 is positioned on bone 1323.

Fixation elements 1317 may pass through jig 1321. Fixation elements 1317 may be inserted into one or more segments of bone 1323. When bone 1323 is fractured, the segments may be defined by one or more fracture lines.

A targeting apparatus may be used to identify an access position on an outer surface of bone 1323. The targeting apparatus may be configured to determine the access position based on a position of the proximal tip of target wire 1315. The targeting apparatus may be configured to determine the access location independent of an orientation of a shaft of target wire 1315.

Base member 1301 defines longitudinal axis $L_{BM}$. The targeting apparatus may be configured to determine the access location independent of an angle between $L_{BM}$ and $L_B$.

A targeting apparatus may include base member 1301. Base member 1301 may define a receptacle (not shown). Target wire 1315 may fit into the receptacle and allow base member 1310 to slide over a shaft of target wire 1315. Base member 1301 may be pivotally affixed to targeting member 1306 by swing arm 1303 and swing arm 1307.

Targeting member 1306 may include passageway 1309 for clearance of swing arm 1303. Targeting member 1306 may include passageway 1311 for clearance of swing arm 1307.

Swing arms 1303 and 1307 include a plurality of holes. The holes may be used to pivotally affix swing arm 1303 or 1307 to targeting member 1306 at locations along axes LSA1 and/or LSA2. The plurality of holes may allow adjustment of spacing between base member 1301 and targeting member 1306. Spacing between base member 1301 and targeting member 1306 may be adjusted to account for differences in patient anatomy.

Swing arm 1303 may define axis $L_{SA1}$. Swing arm 1307 may define axis $L_{SA2}$. Swing arms 1303 and 1307 may be affixed to base member 1301 and to targeting member 1306 such that $L_{SA1}$ is substantially parallel to $L_{SA2}$. Positioning LSA1 parallel to LSA2 may allow indicator 1319 at a proximal end of targeting member 1306 to move along a circumference of a circle centered at the proximal tip of target wire 1315.

Indicator 1319 may identify the access location when indicator 1319 contacts an outer surface of bone 1323. Indicator 1319 may fit into a groove of jig 1321. At the access position, indictor 1319 may direct drill 1313 into bone 1323. Indicator 1313 may direct drill 1313 into bone 1323 at an angle with $L_B$. The angle may direct drill 1313 toward the proximal end of target wire 1315.

Figure 14:
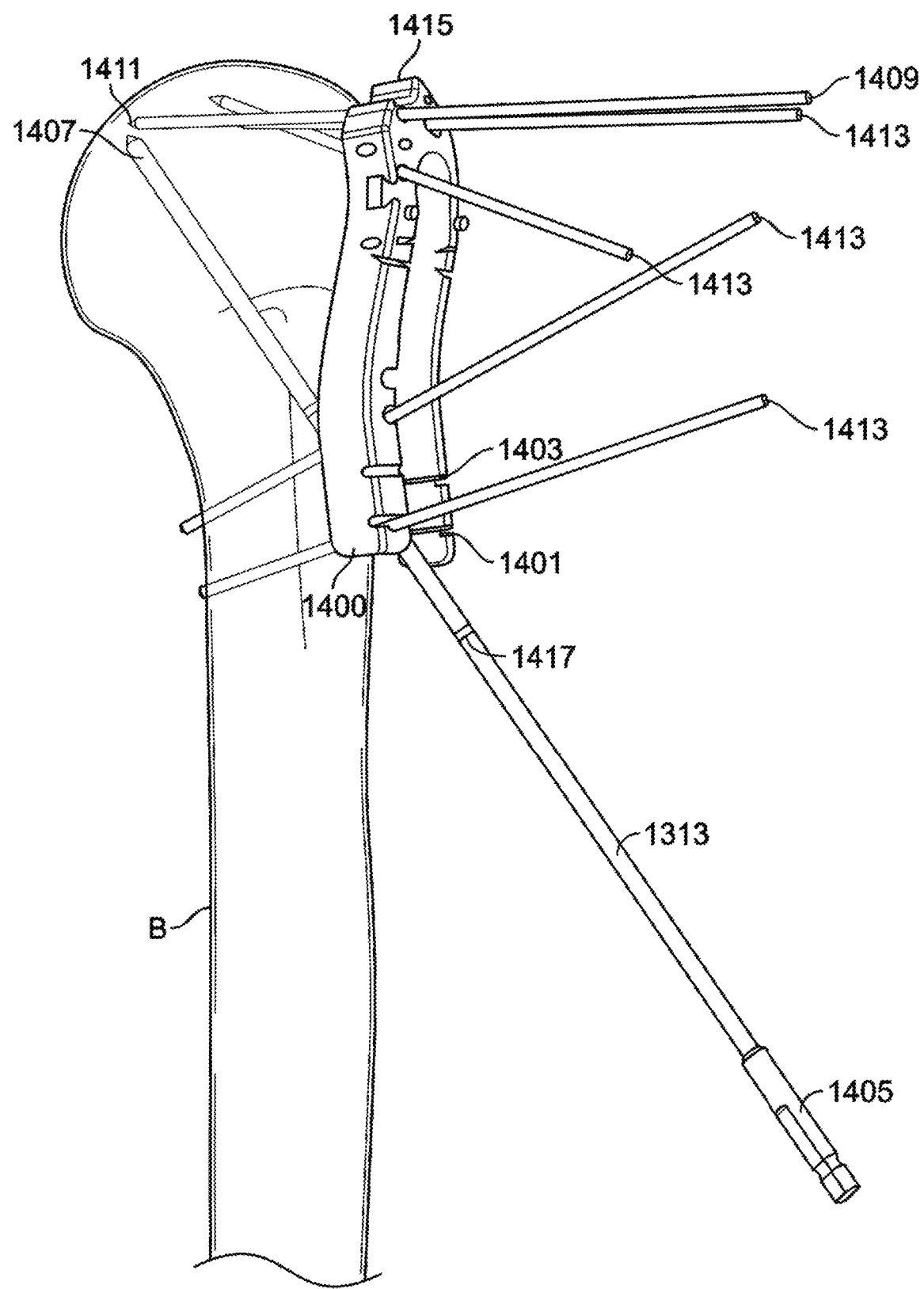
FIG. 14 shows illustrative apparatus and methods in accordance with principles of the invention.

FIG. 14 shows illustrative jig 1400 positioned on bone B. Jig 1400 may include a bottom surface (not shown) complementing a surface contour defined by bone B. In FIG. 14, the bottom surface may be seated complementarily against the surface contour. When the bottom surface is seated complementarily against the surface contour, portion 1415 of jig 1400 may be positioned on top of a greater tuberosity.

Jig 1400 may include indicator 1401 and indicator 1403. Indicator 1401 may indicate a position on bone B for initiating a first access hole. Indicator 14013 may indicate a position on bone B for initiating a second access hole. A distance between the first access hole and a target site may correspond to a first implant length. A distance between the second access hole and the target site may correspond to a second implant length. A practitioner may determine an implant length suitable for implanting in bone B. A practitioner may then determine which set of indicators corresponds to the selected implant length. The practitioner may then initiate an access hole between the selected set of indicators.

Fixation elements 1413 may be driven through jig 1400 and into bone B. Each of fixation elements 1413 may be driven through one of a plurality of holes defined by jig 1400.

Jig 1400 may include a target hole. Target wire 1409 may be driven through the target hole. Tip 1411 of target wire 1409 may be located at the target site in bone B.

FIG. 14 also shows illustrative access drill 1313. Access drill 1313 may include distal protrusion 1405. In FIG. 14, access drill 1313 is shown passing through the first access hole and into an interior of bone B. A practitioner may identify the first access hole using indicator 1401 on the reduction jig, using an access locating jig, using direct visualization or using x-ray fluoroscopy imaging.

Access drill 1313 may be used to start preparation of the first access hole. Tip 1407 of access drill 1313 is shown to be advanced up to the location of tip 1411 of target wire 1409. Advancing access drill 1313 to the target site may create an initial path through the bone. This initial path may be used as a guide channel for subsequent surgical procedures disclosed herein.

Access drill 1313 may include indicators 1417.

A guide and/or a tissue protector (not shown) may be used in conjunction with the procedure illustrated in FIG. 14.

Figure 15:
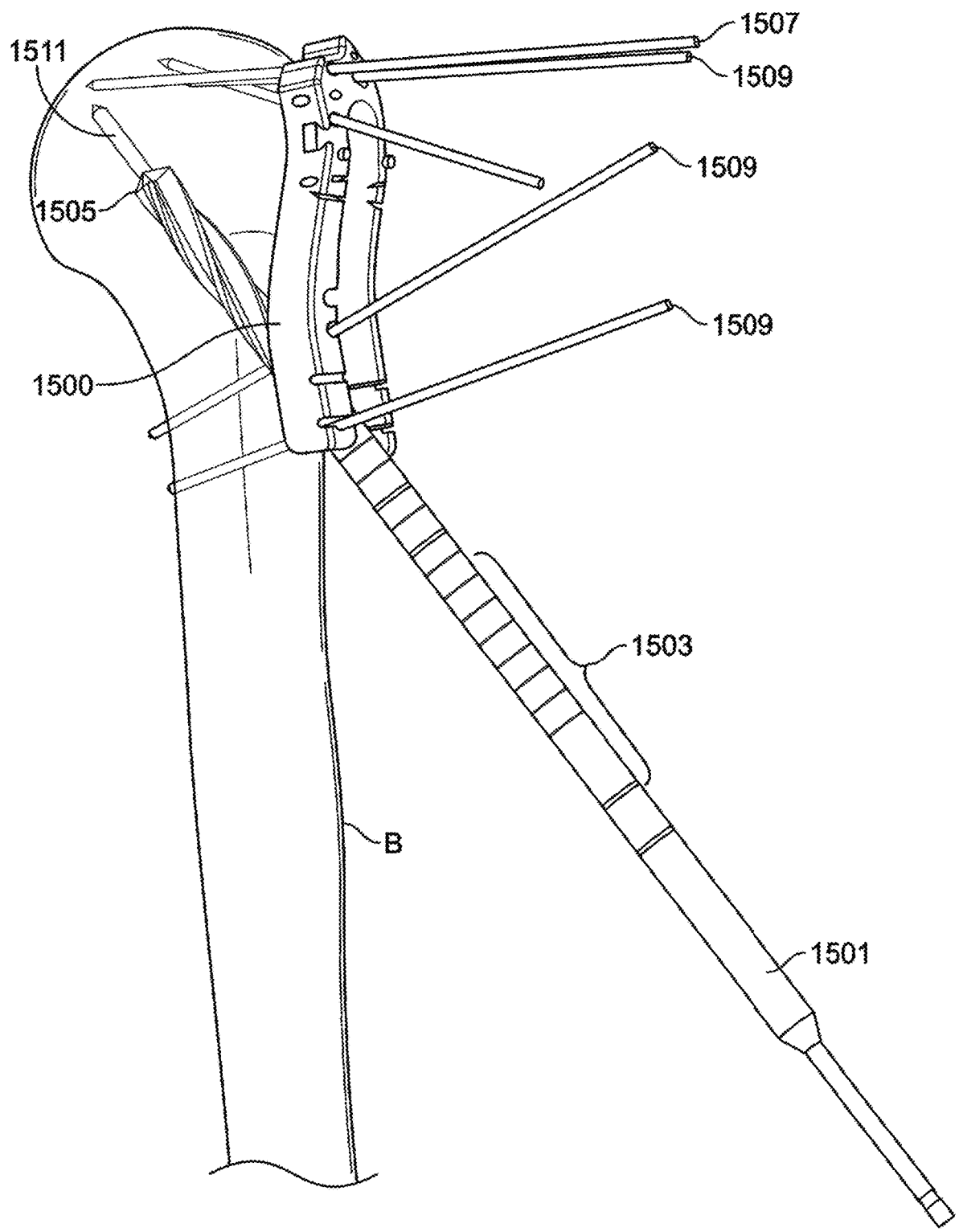
FIG. 15 shows illustrative apparatus and methods in accordance with principles of the invention.

FIG. 15 shows illustrative jig 1500 positioned on bone B. Jig 1500 may include a bottom surface (not shown) complementing a surface contour defined by bone B. In FIG. 15, the bottom surface may be seated complementarily against the surface contour.

Fixation elements 1509 may be driven through holes included in a plurality of holes defined by jig 1500. Target wire 1507 may be driven through a target hole defined by jig 1500 and into an interior of bone B.

FIG. 15 shows illustrative drill 1501. Drill 1501 may be a drill larger than access drill 1313. Drill 1501 may be used to remove cortical bone tissue in an interior of bone B. Drill 1501 may be used to remove cortical bone along the initial path defined by access drill 1313. Drill 1501 may be used to enlarge the initial path.

Drill 1501 may be advanced along the initial path created by access drill 1313 by drilling over pin 1511 placed in the initial path. Drill 1501 may be advanced along the initial path created by access drill 1313 by over drilling over a drill similar to drill 1313 but without distal protrusion 1405. Drill 1501 may be used to enlarge the initial path and create a path large enough for deployment of an implant in an unexpanded state.

Using drills with different widths may reduce the stress applied to cortical bone in bone B when creating the path. Additionally, using access drill 1313 prior to drill 1501 may enable a physician to change a trajectory of an initial path without compromising the cortical bone.

A guide and/or a tissue protector (not shown) may be used in conjunction with the procedure illustrated in FIG. 15.

Figure 16:
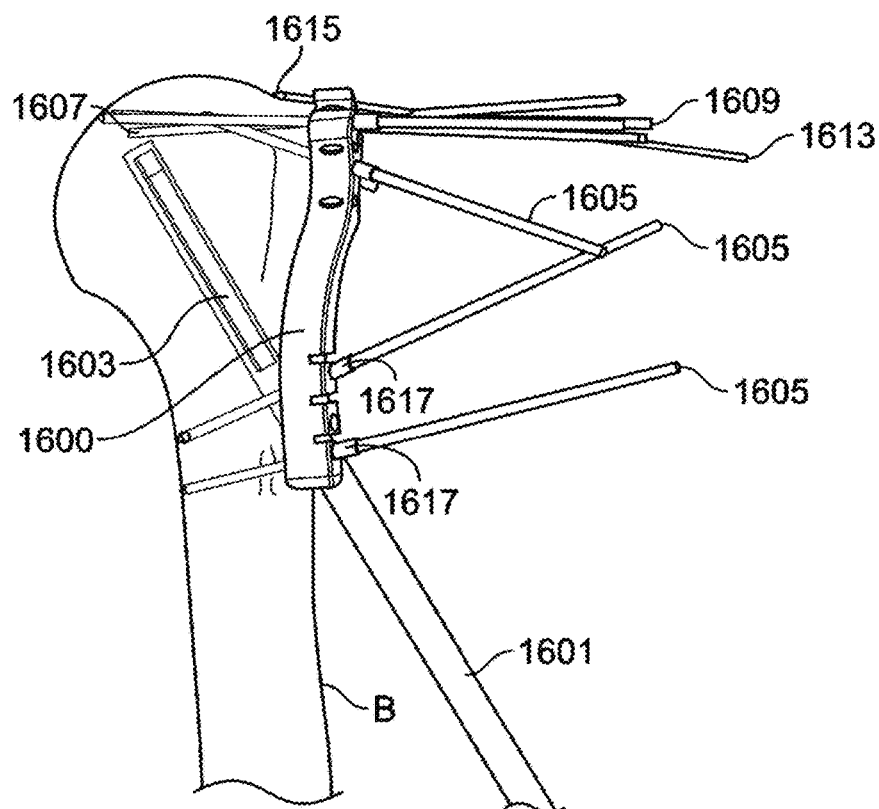
FIG. 16 shows illustrative apparatus and methods in accordance with principles of the invention.

FIG. 16 shows illustrative jig 1600 positioned on bone B. Jig 1600 may include a bottom surface (not shown) complementing a surface contour defined by bone B. In FIG. 16, the bottom surface may be seated complementarily against the surface contour.

Fixation elements 1605 may be driven through holes included in a plurality of holes defined by jig 1600. Fixation elements 1605 may pass through bushings 1617 coupled to the plurality of holes.

Target wire 1609 may be driven through a target hole defined by jig 1600 and into an interior of bone B. Tip 1607 of target wire 1609 may be positioned at a target site.

Jig 1600 may include a positioning hole. Fixation element 1613 may be driven through the positioning hole. Tip 1615 of fixation element 1613 may pass over a top of a greater tuberosity. Tip 1615 may be inserted so as to not violate a portion of the greater tuberosity and/or an articular surface of bone B.

FIG. 16 shows illustrative cavity preparation device 1601. Cavity preparation device 1601 may include broaching member 1603. In FIG. 16, broaching member is illustrated in a collapsed state.

Cavity preparation device 1601 may have a diameter. The diameter of cavity preparation device 1601, when preparation device 1601 is unexpanded, may be equal to, lesser than, or slightly greater than, a diameter of drill 1501. Cavity preparation device 1601 may be inserted through an access hole prepared on the surface of the bone by access drill 1313 and drill 1501. Cavity preparation device 1601 may be advanced along the enlarged initial path created by drill 1501.

Cavity preparation device 1601 may include one or more demarcations along a length of the device. Each demarcation may indicate a length. The length may be a distance between the demarcation and a tip of the cavity preparation device. Each demarcation may indicate a size and/or length of an implant. As the cavity preparation device is being inserted through the access hole, the demarcation visible next to the location at the surface of the access site hole on the bone may correlate to a size and/or length of an implant.

Figure 17:
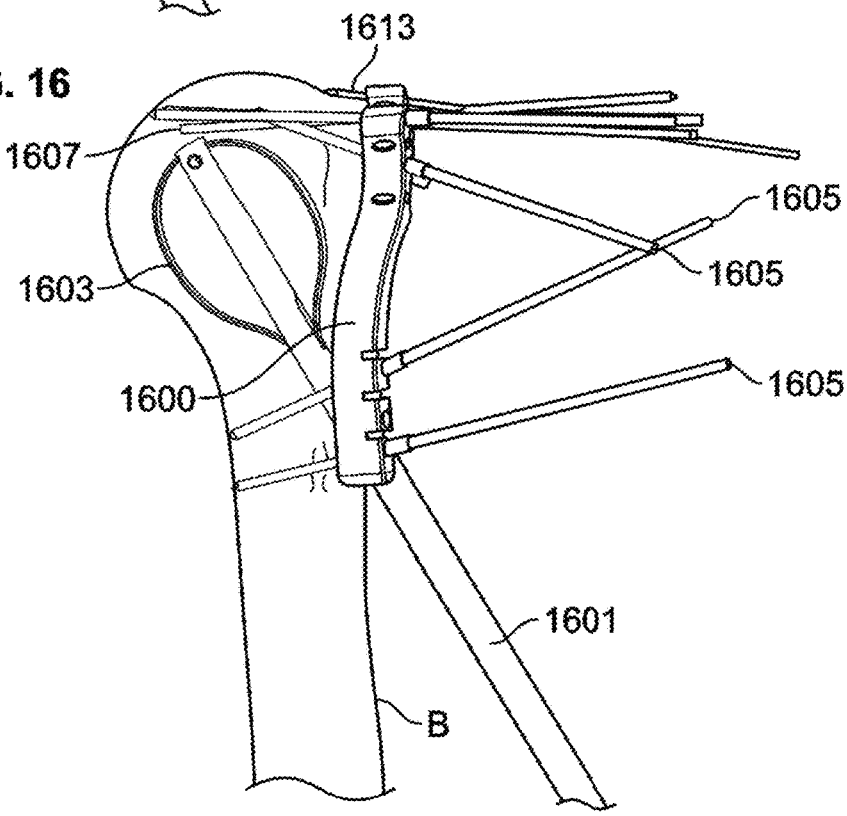
FIG. 17 shows illustrative apparatus and methods in accordance with principles of the invention.

FIG. 17 shows illustrative cavity preparation device 1601 positioned in bone B. In FIG. 17, broaching member 1603 has been expanded using a handle (not shown) coupled to an end of cavity preparation device 1601.

Broaching member 1603 may be expanded in bone B. Broaching member 1603 may rotated in bone B. Broaching member 1603 may be simultaneously expanded and rotated in bone B. Movement of broaching member 1603 in bone B may form a cavity in bone B. Movement of broaching member 1603 in bone B may prepare a site in the interior of bone B for implantation of an implant.

Broaching member 1603 may create the cavity by displacing cancellous bone in bone B. Broaching member 1603 may create the cavity by cutting cancellous bone in the interior of bone B.

The cavity formed by broaching member may have a volume. The volume may be substantially equal to a volume of an implant head when the implant head is expanded to form a mesh cage. A physician may first select a size of an implant for implanting at the target site. The physician may then expand the broaching member to create a cavity having a size substantially equivalent to a size of the selected implant, when the selected implant is expanded.

Exemplary methods for preparing a cavity in the interior of bone B for implantation of an implant may include inserting a fully collapsed cavity preparation device through an access hole. The cavity preparation device may be cavity preparation device 1601, a site preparation instrument, an expandable hand reamer or any other suitable cavity preparation device. The cavity preparation device may be manual or automated.

The cavity preparation device may be advanced through the access hole and along a channel or path previously created by one or more wires or drills. If a deviation from the prepared channel or path is desired, the method may include altering the path of the cavity preparation instrument from the prepared path to facilitate preparation of the cavity in a different, desired location.

The method may include advancing the cavity preparation device to a tip of a target wire positioned in the bone interior. The method may include advancing the cavity preparation device along an access wire. The method may include confirming the position of the cavity preparation device in the bone interior. The position may be confirmed fluoroscopically.

The method may include rotating the cavity preparation device. The cavity preparation device may be rotated any suitable number of times, such as once, twice, three times, five times, or any suitable number of times.

The method may include expanding a broaching member included in the cavity preparation device. The broaching member may be expanded by rotating an expansion knob coupled to an end of the cavity preparation device. The expansion knob may be rotated clockwise. The expansion knob may be rotated counterclockwise. Rotating the expansion knob may expand the broaching member. Rotating the expansion knob may slightly expand the broaching member. Rotating the expansion knob a predetermined amount may result in an audible feedback. For example, rotating the expansion knob ¼ of a turn, ½ a turn, or a full turn, may give off a clicking sound.

The method may include determining a size and/or location of the radial expansion of the broaching member using x-ray fluoroscopy imaging.

The method may include completing preparation of the cavity. A physician may complete the cavity preparation by turning the expansion knob a predetermined number of times and rotating the cavity preparation device a certain number of turns per each expansion knob click. A physician may use one or more of tactile feedback, audible feedback and/or fluoroscopy to determine if the cavity is the proper size. A physician may use one or more of tactile feedback, audible feedback and/or fluoroscopy to determine if the broaching member is nearing a cortical wall of the bone.

The cavity may be prepared when a volume of the cavity has a diameter that will facilitate the expansion of the implant into the interior of the bone.

A broaching member may need to be fully expanded to complete preparation of a cavity.

A broaching member may not need to be fully expanded to complete preparation of a cavity. This may be at least because a plurality of implants, each implant having a different diameter when expanded, may be implanted in the bone. Therefore, cavities of various sizes may be prepared, each cavity being suitable for implanting an implant having a different expanded diameter.

A tip of a target wire may remain at a target site during preparation of the cavity.

The method may include at least partially retracting the target wire during cavity preparation. The target wire may be retracted to enable a physician to fully expand the cavity preparation device.

After the cavity has been prepared, the method may include collapsing the broaching member. The broaching member may be completely collapsed. The broaching member may be collapsed by rotating the expansion knob counter-clockwise. The expansion knob may be rotated fully until it stops.

The method may include determining the size and location of the prepared cavity using x-ray fluoroscopy imaging.

After collapsing the broaching member, the method may include removing the cavity preparation device from the access site. The method may include removing any wires that interfere with the cavity preparation device.

Some, all or none of the bone cut or morselized by the broaching member may be removed from cavity.

The method may include removing cut bone or morselized bone may from the cavity. The method may also include adding material into the cavity. Exemplary material that may be added to the cavity may include bone graft or biological agents to facilitate healing. This material may be removed from, or added to, the cavity through a cannula in the cavity preparation device.

FIG. 18 shows illustrative cavity preparation device 1601 positioned in bone B with broaching member 1603 in an expanded state. In FIG. 18, cavity preparation device 1601 is positioned in bone B without a jig fixed to a surface of bone B.

In some of these embodiments, provisional reduction of bone B may be performed by the physician without using a jig. In some of these embodiments, a physician may select a location on the bone surface for preparing an access hole and/or select an angle for drilling through the access hole without the assistance of one or more jigs.

FIG. 18 shows illustrative handle 1801 coupled to broaching member 1601. Handle 1801, when rotated in a first direction, may expanded broaching member 1603. Handle 1801, when rotated in a second direction opposite the first direction, may collapse broaching member 1603.

Handle 1801 may have a hard stop. The hard stop may prevent a physician from expanding the broaching member more than a predetermined amount.

FIG. 19 shows illustrative cavity preparation device 1601 positioned in bone B with broaching member 1603 in an expanded state.

Figures 20, 21:
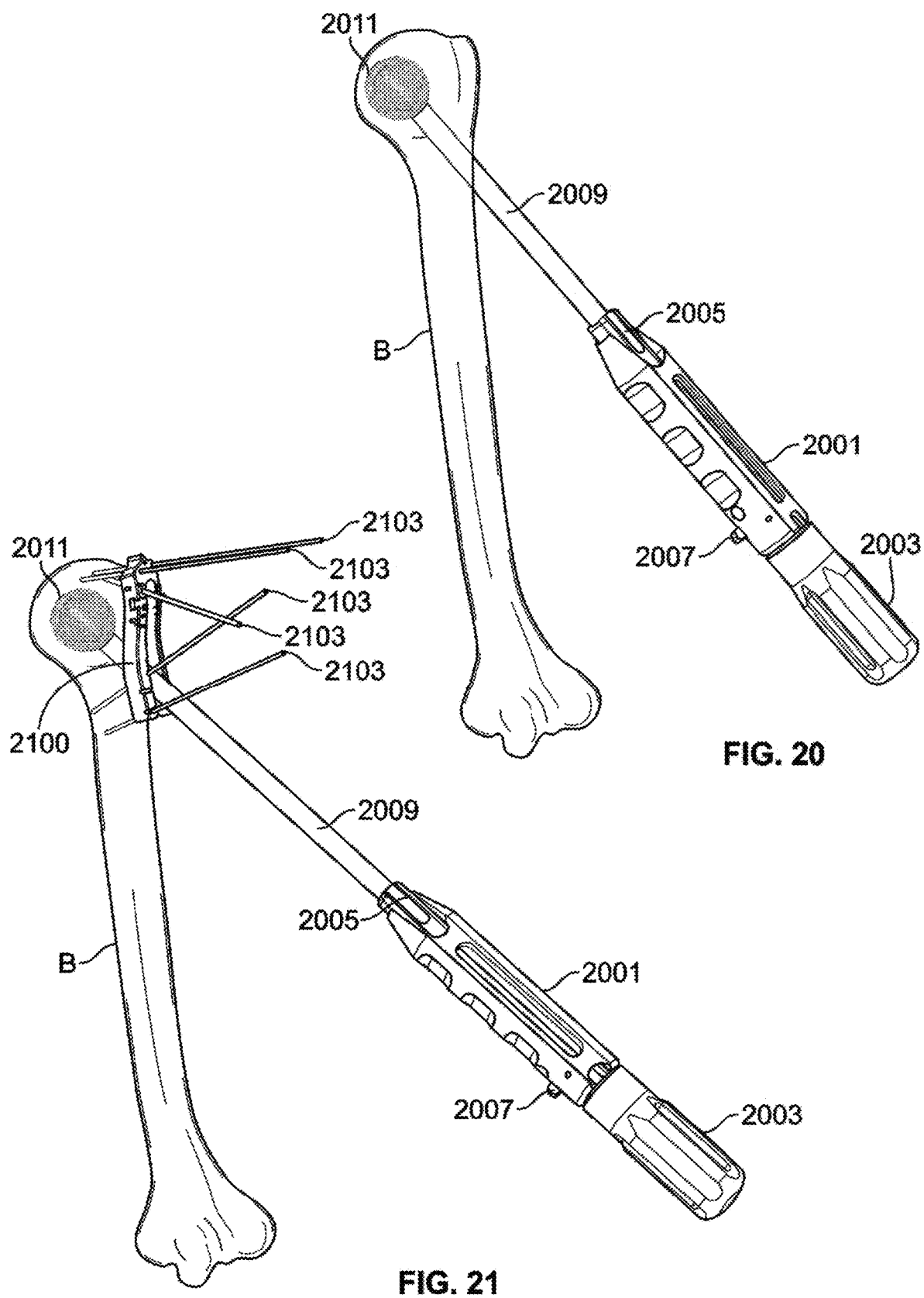
FIG. 20 shows illustrative apparatus and methods in accordance with principles of the invention.
FIG. 21 shows illustrative apparatus and methods in accordance with principles of the invention.

FIG. 20 shows illustrative apparatus for delivering an implant in bone B. Delivering an implant may be referred to alternately herein as deploying an implant.

FIG. 20 shows illustrative delivery device 2001. Illustrative delivery device 2001 may include handle 2003, pin 2007, indentation 2005 and sheath 2009. Implant 2011 may be positioned in sheath 2009. Rotation of handle 2003 may retract sheath 2009 into delivery device 2001. Retraction of shaft 2009 may expose implant 2011. In FIG. 20, sheath 2009 is shown partially retracted. A portion of a head of implant 2011 has been exposed. The head of implant 2011 is illustrated in a partially expanded state.

A method for delivering an implant may include advancing a delivery device through an access hole and up to a tip of a target wire or a target site. When the delivery device is advanced, implant 2011 may be positioned in sheath 2009. The method may include deploying the implant. The deploying may include rotating a knob of the delivery device. Rotation of the knob may retract sheath 2009. Retraction of sheath 2009 may expose implant 2011. A head of the implant, when exposed, may self-expand. When the implant is sufficiently exposed, delivery device 2001 may be removed from implant 2011. Handle 2003 may include a piston for retracting sheath 2009.

Implant 2201 may be deployed in bone B as follows. Implant 2201 may be positioned in a shaft of the delivery device. Implant 2201 may be positioned in the shaft of the delivery device with head 2211 in an unexpanded state. Implant 2201 may not be rigidly coupled to the delivery device.

FIG. 21 shows illustrative apparatus for delivering an implant in bone B. The illustrative apparatus may include delivery device 2001 and illustrative reduction jig 2100. In FIG. 21, illustrative reduction jig 2011 is fixed to bone B by fixation elements 2103. Portion of a head of implant 2011 has been exposed by delivery device 2001. The head of implant 2011 is illustrated in a partially expanded state. Jig 2011 may support to bone B during the deployment of implant 2011.

FIG. 22 shows illustrative implant 2201 implanted in bone B. Illustrative implant 2201 may include implant head 2211, implant tail 2207, and implant shaft 2203. Implant shaft 2203 may include keyseat 2205. Keyseat 2205 may be a laser-cut feature at an end of implant shaft 2203.

FIG. 22 shows illustrative implant 2201 with implant head 2211 fully expanded. In FIG. 22, a delivery device such as delivery device 2001 may be used to deploy implant 2201 in bone B.

Implant tail 2207 may include implant base 2209. Implant tail 2207 may be coupled to implant base 2209 by a snap fit. The snap fit may provide rotational and axial locking. In other embodiments, implant tail 2207 may be welded to implant base 2209, be of unitary construction with implant base 2209, be of monolithic construction with implant base 2209, or coupled to implant base 2209 in any other suitable fashion. Implant tail 2207 may include beveled end 2215. Beveled end 2215 may conform to a surface contour of a bone when shaft 2203 is removed from implant tail 2207.

Implant head 2211 may include proximal end 2213. Proximal end 2213 may be positioned at the target site during deployment of implant 2201. Proximal end 2213 may be positioned adjacent a tip of a target wire during deployment of implant 2201.

FIG. 23 shows illustrative implant 2201 implanted in bone B. FIG. 23 also shows illustrative jig 2301 fixed to bone B by fixation elements 2303.

FIG. 23 shows how fixation elements 2303 driven through jig 2301 and into bone B provide clearance for implant 2211.

FIG. 24 shows illustrative implant 2201 deployed in bone B. FIG. 24 also shows illustrative jig 2401 fixed to bone B by fixation elements 2403.

FIG. 24 shows how fixation elements 2403 driven through jig 2401 and into bone B provide clearance for implant 2211.

FIG. 25 shows illustrative rotation handle 2500. Rotation handle 2500 may be configured to be releasably coupled to an end of an implant shaft. Rotation handle 2500 may removably couple to one or more laser cut features located at an end of the implant shaft. Rotation handle 2500 may include a mechanism for removably coupling to keyseat 2205.

Rotation handle 2500 may include an internal spring mechanism. The internal spring mechanism may include a lever. The lever may pop into a window to facilitate coupling and decoupling rotation handle 2500 with an implant shaft.

When rotation handle 2500 is coupled to an implant shaft, rotation handle 2500 may allow for axial control of the implant. When rotation handle 2500 is coupled to an implant shaft, rotation handle 2500 may allow for rotational control of the implant.

Rotation handle 2500 may include opening 2511. Opening 2511 may be shaped to receive an end of an implant shaft. Rotation handle 2500 may include lever 2509. Lever 2509, when lifted, may decouple an implant shaft from rotation handle 2500.

A method for rotating an implant in a cavity may include attaching a rotation handle to a shaft of the implant. The method may include rotating the implant multiple times. Rotating the implant may assist in seating the implant in the cavity. Rotating the implant may further expand the head of the implant. Rotating the implant may further engage the head of the implant with surrounding tissue or bone. Rotating the implant may move cut up cancellous bone into the head of the implant. Rotating the implant may seat the tail of the implant inside the bone.

The method may also include ensuring that a release lever of the rotation handle is aligned with a center of a jig when rotation is complete. The method may also include confirming expansion of the implant head fluoroscopically. The method may also include tightening an implant locking screw to lock the cage in the expanded state.

Rotation handle 2500 may be used to move the head of the implant further into an interior the bone. Rotation handle 2500 may be used to further advance the head of the implant into the bone. The head of the implant may be further advanced into the bone to position the tail fully within a bone, or to ensure that the tail does not extend away from an outer surface of the bone. Rotation handle 2500 may be used to move the head of the implant away from an interior of the bone.

FIG. 26 shows illustrative jig 2600 fixed to bone B by fixation elements 2605. FIG. 25 shows illustrative rotation handle 2500 coupled to implant shaft 2601.

FIG. 27 shows illustrative rotation handle 2500 coupled to shaft 2701 of an implant.

Figures 28, 29:
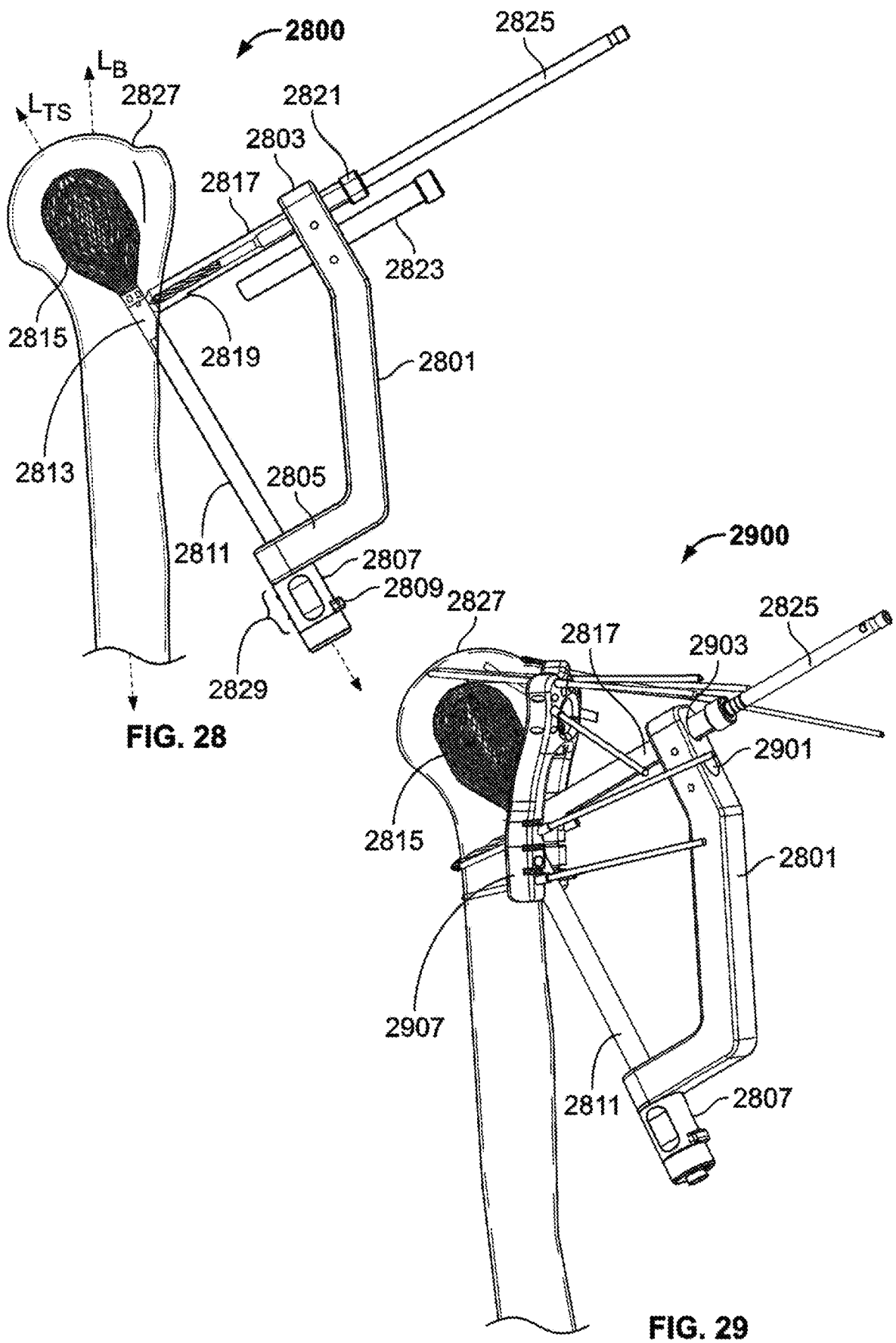
FIG. 28 shows illustrative apparatus and methods in accordance with principles of the invention.
FIG. 29 shows illustrative apparatus and methods in accordance with principles of the invention.

FIG. 28 shows illustrative therapeutic scenario 2800. Scenario 2800 shows apparatus for securing tail 2813 of implant 2815 to bone 2827. Scenario 2800 shows a targeting apparatus that may be used for drilling to anchor receiving features of tail 2813. The targeting apparatus may also be used to direct anchors through bone 2827 and through the anchor receiving features of tail 2813.

The targeting apparatus may include bracket 2801. Bracket 2801 may include end 2805 and end 2803.

End 2805 may include collar 2807. Collar 2807 receives an end of implant shaft 2811. An end of implant shaft 2811 is affixed to tail 2813. Implant shaft 2811 may be inserted concentrically into collar 2807. Implant shaft 2811 may be tubular. Implant shaft 2811 may be locked to collar 2807. Implant shaft 2811 may be locked to collar 2807 axially along axis $L_{TS}$. Implant shaft 2811 may be locked to collar 2807 rotationally about axis $L_{TS}$.

End 2803 may include guide tube 2817 and guide tube 2823. Guide tubes 2817 and 2823 may define longitudinal axes for positioning surgical tools relative to implant 2815. Guide tubes 2817 and 2823 may be moveable with respect to bracket 2801.

Guide tubes may include one or more flanges to prevent guide tubes from separating from bracket 2801. For example, guide tube 2817 may include flanges 2821 and 2819 that may prevent guide tube 2817 from separating from bracket 2801.

When implant shaft 2811 is engaged with collar 2807, guide tube 2817 directs drill 2825 through bone 2827 and through a clearance hole (not shown) in tail 2813. Guide tubes 2817 may direct an anchor through bone 2817 and through the clearance hole in tail 2813.

When an end of implant shaft 2811 is engaged with tail 2813, and an end of implant shaft 2811 is engaged with collar 2807, guide tube 2817 may be aligned with a first clearance hole defined by tail 2813. When an end of implant shaft 2811 is engaged with tail 2813, and an end of implant shaft 2811 is engaged with collar 2807, guide tube 2823 may be aligned with a second clearance hole defined by tail 2813.

Collar 2807 may include a key (not shown) and implant shaft 2811 may include a keyseat (not shown). The key may be configured to be releasably seated in the keyseat when the implant shaft 2811 is inserted into collar 2807. When the key is seated in the keyseat, implant shaft 2811 may be locked axially along $L_{TS}$. When the key is seated in the keyseat, implant shaft 2811 may be locked rotationally about $L_{TS}$.

Collar 2807 may include a keyseat and implant shaft 2811 may include a key.

Collar 2807 may include release 2809. Release 2809 may release the key from the keyseat. Releasing the key from the keyseat may allow implant shaft 2811 to be disengaged from collar 2807.

Collar 2807 may include a releasable key and a static key. For example, collar 2807 may include static key 2829. Static key 2829 may protrude into a cannula defined by collar 2807. Static key 2829 may not be visible on an exterior of collar 2807. Implant shaft 2811 may include a slot (not shown) that may be configured to receive static key 2829. Engagement of static key and the slot may be configured to align a releasable key with the keyseat.

Seating the key of collar 2807 in the keyseat of implant shaft 2811 may align one or more of guide tubes 2817 and 2823 with one or more clearance holes defined by tail 2813.

Implant shaft 2811 may be configured for use with implants of different lengths. Implant shaft 2811 may include a first keyseat and a second keyseat (not shown). Seating the key of collar 2807 in the first keyseat may space collar 2807 a first distance apart from the proximal end of implant shaft 2811. The first distance may align guide tube 2817 with a clearance hole defined by a tail affixed to an implant having a first length.

Engagement of the second keyseat in implant shaft 2811 with the key of collar 2807 may space collar 2807 a second distance from the proximal end of implant shaft 2811. The second distance may align guide tube 2823 with a clearance hole defined by a tail affixed to an implant having a second length.

FIG. 29 shows illustrative therapeutic scenario 2900. Scenario 2900 shows jig 2907 positioned on bone 2827. Jig 2907 positioned on bone 2827 based on positioning jig 2907 relative to one or more anatomical landmarks on bone 2827. Jig 2907 is secured to bone 2827 by one or more fixation elements.

Scenario 2900 shows that bracket 2801 may include passageway 2903. Passageway 2903 holds guide tube 2817. Guide tube 2817 may be slidable in passageway 2903. Passageway 2903 orients guide tube 2817 relative to bracket 2801. For example, passageway 2903 may orient guide tube 2817 along a longitudinal axis defined by passageway 2903.

Bracket 2801 may include passageway 2901. Passageway 2901 may hold a guide tube, such as guide tube 2823 (shown in FIG. 28). Guide tube 2823 may be slidable in passageway 2901. Passageway 2903 may be a first passageway and passageway 2901 may be a second passageway for holding a second guide tube (not shown). Passageways 2901 and 2903 may orient guide tubes relative to collar 2807. Passageways 2901 and 2903 may orient guide tubes relative to clearance holes in an implant tail.

When collar 2807 is engaged with implant shaft 2811, guide tube 2817 may be slidable in the passageway 2903 between bracket 2801 and bone 2827.

Figure 30:
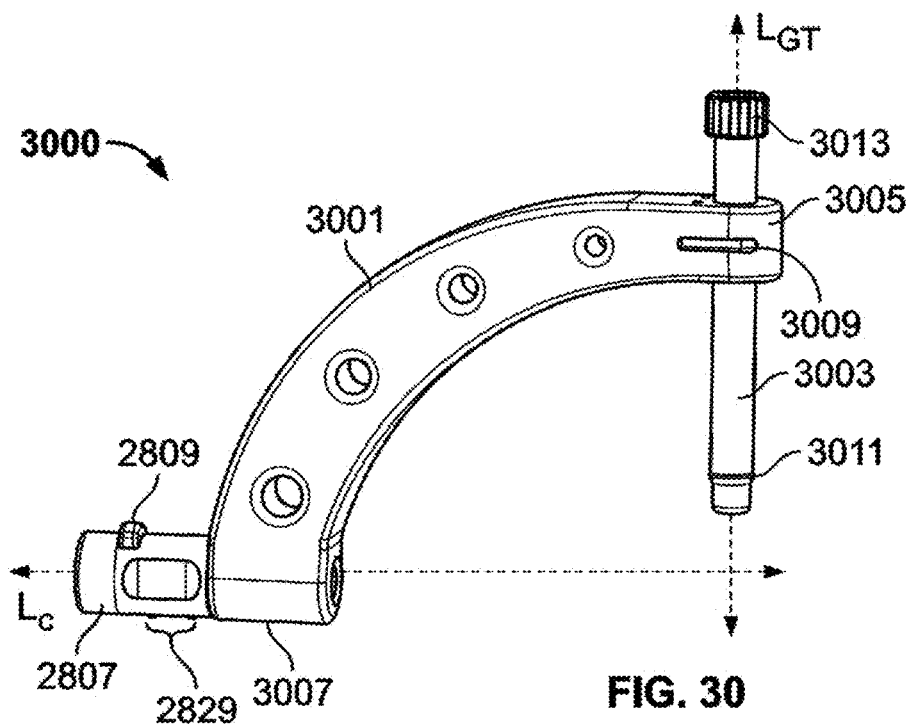
FIG. 30 shows illustrative apparatus in accordance with principles of the invention.

FIG. 30 shows illustrative apparatus 3000. Apparatus 3000 may have or more features in common with apparatus shown in scenario 2800 (shown in FIG. 28) and/or scenario 2900 (shown in FIG. 29). Apparatus 3000 may include bracket 3001. Bracket 3001 may include end 3005 and end 3007.

End 3005 may include guide tube 3003. Guide tube 3003 may be slidable with respect to bracket 3001. Guide tube 3003 may be slidable along axis $L_{GT}$. Gasket 3009 may provide a friction fit around guide tube 3003. Gasket 3009 may hold a position of guide tube 3003 relative to bracket 3001. Gasket 3009 may hold a position of guide tube 3003 along axis $L_{GT}$.

Guide tube 3003 may include flange 3011. Flange 3011 is positioned at a first end of guide tube 3003. Guide tube 3003 may include flange 3013. Flange 3013 is positioned at a second end of guide tube 3003. Flanges 3011 and 3013 may prevent guide tube 3003 from sliding out of bracket 3001.

Apparatus 3003 may include collar 2807. Collar 2807 defines longitudinal axis $L_C$. Bracket 3001 positions axis $L_C$ relative to axis $L_{GT}$. For example, bracket 3001 may position axis $L_C$ perpendicular to axis $L_{GT}$. When a tubular shaft such as implant shaft 2811 (shown in FIG. 28) is engaged with collar 2807, axis $L_{GT}$ may be substantially perpendicular to a longitudinal axis $L_{TS}$ (shown in FIG. 28) defined by implant shaft 2811.

Figure 31:
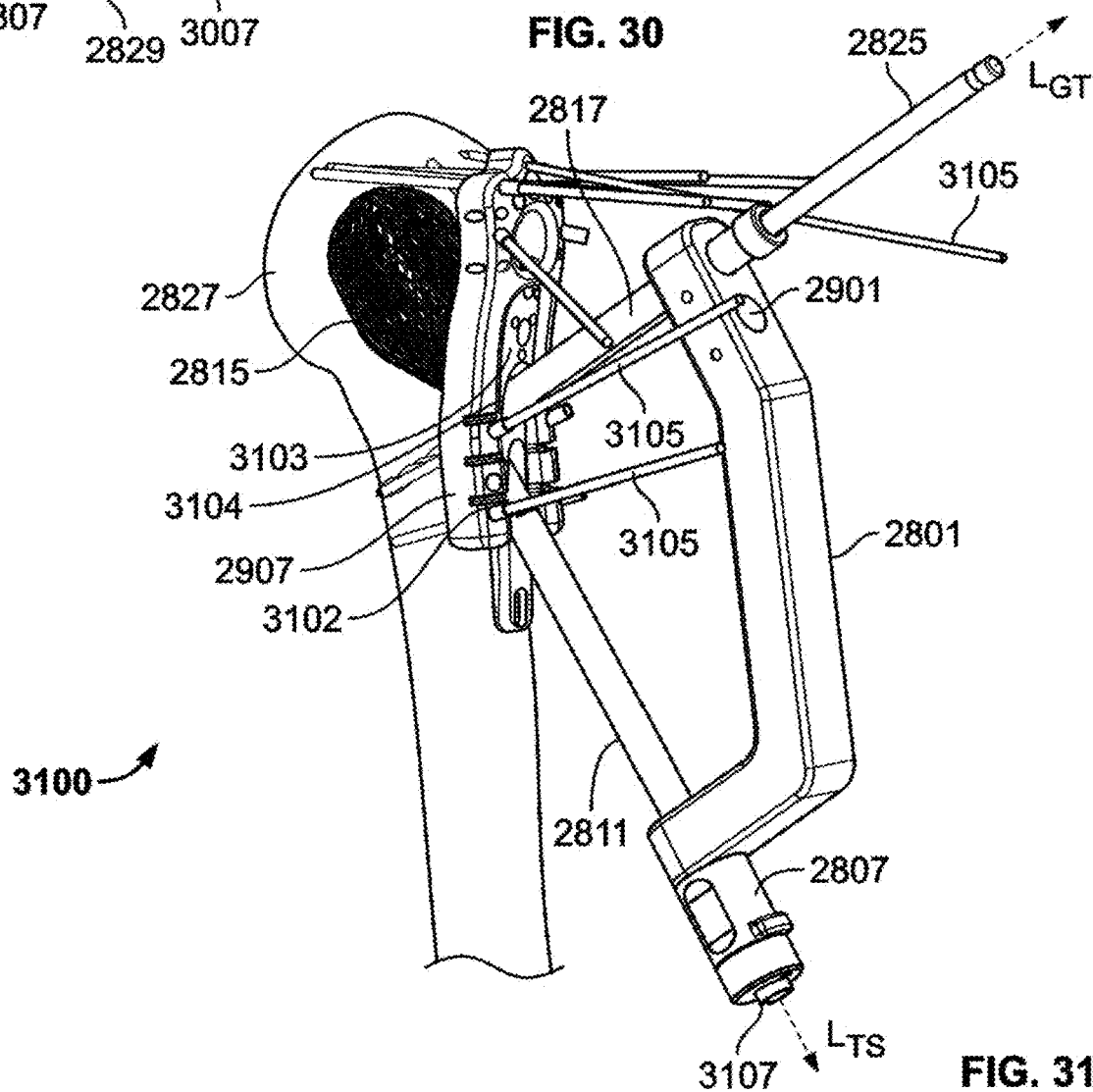
FIG. 31 shows illustrative apparatus and methods in accordance with principles of the invention.

FIG. 31 shows illustrative therapeutic scenario 3100. Scenario 3100 shows plate 3103 positioned on bone 2827. Scenario 3100 shows jig 2907 complementarily seated on bone 2827. Jig 2907 is secured to bone 2827 by one or more fixation elements 3105. Fixation elements 3105 may secure plate 3013 between jig 2907 and bone 2827.

Scenario 3100 shows jig 2907 and plate 3103 being used in concert. Plate 3103 may include opening 3102. Implant shaft 2811 passes through opening 3102. Plate 3103 may include hole 3104. Guide tube 2817 passes through hole 3104. Drill 2825 may pass through guide tube 2817 and thereby be positioned relative to implant 2815.

Scenario 3100 shows implant shaft 2811 engaged with collar 2807. An end of implant shaft 2811 is shown protruding from collar 2811. In scenario 3100, a slot 3107 is visible at the protruding end of implant shaft 2811.

FIG. 32 shows illustrative therapeutic scenario 3200. Scenario 3200 shows apparatus for targeting anchors or screws that engage implant 3219. The apparatus may be used to direct one or more of fixation elements, such as fixation elements 3213) into bone 3202 and into implant 3219.

The apparatus may direct an elongated fixation element from outside bone 3202 into bone 3202 and into a volume defined by a head of implant 3219 positioned inside bone 3202.

Scenario 3200 shows implant shaft 3209. Implant shaft 3209 may include one or more features of implant shaft 2811 shown in FIG. 28. Implant shaft 3215 may include keyseat 3215. Keyseat 3215 may be configured to receive a key of collar 2807 (shown in FIG. 28).

Implant shaft 3209 defines longitudinal axis $L_{TS}$. An end of implant shaft 3209 may be configured to engage a tail of implant 3219. In operation, as shown in scenario 3200, an end of implant shaft 3209 may be configured to extend outside of bone 3202. Collar 3207 may be configured to slidably engage an end of implant shaft 3209 that extends outside of bone 3202. Collar 3207 may slide along axis $L_{TS}$. Collar 3207 may rotate about axis $L_{TS}$.

Collar 3207 may be rigidly affixed to neck 3205. Boom 3201 may be rotatably affixed to neck 3205. Boom 3201 may be configured to rotate about axis $L_{PB}$. Boom 3201 may include elongated passageway 3203. When collar 3207 is slidably engaged with implant shaft 3209, elongated passageway 3203 is positioned to direct fixation element 3211 from outside bone 3202, into bone 3202 and into a volume defined by a head of implant 3219. The volume defined by the head of implant 3219 may correspond to a volume of an expandable web of an implant.

When collar 3207 is slidably engaged with implant shaft 3209, elongated passageway 3203 may be aligned along $L_{TS}$. When elongated passageway 3203 is aligned with axis $L_{TS}$, elongated passageway 203 may direct fixation member 3211 into the volume defined by the head of implant 3219. When elongated passageway 3203 is aligned along $L_{TS}$, elongated passageway 3203 may be configured to direct fixation member 3211 into the volume defined by the head of implant 3219 at or near a center longitudinal axis of implant 3219.

The center longitudinal axis of implant 3219 may correspond to $L_{TS}$. When elongated passageway 3203 is aligned along $L_{TS}$, elongated passageway 3203 may direct fixation element 3211 into the volume defined by the head of implant 319 such that fixation element 3211 is deflected by center axis member 3204 of implant 3219.

Rotating collar 3207 about axis $L_{TS}$ may position elongated passageway 3203 about a perimeter of the head of implant 3219. Pivoting boom 3201 about axis $L_{PB}$ may allow boom 3201 to slide over an end of fixation element 3211 that is operationally external to bone 3202.

After boom 3201 is removed from fixation element 3211, boom 3201 may be repositioned about axis $L_{TS}$. After boom 3201 is removed from fixation element 3211, cannulated screws may be drilled over fixation element 3211. Screws drilled over fixation element 3211 may secure bone 3202 to implant 3219.

Pivoting boom 3201 about axis $L_{PB}$ may also allow boom 3201 to be repositioned without being obstructed by the ends of fixation elements 3213 that are operatively external to bone 3202. Boom 3201 may be repositioned by rotating collar 3207 about axis $L_{TS}$.

FIG. 33 shows illustrative therapeutic scenario 3300. Apparatus shown in scenario 3300 may have one or more features of apparatus shown in scenario 3200.

Scenario 3300 shows jig 3311 complementarily seated on bone 3302. Jig 3311 may be secured to bone 3302 by one or more of fixation elements 3313.

Scenario 3300 shows collar 3306. Collar 3306 may slidably engage implant shaft 3323. Implant shaft 3323 may engage tail 3321.

Collar 3306 may include trough 3301. Collar 3306 may include trough 3305. Kerf 3303 extends between trough 3301 and trough 3305. Collar 3306 may include a pair of opposing kerfs. Collar 3306 may include an internal diameter that is less than an outer diameter of implant shaft 3323. When collar 3306 slidably engages implant shaft 3323, the opposing pair of kerfs may allow implant shaft 3323 to space trough 3301 apart from trough 3305.

Spacing trough 3301 apart from trough 3305 may apply pressure to an outer surface of implant shaft 3323. The pressure applied by troughs 3301 and 3305 may provide a friction fit that holds collar 3306 in a position about longitudinal axis $L_{TS}$.

Scenario 3300 also shows boom 3201. Boom 3201 is pivotable about pin 3307. Scenario 3300 shows that passageway 3203 of boom 3201 may direct fixation element 3317 into head 3309 of an implant. Scenario 330 shows that passageway 3203 may receive, and thereby direct, fixation element 3317 at angle θ. Angle θ corresponds to an angle between length $L_P$ of passageway 3203 and fixation element 3317. Length LP may allow a fixation element to be directed into head 3309 at a range of angles. An illustrative range may be 5°-175°. At any angle θ, passageway 3203 may direct a fixation element into head 3309 at or near axis $L_{TS}$.

Scenario 3300 shows anchor 3315. Anchor 3315 may be cannulated. Anchor 3315 may slide over fixation element 3317. Fixation element 3317 may guide anchor 3315 into bone 3302 and into head 3309 at angle θ. Surgical washer 3314 may provide a surface area that is wider than a surface area of a head of anchor 3315. The wider surface area of surgical washer 3314 may spread pressure applied to bone 3302 when buttressing anchor 3315 against an outer surface of bone 3302. Surgical washer 3314 may also provide apertures for attachment of sutures.

Figure 34:
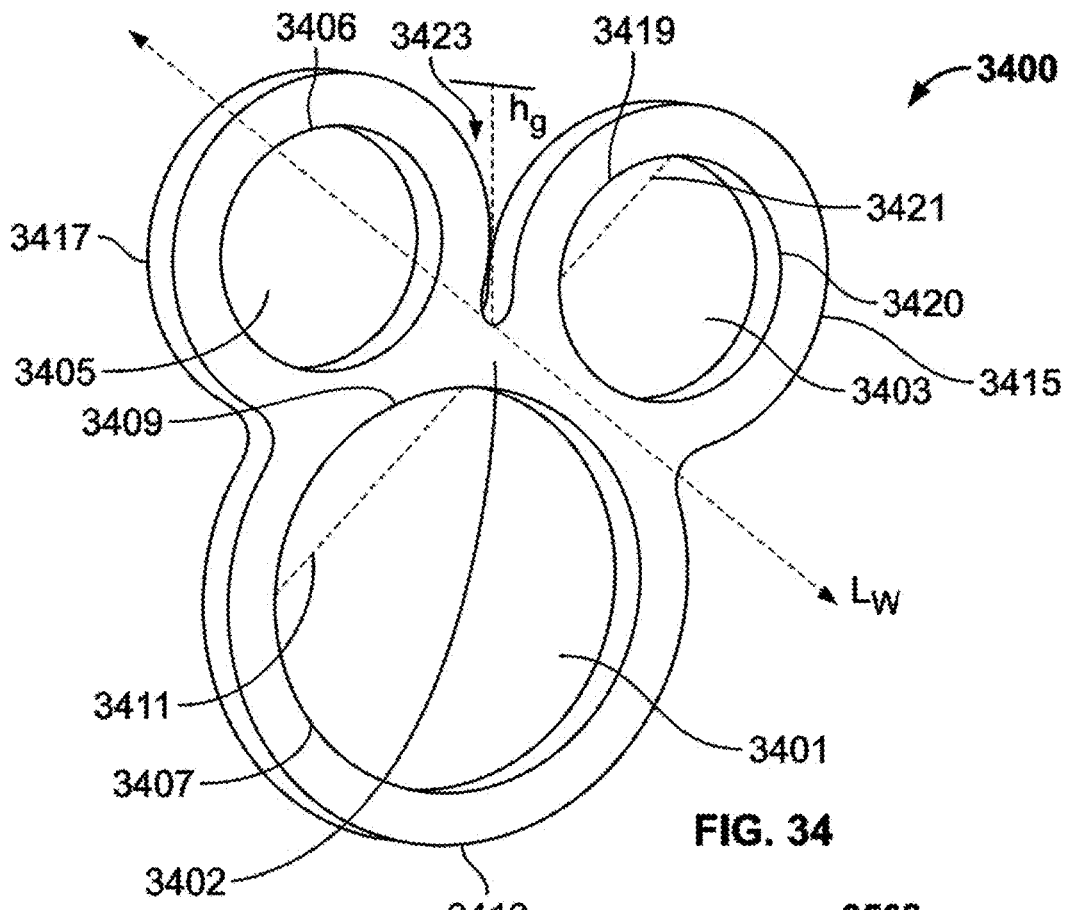
FIG. 34 shows illustrative apparatus in accordance with principles of the invention.

FIG. 34 shows illustrative surgical washer 3400. Surgical washer 3400 may include central aperture 3401. Central aperture may be defined by circumference 3407. Surgical washer 3400 may include offset aperture 3403. Offset aperture 3403 may be a first offset aperture. Surgical washer 3400 may include second offset aperture 3405. Offset aperture 3403 may be a second offset aperture.

Offset aperture 3403 is spaced apart from central aperture 3401 at a position with respect to circumference 3407. Offset aperture 3405 is spaced apart from central aperture 3401 at a position with respect to circumference 3407.

Surgical washer 3400 may include solid material 3402 that joins offset apertures 3405 and 3403 to each other and to central aperture 3401. FIG. 34 shows that an offset aperture (e.g. offset aperture 3403) and central aperture 3401 may form a "Figure eight" shape.

Offset apertures 3405 may provide eyelets for suturing tissue. For example, an anchor may be driven through central aperture 3401. The anchor may secure surgical washer to a bone. Tissue such as tendon, ligaments and/or muscle in the vicinity of the bone may be sutured to one or more of offset apertures 3405 and 3403. Sutures may be tied to an arcuate shaped member (e.g. solid material between inner circumference 3406 and arc 3417) that defines, at least in part, an outer perimeter of offset aperture 3405.

Surgical washer 3400 may include outer perimeter 3413. Outer perimeter 3413 encloses apertures 3401, 3403 and 3405. Outer perimeter 3413 may define one or more of apertures 3401, 3403 and 3405. Surgical washer 3400 may include solid material 3402 between arc 3419 of inner offset circumference 3420 (defined by chord 3421) and a length of outer perimeter 3413 enclosing arc 3419.

Solid material 3419 may vary in thickness between an arc and a length of outer perimeter 3413. For example, surgical washer 3400 may include a first thickness of solid material 3402 between arc 3419 and a first length of outer perimeter 3413. Surgical washer 3400 may include a variable thickness of solid material 3402 between arc 3409 (defined by chord 3411) and outer perimeter 3413.

Outer perimeter 3413 defines height $h_g$ between offset apertures 3403 and 3405. Surgical washer 3400. A value of height $h_g$ may determine a movability of length 3417 of outer perimeter 2413 with respect to inner circumference of 3407 of central aperture 3401. Movability may allow an offset aperture to be bent about axis $L_W$. For a given value of height $h_g$, values higher than the given value may result in less movability than values lower than the given value.

Movability of a surgical washer may also be determined based on a shape of space 3423 between offset aperture 3403 and offset aperture 3405. For example, if solid material reduces space 3423, offset aperture may be less moveable.

Bending an offset aperture about axis $L_W$ may allow a physician to position an offset aperture with respect to tissue. Bending an offset aperture about axis $L_W$ may allow a physician to position an offset aperture with respect to tissue for threading a suture through an offset aperture. Axis $L_W$ may be tangential to inner circumference 3420 and tangential to inner circumference 3407.

FIG. 3400 shows that within space 3423, a first length of outer perimeter 3417 around offset aperture 3405 may be positioned convexly opposing a second length 3415 of outer perimeter 3413. FIG. 34 also shows that arc 3409 may be positioned convexly opposing a length of inner circumference 3406 surrounding offset aperture 3405. Surgical washer 3400 may include solid material 3402 between convexly opposing arcs.

Figure 35:
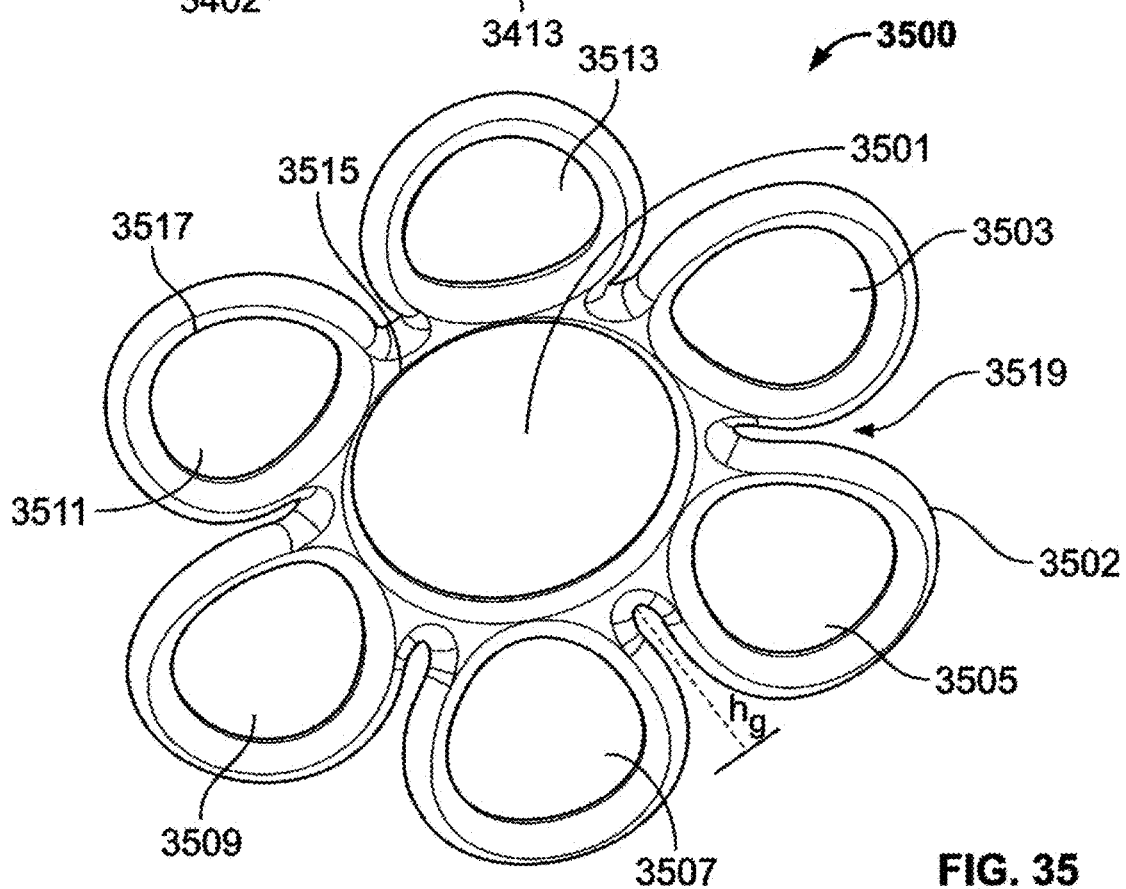
FIG. 35 shows illustrative apparatus in accordance with principles of the invention.

FIG. 35 shows illustrative surgical washer 3500. Surgical washer 3500 may include central aperture 3501. Central aperture 3501 may receive an anchor that presses surgical washer 3500 between a head of the anchor and an outside surface of the bone. Surgical washer 3500 may spread pressure applied by a head of the anchor over a surface area of surgical washer 3500.

An inner circumference 3515 of central aperture 3501 may define a first plane. An outer perimeter of surgical washer 3500 may define a second plane. The first plane may be spaced apart from the second plane.

Surgical washer 3500 may include offset apertures 3503, 3505, 3507, 3509, 3511, and 3513. Outer perimeter 3502 may define height $h_g$ of washer 3500. Movability of an offset aperture relative to the central aperture may be determined based on height $h_g$. A value of height $h_g$ relative to outer perimeter 3502 may define a space between two offset apertures. For example, outer perimeter 3502 may define space 3519 between offset apertures 3505 and 3503.

An offset aperture may be defined by an inner perimeter of the offset aperture. An inner perimeter may be circular, oblong, hexagonal or any other suitable shape. For example, offset aperture 3511 is defined by inner perimeter 3517.

Figure 36:
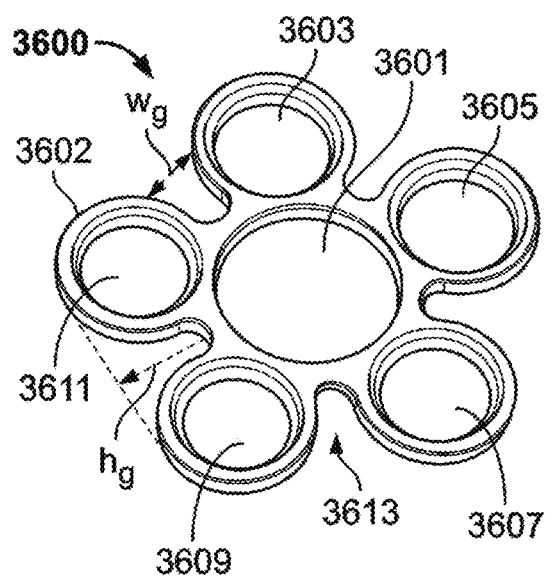
FIG. 36 shows illustrative apparatus in accordance with principles of the invention.

FIG. 36 shows illustrative surgical washer 3600. Surgical washer 3600 may include central aperture 3601. Surgical washer may include offset apertures 3603, 3605, 3607, 3609 and 3611 positioned around central aperture 3601.

FIG. 36 shows that two adjacent offset apertures may be spaced apart by groove 3613. Groove 3613 may have height $h_g$. Groove 3613 may have width $w_g$. Movability of an offset aperture may be determined based on $h_g$ and $w_g$. For example, if solid material reduces $h_g$ and/or $w_g$ and offset aperture may be less moveable.

Figure 37:
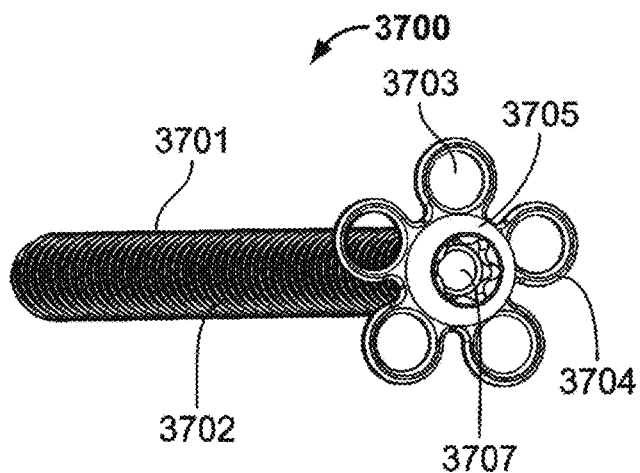
FIG. 37 shows illustrative apparatus in accordance with principles of the invention.

FIG. 37 shows illustrative apparatus 3700. Apparatus 3700 may include an illustrative surgical washer positioned on an anchor. The anchor may include threaded shaft 3701. The anchor may include head 3705. The anchor may include cannula 3707. Cannula 3707 may allow the anchor to slide over a fixation element. Threaded shaft 3701 passes through a central aperture of the surgical washer. The surgical washer also may include offset aperture 3703. Sutures may be threaded through offset aperture 3703.

Figure 38:
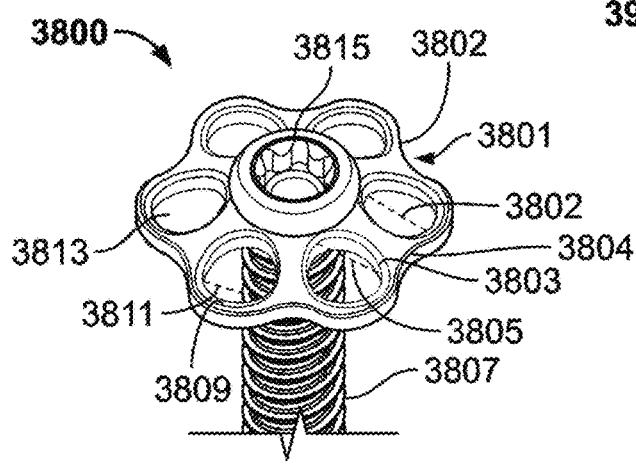
FIG. 38 shows illustrative apparatus in accordance with principles of the invention.

FIG. 38 shows illustrative apparatus 3800. Apparatus 3800 may include surgical washer 3802 abutting head 3815 of anchor 3807. Surgical washer 3802 may include offset apertures such as offset aperture 3813. Adjacent offset apertures may be spaced apart from each other by groove 3801. Groove 3801 is shallower than groove 3613 (shown in FIG. 36). Thus, offset apertures in surgical washer 3600 may be more deformable than offset apertures of surgical washer 3802. Offset apertures of surgical washer 3802 may not be bendable.

Groove 3801 may be defined based on any suitable feature of surgical washer 3802. For example, groove 3801 may be defined by one or more arcs. For example, groove 3801 may be defined based on arc 3809. Arc 3809 may in turn be defined by chord 3811.

Groove 3801 may be defined based on empty space between two adjacent and opposing arcs. For example, groove 3801 may be defined based on empty space between arc 3805 and opposing arc 3804 of an adjacent offset aperture.

Surgical washer 3802 may include a mid-section that extends between a circumference of a central aperture and an outer perimeter of the washer. The mid-section may be curved. For example, apparatus 3800 shows a surgical washer that is convex when positioned abutting head 3815 and viewed from head 3815 looking down a threaded shaft of anchor 3807. Thus, when washer 3802 is buttressed (in the orientation shown in FIG. 38) against a bone by anchor 3807, the curved mid-section spaces head 3815 apart from an outer surface of the bone. When washer 3802 is buttressed (in the orientation shown in FIG. 38) against a bone by anchor 3807, the curved mid-section spaces a rim (not shown) around central aperture of washer 3802 apart from an outer surface of the bone.

A curved mid-section may flatten out before the outer perimeter of the washer. A curved mid-section may flatten out before the circumference of the central aperture. A flattened-out region of a mid-section may form a flange for dispersing pressure applied to a head of an anchor. A flattened-out region of a mid-section may form a flanged outer skirt that encircles a surgical washer.

Figure 39:
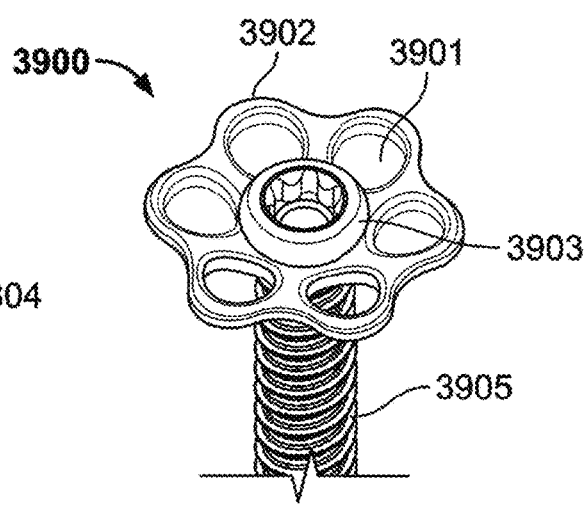
FIG. 39 shows illustrative apparatus in accordance with principles of the invention.

FIG. 39 shows illustrative apparatus 3900. Apparatus 3900 may include surgical washer 3902 and anchor 3905. Surgical washer 3902 may include a curved mid-section. FIG. 39 shows washer 3902 positioned such that when surgical washer 3902 abuts head 3903 of anchor 3905 the curved mid-section is concave, when viewed from a head 3903 looking down a threaded shaft of anchor 3905.

Surgical washer 3902 may be oriented on anchor 3905 as surgical washer 3802 is oriented on anchor 3807 (shown in FIG. 38). Surgical washer 3802 may be oriented on anchor 3807 (shown in FIG. 38) as surgical washer 3902 is oriented on anchor 3905.

When washer 3902 is buttressed (in the orientation shown in FIG. 39) against a bone by anchor 3905, the curved mid-section spaces offset aperture 3901 (and outer perimeter of washer 3902) apart from an outer surface of the bone. Spacing offset aperture apart from the outer surface of the bone may allow sutures to be more easily threaded through the offset aperture than if the mid-section was planar.

When washer 3902 is buttressed (in the orientation shown in FIG. 39) against a bone by anchor 3905, a rim of a central aperture of washer 3902 may be pressed against an outer surface of the bone.

Figure 40:
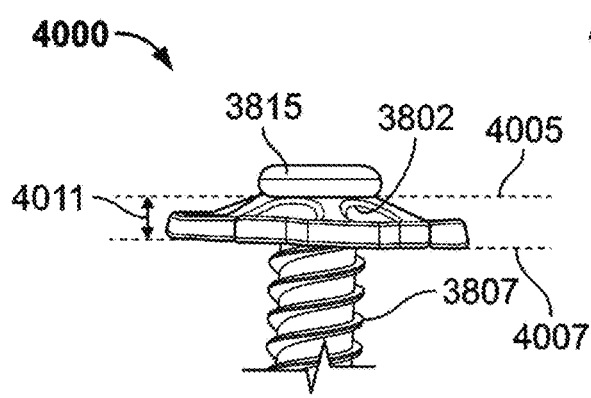
FIG. 40 shows illustrative apparatus in accordance with principles of the invention.

FIG. 40 shows illustrative view 4000 of apparatus 3800 (shown in FIG. 38). FIG. 40 shows that a central aperture of washer 3802 may define first plane 4005. An outer perimeter of washer 3802 may define second plane 4007. A flanged or flattened out region of a mid-section of washer 3802 may define second plane 4007.

View 4000 shows that first plane 4005 is spaced apart from second plane 4007 by distance 4011. In operation, when anchor 3807 buttresses washer 3802 against an outer surface of a bone, distance 4011 may space head 3815 apart from the outer surface of the bone. First plane 4005 may be substantially parallel to second plane 4007.

Figure 41:
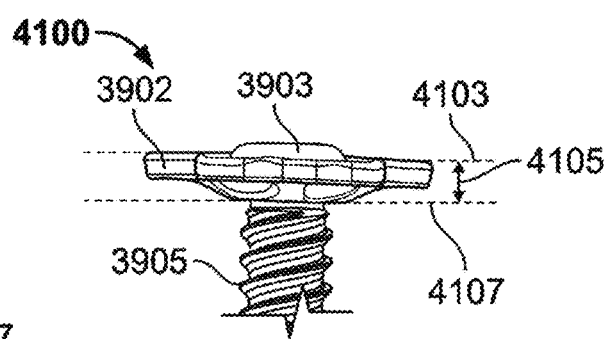
FIG. 41 shows illustrative apparatus in accordance with principles of the invention.

FIG. 41 shows illustrative view 4100 of apparatus 3900 (shown in FIG. 39). FIG. 41 shows that a central aperture of washer 3902 may define first plane 4107. An outer perimeter of washer 3902 may define second plane 4103. A flanged or flattened out region of a mid-section of washer 3902 may define second plane 4013.

View 4100 shows that first plane 4107 is spaced apart from second plane 4103 by distance 4105. In operation, when anchor 3905 buttresses washer 3902 against an outer surface of a bone, distance 4105 may space head 3903 apart from the outer surface of the bone. First plane 4107 may be substantially parallel to second plane 4103.

FIG. 42 shows illustrative therapeutic scenario 4200. FIG. 42 shows implant 4207 being rotated around implant shaft axis $L_{TS}$. Implant shaft axis $L_{TS}$ may be an implant central axis. Implant 4207 may be rotated to seat implant 4207 within bone 4201. Implant 4207 may be rotated to incorporate bone matter into implant head of implant 4207. Implant 4207 may be rotated by handle 2400. Handle 2400 may be coupled to an end of implant shaft 4203.

Scenario 4200 shows jig 4211 positioned on bone 4201. Scenario 4200 shows fixation elements 4213 that releasably couple jig 4211 to bone 4210. When bone 4201 is fractured, one or more of fixation elements 4213 may be inserted into segments of bone 4201. Fixation elements 4213 may be used to position the segments and provisionally reduce the fracture. Scenario 4200 shows targeting wire 4215. Jig 4211 may be positioned on bone 4201 based on an anatomical landmark on bone 4201. Proper positioning of target wire 4215 in bone 4201 may be verified by fluoroscopy or other imaging techniques.

Target wire 4215 may be positioned such that a tip of target wire 4215 positioned in bone 4210 is positioned at a target site. Target wire 4215 may be positioned such that a tip of target wire 4215 positioned in bone 4210 defines end 4217 of an implantation region for implant 4207. Implant 4207 may include tail 4205. Tail 4205 may be affixed to implant shaft 4203. Implant shaft 4203 may be used to manipulate implant 4207 after implant 4207 is deployed inside bone 4201.

Implant shaft 4203 may define a longitudinal axis $L_{TS}$. End 4217 of the implantation region may be at intersection of the proximal end of targeting wire 4215 and longitudinal axis $L_{TS}$.

FIG. 43 shows illustrative therapeutic scenario 4300. Scenario 4300 shows implant 4311 deployed in an implantation region of bone 4313. Implant 4311 may include tail 4315. Tail 4315 may include opposing clearance holes (not shown) for receiving anchor 4309. Anchor 4309 may be positioned in clearance holes by apparatus 3000 (shown in FIG. 30).

Tail 4315 may be affixed to implant shaft 4307. A beveled end 4308 of implant shaft 4307 may fit onto or mate with the beveled end of tail 4315. Beveled end 4308 may include one or more fingers 4317. A finger such as 4317 may fit onto an indentation in an outer surface of tail 4315.

Tail 4315 may include an internally threaded segment (threads not shown). Implant shaft 4307 may include flange 4319. Flange 4319 is positioned inside the hollow implant shaft. Flange 4319 may be positioned at a proximal end of a non-beveled segment of implant shaft 4307.

Scenario 4300 shows locking screw 4305 inside implant shaft 4307. Locking screw 4305 may include a threaded segment (not shown) that slides past flange 4319 when locking screw 4305 is inserted into implant shaft 4307. Locking screw may include a shoulder (not shown) that abuts flange 4319 when locking screw 4305 is inserted into implant shaft 4307 and threadedly engages the internally threaded segment of tail 4315.

When locking screw 4305 threadedly engages the internally threaded segment of tail 4315, locking screw 4305 axially locks implant shaft 4307 to tail 4315. Implant shaft 4307 may include one or more fingers 4317 protruding from beveled end 4307. Tail 4315 may include one or more indentations that are configured to mate with one or more fingers 4317. When locking screw 4305 threadedly engages tail 4315, one or more of fingers 4317 mate with the one or more indentations of tail 4315. When the one or more fingers 4317 mate with the indentations, implant shaft 4307 may be rotational fixed with respect to tail 4317.

Locking screw 4305 may be cannulated. A cannulated locking screw may allow a driver to be inserted through implant shaft 4307, through locking screw 4305, through tail 4315 and engage a locking mechanism of implant 4311. The locking mechanism of implant 4311 may include a screw that locks a shape of implant 4311. Rotating the locking mechanism inside implant 4311 may collapse implant 4311. Collapsing implant 4311 may allow implant 4311 to be removed from bone 4313.

When inserted into implant shaft 4307, head 4303 of driver 4301 may be used to turn locking screw 4305. Driver 4301 may be used to disengage locking screw from tail 4315. Disengaging locking screw 4305 from tail 4315 may allow implant shaft 4307 to be removed from tail 4315. Flange 4319 may prevent locking screw 4305 from falling out of implant shaft 4307 when implant shaft 4307 is removed from tail 4315.

FIG. 44 shows illustrative driver 4400. Driver 4400 may be used to rotate locking screw 4305 when locking screw 4305 is inside implant shaft 4307. Driver 4400 may include shaft 4301. Driver 4400 may include head 4303. Head may have a hexagonal shape or any other suitable shape for rotating locking screw 4305 (shown in FIG. 43).

Figure 45:
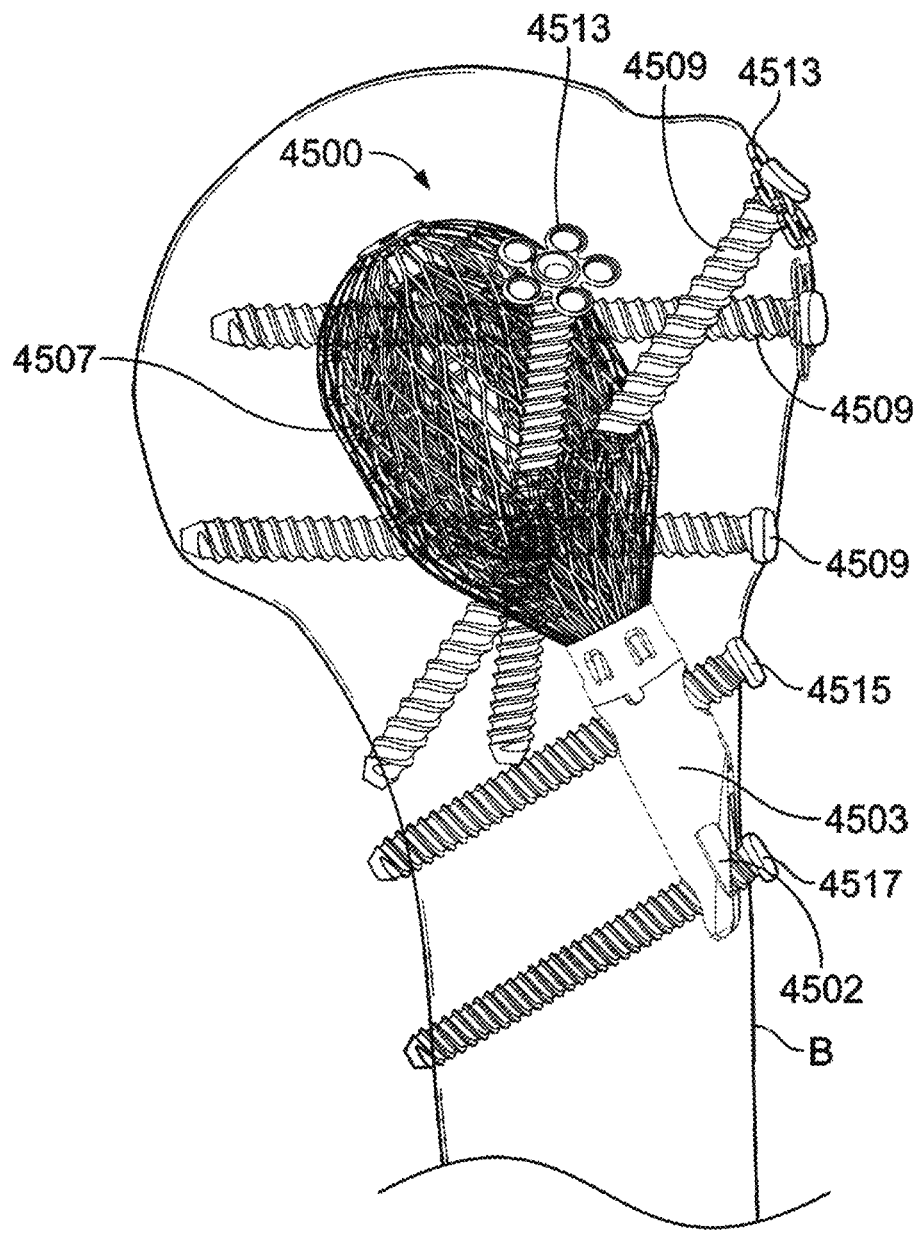
FIG. 45 shows illustrative apparatus and methods in accordance with principles of the invention.

FIG. 45 shows illustrative implant 4500 implanted in bone B. In FIG. 45, screws 4509 are shown anchoring implant head 4507 to bone B. Some of screws 4509 may have washers 4513 coupled to heads of screws 4509. In FIG. 45, screw 4515 is shown passing through a first hole in implant tail 4503. Distal screw 4517 is shown passing through a second hole in implant tail 4503.

FIG. 45 illustrates possible trajectories of screws and washers passing through implant 4500. The trajectories may be used to address fracture patterns. The trajectories may be used to provide fixation and stability to bone B for facilitating bone healing.

FIG. 45 shows illustrative indentation 4502. Indentation 4502 may be configured to mate with a finger 4317 on beveled end 4307 of implant shaft 4307.

FIG. 46 shows illustrative implant 4600 implanted in bone B. In FIG. 46, screws 4611 are shown anchoring implant head 4615 to bone B. Screws 4603 are shown anchoring implant tail 4613 to plate 4601 and to bone B. Screw 4605 is shown anchoring plate 4601 to bone B. Plate 4601 may provide buttress support to bone B.

FIG. 47 shows illustrative implant 4700 implanted in bone B. FIG. 47 shows a plurality of screws anchoring implant head 4721 to bone B, anchoring both plate 4701 and implant head 4721 to bone B, anchoring implant tail and plate 4701 to bone B, and anchoring plate 4701 to bone B. One or more of the screws may include a washer 4725.

FIG. 48 shows illustrative plate 4800. Plate 4800 may define target hole 4811. Plate 4800 may define suture holes 4801. Plate 4800 may define screw holes 4813 and screw holes 4809. Plate 4800 may define slot 4815 and slot 4825. Slot 4815 and slot 4825 may be sized to engage a head of a screw. A screw advanced through one of slot 4815 and slot

4825 may be advanced through the plate at a range of angles relative to a plate longitudinal axis. Slot 4815 and slot 4825 may both be circumscribed by plate 4800. Plate 4800 may define a plurality of holes 4817 sized for receiving fixation elements.

Plate 4800 may include one or more slots for receiving sutures (not shown).

Plate 4800 may define opening 4827. Opening 4827 may define indicators 4823 and indicators 4821.

Plate 4800 may have a bottom surface. The bottom surface may complement a surface contour of a bone. When the bottom surface is seated complementarily against the surface contour, opening 4827 may define an area on the bone for preparing an access hole for accessing a target site in the bone. When the bottom surface is seated complementarily against the surface contour, target hole 4811 may point to the target site.

When the bottom surface is seated complementarily against the surface contour, indicators 4823 may register to a first access position on the bone for accessing the target site. The first access position may be an access position for an implant having a first length. When the bottom surface is seated complementarily against the surface contour, indicators 4821 may register to a second access position on the bone for accessing the target site. The second access position may be an access position for an implant having a second length. The first length may be different from the second length.

When the bottom surface is seated complementarily against the surface contour and an implant is expanded at the target site, screw holes 4813 and screw holes 4809 may point to an implant head. When the bottom surface is seated complementarily against the surface contour and an implant is expanded at the target site, a screw advanced slot 4825 may engage an implant tail. When the bottom surface is seated complementarily against the surface contour and an implant is expanded at the target site, a screw advanced through slot 4815 may engage an implant tail. When the bottom surface is seated complementarily against the surface contour and an implant is expanded at the target site, a screw advanced through slot 4815 may engage an implant head.

Slots 4815 and 4825 may be used for guiding a screw through plate 4800 and into an implant. Slots 4815 and 4825 may provide a physician with a range of access angles for driving the screw through slots 4815 and 4825 and into an implant. One or both of slots 4815 and 4825 may include one or more ridges. Each ridge may extend around the slot. One or more ridges may act as a locking feature for a screw.

FIG. 49 shows illustrative plate 4900. Plate 4900 may define suture holes 4901. Plate 4900 may define screw holes 4909, screw hole 4917 and screw hole 4919. Plate 4900 may define opening 4915. Plate 4900 may define a plurality of holes 4911 for receiving fixation elements. Plate 4900 may define target hole 4907. Plate 4900 may include one or more slots for receiving sutures (not shown).

Plate 4900 may have a bottom surface complementing a surface contour of a bone. When the bottom surface is seated complementarily against the surface contour, opening 4915 may define an area on the bone for preparing an access hole for accessing a target site in the bone. When the bone surface is seated complementarily against the surface contour, target hole 4907 may point to the target site.

Plate 4900 may define slot 4913. Slot 4913 may extend away from opening 4915. Slot 4913 may be partially circumscribed by plate 4900. Slot 4913 may include one or more ridges. Each ridge defined by slot 4813 may extend around slot 4913. The ridges may act as a locking feature for a screw.

Slot 4913 may be used for guiding a screw through plate 4900 and into an implant. Slot 4913 may provide a physician with a range of access angles for driving the screw through slot 4913 and into an implant.

FIG. 50 shows illustrative plate 5000. Plate 5000 may define target hole 5003. Plate 5000 may define screw hole 5001, screw hole 5005, screw hole 5009 and screw hole 5011. Plate 5000 may define a plurality of holes 5007 for receiving fixation elements. Plate 5000 may define suture holes 5017. Plate 5000 may include one or more slots for receiving sutures (not shown).

Plate 5000 may have a bottom surface complementing a surface contour of a bone. When the bottom surface is seated complementarily against the surface contour, opening 5013 may define an area on the bone for preparing an access hole for accessing a target site in the bone. When the bottom surface is seated complementarily against the surface contour, target hole 5003 may point to the target site.

Plate 5000 may define slot 5015 extending away from opening 5013. Slot 5015 may be used for guiding a screw through plate 5000 and into an implant. Slot 5015 may provide a physician with a range of access angles for driving the screw through opening 5015 and into an implant. Slot 5015 may include one or more ridges. The ridges may act as a locking feature for a screw.

The bottom surface of plate 5000 may conform to a surface contour of a left humerus. A proximal end of the plate (including screw holes 5005) may be shaped to cover a greater area of a greater tuberosity of the left humerus compared to plate 4800.

FIG. 51 shows illustrative apparatus 5100. Illustrative apparatus 5100 may include first plate 5101 and second plate 5103.

First plate 5101 may define suture holes 5113. First plate 5101 may include one or more slots for receiving sutures (not shown). First plate 5101 may define target hole 5117. First plate 5101 may define screw holes 5118 and screw hole 5121. First plate 5101 may define a plurality of holes 5119 for receiving fixation elements.

First plate 5101 may define opening 5109. Second plate 5103 may be positioned in opening 5109. Second plate 5103 may be releasably coupled to first plate 5101 by screw 5105. Second plate 5103 may define opening 5107.

First plate 5101 may have a bottom surface complementing a surface contour of a bone. When the bottom surface is seated complementarily against the surface contour, opening 5109 may define an area on the bone for preparing an access hole for accessing a target site in the bone. When an implant is implanted through the access hole and into the bone, a tail of the implant may be positioned in opening 5109. When the implant is implanted into the bone, a tail of the implant may also be positioned in opening 5107. Plate 5103 may be positioned in opening 5109 after the implant is implanted into the bone. The positioning may include positioning an implant shaft in opening 5107 and sliding plate 5103 along the implant shaft and onto plate 5101.

Each of plates 4800, 4900, and 5100 may define a bottom surface. The bottom surface of each of the plates may conform to a surface contour of a right bone and a left bone. The bottom surface may conform to a surface contour of a right proximal humerus and a left proximal humerus. Each of plates 4800, 4900, and 5100 may define a first bottom surface and a second bottom surface. The first bottom surface may conform to a surface contour of a right proximal humerus. The second bottom surface may conform to a surface contour of a left proximal humerus. The first bottom surface and the second bottom surface may define the same bottom surface. The first bottom surface may be different from the second bottom surface. A physician may use plate 4800, plate 4900, or plate 5100 for providing therapy to either a right humerus or a left humerus.

One or more of the screw holes defined by each of plates 4800, 4900, 5000 and 5100 may be threaded. Threaded screw holes may be shaped to receive screws having threaded heads. Threaded screw holes may provide a locking construct between the plates and the screws.

Figure 52:
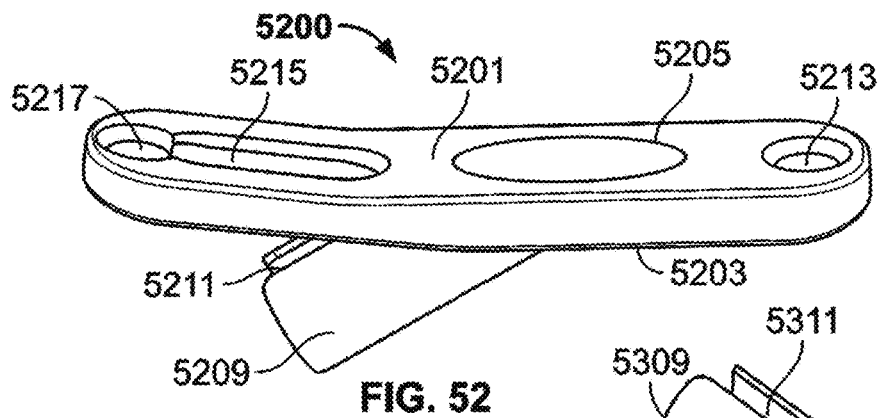
FIG. 52 shows illustrative apparatus in accordance with principles of the invention.

FIG. 52 shows illustrative plate 5200. Plate 5200 may define screw hole 5217, slot 5215 and screw hole 5213. Plate 5200 may include top face 5201. Plate 5200 may include bottom face 5203. Plate 5200 may define opening 5205. Tube 5209 may extend away from opening 5205. Tube 5209 may extend away from opening 5205 at an angle oblique to a longitudinal axis of plate 5200. Tube 5209 may include groove 5211.

Tube 5209 may have an inner diameter. Tube 5209 may have an inner diameter slightly larger than a diameter of an implant tail.

After an implant has been implanted in a bone, bottom face 5203 of plate 5200 may be placed on a surface of bone. Placement of bottom surface 5203 of plate 5200 on a bone may include coaxially mounting tube 5209 onto an implant tail of the implant. Placement of plate 5200 on a bone may include sliding plate 5200 along the implant tail until bottom face 5203 of plate 5200 is seated on a surface of the bone. Slot 5215 and groove 5211 may facilitate the coupling of the implant tail to plate 5200 by defining an opening through which a screw may pass through slot 5215 and groove 5211 and into a bore defined by the implant tail.

Figure 53:
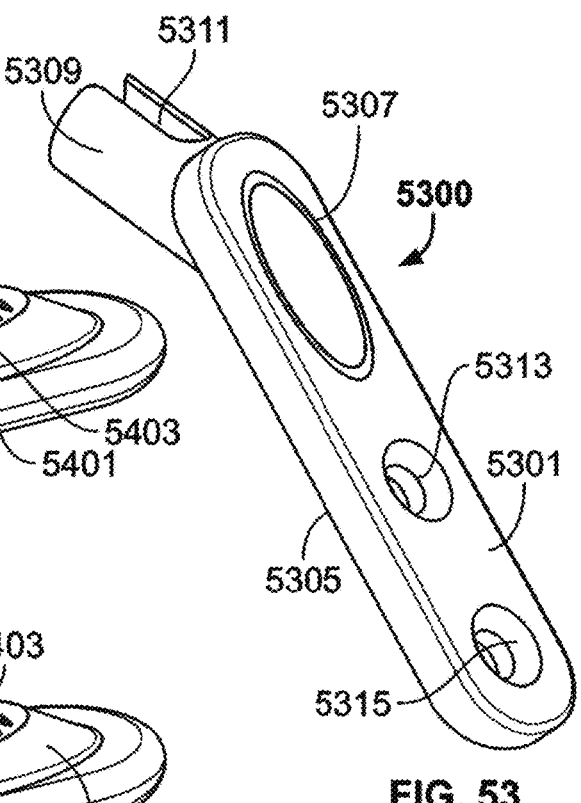
FIG. 53 shows illustrative apparatus in accordance with principles of the invention.

FIG. 53 shows illustrative plate 5300. Plate 5300 may define screw hole 5315 and screw hole 5313. Plate 5300 may include a top face 5301. Plate 5300 may include bottom face 5305. Plate 5300 may define opening 5307. Tube 5309 may extend away from opening 5307. Tube 5309 may extend away from opening 5307 at an angle oblique to a longitudinal axis of plate 5300. Tube 5309 may include groove 5311. Groove 5311 may facilitate the coupling of an implant tail to plate 5300 by providing an opening through which a screw may pass into a bore defined by an implant tail. A screw passed through groove 5311 and into an implant tail may couple tube 5309 and plate 5300 to the implant tail.

Figure 54:
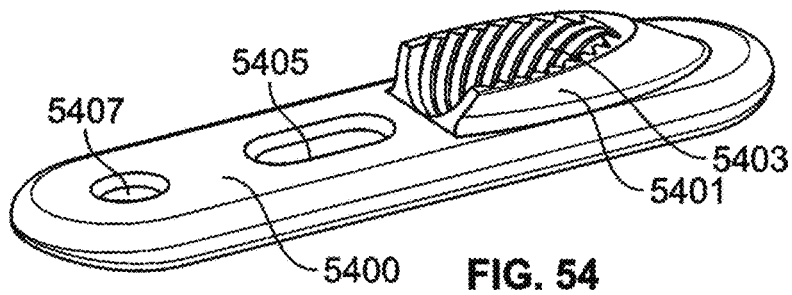
FIG. 54 shows illustrative apparatus in accordance with principles of the invention.

FIG. 54 shows illustrative plate 5400. Plate 5400 may define screw hole 5407 and slot 5405. Plate 5400 may include protrusion 5401. Protrusion 5401 may be internally threaded with threads 5403.

Figure 55:
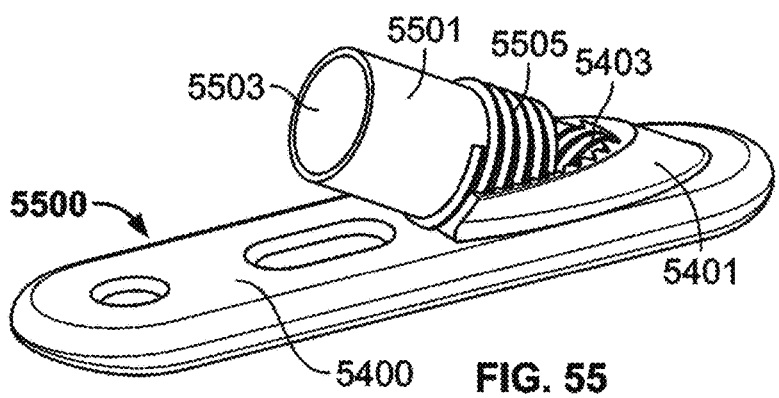
FIG. 55 shows illustrative apparatus in accordance with principles of the invention.

FIG. 55 shows illustrative apparatus 5500. Illustrative apparatus 5500 may include plate 5400 and bushing 5501. Bushing 5501 may be externally threaded with threads 5505. Bushing 5501 may define opening 5503.

In FIG. 55, bushing 5501 is screwed onto a portion of threads 5403. Bushing 5501 may be referred to herein as a first externally threaded tube.

Figure 56:
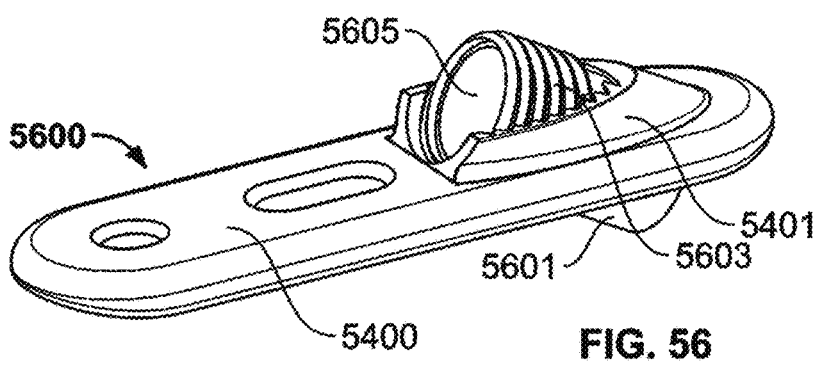
FIG. 56 shows illustrative apparatus in accordance with principles of the invention.

FIG. 56 shows illustrative apparatus 5600. Illustrative apparatus 5600 may include plate 5400 and bushing 5601. Bushing 5605 may be referred to herein as a second externally threaded tube.

Bushing 5601 may be externally threaded with threads 5603. Bushing 5601 may define opening 5605.

A method for preparing a bone for implantation of an implant may include placing plate 5400 on a surface of the bone. The method may include anchoring plate 5400 to the bone by driving a screw through screw hole 5407 and/or slot 5405. The method may include screwing bushing 5501 into threads 5403. The method may include inserting a drill through opening 5503 to create an access hole. The method may include inserting a cavity preparation device through opening 5503 to prepare a cavity in the bone. The method may include passing an implant in an unexpanded form through opening 5503 and into the cavity. The method may include unscrewing bushing 5501 from plate 5400 after the implant is implanted in the cavity. The method may include supporting the implant after implantation. The method may include screwing bushing 5601 into threads 5403. Screwing bushing 5401 into the inner threaded portion of plate 5400 may coaxially mount opening 5605 around a tail of the implant. Bushing 5601 may be placed on an implant shaft of the implant and slid along the implant shaft towards the bone surface. The implant shaft may be removed from an implant tail after bushing 5601 is coupled to plate 5400.

Figures 57, 58, 59:
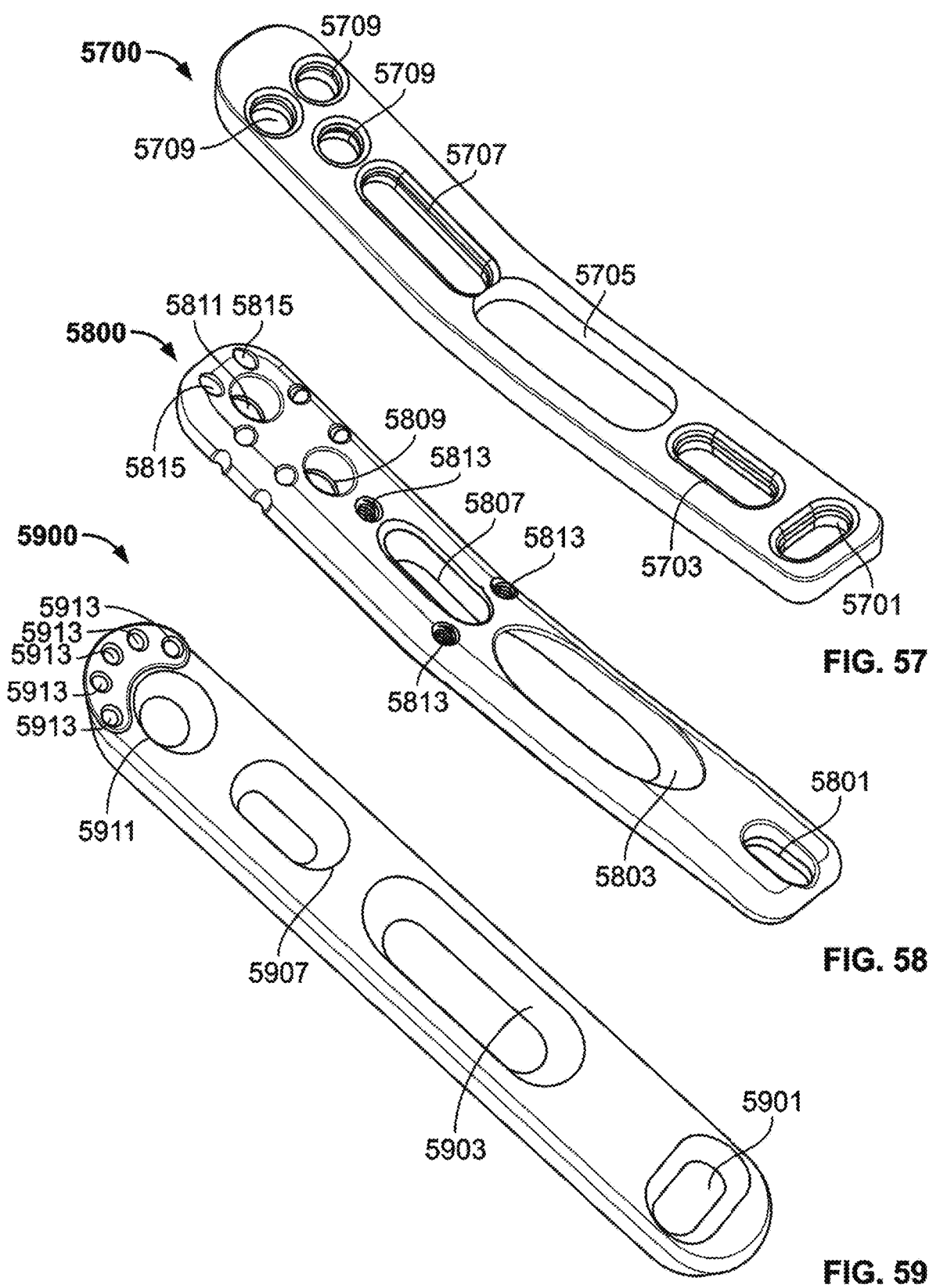
FIG. 57 shows illustrative apparatus in accordance with principles of the invention.
FIG. 58 shows illustrative apparatus in accordance with principles of the invention.
FIG. 59 shows illustrative apparatus in accordance with principles of the invention.

FIG. 57 shows illustrative plate 5700. Plate 5700 may define screw holes 5709, slot 5707, slot 5703 and slot 5701. Plate 5700 may define opening 5705. When plate 5700 is placed on a bone, an access hole may be prepared in an area on the bone defined by opening 5705.

One of more of slot 5707, slot 5703 and slot 5701 may include one or more ridges. The ridges may engage a head of a screw. The ridges may act as a locking feature for a screw.

Plate 5700 may have a bottom surface complementing a surface contour of a bone. When the bottom surface is seated complementarily against the surface contour, opening 5705 may define an area on the bone for preparing an access hole for accessing a target site in the bone.

FIG. 58 shows illustrative plate 5800. Plate 5800 may define suturing holes 5815. Plate 5800 may define target hole 5811. Plate 5800 may define screw hole 5809, slot 5807 and slot 5801. One or both of slot 5807 and slot 5801 may include one or more ridges. The ridges may act as a locking feature for a screw. Plate 5811 may define holes 5813. Holes 5813 may be internally threaded. Holes 5813 may be internally threaded for receiving a bushing. The bushing may be sized for receiving a fixation element. Holes 5813 may be sized to receive a fixation element.

Plate 5800 may define opening 5803. When plate 5800 is placed on a bone B, an access hole may be prepared in an area of the bone defined by opening 5803.

Plate 5800 may have a bottom surface complementing a surface contour of a bone. When the bottom surface is seated complementarily against the surface contour, opening 5803 may define an area on the bone for preparing an access hole for accessing a target site in the bone.

FIG. 59 shows illustrative plate 5900. Plate 5900 may define suture holes 5913. Plate 5900 may include one or more slots for receiving sutures. Plate 5900 may define screw hole 5911, slot 5907 and slot 5901. One or both of slot 5907 and slot 5901 may include one or more ridges. The ridges may act as a locking feature for a screw. Plate 5900 may define opening 5903.

Screw hole 5911 may be tapered. Slot 5907 may be tapered. Slot 5901 may be tapered.

Plate 5900 may have a bottom surface complementing a surface contour of a bone. When the bottom surface is seated complementarily against the surface contour, opening 5903 may define an area on the bone for preparing an access hole for accessing a target site in the bone. When the bottom surface is seated complementarily against the surface contour, an access hole may be prepared in an area of the bone defined by opening 5903. The access hole may be used to access a target site in the interior of the bone.

FIG. 60 shows a bottom view of illustrative jig 6000. Jig 6000 may define slot 6003 sized for receiving a screw. Jig 6000 may define opening 6001 for accessing a surface of a bone through the jig. Opening 6001 may be sized to provide clearance for an implant. Jig may define screw holes 6007. Screw holes 6007 may be used by a practitioner to guide screws into a head of an expanded implant. Jig 6000 may define target hole 6015. Jig 6000 may define positioning hole 6013. Jig 6000 may include slot 6005 sized for receiving a screw.

Jig 6000 may include recess 6009. Recess 6009 may be sized to receive a plate. A plate may be positioned in recess 6009.

Jig 6000 may have a bottom surface complementing a surface contour of a bone. When the bottom surface is seated complementarily against the surface contour, opening 6001 may define an area on the bone for preparing an access hole for accessing a target site in the bone.

FIG. 61 shows a side view of apparatus illustrated in FIG. 60. FIG. 61 shows guide 6101 included in jig 6000. Guide 6101 may extend away from opening 6001. Guide 6101 may receive one or more bushings. Exemplary bushings that may be received by guide 6101 include bushings 7015, 7017, 7019 or 7021 (shown in FIG. 70). One or more devices may be inserted through guide 6101, through opening 6111 and into a bone.

Guide 6101 may receive a fixation element. Guide 6101 may receive a drill. Guide 6101 may receive a cavity preparation device. Guide 6101 may receive an implant. Guide 6101 may receive a bushing sized to receive a fixation element. Guide 6101 may receive a bushing sized to receive a drill. Guide 6101 may receive a bushing sized to receive a cavity preparation device. Guide 6101 may receive a bushing sized to receive an implant.

Guide 6101 may define central axis $G_c$. When the bottom surface is jig 6000 is seated complementarily against the surface contour, central axis $G_c$ may point towards a target site. When the bottom surface is jig 6000 is seated complementarily against the surface contour, central axis $G_c$ may point in a direction that does not transect the target site.

Guide 6101 may define guide opening 6103.

FIG. 62 shows a top view of apparatus illustrated in FIG. 60.

Figure 63:
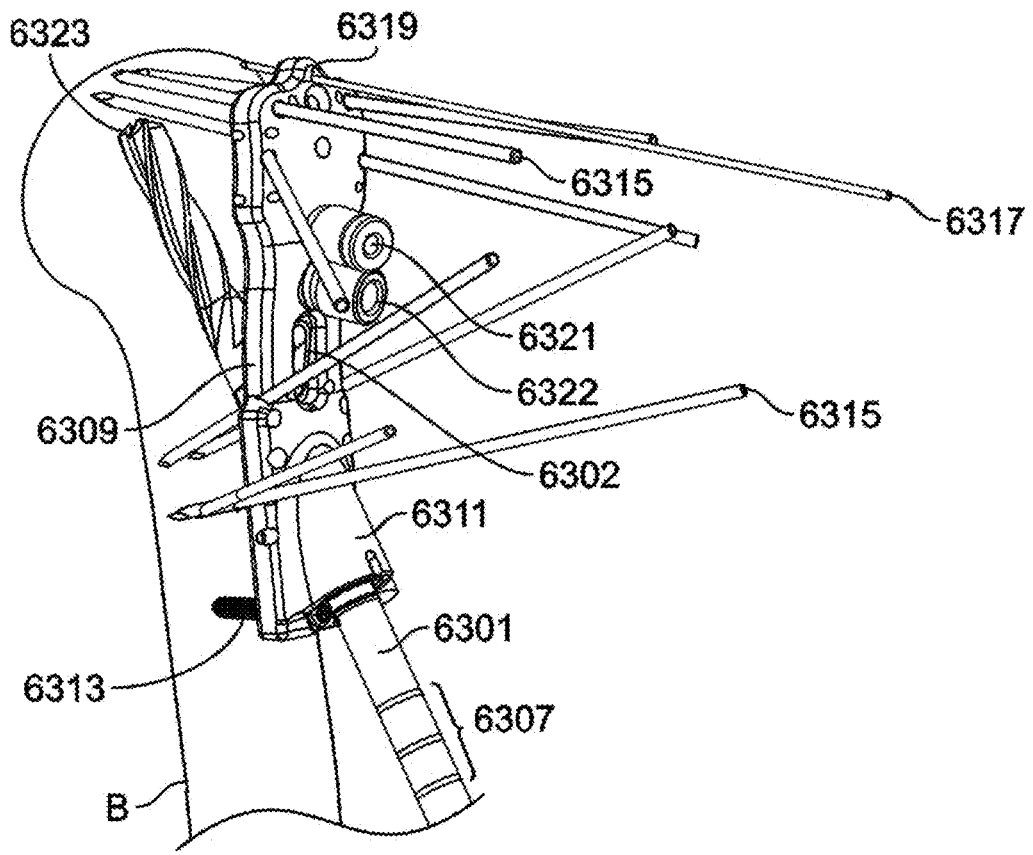
FIG. 63 shows illustrative apparatus and methods in accordance with principles of the invention.

FIG. 63 shows illustrative jig 6309. Jig 6309 may be releasably coupled to bone B by distal screw 6313. Distal screw 6313 may have one or more features in common with distal screw 6507 (illustrated in FIG. 65). Fixation elements 6315 may pass through jig 6309 and into an interior of bone B. Fixation element 6317 may pass through positioning hole 6319 defined by jig 6309.

Jig 6309 may define slot 6302. In operation, slot 6302 may be used by a practitioner to pass a screw into a tail of an expanded implant (not shown). Each of bushing 6321 and bushing 6322 may be releasably coupled to a screw hole defined by jig 6309. Each of bushings 6321 may be used to guide a screw through jig 6309 and into an interior of bone B. When a screw is positioned in bone B, a bushing used to drive the screw into bone B may be removed.

Jig 6309 may include guide 6311. Illustrative drill 6301 may be inserted through guide 6311. Drill 6301 may include demarcations 6307. Tip 6323 of drill 6301 may be advanced to a target site in bone B. Drill 6301 may be used to prepare an access hole in bone B.

Figure 64:
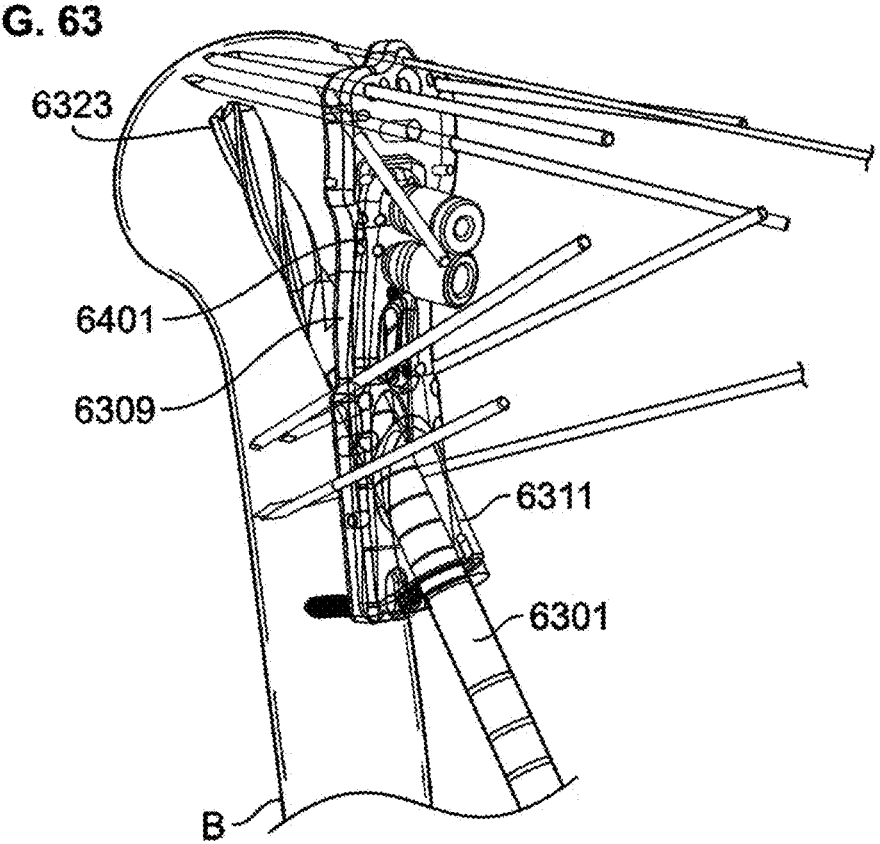
FIG. 64 shows illustrative apparatus and methods in accordance with principles of the invention.

FIG. 64 shows a different view of apparatus illustrated in FIG. 63. In FIG. 64, illustrative plate 6401 is positioned in a recess defined by jig 6309.

Figure 65:
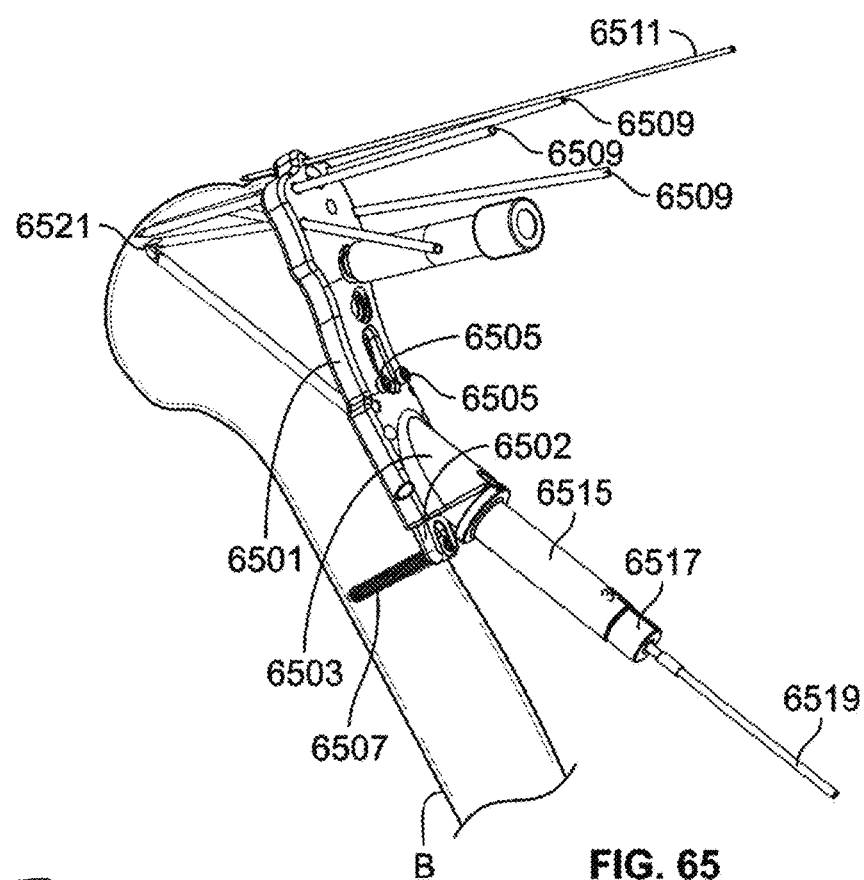
FIG. 65 shows illustrative apparatus and methods in accordance with principles of the invention.

FIG. 65 shows illustrative jig 6501 seated on bone B. Fixation elements 6509 pass through holes defined by jig 6501 and into bone B. Fixation element 6511 passes through a positioning hole located on jig 6501. A distal end of jig 6501 is releasably coupled to bone B by distal screw 6507.

Distal screw 6507 may be a removable screw. Distal screw 6507 may be a non-locking screw. Distal screw 6507 may be inserted through plate 6502 coupled to a bottom of jig 6501 and into bone B. Distal screw 6507 may be inserted through plate 6502 and into bone B during preliminary reduction of bone B. Distal screw 6507 may be used to stabilize bone B. Distal screw 6507 may be used to position plate 6502 onto bone B. Distal screw 6507 may be removed from bone B after reduction is obtained. Distal screw 6507 may be replaced with a screw such a locking screw after an implant is implanted in bone B. Distal screw 6507 may have a length longer than a length of the screw.

Jig 6501 includes guide 6503. Insert 6515 is shown inserted into guide 6503.

Insert 6517 is nested within a lumen defined by insert 6515. Insert 6515 may be sized to receive a drill, cavity preparation device and an implant. Insert 6515 may define a first insert central axis. The insert central axis may point towards a target site. Insert 6517 may be sized to receive a fixation element. Fixation element 6519 is shown passing through insert 6517 and into bone B. Tip 6521 of fixation element 6519 is positioned at a target site in bone B. Insert 6517 may define a second insert central axis. The second insert central axis may be coaxial with the first insert central axis. The second insert central axis may point to the target site. Insert 6517 may guide a target wire to the target site. Insert 6515 may guide one or more of a drill, cavity preparation device and an implant to the target site.

Screws 6505 are shown passing through jig 6501. Screws 6505 may releasably couple jig 6501 with a plate positioned under jig 6501 (not shown).

Figure 66:
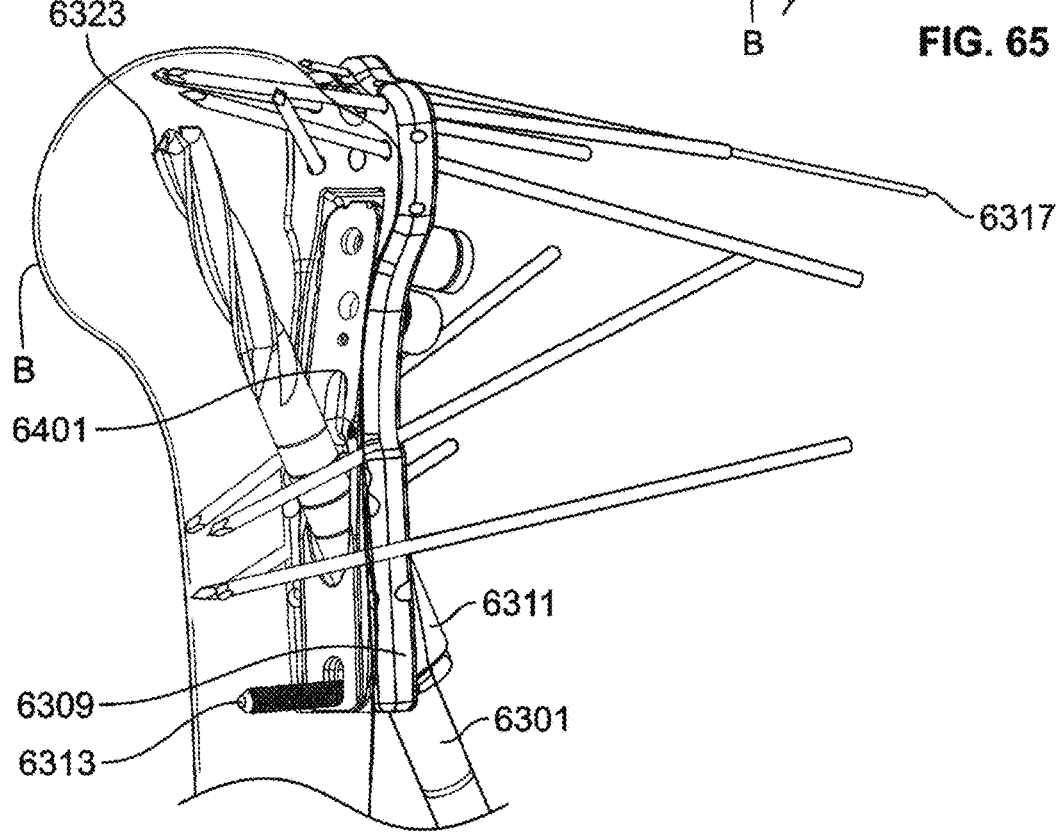
FIG. 66 shows illustrative apparatus and methods in accordance with principles of the invention.

FIG. 66 shows a perspective view of apparatus illustrated in FIGS. 63 and 64. Distal screw 6313 may have one or more features in common with distal screw 6507.

FIG. 67 shows an outline of illustrative implants 6703, 6705 and 6707 positioned in a central location in an interior of bone B. Bone B may be a humerus bone. A humeral head of bone B may define central axis $B_c$.

In FIG. 67, a proximal end of each of implants 6703, 6705 and 6707 is positioned at target site 6701. Each of implants 6703, 6705 and 6707 has a unique length. Additionally, each of implants 6703, 6705 and 6707 defines a unique central axis. Implant 6707 defines central axis 6709. Implant 6705 defines central axis 6711. Implant 6703 defines central axis 6713. As shown in FIG. 67, a tail of each of implants 6703, 6705 and 6707 extends through a surface of bone B at a unique location. Thus, each implant would necessitate preparation of an access hole at a different location on bone B for deployment at target site 6701.

When a practitioner is selecting a size of an implant for implanting at target site 6701 in bone B, each sized implant may require preparation of an access hole at a different location on bone B.

FIG. 68 shows an outline of illustrative implants 6803, 6805 and 6807 positioned in an interior of bone B. Bone B may be a humerus bone. A humeral head of bone B may define a central axis $B_c$.

In FIG. 68, a proximal end of each of implants 6803, 6805 and 6807 is positioned at target site 6801. Each of implants 6803, 6805 and 6807 has a unique length. Additionally, each of implants 6803, 6805 and 6807 defines a unique central axis. Implant 6807 defines central axis 6809. Implant 6805 defines central axis 6811. Implant 6803 defines central axis 6813. As shown in FIG. 68, a tail of each of implants 6803, 6805 and 6807 extends through a surface of bone B at a unique location. Thus, each implant would necessitate preparation of an access hole at a different location on bone B for deployment at target site 6801.

When a practitioner is selecting a size of an implant for implanting at target site 6801 in bone B, each sized implant may require preparation of an access hole at a different location on bone B.

FIG. 69 shows an outline of illustrative implants 6903, 6905 and 6907 positioned in an interior of bone B. Bone B may be a humerus bone. A humeral head of bone B may define a central axis $B_c$.

In FIG. 69, a proximal end of each of implants 6903, 6905 and 6907 is positioned at target site 6901. Each of implants 6903, 6905 and 6907 has a unique length. Additionally, each of implants 6903, 6905 and 6907 defines a unique central axis. Implant 6907 defines central axis 6909. Implant 6905 defines central axis 6911. Implant 6903 defines central axis 6913. As shown in FIG. 69, a tail of each of implants 6903, 6905 and 6907 extends through a surface of bone B at a unique location. Thus, each implant would necessitate preparation of an access hole at a different location on bone B for deployment at target site 6901.

When a practitioner is selecting a size of an implant for implanting at target site 6901 in bone B, each sized implant may require preparation of an access hole at a different location on bone B.

Figure 70:
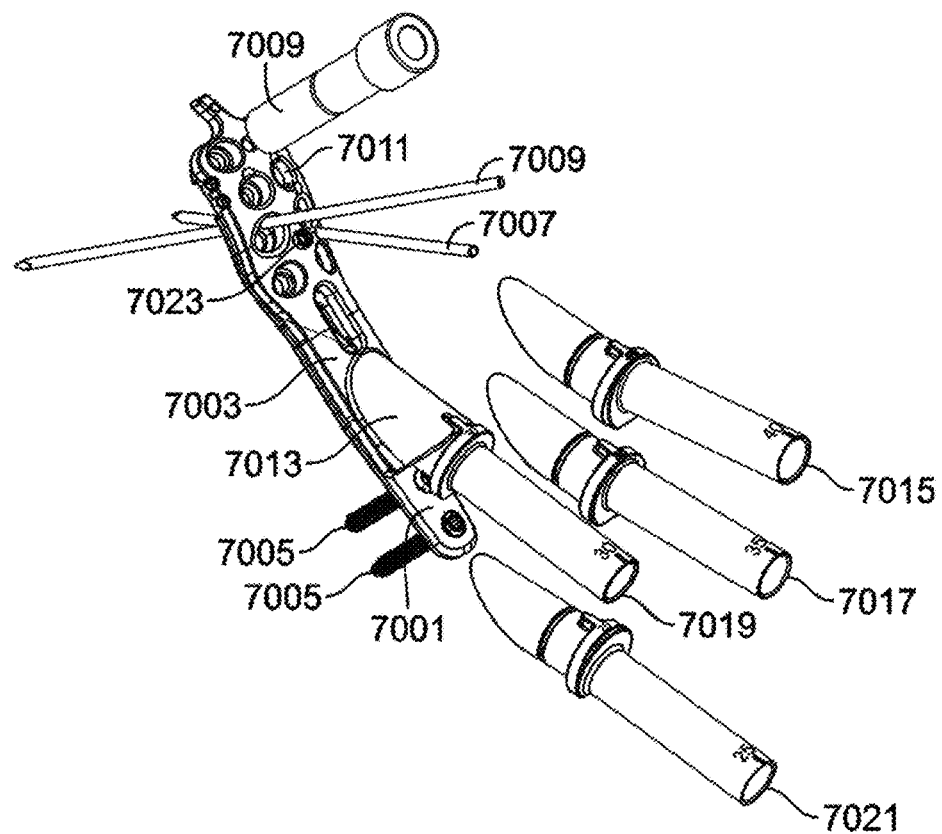
FIG. 70 shows illustrative apparatus in accordance with principles of the invention.

FIG. 70 shows illustrative apparatus including plate 7001 and jig 7003. Plate 7001 may be releasably coupled to a bone (not shown) by distal screws 7005. Distal screws 7005 may have one or more features in common with distal screw 6507. Screw 7023 may releasably couple jig 7003 to plate 7001.

Jig 7003 may define screw hole 7011. Bushing 7009 may be screwed onto a screw hole defined by jig 7003. Each of fixation element 7009 and fixation element 7007 may pass through a first hole defined by jig 7003, through a second hole defined by plate 7001, and into an interior of a bone (not shown).

FIG. 70 shows illustrative insert 7015, illustrative insert 7017, illustrative insert 7019 and illustrative insert 7021. An end of each of the inserts sized to be received by guide 7013 may define an outer shape. The outer shape may be sized to fit into an inner surface of guide 7013.

Figure 71:
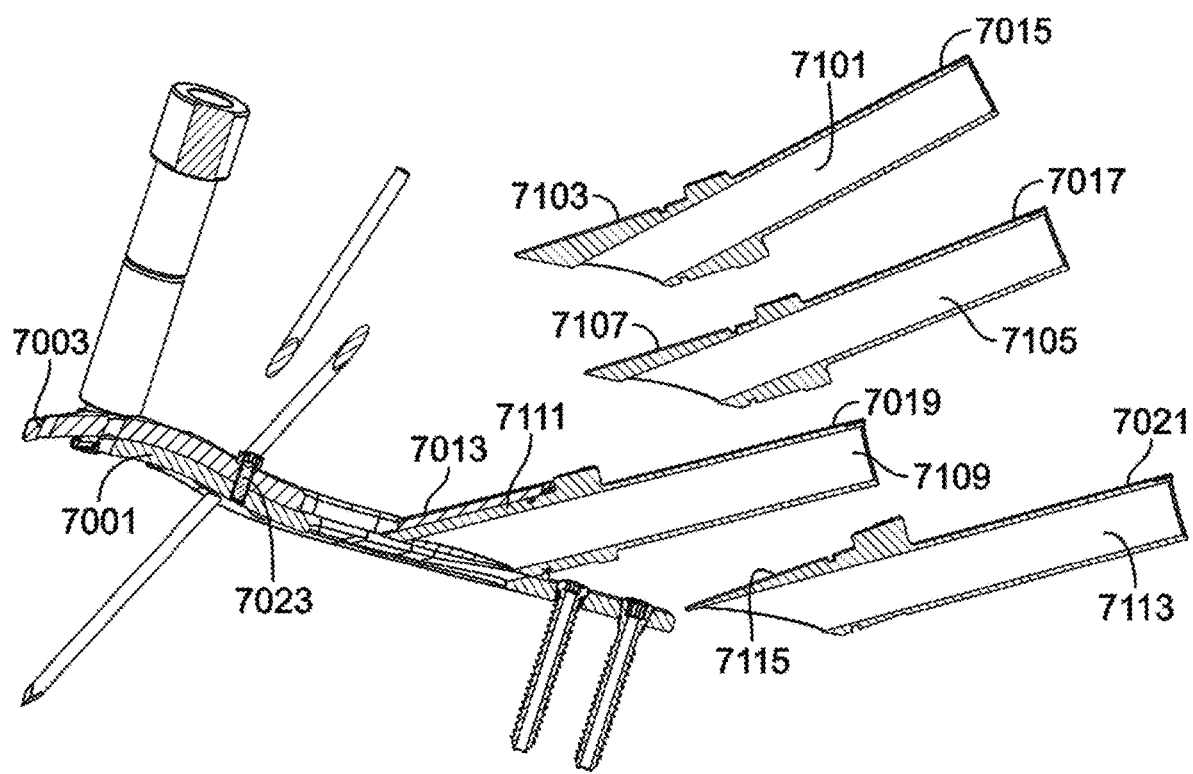
FIG. 71 shows illustrative apparatus in accordance with principles of the invention.

FIG. 71 shows a cross sectional view of apparatus illustrated in FIG. 70.

Insert 7015 may include outer shape 7103 and inner lumen 7101. Insert 7017 may include outer shape 7107 and inner lumen 7105. Insert 7019 may include outer shape 7111 and inner lumen 7109. Insert 7021 may include outer shape 7115 and inner lumen 7113. The inner lumen may have a cylindrical shape.

Each of the outer shapes may be sized to fit into an inner surface of guide 7013. A portion of the outer shapes may define a central axis. The central axis of the outer shapes may be parallel to a central axis of guide 7013.

Each lumen may define a lumen central axis. A lumen central axis defined by each of guides 7015, 7017 and 7021 may not be parallel to the central axis of guide 7013. A lumen central axis defined by guide 7019 may be parallel to the central axis of guide 7013.

When insert 7019 is inserted into guide 7013, insert 7019 may guide a device along a central axis defined by guide 7013 and into a bone B. When one of inserts 7015, 7017 or 7021 are inserted into guide 7013, apparatus advanced through the inserts may be advanced along an access angle different from the central axis of guide 7013. The access angle may be the angle defined by the lumen of the insert. A physician may use inserts 7015, 7017, 7019 and 7021 as apparatus for selecting or modifying an access angle for accessing a bone through an opening defined by plate 7001.

In embodiments where the inner lumen has a cylindrical shape, the inner lumen may be referred to alternatively as an inner cylindrical surface. An inner lumen axis may be referred to alternatively as an insert inner central axis.

Figure 72:
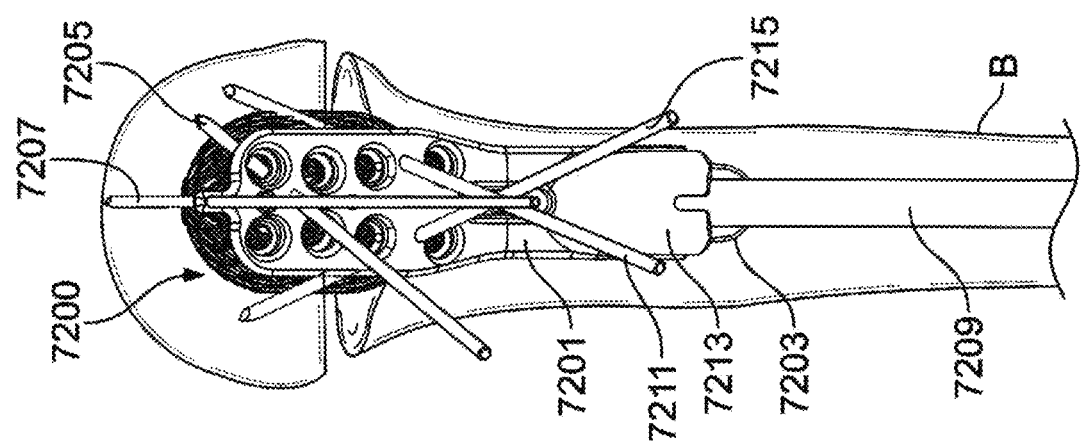
FIG. 72 shows illustrative apparatus and methods in accordance with principles of the invention.

FIG. 72 shows illustrative apparatus including jig 7201, plate 7203 and implant 7200. Plate 7203 may be releasably coupled to a bottom of jig 7201.

In FIG. 72, fixation element 7205, fixation element 72011 and fixation element 7215 may pass through jig 7201 and into an interior of bone B. A hole defined by jig 7201 to receive fixation element 7211 may define a first direction. A hole defined by jig 7201 to receive fixation element 7215 may define a second direction. The second direction may be divergent from the first direction.

Fixation element 7207 may pass through a positioning hole defined by jig 7201. Fixation element 7207 may be seated on a top of a greater tuberosity of bone B. Jig 7201 may include guide 7213. Shaft 7209 of implant 7200 may extend through guide 7213.

Figure 73:
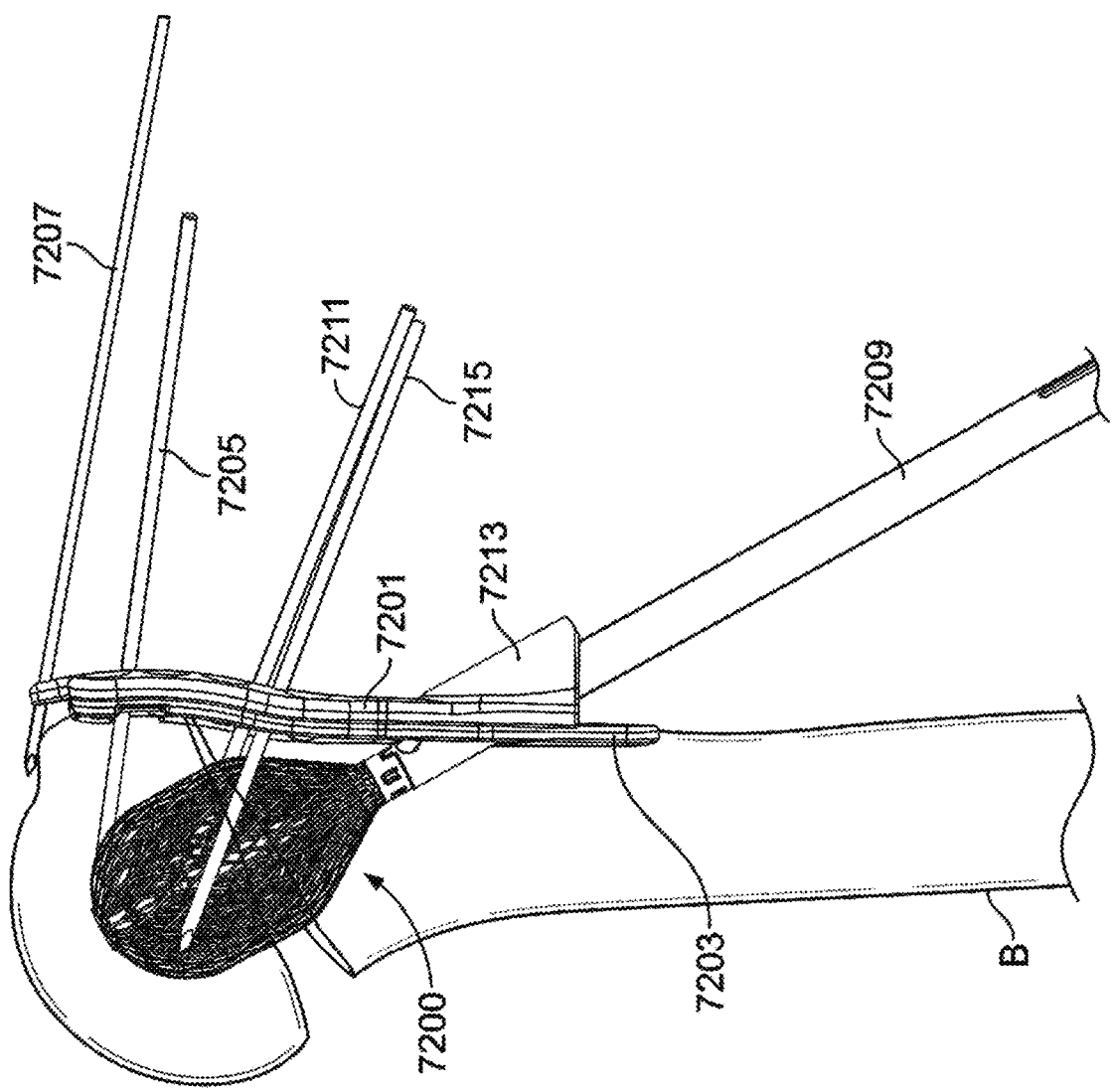
FIG. 73 shows illustrative apparatus and methods in accordance with principles of the invention.

FIG. 73 shows a side view of apparatus illustrated in FIG. 72.

Figure 74:
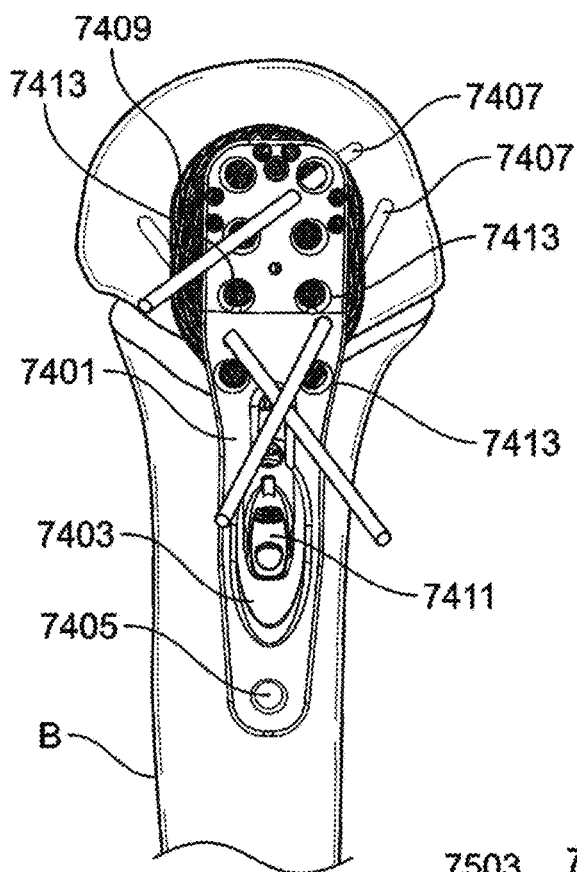
FIG. 74 shows illustrative apparatus and methods in accordance with principles of the invention.

FIG. 74 shows illustrative apparatus including plate 7401 and implant 7409. In FIG. 74, implant has been deployed in bone B so that implant tail 7411 is positioned in opening 7403 defined by plate 7401.

Plate 7401 may include screw hole 7405. Driving a screw through distal screw hole 7405 may releasably couple an end of plate 7401 to bone B. Plate 7401 may define screw holes 7413. Passing a screw through one of screw holes 7413 may guide the screw through the plate, through a surface of bone B and into an implant head of implant 7409. In FIG. 74, fixation elements 7407 are shown passing through plate 7401 and into an interior of bone B.

Figure 75:
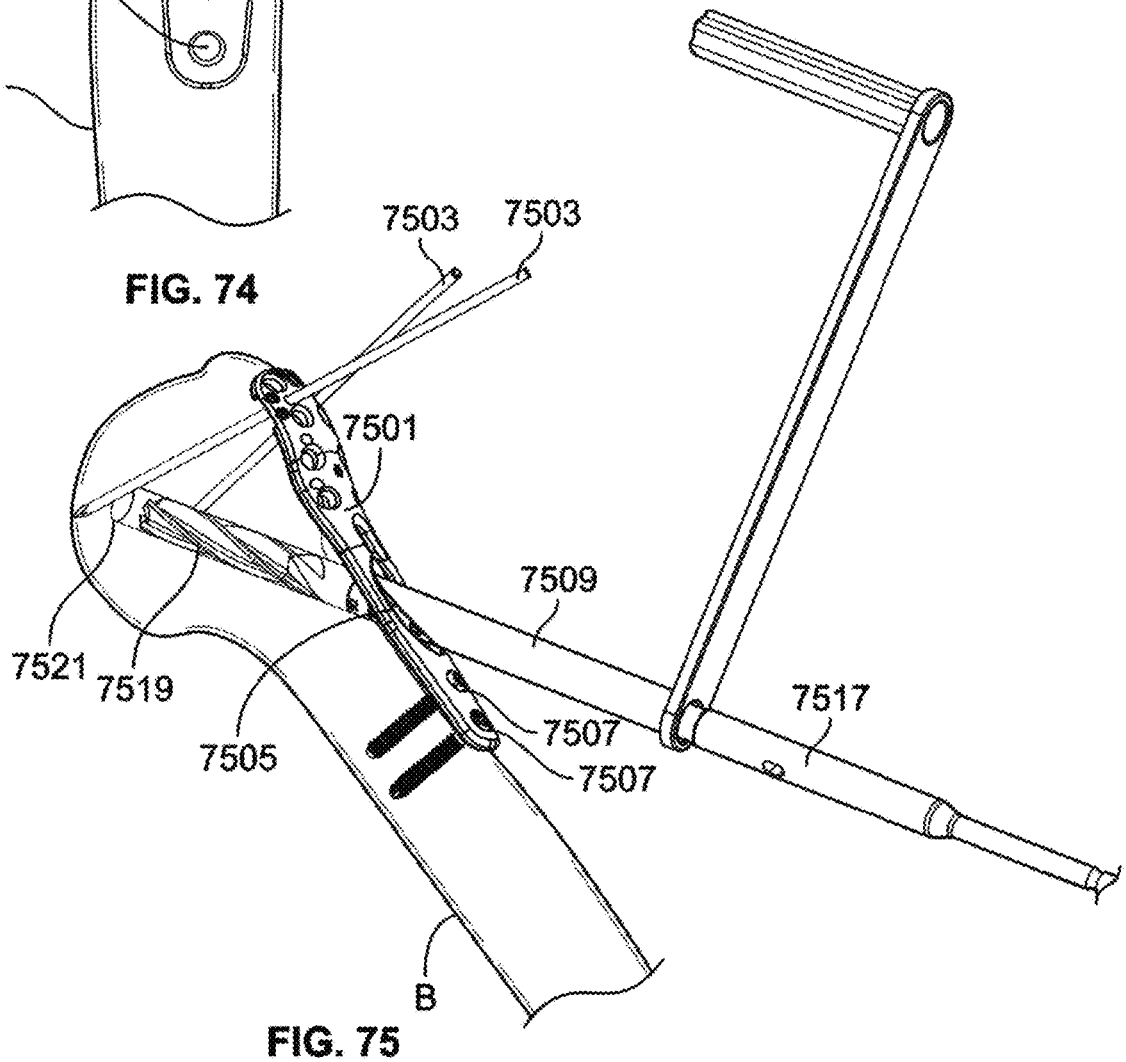
FIG. 75 shows illustrative apparatus and methods in accordance with principles of the invention.

FIG. 75 shows illustrative apparatus including plate 7501, drill 7517 and drill guide 7509.

Fixation elements 7503 may pass through plate 7501 and into an interior of bone B. Distal screws 7507 may releasably couple a portion of plate 7501 to bone B. Distal screws 7507 may have one or more features in common with distal screw 6507. Drill 7517 may pass through opening 7505 of plate 7501 and drill into bone B. In FIG. 75, tip 7519 of drill 7517 is shown advancing along trajectory 7521 in an interior of bone B.

Member 7509 may nest into plate 7501. Opening 7403 of plate 7501 may aide in guiding and stabilizing drill 7517 during penetration of the cortical wall. A skive angle on tube member 7509 may also help facilitate drilling in a desired direction.

FIG. 76 shows illustrative apparatus including plate 7601 anchored to implant 7600 and to bone B.

Screws 7615 may anchor plate 7601 to head 7617 of implant 7600. Screws 7615 may pass through screw holes defined by plate 7601 and into head 7617. Screw 7621 may anchor an end of plate 7601 to bone B. Screws 7613 and 7611 may anchor implant tail 7619 to bone B. Implant 7600 may be deployed in bone B so that implant tail 7619 is positioned in opening 7603 defined by plate 7601.

Plate 7601 may define suturing holes 7609 for suturing tissue to plate 7601.

FIG. 77 shows illustrative apparatus including first plate 7705, second plate 7707 and implant 7700.

In FIG. 77, screws 7711 may anchor implant head 7701 to first plate 7705. Second plate 7707 may be anchored to both first plate 7705 and implant tail 7721 by screw 7715. Screw 7715 is illustrated as passing through slot 7717 defined by second plate 7707. Second plate is anchored to first plate 7705 and bone B by screw 7719.

Second plate 7707 may define opening 7709. Tube 7703 may extend away from opening 7709. Tube 7703 may be coaxially mounted on tail 7721. Placing second plate 7707 on first plate 7705 may coaxially mount tube 7703 onto tail 7721.

Figure 78:
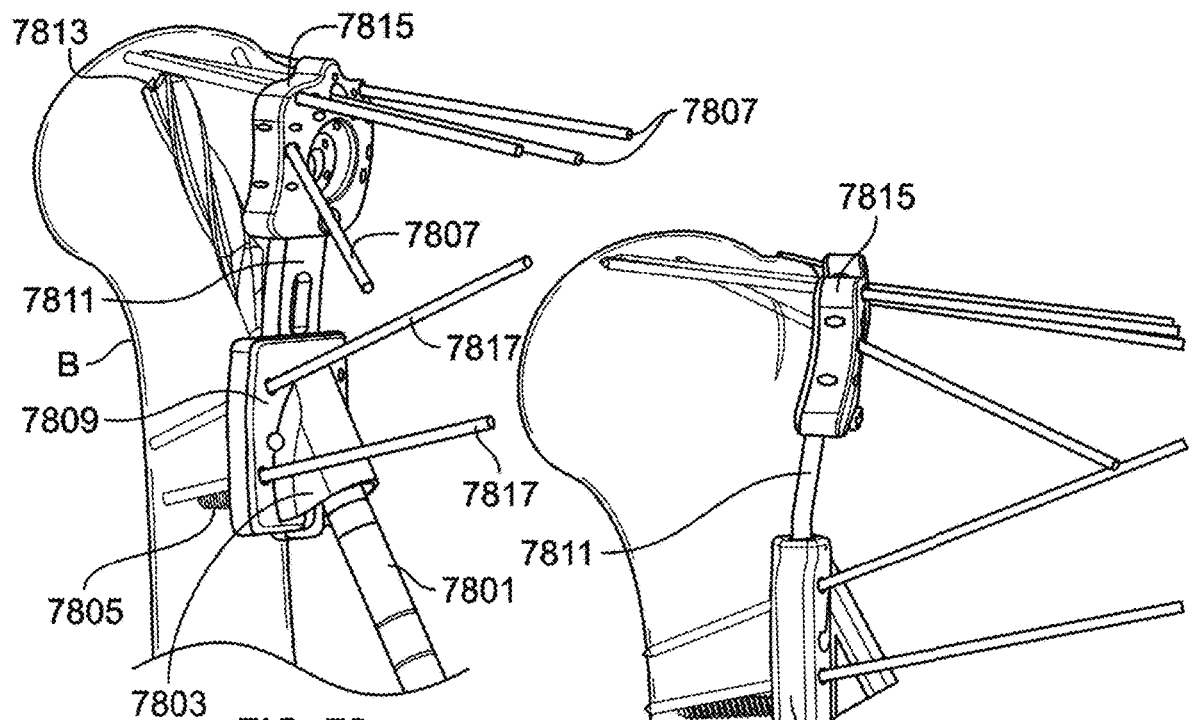
FIG. 78 shows illustrative apparatus and methods in accordance with principles of the invention.

FIG. 78 shows illustrative apparatus including plate 7811, first jig 7815 and second jig 7809. Plate 7811 may be releasably coupled to bone B by distal screw 7805. Distal screw 7805 may have one or more features in common with distal screw 6507. Fixation elements 7807 may pass through first jig 7815 and into bone B. Fixation elements 7817 may pass through second jig 7809 and into bone B.

In FIG. 78, illustrative drill 7801 is shown advanced through guide 7803 included in second jig 7809 and into bone B. Tip 7813 of drill 7801 is shown positioned at a target site for implanting an implant in bone B.

Figure 79:
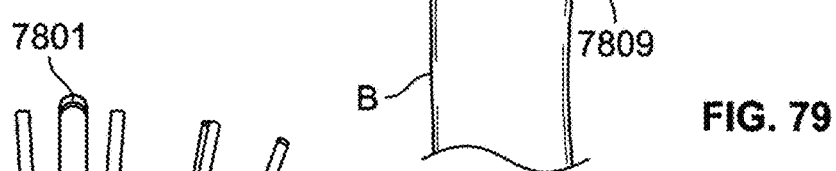
FIG. 79 shows illustrative apparatus and methods in accordance with principles of the invention.

FIG. 79 shows a side view of a portion of the apparatus illustrated in FIG. 78

Figure 80:
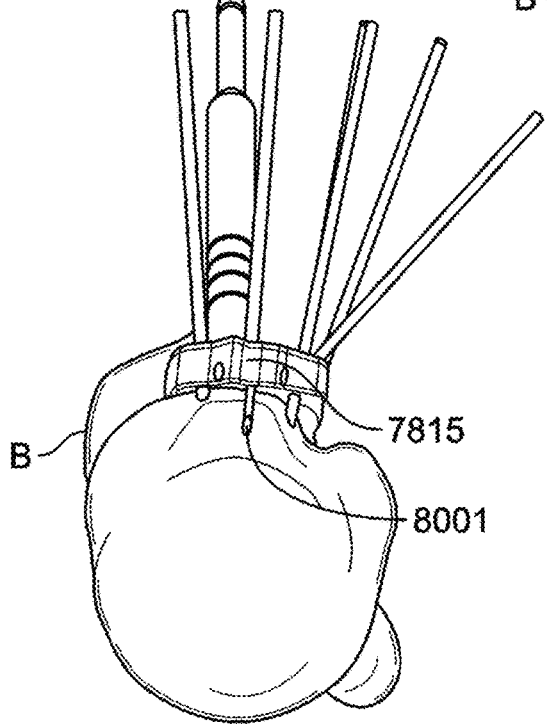
FIG. 80 shows illustrative apparatus and methods in accordance with principles of the invention.

FIG. 80 shows a top view of apparatus illustrated in FIG. 78. In FIG. 80, fixation element 8001 is shown passing through a positioning hole defined by first jig 7815. Fixation element 8001 passes over, and is seated on, a top of a greater tuberosity defined by bone B. In FIG. 80, plate 7811 and first jig 7815 are shown positioned on a lateral surface adjacent the bicipital groove.

FIG. 81 shows illustrative apparatus including plate 8101 and jig 8103. Plate may be releasably coupled to bone B by distal screw 8107. Distal screw 8107 may have one or more features in common with distal screw 6507. Jig 8103 and plate 8101 may be secured to bone B by fixation elements 8105 passing through jig 8103 and into bone B.

FIG. 82 shows illustrative apparatus including plate 8201 and jig 8215. Screw 8217 may releasably couple jig 8215 to plate 8201. Fixation elements 8219 may releasably couple jig 8215 to bone B. Jig 8215 may include positioning hole 8221. Jig 8215 may include target wire 8219 passing through a target hole defined by jig 8215.

Plate 8201 may be anchored to bone B by screw 8209. Distal crew 8209 may be seated in slot 8207. Distal screw 8209 may have one or more features in common with distal screw 6507. Plate 8201 may define slot 8213. A screw may be inserted through hole 8213 after an implant is implanted in bone B. Plate 8201 may define opening 8203. Opening 8203 may be used for one or more of preparation of an access hole, cavity preparation and implant deployment.

Figure 83:
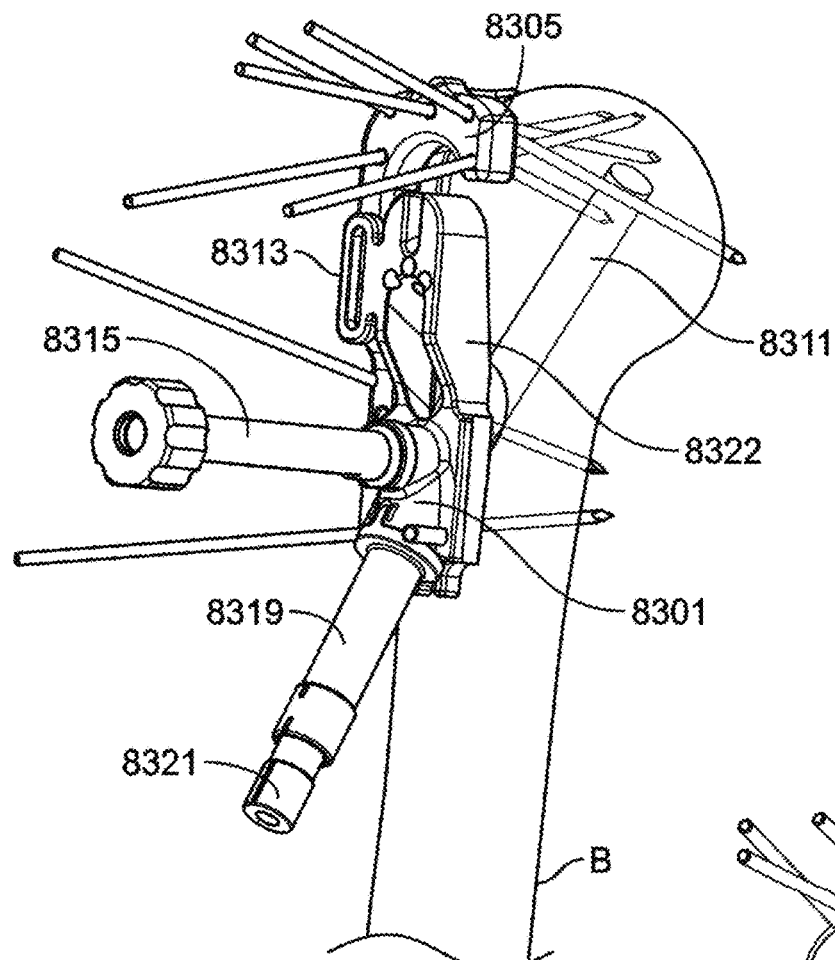
FIG. 83 shows illustrative apparatus and methods in accordance with principles of the invention.

FIG. 83 shows illustrative apparatus including illustrative first jig 8305 and illustrative second jig 8322. Coupling mechanism 8313 may releasably couple second jig 8322 to first jig 8305.

Second jig 8322 may include insert 8319. Insert 8319 may be inserted into guide 8301. First bushing 8321 may be placed in insert 8319. Path 8311 may illustrate an angle and a diameter defined by an inner surface of insert 8319 extending along an inner surface of bone B. Second bushing 8315 may be screwed into a screw hole defined by second jig 8322 (not shown).

Figure 84:
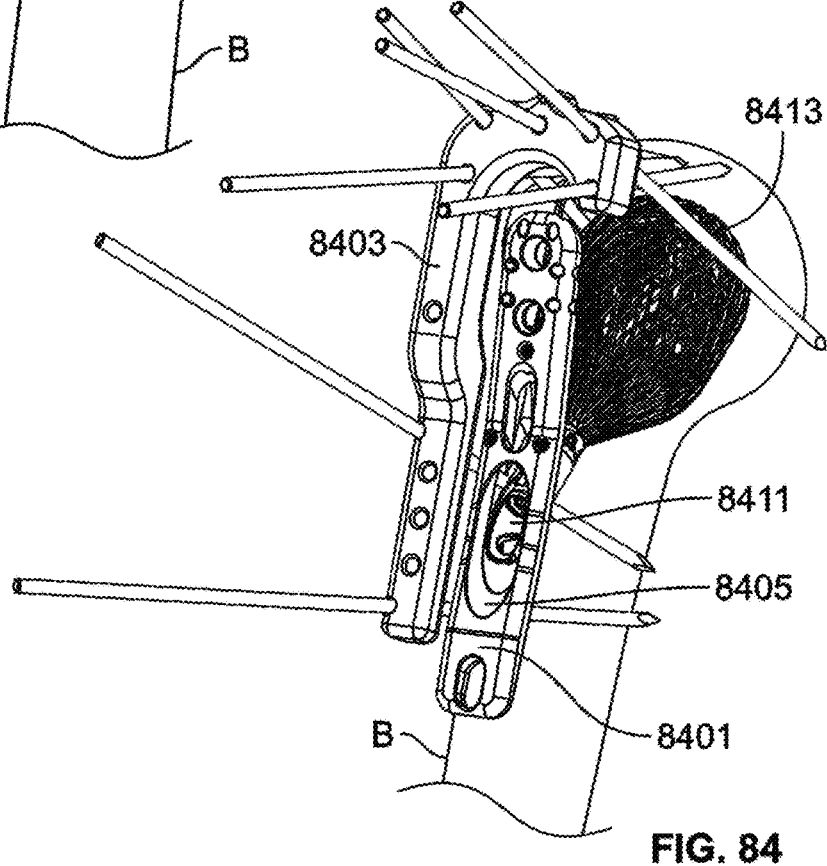
FIG. 84 shows illustrative apparatus and methods in accordance with principles of the invention.

FIG. 84 shows illustrative apparatus including illustrative plate 8401, illustrative jig 8403 and illustrative implant 8413. Implant 8413 may be positioned such that implant tail 8411 is positioned in opening 8405 defined by plate 8401.

Jig 8403 may include a transverse member and a longitudinal member. Plate 8401 may be positioned adjacent jig 8403. Plate 8401 may be positioned adjacent 8403. Plate 8401 may not physically contact jig 8403.

Jig 8403 may define a plurality of holes sized receiving fixation elements. Jig 8403 may define a targeting hole and/or a positioning hole. Plate 8401 may define holes sized for receiving fixation elements. Plate 8401 may define holes for receiving screws. Plate 8401 may be placed on the bone after jig 8403 is used to gain access to an interior of the bone. Plate 8401 may be placed on the bone prior to accessing an interior of the bone.

FIG. 85 shows illustrative apparatus 8500. Apparatus 8500 may be used for percutaneous delivery of an implant into bone 8515. Percutaneous delivery of an implant may utilize a relatively small incision compared to typical surgical techniques for fracture repair. For example, percutaneous delivery may allow for an incision that is smaller in size and less traumatic than a deltopectoral incision or a deltoid split incision.

Percutaneous implant delivery using apparatus 8500 includes apparatus such as implant delivery base 8501 and plate 8509. Implant delivery base 8501 and plate 8509 may be positioned underneath the skin (on the bone surface) during the implantation procedure. Percutaneous implant delivery may also utilize apparatus such as reduction device 8505. Reduction device 8505 may be moved along post 8503. Reduction device 8505 may be moved along post 8503 to be positioned on the skin during the implantation procedure. Reduction device 8515 may be releasably coupled to post 8503. Reduction device 8515 may be secured to post 8503 after implant delivery base 8501 is positioned on bone 8515.

Reduction device 8505 may direct one or more fixation elements 8510, from a location above the skin, to a desired location in an interior of bone 8515. Bone 8515 may be obscured by skin and soft tissue during the procedure. After placing implant delivery base 8501 on a bone, a practitioner may assess the placement. A practitioner may assess the placement by driving fixation elements 8510 into a bone and confirming the position of fixation elements 8510 in the interior. If fixation elements 8510 are placed in a desirable location, the practitioner may further reduce a bone fracture of bone 8515 and prepare to initiate an access hole in the bone through the channel. If fixation elements are not placed in a desirable location, the practitioner may remove fixation elements 8510 from the bone and reposition reduction device 8505 on the surface. When the bone is a proximal humerus, the desirable placement location in the bone may be a calcar region.

Reduction jig 8505 may define holes 8517. The holes may be sized to receive fixation elements. The holes may point into the interior of bone 8515 but not into an implantation region of an implant.

Plate 8509 may define a bottom surface. The bottom surface may conform to a contour of bone 8515. Implant delivery base 8501 may define a bottom surface. The bottom surface may conform to a contour of bone 8515.

Implant delivery base 8501 may include top surface 8521. Top surface 8521 may define two bores. Each bore may extend through an interior of implant delivery base 8501. Fixation elements 8510 are shown extending through the bores. Fixation elements 8510 may releasably couple apparatus 8500 to bone 8515.

Implant delivery base 8501 may define channel 8507. Channel 8507 may extend through implant delivery base

8501 at an angle oblique to an implant delivery base bottom surface. Channel 8507 may be configured to receive bushing 8513.

Implant delivery base 8501 may define a bottom surface (not shown). The bottom surface may conform to a surface contour of bone 8515. The bottom surface may conform to a portion of a top face of plate 8509. Implant delivery base 8501 may be coupled to plate 8509 by any suitable coupling mechanism, such as a screw mechanism, a snap fit mechanism, or any other coupling mechanism known to those skilled in the art.

When apparatus 8500 is seated complementarily on the surface contour, a central axis defined by channel 8507 may point to a target site. When the bottom surface is seated complementarily on the surface contour, a central axis defined by bushing 8515 may point to a target site. Implant delivery base 8501 may conform to a portion of a top surface of plate 8509. Implant delivery base 8501 may include a recess shaped to receive plate 8509.

Post 8503 may be fixedly attached to implant delivery base 8501. Post 8503 may be releasably coupled to implant delivery base 8501. Post 8503 may be secured to implant delivery base 8501 after implant delivery base 8501 is positioned on bone 8515.

Reduction jig 8505 may be slidably affixed to post 8503. In operation, a physician may position reduction device 8505 on the surface of the skin above bone 8515 after apparatus 8500 is seated complementarily on a surface contour of bone 8515. Reduction jig 8505 may be adjustable along post 8503. Reduction jig 8505 may slidable to account for differences in anatomy of patients. For example, different patients may have different thicknesses of soft tissue between a surface of bone 8515 and the patient's skin.

One or more of fixation elements 8510 may be driven through holes 8517 in reduction device 8505 to hold segments of a fracture together. Holes in reduction device 8505 may be perpendicular to a longitudinal axis of bone 8515. Holes that are perpendicular to a longitudinal axis of bone 8505 may allow reduction device 8505 to be moved along post 8503 in order to position reduction device 8505 on the skin of a patient. Holes in reduction device 8505 may transect reduction device 8505 at right angles. Holes that are transect reduction jig at right angles may allow reduction device 8505 to be moved along post 8503 in order to position reduction device 8505 on the skin of a patient.

Reduction jig 8505 may include groove 8520. Groove 8520 may be sized to provide clearance for an anchoring guide to guide a screw into the bone or into a plate positioned on the bone. Groove 8520 may be sized to provide clearance for driving a target wire into bone 8515. Groove 8520 may allow apparatus 8500 to be positioned relative to the target wire. Targeting apparatus (such as the targeting apparatus shown in FIG. 12 or the targeting apparatus shown in FIG. 11) may be used to position the target wire.

After making the incision, a physician may slip plate 8509 into the incision and position plate 8509 onto the surface of bone 8515. Implant delivery base 8501 may be coupled to the plate prior to the plate being positioned on the bone. Implant delivery base 8501 may be coupled to the plate after the plate is positioned on the bone. Fixation elements 8510 may be driven through implant delivery base 8501 to secure it to bone 8515. Fixation elements 8510 may be used to reduce a fracture of bone 8515 (not shown). Reduction device 8505 may be coupled to post 8505. Reduction device may be seated on skin extending around the incision. Fixation elements 8510 may be driven through reduction device 8505 to reduce the fracture of bone 8515. Fixation elements 8510 may target specific anatomical locations such as a calcar region of the humerus. One or more fixation elements may be driven through aperture 8519. A threaded K-wire with a nut may be driven through aperture 8519 and used to provide compressional force to the bone.

After stabilizing the fracture, bushing 8513 may be inserted into channel 8507. Any fixation elements positioned in aperture 8519 may be removed from the bone. Bushing 8513 may be fixedly attached to guide 8507. Bushing 8513 may be inserted into guide 8507.

A fixation element may be driven through a fixation element bushing (not shown) nested in bushing 8513. The fixation element may be used to determine if an access angle defined by bushing 8513 is desirable. The fixation element may be used to determine a longitudinal axis of an implantation region where an implant will reside inside bone 8515. The orientation of the fixation element and, specifically, the location of a tip of the fixation element in the interior of bone 8515 may be verified using fluoroscopy or other imaging techniques.

If the position of a tip of the fixation element inserted through guide 8513 is desirable, the fixation element bushing may be removed. The target wire may be replaced with a drill. The target wire may be over drilled with a cannulated drill. After drilling, a cavity inside bone 8509 may be prepared using a cavity preparation device. After preparing the cavity, an implant may be inserted through guide 8513 and advanced towards the target site. When the implant is positioned at the target site, an implant head of the implant may be expanded to form a mesh cage.

FIG. 86 shows illustrative apparatus 8600. Apparatus 8600 may be used for percutaneous delivery of an implant into a bone such as bone 8515 (shown in FIG. 85). Apparatus 8600 may include implant delivery base 8601. A bottom surface of implant delivery base 8601 may conform to a surface contour of a bone.

Apparatus 8600 may include post 8609. Post 8609 may extend away from top surface 8621 of implant delivery base 8601. Post 8609 may be releasably coupled to implant delivery base 8601. Post 8609 may be fixedly attached to implant delivery base 8601.

Apparatus 8600 may include reduction device 8611. Reduction device 8611 may be slidably coupled to post 8609. Reduction device 8611 may be removably coupled to post 8609. Reduction device 8611 may define a plurality of holes for driving fixation elements into a bone. Holes defined by reduction device 8611 may transect reduction device 8611 at a right angle.

Implant delivery base 8601 may include slot 8607. Slot 8607 may facilitate the coupling or insertion of a screw through slot 8607 and into an implant tail after the implant is implanted in an interior of the bone.

Percutaneous implant delivery may not utilize a plate such as plate 8509. After making the incision, a physician may slip implant delivery base 8601 into the incision and seat the bottom surface on the bone. Fixation elements may then be driven through bores 8603 and 8605 and into the bone, coupling implant delivery base 8601 to the bone. Fixation elements may be driven through reduction device 8611 and into the bone.

Bushing 8613 may be inserted into a channel defined by implant delivery base 8601. Bushing 8613 may be fixedly attached to implant delivery base 8601. When the bottom surface of the implant delivery base is seated complementarily on the surface contour, bushing 8613 may point towards a target site.

Reduction device 8611 may define aperture 8615. Fixation elements may be driven through aperture 8615 and into a bone. Screws may be driven through aperture 8615 and into a bone. Aperture 8615 may allow apparatus 8600 to be positioned over anchors or fixation elements previously inserted into holes in a plate such as plate 8509.

FIG. 87 shows illustrative apparatus 8700. Apparatus 8700 may include implant delivery base 8701. Implant delivery base 8701 may be used alone for percutaneous implant delivery. Implant delivery base 8701 may be used with plate 8725 for percutaneous delivery.

Implant delivery base 8701 may define channel 8705. Bushing 8707 may be removably coupled to channel 8705. Bushing 8707 may be fixedly coupled to channel 8705.

Implant delivery base 8701 may define bores 8709 and 8711. Bores 8709 and 8711 may extend through the implant delivery base at an angle oblique to a bottom surface of the implant delivery base. Bore 8709 may define a central axis. The central axis may pass through slot 8713 and into a bore defined by a bottom face of implant delivery base 8701. Bore 8711 may define a central axis. The central axis may pass through a slot (not shown) and into a bore defined by a bottom face of implant delivery base 8701.

Implant delivery base 8701 may include holes 8715. Holes 8715 may be used to couple implant delivery base 8701 to plate 8725. Driving a screw or fixation element through holes 8715 and into holes defined by plate 8725 and positioned under holes 8715 may releasably couple implant delivery base 8701 with plate 8725.

Apparatus 8700 may include post 8717 extending away from implant delivery base 8701. Post 8717 may extend away from top surface 8703 of implant delivery base 8701. Apparatus 8700 may include reduction device 8719. Reduction device 8719 may be slidably coupled to post 8717. Reduction device 8719 may define holes 8723. Holes 8723 may be sized for receiving fixation elements. Reduction device 8719 may define aperture 8721. Aperture 8721 may be sized for receiving fixation elements. Aperture 8721 may be sized for receiving screws. Reduction device 8719 may include groove 8720.

Groove 8720 may be sized to provide clearance for an anchoring guide to guide a screw into the bone or into a plate positioned on the bone. Groove 8720 may be sized to provide clearance for driving a target wire into a bone. Groove 8720 may allow apparatus to be positioned relative to the target wire. A targeting apparatus (such as the apparatus shown in FIG. 12 or the apparatus shown in FIG. 11) may be used to position the target wire.

Figure 88:
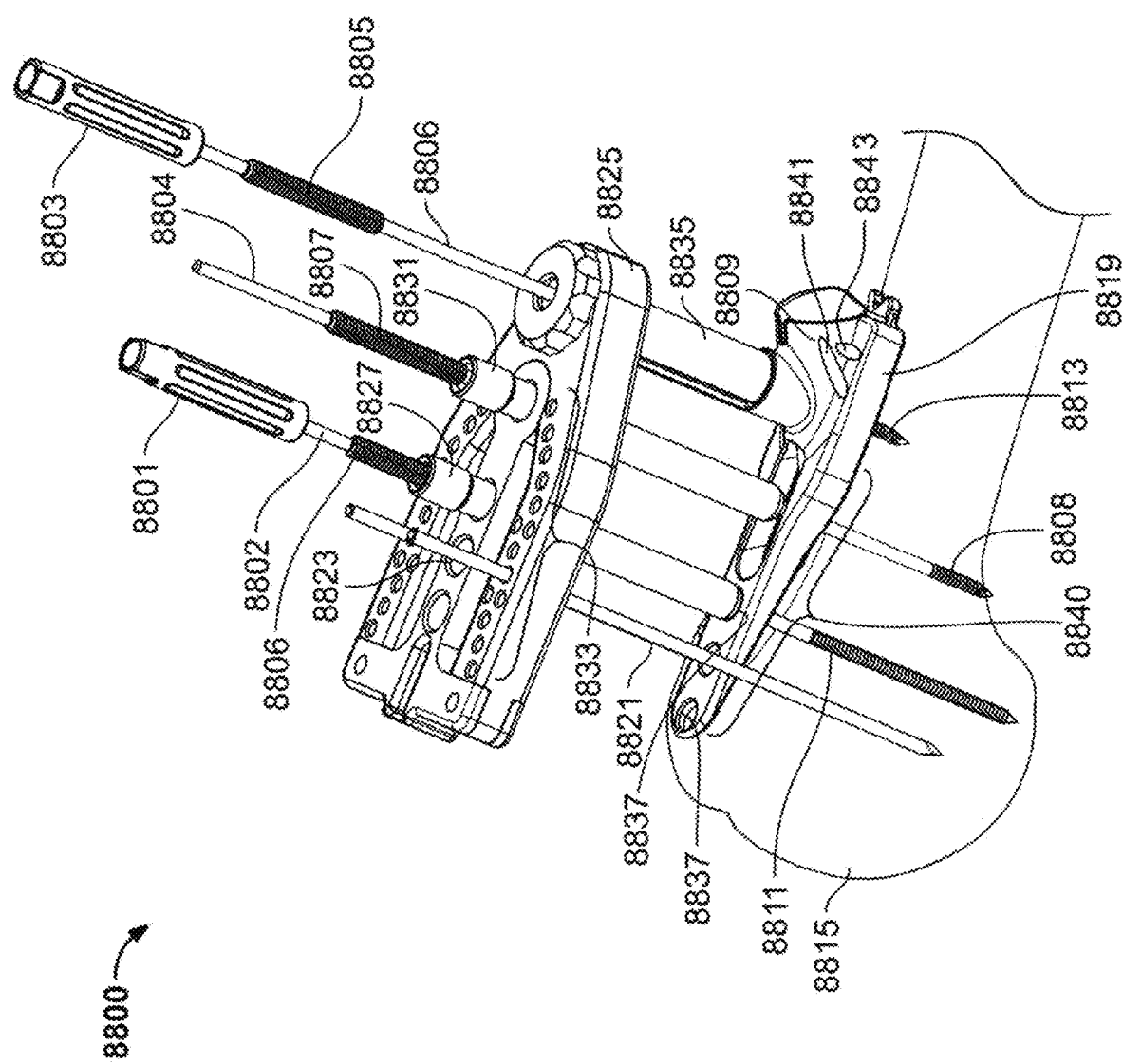
FIG. 88 shows illustrative apparatus and methods in accordance with principles of the invention.

FIG. 88 shows illustrative therapeutic scenario 8800. Apparatus shown in therapeutic scenario 8800 may be used for percutaneous delivery of an implant (not shown) into bone 8515. Implant delivery base 8819 may be slipped onto a surface of bone 8815 through a relatively small incision. Reduction device 8825 may be slidably engaged with post 8835.

Reduction device may define screw holes 8823. Screw holes 8823 may correspond to screw holes 8837 defined by implant delivery base 8819. A central axis one of screw holes 8823 may be coaxial with a central axis of a screw hole defined by implant delivery base 8819. One or more of screw holes 8823 may be threaded. One or more of screw holes 8823 may not be threaded. Screw holes 8823 may be positioned above screw holes defined by a plate coupled to a bottom surface of implant delivery base 8819 (not shown).

Screw holes 8823 may receive a fixation element. Screw holes 8823 may receive a screw. Screw holes 8823 may be receive a bushing sized for receive a fixation element. Screw holes 8823 may receive a bushing sized for receiving a screw. In FIG. 88, bushing 8827 and bushing 8831 are positioned in two of screw holes 8823.

In FIG. 88, fixation element 8802 is advanced through bushing 8827 and into the interior of bone 8815. Fixation element 8802 may be a threaded K-wire. Fixation element 8802 may include threaded portion 8806 and threaded tip 8811. Nut 8801 is positioned on fixation element 8802. Nut 8801 may be internally threaded. A practitioner may screw nut 8801 onto threaded portion 8802 of fixation element 8802. Nut 8801, when screwed onto fixation element 8802, may provide compressional force to bone 8815. Nut 8801 may be used to draw a fragment of bone 8815 towards implant delivery base 8819.

Fixation element 8804 may be a threaded K-wire. Fixation element 8804 may include threaded portion 8807 and threaded tip 8808. A nut screwed onto fixation element 8804 may provide compressional force to bone 8815.

Post 8835 may be cannulated. A fixation element such as fixation element 8806 may be driven through post 8835 and into bone 8815 to obtain provisional reduction of a fracture of a bone. Fixation element 8806 may include threaded portion 8805 and threaded tip 8813. Fixation element 8806 may remain in post 8835 until the bone is stabilized. Fixation element 8806 may be removed from post 8835 before a bushing is inserted through a channel defined by implant delivery base 8819. Shoulder 8809 may define an outer surface of the channel.

In operation, a practitioner may use one, two, three or more fixation elements such as fixation element 8802, fixation element 8804 and fixation element 8806 to reduce a fractured bone. Fixation elements received by screw holes 8806 may remain in a bone while a bone fracture of bone 8815 (now shown) is being reduced. Once reduction is obtained, additional fixation elements such as fixation elements 8823 may be driven through holes 8833 defined by reduction device and into bone 8815. When the bone is stabilized, fixation elements disposed through screw holes 8806 may be removed from the bone.

Implant delivery base 8819 may include a channel extending through an interior of implant delivery base 8819. The channel may support a bushing (not shown).

Implant delivery base 8819 may include first bore 8841. First bore 8841 may be positioned on shoulder 8809. First bore 8841 may extend through the implant delivery base at an angle oblique to an implant delivery base longitudinal axis. First bore 8841 may form a notch on shoulder 8809. Implant delivery base 8819 may include a second bore having the same geometrical properties as the first 8841 bore disposed on an opposite side of shoulder 8809. When fixation elements are advanced through both first bore 8841 and the second bore, and into the bone, implant delivery base 8819 may be releasably coupled to bone 8815. A practitioner may confirm the placement of the fixation elements. Proper placement of the fixation elements within a bone may indicate proper placement of implant delivery base 8819 on the bone. When the bone is a proximal humerus, proper placement may be a location in a calcar region of the bone.

Implant delivery base 8819 may define third bore 8843. Third bore may be disposed on shoulder 8809. Third bore 8843 may extend through the implant delivery base at an angle perpendicular to a longitudinal axis of implant delivery base 8819. The implant delivery base may define a fourth bore having the same geometrical properties as third bore 8843 and disposed on an opposite side of shoulder 8809. Advancing fixation elements through both third bore 8843 and the fourth bore and into the bone may enhance the coupling of implant delivery base 8819 to bone 8815.

Implant delivery base 8819 may include longitudinal member 8840. Longitudinal member 8840 may not include shoulder 8809. Longitudinal member 8840 may define screw holes 8837. Screw holes 8837 may be positioned above screw holes defined by a plate coupled to a bottom of implant delivery base 8819 (not shown). When implant delivery base 8819 is positioned on a bone, screw holes 8837 may point to an implantation region occupied by an implant (not shown).

Reduction device 8825 may be positioned at any suitable position along post 8835. Reduction device 8825 may be slidably coupled to post 8835. For example, in operation, reduction device 8825 may be positioned abutting the skin of a patient. Positioning (and re-positioning) reduction device 8835 may enable a physician to achieve a satisfactory reduction of a fracture.

Reduction device 8825 may include hole sets 8833. Each of hole sets 8883 may correspond to a different size implant. Holes spaced a first distance away from a central axis of reduction device 8825 may form a first hole set. Holes spaced a second distance away from the central axis of reduction device 8825 may form a second hole set. The first hole set may correspond to a first implant defining a first volume, when expanded. The second hole set may correspond to a second implant defining a second volume, when expanded. Implant size may be determined based on a length of an implant. Implant size may be determined based on a volume of an implant, when expanded. Hole sets 8833 may be used to position fixation element 8821 such that fixation element 8821 provides clearance for an implant and does not engage the implant.

After positioning fixation elements through one or more of hole sets 8833 and after implantation of the implant in bone 8815, a portion of reduction device 8825 may be removed. The portion of the reduction device that may be removed is shown in FIG. 88A at step 8814B. Targeting apparatus (such as apparatus 3000, shown in FIG. 30) may then be positioned on an implant shaft of the implant.

A releasable key of the targeting apparatus may engage keyseat 8803. A static key of the targeting apparatus may engage slot 8805. When positioned on implant shaft 8801, the targeting apparatus may be used to drive an anchor into clearance hole 8813 in tail 8811. Cannulated anchors may be driven over fixation element 8821 and into a head of implant 8817.

FIG. 88A shows an illustrative method for inserting an implant in a bone using a percutaneous approach. The illustrative method may include one or more of the steps shown in FIG. 88A. The steps shown in FIG. 88A may be performed in an order different from the order shown in FIG. 88A. The steps may be performed using apparatus and methods disclosed in herein, such as apparatus and methods illustrated in FIGS. 85-88.

Step 8802 and step 8802A may include reducing a bone. The reduction may include guiding a fixation element through the cannulated post and guiding a fixation element through a screw hole defined by the reduction device. The fixation elements may be guided into the bone using a bushing coupled to the cannulated post and through a bushing coupled to the reduction device.

The reduction may include driving a first fixation element through first bore 8841 and into the bone at an angle that is oblique to a longitudinal axis of the bone. The reduction may include driving a second fixation element through a second bore and into the bone at an angle that is oblique to the longitudinal axis of the bone. The second bore may be disposed on an opposite side of a shoulder relative to first bore 8841. The shoulder may be defined by an outer surface of a channel. The channel may extend through an interior of the implant delivery base.

The reduction may include driving a third fixation element through third bore 8843 and into the bone at an angle that is perpendicular to the longitudinal axis of the bone. The reduction may include driving a fourth fixation element into a fourth bore and into the bone in a direction perpendicular to the longitudinal axis of the bone. The fourth bore may be disposed on an opposite side of the shoulder relative to third bore 8843

Step 8804 and step 8804A may include stabilizing the bone. Stabilizing the bone may include driving fixation elements through bores defined by a top surface of the implant delivery base. Fixation elements driven through the bores may transect the bone at an angle oblique to a bone longitudinal axis. After the bone is stabilized, step 8804 may include removing the fixation element positioned in the cannulated post.

The stabilizing may include driving a first fixation element through first bore 8841 and into the bone in a direction oblique to the longitudinal axis of the bone. The stabilizing may include driving a second fixation element through a second bore and into the bone in direction oblique to the longitudinal axis of the bone. The second bore may be disposed on an opposite side of the shoulder relative to first bore 8841.

The stabilizing may include driving a third fixation element through third bore 8843 and into the bone in a direction perpendicular to the longitudinal axis of the bone. The stabilizing may include driving a fourth fixation element into a fourth bore and into the bone in a direction perpendicular to a longitudinal axis of the bone. The fourth bore may be disposed on an opposite side of the shoulder relative to third bore 8843.

Step 8806 may include driving a fixation element through a fixation element bushing nested inside a drill bushing. The fixation element bushing may be nested in a drill bushing. The fixation element bushing may be seated in a channel defined by the implant reduction base. A tip of the fixation element may be advanced through the fixation element bushing and towards a target site. Step 8806 may include removing the fixation element positioned in a screw hole defined by the reduction device.

Step 8808 may include removing the fixation element bushing from the drill bushing and advancing a drill through the drill bushing and into the bone interior.

Step 8810 may include preparing an interior of the bone for implantation of an implant. The preparing may include inserting a cavity preparing device through the drill bushing and into the bone interior. Step 8812 may include deploying an implant in the prepared cavity, rotating the implant in the prepared cavity and locking the implant head in the expanded shape. Step 8814 may include securing the implant to the bone. A device for driving screws into a tail of the implant may be coupled to an implant shaft. The device may be used to drive screws into an implant tail. Step 8816 and 8816A may include fragment fixation. Fragment fixation may include fixing fragments of the bone to the implant head using screws. The screws may be cannulated.

FIG. 89 shows illustrative jig 8901. Jig 8901 may include bushing 8903 for pin 8911. Jig 8901 may include bushing 8905 for pin 8913. Jig 8901 may include bushing 8907 for pin 8915. Jig 8901 may include bushing 8909 for pin 8917.

FIG. 90 shows an illustrative operational view of jig 8901 and implant 9000. In FIG. 990, each of pins 8911, 8913, 8915 and 8917 are shown engaged with implant 9000. Pins 8911 and 8913 are engaged with head 9001 of implant 9000. Pin 8915 is engaged with hole 9035 in tail 9003 of implant 9000. Pin 8917 is engaged with hole 9007 in tail 9003 of implant 9000.

FIG. 91 shows an illustrative operational view of implant 9000. In FIG. 91, pins 8917 and 8915 have been removed from tail 9003 of implant 9000. Pins 8911 and 8913 are engaged with head 9001 of implant 9000. In FIG. 91, implant 9000 is positioned in an inner cavity of bone B.

FIG. 92 shows an illustrative operational view of jig 8901 registered to implant 9000. In FIG. 92, jig 8901 is registered to implant 9000 by engagement of pins 8911 and 8913 with jig 8901. Engaging pins 8911 and 8913 with jig 8901 may align jig 8901 with implant 9000. Aligning jig 8901 with implant 9000 may ensure that a member drilled through bushing 8907 or bushing 8909 passes into a hole defined by tail 9003 of implant 9000. In FIG. 92, screw 9201 is shown anchoring implant 9000 to bone B. Drill 9203 is shown passing through bushing 8909 and through a hole defined by tail 9003 of implant 9000. The hole defined by tail 9003 may be hole 9007 (shown above in FIG. 90).

Figure 92A:
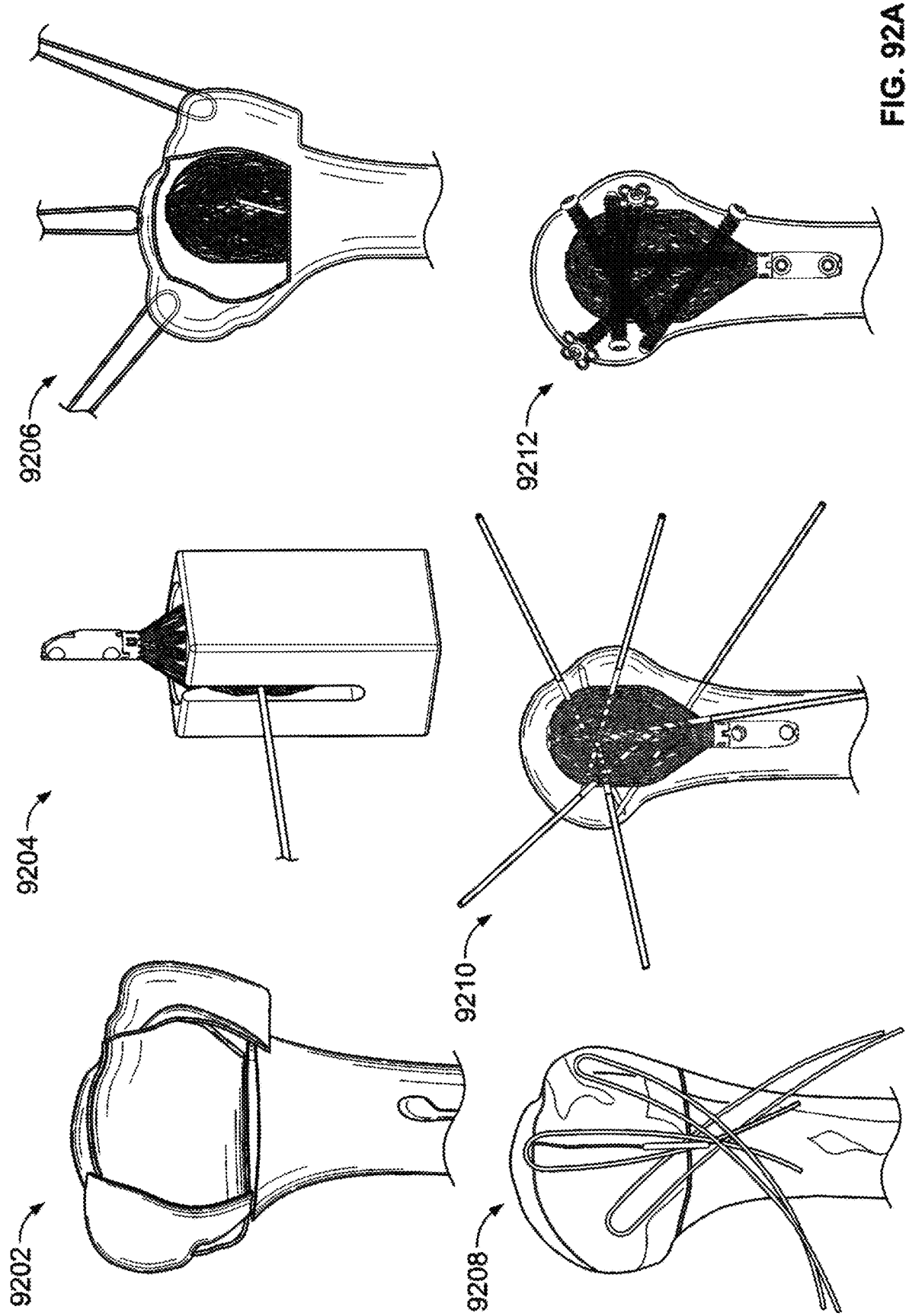
FIG. 92A shows illustrative apparatus and methods in accordance with principles of the invention.

FIG. 92A shows an illustrative antegrade procedure for implanting an implant in a bone. The bone may be proximal humerus bone or any suitable bone shown above in FIG. 3. An antegrade procedure may be a therapeutic procedure performed in a direction normal to a path of blood circulation. The illustrative procedure shown in FIG. 92A may be performed in any other suitable bone in the human body.

The illustrative procedure may include one of more of the steps shown in FIG. 92A. The procedure may include step 9202 for accessing and preparing the bone for implantation of the implant.

The procedure may include step 9204 for deploying and locking the implant. Step 9204 may include deploying the implant outside of a bone in free space. Step 9204 may include locking the implant to a desired expansion diameter. Locking the implant may include constraining a diameter of a head of the implant to a desired diameter. Locking the implant may include constraining a head of the implant to a desired contour. Locking the implant may include engaging a locking screw with a locking mechanism of the implant to limit expansion/collapsing of the implant head. Step 9204 may include inserting pins into the implant. The pins may be inserted into the implant using a jig such as jig 8901.

The procedure may include step 9206 which represents inserting the implant into a fractured bone. The implant may be inserted into the bone with or without a jig such as jig 8901. In embodiments where the implant is inserted into a humerus with a fixation element, such as a pin, pre-positioned in the implant head, step 9206 may include positioning one or more of the pins to protrude from a fracture in the humerus between the greater and lesser tuberosity of the humerus. The procedure may include step 9208 which represents stabilizing the bone and reducing the fractured bone as appropriate.

The procedure may include step 9210 for securing the implant to the bone. Step 9210 may include driving one or more fixation elements through the bone and into the implant. The procedure may include step 9212 for securing the implant to the bone by driving one or more screws through the bone and into the implant head. Step 9212 may also include driving one or more screws through the bone and into the implant tail. The screws may be cannulated and may be driven into an implant component by driving the screw over a previously positioned fixation element. An implant component may include a head, tail, hub, base, locking mechanism or any other suitable implant component.

When the implant is positioned in the bone with one or more pins protruding from the implant, step 9210 may include reapplying the jig to the protruding pins. Embodiments may include removing the pins and driving fixation elements through the screw holes defined by the jig. Step 9212 may include driving cannulated screws over the fixation elements and into the implant. Driving screws through screw holes defined by the jig, may be used to anchor the implant to the bone.

Figure 93:
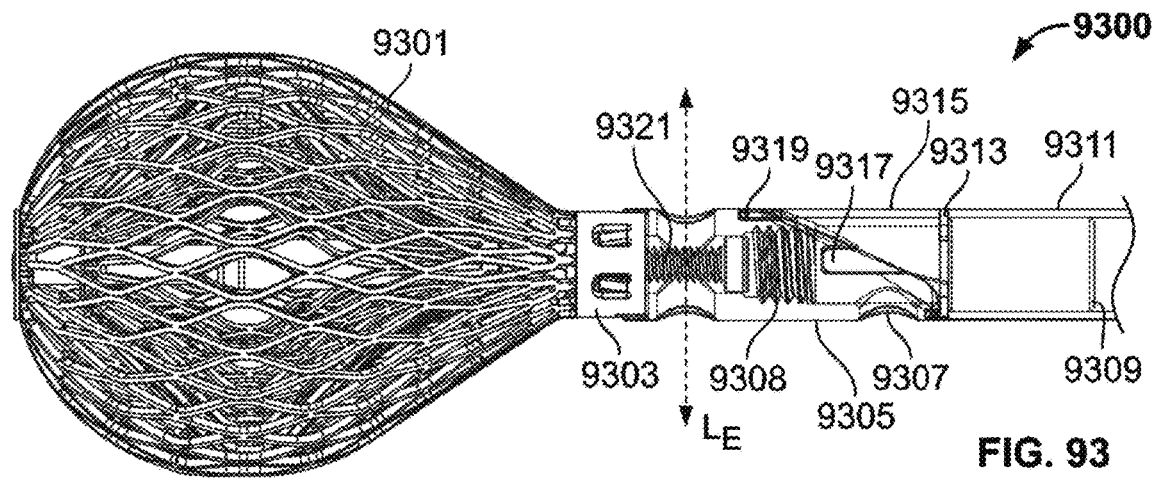
FIG. 93 shows illustrative apparatus in accordance with principles of the invention.

FIG. 93 shows illustrative apparatus 9300. Apparatus 9300 includes implant head 9301. Implant base 9303 may couple head 9301 to tail 9305. Tail 9305 may be snap-fit into Implant base 9303. Locking screw 9321 may be used to lock expansion of head 9301. Locking screw 9321 may lock an expansion of head 9301 by threadedly engaging one or more components (not shown) of an implant.

Tail 9305 includes internal threads 9308. Locking screw 9309 may threadedly engage internal threads 9308. Tail 9305 defines emplacement axis LE. Axis LE may be defined by a pair of opposing clearance holes in tail 9305.

A beveled end of tail 9305 may mate with a beveled end 9315 of implant shaft 9311. Beveled end of tail 9305 may allow tail 9305 to be positioned at or below an outer surface of a bone when head 9301 is positioned inside the bone. Beveled end 9315 of implant shaft 9311 includes fingers 9317 and 9319. Fingers 9317 and 9319 may fit into indentations (not shown) in tail 9305. Fitting fingers 9317 and 9319 into the indentation in tail 9305 may rotational lock tail 9305 with respect to implant shaft 9311.

Implant shaft 9311 may be axially locked with respect to tail 9305 by locking screw 9309. Locking screw 9309 may be inserted into implant shaft 9311 until a head of locking screw 9309 abuts flange 9313. Flange 9313 may reduce an inner diameter of implant shaft 9311. A threaded segment of locking screw 9309 may be sized to pass through flange 9313. For example, major diameter of locking screw 9309 may be less than the diameter of implant shaft 9311 reduced by flange 9313. A threaded segment of locking screw 9309 may threadedly engage internal threads 9308 in tail 9305.

When locking screw 9309 is positioned within implant shaft 9311, threaded engagement locking screw 9309 and internal threads 9308 may position beveled end 9315 of implant shaft 9311 against a beveled end of tail 9305. Threaded engagement of locking screw 9309 and internal threads 9308 may position fingers 9319 and 9317 in indentations on tail 9305.

Tail 9305 includes clearance hole 9307. After positioning head 9301 inside a bone, locking screw 9309 and implant shaft 9311 may be removed from tail 9305. Removing locking screw 9309 and implant shaft 9311 from tail 9305 may expose clearance hole 9307. An anchor may be driven through clearance hole 9307 and into the bone to stabilize a position of head 9301.

Figure 94:
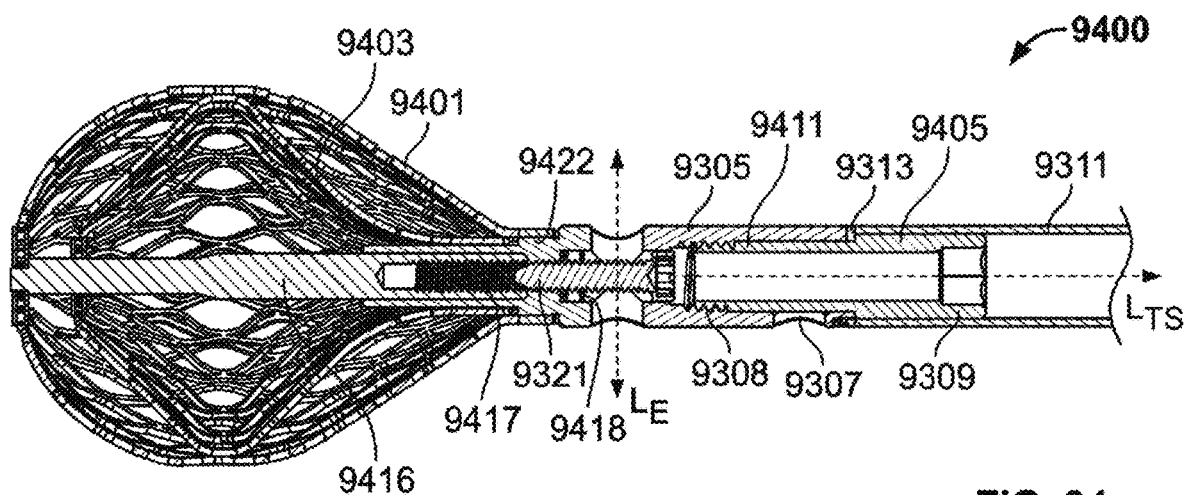
FIG. 94 shows illustrative apparatus in accordance with principles of the invention.

FIG. 94 shows illustrative apparatus 9400. Apparatus 9400 shows that a head of an implant (such as head 9301 shown in FIG. 93) may include outer mesh 9401 and inner mesh 9403. Outer mesh 9401 may be self-expanding. Inner mesh 9403 may be self-expanding. A head of an implant may include one, three or more mesh layers. Locking screw 9321 may be utilized to lock outer mesh 9401 and/or inner mesh 9403 in an expanded state. Inner mesh 9403 may be "free floating" and expand up to a maximum limit allowed by a diameter of outer mesh 9401. In such embodiments, inner mesh 9403 may not be locked. When outer mesh 9401 and/or inner mesh 9403 are locked, locking screw 9321 may not obstruct emplacement axis LE.

Locking screw 9321 may threadedly engage threads 9417 in illustrative implant component 9416. When outer mesh 9401 and/or inner mesh 9403 are locked by locking screw 9321, head 9420 of locking screw 9321 may be seated in recess 9418 of implant component 9422. Tail 9305 may include implant component 9422. Tail 9305 may not include implant component 9422. In such embodiments, implant component 9422 may be separable from tail 9305.

Locking screw 9309 includes threaded end 9411. Locking screw 9309 includes unthreaded end 9405. Threaded end 9411 may have diameter that is less than a diameter of unthreaded end 9405. Threaded end 9411 may slide past flange 9313 and engage internal threads 9308 of tail 9305.

Unthreaded end 9405 may include a first segment having a first diameter. Unthreaded end 9405 may include a second segment having a second diameter. The first diameter may be less than the second diameter. For example, the first segment may slide past flange 9313. The second segment may not slide past flange 9313.

Apparatus 9400 shows tail 9305 locked to implant shaft 9311 by locking screw 9309. When tail 9305 is locked to implant shaft 9311, movement of implant shaft 9311 may adjust a position of implant head 9301 (shown in FIG. 93) inside a bone. When tail 9305 is locked to implant shaft 9311, implant shaft 9311 may be used as a point of reference for inserting fixation elements into an implant component such as implant head 9301 or tail 9305.

Figure 95:
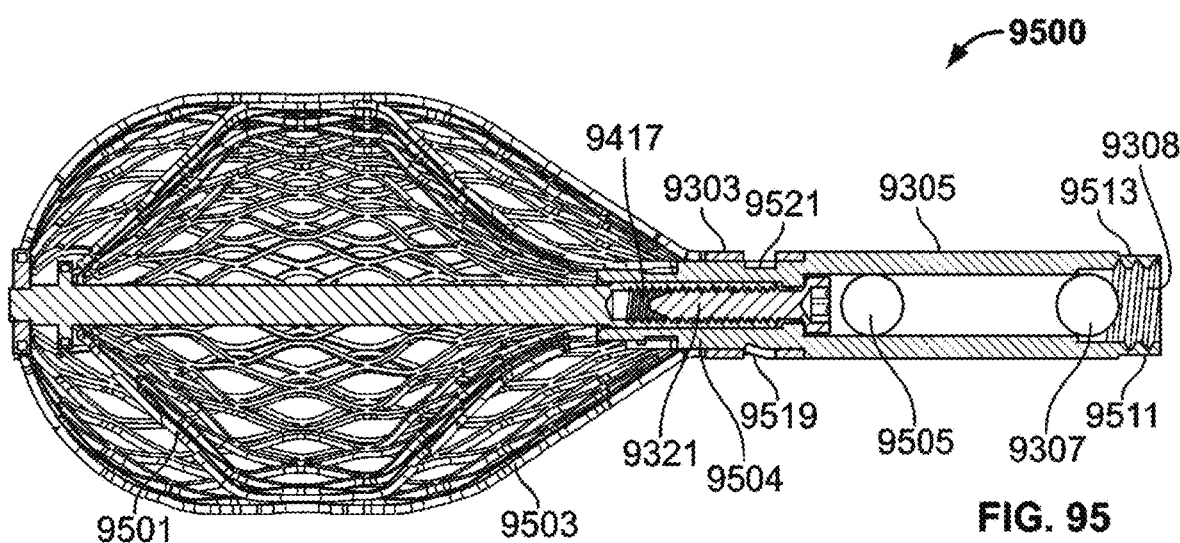
FIG. 95 shows illustrative apparatus in accordance with principles of the invention.

FIG. 95 shows illustrative apparatus 9500. Apparatus 9500 includes outer mesh 9503 and inner mesh 9501. FIG. 95 shows that outer and inner meshes may be constructed to provide different expansion shapes and therapeutic properties (compare to inner and outer meshes shown in FIG. 94).

Apparatus 9500 shows locking screw 9321 engaged with internal threads 9417 in a locked configuration. When locking screw 9321 is in a locked configuration, clearance hole 9505 is not obstructed by locking screw 9321. Clearance hole 9505 may be one of a pair of clearance holes that define an emplacement axis (such as axis LE shown in FIG. 93). Clearance hole 9505 and an associated emplacement axis may be positioned such that they are not obstructed even when locking screw 9321 is in an unlocked position (e.g., not threadedly engaged with threads 9417).

Implant component 9504 (which may be an extension of tail 9305) may fit into implant base 9303. Implant component 9504 may be snap-fit into implant base 9303. For example, detent 9519 of implant base 9303 may be biased to engage an indentation, such as indentation 9521 in implant component 9504. Tail 9305 also includes indentations 9513 and 9511. Indentations 9513 and 9511 may mate with a finger protruding from an implant shaft. For example, indentation 9317 may mate with finger 9317 (shown in FIG. 93).

Figure 96:
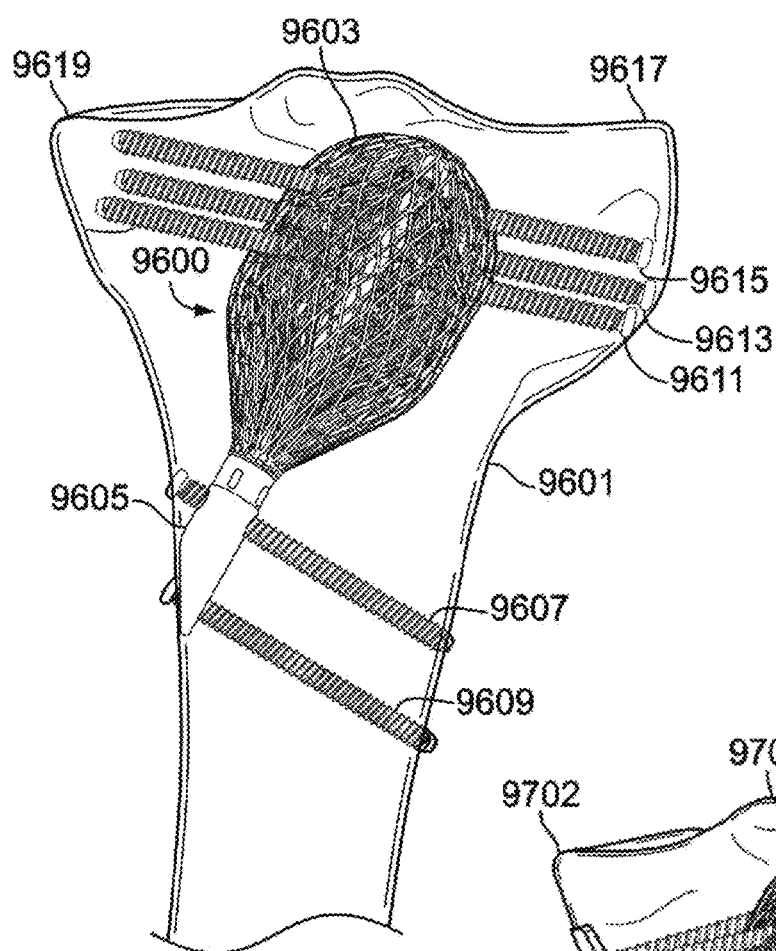
FIG. 96 shows illustrative apparatus and methods in accordance with principles of the invention.

FIG. 96 shows illustrative implant 9600 inside bone 9601. Bone 9601 may be a tibia. Bone 9601 may include medial condyle 9619 and lateral condyle 9617.

Implant 9600 may be implanted in an interior of a proximal portion of the tibia ("proximal tibia"). In FIG. 96, screw 9615, screw 9613 and screw 9611 are shown anchoring implant head 9603 to bone 9601. Screw 9615, screw 9613 and screw 9611 pass through head 9603 of implant 9600 cage and extend underneath medial condyle 9619 of bone 9601.

Screw 9607 and screw 9609 are shown anchoring implant tail 9605 to bone 9601 in a diaphyseal region of bone 9601. Screws 9607 and 9609 are shown passing through a metaphasis region of bone 9601.

Implant 9600 may be advanced into bone 9601 through an access hole prepared at an access site. The access site may be an access site prepared at an anterior side of bone 9601. In other embodiments, an implant may be advanced into a proximal tibia from a medial side of the proximal tibia. An implant may be advanced into a proximal tibia from either a medial side of the proximal tibia or the lateral side of the proximal tibia.

FIG. 96 shows implant 9600 positioned centrally within an interior of bone 9601. However, in other embodiments, an implant may be positioned laterally or medially within an interior of a bone. For example, an implant may be positioned laterally within a head of a proximal tibia to support a fractured lateral condyle. An implant may be positioned medially within a head of a proximal tibia to support a fractured medial condyle.

Figure 97:
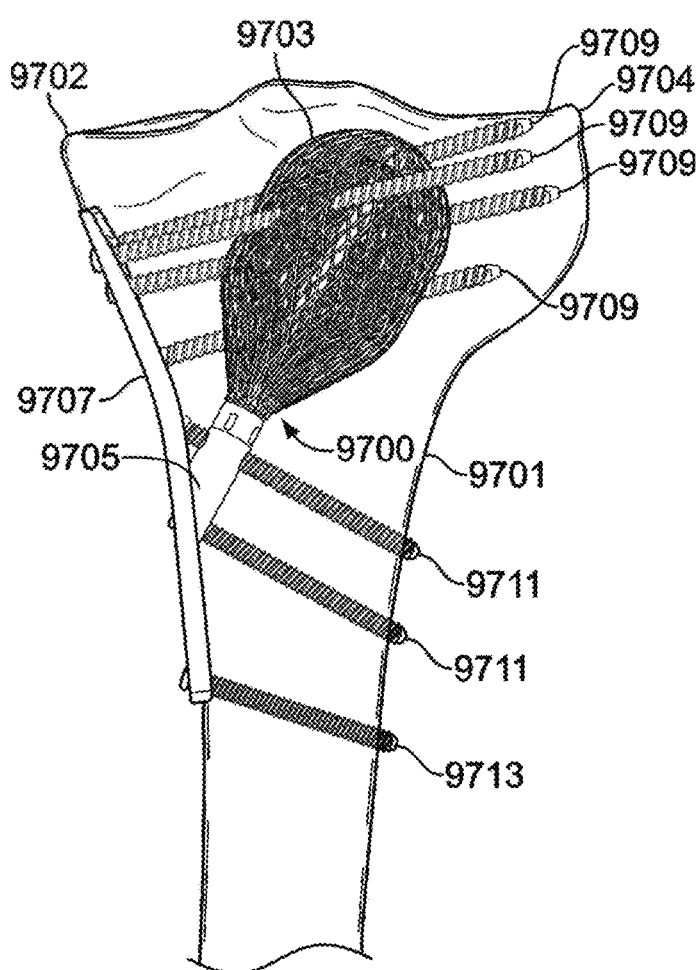
FIG. 97 shows illustrative apparatus and methods in accordance with principles of the invention.

FIG. 97 shows illustrative implant 9700 positioned inside bone 9701. Bone 9701 may be a tibia. Bone 9701 may include medial condyle 9702 and lateral condyle 9704.

Implant 9700 may be implanted in an interior of a proximal portion of the tibia ("proximal tibia"). Implant 9700 may be anchored to bone 9701 and plate 9707.

In FIG. 97, screws 9709 are shown anchoring implant head 9703 to bone 9601 and to plate 9707. Screws 9709 may be inserted medially, pass through the plate and extend underneath lateral condyle 9704.

Screws 9711 may anchor implant tail 9705 bone 9601 in a diaphyseal region of bone 9601. Screws 9711 may anchor implant tail 9705 to plate 9707. Screws 9711 may pass through plate 9707 in a metaphasis region of bone 9701.

Implant 9700 may be advanced into bone 9701 through an access hole prepared at an access site. The access site may be an access site prepared at an anterior side of bone 9701. In other embodiments, an implant may be advanced into a proximal tibia from a medial side of the proximal tibia. An implant may be advanced into a proximal tibia from either a medial side of the proximal tibia or the lateral side of the proximal tibia.

FIG. 97 illustrates implant 9700 positioned centrally within an interior of bone 9701. An implant may be positioned laterally or medially within an interior of the proximal tibia. An implant may be positioned laterally, with respect to a longitudinal axis of bone, within a head of a proximal tibia to support a fractured lateral condyle. An implant may be positioned medially, with respect to a longitudinal axis of bone, within a head of a proximal tibia to support a fractured medial condyle.

Figure 97A:
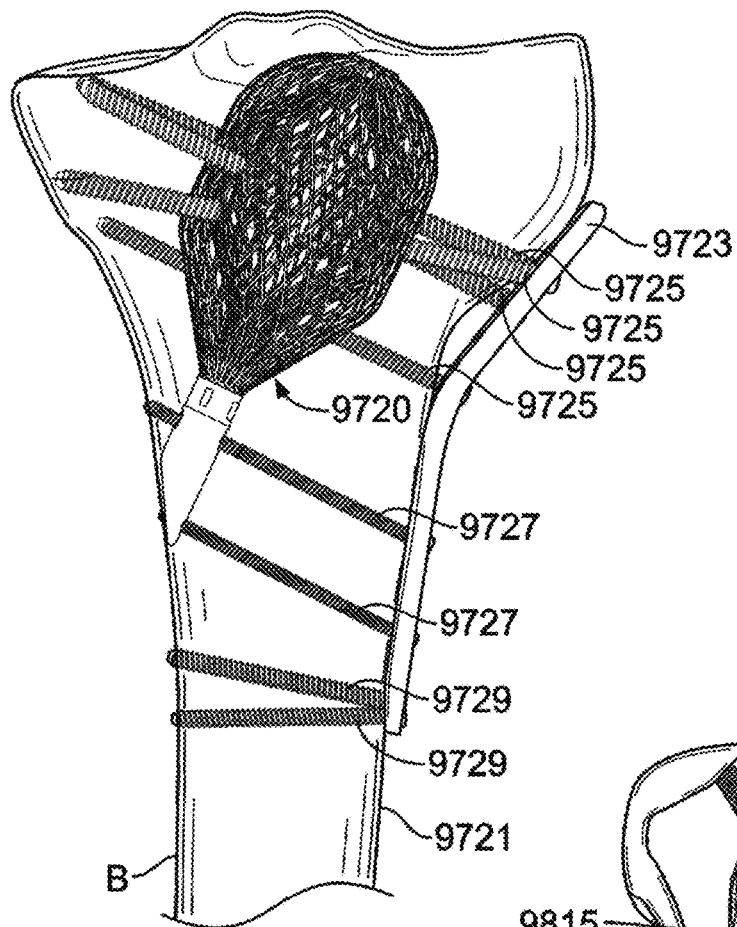
FIG. 97A shows illustrative apparatus and methods in accordance with principles of the invention.

FIG. 97A shows illustrative implant 9720 implanted in bone 9721. Bone 9721 may be a tibia. Implant 9720 may be anchored to bone 9721 and plate 9723.

In FIG. 97A, plate 9723 is affixed to a first side of bone 9721 using a plurality of screws 9725, 9727 and 9729. The first side may be a medial side. The first side of the bone is opposite a second side of the bone. The second side may be a lateral side. In FIG. 97A, an access hole was prepared on the second side for advancing the implant through the surface of the bone and into the interior.

Screws 9725 may pass through plate 9723 and through a head of implant 9720. Screws 9727 may pass through plate 9723 and into a tail of implant 9720. Screws 9729 may pass through plate 9723 and advance along a width of bone 9721.

FIG. 97A illustrates implant 9720 positioned centrally within an interior of bone 9721. Implant 9720 may be positioned laterally or medially within an interior of the proximal tibia. Implant 9720 may be positioned laterally, with respect to a longitudinal axis of bone, within a head of a proximal tibia to support a fractured lateral condyle. Implant 9720 may be positioned medially, with respect to a longitudinal axis of bone, within a head of a proximal tibia to support a fractured medial condyle.

Figure 98:
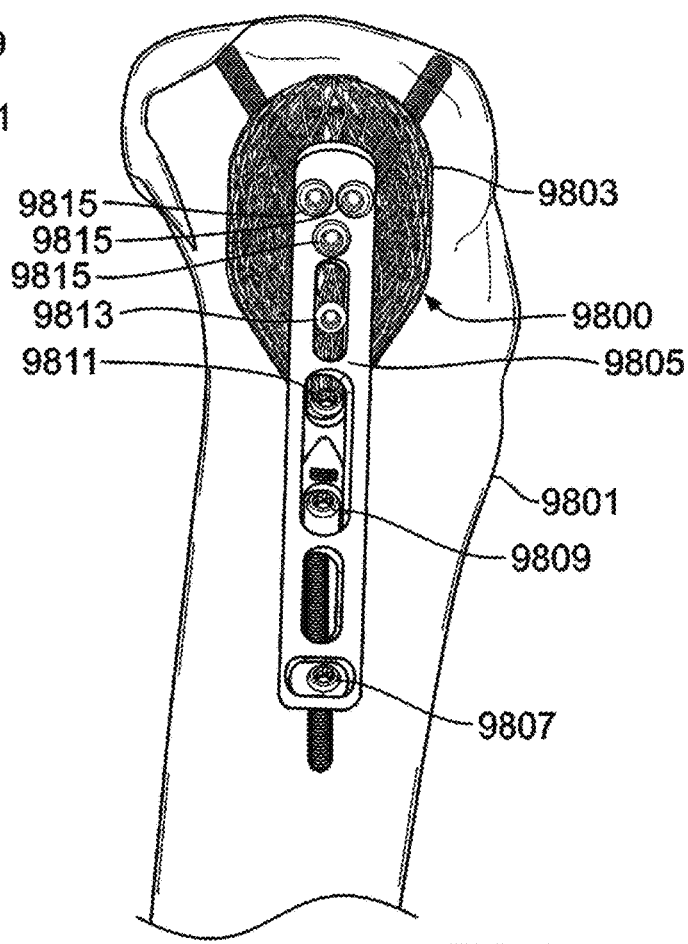
FIG. 98 shows illustrative apparatus and methods in accordance with principles of the invention.

FIG. 98 shows illustrative implant 9800 positioned inside bone 9801. Bone 9801 may be a tibia. Implant 9800 may be implanted in an interior of a proximal portion of the tibia ("proximal tibia"). Implant 9800 may be anchored to bone 9801 and plate 9805. Plate 9805 may be positioned on a medial portion of bone 9801.

Screws 9815 and screw 9813 are shown anchoring plate 9805 to implant head 9803 and bone 9801. Screw 9807 and screw 9809 are shown anchoring plate 9805 to bone 9801. Screw 9811 is shown anchoring an implant tail of implant 9800 to bone 9801.

In FIG. 98, plate 9805 is illustrated as having a substantially rectangular outer perimeter. Plate 9805 may be referred to as a longitudinal member. A plate anchored to an implant positioned within a proximal tibia may be wider than plate 9805.

A plate anchored to an implant positioned within in a tibia may include a longitudinal member and a semi-circular transverse member extending away from the longitudinal member. The semi-circular transverse member may extend away from an end of the longitudinal member and wrap around an anterior or posterior portion of a metaphysis region of the tibia. The semi-circular transverse member may extend away from an end of the longitudinal member and wrap around an anterior or posterior portion of a diaphysis region of the tibia.

A plate anchored to an implant implanted in a proximal tibia may include a longitudinal member and a transverse member extending away from the longitudinal member. The transverse member may wrap around an anterior or posterior portion of a metaphysis region of the tibia. The transverse member may extend away from an end of the longitudinal member and wrap around an anterior or posterior portion of a diaphysis region of the tibia.

Figure 99:
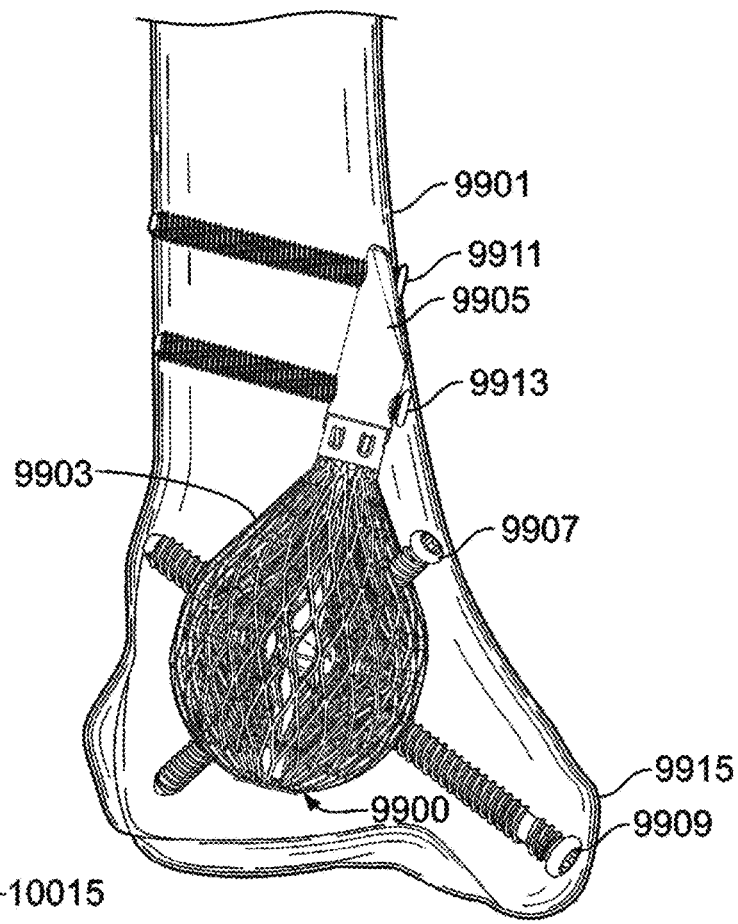
FIG. 99 shows illustrative apparatus and methods in accordance with principles of the invention.

FIG. 99 shows implant 9900 positioned within bone 9901. Bone 9901 may be a tibia. In FIG. 99, implant 9900 is shown positioned in a distal region of the tibia ("distal tibia"). Screw 9911 and screw 9913 are shown anchoring implant tail 9905 to bone 9901. Screws 9911 and 9913 may be positioned in a diaphysis region of bone 9901.

Screw 9907 and screw 9909 are shown anchoring implant head 9903 to a metaphysis region of bone 9901. Screw 9909 is shown anchoring implant head 9903 to lateral malleolus 9915 of the distal tibia.

Figure 100:
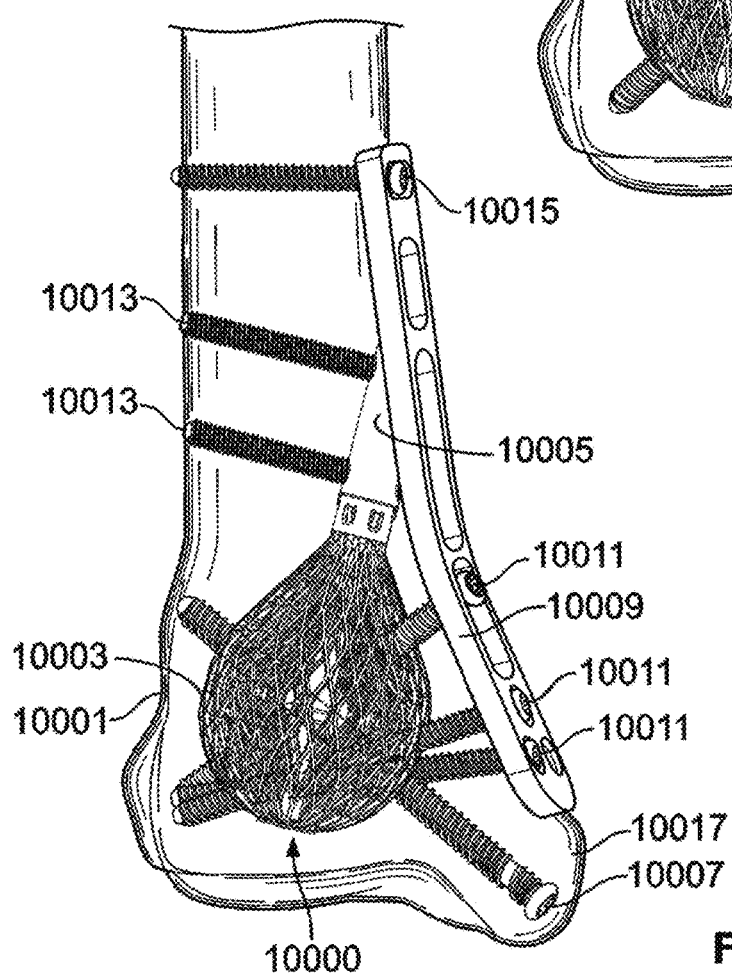
FIG. 100 shows illustrative apparatus and methods in accordance with principles of the invention.

FIG. 100 shows implant 10000 implanted into bone 10001. Bone 10001 may be a tibia. In FIG. 100, implant 10000 is shown implanted into a distal tibia. Screws 10011 are shown anchoring implant head 10003 to plate 10009 and to a metaphysis region of bone 10001.

Screws 10013 are shown anchoring implant tail 10005 to a diaphysis region of bone 10001. Screw 10015 is shown anchoring plate 10009 to a diaphysis region of bone 10001. Screw 10007 is shown anchoring implant head 10003 to lateral malleolus 10017 of the distal tibia.

Figure 101:
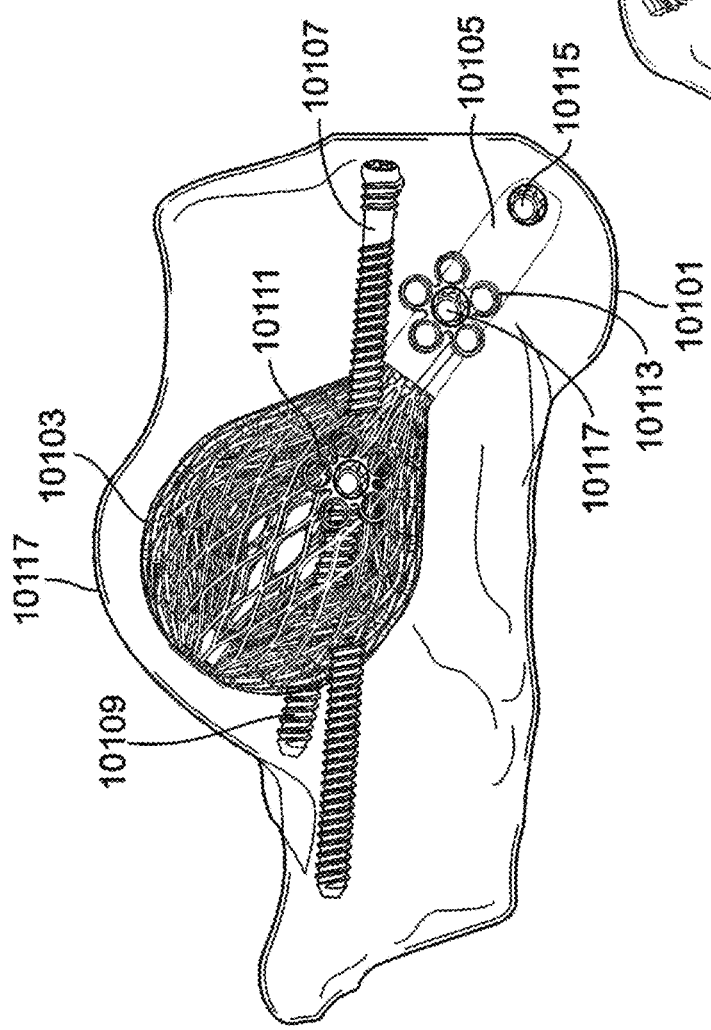
FIG. 101 shows illustrative apparatus and methods in accordance with principles of the invention.

FIG. 101 shows implant 10100 implanted into bone 10101. Bone 10101 may be a calcaneus bone. Implant 10100 may be positioned in bone 10101 such that implant head 10103 supports articular surface 10117 of bone 10101. Implant 10111 may be implanted in bone 10101 through the Achilles tendon at the base of tuberosity.

Screw 10115 is shown anchoring implant tail 10115 to bone 10101. Screw 10107 and screw 10111 are shown anchoring implant head 10103 to bone 10101. Screw 10107 and screw 10111 may support implant head 10103 and articular surface 10117. Screw 10107 and screw 10111 may anchor implant head 10103 with respect to articular surface 101117.

Screws 10115 and 10117 are shown anchoring implant tail 10105 to bone 10101.

Washer 10111 may be coupled to screw 10109. Washer 10111 may distribute load applied to bone 10101 by a head of screw 10109. Washer 10111 may space a head of screw 10119 apart from an outer surface of bone 10101.

Washer 10113 may be coupled to a head of screw 10117. Washer 10113 may distribute load applied to bone 10101 by a head of screw 10117. Washer 10113 may space a head of screw 10117 apart from an outer surface of bone 10101.

Figure 102:
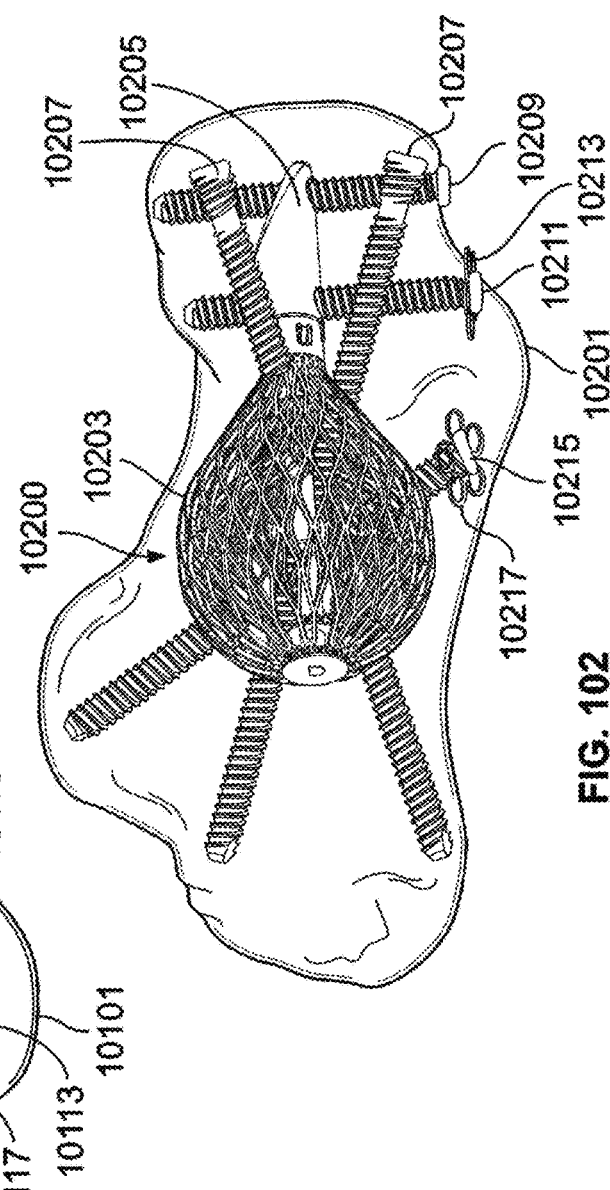
FIG. 102 shows illustrative apparatus and methods in accordance with principles of the invention.

FIG. 102 shows implant 10200 implanted in bone 10201. Bone 10201 may be a calcaneus bone. Screws 10207 and screw 10215 are shown anchoring implant head 10203 to bone 10201. Screw 10209 and 10211 are shown anchoring implant tail 10205 to bone 10201.

Washer 10217 may be coupled to a head of screw 10215. Washer 10213 may be coupled to a head of screw 10211. Washer 10217 and washer 10213 are shown positioned on a lateral surface of calcaneus bone 10201.

Screw 10215 may support an articular surface of bone 10201.

FIG. 102 shows a pattern of screws anchoring implant 10200 to bone 10201 that is representational of a screw pattern that may be used by a practitioner to support a calcaneus fracture. Any other suitable screw pattern may be used to anchor implant 10200 to bone 10201.

Any pattern of screws shown herein for anchoring an implant to a bone is for illustrative purposes only. Any other suitable pattern of screws may be used to anchor an implant to a bone.

Figure 103:
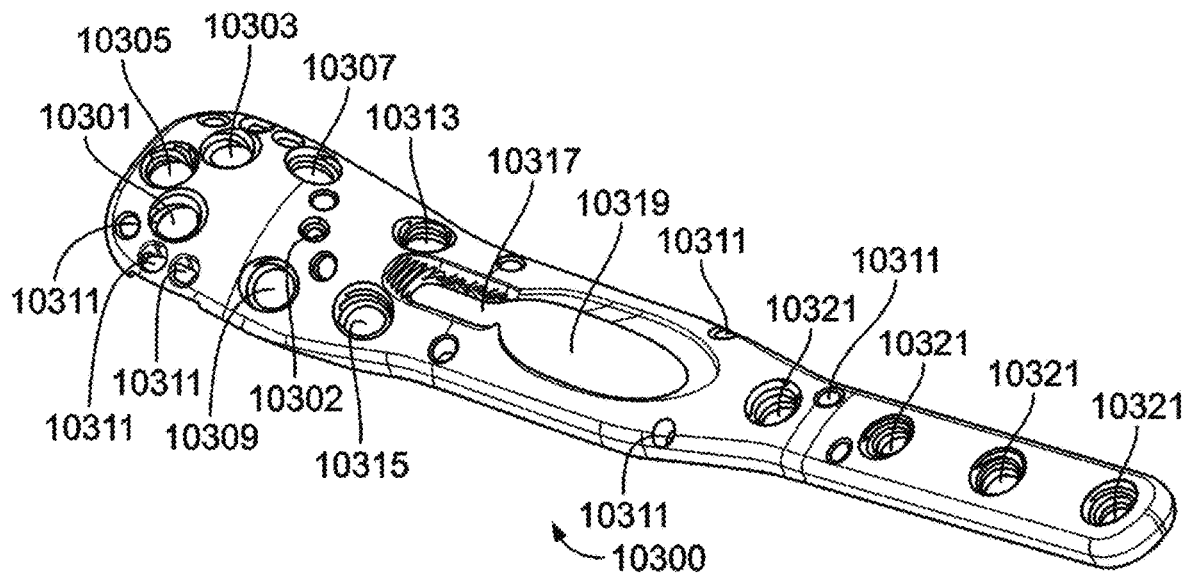
FIG. 103 shows illustrative apparatus in accordance with principles of the invention.

FIG. 103 shows illustrative plate 10300. Plate 10300 may include a bottom face (shown below in FIG. 104). The bottom face may include a bottom surface. The bottom surface may conform to a surface contour of a bone. The surface contour may be defined by an outer surface of a bone.

Plate 10300 may define plurality of holes 10311. Each of the plurality of holes 10311 may be sized to receive a fixation element.

Plate 10300 may define screw hole 10305. When a bottom surface of plate 10300 is seated complementarily on a surface contour of a bone, screw hole 10305 may be configured to position a bushing for directing a screw, or direct a screw, in a direction. The direction defined by screw hole 10305 may direct a screw into an interior of the bone but not into an implantation region occupied by an implant when the implant is positioned within the bone.

Plate 10300 may define screw holes 10301 and 10303. Screw holes 10301 and 10303 may each be configured to 10305 may be configured to direct a screw in a direction. The directions defined by screw holes 10301 and 10303 may intersect an implantation region when a bottom surface of plate 10300 is seated complementarily on a bone surface. The direction defined by screw hole 10301 may diverge from a direction defined by screw hole 10303. In other embodiments, the direction defined by screw hole 10301 may converge with a direction defined by screw hole 10303.

Plate 10300 may define screw hole 10307 and screw hole 10309. Screw holes 10307 and 10309 may define directions that direct screws into an implantation region when a bottom surface of plate 10300 is seated complementarily on a bone surface. The direction defined by screw hole 10307 may converge with a direction defined by screw hole 10309. The direction defined by screw hole 10307 may diverge from a direction defined by screw hole 10309.

Plate 10300 defines screw hole 10313 and screw hole 10315. Screw holes 10313 and 10315 may define directions that direct screws into an implantation region when a bottom surface of plate 10300 is seated complementarily on a bone surface. A direction defined by screw hole 10313 may diverge from a direction defined by screw hole 10315. The direction defined by screw hole 10313 may converge with a direction defined by screw hole 10315.

Plate 10300 may be configured to be coupled to a jig such as jig 10500 (shown below in FIG. 105). Plate 10300, as shown in FIG. 103, defines bore 10302. Bore 10302 may be threaded. Bore 10302 may be configured to receive a screw. The screw may be a screw inserted into a bore defined by a jig, advanced through the jig and into bore 10302, coupling plate 10300 to the jig.

Plate 10300 may define opening 10319. When a bottom surface of plate 10300 is seated complementarily on a surface contour of a bone, opening 10319 may define an access position. An access hole may be prepared at the access position through opening 10319. Plate 10300 also includes locking slot 10317. A locking slot may be defined by the plate. In FIG. 103, locking slot 10317 is partially defined by plate 10300 and extends away from opening 10319. Locking slot 10317 also intersects opening 10319. Locking slot 10317 may be shaped to engage a head of a screw.

Plate 10300 may define screw holes 10321. When a bottom surface of plate 10300 is seated complementarily on a surface contour of a bone, screw holes 10321 may point into an interior of the bone but not into the implantation region.

Figure 104:
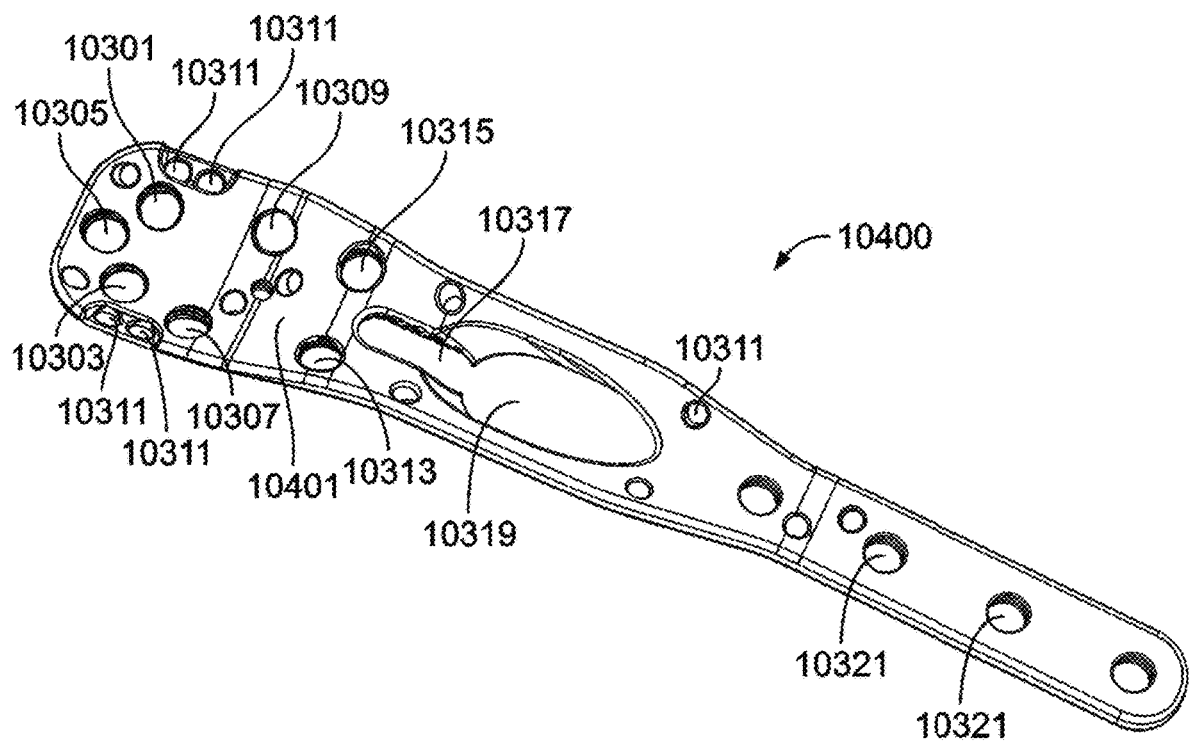
FIG. 104 shows illustrative apparatus in accordance with principles of the invention.

FIG. 104 shows bottom face 10401 of plate 10300. Some or all of bottom face 10401 may define a bottom surface configured to conform to a surface contour of a bone.

Figure 105:
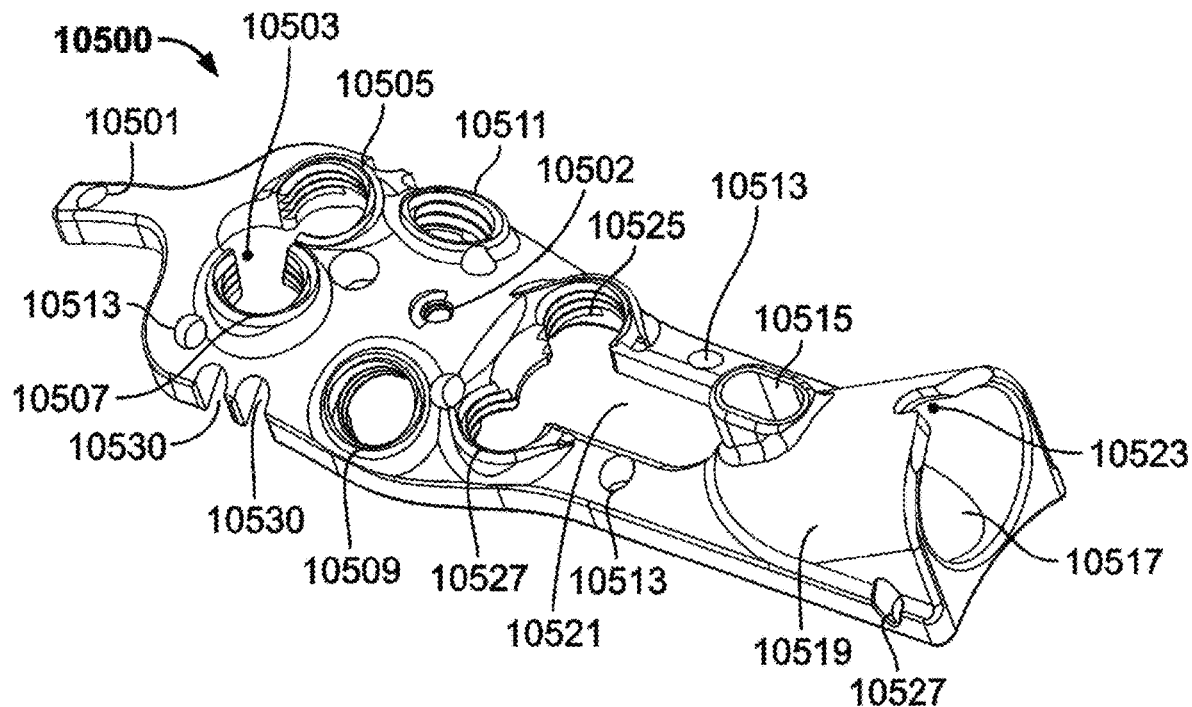
FIG. 105 shows illustrative apparatus in accordance with principles of the invention.

FIG. 105 shows illustrative jig 10500. Jig 10500 may be configured to be seated on, and coupled to, a position on a top face of a plate, such as plate 10300 (shown in FIG. 103). Jig 10500 may define positioning hole 10501.

Jig 10500 may define aperture 10503. Aperture 10503 may include threaded openings 10505 and 10507 for receiving a bushing. A fixation element advanced through a bushing coupled to threaded opening 10505 may be advanced in a first direction. A fixation element advanced through a bushing coupled to threaded opening 10507 may be advanced in a second direction. The first direction may be divergent from the second direction. The first direction may be convergent with the second direction.

Jig 10500 may define screw hole 10511 and screw hole 10509. Screw hole 10511 may define a first direction. Screw hole 10509 may define a second direction. The first direction may be convergent with the second direction. The first direction may be divergent from the second direction.

Jig 10500 may define bore 10502. Bore 10502 may extend though jig 10500. Bore 10502 may be threaded. When jig 10500 is seated on a plate such as plate 10300, a screw advanced through bore 10502 and into a hole in the plate positioned underneath bore 10502 (such as bore 10302 illustrated in FIG. 103) may releasably couple jig 10500 to the plate.

Jig 10500 may include aperture 10521. Aperture 10521 may define opening 10525 for receiving a first bushing and opening 10527 for receiving a second bushing. Opening 10525 may be an open channel that has an arcuate perimeter. Opening 10527 may be an open channel that has an arcuate perimeter.

A fixation element advanced through the first bushing may be directed along a first direction. A fixation element advanced through the second bushing may be directed along a second direction. The first direction may diverge from the second direction. The first direction may be convergent with the second direction.

Jig 10500 may include guide 10519. Guide 10519 may extend away from opening 10517 defined by jig 10500. Guide 10519 may be shaped to receive bushings inserted into guide 10519. Guide 10519 may receive a bushing shaped to receive a target wire. Guide 10519 may receive a bushing shaped to receive a drill. Guide 10519 may receive a bushing shaped to receive a cavity preparation device. Guide 10519 may receive a bushing shaped to receive an unexpanded implant.

Guide 10519 may include slot 10523. Slot 10523 may mate with a protrusion extending away from a bushing inserted into guide 10519. The mating of slot 10523 with a protrusion of a bushing may secure the bushing within guide 10519.

Guide 10519 may define opening 10515. A practitioner may advance a fixation element through opening 10515 to provisionally reduce a fracture. For example, a practitioner may advance a threaded member coupled to a nut into a bone fragment. The nut may rest on an outer surface of opening 10515. The nut may be used to provide compression to the bone fragment.

Jig 10500 may define a plurality of holes sized for receiving fixation elements. The plurality of holes may include holes 10513 and 10527. Holes 10527 may be positioned adjacent a bottom portion of guide 10519. Fixation elements driven though bores 10513 and 10527 when jig 10500 is coupled to a plate seated complementarily on a bone surface may releasably couple jig 10500 to the bone. When jig 10500 is coupled to a plate seated on a bone, bores 10513 and 10527 may point into an interior of the bone but not into an implantation region.

Jig 10500 may also include channels 10530. Each of channels 10530 may be defined by a perimeter of jig 10500. A fixation element may be guided through one of channels 10530 and into a hole defined by a plate coupled to the jig. The hole in the plate may be sized for receiving the fixation element. Channel 10530 may define an arcuate cross section.

Figure 106:
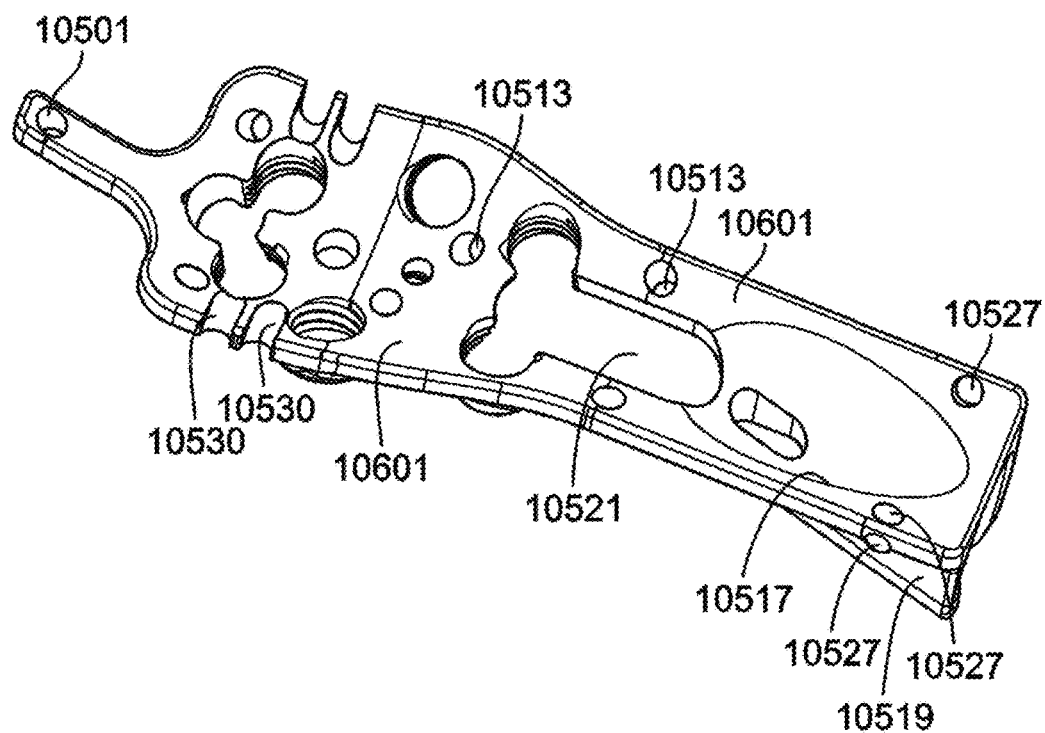
FIG. 106 shows illustrative apparatus in accordance with principles of the invention.

FIG. 106 shows bottom face 10601 of jig 10500. A contour of a first portion of bottom face 10601 may conform to a contour of a portion of a top face of a plate such as plate 10300. A second portion of bottom face 10601 may extend away from a plate (such as plate 10300) when jig 10500 is coupled to the plate. For example, when jig 10500 is coupled to plate 10300, the first portion of bottom face 10601 may rest on plate 10300 and the second portion of bottom face 10601 may not come into contact with plate 10300.

Figure 107A:
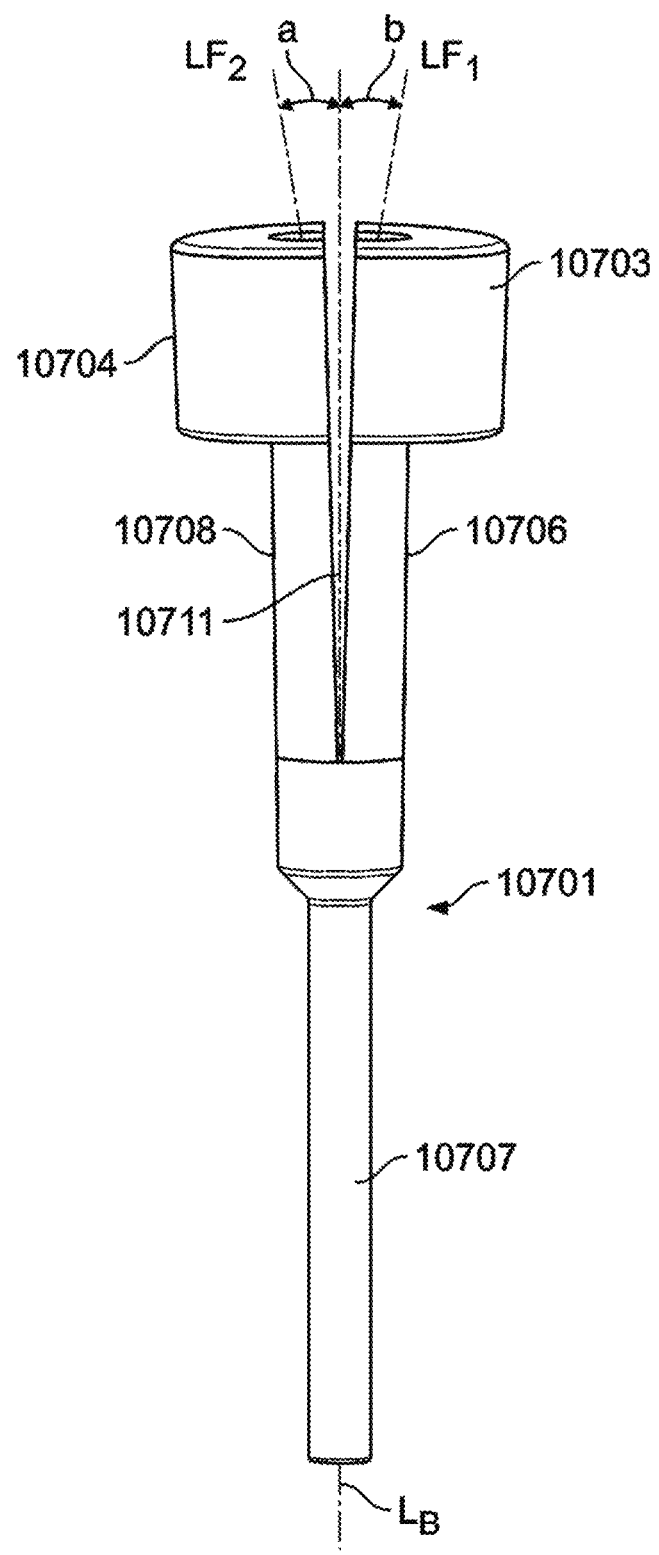
FIG. 107A shows illustrative apparatus in accordance with principles of the invention.
Figure 107B:
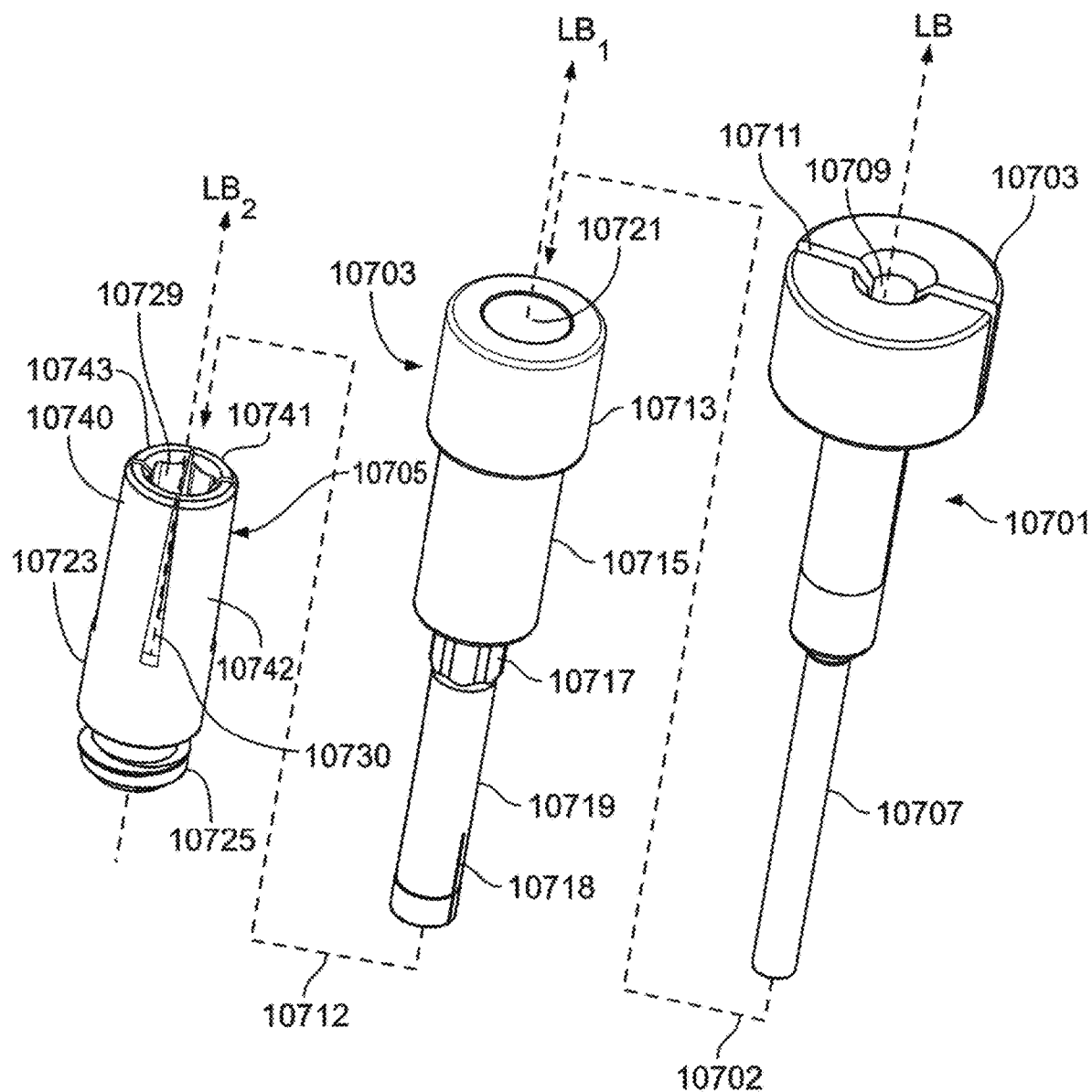
FIG. 107B shows illustrative apparatus in accordance with principles of the invention.

FIG. 107A and FIG. 107B show illustrative bushing 10701. Longitudinal segment 10707 of bushing 10701 defines longitudinal axis $L_B$. Bushing 10707 includes flanged end 10703. Bushing 10707 includes flanged end 10704. In an equilibrium state, kerf 10711 spaces flanged end 10703 apart from flanged end 10704. Flanged end 10703 may be mounted on longitudinal segment 10706. Longitudinal segment 10706 may define longitudinal axis LF1. Flanged end 10704 may be mounted on longitudinal segment 10708. Longitudinal segment 10708 may define longitudinal axis LF2. Longitudinal segment 10706 may have a semi-circular cross section in a plane that is normal to LF1.

Longitudinal segment 10708 may have a semi-circular cross section in plane that is normal to LF2.

FIG. 107A shows bushing 10701 in an equilibrium state. In an equilibrium state, longitudinal axis LF1 may form an angle B with respect to axis $L_B$. In an equilibrium state, longitudinal axis LF1 may form an angle A with respect to axis $L_B$.

Bushing 10701 includes longitudinal segment 10707 that defines longitudinal axis $L_B$. Longitudinal segment 1707 may be cannulated. Longitudinal segment 1707 may define a circular cross section in a plane normal to $L_B$.

FIG. 107B shows illustrative bushing 10703. Bushing 10703 includes flanged end 10713. Flanged end 10713 may be cannulated. Bushing 10703 includes longitudinal segment 10715. Longitudinal segment 10715 may be cannulated. Bushing 10703 includes longitudinal segment 10719. Longitudinal segment 10719 may be cannulated. Each of flanged end 10713, longitudinal segment 10715 and longitudinal segment 10719 may be cannulated such that a cannula of uniform diameter extends along a longitudinal axis LB1 of bushing 10703.

Longitudinal segment 10719 may be cannulated such that it is configured to receive longitudinal segment 10707 of bushing 10701. Longitudinal segment 10715 may be cannulated such that it is configured to receive longitudinal segments 10708 and 10706 (shown in FIG. 107A). A cannula running through longitudinal segment 10719 may be narrower than a cannula running though longitudinal segment 10715. Bushing 10703 may include a cannula that is large enough to receive a surgical drill.

Longitudinal segment 10719 may include kerf 10718. Kerf 10718 may be one of two or more kerfs in longitudinal segment 10719. In operation, when a tool is inserted into cannula 10721, the one or more kerfs may allow longitudinal segment 10719 to expand about longitudinal axis LB1. Expansion of longitudinal segment 10719 may provide a friction fit, along axis Lb1 for a tool inserted into cannula 10721. When longitudinal segment 10719 is nested within longitudinal segment 10723, pressure applied by expansion of the longitudinal segment 10719 may provide a friction fit that holds longitudinal segment 10719 with respect to longitudinal segment 10723.

When bushing 10701 is inserted into cannula 10721 of bushing 10703, flanged end 10713 and longitudinal segment 10715 may compress longitudinal segment 10703 and longitudinal segment 10704 about longitudinal axis LB1. Thus, when bushing 10701 is positioned within bushing 10703, angles A and B may be smaller than in the equilibrium state (shown above in FIG. 107A). When bushing 10701 is positioned within bushing 10703, longitudinal segments 10706 and 10708 may exert pressure on longitudinal segment 10713 and/or longitudinal segment 10715. The exerted pressure may provide a friction fit for bushing 10701 within bushing 10703.

FIG. 107B shows illustrative bushing 10705. Bushing 10705 includes longitudinal segment 10723. Longitudinal segment 10723 defines longitudinal axis LB2.

Bushing 10705 may include one or more kerfs such as kerf 10730. The one or more kerfs may allow bushing 10705 to be formed into a tapered shape along longitudinal axis LB2. The one or more kerfs may define two or more longitudinal segments, such as longitudinal segments 10740, 10741, 10742 and 10743.

In an equilibrium state (when bushings 10705 and 10703 are not nested) longitudinal segments 10740, 10741, 10742 and 10743 may be inwardly biased toward axis LB2. In the equilibrium state, a diameter of cannula 10729 may narrow along axis LB2 when moving from threaded segment 10725 toward a hexagonal cross section of cannula 10729.

Bushing 10703 may be nested within bushing 10705. When bushing 10703 is nested in bushing 10705, longitudinal segment 10719 may expand longitudinal segments 10740, 10741, 10742 and 10743 outward from axis LB2. When bushing 10703 is nested in bushing 10705, longitudinal segments 10740, 10741, 10742 and 10743 may apply pressure to longitudinal segment 10719 of bushing 10703. The pressure may provide a friction fit that maintains a nested position of bushing 10703 within bushing 10705.

Bushing 10705 may include one kerf. For example, kerf 10730 may be the only kerf in bushing 10705. When kerf 10730 is the only kerf, longitudinal segments 10740, 10741, 10742 and 10743 may form a unitary longitudinal segment. When kerf 10730 is the only kerf and bushing 10703 is nested in bushing 10705, the unitary longitudinal segment may apply pressure to longitudinal segment 10719 of bushing 10703. The pressure may provide a friction fit that maintains a nested position of bushing 10703 within bushing 10705.

Bushing 10705 defines cannula 10729. Cannula 10729 may include different cross sections along longitudinal axis LB2. For example, FIG. 107B shows that cannula 10729 may include a hexagonal cross section at or near an end of longitudinal segments 10740, 10741, 10742 and 10743. The hexagonal cross section may be configured to mate with hexagonal protrusions 10717 of bushing 10703. When bushing 10703 is inserted into bushing 10705, a mating of the hexagonal cross section and hexagonal protrusions may lock bushings 10703 and 10705 rotationally, with respect to each other, about axis LB1 and/or LB2.

Bushing 10705 includes threaded segment 10725. Threaded segment 10725 may be configured to threadedly engage jig 10500.

As shown by 10702, Bushing 10701 may be nested within bushing 10703. As shown by 10712, bushing 10703 may be nested within bushing 10705. Bushings 10701, 10703 and 10705 may form nested bushing 10801 (shown in FIG. 108). Nested bushing 10801 may be fixed to jig 10500. Narrow gauge instruments, such as K-wires, may be directed into a bone through cannula 10709 in bushing 10701. Bushing 10701 may direct such instruments into a bone in a direction along axis $L_B$. Bushing 10701, when affixed to a jig, may direct instruments into an implantation region within a bone.

After positioning an instrument using bushing 10701, bushing 10701 may be separated from bushing 10703. Separating bushing 10701 from bushing 10703 may expose cannula 10721 of bushing 10703. Cannula 10721 may have a diameter that is larger than the diameter of cannula 10709. Cannula 10721 may be configured to receive larger gauge instruments than those that would fit into cannula 10709. Cannula 10721 may be sized to receive a drill. The drill may be a cannulated drill that is configured to slide over the K-wire positioned using bushing 10701. Cannula 10721 may direct an instrument along longitudinal axis LB1.

Bushing 10703 may be separated from bushing 10705. Separating bushing 10703 from bushing 10705 may expose cannula 10729. Cannula 10729 may have a diameter that is larger than the diameter of cannula 10721. Cannula 10729 may be configured to received larger gauge instruments than those that would fit into cannula 10721. Cannula 10729 may be sized to receive an anchor or screw. Cannula 10729 may direct an anchor or screw along longitudinal axis LB2. The anchor or screw may be a cannulated and configured to slide over the K-wire positioned using bushing 10701.

Bushing 10705 may be removed from jig 10500.

Figure 108:
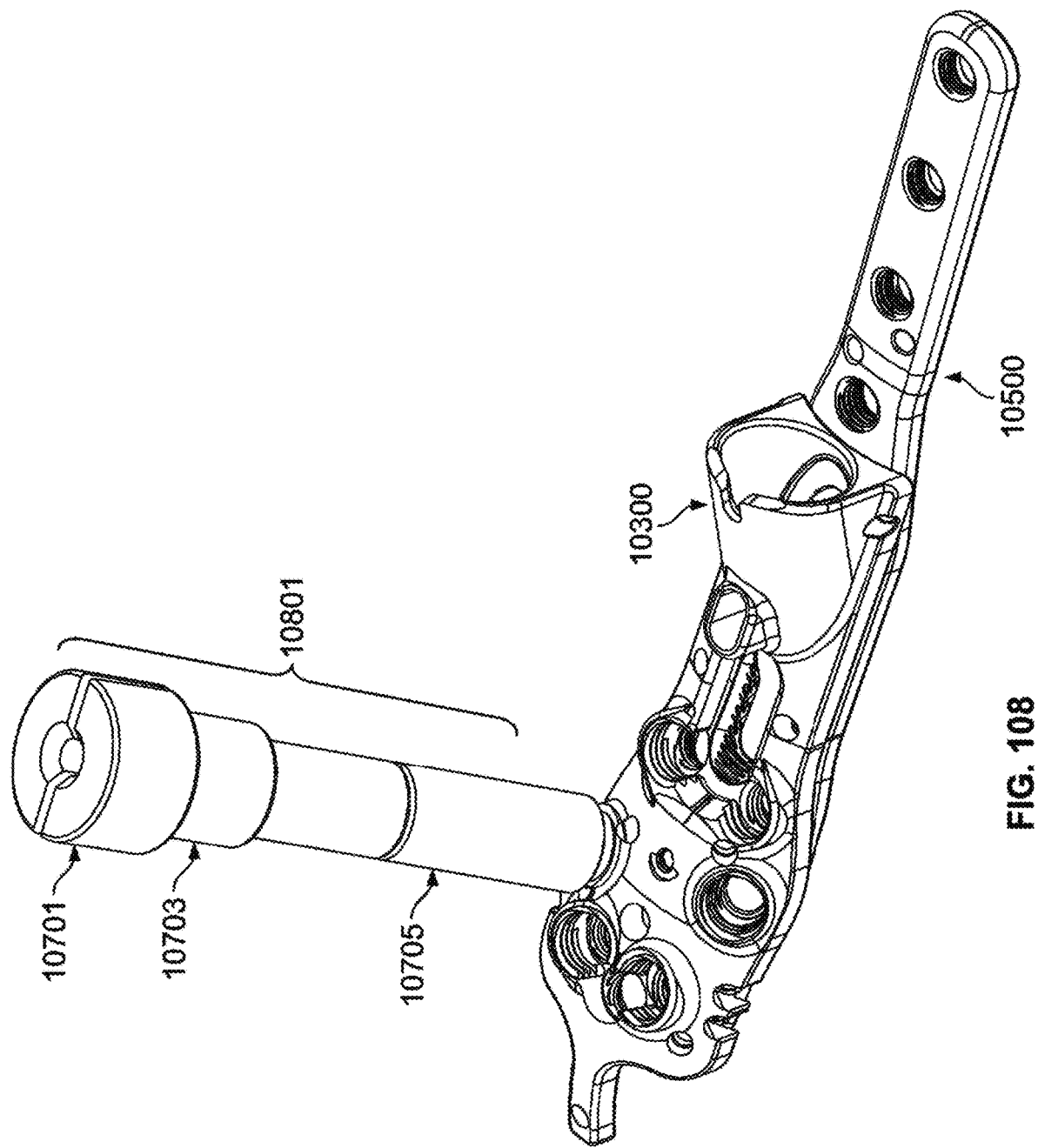
FIG. 108 shows illustrative apparatus in accordance with principles of the invention.

FIG. 108 shows exemplary apparatus. The apparatus shown in FIG. 108 includes jig 10500 releasably coupled to plate 10300. The apparatus shown in FIG. 108 also includes bushings 10701, 10703 and 10705 coupled together to form nested bushing 10801. In FIG. 108, bushings 10701, 10703 and 10705 are coupled together to form nested bushing 10800 and are seated on a screw hole defined by jig 10500. Threaded segment 10725 of bushing 10705 may threadedly engage a screw hole in jig 10500.

Figure 109:
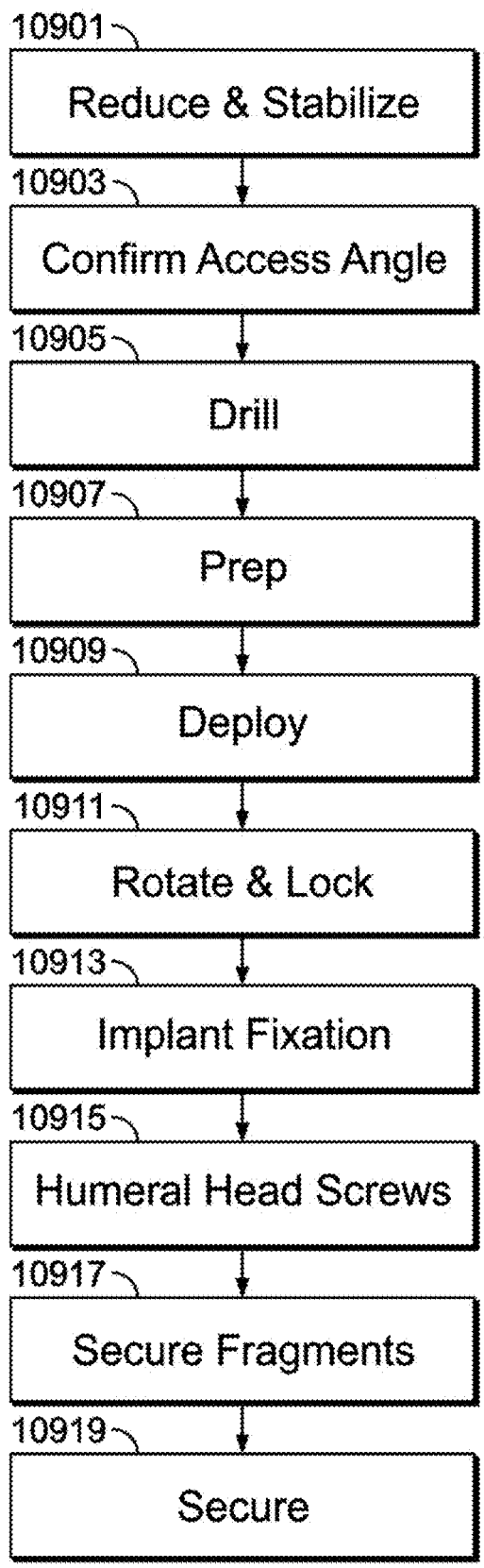
FIG. 109 shows steps of an illustrative procedure accordance with principles of the invention.

FIG. 109 shows an illustrative method for inserting an implant in a bone. The illustrative method may include one or more of the steps shown in FIG. 109. The steps shown in FIG. 109 may be performed in an order different from the order shown in FIG. 109. The steps may be performed using apparatus and methods disclosed herein. The steps may be performed using any plate, jig, or plate and jig combination disclosed herein.

Step 10901 may include reducing and stabilizing a fractured bone. Step 10903 may include confirming an access angle. Step 10905 may include drilling. The drilling may form an access hole towards a target site. Step 10907 may include prepping an interior of the bone for implantation of the implant. Prepping the interior may include creating a cavity within the bone. Step 10909 may include deploying the implant in the cavity. The deploying may include expanding the implant. The implant may be self-expanding. Step 10911 may include rotating and locking the deployed implant. Step 10913 may include fixing the implant to the bone. The fixing the implant may include fixing a tail of the implant to the bone. Step 10915 may include driving screws through the bone and into a head of the implant. Step 10915 may be performed for any suitable bone. In some of the embodiments where the bone is a proximal humerus, the screws may be driven through a humeral head and into a head of the implant. Step 10917 may include securing fragments of the bone. The securing the fragments of the bone may include securing fragments of the bone to the implant head by driving fixation elements through the bone and into the implant head. Step 10919 may include securing the implant to the bone.

Figure 110:
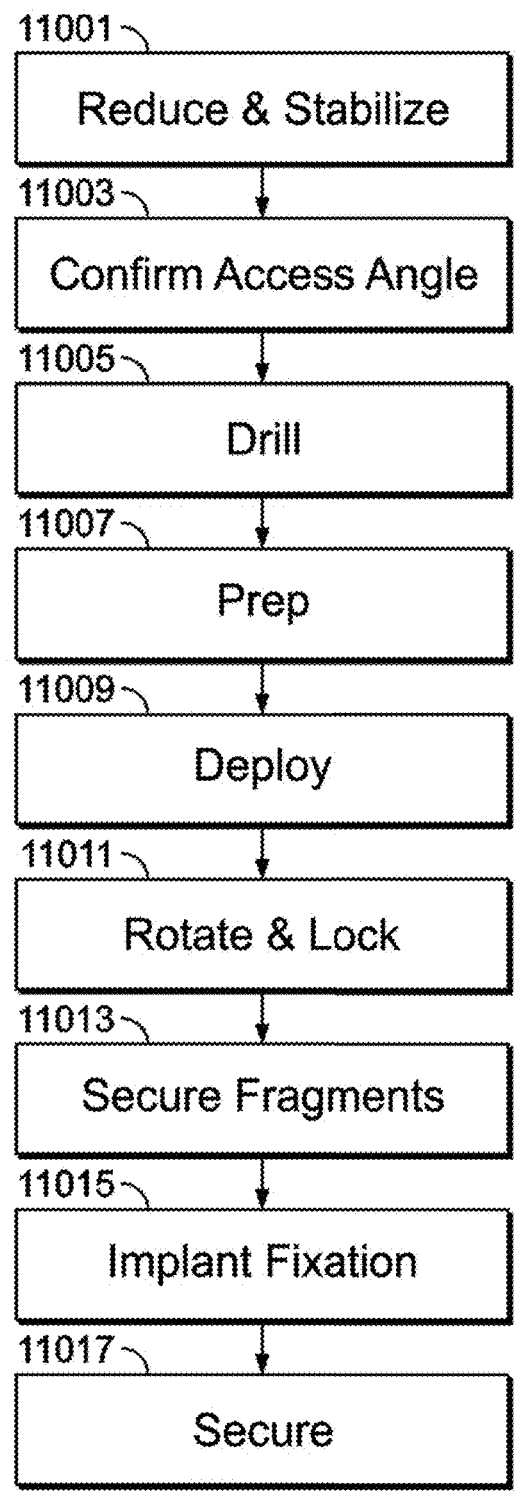
FIG. 110 shows steps of an illustrative procedure accordance with principles of the invention.

FIG. 110 shows an illustrative method for inserting an implant in a bone. The illustrative method may include one or more of the steps shown in FIG. 110. The steps shown in FIG. 110 may be performed in an order different from the order shown in FIG. 110. The steps may be performed using apparatus and methods disclosed herein. The steps may be performed using any plate, jig, or plate and jig combination disclosed herein.

Step 11001 may include reducing and stabilizing a fractured bone. Step 11003 may include confirming an access angle. Step 11005 may include drilling. The drilling may be performed to form an access hole towards a target site. Step 11007 may include prepping an interior of the bone for implantation of the implant. Prepping the interior may include creating a cavity within the bone. Step 11009 may include deploying the implant in the cavity. Step 11011 may include rotating and locking the deployed implant. Step 11013 may include securing fragments of the bone. The securing the fragments of the bone may include securing fragments of the bone to the implant head by driving fixation elements through the bone and into the implant head. Step 11015 may include fixing the implant to the bone. The fixing the implant may include fixing a tail of the implant to the bone. Step 11017 may include securing the implant to the bone.

Figure 111:
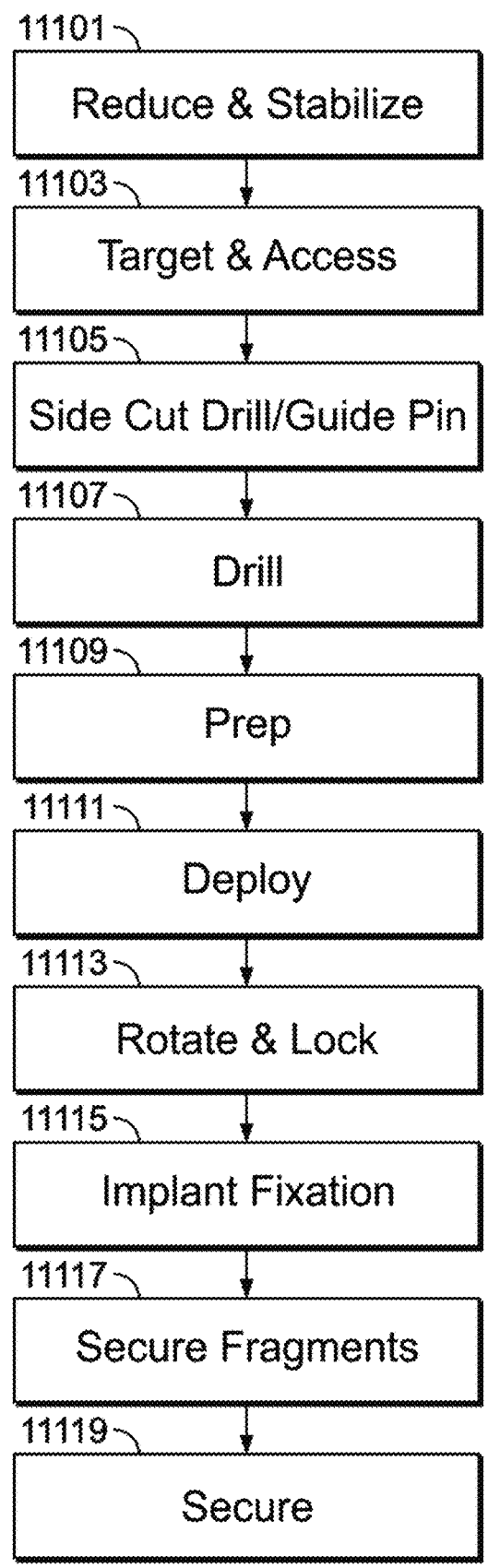
FIG. 111 shows steps of an illustrative procedure accordance with principles of the invention.

FIG. 111 shows an illustrative method for inserting an implant in a bone. The illustrative method may include one or more of the steps shown in FIG. 111. The steps shown in FIG. 111 may be performed in an order different from the order shown in FIG. 111. The steps may be performed using apparatus and methods disclosed herein. The steps may be performed using any plate, jig, or plate and jig combination disclosed herein.

Step 11101 may include reducing and stabilizing a fractured bone. Step 11103 may include target and access. Target and access may include driving a target wire through a target hole and towards a target site. Step 11105 may include using a side cut drill to create an access hole on the bone and driving a target wire through the access hole and towards the target site. The target wire may be used as a guide pin. Step 11107 may include drilling through the access hole and towards the target site. Step 1109 may include prepping an interior of the bone for implantation of the implant. Prepping the interior may include creating a cavity within the bone. Step 11111 may include deploying the implant in the cavity. Step 11113 may include rotating and locking the deployed implant. Step 11115 may include may include fixing the implant to the bone. The fixing the implant may include fixing a tail of the implant to the bone. Step 1117 may include securing fragments of the bone. The securing the fragments of the bone may include securing fragments of the bone to the implant head by driving fixation elements through the bone and into the implant head. Step 11119 may include securing the implant to the bone.

Figure 112:
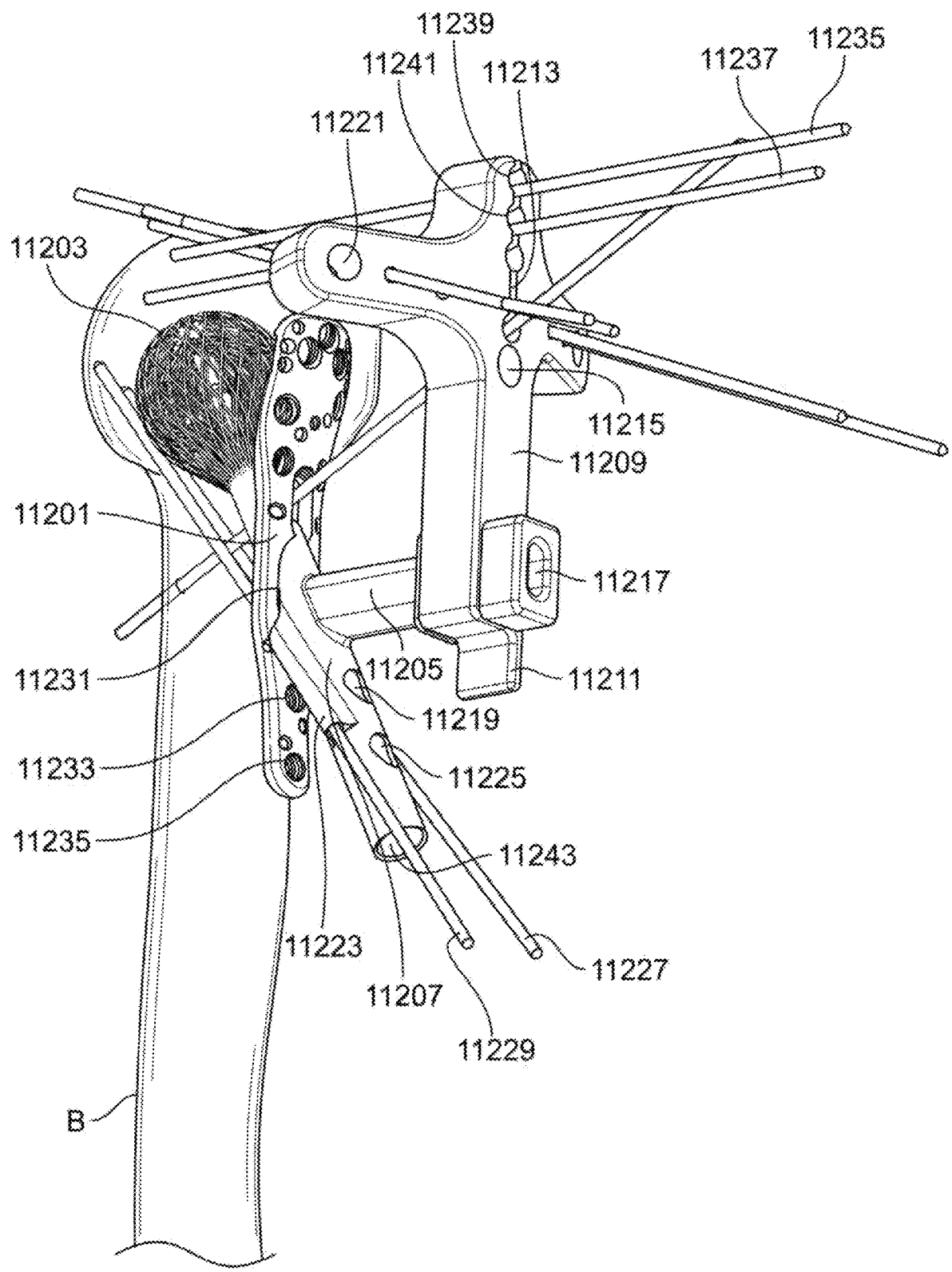
FIG. 112 shows illustrative apparatus and methods in accordance with principles of the invention.

FIG. 112 shows an illustrative therapeutic scenario with illustrative apparatus implanted in bone B. The apparatus may include plate 11201 and implant 11203. The apparatus may also include implant delivery base 11207, post 11205 and reduction device 11209.

The apparatus illustrated in FIG. 112 may be used for the percutaneous delivery of implant 11203 into an interior of bone B. The apparatus illustrated in FIG. 112 may be used to deliver implant 11203 into an interior of bone B using a minimally invasive method, such as a method including splitting the deltoid muscle. The apparatus illustrated in FIG. 112 may be used to deliver implant 11203 into an interior of a bone using an open procedure.

Implant delivery base 11207 may be used alone for percutaneous delivery of implant 11203 in bone B. Implant delivery base 11207 may be used with plate 11201 for percutaneous delivery of implant 11203 in bone B.

Implant delivery base 11207 may have one or more features in common with the implant delivery bases illustrated in FIGS. 85-88A. Post 11205 may have one or more features in common with the posts illustrated in FIGS. 85-88A. Reduction device 11209 may have one or more features in common with the reduction devices illustrated in FIGS. 85-88A.

The implant delivery bases illustrated in FIGS. 85-88A may have one or more features in common with implant delivery base 11207. The posts illustrated in FIGS. 85-88A may have one or more features in common with post 11205. The reduction devices illustrated in FIGS. 85-88A may have one or more features in common with reduction device 11209.

Plate 11203 may be positioned complimentarily on a surface of bone B.

Implant delivery base 11207 may be nested in opening 11231 defined by plate 11201. Implant delivery base 11207 may be seated in opening 11231 defined by plate 11201. A bottom surface of implant delivery base 11207 may be seated on a surface of bone B. A bottom surface of implant delivery base 11207 may be seated in opening 11231. A bottom surface of implant delivery base 11207 may be seated on a face of plate 11201. A first portion of a bottom surface of implant delivery base 11207 may be seated on a surface of bone B and a second portion of a bottom surface of implant delivery base 11207 may be seated on a surface of plate 11201. One or more features of implant delivery base 11207 may snap into plate 11201. Plate 11201 may include a slot shaped to receive a protrusion on a bottom face of implant delivery base 11207.

Implant delivery base 11207 may define channel 11243. Channel 11243 may be sized to receive implant 11203 in an unexpanded state. Channel 11243 may be sized to receive a bushing (not shown). The bushing may be sized to receive implant 11203 in an unexpanded state. The bushing may be sized to receive a drill. The bushing may be removably coupled to channel 11243.

Implant delivery base 11207 may define bore 11223. Implant delivery base 11207 may define a second bore (not shown) opposite bore 11223 across a channel longitudinal axis. Fixation element 11229 may pass through bore 11223. Fixation element 11227 may pass through the second bore. Bore 11223 and the second bore may extend through implant delivery base 11207 at an angle oblique to a bottom surface of implant delivery base 11207. Bore 11223 may define a central axis. Fixation element 11229 may pass through a hole defined by plate 11201 and into the interior of bone B. Fixation element 11227 may pass through a hole defined by plate 11201 and into the interior of bone B. The passing of fixation elements 11227 and 11229 through implant delivery base 11207 and through plate 11201 may couple implant delivery base 11207 to plate 11201. The passing of fixation elements 11227 and 11229 through implant delivery base 11207, through plate 11201 and into bone B may couple implant delivery base 11207 to plate 11201 and to bone B.

A central axis defined by channel 11243 may be non-parallel to a central axis defined by bore 11223 and a central axis defined by the second bore. A first central axis defined by bore 11223 and a second central axis defined by the second bore may point into the interior of bone B, but not into a volume occupied by implant 11203 in the interior when implant 11203 is advanced through the channel, into the interior, positioned at a target site, and radially expanded to form a mesh cage.

Implant delivery base 11207 may include hole 11219 and hole 11225. Implant delivery base 11207 may include a second hole opposite hole 11219 across a base longitudinal axis. Implant delivery base 11207 may include a third hole opposite hole 11225 across a base longitudinal axis. When implant delivery base 11207 is coupled to plate 11201, hole 11219 may be coaxial with hole 11233 and the second hole, and hole 11225 may be coaxial with hole 11235 and the third hole. A practitioner may removably couple implant delivery base 11207 to plate 11201 during the therapeutic procedure by passing a screw through hole 11219 and hole 11233. A practitioner may removably couple implant delivery base 11207 to plate 11201 during the therapeutic procedure by passing a screw through 11225 and hole 11235.

Implant delivery base 11207 may include post 11205 extending away from a top surface of implant delivery base 11207. Post 11205 may be cannulated to define inner lumen 11217. Inner lumen 11217 may be sized to receive a drill. Inner lumen 11217 may be sized to receive a screw. In operation, when implant delivery base 11207 is coupled to plate 11201 and implant 11203 is positioned in bone B, a screw advanced through lumen 11217 may engage a hole defined by a tail of implant 11203.

Implant delivery base 11207 may include reduction device 11209. Reduction device 11209 may be removably coupled to post 11205. Reduction device 11209 may be snapped onto post 11205. Reduction device 11209 may be removed from post 11205 using handle 11211.

Reduction device 11209 may define hole 11215, hole 11241, hole 11239 and hole 11221. Holes defined by reduction device 11209 may be sized to receive fixation elements such as k-wire 11235, k-wire 11237 and screws (not shown). Holes defined by reduction device 11209 may be sized to receive a bushing (not shown). Each of holes 11215, 11241, 11239 and 11221 may point to a volume defined by implant 11203 when the implant is positioned at the target site in bone B and expanded to form a mesh cage.

Reduction device 11209 may define slit 11213. Slit 11213 may run from an end of reduction device 11209 along a central axis of reduction device 11209. Slit 11213 may extend through one or more holes defined by reduction device 11209. A practitioner may drive k-wires into the bone and subsequently slide reduction device over the k-wires by axially sliding an opening defined by slit 11213 along the k-wires.

Arms of reduction device 11209 extending circumferentially about bone B may have any suitable length and width to target desired anatomy of bone B.

Figure 113:
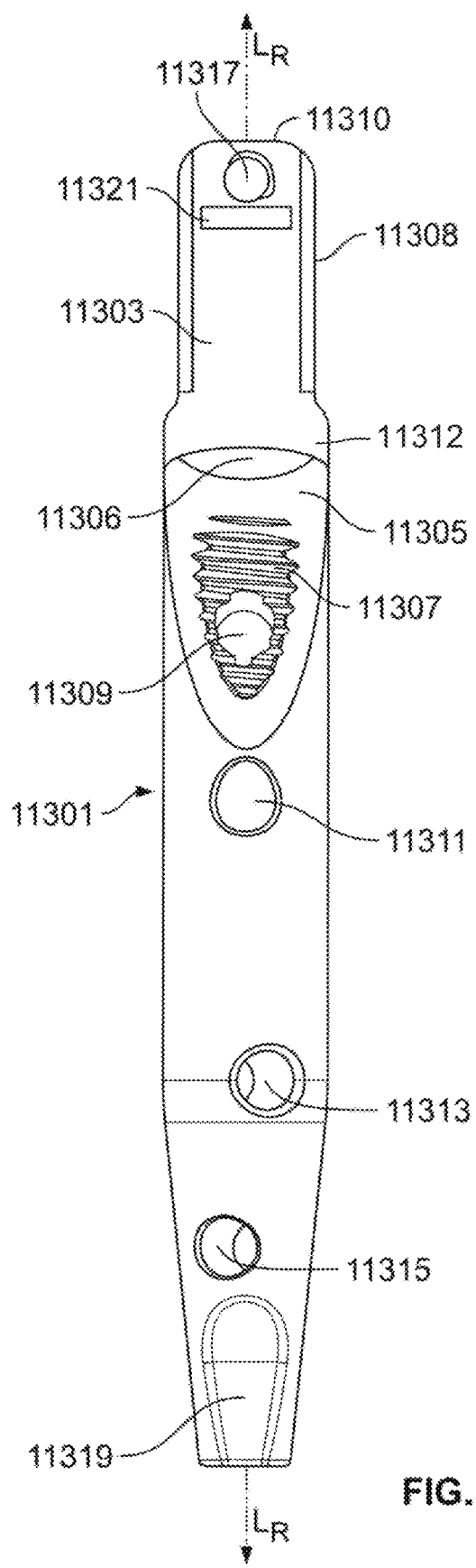
FIG. 113 shows illustrative apparatus in accordance with principles of the invention.

FIG. 113 shows illustrative rod 11301. Rod 11301 may include tapered segment 11319. Tapered segment 11319 may displace tissue in a bone as rod 11301 is inserted into the bone.

Rod 11301 may include anchor receiving feature 11315. Anchor receiving feature 11315 may define a first central longitudinal axis (not shown). The first central longitudinal axis may be oblique to the central longitudinal axis of rod 11301. An anchor driven through anchor receiving feature 11315 may secure rod 11301 to a bone.

Rod 11301 may include anchor receiving feature 11313. Anchor receiving feature 11315 may define a second central longitudinal axis (not shown). The second central longitudinal axis may be oblique to the central longitudinal axis of rod 11301. An anchor driven through anchor receiving feature 11313 may secure rod 11301 to the bone.

A first planar surface (not shown) may include the first central longitudinal axis. A second planar surface (not shown) may include the second central longitudinal axis. The first planar surface may be parallel to the second planar surface.

Rod 11301 may include anchor receiving feature 11311. Anchor receiving feature 11311 may define a third central longitudinal axis (not shown). An anchor driven through anchor receiving feature 11311 may secure rod 11301 to the bone. The third central longitudinal axis may intersect the first and the second planar surfaces.

Rod 11301 may include anchor receiving feature 11309. Anchor receiving feature 11309 may define a fourth central longitudinal axis (not shown). An anchor driven through anchor receiving feature 11309 may secure rod 11301 to the bone. The fourth central longitudinal axis may intersect the first and the second planar surfaces. The fourth central longitudinal axis may be parallel to the third central longitudinal axis defined by anchor receiving feature 11311. The fourth central longitudinal axis may intersect the third central longitudinal axis defined by anchor receiving feature 11311.

Rod 11301 may include guide surface 11305. A segment of rod 11301 that includes guide surface 11305 may be a guide segment. Guide surface 11305 may guide tools into the bone. Guide surface 11305 may guide tools into the bone through aperture 11306. Aperture may be defined by ring-shaped segment 11312. Exemplary tools may include a k-wire, drill, reamer and/or implant. The drill may be any suitable drill, such as drill 1501 (shown in FIG. 15). The reamer may be any suitable reamer, such as reamer 1601 (shown in FIGS. 16-19). The implant may be the implant, such as implant 9720 (shown in FIG. 97A).

Guide surface 11305 may be configured to support the implant tail of the implant.

Rod 11301 may include threaded segment 11307. Threaded segment 11307 may threadedly engage an extension rod (not shown) that extends along central longitudinal rod axis $L_R$. A force may be applied to the extension rod to drive rod 11301 into a bone. The extension rod may be threadedly disengages from rod 11301 after rod is 11301 is positioned in the bone. Appling the force to the extension rod may mitigate a risk of deforming rod 11301 while inserting rod 11301 into the bone.

Rod 11301 may include anchor receiving feature 11309. Anchor receiving feature 11309 may receive an anchor that is driven through the implant tail (not shown). The anchor received by anchor receiving feature 11309 may secure the implant tail to the bone. The anchor received by anchor receiving feature 11309 may secure rod 11301 to the bone. The anchor received by anchor receiving feature 11309 may secure the implant to rod 11301.

Rod 11301 may include elongated extension member 11303. Extension member 11303 may have a length. The length of extension member 11303 may extend parallel to, or substantially parallel to, a central longitudinal axis of rod 13301. An outer surface of rod 11301 may be tubular and define a cylindrical surface. An outer surface of extension member 11303 may be coextensive with the cylindrical surface. An outer surface of extension member 11303 may be coextensive with a portion of the cylindrical surface. An inner surface of extension member 11303 may be coextensive with an inner surface of ring-shaped segment 11312.

An "outer" surface may be a surface of extension member 13303, rod 11301 or ring-shaped segment 11312 that is more distant from a central longitudinal axis of rod 11301. An "inner" surface may be a surface of extension member extension member 13303, rod 11301 or ring-shaped segment 11312 that is closer to the central longitudinal axis of rod 11301. A thickness of extension member 13303, rod 11301 or ring-shaped segment 11312 may be a distance between the inner and outer surfaces.

An outer surface of extension member 11303 may be planar, or substantially planar. An inner surface of extension member 11303 may be planar, or substantially planar.

Extension member 11303 may have a thickness. The thickness may extend between inner and outer surfaces of extension member 11303. The thickness of extension member 11303 may vary along the length of extension member 11303. The thickness of extension member 11303 may be less than a diameter of the cylindrical surface defined by rod 11301. A thickness of elongated extension member 11303 may less than a radius of the cylindrical surface defined by rod 11301. An outside surface of extension member 11303 may not completely encircle aperture 11306. A thickness of elongated extension member 11303 may not obscure aperture 11306. A thickness of elongated extension member 11303 may not obscure a trajectory defined by guide surface 11305.

An outside surface of extension member 11303 may not completely encircle ring-shaped segment 11312. A thickness of ring-shaped segment 11312 may vary along a central longitudinal axis of rod 11301. A thickness of ring-shaped segment 11312 may vary to accommodate the trajectory defined by guide surface 11305. The thickness of ring-shaped segment 11312 may vary about a central longitudinal axis defined by guide surface 11305. The thickness of ring-shaped segment 11312 may vary along the central longitudinal axis defined by guide surface 11305. The thickness of ring-shaped segment 11312 may vary about a central longitudinal axis defined by rod 11301. The thickness of ring-shaped segment 11312 may vary along the central longitudinal axis defined by rod 11301.

Ring-shaped segment 11312 may be thick at or near a joint with extension member 11303. Increased thickness at the joint may provide more robust support for extension member 11303.

An outer surface of extension member 11303 may have an arc length that is less than a circumferential length of the cylindrical surface defined by rod 11301. Elongated extension member 11303 may define a planar surface area. When rod 11301 is positioned inside a bone, elongated extension member 11303 may be positioned between a central longitudinal axis of the bone and cortical bone. When rod 11301 is positioned inside a bone, elongated extension member 11303 may be positioned between a central longitudinal axis of rod 11301 and an outer surface of rod 13301.

Extension member 11303 may include mating feature 11321. Mating feature 11321 may mate with a corresponding mating feature (not shown) in an extension rod (not shown). Mating feature 11321 may position the extension rod such a central longitudinal axis of the extension rod is perpendicular to, or substantially perpendicular, to axis $L_R$.

Extension member 11303 may include anchor receiving feature 11317. Anchor receiving feature 11317 may be configured to receive an anchor that locks rod 11301 to an extension rod. Anchor receiving feature 11317 may be threaded.

Using mating feature 11321 and anchor receiving feature 11317, an extension rod may be securely affixed to rod 11301. A force, applied to the extension rod may drive rod 11301 into the bone. The extension rod may be disengaged from rod 11301 after rod is 11301 is positioned in the bone. Mating feature 11321 may mitigate a risk of deforming rod 11301 while inserting rod 11301 into the bone.

Edge 11310 of extension member 11303 may be a mating feature. A first protrusion (e.g., of an extension rod) may be configured to mate with mating feature 11321. A depth of mating feature 11321 may be less than a thickness of extension member 11303. A second protrusion (e.g., of the extension rod) may be configured to abut edge 11310. Edge 11310 may touch the second protrusion. Edge 11310 may contact the second protrusion when a force is applied to the second protrusion (e.g., via the extension rod). Edge 11310 may have a thickness that is the same as, or different from, a thickness of extension member 11301. Edge 11301 may have a thickness that is at least equal to a depth of mating feature 11321.

Extension member 11303 may include mating feature 11308. Mating feature 11308 may mate with a corresponding mating feature (not shown) in an extension rod (not shown). Mating feature 11308 may position the extension rod such a central longitudinal axis of the extension rod is parallel to, or substantially parallel to, axis $L_R$. Mating feature 11308 may define a track for receiving a corresponding feature of the extension rod.

Figure 114:
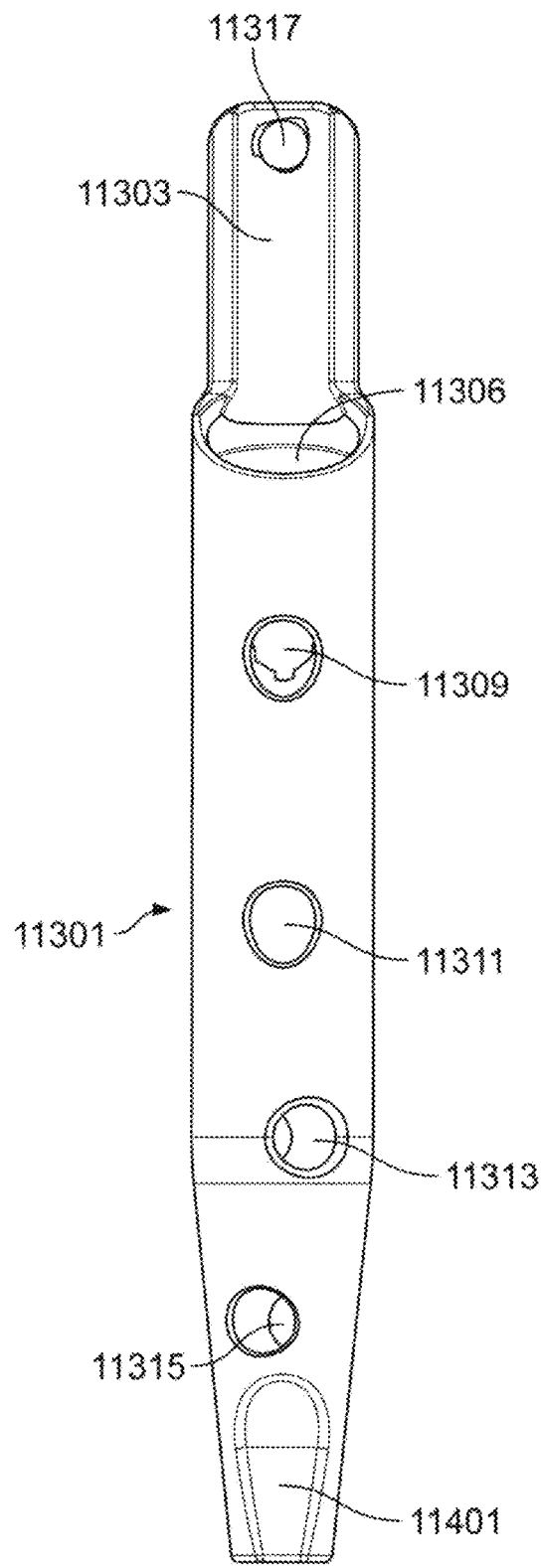
FIG. 114 shows illustrative apparatus in accordance with principles of the invention.

FIG. 114 shows another view of rod 11301. FIG. 114 shows that extension member 11303 does not obstruct aperture 11306. Tools guided by guide surface 11305 (shown in FIG. 113) may pass through aperture 11306 and into the bone without being obstructed by extension member 11303. Extension member 11303 may not obstruct an expansion of an implant inside the bone.

Figure 115:
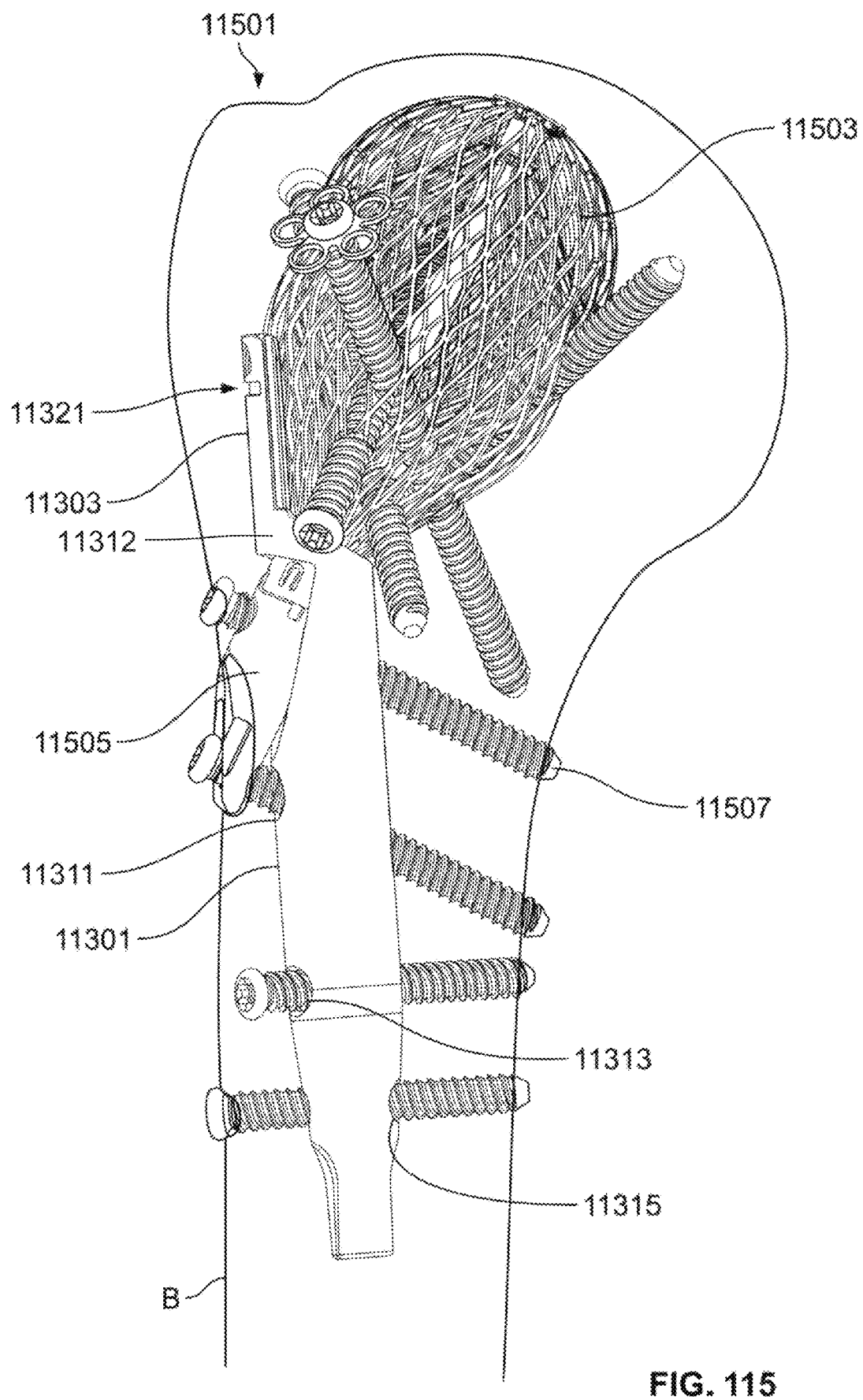
FIG. 115 shows illustrative apparatus and methods in accordance with principles of the invention.

FIG. 115 shows illustrative therapeutic scenario 1501. Scenario 11501 shows rod 11301 positioned inside bone B. Bone B may be any suitable bone. Exemplary bones may include a humerus and femur. Scenario 11501 shows implant 11503 positioned inside bone B. Implant 11503 may be inserted into bone B using guide surface 11305 (shown in FIG. 113). Scenario 11501 shows implant 11503 in an expanded state. Scenario 11501 shows that extension member 11303 does not obstruct expansion of implant 11503.

Scenario 11501 shows another view of mating feature. Scenario 11501 shows anchor 11507 positioned in anchor receiving features 11315, 11313 and 11311. Anchor 11507 may be received by anchor receiving feature 11309 (shown in FIG. 113).

Scenario 11501 shows the guide surface supporting implant tail 11505. Scenario 11501 also shows implant tail 11515 penetrating aperture 11306 defined by ring-shaped segment 11312. Implant head 11503 may also penetrate aperture 11306 defined by ring-shaped segment 11312.

Figure 116:
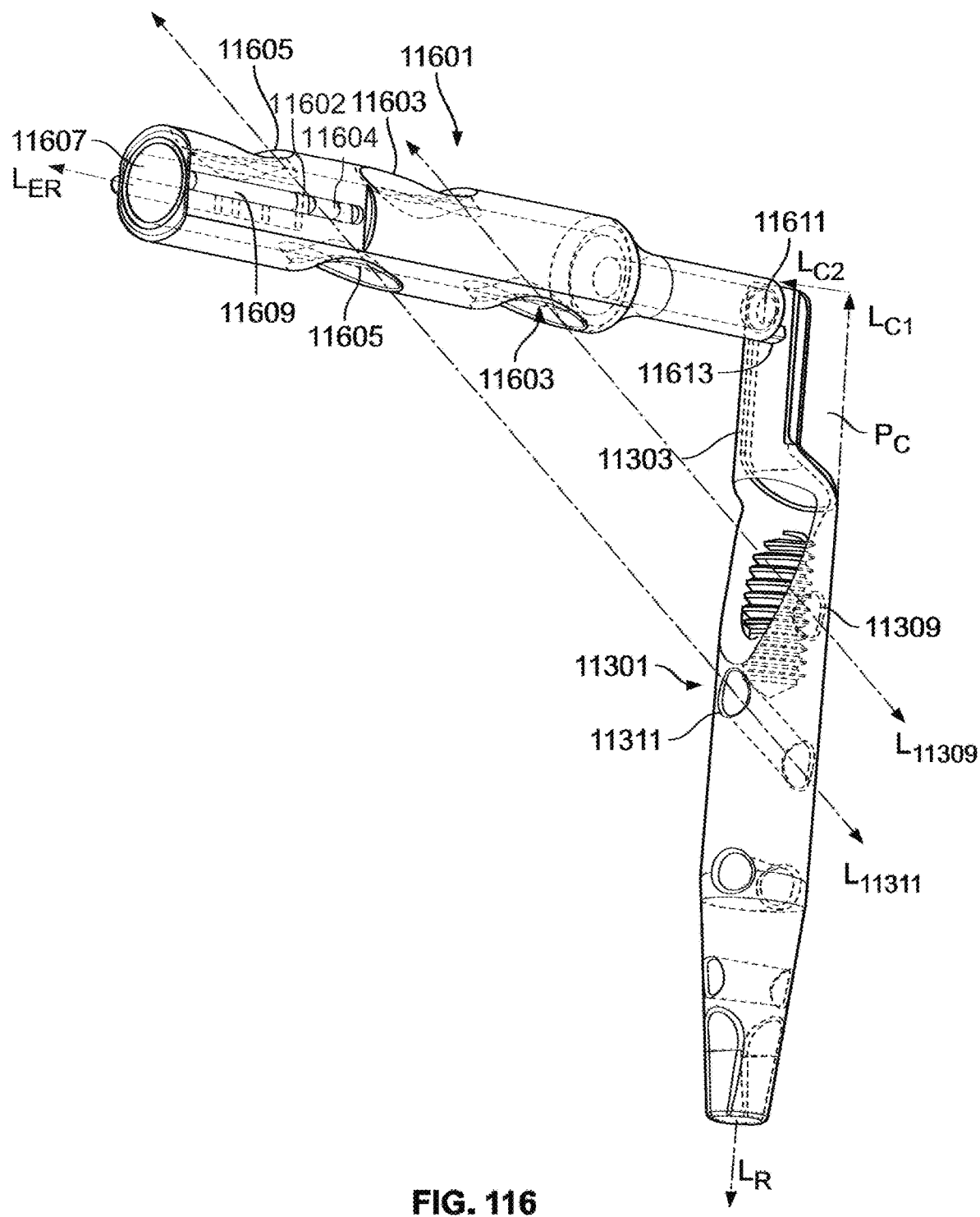
FIG. 116 shows illustrative apparatus and methods in accordance with principles of the invention.

FIG. 116 shows rod 11301 positioned relative to extension rod 11601. A central longitudinal axis $L_R$ of rod 11301 may be positioned perpendicular to, or substantially perpendicular to, a central longitudinal axis $L_{ER}$ of extension rod 11601.

Extension rod 11601 may include mating feature 11613. Mating feature 11613 may mate with mating feature 11321 (shown in FIG. 113) of rod 11301. Extension rod 11601 may include internal bore 11611. Positioning mating feature 11613 within mating feature 11321 may position internal bore 11611 relative to anchor receiving feature 11317 (shown in FIG. 113).

When internal bore 11611 is positioned relative to anchor receiving feature 11317, an anchor (not shown) may be driven through internal bore 11611 into anchor receiving feature 11317. The anchor may be inserted into extension rod 11601 via opening 11607. The anchor may threadedly engage anchor receiving feature 11317. Threaded engagement of the anchor and anchor receiving feature 11317 may lock extension rod 11601 to rod 11301. Extension rod 11601 may be locked to rod 11301 such that $L_R$ is perpendicular to, or substantially perpendicular to, $L_{ER}$. Extension rod 11601 may be locked to rod 11301 before rod 11301 is positioned inside a bone.

When extension rod 11601 is locked relative to rod 11301 mating feature 11613 may be securely mated to mating feature 11321. For example, mating feature 11601 may be received by mating feature 11321. When mating feature 11601 is securely mated to mating feature 11321, a force applied to extension rod 11601 may be transferred to rod 11301 without deforming extension member 11303 or any other component of rod 11301.

When rod 11301 is secured to extension rod 11601, pass-through 11605 may be aligned with central longitudinal axis $L_{11311}$ of anchor receiving feature 11311. Extension rod 11601 may remain affixed to rod 11301 after rod 11301 is positioned inside a bone. Tools may be inserted through pass-through 11605. The tools may be used to position an anchor, from an outside of the bone, within anchor receiving feature 11311.

When rod 11301 is secured to extension rod 11601, pass-through 11603 may be aligned with central longitudinal axis $L_{11309}$ of anchor receiving feature 11309. Extension rod 11601 may remain affixed to rod 11301 after rod 11301 is positioned inside a bone. Tools may be inserted through pass-through 11603. The tools may be used to position an anchor, from an outside of the bone, within anchor receiving feature 11309. For example, pass-through 11603 may be used to position anchor 11507 that secures implant 11503.

Extension rod 11601 may include rib 11609. Rib 11609 may secure targeting tools relative to extension rod 11601. The targeting tools may be used to direct one or more anchors into rod 11301 when rod 11301 is positioned inside the bone. The targeting tools may be used to direct one or more anchors into implant 11503 (shown in FIG. 115) when implant 11503 is positioned inside the bone.

Rib 11609 may include one or more cut-outs. FIG. 116 shows that rib 11609 includes cut-out 11602. FIG. 116 shows that rib 11609 includes cut-out 11604. A cut-out may receive a set screw affixed to targeting tools (not shown). Targeting tools may include a feature that mates with rib 11609. Targeting tools may be secured to extension rod 11601 by mating with rib 11609. A set screw may be driven into cut-outs 11602 and/or 11604 in rib 11609. Driving a set screw into cut-outs 11602 and/or 11604 may provide additional stability to targeting tools secured to rod 11301.

Extension rod 11601 may be unlocked and removed from rod 11301. Extension rod 11601 may be unlocked and removed from rod 11301 after rod 11301 is securely positioned inside a bone.

FIG. 116 shows clearance axis $L_{C1}$. Clearance axis $L_{C1}$ may represent space for positioning of a tool (e.g., drill or implant) inside a bone. Axis $L_{C1}$ may be parallel to an outer surface of rod 11301. FIG. 116 also shows clearance axis $L_{C2}$. Clearance axis $L_{C2}$ may represent space for positioning of a tool (e.g., drill or implant) inside a bone. $L_{C1}$, $L_{C2}$ and an inner surface of extension member 11303 may collectively define a clearance plane $P_C$ for positioning of a tool (e.g., drill or implant) inside a bone.

Clearance may include space for an expandable implant (such as implant 11503, shown in FIG. 115) to fully expand inside a bone. Clearance may include space for an expandable implant to fully expand inside the bone. Clearance may include space for an expandable implant to fully expand inside the bone when the implant is inserted into the bone at an angle, relative to a longitudinal axis of the bone. The angle may be defined by guide surface 11305 (shown in FIG. 113). Clearance may include space for an expandable implant to be therapeutically positioned within the bone. A therapeutic position for an implant may include a position, within the bone, that allows a practitioner to repair a fracture of the bone by securing one or more segments of the bone to the implant. An illustrative therapeutic position for an implant is shown in FIG. 115.

Figure 117:
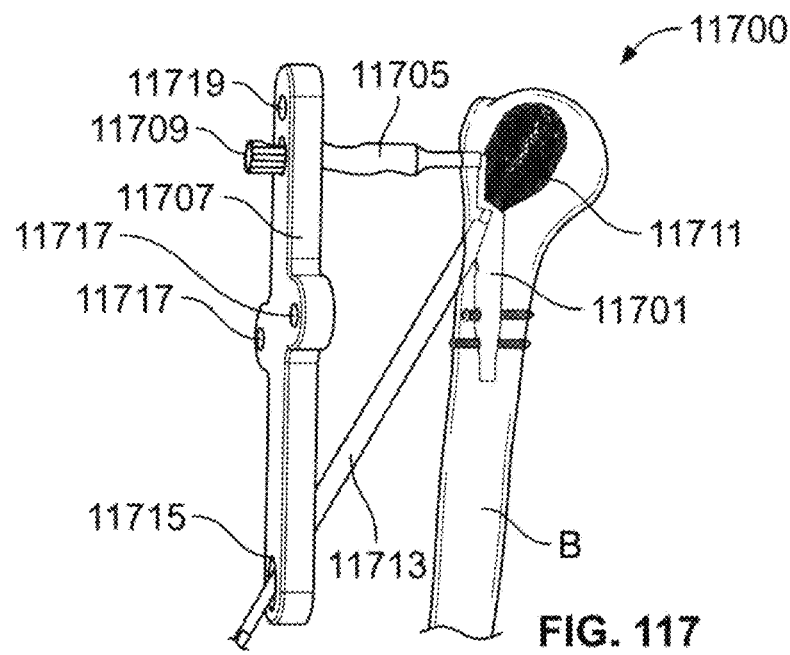
FIG. 117 shows illustrative apparatus and methods in accordance with principles of the invention.

FIG. 117 shows illustrative therapeutic scenario 11700. Scenario 11700 shows extension rod 11705. Extension rod 11705 may have one or more features in common with extension rod 11601 (shown in FIG. 116). Scenario 11700 shows rod 11701. Rod 11701 may have one or more features in common with rod 11301 (shown in FIG. 113). Scenario 11700 shows extension rod 11705 affixed to rod 11701. Rod 11701 is positioned inside bone B. Extension rod 11705 extends out of bone B.

Scenario 11700 shows targeting tool 11707 affixed to extension rod 11705. Set screw 11709 may be used to secure targeting tool 11707 to extension rod 11705. Targeting tool 11707 may include anchor receiving features 11717. Targeting tool 1707 may include anchor receiving feature 11719. When targeting tool 11707 is affixed to extension rod 11705, anchor receiving features 11717 and 11719 may be positioned to direct one or more anchors into target locations on rod 11701 and/or within bone B.

Target tool 11701 may include guide segment 11715. When targeting tool 11701 is affixed to extension rod 11705, and extension rod is affixed to rod 11701, guide segment 11715 may be positioned to direct tool 11713 into guide surface 11305 (shown in FIG. 113). Tool 11713 may be used to deploy implant 11711 inside bone B.

Figure 118:
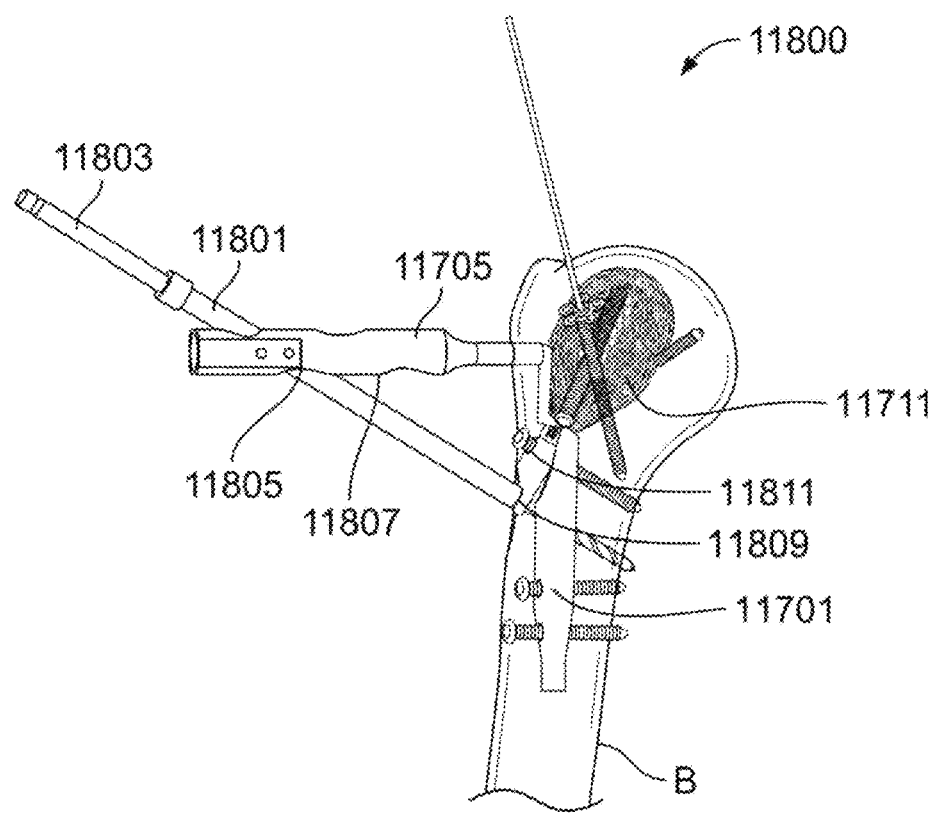
FIG. 118 shows illustrative apparatus and methods in accordance with principles of the invention.

FIG. 118 shows illustrative therapeutic scenario 11800. Scenario 11800 shows extension rod 11705 affixed to rod 11701. Rod 11701 is positioned inside bone B. Extension rod 11705 extends out of bone B. Scenario 11800 shows that when rod 11701 is positioned inside bone B, extension rod 11705 may be used to position tools 11801 and 11803 from an outside of bone B, relative to rod 11701 inside bone B. Scenario 11800 shows that when rod 11701 is positioned inside bone B, extension rod 11705 may be used to position tools 11801 and 11803 from an outside of bone B, relative to implant 11711 inside bone B.

For example, scenario 11800 shows that guide tube 11801 may be positioned within pass-through 11805 of extension rod 11705. Pass-through 11805 may include one or more features of pass-through 11605 (shown in FIG. 116). Positioning guide tube 11801 within the pass-through may allow drill 11803 to be positioned within guide tube 11801 and be aligned with an anchor receiving feature of rod 11701. For example, drill 11803 may create a pilot hole for an anchor that is received by anchor receiving feature 11311 (shown in FIGS. 113 and 115).

Extension rod 11705 may include pass-through 11807. Pass-through 11807 may include one or more features of pass-through 11603 (shown in FIG. 116). Pass-through 11807 may position a drill or other tool relative to anchor receiving feature 11309 (shown in FIGS. 113 and 116). When positioned relative to anchor receiving feature 11309, the drill may create a pilot hole for anchor 11811. Pass-through 11807 may be used to position anchor 11811.

Figure 119:
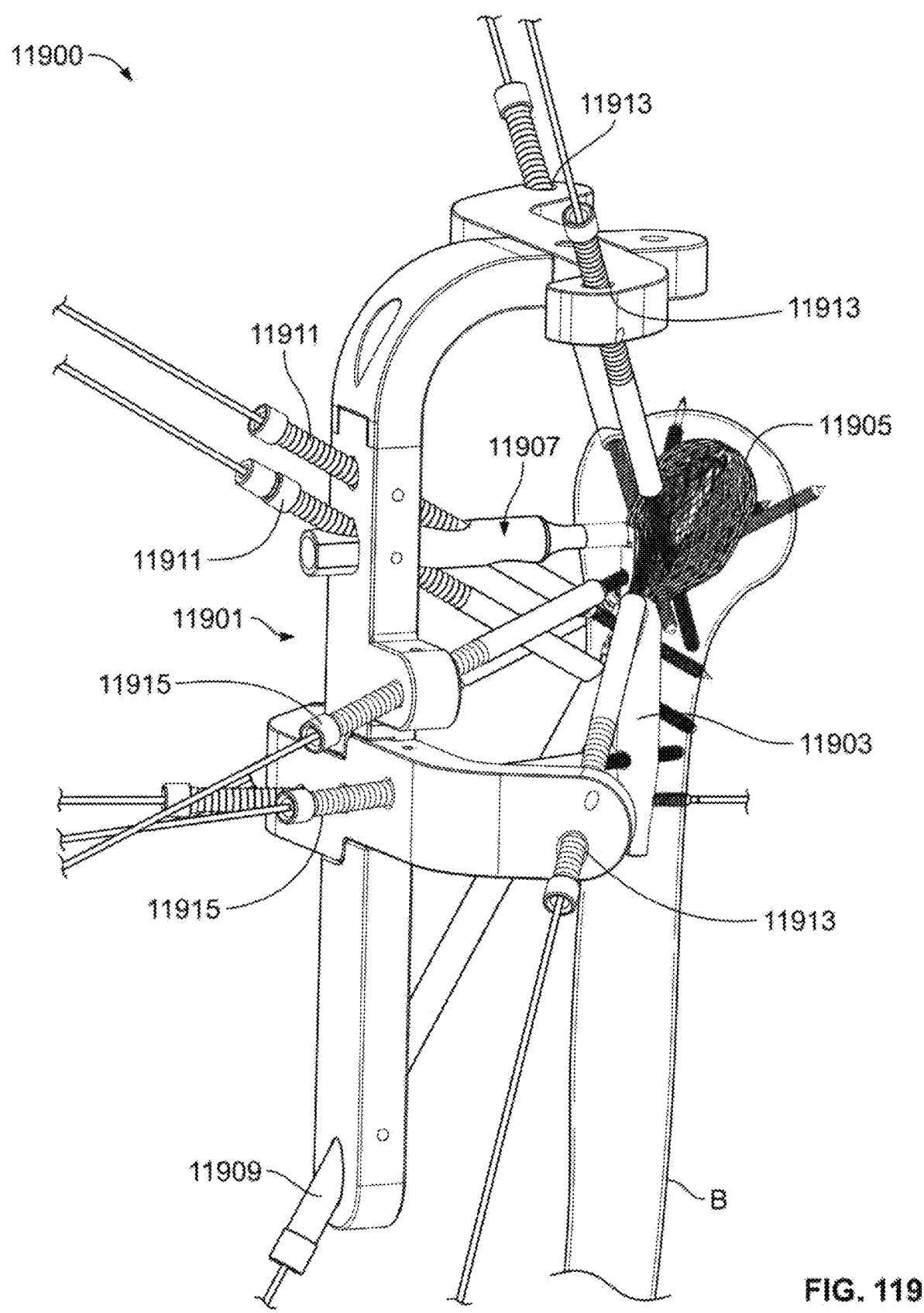
FIG. 119 shows illustrative apparatus and methods in accordance with principles of the invention.

FIG. 119 shows illustrative therapeutic scenario 11900. Scenario 11900 shows extension rod 11907 affixed to rod 11903. Extension rod 11907 may include one or more features of extension rod 11601 (shown in FIG. 116). Rod 11903 may include one or more features of rod 11301 (shown in FIG. 116). Rod 11903 is positioned inside bone B. Extension rod 11907 extends out of bone B.

Scenario 11900 shows that when rod 11903 is positioned inside bone B, targeting tool 11901 may be affixed to extension rod 11907. Targeting tool 11901 may be affixed to extension rod 11907 such that the targeting tools 11901 are positioned outside of bone B. When targeting tool 11901 is affixed to extension rod 11907. Guide surfaces of targeting tool 11901 may be aligned with anchor receiving features, positioned inside bone B, of rod 11903 and/or implant 11905.

Targeting tool 11901 may include one or more guide surfaces. For example, targeting tool 11901 may include guide surfaces that position tools 11909, 11915, 11913, 11911 and 11911. The one or more guide surfaces may direct a k-wire, anchor, drill, reamer wires, guide tubes or other tool into anchor receiving features of rod 11903 after rod 11903 is inside bone B. The one or more guide surfaces may direct a k-wire, anchor, drill, reamer, wires, guide tubes or other tool into anchor receiving features of implant 11905 after implant 11905 is inside bone B. Anchor receiving features of implant 11905 may include anchor receiving features in the implant tail of implant 11905. Anchor receiving features of implant 11905 may include anchor receiving features in the implant head of implant 11905.

Guide surfaces of targeting tool 11901 may be aligned with anchor receiving features of rod 11903 and/or implant 11905 when rod 11701 is positioned inside bone B, extension rod 11705 may be used to position tools 11801 and 11803 from an outside of bone B, relative to implant 11711 inside bone B.

FIG. 120 shows rod 12000. Rod 12000 may include one or more features of rod 11301 (shown in FIG. 113). Rod 11301 may include one or more features of rod 12000.

Rod 12000 may be tubular. Rod 12000 may include rod body 12006. Rod body 12006 may include a length that defines a cylindrical surface. For example, rod body 12006 may define cylindrical surface 12010. Rod body 12006 may include a length that defines a cylindrical surface.

An outer surface of rod body 12006 may define axes $L_{OS1}$ and Lose. Axes $L_{OS1}$ and Lose may be parallel to a central longitudinal axis of rod 12000.

Rod 12000 may include tapered segment 12008. Tapered segment 12008 may define a conical surface. For example, tapered segment 12008 may define conical surface 12012. Tapered segment 12008 may define a conical surface.

Rod 12000 may include anchor receiving feature 12005. Anchor receiving feature 12005 may define a first central longitudinal axis (not shown). The first central longitudinal axis may be oblique to the central longitudinal axis of rod 12000. An anchor driven through anchor receiving feature 12005 may secure rod 12000 to a bone, such as bone B (shown in FIG. 115). An anchor may be driven through anchor receiving feature 12005 at an angle defined by the intersection of central longitudinal axis of anchor receiving feature 12005 and central longitudinal axis of rod 12000.

Rod 12000 may include anchor receiving feature 12003. Anchor receiving feature 12003 may define a second central longitudinal axis (not shown). The second central longitudinal axis may be oblique to a central longitudinal axis of rod 12000. An anchor driven through anchor receiving feature 12003 may secure rod 12000 to a bone, such as bone B (shown in FIG. 115). An anchor may be driven through anchor receiving feature 12003 at an angle defined by the intersection of central longitudinal axis of anchor receiving feature 12003 and central longitudinal axis of rod 12000.

A first planar surface (not shown) may include the first central longitudinal axis defined by anchor receiving feature 12005. A second planar surface (not shown) may include the second central longitudinal axis defined by anchor receiving feature 12003. The first planar surface may be parallel to the second planar surface.

The axes defined by anchor receiving features 12005 and 12003 may direct anchors into a bone at different angles with respect to a central longitudinal axis of rod 12000. The axes defined by anchor receiving features 12005 and 12003 may direct anchors into a bone within parallel planar surfaces. Driving anchors into a bone at different angles and in parallel surfaces may decrease stress risers in the bone. The stress risers may be due to threaded engagement of the anchors with the bone.

An anchor may include a head. The head may not pass through anchor receiving feature 12005 or 12003. The stress risers may be due to threaded engagement of the anchors with the bone and a bracing of the anchor head against an outer surface of rod 12000. The stress risers may be due to threaded engagement of the anchors with the bone and a bracing of the anchor head against an outer surface of the bone.

Rod 12000 may include guide surface 12001. A segment of rod 12000 that includes guide surface 12001 may be a guide segment. Guide surface 12001 may guide tools into the bone. Guide surface 12001 may guide tools into the bone through aperture 12002. Guide surface 12001 may guide tools into the bone at an angle that is oblique to a central longitudinal axis of rod 12000. Exemplary tools may include a k-wire, drill, reamer and/or implant. The drill may be any suitable drill, such as drill 1501 (shown in FIG. 15). The reamer may be any suitable reamer, such as reamer 1601 (shown in FIGS. 16-19). The implant may be any suitable implant, such as implant 9720 (shown in FIG. 97A).

Rod 12000 may include anchor receiving feature 12007. Anchor receiving feature 12007 may define a third central longitudinal axis (not shown). The third central longitudinal axis may be oblique to a central longitudinal axis of rod 12000. An anchor driven through anchor receiving feature 12007 may secure rod 12000 to the bone. The third central longitudinal axis may intersect the first and the second planar surfaces.

Rod 12000 may include anchor receiving feature 12009. Anchor receiving feature 12009 may define a fourth central longitudinal axis (not shown). An anchor driven through anchor receiving feature 12009 may secure rod 12000 to the bone. The fourth central longitudinal axis may intersect the first and the second planar surfaces. The fourth central longitudinal axis may intersect the first and the second planar surfaces.

The fourth central longitudinal axis defined by anchor receiving feature 12009 may be parallel to the third central longitudinal axis defined by anchor receiving feature 12007. The fourth central longitudinal axis defined by anchor receiving feature 12009 may intersect the third central longitudinal axis defined by anchor receiving feature 12007.

Anchor receiving features 12007 and 12009 may receive anchors that secure rod 12000 to a bone. Anchor receiving features 12007 and 12009 may receive anchors that secure an implant to the bone. Anchor receiving features 12007 and 12009 may receive anchors that secure a tail of the implant to rod 12000 and the bone.

Rod 12000 may include elongated extension member 12004. Extension member 12004 may include mating feature 12011 and mating feature 12012. Mating features 12011 and 12012 may mate with corresponding mating features (not shown) in an extension rod (not shown). Mating features 12011 and 12012 may position the extension rod such that a central longitudinal axis of the extension rod is perpendicular to, or substantially perpendicular to, a central longitudinal axis of rod 12000.

Rod 12000 include cannulated segment 12014. Cannulated segment 12014 may be threaded. For example, a threaded tool (e.g., screw or extension rod) may be threadedly inserted into cannulated segment 12014 via aperture 12013. A tool that engages cannulated segment 12014 may be positioned such a central longitudinal axis of the tool is parallel to, or substantially parallel to, a central longitudinal axis of rod 12000.

Cannulated segment 12014 may have a width (or diameter) that is less than a width (or diameter) of rod 12000. The difference in width (or diameter) may allow a tool to slide over cannulated segment 12014 without increasing an overall width (or diameter) of rod 12000. A tool that slides over cannulated segment 12014 may also threadedly engage cannulated segment 12014 via aperture 12013.

Elongated extension member 12004 may include anchor receiving feature 12017. Anchor receiving feature 12017 may be configured to receive an anchor that locks rod 12000 to an extension rod (not shown). Anchor receiving feature 12017 may be threaded.

An extension rod may include mating features that mate with mating feature 12011 and/or mating feature 12012. For example, mating features 12011 and 12012 may include depressions in a surface of rod 12000. An extension rod may include one or more protrusions that fit into the depressions. When mating features of an extension rod are joined to mating features 12011 and 12012, a guide surface of the extension rod may be positioned over anchor receiving feature 12017. An anchor may be driven through the extension rod into anchor receiving feature 12017 and securely affixed the extension rod to rod 12000.

A force, applied to the extension rod may drive rod 12000 into the bone. The extension rod may be disengaged from rod 12000 after rod is 12000 is positioned in the bone. Mating features 12011 and 12012 may mitigate a risk of deforming rod 12000 when applying the force to the extension rod and inserting rod 12000 into the bone.

FIG. 121 shows another view of rod 12000. FIG. 121 shows that elongated extension member 12004 may include an outer surface area that is less than an outer surface area of rod body 12006. For example, rod body 12006 may define a cylindrical surface. In some embodiments, rod body 12006 may define a cylindrical surface.

Rod body 12006 may have an outer surface area that is larger than an outer surface area of elongated extension member 12004. Less outer surface area may provide elongated extension member 12004 with clearance for tools inserted into a bone via guide surface 12001 and aperture 12002.

Clearance may include space for an expandable implant to fully expand inside the bone. Clearance may include space for an expandable implant to fully expand inside the bone. Clearance may include space for an expandable implant to fully expand inside the bone when the implant is inserted into the bone at an angle, relative to a longitudinal axis of the bone, defined by guide surface 12001. Clearance may include space for an expandable implant to be therapeutically positioned within the bone. A therapeutic position for an implant may include a position, within the bone, that allows a practitioner to repair a fracture of the bone by securing one or more segments of the bone to the implant.

FIG. 121 shows that cannulated segment 12014 is spaced apart from aperture 12012 by a length of elongated member 12004. FIG. 121 shows that cannulated segment 12014 may include an outer surface area that is larger than an outer surface area of elongated extension member 12004. FIG. 121 also shows that cannulated segment 12014 may include an outer surface area that is smaller than an outer surface area of rod body 12006.

Figure 122:
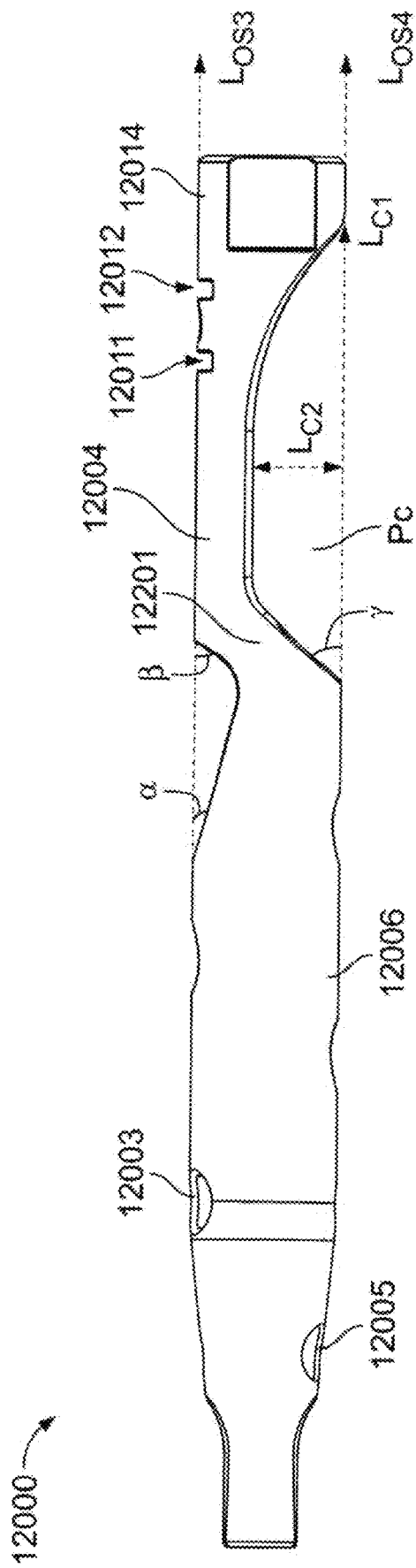
FIG. 122 shows illustrative apparatus accordance with principles of the invention.

FIG. 122 shows another view of rod 12000. FIG. 122 shows that rod body 12006 defines outer surface axes $L_{OS3}$ and $L_{OS4}$. Guide surface 12001 (shown in FIG. 120) may form angle $\alpha$ with axis $L_{OS3}$. A slope of guide surface 12001 may be defined by $\tan(\alpha)$. Ring-shaped segment 12201 may bridge between guide surface 12001 and elongated extension member 12004. Ring-shaped segment 12201 may form angle $\beta$ with $L_{OS3}$. A central longitudinal axis (not shown) of rod 12000 may pass through ring-shaped segment 12201.

FIG. 122 shows clearance axis $L_{C1}$. Axis $L_{C1}$ may be an extension of outer surface axis $L_{OS4}$ defined by rod body 12006. Ring-shaped segment 12201 may define angle $\gamma$ with clearance axis $L_{C1}$. Angle $\gamma$ may be different from angle $\beta$. Angle $\gamma$ may be equal to angle $\beta$.

Clearance axis $L_{C1}$ may represent space for positioning of a tool (e.g., drill or implant) inside a bone. Axis $L_{C1}$ may be parallel to an outer surface axis $L_{OS}$. FIG. 122 also shows clearance axis $L_{C2}$. Clearance axis $L_{C2}$ may also represent space for positioning of a tool (e.g., drill or implant) inside a bone. $L_{C1}$, $L_{C2}$ and an inner surface of extension member 12004 may collectively define a clearance plane $P_C$ for positioning of a tool (e.g., drill or implant) inside a bone. Clearance plane $P_C$ may provide space for positioning the tool inside a bone after the tool is inserted into the bone via aperture 12002 defined by ring-shaped element 12201.

Figure 123:
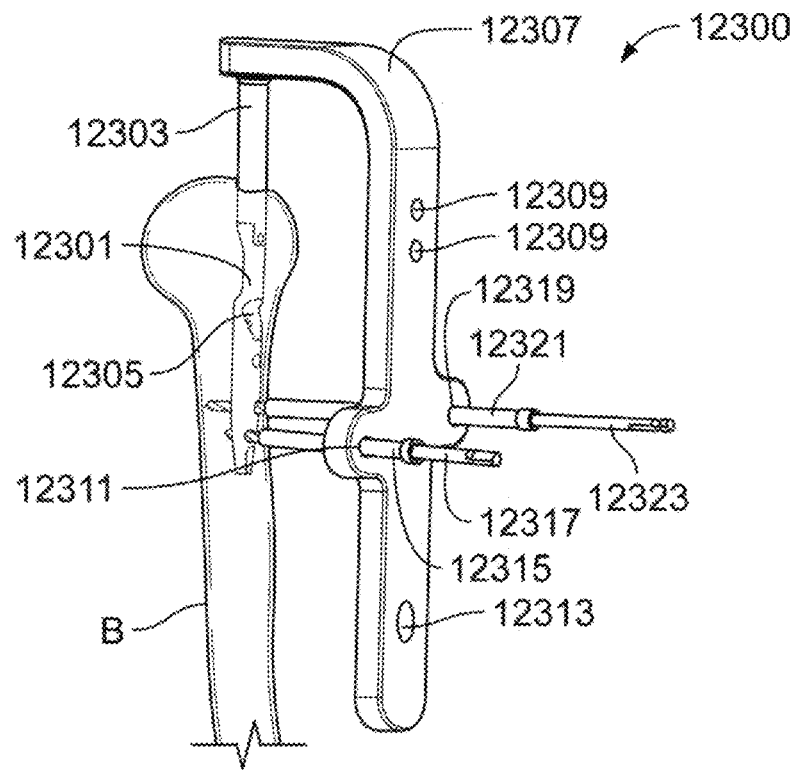
FIG. 123 shows illustrative apparatus and methods in accordance with principles of the invention.

FIG. 123 shows illustrative therapeutic scenario 12300. Scenario 12300 shows rod 12301 positioned inside bone B. Rod 12300 may include one or more features of rod 11301 (shown in FIG. 113), rod 11701 (shown in FIG. 117), rod 11903 (shown in FIG. 119) and rod 12000 (shown in FIG. 120).

Scenario 123 shows extension rod 12303 affixed to rod 12301. Extension rod 12303 may be affixed to rod 12303 by threadedly engaging cannulated segment 12014 (shown in FIG. 120). Extension rod 12303 may slide into a space between surface 12010 and surface 12015 of cannulate segment 12014 (shown in FIG. 120). Extension rod 12303 may be cannulated. An anchor (not shown) a cannulated extension rod 12303 may direct an anchor into cannulate segment 12014. The anchor may threadedly engage cannulated segment 12014 and affix extension rod 12303 to rod 12301.

After rod 12301 is affixed to extension rod 12303, a force may be applied to extension rod 120303. The force may drive rod 12301 into bone B. The force may drive rod 12301 into bone B without deforming rod 12301. Scenario 12300 shows that rod 12301 may be driven into bone B through an articular surface of bone B.

After rod 12301 is positioned inside bone B, a first length of extension rod 12303 may be positioned inside bone B. After rod 12301 is positioned inside bone B, a second length of extension rod 12303 may be positioned outside bone B.

Targeting tools may be affixed to the second length of extension rod 12303 that extends outside of bone B. Scenario 12300 shows targeting tool 12307 affixed to extension rod 12303. Targeting tool may be a jig that includes apertures and guide surfaces. The apertures and guide surface may direct tools (e.g., drill, reamer, k-wire, guide tube, anchor) into targeted positions on rod 12301. Such targeted positions may include anchor receiving features in rod 12301.

For example, scenario 12300 shows tools 12315 and 12317 passing through aperture 12311, through bone B and into an anchor receiving feature of rod 12301. Scenario 12300 also shows tools 12321 and 12323 passing through aperture 12319, through bone B and into an anchor receiving feature of rod 12301.

Targeting tool 12307 may include aperture 12313. Aperture 12313 and an associated guide surface (not shown) may direct tools through bone B and on to guide surface 12305. Guide surface 12305 may include one or more features of guide surface 12001 (shown in FIG. 120).

Targeting tool 12307 may include apertures 12309. Apertures 12309 may be associated with guide surfaces that direct tools into bone B. Apertures 12309 may be associated with guide surfaces that direct tools into an implant positioned inside bone B. Apertures 12309 may be associated with guide surfaces that direct tools into rod 12301 after rod 12301 is positioned inside bone B.

Extension rod 12303 may be removed from bone B after rod 12301 is secured to bone B. Extension rod 12303 may be removed from bone B after a fracture in bone B has been repaired.

Figure 124:
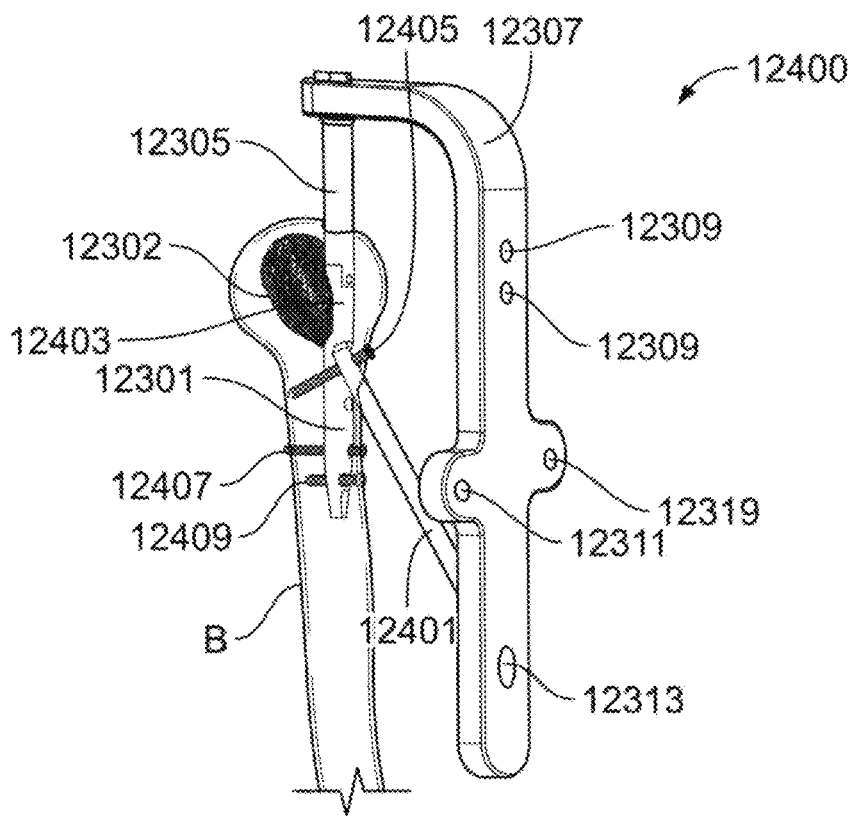
FIG. 124 shows illustrative apparatus and methods in accordance with principles of the invention.

FIG. 124 shows illustrative therapeutic scenario 12400. Scenario 12400 shows targeting tool 12307 affixed to extension rod 12303. Scenario 12400 shows tool 12401 passing through aperture 12313 and on to guide surface 12305 (shown in FIG. 123). Tool 12401 may be used to deploy implant 12403 inside bone B.

Implant 12403 may pass through aperture 12313 and aperture 12002 (shown in FIG. 120) in a collapsed state. Implant 12403 may be expanded inside bone B. Elongated extension member 12302 of rod 12301 may provide clearance for expansion of implant 12403 inside bone B. Elongated extension member 12302 of rod 12301 may provide clearance for positioned of collapsed or expanded implant 12403 inside bone B.

Anchor 12405 may pass through a tail of implant 12403. Anchor 12405 may be directed into implant 12403 and rod 12301 using guide surfaces associated with one or more of apertures 12309 in target tool 12307. Anchor 12409 may be directed into bone B and into rod 12301 using a guide surface associated with aperture 12311. Anchor 12407 may be directed into bone B and into rod 12301 using a guide surface associated with aperture 12319.

Figure 125:
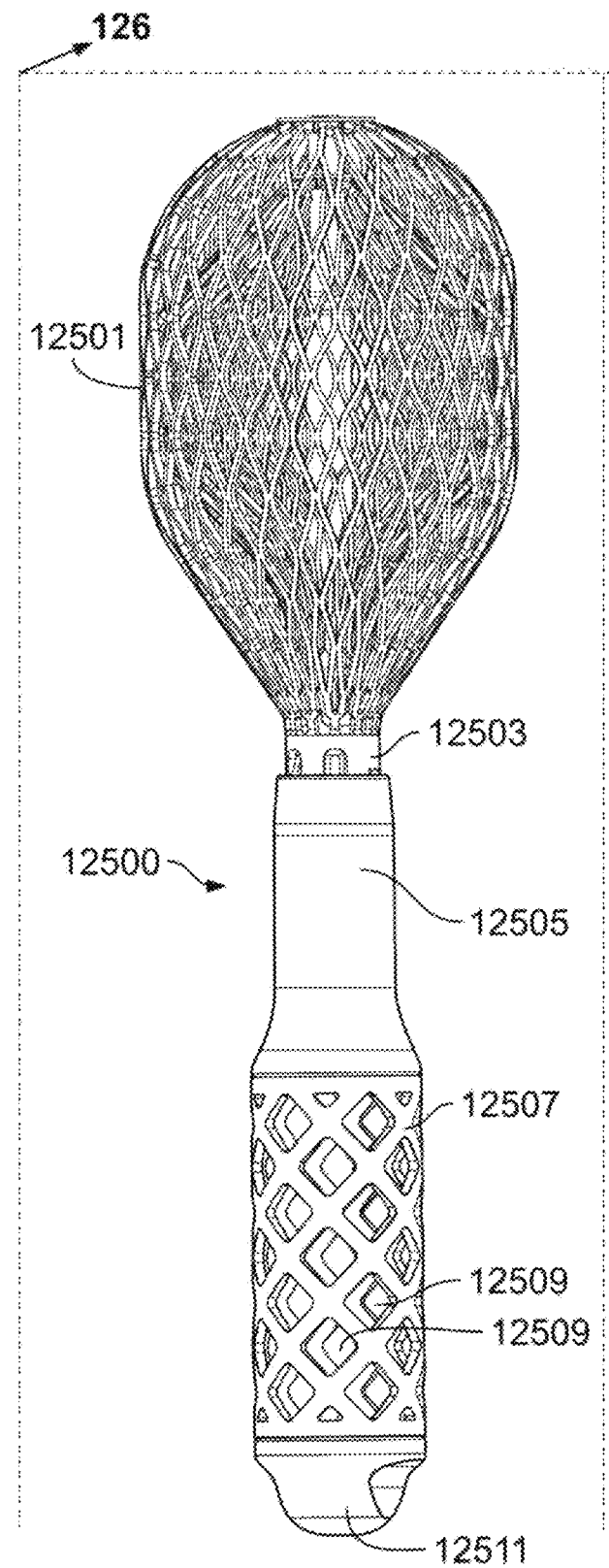
FIG. 125 shows illustrative apparatus in accordance with principles of the invention.

FIG. 125 shows illustrative apparatus 12500. Apparatus 12500 may include the implant. The implant may include implant head 12501 and implant base 12503 positioned between implant head 12501 and implant tail (not shown).

Apparatus 12500 may include an elongated member removably coupled to the implant. The elongated member may include sleeve 12505, anchoring base 12507 and end 12511. End 12511 may be tapered.

Anchoring base 12507 may include a hollow mesh structure defining a plurality of openings 12509. Anchoring base 12507 may extend between sleeve 12505 and end 12511.

Openings 12509 may be sized to receive anchors for fixing anchoring base 12507 to a bone B. The anchors may be screws. A practitioner may drive a screw into anchoring base 12507 without using a jig to register the anchor to an opening 12509.

Apparatus 12500 may be positioned in a bone. Apparatus 12500 may be positioned in a shaft of a bone. Apparatus 12500 may be positioned along a neck of a bone such that the implant head extends into a head of the bone. Apparatus 12500 may be positioned in any other suitable location in a bone.

Figure 126:
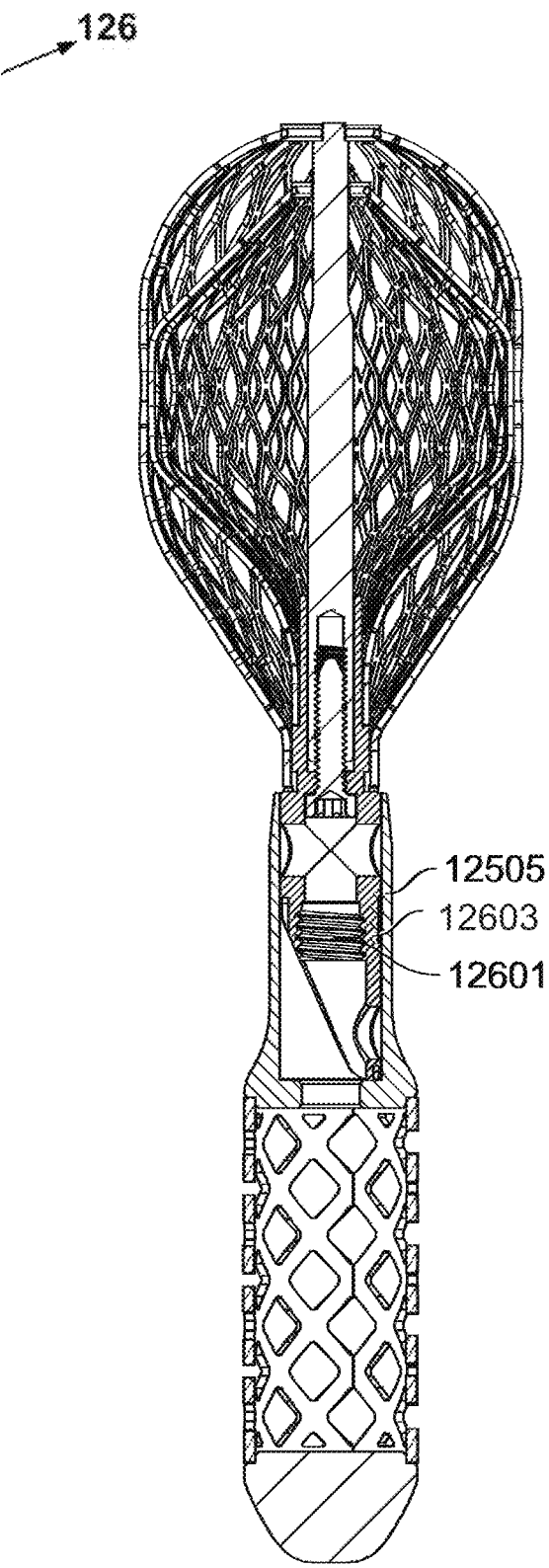
FIG. 126 shows a cross-sectional view of apparatus illustrated in FIG. 125.

FIG. 126 shows a cross-sectional view of apparatus illustrated in FIG. 125 taking along lines 126-126. FIG. 126 shows implant tail 12603 positioned in sleeve 12505. FIG. 126 also shows threaded member 12601 fixed to sleeve 12505. Threaded member 12601 extends along a sleeve longitudinal axis and is spaced radially apart from the sleeve 12505 to define an annular space. Tail 12603 is seated in the annular space. Threaded member 12601 is shown engaged with an inner threaded portion of tail 12603 to couple the elongated member to the implant.

Figure 127:
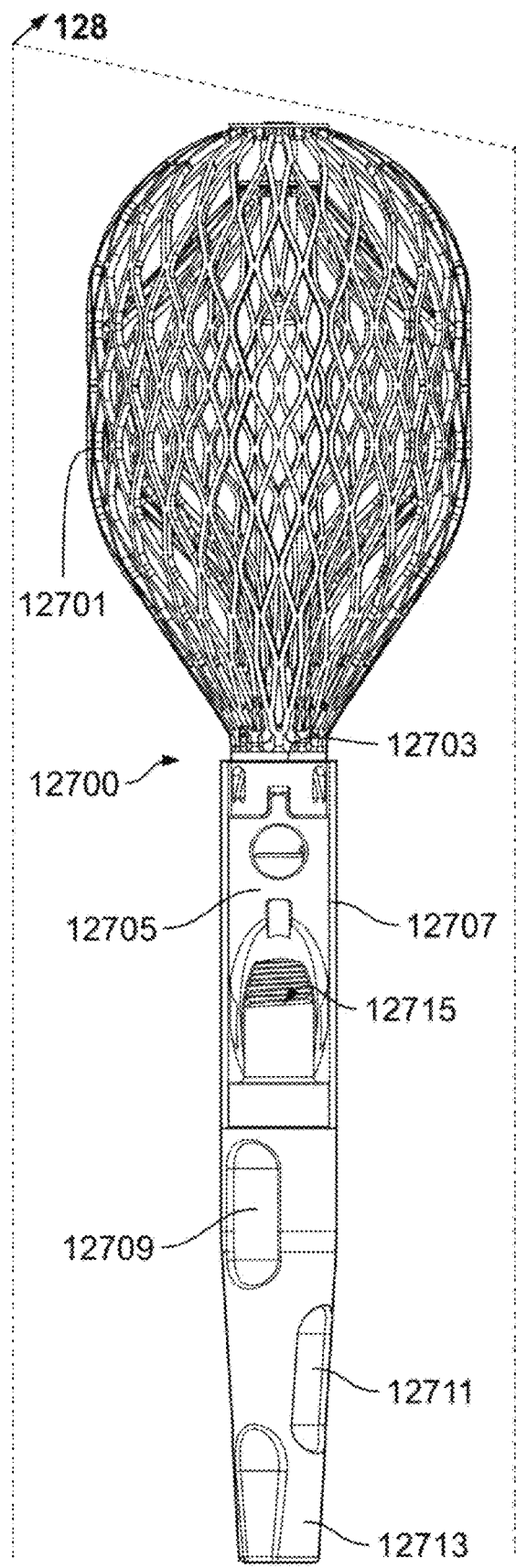
FIG. 127 shows illustrative apparatus in accordance with principles of the invention.

FIG. 127 shows illustrative apparatus 12700. Apparatus 12700 may include the implant. The implant may include implant head 12701 and implant base 12703 positioned between implant head 12701 and implant tail 12705.

Apparatus 12700 may include an elongated member removably coupled to the implant. The elongated member may include sleeve 12707. In FIG. 127, sleeve 12707 is illustrated as transparent to show implant tail 12705 and threaded member 12715 positioned in sleeve 12707.

The elongated member may include threaded member 12715. Threaded member 12715 may be fixed to the sleeve and extend along a sleeve longitudinal axis. Threaded member 12715 may be spaced radially apart from sleeve 12707 to define an annular space.

The elongated member may include end 12713 and an anchoring base extending between sleeve 12707 and end 12713. The anchoring base may define slots 12709 and 12711. End 12713 may be tapered.

Apparatus 12700 may be positioned in a bone. Apparatus 12700 may be positioned in a shaft of a bone. Apparatus 12700 may be positioned along a neck of a bone such that the implant extends into a head of the bone. Apparatus 12700 may be positioned in any other suitable location in the bone.

Figure 128:
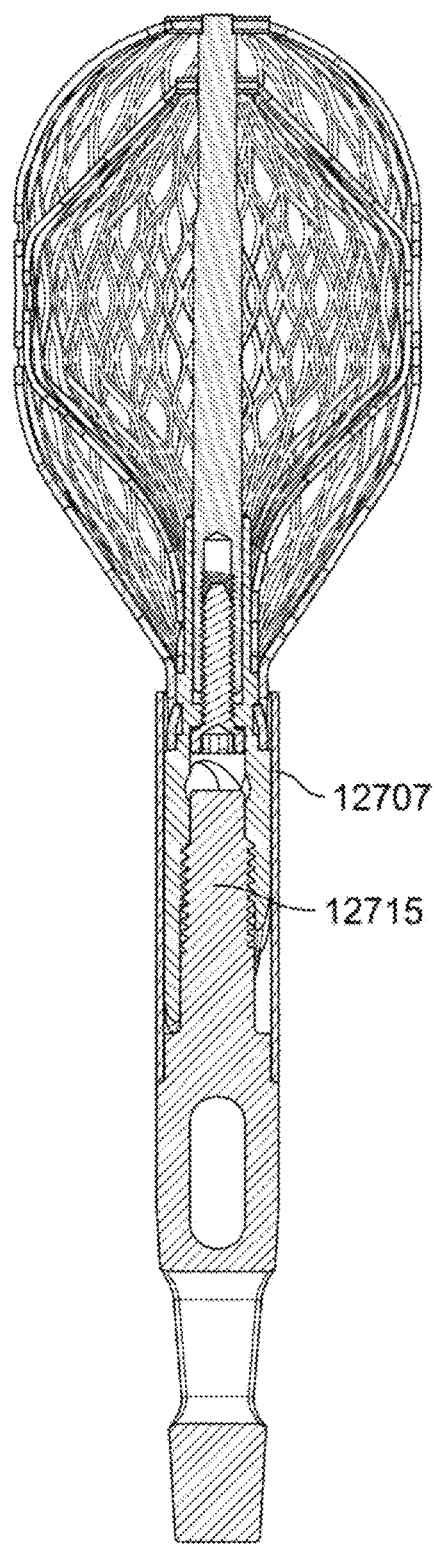
FIG. 128 shows a cross-sectional view of apparatus illustrated in FIG. 127.

FIG. 128 shows a cross-sectional view of apparatus illustrated in FIG. 127 taking along lines 128-128. FIG. 128 shows threaded member 12715 engaged with an inner threaded portion of tail 12705 to couple the elongated member to the implant.

Figure 129:
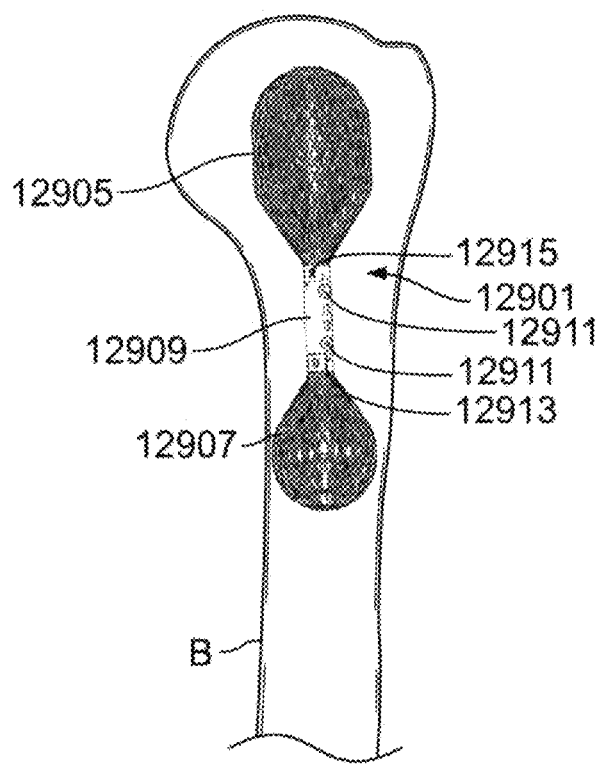
FIG. 129 shows illustrative apparatus and methods in accordance with principles of the invention.

FIG. 129 shows illustrative apparatus 12901 positioned in bone B. Apparatus 12901 may include first implant head 12905 and first implant base 12915 coupled to first implant head 12905. Apparatus 12901 may include second implant head 12907 and second implant base 12913 coupled to second implant head 12907. First implant head 12905 may have one or more features in common with the implant head. Second implant head 12907 may have one or more features in common with the implant head.

First implant head 12905 may be expandable. Second implant head 12907 may be expandable. One or both of implant head 12905 and 12907 may be expanded in bone B. One or both of implant head 12905 and 12907 may be expanded prior to positioning in bone B. One or both of implant head 12905 and 12907 may not be expandable.

First implant head 12905 and second implant head 12907 may self-expand in the bone after being removed from a sheath. First implant head 12905 and second implant head 12907 may be manually expandable. A practitioner may insert apparatus 12901 in the bone prior to expansion of first implant head 12905 and second implant head 12907. A practitioner may insert apparatus 12901 in the bone after the expansion of first implant head 12905 and/or second implant head 12907.

First implant head 12905 may have a first volume. Second implant head 12907 may have a second volume. The first volume may be equal to the second volume. A shape defined by an outer face of first implant head 12905 may be the same as, or different from, a shape defined by an outer face of second implant head 12907.

Apparatus 12901 may include shaft 12909. Shaft 12909 may be straight. Shaft 12909 may include one or more bent sections (not shown) to position implant head 12905 and implant head 12907 in desirable anatomical positions in a bone.

Shaft 12909 may be an implant tail. Shaft 12909 may be an intramedullary rod. Shaft 12909 may be a cannulated tube. Shaft 12909 may be a solid tube.

Shaft 12909 may extend between first implant base 12915 and second implant base 12913. Shaft 12909 may couple the first implant head 12905 to second implant head 12907. A first end of shaft 12909 may be coupled to first implant base 12915. A second end of shaft 12909 may be coupled to second implant base 12915. Shaft 12909 may be rigidly coupled to one or both of first implant base 12915 and second implant base 12913. Shaft 12909 may be configured to be coupled to one or both of first implant base 12915 and second implant base 12913 by threads, snap-fit, friction fit, or any other suitable attachment mechanism described herein or known to those skilled in the art.

Shaft 12909 may define one or both of holes 12911. Shaft 12909 may define additional holes extending through shaft 12909. Holes 12911 may be sized to receive an anchor such as a screw. Shaft 12909 may define a mesh structure extending circumferentially around some or all of a central axis of shaft 12909. Shaft 12909 may define one or more slots.

Figure 130:
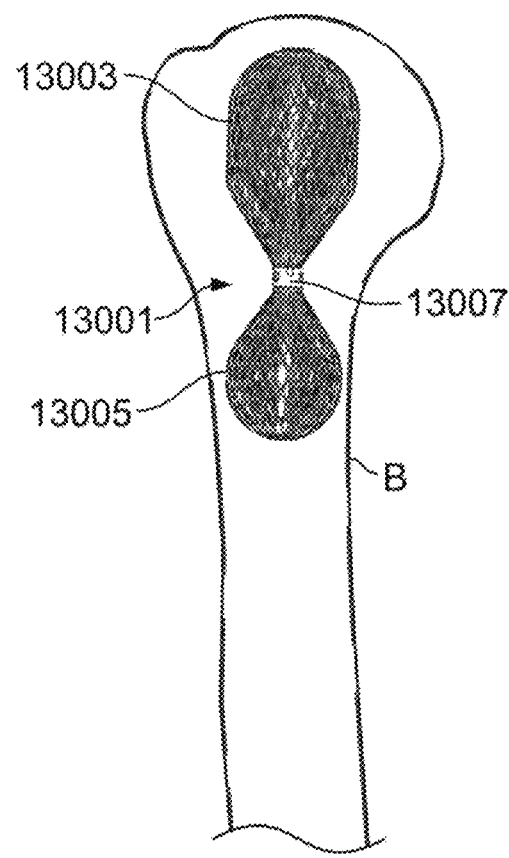
FIG. 130 shows illustrative apparatus and methods in accordance with principles of the invention.

FIG. 130 shows illustrative apparatus 13001 positioned in bone B. Apparatus 13001 may include first implant head 13003 and second implant head 13005. First implant head 13003 may have one or more features in common with the implant head. Second implant head 13005 may have one or more features in common with the implant head.

First implant head 13003 may be expandable. Second implant head 13005 may be expandable. First implant head 13003 and second implant head 13005 may self-expand in bone B after being removed from a sheath. First implant head 13003 and second implant head 13005 may be manually expandable. A practitioner may insert apparatus 13001 in bone B prior to expansion of first implant head 13003 and second implant head 13005. A practitioner may insert apparatus 13001 in bone B after expansion of first implant head 13003 and/or second implant head 13005.

Base 13007 may be positioned between first implant head 13003 and 13005. Base 13007 may be rigidly fixed to first implant head 13003. Base 13007 and first implant head 13003 may be, together, monolithic. Base 13007 may be rigidly fixed to second implant head 13005. Base 13007 and second implant head 13005 may be, together, monolithic. Base 13007 may be rigidly fixed to first implant head 13003 and second implant head 13005. Base 13007, first implant head 13003 and second implant head 13005 may be, together, monolithic.

Base 13007 may be a first base. Base 13007 be rigidly fixed to first implant head 13003. Second implant head 13005 may be rigidly fixed to a second base. The second base may be coupled to an inner face of base 13007 by threads, snap fit, friction fit, or any other suitable attachment mechanism described herein or known to those skilled in the art.

A practitioner may advance one or more screws into first implant head 13003 and second implant head 13005. A practitioner may advance screws into one or both of first and second implant heads without using a jig.

Figure 131:
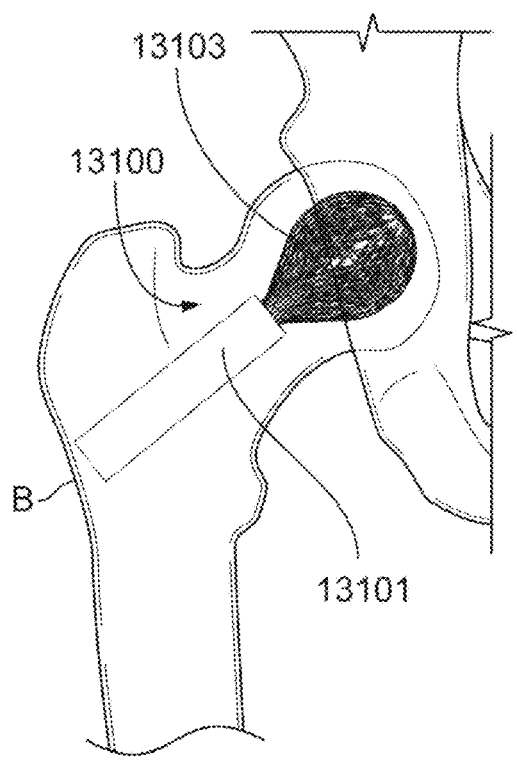
FIG. 131 shows illustrative apparatus and methods in accordance with principles of the invention.

FIG. 131 shows illustrative apparatus 13100 positioned in bone B. Apparatus 13100 may include implant head 13103. Implant head 13103 may have one or more features in common with the implant head. Implant head 13103 may be expandable. Implant head 13103 may be expanded in bone B. Implant head 13103 may be expanded prior to positioning in bone B. Implant head 13101 may be advanced, in an unexpanded state, through rod 13101 after rod 13101 is implanted in bone B and subsequently expanded in bone B. Implant head 13103 may not be expandable.

Apparatus 13100 may include member 13101. Member 13101 may be an intramedullary rod 13101. Intramedullary rod 13101 may be coupled to, and extend away from, implant head 13103. Intramedullary rod 13101 may be cannulated. An end of intramedullary rod 13101 may be coupled to implant head 13103. The end of intramedullary rod 1310 may define an opening in which implant head 13101 is seated. A portion of implant head 13103 may be positioned in intramedullary rod 13101. A portion of an implant base fixed to implant head 13103 may be positioned in intramedullary rod 13101. An implant base fixed to implant head 13103 may be positioned in intramedullary rod 13101. A portion of an implant tail fixed to implant head 13103 may be positioned in intramedullary rod 13101. An implant tail fixed to implant head 13103 may be positioned in intramedullary rod 13101.

Implant head 13103 and intramedullary rod 13101 may be, together, monolithic. Implant head 13103 may be fixedly coupled to intramedullary rod 13101. Implant head 13103 may be removably coupled to intramedullary rod 13101. A portion of rod 13101 may extend through implant head 13103. An end of rod 13101 may mate with an end of implant head 13103.

Implant head may be configured to be coupled to intramedullary rod 13101 by threads, snap fit, friction fit, or any other suitable attachment mechanism described herein or known to those skilled in the art. Intramedullary rod 13101 may be cannulated. Coupling implant head 13103 to rod 13101 may include positioning implant head 13103, the implant base and/or the implant tail in the cannula. Intramedullary rod 13101 may define an opening. Coupling implant head 13103 to rod 13101 may include positioning implant head 13103, the implant base and/or the implant tail in the opening.

Implant head 13103 may extend away from a base. The base may be fixedly coupled to intramedullary rod 13101. The base may be configured to be coupled to intramedullary rod 13101 by threads, snap fit, friction fit, or any other suitable attachment mechanism described herein or known to those skilled in the art. Intramedullary rod 13101 may be cannulated. Coupling the base to rod 13101 may include positioning the base in the cannula. Intramedullary rod 13101 may define an opening. Coupling the base to rod 13101 may include positioning the base in the opening.

Implant head 13103 may include an implant tail. The implant tail may pass through the intramedullary rod. The implant tail may be fixedly coupled to the intramedullary rod. The implant tail may be unitary with the intramedullary rod. The tail may be configured to be coupled to intramedullary rod 13101 by threads, snap fit, friction fit, or any other suitable attachment mechanism described herein or known to those skilled in the art.

Implant head 13103 may be coupled to rod 13101 using apparatus and methods illustrated and described in reference the elongated member including the sleeve. Rod 13101 may include the sleeve and the threaded member extending along a central axis of the rod. Implant head 13103 may be coupled to rod 13101 using apparatus and methods illustrated and described in reference to FIG. 125. Implant head 13103 may be coupled to rod 13101 using apparatus and methods illustrated and described in reference to FIG. 127.

Implant head 13103 may be coupled to a distal end of a screw. The screw may pass through the intramedullary rod. The screw may be fixedly coupled to an end cap positioned on an end of the intramedullary rod opposite the end of the rod to which implant head 13103 is coupled. The screw may be unitary with the intramedullary rod.

Member 13101 may be the implant tail. Member 13101 may be the implant shaft. Member 13101 may be the implant tail coupled to the implant shaft. Member 13101 may be a screw. A portion of implant head 13103 may be positioned in the screw.

A practitioner may advance one or more screws into implant head 13103. A practitioner may advance screws into implant head 13103 without using a jig. A practitioner may anchor a distal end of a screw in a head of bone B by advancing the distal end of the screw into implant head 13103.

Figure 132:
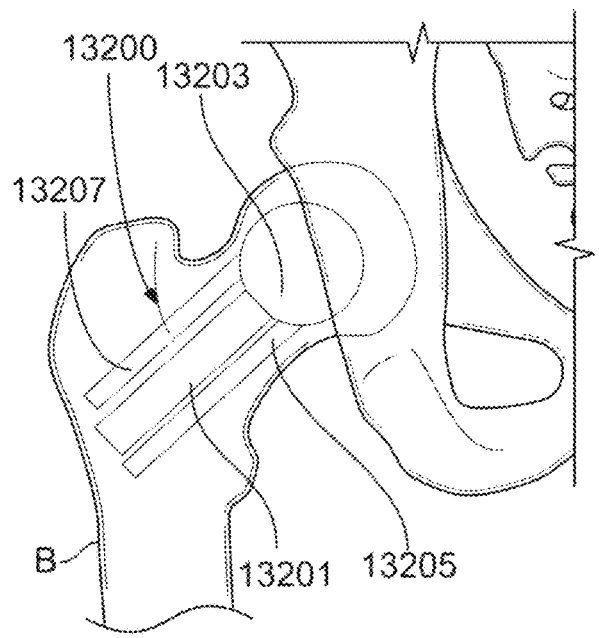
FIG. 132 shows illustrative apparatus and methods in accordance with principles of the invention.

FIG. 132 shows illustrative apparatus 13200 positioned in bone B. The apparatus may include implant head 13203 (mesh structure not shown). Implant head 13203 may have one or more features in common with the implant head. Implant head 13203 may be expandable. Implant head 13203 may be expanded in bone B. Implant head 13203 may be expanded prior to positioning in bone B. Implant head 13203 may not be expandable.

Intramedullary rod 13201 may have one or more features in common with intramedullary rod 13101. Intramedullary rod 13201 may be coupled to implant head 13203. The coupling of implant head 13203 to rod 13201 may have one or more features in common with the coupling of intramedullary rod 13101 to implant head 13103 described at FIG. 131, above.

FIG. 132 also shows illustrative fixation members 13205 and 13207. Fixation member 13205 may be a screw. Fixation member 13207 may be a screw. Fixation members 13205 and 13207 are shown extending through a neck of bone B and into a head of bone B. A distal end of fixation member 13205 is anchored in implant head 13203. A distal end of fixation member 13207 is anchored in implant head 13203.

Figure 133:
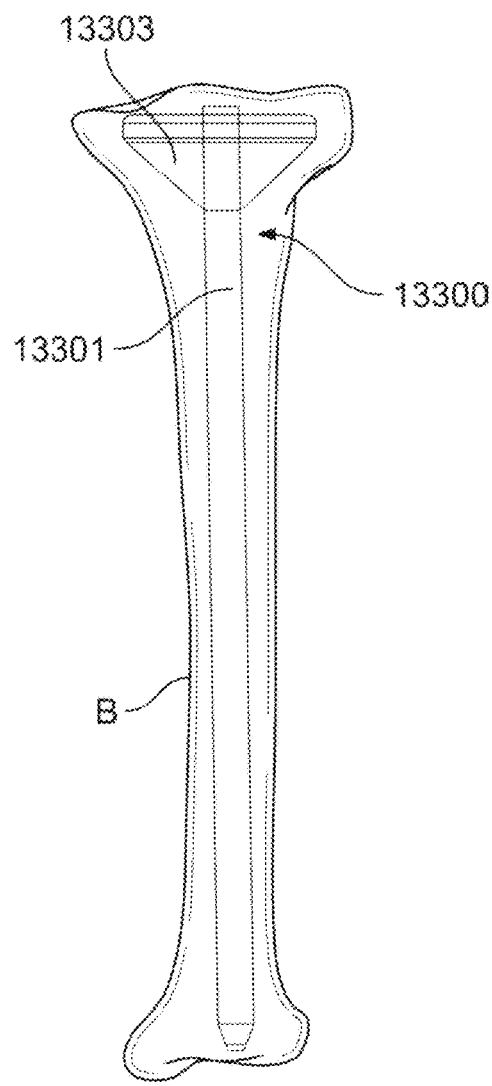
FIG. 133 shows illustrative apparatus and methods in accordance with principles of the invention.

FIG. 133 shows illustrative apparatus 13300 including intramedullary rod 13301 positioned in bone B. Apparatus 13300 may also include implant head 13303 (mesh structure not shown). Implant head 13303 may be fixedly coupled to an end of intramedullary rod 13303. Implant head 13303 may be coupled to an end of intramedullary rod 13303.

Implant head 13303 may have one or more features in common with the implant head. Implant head 13303 may be expandable. Implant head 13303 may be expanded prior to positioning in bone B. Implant head may be expanded in bone B. Implant head 13303 may not be expandable.

Intramedullary rod 13303 may have one or more features in common with intramedullary rod 13101. Intramedullary rod 13303 may be coupled to implant head 13301. The coupling of implant head 13301 to rod 13303 may have one or more features in common with the coupling of intramedullary rod 13101 to implant head 13103 described at FIG. 131, above.

Implant head 13303 may have an outer face shaped in the pseudo-conical shape illustrated in FIG. 133.

Implant head 13303 may be positioned adjacent an articular surface of bone B. A shape of implant head 13303 may support an articular surface of bone B.

Implant head 13303 may be coupled to a first end of rod 13303. Rod 13303 may include a second implant head (not shown) coupled to a second end of rod 13303, opposite the first end. Rod 13303 may include one or more additional implant heads (not shown) coupled to rod 13303 along a length of rod 13303.

Figure 134:
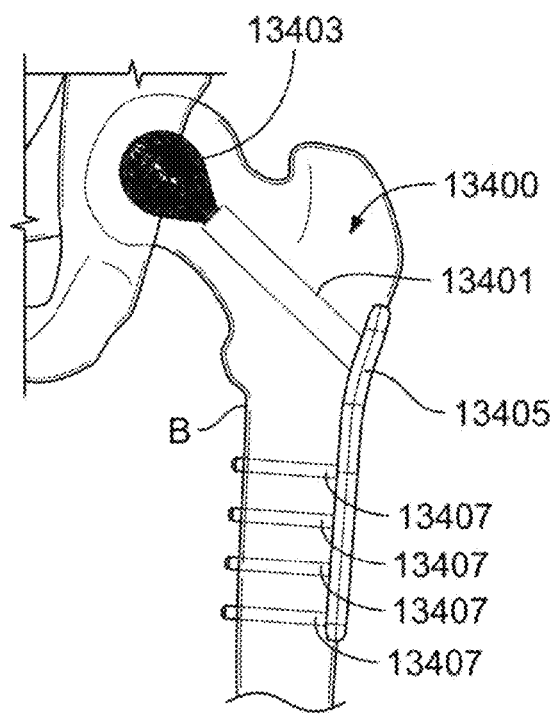
FIG. 134 shows illustrative apparatus and methods in accordance with principles of the invention.

FIG. 134 shows illustrative apparatus 13400 positioned in bone B. Apparatus 13400 may include implant head 13403. Implant head 13403 may have one or more features in common with the implant head. Implant head 13403 may be expandable. Implant head 13403 may be expanded inside bone B. Implant head 13403 may be expanded prior to positioning in bone B. Implant head 13403 may not be expandable.

Apparatus 13400 may include intramedullary rod 13401. Intramedullary rod 13401 may have one or more features in common with intramedullary rod 13101. Intramedullary rod 13401 may be coupled to implant head 13403. The coupling of implant head 13403 to rod 13401 may have one or more features in common with the coupling of intramedullary rod 13101 to implant head 13103 described at FIG. 131, above.

Apparatus 13400 may include plate 13405. A bottom surface of plate 13405 may be positioned on bone B. Rod 13401 may extend through plate 13405. Rod 13401 may extend through an opening in plate 13405, rod 13401 may fixed to plate 13405, and rod 13401 may be coupled to plate 13404 in any other suitable way using known apparatus and methods. Rod 13401 and plate 13405 may together be monolithic. Bi-cortical screws 13407 may be advanced through plate 13405 and across a width of a shaft of bone B.

Figure 135:
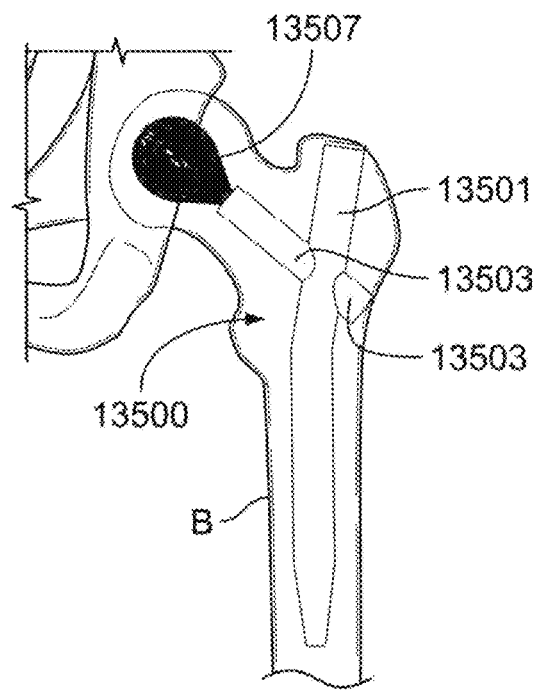
FIG. 135 shows illustrative apparatus and methods in accordance with principles of the invention.

FIG. 135 shows illustrative apparatus 13500 positioned in bone B. Apparatus 13500 may include implant head 13507. Implant head 13507 may have one or more features in common with the implant head. Implant head 13507 may be expandable. Implant head 13507 may be expanded inside bone B. Implant head 13507 may be expanded prior to positioning in bone B. Implant head 13507 may not be expandable.

Apparatus 13500 may include intramedullary rod 13503. Intramedullary rod 13503 may have one or more features in common with intramedullary rod 13101. Intramedullary rod 13503 may be coupled to implant head 13507. The coupling of implant head 13507 to rod 13503 may have one or more features in common with the coupling of intramedullary rod 13101 to implant head 13103 described at FIG. 131, above.

Apparatus may include intramedullary rod 13501. Intramedullary rod 13501 may be extend through an opening in intramedullary rod 13503 and be fixed to rod 13503 using one or more screws, intramedullary rod 13501 may be fixedly attached to rod 13503, and intramedullary rod 13501 may be coupled to intramedullary rod 13503 in any other suitable way known apparatus and methods.

Bone B may be a femur bone. A first end of rod 13501 may be positioned adjacent a greater trochanter of the femur. A length of rod 13501 may extend along a length of the femur. A second end of rod 13501 may be positioned in a femur shaft. Implant head 13507 may be positioned in a head of the femur. Rod 13101 may extend along a neck of the femur.

Figure 136:
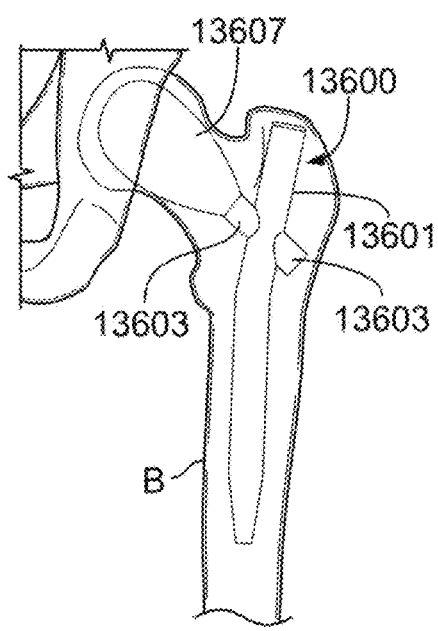
FIG. 136 shows illustrative apparatus and methods in accordance with principles of the invention.

FIG. 136 shows illustrative apparatus positioned in bone B. Apparatus 13600 may include implant head 13607 (mesh structure not shown). Implant head 13607 may have one or more features in common with the implant head. Implant head 13607 may be expandable. Implant head 13607 may be expanded inside bone B. Implant head 13607 may be expanded prior to positioning in bone B. Implant head 13607 may not be expandable.

Apparatus 13600 may include intramedullary rod 13603. Intramedullary rod 13603 may have one or more features in common with intramedullary rod 13101. Intramedullary rod 13603 may be coupled to implant head 13607. The coupling of implant head 13607 to rod 13603 may have one or more features in common with the coupling of intramedullary rod 13101 to implant head 13103 described at FIG. 131, above.

Apparatus may include intramedullary rod 13601. Intramedullary rod 13601 may be coupled to intramedullary rod 13603 as described at FIG. 135, above.

Bone B may be a femur bone. A first end of rod 13601 may be positioned adjacent a greater trochanter of the femur. A length of rod 13601 may extend along a length of the femur. A second end of rod 13601 may be positioned in the femur shaft. Implant head 13607 may be positioned in a head of the femur and extend along a neck of the femur.

Figure 137:
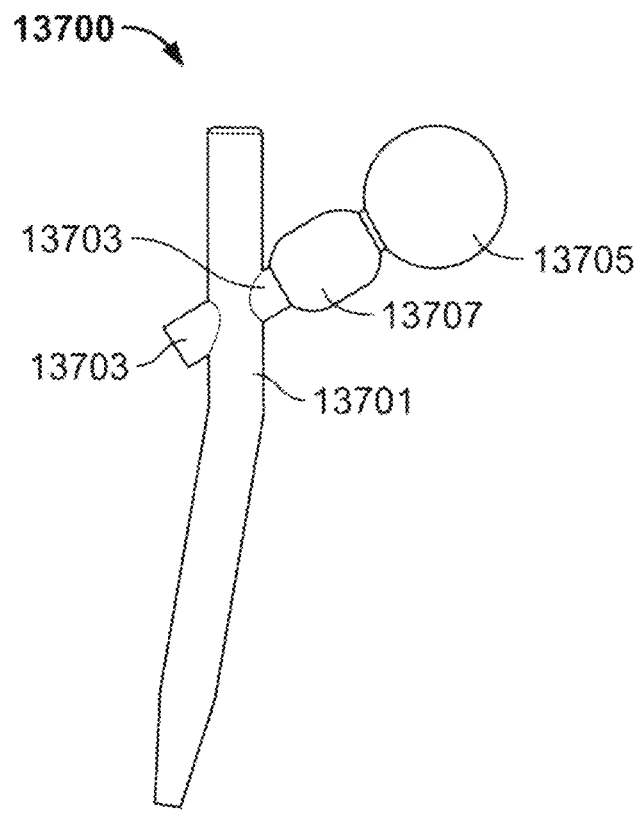
FIG. 137 shows illustrative apparatus in accordance with principles of the invention.

FIG. 137 shows illustrative apparatus 13700 for implanting into a bone such as a humerus, a femur, or any other suitable bone in the body. Apparatus 13700 may include implant head 13705 (mesh structure not shown). Implant head 13705 may have one or more features in common with the implant head. Apparatus 13700 may include implant head 13707 (mesh structure not shown). Implant head 13707 may have one or more features in common with the implant head.

Implant head 13705 may be expandable. Implant head 13705 may be expanded inside bone B. Implant head 13705 may be expanded prior to positioning in bone B. Implant head 13705 may not be expandable.

Implant head 13707 may be expandable. Implant head 13707 may be expanded inside bone B. Implant head 13707 may be expanded prior to positioning in bone B. Implant head 13707 may not be expandable.

Apparatus 13700 may include intramedullary rod 13703. Intramedullary rod 13703 may have one or more features in common with intramedullary rod 13101. Intramedullary rod 13703 may be coupled to implant head 13705. The coupling of implant head 13705 to rod 13703 may have one or more features in common with the coupling of intramedullary rod 13101 to implant head 13103 described at FIG. 131, above. Intramedullary rod 13703 may be coupled to implant head 13707. The coupling of implant head 13707 to rod 13703 may have one or more features in common with the coupling of intramedullary rod 13101 to implant head 13103 described at FIG. 131, above.

Apparatus may include intramedullary rod 13701. Intramedullary rod 13701 may be coupled to intramedullary rod 13703 as described at FIG. 135, above.

Figure 138:
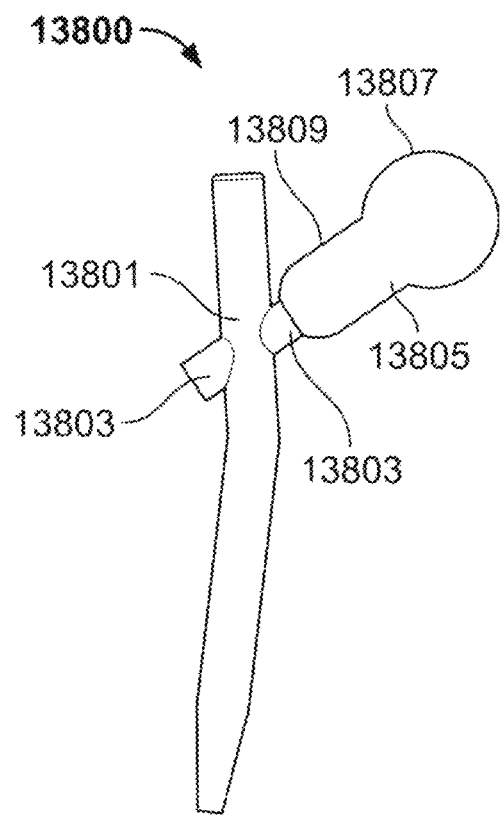
FIG. 138 shows illustrative apparatus in accordance with principles of the invention.

FIG. 138 shows illustrative apparatus 13800 for implanting into a bone such as a humerus, a femur, or any other suitable bone in the body. Apparatus 13800 may include implant head 13805 (mesh structure not shown). Implant head 13805 may have one or more features in common with the implant head. Implant head 13805 may include a first sphere-shaped portion 13807 and a second cylindrically-shaped portion 13809.

Implant head 13805 may be expandable. Implant head 13805 may be expanded inside bone B. Implant head 13805 may be expanded prior to positioning in bone B. Implant head 13805 may not be expandable.

Apparatus 13800 may include intramedullary rod 13803. Intramedullary rod 13803 may have one or more features in common with intramedullary rod 13101. Intramedullary rod 13803 may be coupled to implant head 13805. The coupling of implant head 13805 to rod 13803 may have one or more features in common with the coupling of intramedullary rod 13101 to implant head 13103 described at FIG. 131, above.

Apparatus may include intramedullary rod 13801. Intramedullary rod 13801 may be coupled to intramedullary rod 13803 as described at FIG. 135, above.

Figure 139:
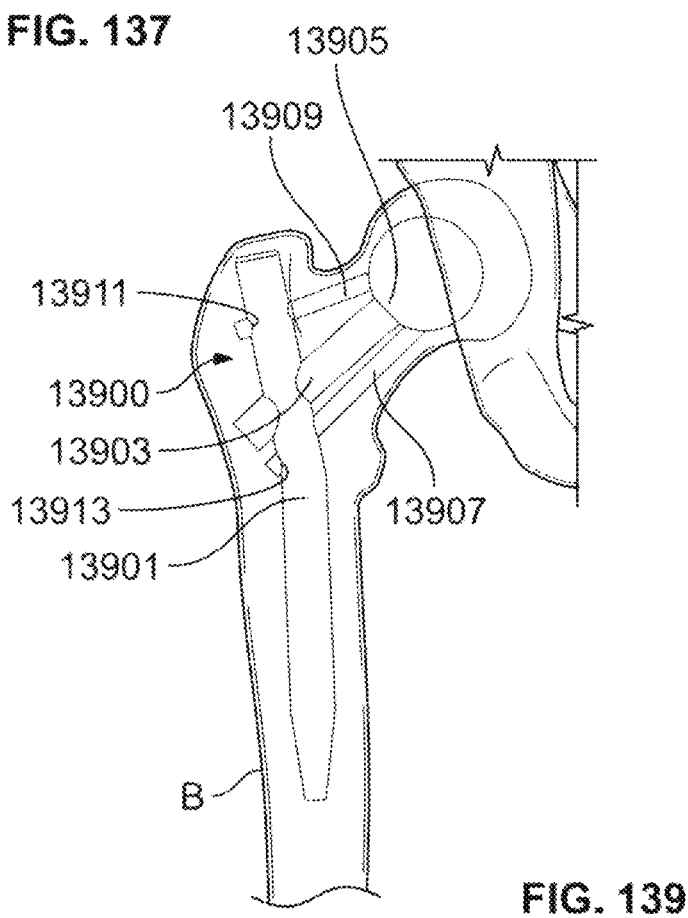
FIG. 139 shows illustrative apparatus and methods in accordance with principles of the invention.

FIG. 139 shows illustrative apparatus 13900 positioned in bone B. Apparatus 13900 may include implant head 13905 (mesh structure not shown). Implant head 13905 may have one or more features in common with the implant head. Implant head 13905 may be expandable. Implant head 13905 may be expanded inside bone B. Implant head 13905 may be expanded prior to positioning in bone B. Implant head 13905 may not be expandable.

Apparatus 13900 may include intramedullary rod 13903. Intramedullary rod 13903 may have one or more features in common with intramedullary rod 13101. Intramedullary rod 13903 may be coupled to implant head 13905. The coupling of implant head 13905 to rod 13903 may have one or more features in common with the coupling of intramedullary rod 13101 to implant head 13103 described at FIG. 131, above.

Apparatus may include intramedullary rod 13901. Intramedullary rod 13901 may be coupled to intramedullary rod 13903 as described at FIG. 135, above. Rod 13901 may define first hole 13911 and second hole 13913. First hole 13911 may define a central axis that points to implant head 13905. Second hole 13913 may define a central axis that points to implant head 13905. When implant head 13905 has not yet been expanded, first hole 13911 and second hole 13913 may each point to a volume that will be occupied by implant head 13905 when expanded in bone B.

A distal tip of fixation element 13909, when advanced through first hole 13911 and into a head of bone B, may be anchored in implant head 13905. A distal tip of fixation element 13907, when advanced through second hole 13913 and into a head of bone B, may be anchored in implant head 13905.

Figure 140:
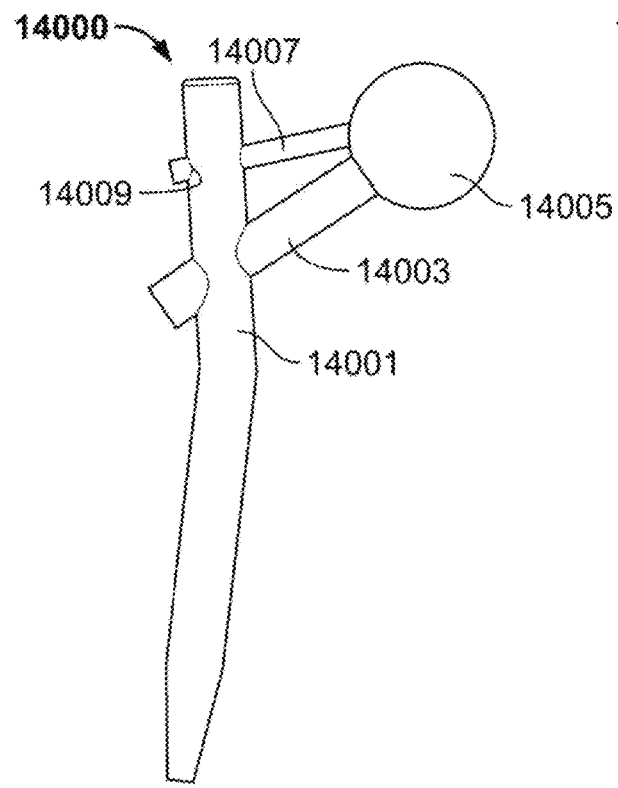
FIG. 140 shows illustrative apparatus and methods in accordance with principles of the invention.

FIG. 140 shows illustrative apparatus 14000 for implanting into a bone such as a humerus, a femur, or any other suitable bone. Apparatus 14000 may include implant head 14005 (mesh structure not shown). Implant head 14005 may have one or more features in common with the implant head. Implant head 14005 may be expandable. Implant head 14005 may be expanded inside the bone. Implant head 14005 may be expanded prior to positioning in the bone. Implant head 14005 may not be expandable. Apparatus 14000 may include intramedullary rod 14003. Intramedullary rod 14003 may have one or more features in common with intramedullary rod 13101. Intramedullary rod 14003 may be coupled to implant head 14005. The coupling of implant head 14005 to rod 14003 may have one or more features in common with the coupling of intramedullary rod 13101 to implant head 13103 described at FIG. 131, above.

Apparatus may include intramedullary rod 14001. Intramedullary rod 14001 may be coupled to intramedullary rod 14003 as described at FIG. 135, above. Rod 14001 may define hole 14009. Hole 14009 may define a central axis that points to implant head 14005. When implant head 14005 has not yet been expanded, hole 14009 may point to a volume that will be occupied by implant head 14005 when expanded in the bone. A distal tip of fixation element 14007, when advanced through first hole 14009 and into the bone, may be anchored in implant head 14005.

Figure 141:
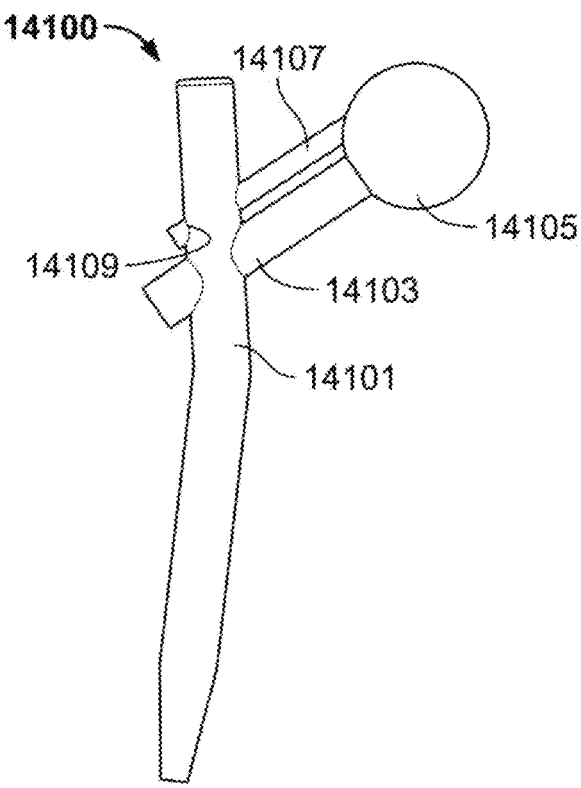
FIG. 141 shows illustrative apparatus and methods in accordance with principles of the invention.

FIG. 141 shows illustrative apparatus 14100 for implanting into a bone such as a humerus, a femur, or any other suitable bone. Apparatus 14100 may include implant head 14105 (mesh structure not shown). Implant head 14105 may have one or more features in common with the implant head. Implant head 14105 may be expandable. Implant head 14105 may be expanded inside the bone. Implant head 14105 may be expanded prior to positioning in the bone. Implant head 14105 may not be expandable. Apparatus 14100 may include intramedullary rod 14103. Intramedullary rod 14103 may have one or more features in common with intramedullary rod 13101. Intramedullary rod 14103 may be coupled to implant head 14105. The coupling of implant head 14105 to rod 14103 may have one or more features in common with the coupling of intramedullary rod 13101 to implant head 13103 described at FIG. 131, above.

Apparatus may include intramedullary rod 14101. Intramedullary rod 14101 may be coupled to intramedullary rod 14103 as described at FIG. 135, above. Rod 14101 may define hole 14109. Hole 14109 may define a central axis that points to implant head 14105. When implant head 14105 has not yet been expanded, hole 14109 may point to a volume that will be occupied by implant head 14105 when expanded in the bone. A distal tip of fixation element 14107, when advanced through first hole 14109 and into the bone, may be anchored in implant head 14105.

Figure 142:
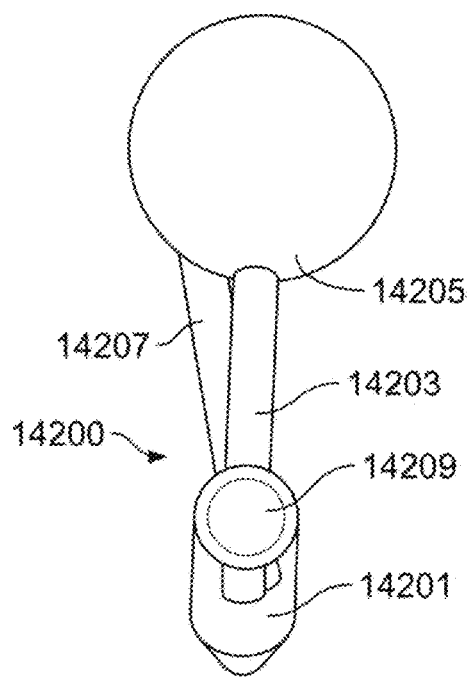
FIG. 142 shows illustrative apparatus and methods in accordance with principles of the invention.

FIG. 142 shows illustrative apparatus 14200 for implanting into a bone such as a humerus, a femur, or any other suitable bone. Apparatus 14200 may include implant head 14205 (mesh structure not shown). Implant head 14205 may have one or more features in common with the implant head. Implant head 14205 may be expandable. Implant head 14205 may be expanded inside the bone. Implant head 14205 may be expanded prior to positioning in the bone. Implant head 14205 may not be expandable. Apparatus 14200 may include intramedullary rod 14203. Intramedullary rod 14203 may have one or more features in common with intramedullary rod 13101. Intramedullary rod 14203 may be coupled to implant head 14205. The coupling of implant head 14205 to rod 14203 may have one or more features in common with the coupling of intramedullary rod 13101 to implant head 13103 described at FIG. 131, above.

Apparatus may include intramedullary rod 14201. Intramedullary rod 14201 may be coupled to intramedullary rod 14203 as described at FIG. 135, above. Rod 14201 may define a hole (not shown). The hole may define a central axis that points to implant head 14205. When implant head 14205 has not yet been expanded, the hole may point to a volume that will be occupied by implant head 14205 when expanded in the bone. A distal tip of fixation element 14207, when advanced through first hole 14209 and into the bone, may be anchored in implant head 14205.

Figure 143:
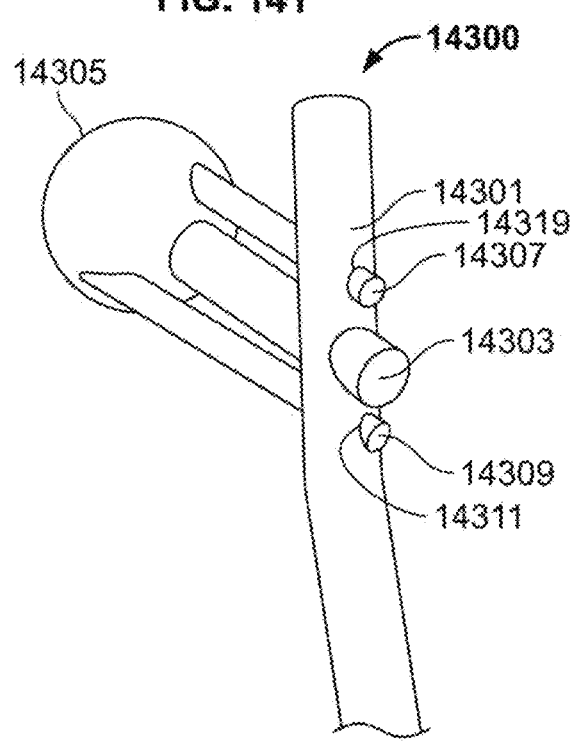
FIG. 143 shows illustrative apparatus and methods in accordance with principles of the invention.

FIG. 143 shows illustrative apparatus 14300 or implanting into a bone such as a humerus, a femur, or any other suitable bone. Apparatus 14300 may include implant head 14305 (mesh structure not shown). Implant head 14305 may have one or more features in common with the implant head. Implant head 14305 may be expandable. Implant head 14305 may be expanded inside the bone. Implant head 14305 may be expanded prior to positioning in the bone. Implant head 14305 may not be expandable. Apparatus 14300 may include intramedullary rod 14303. Intramedullary rod 14303 may have one or more features in common with intramedullary rod 13101. Intramedullary rod 14303 may be coupled to implant head 14305. The coupling of implant head 14305 to rod 14303 may have one or more features in common with the coupling of intramedullary rod 13101 to implant head 13103 described at FIG. 131, above.

Apparatus may include intramedullary rod 14301. Intramedullary rod 14301 may be coupled to intramedullary rod 14303 as described at FIG. 135, above. Rod 14301 may define first hole 14311 and second hole 14313. First hole 14311 may define a central axis that points to implant head 14305. Second hole 14313 may define a central axis that points to implant head 14305. When implant head 14305 has not yet been expanded, first hole 14311 and second hole 14313 may each point to a volume that will be occupied by implant head 14305 when expanded in bone B. A distal tip of fixation element 14309, when advanced through first hole 14311 and into the bone, may be anchored in implant head 14305. A distal tip of fixation element 14307, when advanced through second hole 14313 and into the bone, may be anchored in implant head 14305.

Figure 144:
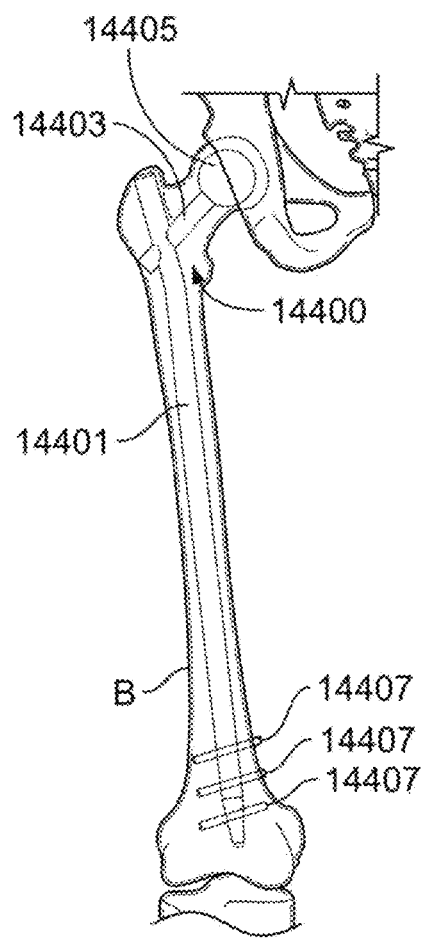
FIG. 144 shows illustrative apparatus and methods in accordance with principles of the invention.

FIG. 144 shows illustrative apparatus 14400 positioned in bone B. Apparatus 14400 may include implant head 14405 (mesh structure not shown). Implant head 14405 may have one or more features in common with the implant head. Implant head 14405 may be expandable. Implant head 14405 may be expanded inside the bone. Implant head 14405 may be expanded prior to positioning in the bone. Implant head 14405 may not be expandable. Apparatus 14400 may include intramedullary rod 14403. Intramedullary rod 14403 may have one or more features in common with intramedullary rod 13101. Intramedullary rod 14403 may be coupled to implant head 14405. The coupling of implant head 14405 to rod 14403 may have one or more features in common with the coupling of intramedullary rod 13101 to implant head 13103 described at FIG. 131, above.

Apparatus may include intramedullary rod 14401. Intramedullary rod 14401 may be coupled to intramedullary rod 14403 as described at FIG. 135, above. Rod 14401 may define one or more holes at an end of rod 14401. Screws 14407 may pass through the holes at the end of rod 14401. Bone B may be a femur bone. A length of intramedullary rod 14401 may extend along a length of the femur bone.

Figure 145:
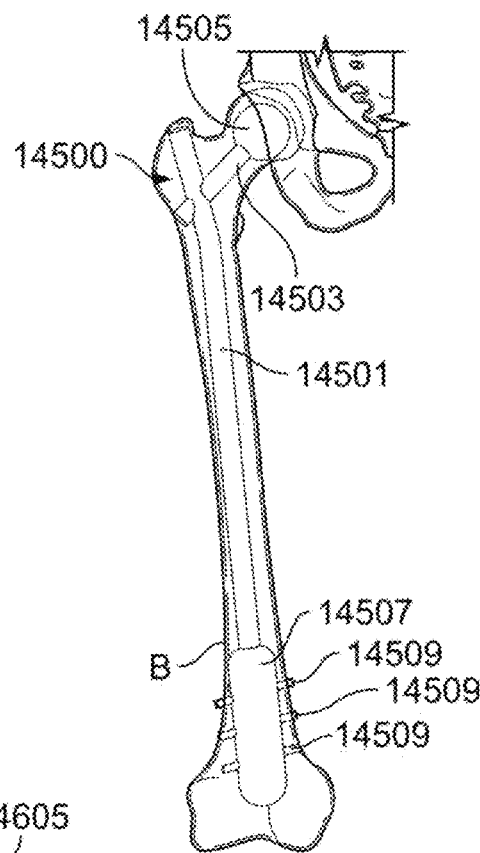
FIG. 145 shows illustrative apparatus and methods in accordance with principles of the invention.

FIG. 145 shows illustrative apparatus 14500 positioned in bone B. Apparatus 14500 may include implant head 14505 (mesh structure not shown). Implant head 14505 may have one or more features in common with the implant head. Implant head 14505 may be expandable. Implant head 14505 may be expanded inside the bone. Implant head 14505 may be expanded prior to positioning in the bone. Implant head 14505 may not be expandable. Apparatus 14500 may include intramedullary rod 14503. Intramedullary rod 14503 may have one or more features in common with intramedullary rod 13101. Intramedullary rod 14503 may be coupled to implant head 14505. The coupling of implant head 14505 to rod 14503 may have one or more features in common with the coupling of intramedullary rod 13101 to implant head 13103 as described at FIG. 131, above.

Apparatus 14500 may include intramedullary rod 14501. Intramedullary rod 14501 may be coupled to intramedullary rod 14503 as described at FIG. 135, above. Apparatus 14500 may include implant head 14507 (mesh structure not shown). Implant head 14507 may have one or more features in common with the implant head. Implant head 14507 may be expandable. Implant head 14507 may be expanded inside the bone. Implant head 14507 may be expanded prior to positioning in the bone. Implant head 14507 may not be expandable. Intramedullary rod 14501 may have one or more features in common with intramedullary rod 13101. Intramedullary rod 14501 may be coupled to implant head 14507. The coupling of implant head 14507 to rod 14501 may have one or more features in common with the coupling of intramedullary rod 13101 to implant head 13103 described at FIG. 131, above. One or more bi-cortical screws 14509 may pass through bone B and implant head 14507. One or more bi-cortical screws 14509 may pass through bone B, implant head 14507 and rod 14501. One or more screws 14509 may pass through bone B and implant head 14507. One or more screws 14509 may pass through bone B, implant head 14507 and rod 14501.

Bone B may be a femur bone. A length of intramedullary rod 14501 may extend along a length of the femur bone. Implant head 14507 may be positioned adjacent lateral and/or medial epicondyles of the femur bone.

Figure 146:
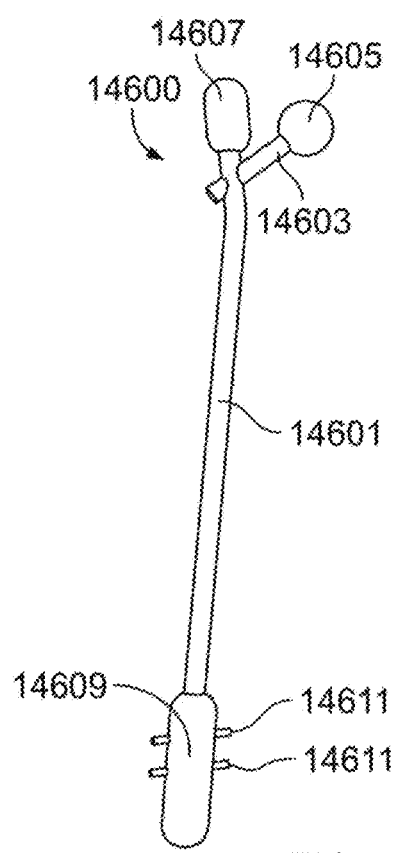
FIG. 146 shows illustrative apparatus in accordance with principles of the invention.

FIG. 146 shows illustrative apparatus 14600 for positioning in a bone such as a femur, a humerus, or any other suitable bone. Apparatus 14600 may include implant head 14605 (mesh structure not shown), implant head 14607 (mesh structure not shown) and implant head 14609 (mesh structure not shown). Implant heads 14605, 14607 and 14609 may each have one or more features in common with the implant head. One or more of implant heads 14605, 14607 and 14609 may be expandable. One or more of implant heads 14605, 14607 and 14609 may be expanded inside the bone. One or more of implant heads 14605, 14607 and 14609 may be expanded prior to positioning in the bone. One or more of implant heads 14605, 14607 and 14609 may not be expandable.

Apparatus 14600 may include intramedullary rod 14603. Intramedullary rod 14603 may have one or more features in common with intramedullary rod 13101. Intramedullary rod 14603 may be coupled to implant head 14605. The coupling of implant head 14605 to rod 14603 may have one or more features in common with the coupling of intramedullary rod 13101 to implant head 13103 as described at FIG. 131, above. Apparatus 14600 may include intramedullary rod 14601. Intramedullary rod 14601 may be coupled to intramedullary rod 14603 as described at FIG. 135, above. Intramedullary rod 14601 may have one or more features in common with intramedullary rod 13101. Intramedullary rod 14601 may be coupled to implant head 14607 and implant head 14609. The coupling of implant head 14607 to rod 14607 and 14609 may have one or more features in common with the coupling of intramedullary rod 13101 to implant head 13103 described at FIG. 131, above.

Screws 14611 may be advanced through implant head 14609. Screws 14611 may be advanced through implant head 14609 and rod 14601. Additional screws (not shown) may be advanced through implant head 14607 and implant head 14605. One or more screws may be advanced through both implant head 14607 and implant head 14605.

Figure 147:
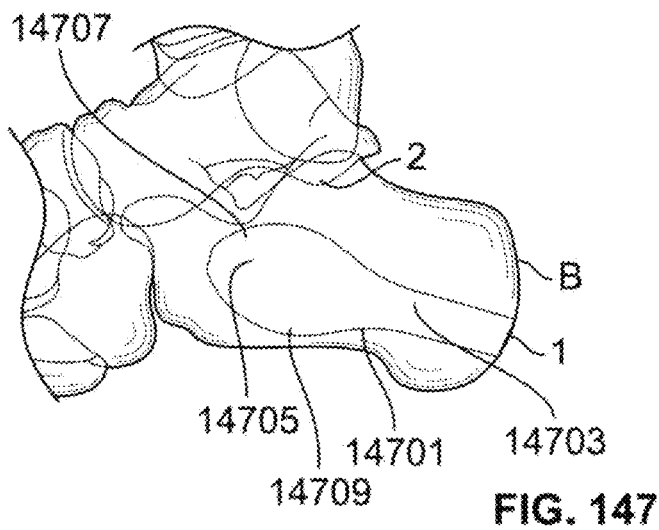
FIG. 147 shows illustrative apparatus and methods in accordance with principles of the invention.

FIG. 147 shows illustrative implant 14701 including implant head 14705 and implant tail 14703 positioned in a bone B. Implant 14701 may have one or more features in common with the implant. Implant head 14705 may have one or more features in common with the implant head. Implant tail 14703 may have one or more features in common with the implant tail.

Bone B may be a calcaneus. Access site '1' may be used by a practitioner to access the interior of the calcaneus. Access site '1' may be positioned at a posterior portion of the calcaneus. Access site '1' may be below the Achilles' tendon termination. Access site '1' may be a primary access site. A practitioner may form a secondary access site on a lateral side of a posterior facet of the calcaneus bone. The secondary access site may be access site '2'. The secondary access site may be used by the practitioner to visualize the sinus relative to the talus. Implant head 14705 may be positioned in the calcaneus and expanded such that first portion 14707 of implant head 14705 is adjacent a sinus tarsi space. Implant head 14705 may be positioned in the calcaneus and expanded such that a second portion 14709 of implant head 14705 is adjacent a distal facet of the calcaneus. The distal facet may be a bottom surface of the calcaneus. The distal facet may be a sole of the foot.

Figure 148:
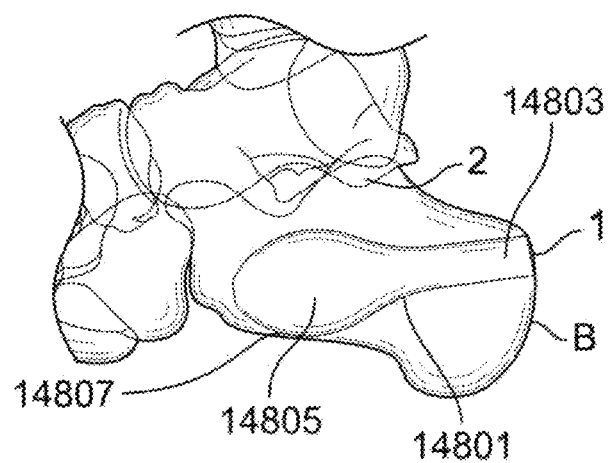
FIG. 148 shows illustrative apparatus and methods in accordance with principles of the invention.

FIG. 148 shows illustrative implant 14801 including implant head 14805 and implant tail 14803 positioned in a bone B. Implant 14801 may have one or more features in common with the implant. Implant head 14805 may have one or more features in common with the implant head. Implant tail 14803 may have one or more features in common with the implant tail.

Bone B may be a calcaneus. Access site '1' may be used by a practitioner to access the interior of the bone. Access site '1' may be located at a posterior heel location on the calcaneus. Access site '1' may be formed through a split made in the Achilles' tendon. Access site '1' may be a primary access site. A practitioner may form a secondary access site on a lateral side of a posterior facet of the calcaneus bone. The secondary access site may be access site '2'. The secondary access site may be used by the practitioner to visualize the sinus relative to the talus. Implant head 14805 may be positioned in the calcaneus and expanded such that a portion 14807 of implant head 14805 is adjacent the distal facet of the calcaneus.

Figure 149:
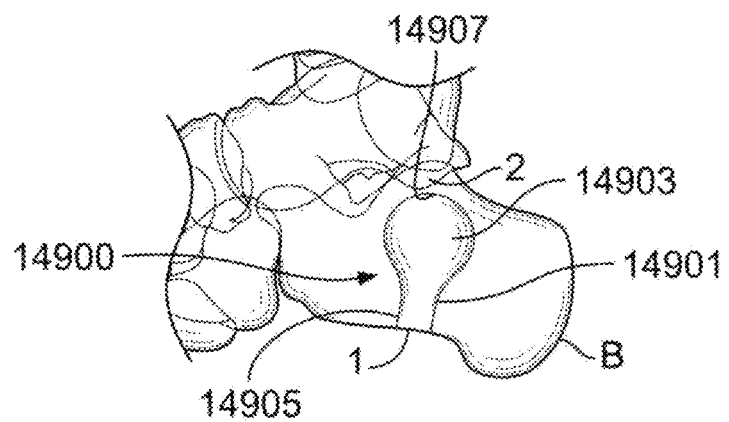
FIG. 149 shows illustrative apparatus and methods in accordance with principles of the invention.

FIG. 149 shows illustrative implant 14901 including implant head 14905 and implant tail 14903 positioned in a bone B. Implant 14901 may have one or more features in common with the implant. Implant head 14905 may have one or more features in common with the implant head.

Implant tail 14903 may have one or more features in common with the implant tail.

Bone B may be a calcaneus. Access site '1' may be used by a practitioner to access the interior of the bone. Access site '1' may be formed through the distal facet of the calcaneus. The implant, when placed in the calcaneus, may define a central axis. The central axis may be perpendicular to the distal facet. Access site '1' may be a primary access site. A practitioner may form a secondary access site on a lateral side of a posterior facet of the calcaneus bone. The secondary access site may be access site '2'. The second access site may be used by the practitioner to visualize the sinus relative to the talus. Implant head 14905 may be positioned in the calcaneus and expanded such that hub 14907 of implant head 14905 is adjacent the talus.

FIG. 150 shows a cross-sectional view of illustrative apparatus 15000. Apparatus 15000 may be implanted in the calcaneus or any other suitable bone. Apparatus 15000 may include first mesh 15001 and second mesh 15003. First mesh 15001 may define a longitudinal axis and may be expandable about the axis. Second mesh 15003 may be expandable about the axis between the axis and first mesh 15001.

First mesh 15001 and second mesh 15003 may together form the implant head of the implant. First mesh 15001 and second mesh 15003 may be configured to be longitudinally fixed to a central axis member that lies along the axis.

First mesh 15001 may have a first thickness. Second mesh 15003 may have a second thickness greater than the first thickness. The first thickness may be in the range 0.010 in. to 0.020 in. The second thickness may be in the range of 0.015 in. to 0.040 in.

First mesh 15001 may have a first stress-strain modulus corresponding to compression of the first mesh along a direction not parallel to the axis. Second mesh 15003 may have a second stress-strain modulus corresponding to compression of the second mesh along the direction. The second modulus may be greater than the first modulus.

First mesh 15001 may have a tear-drop shape. Second mesh 15003 may have a bulbous shape that has a shorter length, along a central axis of the implant, than first mesh 15001.

FIG. 151 shows illustrative apparatus 15100. Apparatus 15100 may be implanted in the calcaneus bone or any other suitable bone. Apparatus 15100 may include a first mesh cage 15101 (mesh not shown), second mesh cage 15103 (mesh not shown), first elongated member 15105 and second elongated member 15107.

First mesh cage 15101 may have one or more features in common with the implant head. Second mesh cage 15103 may have one or more features in common with the implant head.

First mesh cage 15101 may extend between hub 15109 and base 15111. Second mesh cage 15103 may extend between hub 15113 and base 15115.

FIG. 152 shows illustrative apparatus 15200. Apparatus 15200 may be implanted in the calcaneus or any other suitable bone. The apparatus may include mesh cage 15201. Mesh cage 15201 may have one or more features in common with the implant head. Mesh cage 15201 may be expandable. Mesh cage 15201 may not be expandable. Mesh cage may extend between hub 15211 and base 15213.

Mesh cage 15203 may include first bulbous section 15201, second bulbous section 15205 and tapered section 15207. Tapered section may define an outside diameter less than an outside diameter of implant base 15209.

A side profile of mesh cage 15201 may differ from the front profile of mesh cage 15201 illustrated in FIG. 152.

Figure 153:
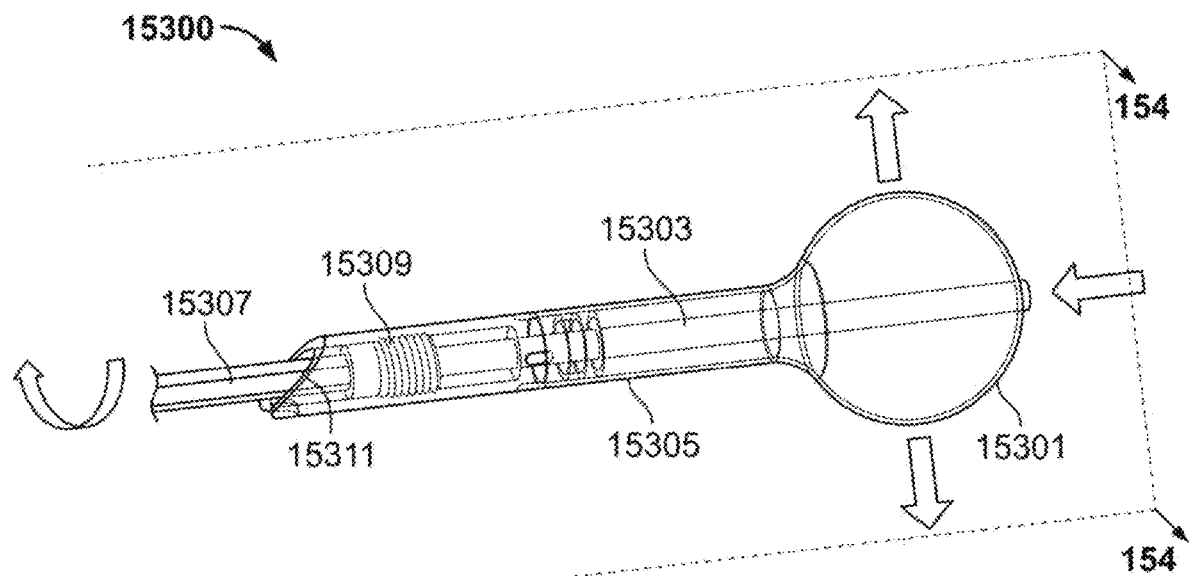
FIG. 153 shows illustrative apparatus and methods in accordance with principles of the invention.

FIG. 153 shows illustrative apparatus 15300. Apparatus 15300 may include implant head 15301 and implant tail 15305. Implant head 15301 may have one or more features in common with the implant head. Implant tail may have one or more features in common with the implant tail. Implant head 15301 may be fixed to an end of central axis member 15303. Implant head 15301 may be expandable.

Implant head 15301 may be manually expanded from a collapsed state to an expanded state. Implant head 15301 may self-expand to a first volume. Implant head 15301 may be manually expanded from the first volume to a second volume. Implant head 15301 may be manually expanded by insertion of rod 15307 into implant tail 15305. Rod 15307 may have an inner threaded portion configured to mate with externally threaded end 15309. When the inner threaded portion of rod 15307 mates with threaded end 15309 of central axis member 15303 and the rod 15307 is turned, central axis member 15303 may be advanced towards implant tail end 15311. As central axis member 15303 advances towards end 15311, implant head 15301 may be expanded.

Implant tail 15305 may be smooth. The smooth tail may allow for micromovement of the implant.

Figure 154:
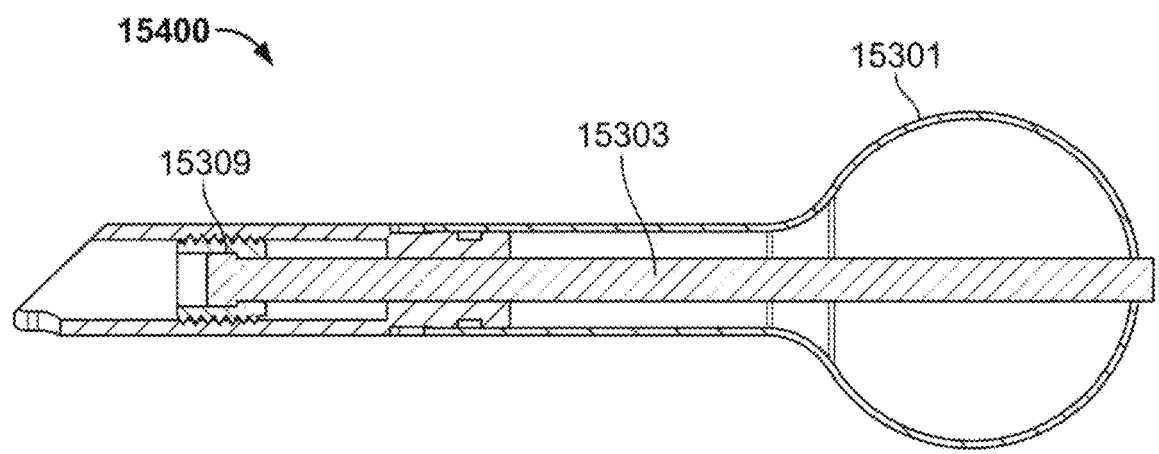
FIG. 154 shows a cross-sectional view of apparatus illustrated in FIG. 153.

FIG. 154 shows a cross-sectional view of the implant shown in FIG. 153 taken along lines 154-154. The cross-sectional view does not include rod 15307.

Figure 155:
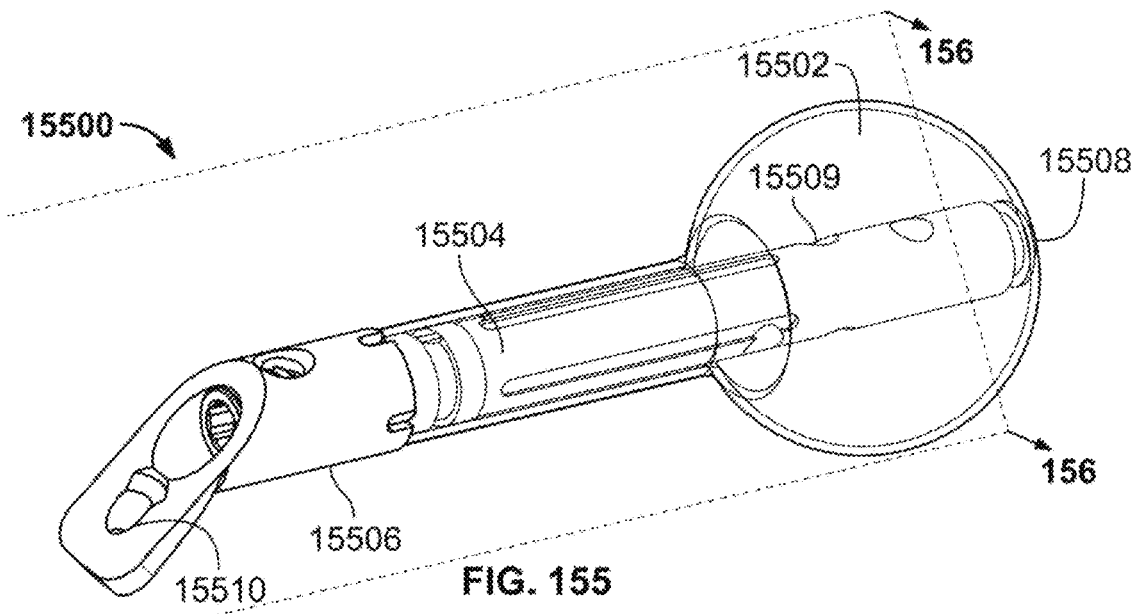
FIG. 155 shows illustrative apparatus in accordance with principles of the invention.

FIG. 155 shows schematically illustrative implant assembly 15500. Assembly 15500 may include implant head 15502. Assembly 15500 may include elongated support 15504. Assembly 15500 may include implant tail 15506.

Implant head 15502 may have one or more features in common with the implant head. Elongated support 15504 may have one or more features in common with central axis member 15303 (shown in FIG. 153). Implant tail 15506 may have one or more features in common with the implant tail.

Implant tail 15506 may include anchor receiving hole 15510.

Elongated support 15504 may engage implant head 15502 at hub 15508. Support 15504 may be engaged with hub 15508 prior insertion of implant head 15502 in a bone. For example, support 15504 may be engaged with hub 15508 at a factory or by a physician in a clinical setting. Support 15504 may be engaged with hub 15508 after insertion of implant head 15502 in a bone. For example, implant head 15502 may be placed in the bone and self-expanded or be expanded by an actuator.

A practitioner may select implant head 15502 from two or more implant heads, each head, when expanded, defining a different volume. A practitioner may select elongated support 15506 from two or more elongated supports, each elongated support defining a different length. A practitioner may select implant tail 15506 for coupling to elongated support 15506. The practitioner may select implant tail 15506 from a group of implant tails, each implant tail having a different length and/or defining a different angle.

Implant head 15502 may not be expanded when a practitioner couples implant head 15502 to elongated support 15502. Implant head 15502 may be expanded when a practitioner couples implant head 15502 to elongated support 15502.

Figure 156:
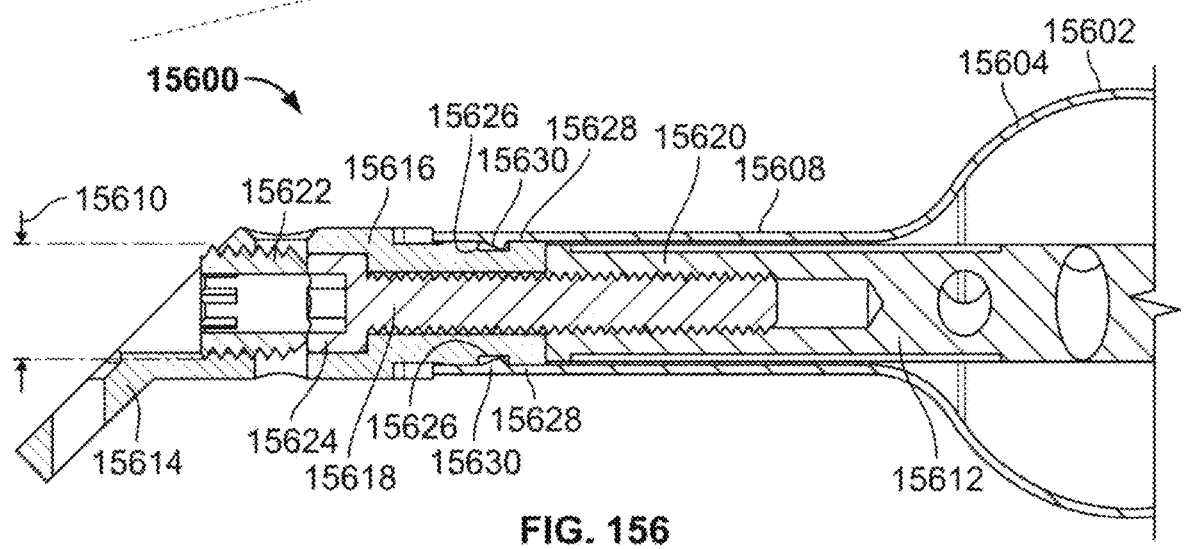
FIG. 156 shows a cross-sectional view of apparatus illustrated in FIG. 155.

FIG. 156 shows in partial cross section a partial view of illustrative implant assembly 15600 that may have one or more features in common with assembly 15500 (shown in FIG. 155). Implant head 15602 may include expandable mesh 15604 (shown schematically). Implant head 15602 may have one or more features in common with the implant head. Implant head 15604 may be fixed to base 15608. Base 15608 may define opening 15610. Opening 15610 may receive elongated support 15612. Implant tail 15614 may extend from elongated support 15612. Implant tail 15614 may have one or more features in common with the implant tail.

Bushing 15616 may provide clearance for threaded rod 15618. Rod 15618 may threadingly engage axial member 15620. Threaded rod 15618 may adjust an axial gap (not shown) between bushing 15616 and axial member 15620. The axial gap may be changed to change the extent of expansion of mesh 15604. Threaded rod 15618 may lock the gap to lock mesh 15604 in a state of expansion. Threaded rod 15618 may lock the gap to lock mesh 15604 in a collapsed state. Set screw 15622 may be tightened against rod 15618 to prevent rod 15618 from rotating. Set screw 15622 may be cannulated to allow access to head 15624 of rod 15618.

Bushing 15616 may include catches 15626. Catches 15626 may include recesses in bushing 15616. Catches 15626 may catch latches 15628. Latches 15628 may include protrusions 15630. Protrusions 15630 may have an equilibrium state in which they rest at a radius from the axis of elongated support 15612 that is smaller than the radius of opening 15610. During insertion of elongated support 15612 into base 15608, elongated support 15612 may displace protrusions 15630 radially outward until catches 15626 align with protrusions 15630. Protrusions 15630 may then elastically relax into catches 15626.

Base 15608 may include arms (not shown) to resiliently support protrusions 15630. The arms may be defined by voids or slots in base 15608. The arms may be cantilevered. Mesh 15604 may be biased to expand radially outward from the axis of elongated support 15612. The bias may urge elongated support 15612 to exit opening 15610. This may increase a force of engagement of catches 15626 with protrusions 15630. The engagement may be frictional. The engagement may be an interference engagement. For example, protrusions 15630 may be shaped to nest in a beveled edge (not shown) of catches 15626.

Figure 157:
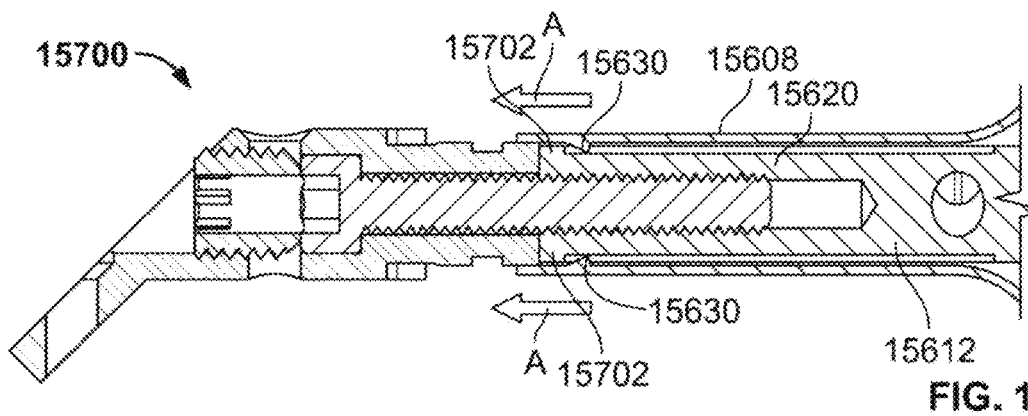
FIG. 157 shows illustrative in accordance with principles of the invention.

FIG. 157 shows illustrative flange 15702 in axial member 15620. When implant head 15602 is joined to elongated support 15612, protrusions 15630 may ride over flange 15702 before nesting in catches 15626. Flange 15702 may provide sufficient resistance to implant head 15602 to reduce the likelihood of inadvertent engagement with catches 15626. Arrows A show the direction of motion of implant head 15602 relative to elongated support 15612 during "snapping on" of implant head 15602 to elongated support 15612.

Figure 158:
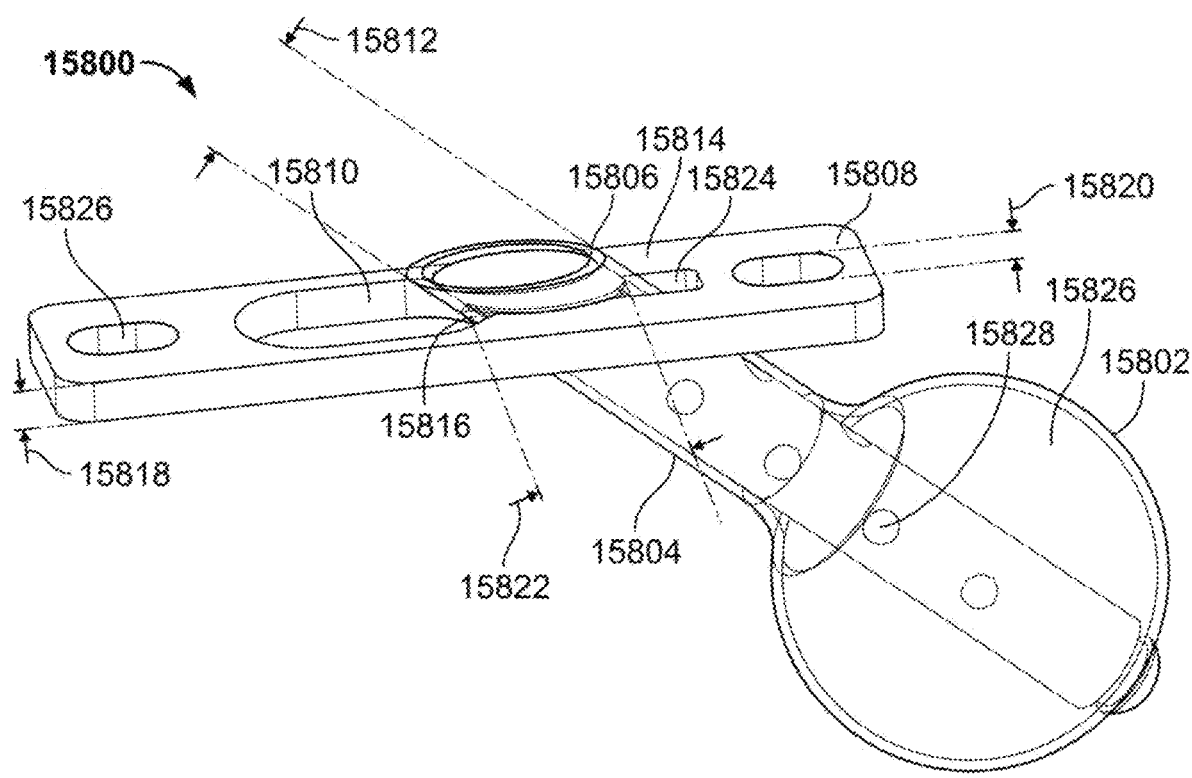
FIG. 158 shows illustrative apparatus and methods in accordance with principles of the invention.

FIG. 158 shows illustrative implant assembly 15800. Assembly 15800 may include the implant. The implant may include implant head 15802. The implant may include elongated support 15804. The implant may include implant tail 15806. Assembly 15800 may include keyed plate 15808.

Implant head 15802 may have one or more features in common with the implant head. Elongated support 15804 may have one or more features in common with central axis member 15303 (shown in FIG. 153). Implant tail 15806 may have one or more features in common with the implant tail. Keyed plate 15808 may have one or more features in common with the plate.

Implant head 15802 may include an expandable mesh anchoring substrate (expandable mesh not shown).

Plate 15808 may include clearance hole 15810. Hole 15810 may be large enough to permit the passage of implant head 15802 in a collapsed state. Hole 15810 may be large enough to permit the passage of a diameter of implant head 15802 in the collapsed state. Hole 15810 may be large enough to permit the passage of diameter 15812 of elongated support 15804. The diameter may be a "primary" diameter.

Plate 15808 may have a thickness 15818. Plate 15808 may include slot 15814.

Implant tail 15806 may include grooves 15816 on opposite sides of tail 15806. Groove 15816 may have a height that is sufficient to accommodate thickness 15818. Grooves 15816 may have depth such that tail 15806 has a minor diameter 15820 such that tail 15806 can slide into slot 15814. Grooves 15816 may have a length 15822 to be constrained by walls 15824 of slot 15814 with sufficient moment to prevent rotation of tail 15806 about a normal (not shown) to plate 15808. Grooves 15816 may have a length 15822 to be constrained by walls 15824 of slot 15814 with sufficient moment to prevent rotation of tail 15806 about a longitudinal axis of support 15804.

Anchor receiving holes may be used to fix plate 15808 to the bone. Tail 15806 may be seated sufficiently snuggly in slot 15814, when plate 15808 is fixed to the bone, so that plate 15808 prevents or reduces rotation of the implant about the longitudinal axis of the implant. Tail 15806 may be seated sufficiently snuggly in slot 15814, when plate 15808 is fixed to the bone, so that plate 15808 prevents or reduces rotation of the implant with respect to plate 15808.

Tail 15806 may be seated sufficiently snuggly in slot 15814, when plate 15808 is fixed to the bone, so that plate 15808 prevents or reduces translation of the implant along the longitudinal axis of the implant.

Tail 15806 may be seated sufficiently snuggly in slot 15814, when plate 15808 is fixed to the bone, so that plate 15808 prevents or reduces translation of the implant with respect to plate 15808. Plate 15808 may include a set screw (not shown) or other fixation device to lock tail 15806 in slot 15814. One or more set screws may traverse plate 15808 at a position along slot 15814, and contact tail 15806 at one or both of grooves 15816.

Elongated support 15804 may include one or more anchor passing holes 15828.

Anchor passing holes 15828 may receive an anchor engaged with implant head 15802. A practitioner may pass one or more anchors through implant head 15802 and into anchor passing holes 15828.

Figure 159:
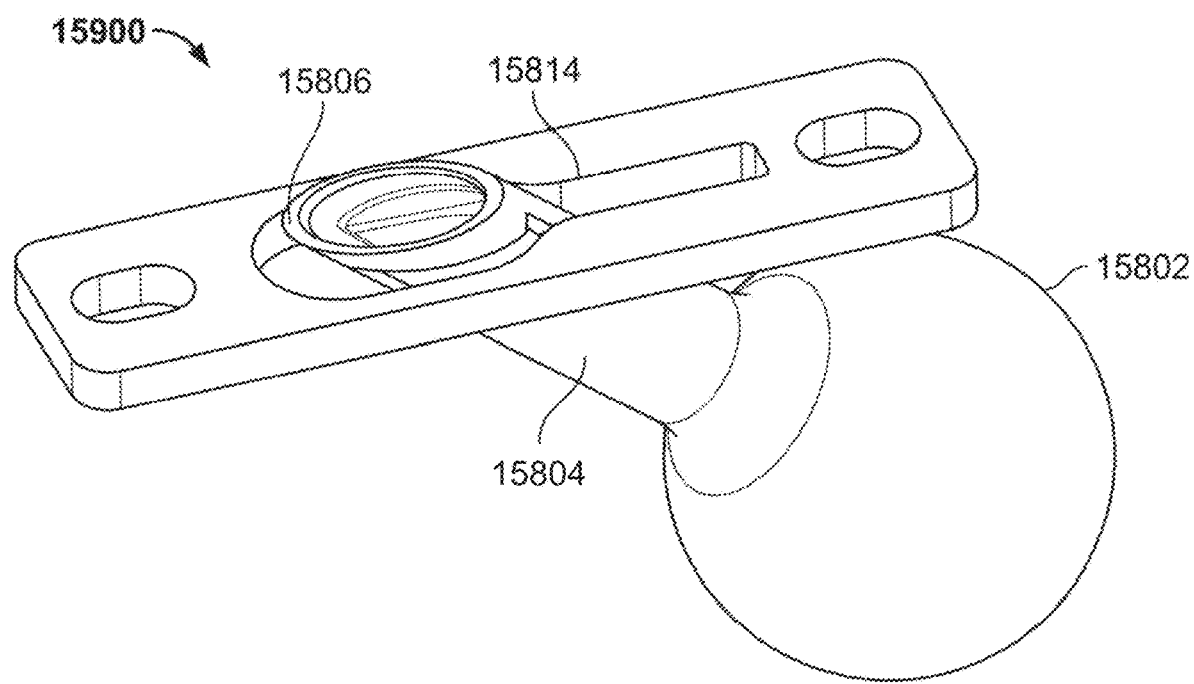
FIG. 159 shows illustrative apparatus and methods in accordance with principles of the invention.

FIG. 159 shows the implant in clearance hole 15810 prior to insertion in slot 15814.

A practitioner may insert implant tail 15802 into slot 15814 after the implant is positioned in the bone by sliding plate 15808 along a surface of the bone.

When implant tail 15802 is positioned in slot 15814, a practitioner may secure the implant to the bone using screws. The screws may pass through plate 15802 and into the bone. The screws may pass through the bone and into the implant. The screws may pass through plate 15802 and the implant.

Thus, apparatus and methods for bone fracture repair have been provided. Persons skilled in the art will appreciate that the present invention can be practiced by other than the described examples, which are presented for purposes of illustration rather than of limitation.

What is claimed is:

1. Apparatus for placement in an interior of a bone, the apparatus comprising:
   a first intramedullary rod defining a screw hole having a central axis;
   a second intramedullary rod configured to be coupled to the first rod;

an implant configured to be coupled to an end of the second rod, the implant including an expandable implant head that, when expanded, defines a volume; and an elongated member configured to be advanced through the screw hole and to be anchored in the implant head when the implant head is expanded;

wherein, in operation, the second rod is coupled to the first rod, the implant is coupled to the second rod, the implant head is in an expanded state, the central axis points to the volume, the elongated member is seated in the screw hole and is anchored in the implant head.

2. The apparatus of claim 1 wherein:

the hole is a first hole and the central axis is a first central axis;

the first rod defines a second hole; and the second hole defines a second central axis oblique to the first central axis; wherein, in operation, the second rod is coupled to the first rod, the implant is coupled to the second rod, the implant head is in an expanded state and the second central axis points to the volume.

3. The apparatus of claim 1 wherein:

the implant includes an implant base extending away from the implant head; and the end of the second rod defines an opening sized to receive the implant base.

4. The apparatus of claim 1, when the implant is a first implant and the expandable head is a first expandable head, further comprising a second implant including a second expandable head, the second implant being configured to be coupled to an end of the first rod.

5. The apparatus of claim 4 wherein:

the second implant includes a base extending away from the second head; and the end of the first rod defines an opening sized to receive the second implant base.

6. The apparatus of claim 4, when the end of the first rod is a first end, further comprising:

a third implant including a third expandable head configured to be coupled to a second end of the first rod.

7. The apparatus of claim 6 wherein:

the third implant includes a base extending away from the third head; and the end of the first rod defines an opening sized to receive the third base.

* * * * *